US010006038B2

(12) United States Patent
Raab et al.

(10) Patent No.: US 10,006,038 B2
(45) **Date of Patent: *Jun. 26, 2018**

(54) CONSOLIDATED PRETREATMENT AND HYDROLYSIS OF PLANT BIOMASS EXPRESSING CELL WALL DEGRADING ENZYMES

(71) Applicant: Agrivida, Inc., Medford, MA (US)

(72) Inventors: R. Michael Raab, Arlington, MA (US); Dongcheng Zhang, Medford, MA (US); Oleg Bougri, Boise, ID (US)

(73) Assignee: AGRIVIDA, INC., Medford, MA (US)

( * ) Notice: Subject to any disclaimer, the term of this patent is extended or adjusted under 35 U.S.C. 154(b) by 67 days.

This patent is subject to a terminal disclaimer.

(21) Appl. No.: 14/961,426

(22) Filed: Dec. 7, 2015

(65) Prior Publication Data

US 2016/0138035 A1 May 19, 2016

Related U.S. Application Data

(63) Continuation of application No. 13/414,627, filed on Mar. 7, 2012, now Pat. No. 9,249,474, which is a continuation-in-part of application No. 12/590,444, filed on Nov. 6, 2009, now Pat. No. 8,420,387, and a continuation-in-part of application No. 13/004,713, filed on Jan. 11, 2011, now Pat. No. 8,247,647, and a continuation-in-part of application No. PCT/US2010/055746, filed on Nov. 5, 2010, which is a continuation-in-part of application No. 12/590,444, filed on Nov. 6, 2009, now Pat. No. 8,420,387, said application No. 13/414,627 is a continuation-in-part of application No. PCT/US2010/055669, filed on Nov. 5, 2010, which is a continuation-in-part of application No. 12/590,444, filed on Nov. 6, 2009, now Pat. No. 8,420,387, said application No. 13/414,627 is a continuation-in-part of application No. PCT/US2010/055751, filed on Nov. 5, 2010, which is a continuation-in-part of application No. 12/590,444, filed on Nov. 6, 2009, now Pat. No. 8,420,387.

(60) Provisional application No. 61/449,769, filed on Mar. 7, 2011, provisional application No. 61/280,635, filed on Nov. 6, 2009, provisional application No. 61/398,589, filed on Jun. 28, 2010.

(51) Int. Cl.

| | |
|---|---|
| ***C12N 15/82*** | (2006.01) |
| ***C12N 9/24*** | (2006.01) |
| ***C12N 9/42*** | (2006.01) |
| ***C12P 19/14*** | (2006.01) |

(52) U.S. Cl.

CPC ......... *C12N 15/8246* (2013.01); *C12N 9/248* (2013.01); *C12N 9/2437* (2013.01); *C12N 9/2445* (2013.01); *C12N 15/8216* (2013.01); *C12P 19/14* (2013.01); *C12Y 302/01004* (2013.01); *C12Y 302/01008* (2013.01); *C12Y 302/01021* (2013.01); *Y02E 50/10* (2013.01); *Y02E 50/30* (2013.01)

(58) Field of Classification Search

None

See application file for complete search history.

(56) References Cited

U.S. PATENT DOCUMENTS

| | | | | |
|---|---|---|---|---|
| 5,432,074 | A | 7/1995 | Evans et al. | |
| 5,496,714 | A | 3/1996 | Comb et al. | |
| 5,654,184 | A | 8/1997 | Curtiss et al. | |
| 5,780,708 | A | 7/1998 | Lundquist et al. | |
| 5,834,247 | A | 11/1998 | Comb et al. | |
| 5,981,835 | A | 11/1999 | Austin-Phillips et al. | |
| 6,013,863 | A | 1/2000 | Lundquist et al. | |
| 6,022,846 | A | 2/2000 | Van Ooijen et al. | |
| 6,160,208 | A | 12/2000 | Lundquist et al. | |
| 6,395,966 | B1 | 5/2002 | Mumm et al. | |
| 6,531,316 | B1 | 3/2003 | Patten et al. | |
| 6,800,792 | B1 | 10/2004 | Howard et al. | |
| 6,858,775 | B1 | 2/2005 | Xu et al. | |
| 6,933,362 | B1 | 8/2005 | Belfort et al. | |
| 7,049,485 | B2 | 5/2006 | Sticklen et al. | |
| 7,102,057 | B2 | 9/2006 | Lanahan et al. | |
| 7,186,898 | B1 | 3/2007 | Kossmann and Emmermann | |
| 7,361,806 | B2 | 4/2008 | Lebel et al. | |
| 7,557,262 | B2 | 7/2009 | Lanahan et al. | |
| 7,709,697 | B2 | 5/2010 | Raab | |
| 7,741,530 | B2 | 6/2010 | Snell | |
| 7,838,732 | B2 | 11/2010 | Lebel et al. | |
| 7,855,322 | B2 | 12/2010 | Lanahan et al. | |
| 7,906,704 | B2 | 3/2011 | Raab et al. | |
| 7,919,681 | B2 | 4/2011 | Lanahan et al. | |
| 7,919,682 | B2 | 4/2011 | Frohberg et al. | |
| 8,093,456 | B2 | 1/2012 | Sticklen | |
| 8,101,392 | B2 | 1/2012 | Gray et al. | |
| 8,101,393 | B2 * | 1/2012 | Gray | C12N 9/2402 424/94.61 |
| 8,247,647 | B2 | 8/2012 | Raab | |
| 8,257,502 | B2 | 9/2012 | Frohberg et al. | |
| 8,343,747 | B2 | 1/2013 | Burke et al. | |
| 8,455,715 | B2 | 6/2013 | Paul et al. | |
| 8,481,810 | B2 | 7/2013 | Lebel et al. | |
| 8,664,476 | B2 | 3/2014 | Raab | |
| 9,249,474 | B2 * | 2/2016 | Raab | C12N 9/2437 |

(Continued)

FOREIGN PATENT DOCUMENTS

| | | | |
|---|---|---|---|
| CN | 101200734 | A | 6/2008 |
| CN | 101283092 | | 10/2008 |

(Continued)

OTHER PUBLICATIONS

Caspers et al 2001 The Plant Journal 26:191-204.*

(Continued)

*Primary Examiner* — Brent T Page

(74) *Attorney, Agent, or Firm* — Volpe and Koenig, P.C.

(57) ABSTRACT

Methods for consolidated pretreatment and hydrolysis of genetically engineered plants expressing cell wall degrading enzymes are provided. Expression cassettes and vectors for making transgenic plants are described. Plants engineered to express one or more cell wall degrading enzymes using expression cassettes and vectors of the invention are also provided.

8 Claims, 29 Drawing Sheets

(56) References Cited

U.S. PATENT DOCUMENTS

| | | | |
|---|---|---|---|
| 2002/0138878 A1 | 9/2002 | Sticklen et al. | |
| 2003/0131376 A1 | 7/2003 | Okubara et al. | |
| 2003/0159182 A1 | 8/2003 | Tackaberry et al. | |
| 2003/0167533 A1 | 9/2003 | Yadav et al. | |
| 2003/0180895 A1 | 9/2003 | Sibbesen et al. | |
| 2003/0233675 A1 | 12/2003 | Cao et al. | |
| 2004/0123343 A1 | 6/2004 | La Rosa et al. | |
| 2005/0125860 A1 | 6/2005 | Raab et al. | |
| 2005/0283850 A1 | 12/2005 | Snell et al. | |
| 2006/0179513 A1 | 8/2006 | Sticklen et al. | |
| 2007/0192900 A1 | 8/2007 | Sticklen et al. | |
| 2007/0218530 A1 | 9/2007 | Duck et al. | |
| 2007/0250961 A1 | 10/2007 | Blaylock et al. | |
| 2008/0115243 A1 | 5/2008 | Raab et al. | |
| 2008/0220125 A1 | 9/2008 | Abbas et al. | |
| 2009/0119800 A1 | 5/2009 | Lanahan et al. | |
| 2009/0155238 A1 | 6/2009 | Weiner et al. | |
| 2009/0193541 A1 | 7/2009 | Miles | |
| 2009/0258930 A1 | 10/2009 | Pachuk et al. | |
| 2009/0298149 A1 | 12/2009 | Wang et al. | |
| 2009/0320831 A1 | 12/2009 | Lanahan et al. | |
| 2010/0124771 A1 | 5/2010 | Sabesan et al. | |
| 2010/0143967 A1 | 6/2010 | McFarland | |
| 2010/0159494 A1 | 6/2010 | Sweeney and Vlasenko | |
| 2010/0159510 A1 | 6/2010 | Raab | |
| 2010/0159519 A1 | 6/2010 | Diner et al. | |
| 2011/0045127 A1 | 2/2011 | Ral et al. | |
| 2011/0111442 A1 | 5/2011 | Shen et al. | |
| 2012/0040409 A1* | 2/2012 | Hau | C12N 15/74 435/99 |
| 2012/0054915 A1 | 3/2012 | Steffens | |
| 2012/0258503 A1 | 10/2012 | Raab et al. | |
| 2013/0318655 A1 | 11/2013 | Raab | |

FOREIGN PATENT DOCUMENTS

| | | |
|---|---|---|
| CN | 101979548 | 2/2011 |
| EP | 0602899 | 6/1994 |
| JP | 70200 | 3/1995 |
| RU | 2291901 C2 | 1/2007 |
| WO | 199701642 | 1/1997 |
| WO | 199821348 | 5/1998 |
| WO | 2000005381 | 2/2000 |
| WO | 200036093 | 6/2000 |
| WO | 200052155 | 9/2000 |
| WO | 2000071701 | 11/2000 |
| WO | 2001057183 | 8/2001 |
| WO | 2001059091 | 8/2001 |
| WO | 2003050265 | 6/2003 |
| WO | 2003056904 | 7/2003 |
| WO | 2005095618 | 10/2005 |
| WO | 2005095619 | 10/2005 |
| WO | 2007041419 A1 | 4/2007 |
| WO | 2007100897 | 9/2007 |
| WO | 2007146944 | 12/2007 |
| WO | 2008064314 | 5/2008 |
| WO | 2009067751 | 6/2009 |
| WO | 2009155601 | 12/2009 |
| WO | 2010060056 | 5/2010 |
| WO | 2010096510 | 8/2010 |
| WO | 2011057159 | 5/2011 |
| WO | 2011163659 | 12/2011 |
| WO | 2012027395 A2 | 3/2012 |

OTHER PUBLICATIONS

Ritte et al., "The starch-related R1 protein is an alpha-glucan, water dikinase"; PNAS, 99:7166-7171.

James D. McMillan, "Pretreatment of Lignocellulosic Biomass", Enzymatic Conversion of Biomass for Fuels Production, ACS Symposium Series, (1994) ISBN 13: 978084 1229563, pp. 292-324.

Chinese Office Action issued in Chinese Application No. 201410108640.4 (with English Translation).

Australian Examination Report for Australian Patent Application No. 2012225487.

Morris et al. "Accession number: AAC46361, beta-1,4xylanase229B, [Dictyoglomus thermophilum]," Genbank, published Dec. 14, 2009.

Morris et al., "Cloning of the xynB Gene from Dictyoglomus thermophilum Rt46B.1 and Action of the Gene Product on Kraft Pulp," Applied and Envoronmental Microbiology, 1998, 64(5):1759-1765.

Mosier et al., "Features of Promising Technologies for Pretreatment of Lignocellulosic Biomass," Bioresource Biotechnology, 2005, 96: 673-686.

Murashige et al., "A Revised Medium for Rapid Growth and Bio Assays with Tobacco Tissue Cultures," Physiologia Plantarum, vol. 15, pp. 473-497 (1962).

Negrotto et al., "The Use of Phosphomannose-Isomerase As a Selectable Marker to recover Transgenic Maize plants (*Zea mays* L) via Agrobacterium transformation," Plant Cell Reports, 2000, 19 (8): 798-803.

Ng et al., (2000) Genome sequence of Halobacterium species NRC-1. Proc Natl Acad Sci U S A. 97(22): 12176-81.

Niehaus et al., (1997) Cloning and characterisation of a thermostable alpha-DNA polymerase from the hyperthermophilic archaeon *Thermococcus* sp. TY. Gene 204(1-2): 153-8.

Nishioka et al., (1998) Characterization of two intein homing endonucleases encoded in the DNA polymerase gene of Pyrococcus kodakaraensis strain KOD1. Nucleic Acids Res 26(19): 4409-12.

Olsson et al., "Fermentation of lignocellulosic Hydrolysates for Ethanol Production," Enzyme and Microbial Technology, vol. 18, 1996, pp. 312-331.

Otomo et al., (1999) Improved segmental isotope labeling of proteins and application to a larger protein. J Biomol NMR 14(2): 105-14.

Otomo et al., (1999B) NMR observation of selected segments in a larger protein: central-segment isotope labeling through intein-mediated ligation. Biochemistry 38(49): 16040-4.

Park et al., "Enhancement of Growth and Cellulose Accumulation by Overexpression of Xyloglucanase in Poplar," FEBS Letters, 2004, 564: pp. 183-187.

Parsons et al., "Transformation of Poplar by Agrobacterium Tumefaciens," Biotechnology, vol. 4, Jun. 1986, pp. 533-536.

Patel et al., "Transgenic Barley Expressing a Fungal Xylanase Gene in the Endosperm of the Developing Grains," Molecular Breeding, 2000, 6:113-123.

Perler et al., (1992) Intervening sequences in an Archaea DNA polymerase gene. Proc Natl Acad Sci U S A. 89(12): 5577-81.

Perler, "InBase: the Intein Database" Aug. 31, 2001, Nucleic Acids Research, vol. 30, No. 1. pp. 383-384.

Perler et al. (1997) Compilation and analysis of intein sequences. Nucleic Acids Res 25(6): 1087-93.

Perler et al., "Protein Splicing Elements; Inteins and Exteins—A Definition of Terms and Recommended Nomenclature", Nucleic Acids Research, vol. 22, No. 7, Feb. 24, 1993, pp. 1125-1127.

Pietrokovski, "Conserved Sequence Features of Inteins (Protein Introns) and Their Use in Identifying New Inteins and Related Proteins" Aug. 10, 1994, Protein Science, vol. 3, pp. 2340-2350.

Pietrokovski (1998) Modular organization of inteins and C-terminal autocatalytic domains. Protein Sci 7(1): 64-71.

Poirier, "Green Chemistry Yields a Better Plastic," Nature Biotechnology, vol. 17, Oct. 1999, pp. 960-961.

*Pyrococcus* sp. Deep Vent DNA Polymerase Precursor Gene (ncbi.nlm.gov/nuccore/436492) GenBank, May 24, 1995.

Ransom et al., "Heterologous Acidothermus cellulolyticus 1,4,β-Endoglucanase E1 Produced Within the Corn Biomass Converts Corn Stover Into Glucose," Applied Biochemistry and Biotechnology, 2007, 36:207-220.

Riera et al., (1997) Ribonucleotide reductase in the archaeon Pyrococcus furiosus: a critical enzyme in the evolution of DNA genomes?. Proc Natl Acad Sci U S A 94(2): 475-8.

Rocha-Sosa et al., "Both Developmental and Metabolic Signals Activate the Promoter of a Class I Patatin Gene," The EMBO Journal, vol. 8, No. 1, 1989, pp. 23-29.

(56) References Cited

OTHER PUBLICATIONS

Ruepp et al., (2000) The genome sequence of the thermoacidophilic scavenger Thermoplasma acidophilum. Nature. 407(6803): 508-13.
Ryan et al., Genomic Sequence of a 12S Seed Storage Protein from Oilseed Rape, Nucleic Acids Research, vol. 17, No. 9, 1989, p. 3584.
Sainz, "Commercial Cellulosic Ethanol: The Role of Plant-Expressed Enzymes," In Vitro Cellular and Developmental Biology, 2009, 45: 314-329.
Sandum Fernando, et al., "Biorefineries: Current Status, Challenges, and Future Direction," Energy & Fuels, 2006, 1727-1737.
Saves et al., (2000) Inteins of Thermococcus fumicolans DNA polymerase are endonucleases with distinct enzymatic behaviors. J Biol Chem 275(4): 2335-41.
Saves et al., (2000C) The Thy pol-2 intein of Thermococcus hydrothermalis is an isoschizomer of PI-TliI and PI-TfuII endonucleases: Nucleic Acids Res 28(21): 4391-6.
Schreier et al., The Use of Nuclear-Encoded Sequences to Direct the Light-Regulated Synthesis and Transport of a Foreign Protein into Plant Chloroplasts, The EMBO Journal, vol. 4, No. 1, 1985, pp. 25-32.
Senejani et al., (2001) The intein of the Thermoplasma A-ATPase A subunit: structure, evolution and expression in *E. coli.* BMC Biochem 2: 13.
Shao et al., (1995) Protein splicing: characterization of the aminosuccinimide residue at the carboxyl terminus of the excised intervening sequence. Biochemistry 34(34): 10844-50.
Shao et al., (1996) Protein splicing: evidence for an N—O acyl rearrangement as the initial step in the splicing process. Biochemistry 35(12): 3810-5.
Shen et al., (2001) Invariant Asp-1122 and Asp-1124 are essential residues for polymerization catalysis of family D DNA polymerase from Pyrococcus horikoshii. J Biol Chem 276(29): 27376-83.
Shill et al., "Ionic Liquid Pretreatment of Cellulosic Biomass: Enzymatc Hydrolysis and Ionic Liquid Recycle," Biotechnology and Bioengineering, 2011, 108(3): 511-520.
Shimamoto et al., Fertile Transgenic Rice Plants Regenerated from Transformed Protoplasts, Nature, vol. 338, Mar. 1989, pp. 274-276.
Shingledecker et al., "Reactivity of the Cysteine Residues in the Protein Splicing Active Center of the *Mycobacterium tuberculosis* RecA intein" Mar. 1, 2000, Archives of biochemistry and biophysics, vol. 375, No. 1, pp. 138-144.
Sijmons et al., Production of Correctly Processed Human Serum Albumin in Transgenic Plants, Biotechnology, vol. 8, Mar. 1990, pp. 217-221.
Sivamani et al. "Expression enhancement of a rice polyubiquitin gene promoter" Plant Molecular Biology 60, pp. 225-239 (2006).
Smeekens et al., "Protein Transport into and Within Chloroplasts," Trends in Biochemical Sciences, vol. 15, Feb. 1990, pp. 73-76.
Smith et al., (1997B) Complete genome sequence of Methanobacterium thermoautotrophicum deltaH: functional analysis and comparative genomics. J Bacteriol 179(22): 7135-55.
Southworth et al., (1998) Control of protein splicing by intein fragment reassembly. Embo J 17(4): 918-26.
Southworth et al., (1999) Purification of proteins fused to either the amino or carboxy terminus of the *Mycobacterium xenopi* gyrase A intein. Biotechniques 27(1): 110-4, 116, 118-20.
Southworth et al., (2000) An alternative protein splicing mechanism for inteins lacking an N-terminal nucleophile. Embo J 19(18): 5019-26.
Sreenath et al., "Production of Ethanol from Wood Hydrolyzate by Yeasts," Bioresource Technology, vol. 72, No. 3, 2000, pp. 253-260.
Staub et al., "High-Yield Production of a Human Therapeutic Protein in Tobacco Chloroplasts," Nature Biotechnology, vol. 18, Mar. 2000, pp. 333-338.
Sticklen, "Plant Genetic Engineering for Biofuel Production: Towards Affordable Cellulosic Ethanol," Nature Reviews: Genetics, 2008, 9: 433-443.
Stoddard et al., (1998) Breaking up is hard to do. Nat Struct Biol 5(1): 3-5.
Chinese Office Action Issued for Chinese Patent Application No. 201410108640.4 (English Translation).
Practical Self-help Manual Against Agricultural Disasters, Harbin Institute of Technology Press, Compiled by Xiao-ping Zhang (with English Translation of pp. 179-182).
Streatfield et al. "Corn as a production system for human and animal vaccines", Vaccine 21, pp. 812-815 (2003).
Sun et al., "Protein trans-Splicing to Produce Herbicide-Resistant Acetolactate Synthase," Applied and Environmental Microbiology, vol. 67, No. 3, pp. 1025-1029 (Mar. 2001).
Tague et al., "A Short Domain of the Plant Vacuolar Protein Phytohemagglutinin Targets Invertase to the Yeast Vacuole," The Plant Cell, vol. 2, Jun. 1990, pp. 533-546.
Takagi et al., (1997) Characterization of DNA polymerase from *Pyrococcus* sp. strain KOD1 and its application to PCR. Appl Environ Microbiol 63(11): 4504-10.
Taylor et al., "Dry-Grind Process for Fuel Ethanol by Continuous Fermentation and Stripping," Biotechnology Progress, vol. 16, 2000. pp. 541-547.
Telenti et al., (1997) The *Mycobacterium xenopi* GyrA protein splicing element: characterization of a minimal intein. J Bacteriol 179(20): 6378-8.
Tetsuya Kimura et al., "Stable Expression of a Thermostable Xylanase of Clostridium thermocellum in Cultured Tobacco Cells," Journal of Bioscience and Bioengineering, 2003, 95(4): 397-400.
Tingey et al., "Glutamine Synthetase Genes of Pea Encode Distinct Polypeptides Which are Differentially Expressed in Leaves, Roots and Nodules," The EMBO Journal, vol. 6, No. 1, 1987, pp. 1-9.
Tokuda et al. Cellulose Digestion in the Wood-Eating Higher Termite Nasutitermes takasagoensis (Shiraki): Distribution of Cellulases and Properties of Endo-β-1,4-glucanases, Zoological Science 14: 83-93(1997).
Tokuda et al. "Metazoan cellulase genes from termites: intron/exon structures and sites of expression", Biochimica et Biophysica Acta 1447, pp. 146-159 (1999).
Toshihiko Komari et al., "Vectors Carrying Two Separate T-DNAs for Co-transformation of Higher Plants Mediated by Agrobacterium tumefaciens and Segregations of Trsnformants Free From Selection Markers," The Plant Journal, 199, 10(1): 165-174.
Ulgen et. al., "Bioconversion of Starch Into Ethanol by a Recombinant Saccharomyces cerevisiae Strain YPG-AB," Process Biochemistry, vol. 37, 2002, pp. 1157-1168.
Van Den Broeck et al., Targeting of a Foreign Protein to Chloroplasts by Fusions to the Transmit Peptide from the Small Subunit of Ribulose 1,5-Bisphosphate Carboxylase, Nature, vol. 313, Ksmistu 1985, pp. 358-363.
Verma et al., Microwave Assisted Pretreatment of Woody Biomass with Ammonium Molibdate Activated by H2O2, Bioresource Technology, 2011, 102(4):3941-3945.
Von Heijne, "Towards a Comparative Anatomy of N-Terminal Topogenic Protein Sequences," Journal of Molecular Biology, vol. 189, 1986, pp. 239-242.
Wallace, "The Curious Case of Protein Splicing: Mechanistic Insights Suggested by Protein Semisynthesis," Protein Science, vol. 2, pp. 697-705 (1993).
Wang et al., "Identification of an Unusual Intein in Chloroplast ClpP Protease of Chlamydomonas Eugametos" May 2, 1997, Journal of Biological Chemistry, vol. 272, No. 18, pp. 11869-11873.
Wenzler et al., "Analysis of a Chimeric Class-I Patatin-GUS Gene in Transgenic Potato Plants: High-Level Expression in Tubers and Sucrose-Inducible Expressions in Cultured Leaf and Stem Explants," Plant Molecular Biology, vol. 12, 1989, pp. 41-50.
Wood et al., "Optimized Single-Step Affinity Purification with a Self-Cleaving Intein Applied to Human Acidic Fibroblast Growth Factor," Biotechnology Progress, vol. 16, 2000, pp. 1055-1063.
Wood et al., "A Genertic System yields self-cleaving inteins for bioseparations," Nature Biotech, 1999, 17:889-892.
Wyman et al., "Coordinated Development of Leading Biomass Pretreatment Technologies," Bioresource Biotechnology, 2005, 96:1959-1966.
Xu et al., (1994) Protein splicing: an analysis of the branched intermediate and its resolution by succinimide formation. Embo J 13(23): 5517-22.

(56) References Cited

OTHER PUBLICATIONS

Xu and Cheng "Pretreatment of Switchgrass for Sugar Production with the Combination of Sodium Hydroxide and Lime," Bioresource Technology, 2011, 102(4):3861-3868.
Xu et al., "In Vitro Protein Splicing of Purified Precursor and the Identification of Branched Intermediate," Cell, vol. 75, Dec. 31, 1993, pp. 1371-1377.
Xu et al., "The Mechanism of Protein Splicing in its Modulation by Mutation," The EMBO Journal, vol. 15, No. 19, 1996, pp. 5146-5153.
Yamazaki et al., (1998) Segmental isotope labeling for protein NMR using peptide splicing. J. Am. Chem. Soc. 120: 5591-5592.
Yang et al., "Intein-mediated assembly of a functional .beta.-glucuronidase in transgenic plants," PNAS, vol. 100, No. 6, pp. 3513-3518 (2003).
Yang Peilong et al., Expression of Xylanase with High Specific Activity from Streptomyces olivaceoviridis A1 in Transgenic Potato Plants (*Solanum tuberosum* L.), Biotechnology Letters, 2007, 29: 659-667.
Yukoh Hiei and Toshihiko Komari, "Improved Protocols for Transformation of Indica Rice Mediated by Agrobacterium tumefaciens," 2006 Plant Cell Tissue and Organ Culture, 2006, 85: 271-283.
Yukoh Hiei, et al., "Efficient Transformation of Rice (*Oryza saliva* L.) mediated by Agrobacterium and sequence analysis of the boundaries of the T-DNA,"The Plant Journal, 1994, 6(2): 271-282.
Yumiko Obana et al., "Enhanced turnover of transitory starch by expression of up-regulared ADP-glucose pyrophosphorylases in *Arabidopsis thaliana*", Plant Science, vol. 170, 1-11, 2006.
Zeng et al., "Biological Pretreatment of Wheat Straw by Phanerochaete chrysosporium Supplemented with Inorganic Salts," Bioresource Technology, 2011, 102(3) 3206-3214.
Zhu et al., "Structural Features Affecting Biomass Enzymatic Digestability," Bioresource Biotechnology, 2008, 99: 3817-3828.
Zhu et al., "Pretreatment of Woody Biomass for Biofuel Production: Energy Efficiency, Technologies, and Recalcitrance," Applied Microbiology & Biotechnology, 2010, 87(3):847-857.
Ziegelhoffer et al., "Dramatic Effects of Truncation and Sub-cellular Targeting on the Accumulation of recombinant Microbial Cellulase in Tobacco," Molecular Breeding, 2001, 8: 147-158.
Ziegelhoffer et al., "Expression of Bacterial Cellulase Genes in Transgenic Alfalfa (*Medicago sativa* L.), potato (*Solanum tuberosum* L.) and tobacco (Nicotiana tabacum)," Molecular Breeding, 1999, 5: 309-318.
Ziegler et al., "Accumulation of Thermostable Endo-1,4-.beta.-D-Glucanase in the Apoplast of *Arabidposis thaliana* Leaves," Molecular Breeding, vol. 6, 2000, pp. 37-46.
Ziyu Dai et al., "Improved Plant-Based Production of E1 Endoglucanase Using Potato: Expression Optimization and Tissue Targeting," Molecular Breeding, 2000, 6:277-285.
U.S. Office Action issued in U.S. Appl. No. 13/508,280.
Chinese Office Action issued in Chinse Application No. 201080060542.8.
Morris D. D. et al., UniProtKB—P77853 (P77853_DICTH); 6-7; 16-17, Dec. 31, 1998.
Office Action Issued in corresponding Indian Patent Application No. 1338/KOLNP/2012 dated Feb. 12, 2018, consisting of 6 pp.
Abramson et al., "Plant Cell Wall Reconstruction Toward Improved Lignocellulosic Production and Processability," Plant Science, 2010, 178: 61-72.
Altintas et al., "Improvement of Ethanol Production from Starch by Recombinant Yeast Through Manipulation of Environmental Factors," Enzyme and Microbial Technology, vol. 31, No. 5, 2002, pp. 640-647.
Alvira et al., "Pretreatment technologies for an efficient bioethanol production process based on enzymatic hydrolysis: A review," Bioresource Technology, vol. 101, 4851-4861, 2010.
Aspegren, K., et al., "Secretion of Heat-Stable Fungal .beta.-Glucanase from Transgenic, Suspension-Cultured Barley Cells," Molecular Breeding, 1995, pp. 91-99.
Bae et al., Dual Targeting of Xylanase to Chloroplasts and Peroxisomes as a Means to Increase Protein Accumulation in Plant Cells, Journal of Experimental Botany, 2006, 57 (1): 161-169.
Bae et al. "Production of Recombinant Xylanase in Plants and its Potential for Pulp Biobleaching Applications," Bioresource Technology, Elseview, BV, GB, vol. 99, No. 9, 22 (Aug. 22, 2008), pp. 3513-3519.
Banerjee and Scott-Craig "Improving Enzymes for Biomass Conversion: A Basic Research Perspective," BioEnergy Research, 2010, 3: 82-92.
Belknap et al. "pBINPLUS/ARS: an improved plant transformation vector based on pBINPLUS" BioTechniques vol. 44, No. 6, pp. 753-756 (May 2008).
Bhiri et al. "Accession No. AAT99321, cellobiohydrolase 1[Penicillium occitanis]," Genbank, published Oct. 8, 2008.
Birch, "Plant Transformation: Problems and Strategies for Practical Application," Annual Review of Plant Physiology and Plant Molecular Biology, vol. 48, Jun. 1997, pp. 297-326.
Bird et al., The Tomato Polygalacturonase Gene and Ripening-Specific Expressions in Transgenic Plants, Plant Molecular Biology, 1988, pp. 651-662.
Biswas et al., "Expression of Biologically Active Acidothermus cellulolyticus Endoglucanase in Transgenic Maize Plants," Plant Science, 2006, pp. 617-623.
Borkhardt et al., "Autohydrolysis of Plant Xylans by Apoplastic Expression of Thermophilic Bacterial Endo-Xylanases," Plant Biotechnology Journal, 2010, 8: pp. 363-374.
Brederode et al., Complete Nucleotide Sequence of Alfalfa Mosaic Virus RNA 4, Nucleic Acids Research, vol. 8, No. 10, 1980, pp. 2213-2223.
Broothaerts el al., "Gene Transfer to Plants by Diverse Species of Bacteria," Nature, vol. 433, Feb. 2005, pp. 629-633.
Brunecky et al., "In planta Expression of A. cellulоticus Cel5A Endocellulase Reduces Cell Wall Recalcitrance in Tobacco and Maize," Biotechnology for Biofuels, 2011, 4: pp. 1-10.
Bult et al., (1996) Complete genome sequence of the methanogenic archaeon, Methanococcus jannaschii. Science 273(5278): 1058-73.
Cambon-Bonavita et al., (2000) Cloning, expression, and characterization of DNA polymerase I from the hyperthermophilic archaea Thermococcus fumicolans. Extremophiles 4(4): 215-25.
Cameron et al., "Metabolic Engineering of Propanediol Pathways," Biotechnology Progress, 1998, pp. 116-125.
Chen et al., (2000) Protein splicing in the absence of an intein penultimate histidine. J Biol Chem 275(27): pp. 20431-20435.
Chen et al., "Herbicide Resistance from a Divided EPSPS Protein: The Split Synechocystis DnaE Intein as an In Vivo Affinity Domain" Gene: An International Journal of Genes and Genomes, vol. 263, pp. 39-48 (2001).
Cheon et al., "Ovexpression of Human Erythropoietin (EPO) Affects Plant Morphologies: Retarded Vegetative Growth in Tobacco and Male Sterility in Tobacco and *Arabidopsis*," Transgenic Research, 2004, pp. 541-549.
Chih-Ching et al., "Establishment of an Efficient Medium for Anther Culture of Rice Through Comparative Experiments on the Nitrogen Sources," Scientia Sinica, vol. 18, No. 3, 1975, pp. 659-668.
Chin et al., Protein trans-splicing in transgenic plant chloroplast: Reconstruction of herbicide resistance from split genes, PNAS, vol. 100, No. 8, pp. 4510-4515 (2003).
Chong et al., "Modulation of Protein Splicing of the *Saccharomyces cerevisiae* Vacuolar Membrane ATPase Intein," The Journal of Biological Chemistry, vol. 273, No. 17, pp. 10567-10577. (Apr. 24, 1998).
Chong et al., "Single-column purification of free recombinant proteins using a self-cleavable affinity tag derived from a protein splicing element," Gene: An International Journal of Genes Genomes, vol. 192, pp. 271-281 (1997).
Christian et al. "The yield and composition of switchgrass and coastal panic grass grown as a biofuel in Southern England" Bioresource Technology 83, pp. 115-124 (2002).
Chute et al., (1998) A topA intein in Pyrococcus furiosus and its relatedness to the r-gyr intein of Methanococcus annaschii. Gene 210(1): pp. 85-92.

(56) References Cited

OTHER PUBLICATIONS

Clarke, "A Proposed Mechanism for the Self-Splicing of Proteins," Proceedings of the National Academy of Science, USA, vol. 91, pp. 11084-11088, Nov. 1994.
Coruzzi et al., "Tissue-Specific and Light-Regulated Expression of Pea Nuclear Gene Coding the Small Subunit of Ribulose-1, 5-Bisphosphate Carboxylase," The EMBO Journal, 1984, pp. 1671-1679.
Dai et al., "Improved Plant-Based Production of E1 Endoglucanase Using Potato: Expression Optimization and Tissue Targeting," Molecular Breeding, 2000, pp. 277-285.
Dai et al., "Expression of Acidothermus cellulolyticus E1 in Transgenic Tobacco: Biochemical Characteristics and Physiological Effects," Transgenic Research, 2000, 9: pp. 43-54.
Dale "Biobased Industrial Products: Bioprocess Engineering When Costs Really Count," Biotechnology Progress, 1999, pp. 775-776.
Dalgaard et al., (1997) Statistical modeling, phylogenetic analysis and structure prediction of a protein splicing domain common to inteins and hedgehog proteins. J Comput Biol 4(2): pp. 193-214.
Davis et al., "Protein Sprucing: The Lengths Some Proteins Will Go to," 1995, Antonie van Leeuwenhoek, vol. 67, pp. 131-137.
Davis et al., "Novel Structure of the recA Locus of *Mycobacterium tuberculosis* Implies Processing of the Gene Product," Journal of Bacteriology, vol. 173, No. 18, Sep. 1991, pp. 5653-5662.
Davis et al., "Protein Splicing in the Maturation of *M. Tuberculosis* RecA Protein: A Mechanism for Tolerating a Novel Class of Intervening Sequence," Cell Press, vol. 71, Oct. 16, 1992, pp. 201-210.
Deckert et al., (1998) The complete genome of the hyperthermophilic bacterium Aquifex aeolicus. Nature. 392(6674): pp. 353-358.
Derbyshire et al., "Lightning Strikes Twice: Intron-Intein Coincidence," Proceedings of the National Academy of Science, USA, vol. 95, pp. 1356-1357, Feb. 17, 1998.
Dodd and Cann, "Enzymatic Deconstruction of Xylan for Biofuel Production," Global Change Biology Bioenergy, 2009, 1(1): pp. 2-17.
Evans et al., (1999) The in vitro ligation of bacterially expressed proteins using an intein from Methanobacterium thermoautotrophicum. J Biol Chem 274(7): pp. 3923-3926.
Evans et al., "Semisynthesis of Cytotoxic Proteins Using a Modified Protein Splicing Element," Protein Science, vol. 7: pp. 2256-2264.
Galbe et al., "A Review of the Production of Ethanol from Softwood," Applied Microbiology Biotechnology, 2002, 59:618-628.
Gangopadhyay et. al., "In Vitro Splicing of Erythropoietin by the *Mycobacterium tuberculosis* RecA Intein Without Substituting Amino Acids at the Splice Junctions," Biochimica et Biophysica Acta, vol. 1619, (2003), pp. 193-200.
GenBank Accession No. BAA33708, first available Oct. 8, 1999.
Genschik et al., (1997) The human RNA 3'-terminal phosphate cyclase is a member of a new family of proteins conserved in Eucarya, Bacteria and Archaea. Embo J. 16(10): pp. 2955-2967.
Genschik et al., (1998) Characterization of the *Escherichia coli* RNA 3'-terminal phosphate cyclase and its sigma54-regulated operon. J Biol Chem. 273(39): pp. 25516-25526.
Gimble, "Invasion of a Multitude of Genetic Niches by Mobile Endonuclease Genes," Feb. 8, 2000, FEMS Microbiology Letters, vol. 185, pp. 99-107.
Gordon-Kamm et al., "Transformation of Maize Cells and Regeneration of Fertile Transgenic Plants," The Plant Cell, vol. 2, pp. 603-618, Jul. 1990.
Gray et al., "Global and Grain-Specific Accumulation of Glycoside Hydrolase Family 10 Xylanases in Transgenic Maize (*Zea mays*)," Plant Biotechnology Journal, 2011, 9:1100-1108.
Decision on Grant Issued in corresponding Russian Patent Application No. 2016147539 dated Apr. 2, 2018, consisting of 14 pp. (English Translation Provided).

* cited by examiner

FIG.5A
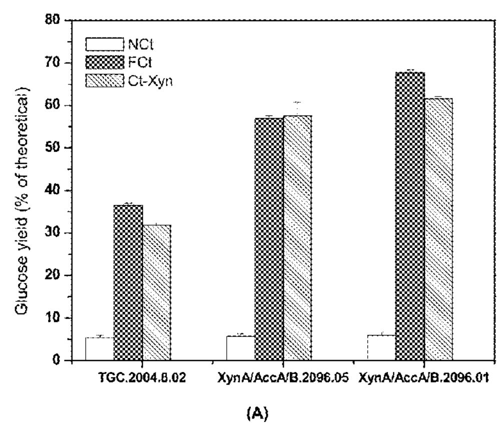
FIG.5B
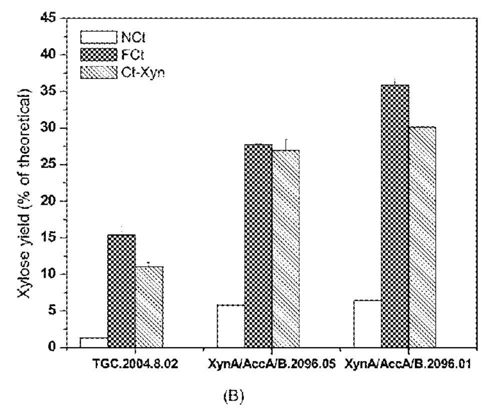
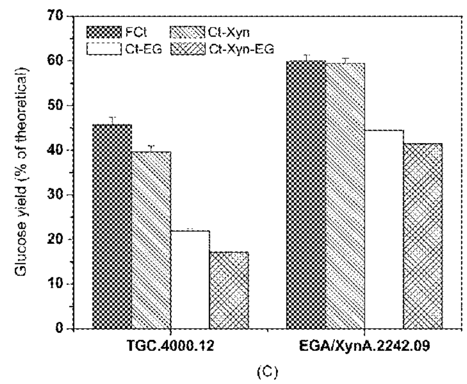
FIG. 5C
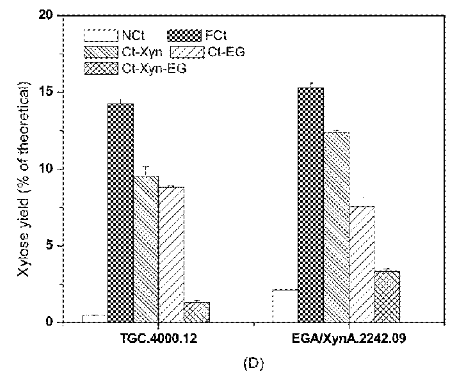
FIG.5D

FIG.16A
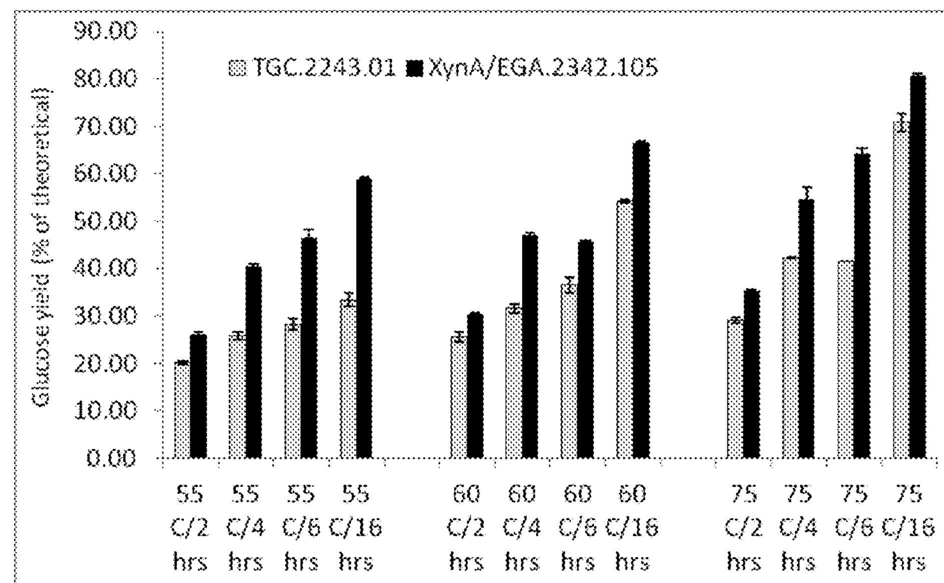
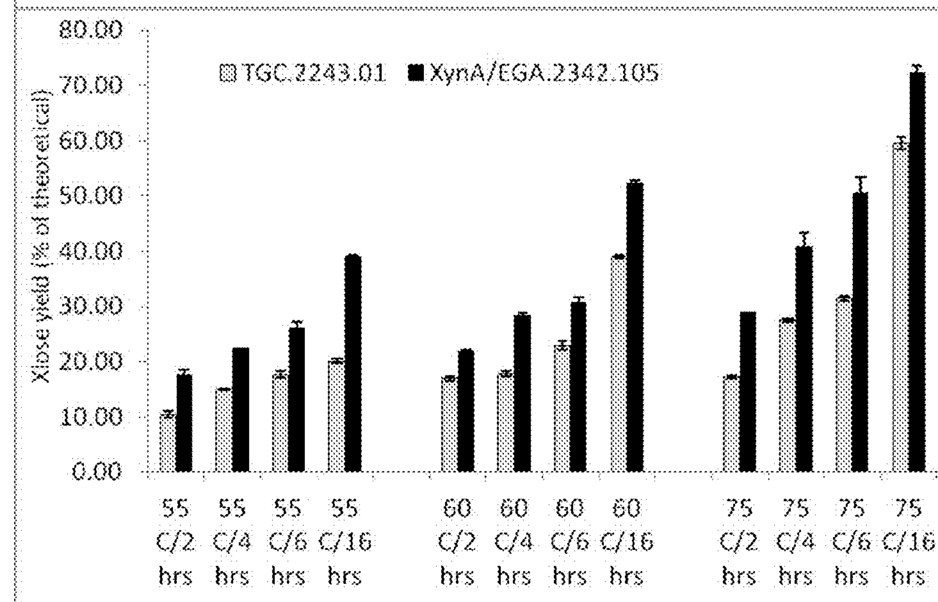
FIG.16B

FIG.20A
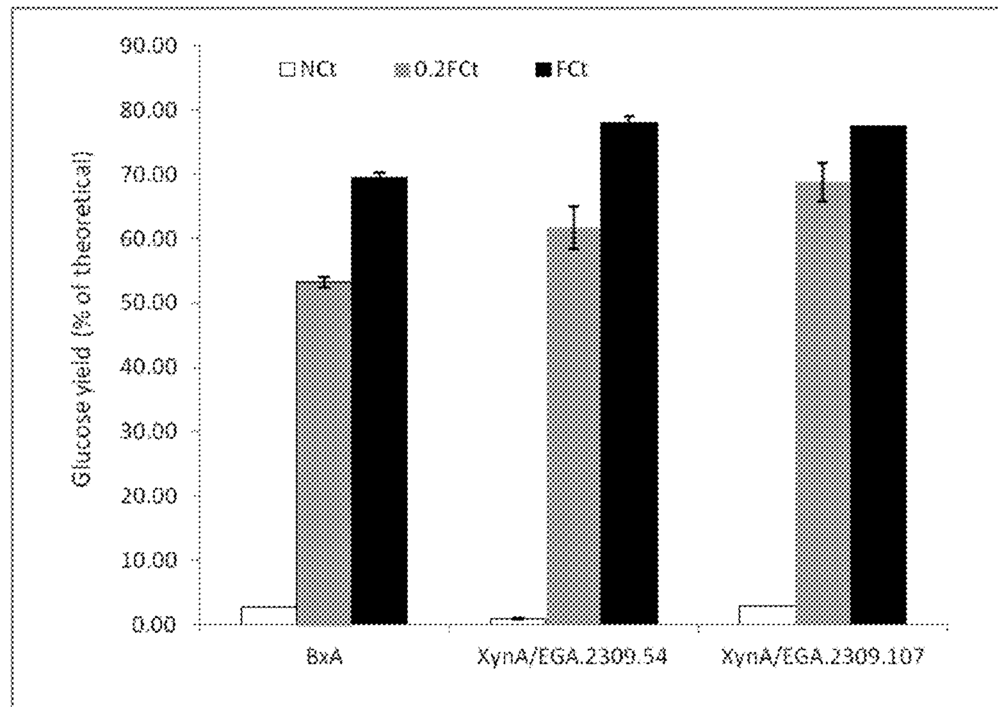
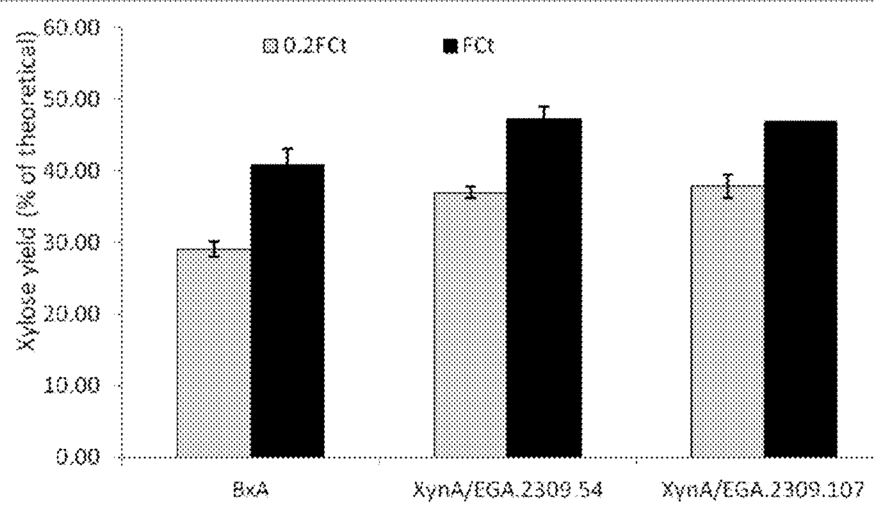
FIG.20B

FIG.24A
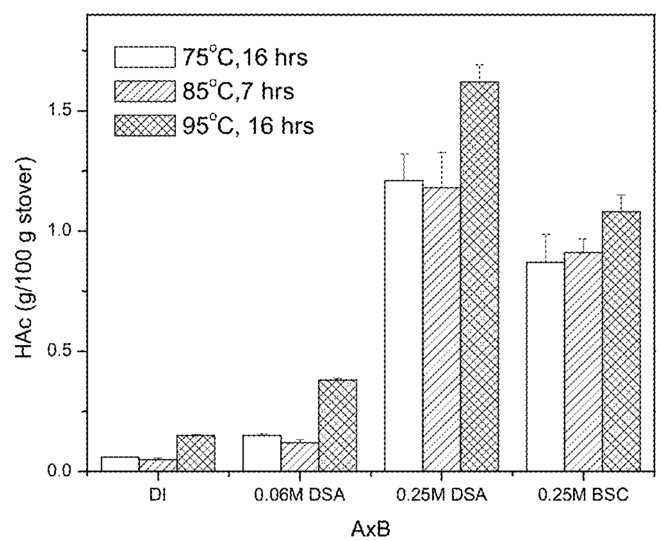
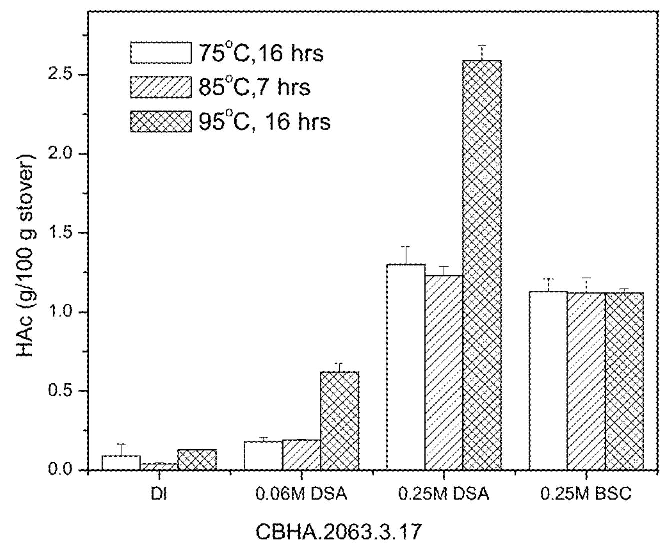
FIG. 24B

FIG.25A
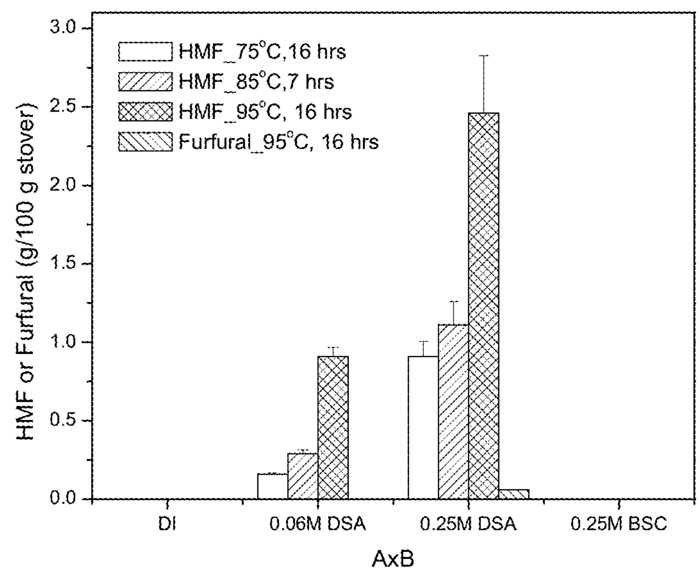
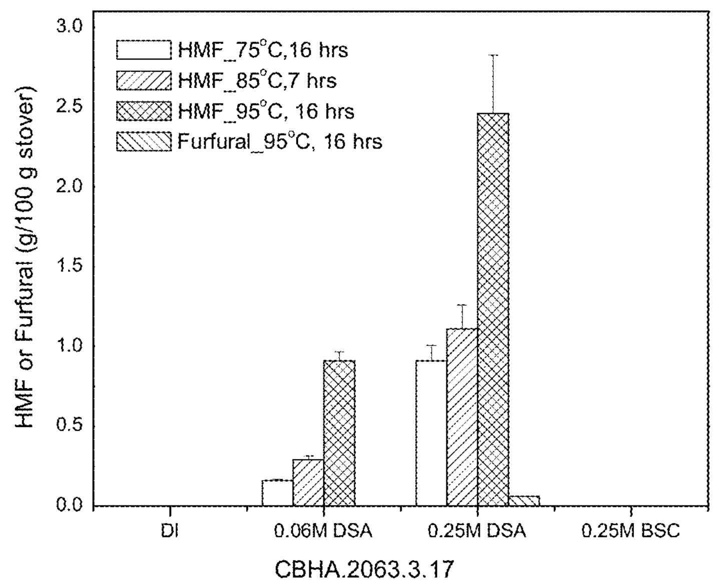
FIG. 25B

SEQUENCE LISTING

```
<160> NUMBER OF SEQ ID NOS: 85

<210> SEQ ID NO 1
<211> LENGTH: 337
<212> TYPE: PRT
<213> ORGANISM: Dictyoglomus thermophilum

<400> SEQUENCE: 1

Met Gln Thr Ser Ile Thr Leu Thr Ser Asn Ala Ser Gly Thr Phe Asp
1               5                   10                  15

Gly Tyr Tyr Tyr Glu Leu Trp Lys Asp Thr Gly Asn Thr Thr Met Thr
            20                  25                  30

Val Tyr Thr Gln Gly Arg Phe Ser Cys Gln Trp Ser Asn Ile Asn Asn
        35                  40                  45

Ala Leu Phe Arg Thr Gly Lys Lys Tyr Asn Gln Asn Trp Gln Ser Leu
    50                  55                  60

Gly Thr Ile Arg Ile Thr Tyr Ser Ala Thr Tyr Asn Pro Asn Gly Asn
65                  70                  75                  80

Ser Tyr Leu Cys Ile Tyr Gly Trp Ser Thr Asn Pro Leu Val Glu Phe
                85                  90                  95
```

```
Tyr Ile Val Glu Ser Trp Gly Asn Trp Arg Pro Pro Gly Ala Thr Ser
            100                 105                 110

Leu Gly Gln Val Thr Ile Asp Gly Gly Thr Tyr Asp Ile Tyr Arg Thr
        115                 120                 125

Thr Arg Val Asn Gln Pro Ser Ile Val Gly Thr Ala Thr Phe Asp Gln
    130                 135                 140

Tyr Trp Ser Val Arg Thr Ser Lys Arg Thr Ser Gly Thr Val Thr Val
145                 150                 155                 160

Thr Asp His Phe Arg Ala Trp Ala Asn Arg Gly Leu Asn Leu Gly Thr
                165                 170                 175

Ile Asp Gln Ile Thr Leu Cys Val Glu Gly Tyr Gln Ser Ser Gly Ser
            180                 185                 190

Ala Asn Ile Thr Gln Asn Thr Phe Ser Gln Gly Ser Ser Ser Gly Ser
        195                 200                 205

Ser Gly Gly Ser Ser Gly Ser Thr Thr Thr Thr Arg Ile Glu Cys Glu
    210                 215                 220

Asn Met Ser Leu Ser Gly Pro Tyr Val Ser Arg Ile Thr Asn Pro Phe
225                 230                 235                 240

Asn Gly Ile Ala Leu Tyr Ala Asn Gly Asp Thr Ala Arg Ala Thr Val
                245                 250                 255

Asn Phe Pro Ala Ser Arg Asn Tyr Asn Phe Arg Leu Arg Gly Cys Gly
            260                 265                 270

Asn Asn Asn Asn Leu Ala Arg Val Asp Leu Arg Ile Asp Gly Arg Thr
        275                 280                 285

Val Gly Thr Phe Tyr Tyr Gln Gly Thr Tyr Pro Trp Glu Ala Pro Ile
    290                 295                 300

Asp Asn Val Tyr Val Ser Ala Gly Ser His Thr Val Glu Ile Thr Val
305                 310                 315                 320

Thr Ala Asp Asn Gly Thr Trp Asp Val Tyr Ala Asp Tyr Leu Val Ile
                325                 330                 335

Gln


<210> SEQ ID NO 2
<211> LENGTH: 261
<212> TYPE: PRT
<213> ORGANISM: Aspergillus niger

<400> SEQUENCE: 2

Met Ala Ser Thr Gln Gly Ile Ser Glu Asp Leu Tyr Asn Arg Leu Val
1               5                   10                  15

Glu Met Ala Thr Ile Ser Gln Ala Ala Tyr Ala Asp Leu Cys Asn Ile
            20                  25                  30

Pro Ser Thr Ile Ile Lys Gly Glu Lys Ile Tyr Asn Ala Gln Thr Asp
        35                  40                  45

Ile Asn Gly Trp Ile Leu Arg Asp Asp Thr Ser Lys Glu Ile Ile Thr
    50                  55                  60

Val Phe Arg Gly Thr Gly Ser Asp Thr Asn Leu Gln Leu Asp Thr Asn
65                  70                  75                  80

Tyr Thr Leu Thr Pro Phe Asp Thr Leu Pro Gln Cys Asn Asp Cys Glu
                85                  90                  95

Val His Gly Gly Tyr Tyr Ile Gly Trp Ile Ser Val Gln Asp Gln Val
            100                 105                 110

Glu Ser Leu Val Lys Gln Gln Ala Ser Gln Tyr Pro Asp Tyr Ala Leu
        115                 120                 125
```

```
Thr Val Thr Gly His Ser Leu Gly Ala Ser Met Ala Ala Leu Thr Ala
    130                 135                 140

Ala Gln Leu Ser Ala Thr Tyr Asp Asn Val Arg Leu Tyr Thr Phe Gly
145                 150                 155                 160

Glu Pro Arg Ser Gly Asn Gln Ala Phe Ala Ser Tyr Met Asn Asp Ala
                165                 170                 175

Phe Gln Val Ser Ser Pro Glu Thr Thr Gln Tyr Phe Arg Val Thr His
            180                 185                 190

Ser Asn Asp Gly Ile Pro Asn Leu Pro Pro Ala Asp Glu Gly Tyr Ala
        195                 200                 205

His Gly Gly Val Glu Tyr Trp Ser Val Asp Pro Tyr Ser Ala Gln Asn
    210                 215                 220

Thr Phe Val Cys Thr Gly Asp Glu Val Gln Cys Cys Glu Ala Gln Gly
225                 230                 235                 240

Gly Gln Gly Val Asn Asp Ala His Thr Thr Tyr Phe Gly Met Thr Ser
                245                 250                 255

Gly Ala Cys Thr Trp
            260


<210> SEQ ID NO 3
<211> LENGTH: 505
<212> TYPE: PRT
<213> ORGANISM: Aspergillus niger

<400> SEQUENCE: 3

Met Ala Thr Asp Pro Phe Gln Ser Arg Cys Asn Glu Phe Gln Asn Lys
1               5                   10                  15

Ile Asp Ile Ala Asn Val Thr Val Arg Ser Val Ala Tyr Val Ala Ala
            20                  25                  30

Gly Gln Asn Ile Ser Gln Ala Glu Val Ala Ser Val Cys Lys Ala Ser
        35                  40                  45

Val Gln Ala Ser Val Asp Leu Cys Arg Val Thr Met Asn Ile Ser Thr
    50                  55                  60

Ser Asp Arg Ser His Leu Trp Ala Glu Ala Trp Leu Pro Arg Asn Tyr
65                  70                  75                  80

Thr Gly Arg Phe Val Ser Thr Gly Asn Gly Gly Leu Ala Gly Cys Val
                85                  90                  95

Gln Glu Thr Asp Leu Asn Phe Ala Ala Asn Phe Gly Phe Ala Thr Val
            100                 105                 110

Gly Thr Asn Gly Gly His Asp Gly Asp Thr Ala Lys Tyr Phe Leu Asn
        115                 120                 125

Asn Ser Glu Val Leu Ala Asp Phe Ala Tyr Arg Ser Val His Glu Gly
    130                 135                 140

Thr Val Val Gly Lys Gln Leu Thr Gln Leu Phe Tyr Asp Glu Gly Tyr
145                 150                 155                 160

Asn Tyr Ser Tyr Tyr Leu Gly Cys Ser Thr Gly Gly Arg Gln Gly Tyr
                165                 170                 175

Gln Gln Val Gln Arg Phe Pro Asp Asp Tyr Asp Gly Val Ile Ala Gly
            180                 185                 190

Ser Ala Ala Met Asn Phe Ile Asn Leu Ile Ser Trp Gly Ala Phe Leu
        195                 200                 205

Trp Lys Ala Thr Gly Leu Ala Asp Asp Pro Asp Phe Ile Ser Ala Asn
    210                 215                 220

Leu Trp Ser Val Ile His Gln Glu Ile Val Arg Gln Cys Asp Leu Val
225                 230                 235                 240
```

```
Asp Gly Ala Leu Asp Gly Ile Ile Glu Asp Pro Asp Phe Cys Ala Pro
            245                 250                 255

Val Ile Glu Arg Leu Ile Cys Asp Gly Thr Thr Asn Gly Thr Ser Cys
            260                 265                 270

Ile Thr Gly Ala Gln Ala Ala Lys Val Asn Arg Ala Leu Ser Asp Phe
        275                 280                 285

Tyr Gly Pro Asp Gly Thr Val Tyr Tyr Pro Arg Leu Asn Tyr Gly Gly
    290                 295                 300

Glu Ala Asp Ser Ala Ser Leu Tyr Phe Thr Gly Ser Met Tyr Ser Arg
305                 310                 315                 320

Thr Glu Glu Trp Tyr Lys Tyr Val Val Tyr Asn Asp Thr Asn Trp Asn
                325                 330                 335

Ser Ser Gln Trp Thr Leu Glu Ser Ala Lys Leu Ala Leu Glu Gln Asn
            340                 345                 350

Pro Phe Asn Ile Gln Ala Phe Asp Pro Asn Ile Thr Ala Phe Arg Asp
        355                 360                 365

Arg Gly Gly Lys Leu Leu Ser Tyr His Gly Thr Gln Asp Pro Ile Ile
    370                 375                 380

Ser Ser Thr Asp Ser Lys Leu Tyr Tyr Arg Arg Val Ala Asn Ala Leu
385                 390                 395                 400

Asn Ala Ala Pro Ser Glu Leu Asp Glu Phe Tyr Arg Phe Phe Gln Ile
                405                 410                 415

Ser Gly Met Gly His Cys Gly Asp Gly Thr Gly Ala Ser Tyr Ile Gly
            420                 425                 430

Gln Gly Tyr Gly Thr Tyr Thr Ser Lys Ala Pro Gln Val Asn Leu Leu
        435                 440                 445

Arg Thr Met Val Asp Trp Val Glu Asn Gly Lys Ala Pro Glu Tyr Met
    450                 455                 460

Pro Gly Asn Lys Leu Asn Ala Asn Gly Ser Ile Glu Tyr Met Arg Lys
465                 470                 475                 480

His Cys Arg Tyr Pro Lys His Asn Ile His Thr Gly Pro Gly Asn Tyr
                485                 490                 495

Thr Asp Pro Asn Ser Trp Thr Cys Val
            500                 505


<210> SEQ ID NO 4
<211> LENGTH: 433
<212> TYPE: PRT
<213> ORGANISM: Nasutitermes takasagoensis

<400> SEQUENCE: 4

Met Ala Tyr Asp Tyr Lys Gln Val Leu Arg Asp Ser Leu Leu Phe Tyr
1               5                   10                  15

Glu Ala Gln Arg Ser Gly Arg Leu Pro Ala Asp Gln Lys Val Thr Trp
            20                  25                  30

Arg Lys Asp Ser Ala Leu Asn Asp Gln Gly Asp Gln Gly Gln Asp Leu
        35                  40                  45

Thr Gly Gly Tyr Phe Asp Ala Gly Asp Phe Val Lys Phe Gly Phe Pro
    50                  55                  60

Met Ala Tyr Thr Ala Thr Val Leu Ala Trp Gly Leu Ile Asp Phe Glu
65                  70                  75                  80

Ala Gly Tyr Ser Ser Ala Gly Ala Leu Asp Asp Gly Arg Lys Ala Val
                85                  90                  95

Lys Trp Ala Thr Asp Tyr Phe Ile Lys Ala His Thr Ser Gln Asn Glu
```

```
            100                 105                 110

Phe Tyr Gly Gln Val Gly Gln Gly Asp Ala Asp His Ala Phe Trp Gly
        115                 120                 125

Arg Pro Glu Asp Met Thr Met Ala Arg Pro Ala Tyr Lys Ile Asp Thr
    130                 135                 140

Ser Arg Pro Gly Ser Asp Leu Ala Gly Glu Thr Ala Ala Ala Leu Ala
145                 150                 155                 160

Ala Ala Ser Ile Val Phe Arg Asn Val Asp Gly Thr Tyr Ser Asn Asn
                165                 170                 175

Leu Leu Thr His Ala Arg Gln Leu Phe Asp Phe Ala Asn Asn Tyr Arg
            180                 185                 190

Gly Lys Tyr Ser Asp Ser Ile Thr Asp Ala Arg Asn Phe Tyr Ala Ser
        195                 200                 205

Ala Asp Tyr Arg Asp Glu Leu Val Trp Ala Ala Ala Trp Leu Tyr Arg
    210                 215                 220

Ala Thr Asn Asp Asn Thr Tyr Leu Asn Thr Ala Glu Ser Leu Tyr Asp
225                 230                 235                 240

Glu Phe Gly Leu Gln Asn Trp Gly Gly Gly Leu Asn Trp Asp Ser Lys
                245                 250                 255

Val Ser Gly Val Gln Val Leu Leu Ala Lys Leu Thr Asn Lys Gln Ala
            260                 265                 270

Tyr Lys Asp Thr Val Gln Ser Tyr Val Asn Tyr Leu Ile Asn Asn Gln
        275                 280                 285

Gln Lys Thr Pro Lys Gly Leu Leu Tyr Ile Asp Met Trp Gly Thr Leu
    290                 295                 300

Arg His Ala Ala Asn Ala Ala Phe Ile Met Leu Glu Ala Ala Glu Leu
305                 310                 315                 320

Gly Leu Ser Ala Ser Ser Tyr Arg Gln Phe Ala Gln Thr Gln Ile Asp
                325                 330                 335

Tyr Ala Leu Gly Asp Gly Gly Arg Ser Phe Val Cys Gly Phe Gly Ser
            340                 345                 350

Asn Pro Pro Thr Arg Pro His His Arg Ser Ser Ser Cys Pro Pro Ala
        355                 360                 365

Pro Ala Thr Cys Asp Trp Asn Thr Phe Asn Ser Pro Asp Pro Asn Tyr
    370                 375                 380

His Val Leu Ser Gly Ala Leu Val Gly Gly Pro Asp Gln Asn Asp Asn
385                 390                 395                 400

Tyr Val Asp Asp Arg Ser Asp Tyr Val His Asn Glu Val Ala Thr Asp
                405                 410                 415

Tyr Asn Ala Gly Phe Gln Ser Ala Leu Ala Ala Leu Val Ala Leu Gly
            420                 425                 430

Tyr


<210> SEQ ID NO 5
<211> LENGTH: 194
<212> TYPE: PRT
<213> ORGANISM: Unknown
<220> FEATURE:
<223> OTHER INFORMATION: EU591743 from unknown bacterium

<400> SEQUENCE: 5

Met Ala Gln Thr Cys Leu Thr Ser Pro Gln Thr Gly Phe His Asn Gly
1               5                   10                  15

Phe Phe Tyr Ser Phe Trp Lys Asp Ser Pro Gly Thr Val Asn Phe Cys
            20                  25                  30
```

Leu Leu Glu Gly Gly Arg Tyr Thr Ser Asn Trp Ser Gly Ile Asn Asn
35 40 45

Trp Val Gly Gly Lys Gly Trp Gln Thr Gly Ser Arg Arg Asn Ile Thr
50 55 60

Tyr Ser Gly Ser Phe Asn Thr Pro Gly Asn Gly Tyr Leu Ala Leu Tyr
65 70 75 80

Gly Trp Thr Thr Asn Pro Leu Val Glu Tyr Tyr Val Val Asp Ser Trp
85 90 95

Gly Ser Trp Arg Pro Pro Gly Ser Asp Gly Thr Phe Leu Gly Thr Val
100 105 110

Asn Ser Asp Gly Gly Thr Tyr Asp Ile Tyr Arg Ala Gln Arg Val Asn
115 120 125

Ala Pro Ser Ile Ile Gly Asn Ala Thr Phe Tyr Gln Tyr Trp Ser Val
130 135 140

Arg Gln Ser Lys Arg Val Gly Gly Thr Ile Thr Thr Gly Asn His Phe
145 150 155 160

Asp Ala Trp Ala Ser Val Gly Leu Asn Leu Gly Thr His Asn Tyr Gln
165 170 175

Ile Met Ala Thr Glu Gly Tyr Gln Ser Ser Gly Ser Ser Asp Ile Thr
180 185 190

Val Ser

<210> SEQ ID NO 6
<211> LENGTH: 207
<212> TYPE: PRT
<213> ORGANISM: Thermomyces lanuginosus

<400> SEQUENCE: 6

Met Phe Pro Ala Gly Asn Ala Thr Glu Leu Glu Lys Arg Gln Thr Thr
1 5 10 15

Pro Asn Ser Glu Gly Trp His Asp Gly Tyr Tyr Tyr Ser Trp Trp Ser
20 25 30

Asp Gly Gly Ala Gln Ala Thr Tyr Thr Asn Leu Glu Gly Gly Thr Tyr
35 40 45

Glu Ile Ser Trp Gly Asp Gly Gly Asn Leu Val Gly Gly Lys Gly Trp
50 55 60

Asn Pro Gly Leu Asn Ala Arg Ala Ile His Phe Glu Gly Val Tyr Gln
65 70 75 80

Pro Asn Gly Asn Ser Tyr Leu Ala Val Tyr Gly Trp Thr Arg Asn Pro
85 90 95

Leu Val Glu Tyr Tyr Ile Val Glu Asn Phe Gly Thr Tyr Asp Pro Ser
100 105 110

Ser Gly Ala Thr Asp Leu Gly Thr Val Glu Cys Asp Gly Ser Ile Tyr
115 120 125

Arg Leu Gly Lys Thr Thr Arg Val Asn Ala Pro Ser Ile Asp Gly Thr
130 135 140

Gln Thr Phe Asp Gln Tyr Trp Ser Val Arg Gln Asp Lys Arg Thr Ser
145 150 155 160

Gly Thr Val Gln Thr Gly Cys His Phe Asp Ala Trp Ala Arg Ala Gly
165 170 175

Leu Asn Val Asn Gly Asp His Tyr Tyr Gln Ile Val Ala Thr Glu Gly
180 185 190

Tyr Phe Ser Ser Gly Tyr Ala Arg Ile Thr Val Ala Asp Val Gly
195 200 205

<210> SEQ ID NO 7
<211> LENGTH: 761
<212> TYPE: PRT
<213> ORGANISM: Artificial Sequence
<220> FEATURE:
<223> OTHER INFORMATION: Synthetic construct, P77853:T134-100-101

<400> SEQUENCE: 7

```
Met Gln Thr Ser Ile Thr Leu Thr Ser Asn Ala Ser Gly Thr Phe Asp
1               5                   10                  15

Gly Tyr Tyr Tyr Glu Leu Trp Lys Asp Thr Gly Asn Thr Thr Met Thr
            20                  25                  30

Val Tyr Thr Gln Gly Arg Phe Ser Cys Gln Trp Ser Asn Ile Asn Asn
        35                  40                  45

Ala Leu Phe Arg Thr Gly Lys Lys Tyr Asn Gln Asn Trp Gln Ser Leu
    50                  55                  60

Gly Thr Ile Arg Ile Thr Tyr Ser Ala Thr Tyr Asn Pro Asn Gly Asn
65                  70                  75                  80

Ser Tyr Leu Cys Ile Tyr Gly Trp Ser Thr Asn Pro Leu Val Glu Phe
                85                  90                  95

Tyr Ile Val Glu Ser Trp Gly Asn Trp Arg Pro Pro Gly Ala Cys Leu
            100                 105                 110

Ala Glu Gly Ser Leu Val Leu Asp Ala Ala Thr Gly Gln Arg Val Pro
        115                 120                 125

Ile Glu Lys Val Arg Pro Gly Met Glu Val Phe Ser Leu Gly Pro Asp
    130                 135                 140

Tyr Arg Leu Tyr Arg Val Pro Val Leu Glu Val Leu Glu Ser Gly Val
145                 150                 155                 160

Arg Glu Val Val Arg Leu Arg Thr Arg Ser Gly Arg Thr Leu Val Leu
                165                 170                 175

Thr Pro Asp His Pro Leu Leu Thr Pro Glu Gly Trp Lys Pro Leu Cys
            180                 185                 190

Asp Leu Pro Leu Gly Thr Pro Ile Ala Val Pro Ala Glu Leu Pro Val
        195                 200                 205

Ala Gly His Leu Ala Pro Pro Glu Glu Arg Val Thr Leu Leu Ala Leu
    210                 215                 220

Leu Leu Gly Asp Gly Asn Thr Lys Leu Ser Gly Arg Arg Gly Thr Arg
225                 230                 235                 240

Pro Asn Ala Phe Phe Tyr Ser Lys Asn Pro Glu Leu Leu Ala Ala Tyr
                245                 250                 255

Arg Arg Cys Ala Glu Ala Leu Gly Ala Lys Val Lys Ala Tyr Val His
            260                 265                 270

Pro Thr Thr Gly Val Val Thr Leu Ala Thr Leu Ala Pro Arg Pro Gly
        275                 280                 285

Ala Gln Asp Pro Val Lys Arg Leu Val Val Glu Ala Gly Met Val Ala
    290                 295                 300

Lys Ala Glu Glu Lys Arg Val Pro Glu Glu Val Phe Arg Tyr Arg Arg
305                 310                 315                 320

Glu Ala Leu Ala Leu Phe Leu Gly Arg Leu Phe Ser Thr Asp Gly Ser
                325                 330                 335

Val Glu Lys Lys Arg Ile Ser Tyr Ser Ser Ala Ser Leu Gly Leu Ala
            340                 345                 350

Gln Asp Val Ala His Leu Leu Leu Arg Leu Gly Ile Thr Ser Gln Leu
        355                 360                 365
```

```
Arg Ser Arg Gly Pro Arg Ala His Glu Val Leu Ile Ser Gly Arg Glu
    370                 375                 380

Asp Ile Leu Arg Phe Ala Glu Leu Ile Gly Pro Tyr Leu Leu Gly Ala
385                 390                 395                 400

Lys Arg Glu Arg Leu Ala Ala Leu Glu Ala Glu Ala Arg Arg Arg Leu
                405                 410                 415

Pro Gly Gln Gly Trp His Leu Arg Leu Val Leu Pro Ala Val Ala Tyr
            420                 425                 430

Arg Val Gly Glu Ala Glu Arg Arg Ser Gly Phe Ser Trp Ser Glu Ala
        435                 440                 445

Gly Arg Arg Val Ala Val Ala Gly Ser Cys Leu Ser Ser Gly Leu Asn
    450                 455                 460

Leu Lys Leu Pro Arg Arg Tyr Leu Ser Arg His Arg Leu Ser Leu Leu
465                 470                 475                 480

Gly Glu Ala Phe Ala Asp Pro Gly Leu Glu Ala Leu Ala Glu Gly Gln
                485                 490                 495

Val Leu Trp Asp Pro Ile Val Ala Val Glu Pro Ala Gly Lys Ala Arg
            500                 505                 510

Thr Phe Asp Leu Arg Val Pro Pro Phe Ala Asn Phe Val Ser Glu Asp
        515                 520                 525

Leu Val Val His Asn Thr Val Pro Leu Gly Gln Val Thr Ile Asp Gly
    530                 535                 540

Gly Thr Tyr Asp Ile Tyr Arg Thr Thr Arg Val Asn Gln Pro Ser Ile
545                 550                 555                 560

Val Gly Thr Ala Thr Phe Asp Gln Tyr Trp Ser Val Arg Thr Ser Lys
                565                 570                 575

Arg Thr Ser Gly Thr Val Thr Val Thr Asp His Phe Arg Ala Trp Ala
            580                 585                 590

Asn Arg Gly Leu Asn Leu Gly Thr Ile Asp Gln Ile Thr Leu Cys Val
        595                 600                 605

Glu Gly Tyr Gln Ser Ser Gly Ser Ala Asn Ile Thr Gln Asn Thr Phe
    610                 615                 620

Ser Gln Gly Ser Ser Ser Gly Ser Ser Gly Gly Ser Ser Gly Ser Thr
625                 630                 635                 640

Thr Thr Thr Arg Ile Glu Cys Glu Asn Met Ser Leu Ser Gly Pro Tyr
                645                 650                 655

Val Ser Arg Ile Thr Asn Pro Phe Asn Gly Ile Ala Leu Tyr Ala Asn
            660                 665                 670

Gly Asp Thr Ala Arg Ala Thr Val Asn Phe Pro Ala Ser Arg Asn Tyr
        675                 680                 685

Asn Phe Arg Leu Arg Gly Cys Gly Asn Asn Asn Asn Leu Ala Arg Val
    690                 695                 700

Asp Leu Arg Ile Asp Gly Arg Thr Val Gly Thr Phe Tyr Tyr Gln Gly
705                 710                 715                 720

Thr Tyr Pro Trp Glu Ala Pro Ile Asp Asn Val Tyr Val Ser Ala Gly
                725                 730                 735

Ser His Thr Val Glu Ile Thr Val Thr Ala Asp Asn Gly Thr Trp Asp
            740                 745                 750

Val Tyr Ala Asp Tyr Leu Val Ile Gln
        755                 760

<210> SEQ ID NO 8
<211> LENGTH: 760
```

```
<212> TYPE: PRT
<213> ORGANISM: Artificial Sequence
<220> FEATURE:
<223> OTHER INFORMATION: Synthetic construct, P77853:S158-30-108-35

<400> SEQUENCE: 8

Met Gln Thr Ser Ile Thr Leu Thr Ser Asn Ala Ser Gly Thr Phe Asp
1               5                   10                  15

Gly Tyr Asn Tyr Glu Leu Trp Lys Asp Thr Gly Asn Thr Thr Met Thr
            20                  25                  30

Val Tyr Thr Gln Gly Arg Phe Ser Cys Gln Trp Ser Asn Ile Asn Asn
        35                  40                  45

Ala Leu Phe Arg Thr Gly Lys Lys Tyr Asn Gln Asn Trp Gln Ser Leu
    50                  55                  60

Gly Thr Ile Arg Ile Thr Tyr Ser Ala Thr Tyr Asn Pro Asn Gly Asn
65                  70                  75                  80

Ser Tyr Met Cys Ile Tyr Gly Trp Ser Thr Asn Pro Leu Val Glu Phe
                85                  90                  95

Tyr Ile Val Glu Ser Trp Gly Asn Trp Arg Pro Pro Gly Ala Thr Ser
            100                 105                 110

Leu Gly Gln Val Thr Ile Asp Gly Gly Thr Tyr Asp Ile Tyr Arg Thr
        115                 120                 125

Thr Arg Val Asn Gln Pro Cys Leu Ala Glu Gly Ser Leu Val Leu Asp
    130                 135                 140

Ala Ala Thr Gly Gln Arg Val Pro Ile Glu Lys Val Arg Pro Gly Met
145                 150                 155                 160

Glu Val Phe Ser Leu Gly Pro Asp Tyr Arg Leu Tyr Arg Val Pro Val
                165                 170                 175

Leu Glu Val Leu Glu Ser Gly Val Gly Glu Val Val Arg Leu Arg Thr
            180                 185                 190

Arg Ser Gly Arg Thr Leu Val Leu Thr Pro Glu His Pro Leu Leu Thr
        195                 200                 205

Pro Glu Gly Trp Lys Pro Leu Cys Asp Leu Pro Leu Gly Thr Pro Ile
    210                 215                 220

Ala Val Pro Ala Glu Leu Pro Val Ala Gly His Leu Ala Pro Pro Glu
225                 230                 235                 240

Glu Arg Val Met Leu Leu Ala Leu Leu Leu Gly Asp Gly Asn Thr Lys
                245                 250                 255

Leu Ser Gly Arg Arg Gly Thr Arg Pro Asn Ala Phe Phe Tyr Ser Lys
            260                 265                 270

Asp Ser Glu Leu Leu Ala Ala Tyr Arg Arg Cys Ala Glu Ala Leu Gly
        275                 280                 285

Ala Lys Val Lys Ala Tyr Val His Pro Thr Thr Gly Val Val Thr Leu
    290                 295                 300

Ala Thr Leu Ala Pro Arg Pro Gly Ala Gln Asp Pro Val Lys Arg Leu
305                 310                 315                 320

Val Val Glu Ala Gly Met Val Ala Lys Val Glu Glu Lys Arg Val Pro
                325                 330                 335

Glu Glu Val Phe Arg Tyr Arg Arg Glu Ala Leu Ala Leu Phe Leu Gly
            340                 345                 350

Arg Leu Phe Ser Thr Asp Gly Ser Val Glu Lys Lys Arg Ile Ser Tyr
        355                 360                 365

Ser Ser Ala Ser Leu Gly Leu Ala Gln Asp Val Ala His Leu Leu Leu
    370                 375                 380
```

```
Arg Leu Gly Ile Thr Ser Gln Leu Arg Ser Arg Gly Pro Arg Ala His
385                 390                 395                 400

Lys Val Leu Ile Ser Gly Arg Glu Asp Ile Leu Arg Phe Ala Glu Leu
                405                 410                 415

Ile Gly Pro Tyr Leu Leu Gly Ala Lys Arg Glu Arg Leu Ala Ala Leu
            420                 425                 430

Glu Ala Glu Ala Arg Arg Arg Leu Pro Gly Gln Gly Trp His Leu Arg
        435                 440                 445

Pro Val Leu Pro Ala Val Ala Tyr Arg Val Ser Glu Ala Lys Arg Arg
    450                 455                 460

Ser Gly Phe Ser Trp Ser Glu Ala Gly Arg Arg Val Ala Val Ala Gly
465                 470                 475                 480

Ser Cys Leu Ser Ser Gly Leu Asn Leu Lys Leu Pro Arg Arg Tyr Leu
                485                 490                 495

Ser Arg His Arg Leu Ser Leu Leu Gly Glu Ala Phe Ala Asp Pro Gly
            500                 505                 510

Leu Glu Ala Leu Ala Glu Gly Gln Val Leu Trp Asp Pro Ile Val Ala
        515                 520                 525

Val Glu Pro Ala Gly Lys Ala Arg Thr Phe Asp Leu Arg Val Pro Pro
    530                 535                 540

Phe Ala Asn Phe Val Ser Glu Asp Leu Val Val His Asn Ser Ile Val
545                 550                 555                 560

Gly Thr Ala Thr Phe Asp Gln Tyr Trp Ser Val Arg Thr Ser Lys Arg
                565                 570                 575

Thr Ser Gly Thr Val Thr Val Thr Asp His Phe Arg Ala Trp Ala Asn
            580                 585                 590

Arg Gly Leu Asn Leu Gly Thr Ile Asp Gln Ile Thr Leu Cys Val Glu
        595                 600                 605

Gly Tyr Gln Ser Ser Gly Ser Ala Asn Ile Thr Gln Asn Thr Phe Ser
    610                 615                 620

Gln Gly Ser Ser Ser Gly Ser Ser Gly Gly Ser Ser Gly Ser Thr Thr
625                 630                 635                 640

Thr Thr Arg Ile Glu Cys Glu Asn Met Ser Leu Ser Gly Pro Tyr Val
                645                 650                 655

Ser Arg Ile Thr Asn Pro Phe Asn Gly Ile Ala Leu Tyr Ala Asn Gly
            660                 665                 670

Asp Thr Ala Arg Ala Thr Val Asn Phe Pro Ala Ser Arg Asn Tyr Asn
        675                 680                 685

Phe Arg Leu Arg Gly Cys Gly Asn Ser Asn Asn Leu Ala Arg Val Asp
    690                 695                 700

Leu Arg Ile Asp Gly Arg Thr Val Gly Thr Phe Tyr Tyr Gln Gly Thr
705                 710                 715                 720

Tyr Pro Trp Glu Ala Pro Ile Asp Asn Val Tyr Val Ser Ala Gly Ser
                725                 730                 735

His Thr Val Glu Ile Thr Val Thr Ala Asp Asn Gly Thr Arg Asp Val
            740                 745                 750

Tyr Ala Asp Tyr Leu Val Ile Gln
        755                 760
```

<210> SEQ ID NO 9
<211> LENGTH: 244
<212> TYPE: PRT
<213> ORGANISM: Rhodothermus marinus

<400> SEQUENCE: 9

```
Met Cys Asp Trp Leu Phe Pro Asp Gly Asp Asn Gly Lys Glu Pro Glu
1               5                   10                  15

Pro Glu Pro Glu Pro Thr Val Glu Leu Cys Gly Arg Trp Asp Ala Arg
            20                  25                  30

Asp Val Ala Gly Gly Arg Tyr Arg Val Ile Asn Asn Val Trp Gly Ala
        35                  40                  45

Glu Thr Ala Gln Cys Ile Glu Val Gly Leu Glu Thr Gly Asn Phe Thr
    50                  55                  60

Ile Thr Arg Ala Asp His Asp Asn Gly Asn Asn Val Ala Ala Tyr Pro
65                  70                  75                  80

Ala Ile Tyr Phe Gly Cys His Trp Ala Pro Ala Arg Ala Ile Arg Asp
                85                  90                  95

Cys Ala Ala Arg Ala Gly Ala Val Arg Arg Ala His Glu Leu Asp Val
            100                 105                 110

Thr Pro Ile Thr Thr Gly Arg Trp Asn Ala Ala Tyr Asp Ile Trp Phe
        115                 120                 125

Ser Pro Val Thr Asn Ser Gly Asn Gly Tyr Ser Gly Gly Ala Glu Leu
    130                 135                 140

Met Ile Trp Leu Asn Trp Asn Gly Gly Val Met Pro Gly Gly Ser Arg
145                 150                 155                 160

Val Ala Thr Val Glu Leu Ala Gly Ala Thr Trp Glu Val Trp Tyr Ala
                165                 170                 175

Asp Trp Asp Trp Asn Tyr Ile Ala Tyr Arg Arg Thr Thr Pro Thr Thr
            180                 185                 190

Ser Val Ser Glu Leu Asp Leu Lys Ala Phe Ile Asp Asp Ala Val Ala
        195                 200                 205

Arg Gly Tyr Ile Arg Pro Glu Trp Tyr Leu His Ala Val Glu Thr Gly
    210                 215                 220

Phe Glu Leu Trp Glu Gly Gly Ala Gly Leu Arg Thr Ala Asp Phe Ser
225                 230                 235                 240

Val Thr Val Gln


<210> SEQ ID NO 10
<211> LENGTH: 869
<212> TYPE: PRT
<213> ORGANISM: Clostridium thermocellum

<400> SEQUENCE: 10

Met Leu Glu Asp Lys Ser Pro Lys Leu Pro Asp Tyr Lys Asn Asp Leu
1               5                   10                  15

Leu Tyr Glu Arg Thr Phe Asp Glu Gly Leu Cys Phe Pro Trp His Thr
            20                  25                  30

Cys Glu Asp Ser Gly Gly Lys Cys Asp Phe Ala Val Val Asp Val Pro
        35                  40                  45

Gly Glu Pro Gly Asn Lys Ala Phe Arg Leu Thr Val Ile Asp Lys Gly
    50                  55                  60

Gln Asn Lys Trp Ser Val Gln Met Arg His Arg Gly Ile Thr Leu Glu
65                  70                  75                  80

Gln Gly His Thr Tyr Thr Val Arg Phe Thr Ile Trp Ser Asp Lys Ser
                85                  90                  95

Cys Arg Val Tyr Ala Lys Ile Gly Gln Met Gly Glu Pro Tyr Thr Glu
            100                 105                 110

Tyr Trp Asn Asn Asn Trp Asn Pro Phe Asn Leu Thr Pro Gly Gln Lys
        115                 120                 125
```

```
Leu Thr Val Glu Gln Asn Phe Thr Met Asn Tyr Pro Thr Asp Asp Thr
    130                 135                 140

Cys Glu Phe Thr Phe His Leu Gly Gly Glu Leu Ala Ala Gly Thr Pro
145                 150                 155                 160

Tyr Tyr Val Tyr Leu Asp Asp Val Ser Leu Tyr Asp Pro Arg Phe Val
                165                 170                 175

Lys Pro Val Glu Tyr Val Leu Pro Gln Pro Asp Val Arg Val Asn Gln
            180                 185                 190

Val Gly Tyr Leu Pro Phe Ala Lys Lys Tyr Ala Thr Val Val Ser Ser
        195                 200                 205

Ser Thr Ser Pro Leu Lys Trp Gln Leu Leu Asn Ser Ala Asn Gln Val
    210                 215                 220

Val Leu Glu Gly Asn Thr Ile Pro Lys Gly Leu Asp Lys Asp Ser Gln
225                 230                 235                 240

Asp Tyr Val His Trp Ile Asp Phe Ser Asn Phe Lys Thr Glu Gly Lys
                245                 250                 255

Gly Tyr Tyr Phe Lys Leu Pro Thr Val Asn Ser Asp Thr Asn Tyr Ser
            260                 265                 270

His Pro Phe Asp Ile Ser Ala Asp Ile Tyr Ser Lys Met Lys Phe Asp
        275                 280                 285

Ala Leu Ala Phe Phe Tyr His Lys Arg Ser Gly Ile Pro Ile Glu Met
    290                 295                 300

Pro Tyr Ala Gly Gly Glu Gln Trp Thr Arg Pro Ala Gly His Ile Gly
305                 310                 315                 320

Val Ala Pro Asn Lys Gly Asp Thr Asn Val Pro Thr Trp Pro Gln Asp
                325                 330                 335

Asp Glu Tyr Ala Gly Arg Pro Gln Lys Tyr Tyr Thr Lys Asp Val Thr
            340                 345                 350

Gly Gly Trp Tyr Asp Ala Gly Asp His Gly Lys Tyr Val Val Asn Gly
        355                 360                 365

Gly Ile Ala Val Trp Thr Leu Met Asn Met Tyr Glu Arg Ala Lys Ile
    370                 375                 380

Arg Gly Ile Ala Asn Gln Gly Ala Tyr Lys Asp Gly Gly Met Asn Ile
385                 390                 395                 400

Pro Glu Arg Asn Asn Gly Tyr Pro Asp Ile Leu Asp Glu Ala Arg Trp
                405                 410                 415

Glu Ile Glu Phe Phe Lys Lys Met Gln Val Thr Glu Lys Glu Asp Pro
            420                 425                 430

Ser Ile Ala Gly Met Val His His Lys Ile His Asp Phe Arg Trp Thr
        435                 440                 445

Ala Leu Gly Met Leu Pro His Glu Asp Pro Gln Pro Arg Tyr Leu Arg
    450                 455                 460

Pro Val Ser Thr Ala Ala Thr Leu Asn Phe Ala Ala Thr Leu Ala Gln
465                 470                 475                 480

Ser Ala Arg Leu Trp Lys Asp Tyr Asp Pro Thr Phe Ala Ala Asp Cys
                485                 490                 495

Leu Glu Lys Ala Glu Ile Ala Trp Gln Ala Ala Leu Lys His Pro Asp
            500                 505                 510

Ile Tyr Ala Glu Tyr Thr Pro Gly Ser Gly Gly Pro Gly Gly Gly Pro
        515                 520                 525

Tyr Asn Asp Asp Tyr Val Gly Asp Glu Phe Tyr Trp Ala Ala Cys Glu
    530                 535                 540
```

```
Leu Tyr Val Thr Thr Gly Lys Asp Glu Tyr Lys Asn Tyr Leu Met Asn
545                 550                 555                 560

Ser Pro His Tyr Leu Glu Met Pro Ala Lys Met Gly Glu Asn Gly Gly
                565                 570                 575

Ala Asn Gly Glu Asp Asn Gly Leu Trp Gly Cys Phe Thr Trp Gly Thr
            580                 585                 590

Thr Gln Gly Leu Gly Thr Ile Thr Leu Ala Leu Val Glu Asn Gly Leu
        595                 600                 605

Pro Ser Ala Asp Ile Gln Lys Ala Arg Asn Asn Ile Ala Lys Ala Ala
    610                 615                 620

Asp Lys Trp Leu Glu Asn Ile Glu Glu Gln Gly Tyr Arg Leu Pro Ile
625                 630                 635                 640

Lys Gln Ala Glu Asp Glu Arg Gly Gly Tyr Pro Trp Gly Ser Asn Ser
                645                 650                 655

Phe Ile Leu Asn Gln Met Ile Val Met Gly Tyr Ala Tyr Asp Phe Thr
            660                 665                 670

Gly Asn Ser Lys Tyr Leu Asp Gly Met Gln Asp Gly Met Ser Tyr Leu
        675                 680                 685

Leu Gly Arg Asn Gly Leu Asp Gln Ser Tyr Val Thr Gly Tyr Gly Glu
    690                 695                 700

Arg Pro Leu Gln Asn Pro His Asp Arg Phe Trp Thr Pro Gln Thr Ser
705                 710                 715                 720

Lys Lys Phe Pro Ala Pro Pro Pro Gly Ile Ile Ala Gly Gly Pro Asn
                725                 730                 735

Ser Arg Phe Glu Asp Pro Thr Ile Thr Ala Ala Val Lys Lys Asp Thr
            740                 745                 750

Pro Pro Gln Lys Cys Tyr Ile Asp His Thr Asp Ser Trp Ser Thr Asn
        755                 760                 765

Glu Ile Thr Ile Asn Trp Asn Ala Pro Phe Ala Trp Val Thr Ala Tyr
    770                 775                 780

Leu Asp Glu Ile Asp Leu Ile Thr Pro Pro Gly Gly Val Asp Pro Glu
785                 790                 795                 800

Glu Pro Glu Val Ile Tyr Gly Asp Cys Asn Gly Asp Gly Lys Val Asn
                805                 810                 815

Ser Thr Asp Ala Val Ala Leu Lys Arg Tyr Ile Leu Arg Ser Gly Ile
            820                 825                 830

Ser Ile Asn Thr Asp Asn Ala Asp Val Asn Ala Asp Gly Arg Val Asn
        835                 840                 845

Ser Thr Asp Leu Ala Ile Leu Lys Arg Tyr Ile Leu Lys Glu Ile Asp
    850                 855                 860

Val Leu Pro His Lys
865
```

<210> SEQ ID NO 11
<211> LENGTH: 522
<212> TYPE: PRT
<213> ORGANISM: Acidothermus cellulolyticus

<400> SEQUENCE: 11

```
Met Ala Gly Gly Gly Tyr Trp His Thr Ser Gly Arg Glu Ile Leu Asp
1               5                   10                  15

Ala Asn Asn Val Pro Val Arg Ile Ala Gly Ile Asn Trp Phe Gly Phe
            20                  25                  30

Glu Thr Cys Asn Tyr Val Val His Gly Leu Trp Ser Arg Asp Tyr Arg
        35                  40                  45
```

```
Ser Met Leu Asp Gln Ile Lys Ser Leu Gly Tyr Asn Thr Ile Arg Leu
    50                  55                  60

Pro Tyr Ser Asp Asp Ile Leu Lys Pro Gly Thr Met Pro Asn Ser Ile
65                  70                  75                  80

Asn Phe Tyr Gln Met Asn Gln Asp Leu Gln Gly Leu Thr Ser Leu Gln
                85                  90                  95

Val Met Asp Lys Ile Val Ala Tyr Ala Gly Gln Ile Gly Leu Arg Ile
            100                 105                 110

Ile Leu Asp Arg His Arg Pro Asp Cys Ser Gly Gln Ser Ala Leu Trp
        115                 120                 125

Tyr Thr Ser Ser Val Ser Glu Ala Thr Trp Ile Ser Asp Leu Gln Ala
    130                 135                 140

Leu Ala Gln Arg Tyr Lys Gly Asn Pro Thr Val Val Gly Phe Asp Leu
145                 150                 155                 160

His Asn Glu Pro His Asp Pro Ala Cys Trp Gly Cys Gly Asp Pro Ser
                165                 170                 175

Ile Asp Trp Arg Leu Ala Ala Glu Arg Ala Gly Asn Ala Val Leu Ser
            180                 185                 190

Val Asn Pro Asn Leu Leu Ile Phe Val Glu Gly Val Gln Ser Tyr Asn
        195                 200                 205

Gly Asp Ser Tyr Trp Trp Gly Gly Asn Leu Gln Gly Ala Gly Gln Tyr
    210                 215                 220

Pro Val Val Leu Asn Val Pro Asn Arg Leu Val Tyr Ser Ala His Asp
225                 230                 235                 240

Tyr Ala Thr Ser Val Tyr Pro Gln Thr Trp Phe Ser Asp Pro Thr Phe
                245                 250                 255

Pro Asn Asn Met Pro Gly Ile Trp Asn Lys Asn Trp Gly Tyr Leu Phe
            260                 265                 270

Asn Gln Asn Ile Ala Pro Val Trp Leu Gly Glu Phe Gly Thr Thr Leu
        275                 280                 285

Gln Ser Thr Thr Asp Gln Thr Trp Leu Lys Thr Leu Val Gln Tyr Leu
    290                 295                 300

Arg Pro Thr Ala Gln Tyr Gly Ala Asp Ser Phe Gln Trp Thr Phe Trp
305                 310                 315                 320

Ser Trp Asn Pro Asp Ser Gly Asp Thr Gly Gly Ile Leu Lys Asp Asp
                325                 330                 335

Trp Gln Thr Val Asp Thr Val Lys Asp Gly Tyr Leu Ala Pro Ile Lys
            340                 345                 350

Ser Ser Ile Phe Asp Pro Val Gly Ala Ser Ala Ser Pro Ser Ser Gln
        355                 360                 365

Pro Ser Pro Ser Val Ser Pro Ser Pro Ser Pro Ser Pro Ser Ala Ser
    370                 375                 380

Arg Thr Pro Thr Pro Thr Pro Thr Pro Thr Ala Ser Pro Thr Pro Thr
385                 390                 395                 400

Leu Thr Pro Thr Ala Thr Pro Thr Pro Thr Ala Ser Pro Thr Pro Ser
                405                 410                 415

Pro Thr Ala Ala Ser Gly Ala Arg Cys Thr Ala Ser Tyr Gln Val Asn
            420                 425                 430

Ser Asp Trp Gly Asn Gly Phe Thr Val Thr Val Ala Val Thr Asn Ser
        435                 440                 445

Gly Ser Val Ala Thr Lys Thr Trp Thr Val Ser Trp Thr Phe Gly Gly
    450                 455                 460
```

```
Asn Gln Thr Ile Thr Asn Ser Trp Asn Ala Ala Val Thr Gln Asn Gly
465                 470                 475                 480

Gln Ser Val Thr Ala Arg Asn Met Ser Tyr Asn Asn Val Ile Gln Pro
                485                 490                 495

Gly Gln Asn Thr Thr Phe Gly Phe Gln Ala Ser Tyr Thr Gly Ser Asn
            500                 505                 510

Ala Ala Pro Thr Val Ala Cys Ala Ala Ser
        515                 520


<210> SEQ ID NO 12
<211> LENGTH: 513
<212> TYPE: PRT
<213> ORGANISM: Penicillium funiculosum

<400> SEQUENCE: 12

Met Gln Gln Ile Gly Thr Tyr Thr Ala Glu Thr His Pro Ser Leu Ser
1               5                   10                  15

Trp Ser Thr Cys Lys Ser Gly Gly Ser Cys Thr Thr Asn Ser Gly Ala
            20                  25                  30

Ile Thr Leu Asp Ala Asn Trp Arg Trp Val His Gly Val Asn Thr Ser
        35                  40                  45

Thr Asn Cys Tyr Thr Gly Asn Thr Trp Asn Thr Ala Ile Cys Asp Thr
    50                  55                  60

Asp Ala Ser Cys Ala Gln Asp Cys Ala Leu Asp Gly Ala Asp Tyr Ser
65                  70                  75                  80

Gly Thr Tyr Gly Ile Thr Thr Ser Gly Asn Ser Leu Arg Leu Asn Phe
                85                  90                  95

Val Thr Gly Ser Asn Val Gly Ser Arg Thr Tyr Leu Met Ala Asp Asn
            100                 105                 110

Thr His Tyr Gln Ile Phe Asp Leu Leu Asn Gln Glu Phe Thr Phe Thr
        115                 120                 125

Val Asp Val Ser His Leu Pro Cys Gly Leu Asn Gly Ala Leu Tyr Phe
    130                 135                 140

Val Thr Met Asp Ala Asp Gly Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
            180                 185                 190

Ser Ser Asn Asn Ala Asn Thr Gly Leu Gly Asn His Gly Ala Cys Cys
        195                 200                 205

Ala Glu Leu Asp Ile Trp Glu Ala Asn Ser Ile Ser Glu Ala Leu Thr
    210                 215                 220

Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
                245                 250                 255

Asp Gly Cys Asp Phe Asn Pro Tyr Arg Leu Gly Val Thr Asp Phe Tyr
            260                 265                 270

Gly Ser Gly Lys Thr Val Asp Thr Thr Lys Pro Ile Thr Val Val Thr
        275                 280                 285

Gln Phe Val Thr Asp Asp Gly Thr Ser Thr Gly Thr Leu Ser Glu Ile
    290                 295                 300

Arg Arg Tyr Tyr Val Gln Asn Gly Val Val Ile Pro Gln Pro Ser Ser
305                 310                 315                 320
```

```
Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
            340                 345                 350

Gly Leu Ala Lys Met Gly Ala Gly Met Glu Ala Gly Met Val Leu Val
        355                 360                 365

Met Ser Leu Trp Asp Asp Tyr Ser Val Asn Met Leu Trp Leu Asp Ser
    370                 375                 380

Thr Tyr Pro Thr Asn Ala Thr Gly Thr Pro Gly Ala Ala Arg Gly Ser
385                 390                 395                 400

Cys Pro Thr Thr Ser Gly Asp Pro Lys Thr Val Glu Ser Gln Ser Gly
                405                 410                 415

Ser Ser Tyr Val Thr Phe Ser Asp Ile Arg Val Gly Pro Phe Asn Ser
            420                 425                 430

Thr Phe Ser Gly Gly Ser Ser Thr Gly Gly Ser Ser Thr Thr Thr Ala
        435                 440                 445

Ser Gly Thr Thr Thr Thr Lys Ala Ser Ser Thr Ser Thr Ser Ser Thr
    450                 455                 460

Ser Thr Gly Thr Gly Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
                485                 490                 495

Val Asn Pro Tyr Tyr Ser Gln Cys Leu Asp Glu Leu Lys Ala Glu Ala
            500                 505                 510

Lys


<210> SEQ ID NO 13
<211> LENGTH: 26
<212> TYPE: PRT
<213> ORGANISM: Artificial Sequence
<220> FEATURE:
<223> OTHER INFORMATION: Synthetic construct, targeting peptide BAASS

<400> SEQUENCE: 13

Met Ala Asn Lys His Leu Ser Leu Ser Leu Phe Leu Val Leu Leu Gly
1               5                   10                  15

Leu Ser Ala Ser Leu Ala Ser Gly Gln Val
            20                  25


<210> SEQ ID NO 14
<211> LENGTH: 43
<212> TYPE: PRT
<213> ORGANISM: Hordeum vulgare

<400> SEQUENCE: 14

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr
        35                  40


<210> SEQ ID NO 15
<211> LENGTH: 30
<212> TYPE: PRT
<213> ORGANISM: Artificial Sequence
<220> FEATURE:
<223> OTHER INFORMATION: Synthetic construct, targeting peptide PR1a
```

```
<400> SEQUENCE: 15

Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala
            20                  25                  30


<210> SEQ ID NO 16
<211> LENGTH: 19
<212> TYPE: PRT
<213> ORGANISM: Zea mays

<400> SEQUENCE: 16

Met Arg Val Leu Leu Val Ala Leu Ala Leu Leu Ala Leu Ala Ala Ser
1               5                   10                  15

Ala Thr Ser


<210> SEQ ID NO 17
<211> LENGTH: 24
<212> TYPE: PRT
<213> ORGANISM: Oryza sativa

<400> SEQUENCE: 17

Met Ala Thr Ile Ala Phe Ser Arg Leu Ser Ile Tyr Phe Cys Val Leu
1               5                   10                  15

Leu Leu Cys His Gly Ser Met Ala
            20


<210> SEQ ID NO 18
<211> LENGTH: 361
<212> TYPE: PRT
<213> ORGANISM: Artificial Sequence
<220> FEATURE:
<223> OTHER INFORMATION: Synthetic construct, BAASS:P77853

<400> SEQUENCE: 18

Met Ala Asn Lys His Leu Ser Leu Ser Leu Phe Leu Val Leu Leu Gly
1               5                   10                  15

Leu Ser Ala Ser Leu Ala Ser Gly Gln Gln Thr Ser Ile Thr Leu Thr
            20                  25                  30

Ser Asn Ala Ser Gly Thr Phe Asp Gly Tyr Tyr Tyr Glu Leu Trp Lys
        35                  40                  45

Asp Thr Gly Asn Thr Thr Met Thr Val Tyr Thr Gln Gly Arg Phe Ser
    50                  55                  60

Cys Gln Trp Ser Asn Ile Asn Asn Ala Leu Phe Arg Thr Gly Lys Lys
65                  70                  75                  80

Tyr Asn Gln Asn Trp Gln Ser Leu Gly Thr Ile Arg Ile Thr Tyr Ser
                85                  90                  95

Ala Thr Tyr Asn Pro Asn Gly Asn Ser Tyr Leu Cys Ile Tyr Gly Trp
            100                 105                 110

Ser Thr Asn Pro Leu Val Glu Phe Tyr Ile Val Glu Ser Trp Gly Asn
        115                 120                 125

Trp Arg Pro Pro Gly Ala Thr Ser Leu Gly Gln Val Thr Ile Asp Gly
    130                 135                 140

Gly Thr Tyr Asp Ile Tyr Arg Thr Thr Arg Val Asn Gln Pro Ser Ile
145                 150                 155                 160

Val Gly Thr Ala Thr Phe Asp Gln Tyr Trp Ser Val Arg Thr Ser Lys
                165                 170                 175
```

```
Arg Thr Ser Gly Thr Val Thr Val Thr Asp His Phe Arg Ala Trp Ala
            180                 185                 190

Asn Arg Gly Leu Asn Leu Gly Thr Ile Asp Gln Ile Thr Leu Cys Val
        195                 200                 205

Glu Gly Tyr Gln Ser Ser Gly Ser Ala Asn Ile Thr Gln Asn Thr Phe
    210                 215                 220

Ser Gln Gly Ser Ser Ser Gly Ser Ser Gly Gly Ser Ser Gly Ser Thr
225                 230                 235                 240

Thr Thr Thr Arg Ile Glu Cys Glu Asn Met Ser Leu Ser Gly Pro Tyr
                245                 250                 255

Val Ser Arg Ile Thr Asn Pro Phe Asn Gly Ile Ala Leu Tyr Ala Asn
            260                 265                 270

Gly Asp Thr Ala Arg Ala Thr Val Asn Phe Pro Ala Ser Arg Asn Tyr
        275                 280                 285

Asn Phe Arg Leu Arg Gly Cys Gly Asn Asn Asn Asn Leu Ala Arg Val
    290                 295                 300

Asp Leu Arg Ile Asp Gly Arg Thr Val Gly Thr Phe Tyr Tyr Gln Gly
305                 310                 315                 320

Thr Tyr Pro Trp Glu Ala Pro Ile Asp Asn Val Tyr Val Ser Ala Gly
                325                 330                 335

Ser His Thr Val Glu Ile Thr Val Thr Ala Asp Asn Gly Thr Trp Asp
            340                 345                 350

Val Tyr Ala Asp Tyr Leu Val Ile Gln
        355                 360


<210> SEQ ID NO 19
<211> LENGTH: 270
<212> TYPE: PRT
<213> ORGANISM: Artificial Sequence
<220> FEATURE:
<223> OTHER INFORMATION: Synthetic construct, BAASS:033897

<400> SEQUENCE: 19

Met Ala Asn Lys His Leu Ser Leu Ser Leu Phe Leu Val Leu Leu Gly
1               5                   10                  15

Leu Ser Ala Ser Leu Ala Ser Gly Gln Gln Val Cys Asp Trp Leu Phe
            20                  25                  30

Pro Asp Gly Asp Asn Gly Lys Glu Pro Glu Pro Glu Pro Glu Pro Thr
        35                  40                  45

Val Glu Leu Cys Gly Arg Trp Asp Ala Arg Asp Val Ala Gly Gly Arg
    50                  55                  60

Tyr Arg Val Ile Asn Asn Val Trp Gly Ala Glu Thr Ala Gln Cys Ile
65                  70                  75                  80

Glu Val Gly Leu Glu Thr Gly Asn Phe Thr Ile Thr Arg Ala Asp His
                85                  90                  95

Asp Asn Gly Asn Asn Val Ala Ala Tyr Pro Ala Ile Tyr Phe Gly Cys
            100                 105                 110

His Trp Ala Pro Ala Arg Ala Ile Arg Asp Cys Ala Ala Arg Ala Gly
        115                 120                 125

Ala Val Arg Arg Ala His Glu Leu Asp Val Thr Pro Ile Thr Thr Gly
    130                 135                 140

Arg Trp Asn Ala Ala Tyr Asp Ile Trp Phe Ser Pro Val Thr Asn Ser
145                 150                 155                 160

Gly Asn Gly Tyr Ser Gly Gly Ala Glu Leu Met Ile Trp Leu Asn Trp
                165                 170                 175
```

```
Asn Gly Gly Val Met Pro Gly Gly Ser Arg Val Ala Thr Val Glu Leu
            180                 185                 190

Ala Gly Ala Thr Trp Glu Val Trp Tyr Ala Asp Trp Asp Trp Asn Tyr
        195                 200                 205

Ile Ala Tyr Arg Arg Thr Thr Pro Thr Thr Ser Val Ser Glu Leu Asp
    210                 215                 220

Leu Lys Ala Phe Ile Asp Asp Ala Val Ala Arg Gly Tyr Ile Arg Pro
225                 230                 235                 240

Glu Trp Tyr Leu His Ala Val Glu Thr Gly Phe Glu Leu Trp Glu Gly
                245                 250                 255

Gly Ala Gly Leu Arg Thr Ala Asp Phe Ser Val Thr Val Gln
            260                 265                 270


<210> SEQ ID NO 20
<211> LENGTH: 475
<212> TYPE: PRT
<213> ORGANISM: Artificial Sequence
<220> FEATURE:
<223> OTHER INFORMATION: Synthetic construct, HvAleSP:NtEGM

<400> SEQUENCE: 20

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Ala Tyr Asp Tyr Lys
        35                  40                  45

Gln Val Leu Arg Asp Ser Leu Leu Phe Tyr Glu Ala Gln Arg Ser Gly
    50                  55                  60

Arg Leu Pro Ala Asp Gln Lys Val Thr Trp Arg Lys Asp Ser Ala Leu
65                  70                  75                  80

Asn Asp Gln Gly Asp Gln Gly Gln Asp Leu Thr Gly Gly Tyr Phe Asp
                85                  90                  95

Ala Gly Asp Phe Val Lys Phe Gly Phe Pro Met Ala Tyr Thr Ala Thr
            100                 105                 110

Val Leu Ala Trp Gly Leu Ile Asp Phe Glu Ala Gly Tyr Ser Ser Ala
        115                 120                 125

Gly Ala Leu Asp Asp Gly Arg Lys Ala Val Lys Trp Ala Thr Asp Tyr
    130                 135                 140

Phe Ile Lys Ala His Thr Ser Gln Asn Glu Phe Tyr Gly Gln Val Gly
145                 150                 155                 160

Gln Gly Asp Ala Asp His Ala Phe Trp Gly Arg Pro Glu Asp Met Thr
                165                 170                 175

Met Ala Arg Pro Ala Tyr Lys Ile Asp Thr Ser Arg Pro Gly Ser Asp
            180                 185                 190

Leu Ala Gly Glu Thr Ala Ala Ala Leu Ala Ala Ala Ser Ile Val Phe
        195                 200                 205

Arg Asn Val Asp Gly Thr Tyr Ser Asn Asn Leu Leu Thr His Ala Arg
    210                 215                 220

Gln Leu Phe Asp Phe Ala Asn Asn Tyr Arg Gly Lys Tyr Ser Asp Ser
225                 230                 235                 240

Ile Thr Asp Ala Arg Asn Phe Tyr Ala Ser Ala Asp Tyr Arg Asp Glu
                245                 250                 255

Leu Val Trp Ala Ala Ala Trp Leu Tyr Arg Ala Thr Asn Asp Asn Thr
            260                 265                 270
```

```
Tyr Leu Asn Thr Ala Glu Ser Leu Tyr Asp Glu Phe Gly Leu Gln Asn
        275                 280                 285

Trp Gly Gly Gly Leu Asn Trp Asp Ser Lys Val Ser Gly Val Gln Val
    290                 295                 300

Leu Leu Ala Lys Leu Thr Asn Lys Gln Ala Tyr Lys Asp Thr Val Gln
305                 310                 315                 320

Ser Tyr Val Asn Tyr Leu Ile Asn Asn Gln Gln Lys Thr Pro Lys Gly
                325                 330                 335

Leu Leu Tyr Ile Asp Met Trp Gly Thr Leu Arg His Ala Ala Asn Ala
            340                 345                 350

Ala Phe Ile Met Leu Glu Ala Ala Glu Leu Gly Leu Ser Ala Ser Ser
        355                 360                 365

Tyr Arg Gln Phe Ala Gln Thr Gln Ile Asp Tyr Ala Leu Gly Asp Gly
    370                 375                 380

Gly Arg Ser Phe Val Cys Gly Phe Gly Ser Asn Pro Pro Thr Arg Pro
385                 390                 395                 400

His His Arg Ser Ser Ser Cys Pro Pro Ala Pro Ala Thr Cys Asp Trp
                405                 410                 415

Asn Thr Phe Asn Ser Pro Asp Pro Asn Tyr His Val Leu Ser Gly Ala
            420                 425                 430

Leu Val Gly Gly Pro Asp Gln Asn Asp Asn Tyr Val Asp Asp Arg Ser
        435                 440                 445

Asp Tyr Val His Asn Glu Val Ala Thr Asp Tyr Asn Ala Gly Phe Gln
    450                 455                 460

Ser Ala Leu Ala Ala Leu Val Ala Leu Gly Tyr
465                 470                 475


<210> SEQ ID NO 21
<211> LENGTH: 784
<212> TYPE: PRT
<213> ORGANISM: Artificial Sequence
<220> FEATURE:
<223> OTHER INFORMATION: Synthetic construct, BAASS:P77853:S158-30-
      108-35

<400> SEQUENCE: 21

Met Ala Asn Lys His Leu Ser Leu Ser Leu Phe Leu Val Leu Leu Gly
1               5                   10                  15

Leu Ser Ala Ser Leu Ala Ser Gly Gln Gln Thr Ser Ile Thr Leu Thr
            20                  25                  30

Ser Asn Ala Ser Gly Thr Phe Asp Gly Tyr Asn Tyr Glu Leu Trp Lys
        35                  40                  45

Asp Thr Gly Asn Thr Thr Met Thr Val Tyr Thr Gln Gly Arg Phe Ser
    50                  55                  60

Cys Gln Trp Ser Asn Ile Asn Asn Ala Leu Phe Arg Thr Gly Lys Lys
65                  70                  75                  80

Tyr Asn Gln Asn Trp Gln Ser Leu Gly Thr Ile Arg Ile Thr Tyr Ser
                85                  90                  95

Ala Thr Tyr Asn Pro Asn Gly Asn Ser Tyr Met Cys Ile Tyr Gly Trp
            100                 105                 110

Ser Thr Asn Pro Leu Val Glu Phe Tyr Ile Val Glu Ser Trp Gly Asn
        115                 120                 125

Trp Arg Pro Pro Gly Ala Thr Ser Leu Gly Gln Val Thr Ile Asp Gly
    130                 135                 140

Gly Thr Tyr Asp Ile Tyr Arg Thr Thr Arg Val Asn Gln Pro Cys Leu
145                 150                 155                 160
```

```
Ala Glu Gly Ser Leu Val Leu Asp Ala Ala Thr Gly Gln Arg Val Pro
                165                 170                 175

Ile Glu Lys Val Arg Pro Gly Met Glu Val Phe Ser Leu Gly Pro Asp
            180                 185                 190

Tyr Arg Leu Tyr Arg Val Pro Val Leu Glu Val Leu Glu Ser Gly Val
        195                 200                 205

Gly Glu Val Val Arg Leu Arg Thr Arg Ser Gly Arg Thr Leu Val Leu
    210                 215                 220

Thr Pro Glu His Pro Leu Leu Thr Pro Glu Gly Trp Lys Pro Leu Cys
225                 230                 235                 240

Asp Leu Pro Leu Gly Thr Pro Ile Ala Val Pro Ala Glu Leu Pro Val
                245                 250                 255

Ala Gly His Leu Ala Pro Pro Glu Glu Arg Val Met Leu Leu Ala Leu
            260                 265                 270

Leu Leu Gly Asp Gly Asn Thr Lys Leu Ser Gly Arg Arg Gly Thr Arg
        275                 280                 285

Pro Asn Ala Phe Phe Tyr Ser Lys Asp Ser Glu Leu Leu Ala Ala Tyr
    290                 295                 300

Arg Arg Cys Ala Glu Ala Leu Gly Ala Lys Val Lys Ala Tyr Val His
305                 310                 315                 320

Pro Thr Thr Gly Val Val Thr Leu Ala Thr Leu Ala Pro Arg Pro Gly
                325                 330                 335

Ala Gln Asp Pro Val Lys Arg Leu Val Val Glu Ala Gly Met Val Ala
            340                 345                 350

Lys Val Glu Glu Lys Arg Val Pro Glu Glu Val Phe Arg Tyr Arg Arg
        355                 360                 365

Glu Ala Leu Ala Leu Phe Leu Gly Arg Leu Phe Ser Thr Asp Gly Ser
    370                 375                 380

Val Glu Lys Lys Arg Ile Ser Tyr Ser Ser Ala Ser Leu Gly Leu Ala
385                 390                 395                 400

Gln Asp Val Ala His Leu Leu Leu Arg Leu Gly Ile Thr Ser Gln Leu
                405                 410                 415

Arg Ser Arg Gly Pro Arg Ala His Lys Val Leu Ile Ser Gly Arg Glu
            420                 425                 430

Asp Ile Leu Arg Phe Ala Glu Leu Ile Gly Pro Tyr Leu Leu Gly Ala
        435                 440                 445

Lys Arg Glu Arg Leu Ala Ala Leu Glu Ala Glu Ala Arg Arg Arg Leu
    450                 455                 460

Pro Gly Gln Gly Trp His Leu Arg Pro Val Leu Pro Ala Val Ala Tyr
465                 470                 475                 480

Arg Val Ser Glu Ala Lys Arg Arg Ser Gly Phe Ser Trp Ser Glu Ala
                485                 490                 495

Gly Arg Arg Val Ala Val Ala Gly Ser Cys Leu Ser Ser Gly Leu Asn
            500                 505                 510

Leu Lys Leu Pro Arg Arg Tyr Leu Ser Arg His Arg Leu Ser Leu Leu
        515                 520                 525

Gly Glu Ala Phe Ala Asp Pro Gly Leu Glu Ala Leu Ala Glu Gly Gln
    530                 535                 540

Val Leu Trp Asp Pro Ile Val Ala Val Glu Pro Ala Gly Lys Ala Arg
545                 550                 555                 560

Thr Phe Asp Leu Arg Val Pro Pro Phe Ala Asn Phe Val Ser Glu Asp
                565                 570                 575
```

```
Leu Val Val His Asn Ser Ile Val Gly Thr Ala Thr Phe Asp Gln Tyr
            580                 585                 590

Trp Ser Val Arg Thr Ser Lys Arg Thr Ser Gly Thr Val Thr Val Thr
        595                 600                 605

Asp His Phe Arg Ala Trp Ala Asn Arg Gly Leu Asn Leu Gly Thr Ile
    610                 615                 620

Asp Gln Ile Thr Leu Cys Val Glu Gly Tyr Gln Ser Ser Gly Ser Ala
625                 630                 635                 640

Asn Ile Thr Gln Asn Thr Phe Ser Gln Gly Ser Ser Ser Gly Ser Ser
                645                 650                 655

Gly Gly Ser Ser Gly Ser Thr Thr Thr Thr Arg Ile Glu Cys Glu Asn
            660                 665                 670

Met Ser Leu Ser Gly Pro Tyr Val Ser Arg Ile Thr Asn Pro Phe Asn
        675                 680                 685

Gly Ile Ala Leu Tyr Ala Asn Gly Asp Thr Ala Arg Ala Thr Val Asn
    690                 695                 700

Phe Pro Ala Ser Arg Asn Tyr Asn Phe Arg Leu Arg Gly Cys Gly Asn
705                 710                 715                 720

Ser Asn Asn Leu Ala Arg Val Asp Leu Arg Ile Asp Gly Arg Thr Val
                725                 730                 735

Gly Thr Phe Tyr Tyr Gln Gly Thr Tyr Pro Trp Glu Ala Pro Ile Asp
            740                 745                 750

Asn Val Tyr Val Ser Ala Gly Ser His Thr Val Glu Ile Thr Val Thr
        755                 760                 765

Ala Asp Asn Gly Thr Arg Asp Val Tyr Ala Asp Tyr Leu Val Ile Gln
    770                 775                 780
```

<210> SEQ ID NO 22
<211> LENGTH: 6
<212> TYPE: PRT
<213> ORGANISM: Artificial Sequence
<220> FEATURE:
<223> OTHER INFORMATION: Synthetic construct, SEKDEL

<400> SEQUENCE: 22

```
Ser Glu Lys Asp Glu Leu
1               5
```

<210> SEQ ID NO 23
<211> LENGTH: 4
<212> TYPE: PRT
<213> ORGANISM: Artificial Sequence
<220> FEATURE:
<223> OTHER INFORMATION: Synthetic construct, KDEL

<400> SEQUENCE: 23

```
Lys Asp Glu Leu
1
```

<210> SEQ ID NO 24
<211> LENGTH: 8
<212> TYPE: PRT
<213> ORGANISM: Hordeum vulgare

<400> SEQUENCE: 24

```
Asp Glu Leu Lys Ala Glu Ala Lys
1               5
```

<210> SEQ ID NO 25
<211> LENGTH: 536

```
<212> TYPE: PRT
<213> ORGANISM: Artificial Sequence
<220> FEATURE:
<223> OTHER INFORMATION: Synthetic construct, BAASS:AnfaeB:SEKDEL

<400> SEQUENCE: 25

Met Ala Asn Lys His Leu Ser Leu Ser Leu Phe Leu Val Leu Leu Gly
1               5                   10                  15

Leu Ser Ala Ser Leu Ala Ser Gly Gln Val Ala Thr Asp Pro Phe Gln
            20                  25                  30

Ser Arg Cys Asn Glu Phe Gln Asn Lys Ile Asp Ile Ala Asn Val Thr
        35                  40                  45

Val Arg Ser Val Ala Tyr Val Ala Ala Gly Gln Asn Ile Ser Gln Ala
    50                  55                  60

Glu Val Ala Ser Val Cys Lys Ala Ser Val Gln Ala Ser Val Asp Leu
65                  70                  75                  80

Cys Arg Val Thr Met Asn Ile Ser Thr Ser Asp Arg Ser His Leu Trp
                85                  90                  95

Ala Glu Ala Trp Leu Pro Arg Asn Tyr Thr Gly Arg Phe Val Ser Thr
            100                 105                 110

Gly Asn Gly Gly Leu Ala Gly Cys Val Gln Glu Thr Asp Leu Asn Phe
        115                 120                 125

Ala Ala Asn Phe Gly Phe Ala Thr Val Gly Thr Asn Gly Gly His Asp
    130                 135                 140

Gly Asp Thr Ala Lys Tyr Phe Leu Asn Asn Ser Glu Val Leu Ala Asp
145                 150                 155                 160

Phe Ala Tyr Arg Ser Val His Glu Gly Thr Val Val Gly Lys Gln Leu
                165                 170                 175

Thr Gln Leu Phe Tyr Asp Glu Gly Tyr Asn Tyr Ser Tyr Tyr Leu Gly
            180                 185                 190

Cys Ser Thr Gly Gly Arg Gln Gly Tyr Gln Gln Val Gln Arg Phe Pro
        195                 200                 205

Asp Asp Tyr Asp Gly Val Ile Ala Gly Ser Ala Ala Met Asn Phe Ile
    210                 215                 220

Asn Leu Ile Ser Trp Gly Ala Phe Leu Trp Lys Ala Thr Gly Leu Ala
225                 230                 235                 240

Asp Asp Pro Asp Phe Ile Ser Ala Asn Leu Trp Ser Val Ile His Gln
                245                 250                 255

Glu Ile Val Arg Gln Cys Asp Leu Val Asp Gly Ala Leu Asp Gly Ile
            260                 265                 270

Ile Glu Asp Pro Asp Phe Cys Ala Pro Val Ile Glu Arg Leu Ile Cys
        275                 280                 285

Asp Gly Thr Thr Asn Gly Thr Ser Cys Ile Thr Gly Ala Gln Ala Ala
    290                 295                 300

Lys Val Asn Arg Ala Leu Ser Asp Phe Tyr Gly Pro Asp Gly Thr Val
305                 310                 315                 320

Tyr Tyr Pro Arg Leu Asn Tyr Gly Gly Glu Ala Asp Ser Ala Ser Leu
                325                 330                 335

Tyr Phe Thr Gly Ser Met Tyr Ser Arg Thr Glu Glu Trp Tyr Lys Tyr
            340                 345                 350

Val Val Tyr Asn Asp Thr Asn Trp Asn Ser Ser Gln Trp Thr Leu Glu
        355                 360                 365

Ser Ala Lys Leu Ala Leu Glu Gln Asn Pro Phe Asn Ile Gln Ala Phe
    370                 375                 380
```

```
Asp Pro Asn Ile Thr Ala Phe Arg Asp Arg Gly Gly Lys Leu Leu Ser
385                 390                 395                 400

Tyr His Gly Thr Gln Asp Pro Ile Ile Ser Ser Thr Asp Ser Lys Leu
                405                 410                 415

Tyr Tyr Arg Arg Val Ala Asn Ala Leu Asn Ala Ala Pro Ser Glu Leu
            420                 425                 430

Asp Glu Phe Tyr Arg Phe Phe Gln Ile Ser Gly Met Gly His Cys Gly
        435                 440                 445

Asp Gly Thr Gly Ala Ser Tyr Ile Gly Gln Gly Tyr Gly Thr Tyr Thr
    450                 455                 460

Ser Lys Ala Pro Gln Val Asn Leu Leu Arg Thr Met Val Asp Trp Val
465                 470                 475                 480

Glu Asn Gly Lys Ala Pro Glu Tyr Met Pro Gly Asn Lys Leu Asn Ala
                485                 490                 495

Asn Gly Ser Ile Glu Tyr Met Arg Lys His Cys Arg Tyr Pro Lys His
            500                 505                 510

Asn Ile His Thr Gly Pro Gly Asn Tyr Thr Asp Pro Asn Ser Trp Thr
        515                 520                 525

Cys Val Ser Glu Lys Asp Glu Leu
    530                 535


<210> SEQ ID NO 26
<211> LENGTH: 292
<212> TYPE: PRT
<213> ORGANISM: Artificial Sequence
<220> FEATURE:
<223> OTHER INFORMATION: Synthetic construct, BAASS:AnfaeA:SEKDEL

<400> SEQUENCE: 26

Met Ala Asn Lys His Leu Ser Leu Ser Leu Phe Leu Val Leu Leu Gly
1               5                   10                  15

Leu Ser Ala Ser Leu Ala Ser Gly Gln Val Ala Ser Thr Gln Gly Ile
            20                  25                  30

Ser Glu Asp Leu Tyr Asn Arg Leu Val Glu Met Ala Thr Ile Ser Gln
        35                  40                  45

Ala Ala Tyr Ala Asp Leu Cys Asn Ile Pro Ser Thr Ile Ile Lys Gly
    50                  55                  60

Glu Lys Ile Tyr Asn Ala Gln Thr Asp Ile Asn Gly Trp Ile Leu Arg
65                  70                  75                  80

Asp Asp Thr Ser Lys Glu Ile Ile Thr Val Phe Arg Gly Thr Gly Ser
                85                  90                  95

Asp Thr Asn Leu Gln Leu Asp Thr Asn Tyr Thr Leu Thr Pro Phe Asp
            100                 105                 110

Thr Leu Pro Gln Cys Asn Asp Cys Glu Val His Gly Gly Tyr Tyr Ile
        115                 120                 125

Gly Trp Ile Ser Val Gln Asp Gln Val Glu Ser Leu Val Lys Gln Gln
    130                 135                 140

Ala Ser Gln Tyr Pro Asp Tyr Ala Leu Thr Val Thr Gly His Ser Leu
145                 150                 155                 160

Gly Ala Ser Met Ala Ala Leu Thr Ala Ala Gln Leu Ser Ala Thr Tyr
                165                 170                 175

Asp Asn Val Arg Leu Tyr Thr Phe Gly Glu Pro Arg Ser Gly Asn Gln
            180                 185                 190

Ala Phe Ala Ser Tyr Met Asn Asp Ala Phe Gln Val Ser Ser Pro Glu
        195                 200                 205
```

```
Thr Thr Gln Tyr Phe Arg Val Thr His Ser Asn Asp Gly Ile Pro Asn
    210                 215                 220

Leu Pro Pro Ala Asp Glu Gly Tyr Ala His Gly Gly Val Glu Tyr Trp
225                 230                 235                 240

Ser Val Asp Pro Tyr Ser Ala Gln Asn Thr Phe Val Cys Thr Gly Asp
                245                 250                 255

Glu Val Gln Cys Cys Glu Ala Gln Gly Gly Gln Gly Val Asn Asp Ala
            260                 265                 270

His Thr Thr Tyr Phe Gly Met Thr Ser Gly Ala Cys Thr Trp Ser Glu
        275                 280                 285

Lys Asp Glu Leu
    290


<210> SEQ ID NO 27
<211> LENGTH: 468
<212> TYPE: PRT
<213> ORGANISM: Artificial Sequence
<220> FEATURE:
<223> OTHER INFORMATION: Synthetic construct, PR1a:NtEGM:SEKDEL

<400> SEQUENCE: 27

Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala Ala Tyr
            20                  25                  30

Asp Tyr Lys Gln Val Leu Arg Asp Ser Leu Leu Phe Tyr Glu Ala Gln
        35                  40                  45

Arg Ser Gly Arg Leu Pro Ala Asp Gln Lys Val Thr Trp Arg Lys Asp
    50                  55                  60

Ser Ala Leu Asn Asp Gln Gly Asp Gln Gly Gln Asp Leu Thr Gly Gly
65                  70                  75                  80

Tyr Phe Asp Ala Gly Asp Phe Val Lys Phe Gly Phe Pro Met Ala Tyr
                85                  90                  95

Thr Ala Thr Val Leu Ala Trp Gly Leu Ile Asp Phe Glu Ala Gly Tyr
            100                 105                 110

Ser Ser Ala Gly Ala Leu Asp Asp Gly Arg Lys Ala Val Lys Trp Ala
        115                 120                 125

Thr Asp Tyr Phe Ile Lys Ala His Thr Ser Gln Asn Glu Phe Tyr Gly
    130                 135                 140

Gln Val Gly Gln Gly Asp Ala Asp His Ala Phe Trp Gly Arg Pro Glu
145                 150                 155                 160

Asp Met Thr Met Ala Arg Pro Ala Tyr Lys Ile Asp Thr Ser Arg Pro
                165                 170                 175

Gly Ser Asp Leu Ala Gly Glu Thr Ala Ala Ala Leu Ala Ala Ala Ser
            180                 185                 190

Ile Val Phe Arg Asn Val Asp Gly Thr Tyr Ser Asn Asn Leu Leu Thr
        195                 200                 205

His Ala Arg Gln Leu Phe Asp Phe Ala Asn Asn Tyr Arg Gly Lys Tyr
    210                 215                 220

Ser Asp Ser Ile Thr Asp Ala Arg Asn Phe Tyr Ala Ser Ala Asp Tyr
225                 230                 235                 240

Arg Asp Glu Leu Val Trp Ala Ala Ala Trp Leu Tyr Arg Ala Thr Asn
                245                 250                 255

Asp Asn Thr Tyr Leu Asn Thr Ala Glu Ser Leu Tyr Asp Glu Phe Gly
            260                 265                 270
```

```
Leu Gln Asn Trp Gly Gly Gly Leu Asn Trp Asp Ser Lys Val Ser Gly
        275                 280                 285

Val Gln Val Leu Leu Ala Lys Leu Thr Asn Lys Gln Ala Tyr Lys Asp
    290                 295                 300

Thr Val Gln Ser Tyr Val Asn Tyr Leu Ile Asn Asn Gln Gln Lys Thr
305                 310                 315                 320

Pro Lys Gly Leu Leu Tyr Ile Asp Met Trp Gly Thr Leu Arg His Ala
                325                 330                 335

Ala Asn Ala Ala Phe Ile Met Leu Glu Ala Ala Glu Leu Gly Leu Ser
            340                 345                 350

Ala Ser Ser Tyr Arg Gln Phe Ala Gln Thr Gln Ile Asp Tyr Ala Leu
        355                 360                 365

Gly Asp Gly Gly Arg Ser Phe Val Cys Gly Phe Gly Ser Asn Pro Pro
    370                 375                 380

Thr Arg Pro His His Arg Ser Ser Ser Cys Pro Pro Ala Pro Ala Thr
385                 390                 395                 400

Cys Asp Trp Asn Thr Phe Asn Ser Pro Asp Pro Asn Tyr His Val Leu
                405                 410                 415

Ser Gly Ala Leu Val Gly Gly Pro Asp Gln Asn Asp Asn Tyr Val Asp
            420                 425                 430

Asp Arg Ser Asp Tyr Val His Asn Glu Val Ala Thr Asp Tyr Asn Ala
        435                 440                 445

Gly Phe Gln Ser Ala Leu Ala Ala Leu Val Ala Leu Gly Tyr Ser Glu
    450                 455                 460

Lys Asp Glu Leu
465


<210> SEQ ID NO 28
<211> LENGTH: 791
<212> TYPE: PRT
<213> ORGANISM: Artificial Sequence
<220> FEATURE:
<223> OTHER INFORMATION: Synthetic construct, BAASS:P77853:T134-100-
      101:SEKDEL

<400> SEQUENCE: 28

Met Ala Asn Lys His Leu Ser Leu Ser Leu Phe Leu Val Leu Leu Gly
1               5                   10                  15

Leu Ser Ala Ser Leu Ala Ser Gly Gln Gln Thr Ser Ile Thr Leu Thr
            20                  25                  30

Ser Asn Ala Ser Gly Thr Phe Asp Gly Tyr Tyr Tyr Glu Leu Trp Lys
        35                  40                  45

Asp Thr Gly Asn Thr Thr Met Thr Val Tyr Thr Gln Gly Arg Phe Ser
    50                  55                  60

Cys Gln Trp Ser Asn Ile Asn Asn Ala Leu Phe Arg Thr Gly Lys Lys
65                  70                  75                  80

Tyr Asn Gln Asn Trp Gln Ser Leu Gly Thr Ile Arg Ile Thr Tyr Ser
                85                  90                  95

Ala Thr Tyr Asn Pro Asn Gly Asn Ser Tyr Leu Cys Ile Tyr Gly Trp
            100                 105                 110

Ser Thr Asn Pro Leu Val Glu Phe Tyr Ile Val Glu Ser Trp Gly Asn
        115                 120                 125

Trp Arg Pro Pro Gly Ala Cys Leu Ala Glu Gly Ser Leu Val Leu Asp
    130                 135                 140

Ala Ala Thr Gly Gln Arg Val Pro Ile Glu Lys Val Arg Pro Gly Met
145                 150                 155                 160
```

```
Glu Val Phe Ser Leu Gly Pro Asp Tyr Arg Leu Tyr Arg Val Pro Val
                165                 170                 175

Leu Glu Val Leu Glu Ser Gly Val Arg Glu Val Val Arg Leu Arg Thr
            180                 185                 190

Arg Ser Gly Arg Thr Leu Val Leu Thr Pro Asp His Pro Leu Leu Thr
        195                 200                 205

Pro Glu Gly Trp Lys Pro Leu Cys Asp Leu Pro Leu Gly Thr Pro Ile
    210                 215                 220

Ala Val Pro Ala Glu Leu Pro Val Ala Gly His Leu Ala Pro Pro Glu
225                 230                 235                 240

Glu Arg Val Thr Leu Leu Ala Leu Leu Leu Gly Asp Gly Asn Thr Lys
                245                 250                 255

Leu Ser Gly Arg Arg Gly Thr Arg Pro Asn Ala Phe Phe Tyr Ser Lys
            260                 265                 270

Asn Pro Glu Leu Leu Ala Ala Tyr Arg Arg Cys Ala Glu Ala Leu Gly
        275                 280                 285

Ala Lys Val Lys Ala Tyr Val His Pro Thr Thr Gly Val Val Thr Leu
    290                 295                 300

Ala Thr Leu Ala Pro Arg Pro Gly Ala Gln Asp Pro Val Lys Arg Leu
305                 310                 315                 320

Val Val Glu Ala Gly Met Val Ala Lys Ala Glu Glu Lys Arg Val Pro
                325                 330                 335

Glu Glu Val Phe Arg Tyr Arg Arg Glu Ala Leu Ala Leu Phe Leu Gly
            340                 345                 350

Arg Leu Phe Ser Thr Asp Gly Ser Val Glu Lys Lys Arg Ile Ser Tyr
        355                 360                 365

Ser Ser Ala Ser Leu Gly Leu Ala Gln Asp Val Ala His Leu Leu Leu
    370                 375                 380

Arg Leu Gly Ile Thr Ser Gln Leu Arg Ser Arg Gly Pro Arg Ala His
385                 390                 395                 400

Glu Val Leu Ile Ser Gly Arg Glu Asp Ile Leu Arg Phe Ala Glu Leu
                405                 410                 415

Ile Gly Pro Tyr Leu Leu Gly Ala Lys Arg Glu Arg Leu Ala Ala Leu
            420                 425                 430

Glu Ala Glu Ala Arg Arg Arg Leu Pro Gly Gln Gly Trp His Leu Arg
        435                 440                 445

Leu Val Leu Pro Ala Val Ala Tyr Arg Val Gly Glu Ala Glu Arg Arg
    450                 455                 460

Ser Gly Phe Ser Trp Ser Glu Ala Gly Arg Arg Val Ala Val Ala Gly
465                 470                 475                 480

Ser Cys Leu Ser Ser Gly Leu Asn Leu Lys Leu Pro Arg Arg Tyr Leu
                485                 490                 495

Ser Arg His Arg Leu Ser Leu Leu Gly Glu Ala Phe Ala Asp Pro Gly
            500                 505                 510

Leu Glu Ala Leu Ala Glu Gly Gln Val Leu Trp Asp Pro Ile Val Ala
        515                 520                 525

Val Glu Pro Ala Gly Lys Ala Arg Thr Phe Asp Leu Arg Val Pro Pro
    530                 535                 540

Phe Ala Asn Phe Val Ser Glu Asp Leu Val Val His Asn Thr Val Pro
545                 550                 555                 560

Leu Gly Gln Val Thr Ile Asp Gly Gly Thr Tyr Asp Ile Tyr Arg Thr
                565                 570                 575
```

```
Thr Arg Val Asn Gln Pro Ser Ile Val Gly Thr Ala Thr Phe Asp Gln
            580                 585                 590

Tyr Trp Ser Val Arg Thr Ser Lys Arg Thr Ser Gly Thr Val Thr Val
        595                 600                 605

Thr Asp His Phe Arg Ala Trp Ala Asn Arg Gly Leu Asn Leu Gly Thr
    610                 615                 620

Ile Asp Gln Ile Thr Leu Cys Val Glu Gly Tyr Gln Ser Ser Gly Ser
625                 630                 635                 640

Ala Asn Ile Thr Gln Asn Thr Phe Ser Gln Gly Ser Ser Ser Gly Ser
                645                 650                 655

Ser Gly Gly Ser Ser Gly Ser Thr Thr Thr Thr Arg Ile Glu Cys Glu
            660                 665                 670

Asn Met Ser Leu Ser Gly Pro Tyr Val Ser Arg Ile Thr Asn Pro Phe
        675                 680                 685

Asn Gly Ile Ala Leu Tyr Ala Asn Gly Asp Thr Ala Arg Ala Thr Val
    690                 695                 700

Asn Phe Pro Ala Ser Arg Asn Tyr Asn Phe Arg Leu Arg Gly Cys Gly
705                 710                 715                 720

Asn Asn Asn Asn Leu Ala Arg Val Asp Leu Arg Ile Asp Gly Arg Thr
                725                 730                 735

Val Gly Thr Phe Tyr Tyr Gln Gly Thr Tyr Pro Trp Glu Ala Pro Ile
            740                 745                 750

Asp Asn Val Tyr Val Ser Ala Gly Ser His Thr Val Glu Ile Thr Val
        755                 760                 765

Thr Ala Asp Asn Gly Thr Trp Asp Val Tyr Ala Asp Tyr Leu Val Ile
    770                 775                 780

Gln Ser Glu Lys Asp Glu Leu
785                 790


<210> SEQ ID NO 29
<211> LENGTH: 481
<212> TYPE: PRT
<213> ORGANISM: Artificial Sequence
<220> FEATURE:
<223> OTHER INFORMATION: Synthetic construct, HvAleSP:NtEGM:SEKDEL

<400> SEQUENCE: 29

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Ala Tyr Asp Tyr Lys
        35                  40                  45

Gln Val Leu Arg Asp Ser Leu Leu Phe Tyr Glu Ala Gln Arg Ser Gly
    50                  55                  60

Arg Leu Pro Ala Asp Gln Lys Val Thr Trp Arg Lys Asp Ser Ala Leu
65                  70                  75                  80

Asn Asp Gln Gly Asp Gln Gly Gln Asp Leu Thr Gly Gly Tyr Phe Asp
                85                  90                  95

Ala Gly Asp Phe Val Lys Phe Gly Phe Pro Met Ala Tyr Thr Ala Thr
            100                 105                 110

Val Leu Ala Trp Gly Leu Ile Asp Phe Glu Ala Gly Tyr Ser Ser Ala
        115                 120                 125

Gly Ala Leu Asp Asp Gly Arg Lys Ala Val Lys Trp Ala Thr Asp Tyr
    130                 135                 140
```

```
Phe Ile Lys Ala His Thr Ser Gln Asn Glu Phe Tyr Gly Gln Val Gly
145                 150                 155                 160

Gln Gly Asp Ala Asp His Ala Phe Trp Gly Arg Pro Glu Asp Met Thr
                165                 170                 175

Met Ala Arg Pro Ala Tyr Lys Ile Asp Thr Ser Arg Pro Gly Ser Asp
            180                 185                 190

Leu Ala Gly Glu Thr Ala Ala Ala Leu Ala Ala Ala Ser Ile Val Phe
        195                 200                 205

Arg Asn Val Asp Gly Thr Tyr Ser Asn Asn Leu Leu Thr His Ala Arg
    210                 215                 220

Gln Leu Phe Asp Phe Ala Asn Asn Tyr Arg Gly Lys Tyr Ser Asp Ser
225                 230                 235                 240

Ile Thr Asp Ala Arg Asn Phe Tyr Ala Ser Ala Asp Tyr Arg Asp Glu
                245                 250                 255

Leu Val Trp Ala Ala Ala Trp Leu Tyr Arg Ala Thr Asn Asp Asn Thr
            260                 265                 270

Tyr Leu Asn Thr Ala Glu Ser Leu Tyr Asp Glu Phe Gly Leu Gln Asn
        275                 280                 285

Trp Gly Gly Gly Leu Asn Trp Asp Ser Lys Val Ser Gly Val Gln Val
    290                 295                 300

Leu Leu Ala Lys Leu Thr Asn Lys Gln Ala Tyr Lys Asp Thr Val Gln
305                 310                 315                 320

Ser Tyr Val Asn Tyr Leu Ile Asn Asn Gln Gln Lys Thr Pro Lys Gly
                325                 330                 335

Leu Leu Tyr Ile Asp Met Trp Gly Thr Leu Arg His Ala Ala Asn Ala
            340                 345                 350

Ala Phe Ile Met Leu Glu Ala Ala Glu Leu Gly Leu Ser Ala Ser Ser
        355                 360                 365

Tyr Arg Gln Phe Ala Gln Thr Gln Ile Asp Tyr Ala Leu Gly Asp Gly
    370                 375                 380

Gly Arg Ser Phe Val Cys Gly Phe Gly Ser Asn Pro Pro Thr Arg Pro
385                 390                 395                 400

His His Arg Ser Ser Ser Cys Pro Pro Ala Pro Ala Thr Cys Asp Trp
                405                 410                 415

Asn Thr Phe Asn Ser Pro Asp Pro Asn Tyr His Val Leu Ser Gly Ala
            420                 425                 430

Leu Val Gly Gly Pro Asp Gln Asn Asp Asn Tyr Val Asp Asp Arg Ser
        435                 440                 445

Asp Tyr Val His Asn Glu Val Ala Thr Asp Tyr Asn Ala Gly Phe Gln
    450                 455                 460

Ser Ala Leu Ala Ala Leu Val Ala Leu Gly Tyr Ser Glu Lys Asp Glu
465                 470                 475                 480

Leu
```

<210> SEQ ID NO 30
<211> LENGTH: 238
<212> TYPE: PRT
<213> ORGANISM: Artificial Sequence
<220> FEATURE:
<223> OTHER INFORMATION: Synthetic construct, BAASS:O43097:SEKDEL

<400> SEQUENCE: 30

```
Met Ala Asn Lys His Leu Ser Leu Ser Leu Phe Leu Val Leu Leu Gly
1               5                   10                  15

Leu Ser Ala Ser Leu Ala Ser Gly Gln Val Phe Pro Ala Gly Asn Ala
```

```
            20                  25                  30

Thr Glu Leu Glu Lys Arg Gln Thr Thr Pro Asn Ser Glu Gly Trp His
        35                  40                  45

Asp Gly Tyr Tyr Tyr Ser Trp Trp Ser Asp Gly Gly Ala Gln Ala Thr
    50                  55                  60

Tyr Thr Asn Leu Glu Gly Gly Thr Tyr Glu Ile Ser Trp Gly Asp Gly
65                  70                  75                  80

Gly Asn Leu Val Gly Gly Lys Gly Trp Asn Pro Gly Leu Asn Ala Arg
                85                  90                  95

Ala Ile His Phe Glu Gly Val Tyr Gln Pro Asn Gly Asn Ser Tyr Leu
            100                 105                 110

Ala Val Tyr Gly Trp Thr Arg Asn Pro Leu Val Glu Tyr Tyr Ile Val
        115                 120                 125

Glu Asn Phe Gly Thr Tyr Asp Pro Ser Ser Gly Ala Thr Asp Leu Gly
    130                 135                 140

Thr Val Glu Cys Asp Gly Ser Ile Tyr Arg Leu Gly Lys Thr Thr Arg
145                 150                 155                 160

Val Asn Ala Pro Ser Ile Asp Gly Thr Gln Thr Phe Asp Gln Tyr Trp
                165                 170                 175

Ser Val Arg Gln Asp Lys Arg Thr Ser Gly Thr Val Gln Thr Gly Cys
            180                 185                 190

His Phe Asp Ala Trp Ala Arg Ala Gly Leu Asn Val Asn Gly Asp His
        195                 200                 205

Tyr Tyr Gln Ile Val Ala Thr Glu Gly Tyr Phe Ser Ser Gly Tyr Ala
    210                 215                 220

Arg Ile Thr Val Ala Asp Val Gly Ser Glu Lys Asp Glu Leu
225                 230                 235


<210> SEQ ID NO 31
<211> LENGTH: 531
<212> TYPE: PRT
<213> ORGANISM: Artificial Sequence
<220> FEATURE:
<223> OTHER INFORMATION: Synthetic construct, xGZein27ss-02:BD22308:
      HvVSD-01

<400> SEQUENCE: 31

Met Arg Val Leu Leu Val Ala Leu Ala Leu Leu Ala Leu Ala Ala Ser
1               5                   10                  15

Ala Thr Ser Gln Gln Ile Gly Thr Tyr Thr Ala Glu Thr His Pro Ser
            20                  25                  30

Leu Ser Trp Ser Thr Cys Lys Ser Gly Gly Ser Cys Thr Thr Asn Ser
        35                  40                  45

Gly Ala Ile Thr Leu Asp Ala Asn Trp Arg Trp Val His Gly Val Asn
    50                  55                  60

Thr Ser Thr Asn Cys Tyr Thr Gly Asn Thr Trp Asn Thr Ala Ile Cys
65                  70                  75                  80

Asp Thr Asp Ala Ser Cys Ala Gln Asp Cys Ala Leu Asp Gly Ala Asp
                85                  90                  95

Tyr Ser Gly Thr Tyr Gly Ile Thr Thr Ser Gly Asn Ser Leu Arg Leu
            100                 105                 110

Asn Phe Val Thr Gly Ser Asn Val Gly Ser Arg Thr Tyr Leu Met Ala
        115                 120                 125

Asp Asn Thr His Tyr Gln Ile Phe Asp Leu Leu Asn Gln Glu Phe Thr
    130                 135                 140
```

```
Phe Thr Val Asp Val Ser His Leu Pro Cys Gly Leu Asn Gly Ala Leu
145                 150                 155                 160

Tyr Phe Val Thr Met Asp Ala Asp Gly Gly Val Ser Lys Tyr Pro Asn
                165                 170                 175

Asn Lys Ala Gly Ala Gln Tyr Gly Val Gly Tyr Cys Asp Ser Gln Cys
            180                 185                 190

Pro Arg Asp Leu Lys Phe Ile Ala Gly Gln Ala Asn Val Glu Gly Trp
        195                 200                 205

Thr Pro Ser Ser Asn Asn Ala Asn Thr Gly Leu Gly Asn His Gly Ala
    210                 215                 220

Cys Cys Ala Glu Leu Asp Ile Trp Glu Ala Asn Ser Ile Ser Glu Ala
225                 230                 235                 240

Leu Thr Pro His Pro Cys Asp Thr Pro Gly Leu Ser Val Cys Thr Thr
                245                 250                 255

Asp Ala Cys Gly Gly Thr Tyr Ser Ser Asp Arg Tyr Ala Gly Thr Cys
            260                 265                 270

Asp Pro Asp Gly Cys Asp Phe Asn Pro Tyr Arg Leu Gly Val Thr Asp
        275                 280                 285

Phe Tyr Gly Ser Gly Lys Thr Val Asp Thr Thr Lys Pro Ile Thr Val
    290                 295                 300

Val Thr Gln Phe Val Thr Asp Asp Gly Thr Ser Thr Gly Thr Leu Ser
305                 310                 315                 320

Glu Ile Arg Arg Tyr Tyr Val Gln Asn Gly Val Val Ile Pro Gln Pro
                325                 330                 335

Ser Ser Lys Ile Ser Gly Val Ser Gly Asn Val Ile Asn Ser Asp Phe
            340                 345                 350

Cys Asp Ala Glu Ile Ser Thr Phe Gly Glu Thr Ala Ser Phe Ser Lys
        355                 360                 365

His Gly Gly Leu Ala Lys Met Gly Ala Gly Met Glu Ala Gly Met Val
    370                 375                 380

Leu Val Met Ser Leu Trp Asp Asp Tyr Ser Val Asn Met Leu Trp Leu
385                 390                 395                 400

Asp Ser Thr Tyr Pro Thr Asn Ala Thr Gly Thr Pro Gly Ala Ala Arg
                405                 410                 415

Gly Ser Cys Pro Thr Thr Ser Gly Asp Pro Lys Thr Val Glu Ser Gln
            420                 425                 430

Ser Gly Ser Ser Tyr Val Thr Phe Ser Asp Ile Arg Val Gly Pro Phe
        435                 440                 445

Asn Ser Thr Phe Ser Gly Gly Ser Ser Thr Gly Gly Ser Ser Thr Thr
    450                 455                 460

Thr Ala Ser Gly Thr Thr Thr Thr Lys Ala Ser Ser Thr Ser Thr Ser
465                 470                 475                 480

Ser Thr Ser Thr Gly Thr Gly Val Ala Ala His Trp Gly Gln Cys Gly
                485                 490                 495

Gly Gln Gly Trp Thr Gly Pro Thr Thr Cys Ala Ser Gly Thr Thr Cys
            500                 505                 510

Thr Val Val Asn Pro Tyr Tyr Ser Gln Cys Leu Asp Glu Leu Lys Ala
        515                 520                 525

Glu Ala Lys
    530

<210> SEQ ID NO 32
<211> LENGTH: 1014
<212> TYPE: DNA
```

<213> ORGANISM: Artificial Sequence
<220> FEATURE:
<223> OTHER INFORMATION: Synthetic construct, plant optimized P77853

<400> SEQUENCE: 32

```
atgcaaacaa gcattactct gacatccaac gcatccggta cgtttgacgg ttactattac     60

gaactctgga aggatactgg caatacaaca atgacggtct acactcaagg tcgcttttcc    120

tgccagtggt cgaacatcaa taacgcgttg tttaggaccg ggaagaaata caaccagaat    180

tggcagtctc ttggcacaat ccggatcacg tactctgcga cttacaaccc aaacgggaac    240

tcctacttgt gtatctatgg ctggtctacc aacccattgg tcgagttcta catcgttgag    300

tcctggggga actggagacc gcctggtgcc acgtccctgg gccaagtgac aatcgatggc    360

gggacctacg acatctatag gacgacacgc gtcaaccagc cttccattgt ggggacagcc    420

acgttcgatc agtactggag cgtgcgcacc tctaagcgga cttcaggaac agtgaccgtg    480

accgatcact tccgcgcctg ggcgaaccgg ggcctgaacc tcggcacaat agaccaaatt    540

acattgtgcg tggagggtta ccaaagctct ggatcagcca acatcaccca gaacaccttc    600

tctcagggct cttcttccgg cagttcgggt ggctcatccg gctccacaac gactactcgc    660

atcgagtgtg agaacatgtc cttgtccgga ccctacgtta gcaggatcac caatcccttt    720

aatggtattg cgctgtacgc caacggagac acagcccgcg ctaccgttaa cttccccgca    780

agtcgcaact acaatttccg cctgcggggt tgcggcaaca acaataatct tgcccgtgtg    840

gacctgagga tcgacggacg gaccgtcggg accttttatt accagggcac atacccctgg    900

gaggccccaa ttgacaatgt ttatgtcagt gcggggagtc atacagtcga aatcactgtt    960

actgcggata acggcacatg ggacgtgtat gccgactacc tggtgataca gtga         1014
```

<210> SEQ ID NO 33
<211> LENGTH: 786
<212> TYPE: DNA
<213> ORGANISM: Artificial Sequence
<220> FEATURE:
<223> OTHER INFORMATION: Synthetic construct, plant optimized Anfae A

<400> SEQUENCE: 33

```
atggcatcca cgcagggtat ctctgaggac ctgtataatc gcctcgtgga aatggccaca     60

atttcacaag cggcttacgc agatctttgt aatatccctt cgacaattat caagggagag    120

aaaatctata acgcccagac tgacatcaac ggctggatac tgcgggatga cacgagcaag    180

gaaattatca cagtctttag agggaccggt tccgatacaa atttgcagtt ggacacgaat    240

tacacactga ccccttcga tactctccct caatgcaacg actgtgaggt tcacggtggg    300

tactatattg gctggatctc tgttcaagac caagtcgagt cacttgttaa gcagcaagcg    360

tcgcagtacc cggactacgc attgacggtg acagggcaca gcctgggtgc ctcgatggca    420

gcgctcaccg ctgcccagct ttctgcaacc tacgataatg tcaggctgta cactttcgga    480

gaaccacgct caggcaacca agcgtttgct tcgtatatga acgacgcttt ccaggttagc    540

tcccccgaga cgacacaata ctttcgggtg acccattcta acgacgggat tcctaacctc    600

ccgccagccg acgaaggtta cgcacacggg ggtgtcgagt actggtcagt ggacccctac    660

agcgcgcaga atactttcgt ttgcacgggc gatgaggtcc agtgctgtga agctcaaggg    720

ggtcagggag tgaatgatgc acacacaacc tatttcggaa tgacttccgg ggcttgcacg    780

tggtga                                                               786
```

<210> SEQ ID NO 34
<211> LENGTH: 1518
<212> TYPE: DNA
<213> ORGANISM: Artificial Sequence
<220> FEATURE:
<223> OTHER INFORMATION: Synthetic construct, plant optimized Anfae B

<400> SEQUENCE: 34

```
atggctactg atcccttcca gtctcgctgt aacgagtttc aaaacaaaat tgatatcgca     60

aacgtcacgg ttaggtcggt cgcctacgtc gcggctggtc agaatatctc tcaagcagaa    120

gtcgcttcgg tttgcaaggc aagcgtccag gcctccgtgg acctctgtag agtgacaatg    180

aatattagca cctcggatag gagccacctt tgggccgagg cttggctgcc tcgcaattat    240

actggacggt tcgtctccac tgggaacggg ggcctggctg gatgcgtgca ggaaacagac    300

ttgaatttcg ctgccaactt tggcttcgca accgttggca ctaatggagg gcacgatgga    360

gacacggcga aatactttct gaataactct gaggtcctcg ctgatttcgc ctatcgcagc    420

gttcacgagg gcactgtggt cgggaagcaa cttacccagt tgttctacga cgaaggttac    480

aattattcgt actatctggg ctgcagcacc ggaggcaggc aaggctatca gcaagtgcag    540

cgctttccgg atgactacga tggtgttatt gccggaagtg cagcgatgaa ctttatcaat    600

ttgatttctt ggggcgcttt tctttggaag gccacgggac tcgcagacga cccagatttt    660

atctcagcga acctctggag cgttatccac caggagattg tgcggcagtg tgacttggtt    720

gatggtgctc ttgacggaat tattgaagat cctgacttct gcgcccctgt tatcgagaga    780

ctgatttgtg atgggactac caacggcacc tcctgtatca ctggggcaca agcggctaaa    840

gtgaataggg ccctctcgga cttttatggt ccggatggga cagtctacta tccacgcttg    900

aactacggag gggaggcaga ctctgcgagc ctgtacttca caggctccat gtattcacgg    960

accgaagagt ggtacaagta cgtcgtgtac aacgatacta actggaatag ttctcaatgg   1020

acgctcgaaa gcgctaagtt ggccttggag cagaacccct ttaatattca ggcattcgac   1080

cctaatatca cagcgttcag ggaccgcggt ggaaaactct tgagctacca cggcacccaa   1140

gatccgatta tttcatcgac tgacagcaag ttgtattaca gaagagttgc taacgccctt   1200

aacgctgccc catccgaact cgacgagttt tatcgcttct ttcagatctc tgggatgggt   1260

cactgcggcg acggaaccgg ggcttcatac attggccagg gatacggcac gtatacctcg   1320

aaggccccac aggtcaactt gcttcggact atggtggatt gggttgagaa tggaaaagct   1380

ccggaatata tgcctgggaa taagttgaac gccaacggtt cgatcgagta tatgagaaag   1440

cactgtcgtt acccaaaaca caatattcac acgggcccag gtaactacac ggaccctaac   1500

tcctggacct gcgtctga                                                 1518
```

<210> SEQ ID NO 35
<211> LENGTH: 1302
<212> TYPE: DNA
<213> ORGANISM: Artificial Sequence
<220> FEATURE:
<223> OTHER INFORMATION: Synthetic construct, plant optimized NtEGM

<400> SEQUENCE: 35

```
atggcttacg actacaagca ggtgttgcgg gactcgctac tattctatga ggcccagaga     60

tccggccggc tcccagccga ccagaaggtc acgtggagga aggatagcgc gctgaatgac    120

cagggtgacc agggacaaga cttgaccggc ggctactttg acgctgggga cttcgtcaag    180

ttcgggttcc ccatggctta taccgcaacc gtgctggcat ggggcctcat agattttgag    240
```

gccggctaca gcagtgccgg ggccttggat gatggacgga aggctgtcaa atgggccacc 300
gactatttca taaaggccca cacaagtcaa aatgagttct atggtcaggt cggccagggt 360
gacgccgatc acgctttctg ggaagacca gaggatatga cgatggcgcg cccggcgtac 420
aagatagaca cctcaaggcc tggctctgat ctggcaggcg agacagcggc tgctcttgcc 480
gctgcttcaa tcgtgttccg gaacgtcgat ggcacttact caaataacct gttaacacac 540
gctcgccagc tattcgactt cgcgaacaac taccggggaa agtatagtga ctctattact 600
gacgcaagaa atttctacgc aagcgcagac tacagagacg agttggtttg ggctgctgcg 660
tggttataca gagcgaccaa cgacaacacc tacctcaaca ctgctgagtc actgtacgat 720
gagtttgggc tacagaactg gggggggggc ctgaactggg atagcaaggt gtctggcgtg 780
caggtgttgt tggccaagct taccaataag caggcctaca aggacacggt gcagtcttac 840
gtcaattacc taattaataa ccagcagaag actcccaagg gcctcctcta catcgacatg 900
tggggcaccc ttcgccacgc tgccaacgcc gcattcatca tgctcgaagc cgccgagctg 960
ggcttgtccg cctcctctta tagacagttc gcgcaaacgc aaatcgacta cgccctgggc 1020
gatggtggcc gctcctttgt gtgcgggttc gggagtaatc ctcctacgag accgcaccac 1080
agatcctcgt cgtgcccgcc agctcccgct acttgcgact ggaatacatt caactcacct 1140
gacccaaact accacgtcct ctctggggcc ctagtgggcg gacctgatca gaatgacaac 1200
tacgtcgatg accgttcaga ctatgttcac aacgaagtcg ccactgatta caacgcgggt 1260
ttccagtccg cgttagctgc tttggtggcc cttggttact ga 1302

<210> SEQ ID NO 36
<211> LENGTH: 585
<212> TYPE: DNA
<213> ORGANISM: Artificial Sequence
<220> FEATURE:
<223> OTHER INFORMATION: Synthetic construct, plant optimized EU591743

<400> SEQUENCE: 36
atggcccaaa catgtctgac cagcccacaa acaggattcc acaacggctt cttttactcg 60
ttttggaaag attctcctgg tactgttaac ttttgccttc ttgaaggggg aagatatacc 120
tccaattggt ctgggataaa caattgggtc ggtggcaagg gctggcagac cggtagtagg 180
cgcaacatca cgtattccgg gagcttcaat acaccaggga atggatacct ggctctctac 240
ggttggacca ccaacccgtt ggttgagtac tatgttgtcg atagctgggg ctcctggcgc 300
cctcccggaa gtgatgggac atttcttggc acagtgaact cagacggcgg cacgtatgac 360
atctacaggg cgcaaagagt caacgcaccg agcatcattg gcaatgccac cttctaccag 420
tattggtccg tgcggcagtc caagcgtgtc ggtgggacaa tcacgactgg caaccacttc 480
gacgcgtggg ccagcgtggg cctcaacctc gggactcata actaccagat aatggctact 540
gagggttacc agtcgtcagg atcttcagac attacggtgt catga 585

<210> SEQ ID NO 37
<211> LENGTH: 624
<212> TYPE: DNA
<213> ORGANISM: Artificial Sequence
<220> FEATURE:
<223> OTHER INFORMATION: Synthetic construct, plant optimized O43097

<400> SEQUENCE: 37
atgttcccag ctggaaacgc aacggaattg gagaaaagac aaaccacccc taactctgag 60
ggctggcatg acggatacta ctactcttgg tggagcgatg gtggtgcaca ggccacctat 120

```
acaaacctcg aaggcggcac ttatgagatt tcatggggtg acggtggcaa ccttgtcggc    180

ggaaaggggt ggaaccccgg acttaacgcc agggcaatcc acttcgaagg ggtgtaccag    240

cccaatggca actcatacct ggccgtctac gggtggacgc gcaatccgct ggttgagtac    300

tatatcgtgg agaatttcgg aacttatgac cctagctccg gtgccacgga cctcgggaca    360

gtcgagtgtg acggaagcat ctacaggctg ggtaaaacta cccgcgttaa tgctccatcg    420

atcgacggca cgcaaacatt tgatcaatac tggtccgtgc ggcaggataa gaggacaagc    480

ggcacagttc agacgggttg ccactttgat gcctgggcaa gagcggggct caatgtgaat    540

ggggaccact actatcagat tgtggcgacc gagggctatt tctccagtgg ctatgcgcgt    600

ataaccgtcg ctgatgttgg atga                                            624
```

<210> SEQ ID NO 38
<211> LENGTH: 2286
<212> TYPE: DNA
<213> ORGANISM: Artificial Sequence
<220> FEATURE:
<223> OTHER INFORMATION: Synthetic construct, plant optimized P77853: T134-100-101

<400> SEQUENCE: 38

```
atgcaaacaa gcattactct gacatccaac gcatccggta cgtttgacgg ttactattac     60

gaactctgga aggatactgg caatacaaca atgacggtct acactcaagg tcgcttttcc    120

tgccagtggt cgaacatcaa taacgcgttg tttaggaccg ggaagaaata caaccagaat    180

tggcagtctc ttggcacaat ccggatcacg tactctgcga cttacaaccc aaacgggaac    240

tcctacttgt gtatctatgg ctggtctacc aacccattgg tcgagttcta catcgttgag    300

tcctggggga actggagacc gcctggtgcc tgcctggccg agggctcgct cgtcttggac    360

gcggctaccg ggcagagggt ccctatcgaa aaggtgcgtc cggggatgga agttttctcc    420

ttgggacctg attacagact gtatcgggtg cccgttttgg aggtccttga gagcggggtt    480

agggaagttg tgcgcctcag aactcggtca gggagaacgc tggtgttgac accagatcac    540

ccgcttttga cccccgaagg ttggaaacct ctttgtgacc tcccgcttgg aactccaatt    600

gcagtccccg cagaactgcc tgtggcgggc cacttggccc cacctgaaga acgtgttacg    660

ctcctggctc ttctgttggg ggatgggaac acaaagctgt cgggtcggag aggtacacgt    720

cctaatgcct tcttctacag caaaaacccc gaattgctcg cggcttatcg ccggtgtgca    780

gaagccttgg gtgcaaaggt gaaagcatac gtccacccga ctacgggggt ggttacactc    840

gcaaccctcg ctccacgtcc tggagctcaa gatcctgtca aacgcctcgt tgtcgaggcg    900

ggaatggttg ctaaagccga agagaagagg gtcccggagg aggtgtttcg ttaccggcgt    960

gaggcgttgg cccttttctt gggccgtttg ttctcgacag acggctctgt tgaaaagaag   1020

aggatctctt attcaagtgc cagtttggga ctggcccagg atgtcgcaca tctcttgctg   1080

cgccttggaa ttacatctca actccgttcg agagggccac gggctcacga ggttcttata   1140

tcgggccgcg aggatatttt gcggtttgct gaacttatcg gaccctacct cttgggggcc   1200

aagagggaga gacttgcagc gctggaagct gaggcccgca ggcgtttgcc tggacaggga   1260

tggcacttgc ggcttgttct tcctgccgtg gcgtacagag tgggcgaggc ggaaaggcgc   1320

tcgggatttt cgtggagtga agccggtcgg cgcgtcgcag ttgcgggatc gtgtttgtca   1380

tctggactca acctcaaatt gcccagacgc tacctttctc ggcaccggtt gtcgctgctc   1440

ggtgaggctt ttgccgaccc tgggctggaa gcgctcgcgg aaggccaagt gctctgggac   1500
```

```
cctattgttg ctgtcgaacc ggccggtaag gcgagaacat tcgacttgcg cgttccaccc   1560

tttgcaaact tcgtgagcga ggacctggtg gtgcataaca ccgtcccccct gggccaagtg   1620

acaatcgatg gcgggaccta cgacatctat aggacgacac gcgtcaacca gccttccatt   1680

gtggggacag ccacgttcga tcagtactgg agcgtgcgca cctctaagcg gacttcagga   1740

acagtgaccg tgaccgatca cttccgcgcc tgggcgaacc ggggcctgaa cctcggcaca   1800

atagaccaaa ttacattgtg cgtggagggt taccaaagct ctggatcagc caacatcacc   1860

cagaacacct tctctcaggg ctcttcttcc ggcagttcgg gtggctcatc cggctccaca   1920

acgactactc gcatcgagtg tgagaacatg tccttgtccg gaccctacgt tagcaggatc   1980

accaatccct ttaatggtat tgcgctgtac gccaacggag acacagcccg cgctaccgtt   2040

aacttccccg caagtcgcaa ctacaatttc cgcctgcggg gttgcggcaa caacaataat   2100

cttgcccgtg tggacctgag gatcgacgga cggaccgtcg ggacctttta ttaccagggc   2160

acatacccct gggaggcccc aattgacaat gtttatgtca gtgcggggag tcatacagtc   2220

gaaatcactg ttactgcgga taacggcaca tgggacgtgt atgccgacta cctggtgata   2280

cagtga                                                              2286
```

```
<210> SEQ ID NO 39
<211> LENGTH: 2283
<212> TYPE: DNA
<213> ORGANISM: Artificial Sequence
<220> FEATURE:
<223> OTHER INFORMATION: Synthetic construct, plant optimized  P77853:
      S158-30-108-35

<400> SEQUENCE: 39

atgcaaacaa gcattactct gacatccaac gcatccggta cgtttgacgg ttacaattac     60

gaactctgga aggatactgg caatacaaca atgacggtct acactcaagg tcgcttttcc    120

tgccagtggt cgaacatcaa taacgcgttg tttaggaccg ggaagaaata caaccagaat    180

tggcagtctc tcggcacaat ccggatcacg tactctgcga cttacaaccc aaacgggaac    240

tcctacatgt gtatctatgg ctggtctacc aacccattgg tcgagttcta catcgttgag    300

tcctggggga actggagacc gcctggtgcc acgtccctgg gccaagtgac aatcgatggc    360

gggacctacg acatctatag gacgacacgc gtcaaccagc cttgcctggc cgagggctcg    420

ctcgtcttgg acgcggctac cgggcagagg gtccctatcg aaaaggtgcg tccggggatg    480

gaagttttct ccttgggacc tgattacaga ctgtatcggg tgcccgtttt ggaggtcctt    540

gagagcgggg ttggggaagt tgtgcgcctc cgaactcggt cagggagaac gctggtgttg    600

acaccagaac acccgctttt gacccccgaa ggttggaaac ctctttgtga cctcccgctt    660

ggaactccaa ttgcagtccc cgcagaactg cctgtggcgg gccacttggc cccacctgaa    720

gaacgtgtta tgctcctggc tcttctgttg gggggatggga acacaaagct gtcgggtcgg    780

agaggtacac gtcctaatgc cttcttctac agcaaagact ccgaattgct cgcggcttat    840

cgccggtgtg cagaagcctt gggtgcaaag gtgaaagcat acgtccaccc gactacgggg    900

gtggttacac tcgcaaccct cgctccacgt cctggagctc aagatcctgt caaacgcctc    960

gttgtcgagg cgggaatggt tgctaaagtc gaagagaaga gggtcccgga ggaggtgttt   1020

cgttaccggc gtgaggcgtt ggccctttc ttgggccgtt tgttctcgac agacggctct   1080

gttgaaaaga agaggatctc ttattcaagt gccagtttgg gactggccca ggatgtcgca   1140

catctcttgc tgcgccttgg aattacatct caactccgtt cgagagggcc acgggctcac   1200
```

```
aaggttctta tatcgggccg cgaggatatt ttgcggtttg ctgaacttat cggaccctac   1260

ctcttggggg ccaagaggga gagacttgca gcgctggaag ctgaggcccg caggcgtttg   1320

cctggacagg gatggcactt gcggcctgtt cttcctgccg tggcgtacag agtgagcgag   1380

gctaaaaggc gctcgggatt ttcgtggagt gaagccggtc ggcgcgtcgc agttgcggga   1440

tcgtgtttgt catctggact caacctcaaa ttgcccagac gctacctttc tcggcaccgg   1500

ttgtcgctgc tcggtgaggc ttttgccgac cctgggctgg aagcgctcgc ggaaggccaa   1560

gtgctctggg accctattgt tgctgtcgaa ccggccggta aggcgagaac attcgacttg   1620

cgcgtcccac cctttgcaaa cttcgtgagc gaggacctgg tggtgcataa ctccattgtg   1680

gggacagcca cgttcgatca gtactggagc gtgcgcacct ctaagcggac ttcaggaaca   1740

gtgaccgtga ccgatcactt ccgcgcctgg gcgaaccggg gcctgaacct cggcacaata   1800

gaccaaatta cattgtgcgt ggagggttac caaagctctg gatcagccaa catcacccag   1860

aacaccttct ctcagggctc ttcttccggc agttcgggtg gctcatccgg ctccacaacg   1920

actactcgca tcgagtgtga gaacatgtcc ttgtccggac cctacgttag caggatcacc   1980

aatcccttta atggtattgc gctgtacgcc aacggagaca cagcccgcgc taccgttaac   2040

ttccccgcaa gtcgcaacta caatttccgc ctgcggggtt gcggcaacag caataatctt   2100

gcccgtgtgg acctgaggat cgacggacgg accgtcggga ccttttatta ccagggcaca   2160

tacccctggg aggccccaat tgacaatgtt tatgtcagtg cggggagtca tacagtcgaa   2220

atcactgtta ctgcggataa cggcacacgg gacgtgtatg ccgactacct ggtgatacag   2280

tga                                                                 2283
```

<210> SEQ ID NO 40
<211> LENGTH: 735
<212> TYPE: DNA
<213> ORGANISM: Artificial Sequence
<220> FEATURE:
<223> OTHER INFORMATION: Synthetic construct, plant optimized 033897

<400> SEQUENCE: 40

```
atgtgcgatt ggctgttccc tgatggagat aatggaaagg agcccgaacc agaaccagaa     60

ccaacggtag agctctgcgg aagatgggat gcaagagacg tagcgggagg aagatataga    120

gttattaaca atgtgtgggg ggccgaaaca gcacagtgta tagaagtagg tcttgaaaca    180

ggtaatttta cgataacaag agccgatcat gacaatggta ataatgttgc agcatatcca    240

gcaatttact tcggatgtca ttgggcacca gcgagagcaa taagggattg tgccgcgcgt    300

gcgggagcgg ttaggagagc acacgaattg gatgttacac caattaccac gggaagatgg    360

aacgcagctt acgatatatg gtttagtccg gtaacaaact ctggtaacgg gtactcggga    420

ggcgccgaac ttatgatatg gctgaattgg aatggtggcg taatgccagg aggatcacgg    480

gtagcaactg tcgaattggc tggagcgaca tgggaagtgt ggtatgcaga ttggattgg     540

aattacatcg catatagaag aacgactccg acaacctcag tgagtgaact tgacttgaaa    600

gcctttattg atgatgcagt agcgagagga tacataaggc cagaatggta tctgcatgca    660

gtggaaacgg gatttgaatt gtgggaaggg ggggctgggt tgaggacagc agattttagc    720

gtaactgtac agtga                                                     735
```

<210> SEQ ID NO 41
<211> LENGTH: 2610
<212> TYPE: DNA

<213> ORGANISM: Artificial Sequence
<220> FEATURE:
<223> OTHER INFORMATION: Synthetic construct, plant optimized O68438

<400> SEQUENCE: 41

```
atgctggagg acaagtctcc caaactgcct gattataaga acgaccttct gtacgaacgc     60
acattcgacg aggggctctg cttcccgtgg cacacgtgcg aagattcagg agggaaatgc    120
gattttgccg tggtcgacgt tccaggcgag cctgggaaca aggcgttcag gctcactgtt    180
atcgataagg gtcagaacaa gtggtcggtc caaatgagac accggggtat cacgttggag    240
caggggcaca catacaccgt tcggtttact atctggagcg acaagagctg ccgcgtgtat    300
gccaaaatcg gccaaatggg tgaaccctac acggagtact ggaacaataa ctggaatccg    360
ttcaacctca ctccggggca gaaattgacg gtggaacaga actttactat gaattatccc    420
acggacgaca cgtgtgagtt taccttccac ttgggagggg aactggcagc cgggacccct    480
tactacgtgt acctcgacga cgtttctctt tacgatcccc gctttgtcaa gccagtggaa    540
tacgtcctgc ctcaaccgga tgtcagggtt aatcaagttg gatacctccc ttttgctaag    600
aaatatgcta ctgtcgtgtc atcgagcacg tccccattga agtggcaact tctgaatagt    660
gcaaaccaag ttgtcttgga gggcaataca atccccaagg gactggacaa agattcacaa    720
gactacgttc attggatcga tttctcgaac tttaagaccg aaggcaaggg gtactatttc    780
aagttgccca ctgtgaactc cgatactaac tactcccacc cgtttgatat ttctgcagat    840
atctattcaa agatgaagtt cgacgcgctc gctttctttt accataaaag gtcgggaata    900
ccaatcgaga tgccctacgc cgggggagag cagtggacaa ggcccgcagg gcacattggt    960
gtcgcgccga acaagggcga cacgaatgtg ccaacttggc cccaggatga cgaatatgct   1020
ggacgccccc agaaatacta tacgaaagac gtgaccggcg ggtggtacga tgccggtgac   1080
cacggcaagt acgtcgtgaa cggggggtatc gcagtttgga cccttatgaa tatgtacgag   1140
agagcaaaga ttagaggaat cgctaaccag ggtgcctaca aagatggagg aatgaatatc   1200
ccggaaagga ataacggcta tcctgatatt ctggacgagg ccagatggga gatcgaattt   1260
tttaagaaga tgcaagtcac tgagaaagaa gatccgtcga ttgcaggtat ggtgcaccac   1320
aagatccacg atttcaggtg gacggcgctc ggaatgttgc ctcacgagga cccccagcca   1380
cgctaccttc ggcccgtcag cacagcggca accctgaatt tcgcagcgac cctcgctcag   1440
tctgccagat tgtggaagga ttacgacccg acttttgcag cggactgcct tgagaaagct   1500
gaaattgcct ggcaagcagc actcaaacac ccggacatct acgctgagta cacgccagga   1560
agcggtgggc cgggtggagg tccttataat gacgattatg tcggggacga gttctactgg   1620
gccgcttgtg aactctatgt gacaaccggt aaggatgagt acaagaatta cttgatgaat   1680
agtccgcact atctggaaat gccagcgaag atgggcgaga acggaggggc taacggcgag   1740
gacaacggtc tctggggctg ctttacttgg ggaacgacac aggggttggg tacaattacc   1800
cttgccctcg ttgaaaacgg cctcccttcg gcggatattc aaaaggcccg caacaatatc   1860
gctaaagccg cagataagtg gcttgagaat attgaagaac aaggttaccg cctgcctatc   1920
aaacaagcgg aggatgaacg gggcggatac ccgtggggta gtaattcttt cattctcaac   1980
cagatgatcg tcatgggcta cgcttacgac ttcacgggaa acagcaagta tcttgacggg   2040
atgcaggacg gcatgtccta cctgctcggt agaaacggac ttgatcaatc gtacgttact   2100
gggtacgggg agaggccact tcagaacccc cacgaccgct tttggacccc tcaaacttcg   2160
aagaaattcc cggccccacc ccctggtatt atcgcaggcg ggccgaatag ccggtttgaa   2220
```

```
gatccaacga tcactgcagc ggttaagaag gatacacccc cgcagaagtg ctatattgac   2280

cacaccgatt cctggtctac taacgagatc acgattaatt ggaacgcccc cttcgcgtgg   2340

gtcacagcgt atctggacga aattgacttg attaccccac ccggcggagt ggaccctgaa   2400

gagccggaag ttatctacgg tgattgtaac ggcgacggaa aggttaattc gaccgatgct   2460

gtggccctta aaaggtatat cctccgcagc ggtatctcga tcaacacgga caacgcggac   2520

gttaatgcag atggtcgcgt gaatagcact gacctcgcta ttttgaagcg ctatattttg   2580

aaggagatcg atgttcttcc tcacaagtga                                    2610
```

<210> SEQ ID NO 42
<211> LENGTH: 1569
<212> TYPE: DNA
<213> ORGANISM: Artificial Sequence
<220> FEATURE:
<223> OTHER INFORMATION: Synthetic construct, plant optimized P54583

<400> SEQUENCE: 42

```
atggctggag gaggatactg gcacacttcc ggcagggaga tcctcgacgc aaataacgtt     60

ccagtcagaa tcgccgggat taattggttt ggcttcgaaa cgtgtaacta cgtggttcac    120

ggcctgtggt ctcgggatta cagatcaatg ctcgaccaga tcaaatcctt ggggtataat    180

acaattaggc tgccctacag cgatgacatt cttaagcctg gaaccatgcc gaactcgatt    240

aatttctacc aaatgaacca ggatctgcag ggattgactt ctctgcaggt tatggacaag    300

atcgtggcgt acgccggcca aatcgggctc agaattattt tggatcggca caggccagac    360

tgctcaggtc agtcggccct gtggtacaca agctccgtgt cagaggcaac atggatttca    420

gatcttcaag ccctcgcaca acgctataaa ggcaacccca cggttgtggg attcgacctt    480

cacaacgaac ctcacgatcc ggcctgttgg ggctgcgggg acccttcgat cgactggaga    540

ctggcagcgg agagggctgg taacgccgtt ctcagcgtca atcccaactt gctgatcttt    600

gtggagggag ttcagtccta caacggcgat tcttactggt ggggcggaaa tctccaaggc    660

gcagggcagt atcctgtcgt gcttaacgtt ccgaatcgcc tggtctactc agcacacgac    720

tacgcgacta gcgtgtaccc acagacgtgg ttctccgatc ccacatttcc taacaatatg    780

ccgggaatct ggaacaagaa ttggggttac ttgtttaacc aaaacattgc tccagtttgg    840

ttgggtgaat ttggcaccac tcttcagtcg acgacagacc aaacctggct gaaaaccctc    900

gtccagtatt tgcggccaac tgctcagtac ggagcagatt cttttcaatg gacgttctgg    960

tcttggaatc ctgactccgg ggatacaggc ggtatcctga aagacgattg gcagaccgtg   1020

gacactgtta aggacgggta cttggcgccg attaaaagct cgatctttga cccagtcggc   1080

gctagcgctt ccccatcttc acaaccttcg ccgagcgtca gccccagccc aagcccaagc   1140

ccgtctgcca gcagaacccc cactcccaca cctaccccca cggcctcacc aactccgacg   1200

ctcactccta cggcgacgcc aacaccaact gcttcaccca ctcctagccc caccgcagcg   1260

agcggggcta ggtgcaccgc ttcttaccag gtcaactctg actggggtaa tggcttcacc   1320

gtgactgtgg cggtcactaa ctcaggaagc gtcgcgacga aaacctggac tgtgtcctgg   1380

acgttcgggg gcaaccaaac aatcaccaac agctggaacg ctgcagttac gcagaatggg   1440

caaagcgtca cggcgcgcaa tatgagctac aacaacgtga ttcaaccagg ccagaatacc   1500

acattcggtt ttcaagcaag ctataccggg tcaaacgctg ccccaactgt cgcttgtgct   1560

gcctcatga                                                           1569
```

<210> SEQ ID NO 43
<211> LENGTH: 1542
<212> TYPE: DNA
<213> ORGANISM: Artificial Sequence
<220> FEATURE:
<223> OTHER INFORMATION: Synthetic construct, plant optimized BD22308

<400> SEQUENCE: 43

```
atgcagcaga tcggcaccta caccgccgag acccacccaa gcctgagctg gtccacctgc      60
aagagcggcg gttcctgcac gaccaacagc ggcgccatca cccttgatgc gaactggcgc     120
tgggtgcacg gcgtgaacac cagcaccaac tgctacacgg gtaacacgtg gaacaccgcc     180
atctgcgaca cggacgcttc ctgcgcccag gactgcgcgc ttgatggcgc cgactactcc     240
ggcacctacg gcatcaccac ctccggcaac agcctgcgcc tgaacttcgt gaccggcagc     300
aatgtgggca gccgcaccta cctgatggcc gacaacaccc actaccagat cttcgacctg     360
ctgaaccagg agttcacctt caccgtcgac gtgtcccacc tgccctgcgg cctgaacggc     420
gccctctact tcgtgacgat ggacgccgac ggcggcgtgt ccaagtaccc gaacaacaag     480
gctggcgccc agtacggtgt gggctactgc gacagccagt gcccgaggga cctgaagttc     540
atcgccggcc aggccaacgt ggagggctgg accccgagca gcaacaacgc caacaccggc     600
ctgggcaacc acggcgcctg ctgcgccgag ctggacatct gggaggccaa cagcatcagc     660
gaggccctga ccccacaccc atgcgacacc ccaggcctgt ctgtgtgcac caccgacgcc     720
tgcggcggca cctactccag cgaccgctac gccggcacct gcgacccaga cggctgcgac     780
ttcaacccgt accgcctggg cgtgaccgac ttctacggca gcggcaagac cgtggacacc     840
accaagccga tcaccgtggt gacccagttc gtgaccgacg acggcaccag caccggcacc     900
ctgagcgaga tccgccgcta ctacgtccag aacggcgtgg tgatcccgca gccgagcagc     960
aagatcagcg gcgtgtccgg caacgtgatc aacagcgact tctgcgacgc cgagatcagc    1020
accttcggcg agaccgccag cttcagcaag cacggcggcc tggccaagat gggcgctggc    1080
atggaagccg gcatggtgct ggtgatgagc ctgtgggacg actactccgt gaacatgctg    1140
tggctggaca gcacctaccc gaccaacgcc accgggacgc caggcgctgc caggggcagc    1200
tgcccaacca cctcgggcga ccccaagacc gtcgagagcc agagcggcag cagctacgtg    1260
accttcagcg acatccgcgt gggcccgttc aactccacgt tcagcggtgg ctctagcacg    1320
ggcggctcct ccaccaccac cgccagcggc accaccacca ccaaggcctc cagcacgtct    1380
actagctcca cctctaccgg caccggcgtt gctgcccatt ggggccagtg cggtggccag    1440
ggctggacgg gtccaacgac ttgcgcctcc ggcaccacct gcaccgtggt caatccgtac    1500
tactcccagt gcctggacga gctgaaggcc gaggccaagt ga                        1542
```

<210> SEQ ID NO 44
<211> LENGTH: 78
<212> TYPE: DNA
<213> ORGANISM: Artificial Sequence
<220> FEATURE:
<223> OTHER INFORMATION: Synthetic construct, BAASS

<400> SEQUENCE: 44

```
atggcgaaca aacatttgtc cctctccctc ttcctcgtcc tccttggcct gtcggccagc      60
ttggcctccg ggcaagtc                                                    78
```

<210> SEQ ID NO 45
<211> LENGTH: 129

<212> TYPE: DNA
<213> ORGANISM: Artificial Sequence
<220> FEATURE:
<223> OTHER INFORMATION: Synthetic construct, HvAleSP

<400> SEQUENCE: 45
atggcccacg cccgcgtcct cctcctggcg ctcgccgtcc tggccaccgc cgccgtcgcc 60
gtcgcctcct cctcctcctt cgccgactcc aacccgatcc gcccggtgac cgaccgcgcc 120
gcctccacc 129

<210> SEQ ID NO 46
<211> LENGTH: 90
<212> TYPE: DNA
<213> ORGANISM: Artificial Sequence
<220> FEATURE:
<223> OTHER INFORMATION: Synthetic construct, PR1a

<400> SEQUENCE: 46
atgggcttcg tgctcttctc ccagctgcct tccttccttc ttgtctccac cctgctcttg 60
ttcctcgtga tctcccactc ctgccgcgcc 90

<210> SEQ ID NO 47
<211> LENGTH: 57
<212> TYPE: DNA
<213> ORGANISM: Artificial Sequence
<220> FEATURE:
<223> OTHER INFORMATION: Synthetic construct, xGZein27ss-02

<400> SEQUENCE: 47
atgcgcgtgc tgctcgtggc cctggccctg ctggctcttg ctgccagcgc cacctct 57

<210> SEQ ID NO 48
<211> LENGTH: 72
<212> TYPE: DNA
<213> ORGANISM: Artificial Sequence
<220> FEATURE:
<223> OTHER INFORMATION: Synthetic construct, GluB4SP

<400> SEQUENCE: 48
atggccacca tcgctttctc ccgcttgtcc atctacttct gcgtgcttct cctgtgccac 60
ggctccatgg cc 72

<210> SEQ ID NO 49
<211> LENGTH: 18
<212> TYPE: DNA
<213> ORGANISM: Artificial Sequence
<220> FEATURE:
<223> OTHER INFORMATION: Synthetic construct, SEKDEL

<400> SEQUENCE: 49
agcgagaagg acgagctg 18

<210> SEQ ID NO 50
<211> LENGTH: 12
<212> TYPE: DNA
<213> ORGANISM: Artificial Sequence
<220> FEATURE:
<223> OTHER INFORMATION: Synthetic construct, KDEL

<400> SEQUENCE: 50
aaggacgagc tg 12

<210> SEQ ID NO 51

<211> LENGTH: 24
<212> TYPE: DNA
<213> ORGANISM: Artificial Sequence
<220> FEATURE:
<223> OTHER INFORMATION: Synthetic construct, HvVSD

<400> SEQUENCE: 51
gacgagctga aggccgaggc caag 24

<210> SEQ ID NO 52
<211> LENGTH: 1086
<212> TYPE: DNA
<213> ORGANISM: Artificial Sequence
<220> FEATURE:
<223> OTHER INFORMATION: Synthetic construct, BAASS:P77853

<400> SEQUENCE: 52
atggcgaaca aacatttgtc cctctccctc ttcctcgtcc tccttggcct gtcggccagc 60
ttggcctccg ggcaacaaac aagcattact ctgacatcca acgcatccgg tacgtttgac 120
ggttactatt acgaactctg gaaggatact ggcaatacaa caatgacggt ctacactcaa 180
ggtcgctttt cctgccagtg gtcgaacatc aataacgcgt tgtttaggac cgggaagaaa 240
tacaaccaga attggcagtc tcttggcaca atccggatca cgtactctgc gacttacaac 300
ccaaacggga actcctactt gtgtatctat ggctggtcta ccaacccatt ggtcgagttc 360
tacatcgttg agtcctgggg gaactggaga ccgcctggtg ccacgtccct gggccaagtg 420
acaatcgatg gcgggaccta cgacatctat aggacgacac gcgtcaacca gccttccatt 480
gtggggacag ccacgttcga tcagtactgg agcgtgcgca cctctaagcg gacttcagga 540
acagtgaccg tgaccgatca cttccgcgcc tgggcgaacc ggggcctgaa cctcggcaca 600
atagaccaaa ttacattgtg cgtggagggt taccaaagct ctggatcagc caacatcacc 660
cagaacacct tctctcaggg ctcttcttcc ggcagttcgg gtggctcatc cggctccaca 720
acgactactc gcatcgagtg tgagaacatg tccttgtccg gaccctacgt tagcaggatc 780
accaatccct ttaatggtat tgcgctgtac gccaacggag acacagcccg cgctaccgtt 840
aacttccccg caagtcgcaa ctacaatttc cgcctgcggg gttgcggcaa caacaataat 900
cttgcccgtg tggacctgag gatcgacgga cggaccgtcg ggacctttta ttaccagggc 960
acatacccct gggaggcccc aattgacaat gtttatgtca gtgcggggag tcatacagtc 1020
gaaatcactg ttactgcgga taacggcaca tgggacgtgt atgccgacta cctggtgata 1080
cagtga 1086

<210> SEQ ID NO 53
<211> LENGTH: 813
<212> TYPE: DNA
<213> ORGANISM: Artificial Sequence
<220> FEATURE:
<223> OTHER INFORMATION: Synthetic construct, BAASS:O33897

<400> SEQUENCE: 53
atggcgaaca aacatttgtc cctctccctc ttcctcgtcc tccttggcct gtcggccagc 60
ttggcctccg ggcaacaggt gtgcgattgg ctgttccctg atggagataa tggaaaggag 120
cccgaaccag aaccagaacc aacggtagag ctctgcggaa gatgggatgc aagagacgta 180
gcgggaggaa gatatagagt tattaacaat gtgtgggggg ccgaaacagc acagtgtata 240
gaagtaggtc ttgaaacagg taattttacg ataacaagag ccgatcatga caatggtaat 300
aatgttgcag catatccagc aatttacttc ggatgtcatt gggcaccagc gagagcaata 360

```
agggattgtg ccgcgcgtgc gggagcggtt aggagagcac acgaattgga tgttacacca    420

attaccacgg gaagatggaa cgcagcttac gatatatggt ttagtccggt aacaaactct    480

ggtaacgggt actcgggagg cgccgaactt atgatatggc tgaattggaa tggtggcgta    540

atgccaggag gatcacgggt agcaactgtc gaattggctg gagcgacatg ggaagtgtgg    600

tatgcagatt gggattggaa ttacatcgca tatagaagaa cgactccgac aacctcagtg    660

agtgaacttg acttgaaagc ctttattgat gatgcagtag cgagaggata cataaggcca    720

gaatggtatc tgcatgcagt ggaaacggga tttgaattgt gggaaggggg ggctgggttg    780

aggacagcag attttagcgt aactgtacag tga                                 813
```

```
<210> SEQ ID NO 54
<211> LENGTH: 1428
<212> TYPE: DNA
<213> ORGANISM: Artificial Sequence
<220> FEATURE:
<223> OTHER INFORMATION: Synthetic construct, HvAleSP:NtEGM

<400> SEQUENCE: 54

atggcccacg cccgcgtcct cctcctggcg ctcgccgtcc tggccaccgc cgccgtcgcc     60

gtcgcctcct cctcctcctt cgccgactcc aacccgatcc gcccggtgac cgaccgcgcc    120

gcctccaccg cttacgacta caagcaggtg ttgcgggact cgctactatt ctatgaggcc    180

cagagatccg gccggctccc agccgaccag aaggtcacgt ggaggaagga tagcgcgctg    240

aatgaccagg gtgaccaggg acaagacttg accggcggct actttgacgc tggggacttc    300

gtcaagttcg ggttccccat ggcttatacc gcaaccgtgc tggcatgggg cctcatagat    360

tttgaggccg gctacagcag tgccggggcc ttggatgatg gacggaaggc tgtcaaatgg    420

gccaccgact atttcataaa ggcccacaca agtcaaaatg agttctatgg tcaggtcggc    480

cagggtgacg ccgatcacgc tttctgggga agaccagagg atatgacgat ggcgcgcccg    540

gcgtacaaga tagacacctc aaggcctggc tctgatctgg caggcgagac agcggctgct    600

cttgccgctg cttcaatcgt gttccggaac gtcgatggca cttactcaaa taacctgtta    660

acacacgctc gccagctatt cgacttcgcg aacaactacc ggggaaagta tagtgactct    720

attactgacg caagaaattt ctacgcaagc gcagactaca gagacgagtt ggtttgggct    780

gctgcgtggt tatacagagc gaccaacgac aacacctacc tcaacactgc tgagtcactg    840

tacgatgagt ttgggctaca gaactggggg gggggcctga actgggatag caaggtgtct    900

ggcgtgcagg tgttgttggc caagcttacc aataagcagg cctacaagga cacggtgcag    960

tcttacgtca attacctaat taataaccag cagaagactc ccaagggcct cctctacatc   1020

gacatgtggg gcacccttcg ccacgctgcc aacgccgcat tcatcatgct cgaagccgcc   1080

gagctgggct tgtccgcctc ctcttataga cagttcgcgc aaacgcaaat cgactacgcc   1140

ctgggcgatg gtggccgctc ctttgtgtgc gggttcggga gtaatcctcc tacgagaccg   1200

caccacagat cctcgtcgtg cccgccagct cccgctactt gcgactggaa tacattcaac   1260

tcacctgacc caaactacca cgtcctctct ggggccctag tgggcggacc tgatcagaat   1320

gacaactacg tcgatgaccg ttcagactat gttcacaacg aagtcgccac tgattacaac   1380

gcgggtttcc agtccgcgtt agctgctttg gtggcccttg gttactga                1428
```

```
<210> SEQ ID NO 55
<211> LENGTH: 2355
<212> TYPE: DNA
```

<213> ORGANISM: Artificial Sequence
<220> FEATURE:
<223> OTHER INFORMATION: Synthetic construct, BAASS:P77853:S158-30-108-35

<400> SEQUENCE: 55

```
atggcgaaca aacatttgtc cctctccctc ttcctcgtcc tccttggcct gtcggccagc     60

ttggcctccg ggcaacaaac aagcattact ctgacatcca acgcatccgg tacgtttgac    120

ggttacaatt acgaactctg gaaggatact ggcaatacaa caatgacggt ctacactcaa    180

ggtcgctttt cctgccagtg gtcgaacatc aataacgcgt tgtttaggac cgggaagaaa    240

tacaaccaga attggcagtc tctcggcaca atccggatca cgtactctgc gacttacaac    300

ccaaacggga actcctacat gtgtatctat ggctggtcta ccaacccatt ggtcgagttc    360

tacatcgttg agtcctgggg gaactggaga ccgcctggtg ccacgtccct gggccaagtg    420

acaatcgatg gcgggaccta cgacatctat aggacgacac gcgtcaacca gccttgcctg    480

gccgagggct cgctcgtctt ggacgcggct accgggcaga gggtccctat cgaaaaggtg    540

cgtccgggga tggaagtttt ctccttggga cctgattaca gactgtatcg ggtgcccgtt    600

ttggaggtcc ttgagagcgg ggttggggaa gttgtgcgcc tccgaactcg gtcagggaga    660

acgctggtgt tgacaccaga acacccgctt ttgacccccg aaggttggaa acctctttgt    720

gacctcccgc ttggaactcc aattgcagtc cccgcagaac tgcctgtggc gggccacttg    780

gccccacctg aagaacgtgt tatgctcctg gctcttctgt tgggggatgg gaacacaaag    840

ctgtcgggtc ggagaggtac acgtcctaat gccttcttct acagcaaaga ctccgaattg    900

ctcgcggctt atcgccggtg tgcagaagcc ttgggtgcaa aggtgaaagc atacgtccac    960

ccgactacgg gggtggttac actcgcaacc ctcgctccac gtcctggagc tcaagatcct   1020

gtcaaacgcc tcgttgtcga ggcgggaatg gttgctaaag tcgaagagaa gagggtcccg   1080

gaggaggtgt ttcgttaccg gcgtgaggcg ttggcccttt tcttgggccg tttgttctcg   1140

acagacggct ctgttgaaaa gaagaggatc tcttattcaa gtgccagttt gggactggcc   1200

caggatgtcg cacatctctt gctgcgcctt ggaattacat ctcaactccg ttcgagaggg   1260

ccacgggctc acaaggttct tatatcgggc cgcgaggata ttttgcggtt tgctgaactt   1320

atcggaccct acctcttggg ggccaagagg gagagacttg cagcgctgga agctgaggcc   1380

cgcaggcgtt tgcctggaca gggatggcac ttgcggcctg ttcttcctgc cgtggcgtac   1440

agagtgagcg aggctaaaag gcgctcggga ttttcgtgga gtgaagccgg tcggcgcgtc   1500

gcagttgcgg gatcgtgttt gtcatctgga ctcaacctca aattgcccag acgctacctt   1560

tctcggcacc ggttgtcgct gctcggtgag gcttttgccg accctgggct ggaagcgctc   1620

gcggaaggcc aagtgctctg ggaccctatt gttgctgtcg aaccggccgg taaggcgaga   1680

acattcgact tgcgcgtccc accctttgca aacttcgtga gcgaggacct ggtggtgcat   1740

aactccattg tggggacagc cacgttcgat cagtactgga gcgtgcgcac ctctaagcgg   1800

acttcaggaa cagtgaccgt gaccgatcac ttccgcgcct gggcgaaccg gggcctgaac   1860

ctcggcacaa tagaccaaat tacattgtgc gtggagggtt accaaagctc tggatcagcc   1920

aacatcaccc agaacacctt ctctcagggc tcttcttccg gcagttcggg tggctcatcc   1980

ggctccacaa cgactactcg catcgagtgt gagaacatgt ccttgtccgg accctacgtt   2040

agcaggatca ccaatccctt taatggtatt gcgctgtacg ccaacggaga cacagcccgc   2100

gctaccgtta acttccccgc aagtcgcaac tacaatttcc gcctgcgggg ttgcggcaac   2160
```

agcaataatc ttgcccgtgt ggacctgagg atcgacggac ggaccgtcgg gacctttat 2220 taccagggca catacccctg ggaggcccca attgacaatg tttatgtcag tgcggggagt 2280
catacagtcg aaatcactgt tactgcggat aacggcacac gggacgtgta tgccgactac 2340
ctggtgatac agtga 2355

<210> SEQ ID NO 56
<211> LENGTH: 1611
<212> TYPE: DNA
<213> ORGANISM: Artificial Sequence
<220> FEATURE:
<223> OTHER INFORMATION: Synthetic construct, BAASS:AnfaeB:SEKDEL

<400> SEQUENCE: 56
atggcgaaca aacatttgtc cctctccctc ttcctcgtcc tccttggcct gtcggccagc 60
ttggcctccg ggcaagtcgc tactgatccc ttccagtctc gctgtaacga gtttcaaaac 120
aaaattgata tcgcaaacgt cacggttagg tcggtcgcct acgtcgcggc tggtcagaat 180
atctctcaag cagaagtcgc ttcggtttgc aaggcaagcg tccaggcctc cgtggacctc 240
tgtagagtga caatgaatat tagcacctcg gataggagcc acctttgggc cgaggcttgg 300
ctgcctcgca attatactgg acggttcgtc tccactggga acgggggcct ggctggatgc 360
gtgcaggaaa cagacttgaa tttcgctgcc aactttggct tcgcaaccgt tggcactaat 420
ggagggcacg atggagacac ggcgaaatac tttctgaata actctgaggt cctcgctgat 480
ttcgcctatc gcagcgttca cgagggcact gtggtcggga agcaacttac ccagttgttc 540
tacgacgaag gttacaatta ttcgtactat ctgggctgca gcaccggagg caggcaaggc 600
tatcagcaag tgcagcgctt tccggatgac tacgatggtg ttattgccgg aagtgcagcg 660
atgaacttta tcaatttgat ttcttggggc gcttttcttt ggaaggccac gggactcgca 720
gacgacccag attttatctc agcgaacctc tggagcgtta tccaccagga gattgtgcgg 780
cagtgtgact tggttgatgg tgctcttgac ggaattattg aagatcctga cttctgcgcc 840
cctgttatcg agagactgat ttgtgatggg actaccaacg gcacctcctg tatcactggg 900
gcacaagcgg ctaaagtgaa tagggccctc tcggactttt atggtccgga tgggacagtc 960
tactatccac gcttgaacta cggaggggag gcagactctg cgagcctgta cttcacaggc 1020
tccatgtatt cacggaccga agagtggtac aagtacgtcg tgtacaacga tactaactgg 1080
aatagttctc aatggacgct cgaaagcgct aagttggcct tggagcagaa ccccttaat 1140 attcaggcat tcgaccctaa tatcacagcg ttcagggacc gcggtggaaa actcttgagc 1200
taccacggca cccaagatcc gattatttca tcgactgaca gcaagttgta ttacagaaga 1260
gttgctaacg cccttaacgc tgccccatcc gaactcgacg agttttatcg cttctttcag 1320
atctctggga tgggtcactg cggcgacgga accggggctt catacattgg ccagggatac 1380
ggcacgtata cctcgaaggc cccacaggtc aacttgcttc ggactatggt ggattgggtt 1440
gagaatggaa aagctccgga atatatgcct gggaataagt tgaacgccaa cggttcgatc 1500
gagtatatga gaaagcactg tcgttaccca aaacacaata ttcacacggg cccaggtaac 1560
tacacggacc ctaactcctg gacctgcgtc agcgagaagg acgagctgtg a 1611

<210> SEQ ID NO 57
<211> LENGTH: 879
<212> TYPE: DNA
<213> ORGANISM: Artificial Sequence
<220> FEATURE:
<223> OTHER INFORMATION: Synthetic construct, BAASS:AnfaeA:SEKDEL

<400> SEQUENCE: 57

```
atggcgaaca aacatttgtc cctctccctc ttcctcgtcc tccttggcct gtcggccagc     60
ttggcctccg ggcaagtcgc atccacgcag ggtatctctg aggacctgta taatcgcctc    120
gtggaaatgg ccacaatttc acaagcggct tacgcagatc tttgtaatat cccttcgaca    180
attatcaagg gagagaaaat ctataacgcc cagactgaca tcaacggctg gatactgcgg    240
gatgacacga gcaaggaaat tatcacagtc tttagaggga ccggttccga tacaaatttg    300
cagttggaca cgaattacac actgaccccc ttcgatactc tccctcaatg caacgactgt    360
gaggttcacg gtgggtacta tattggctgg atctctgttc aagaccaagt cgagtcactt    420
gttaagcagc aagcgtcgca gtacccggac tacgcattga cggtgacagg gcacagcctg    480
ggtgcctcga tggcagcgct caccgctgcc cagctttctg caacctacga taatgtcagg    540
ctgtacactt tcggagaacc acgctcaggc aaccaagcgt ttgcttcgta tatgaacgac    600
gctttccagg ttagctcccc cgagacgaca caatactttc gggtgaccca ttctaacgac    660
gggattccta acctcccgcc agccgacgaa ggttacgcac acgggggtgt cgagtactgg    720
tcagtggacc cctacagcgc gcagaatact ttcgtttgca cgggcgatga ggtccagtgc    780
tgtgaagctc aagggggtca gggagtgaat gatgcacaca caacctattt cggaatgact    840
tccggggctt gcacgtggag cgagaaggac gagctgtga                           879
```

<210> SEQ ID NO 58
<211> LENGTH: 1407
<212> TYPE: DNA
<213> ORGANISM: Artificial Sequence
<220> FEATURE:
<223> OTHER INFORMATION: Synthetic construct, PR1a:NtEGM:SEKDEL

<400> SEQUENCE: 58

```
atgggcttcg tgctcttctc ccagctgcct tccttccttc ttgtctccac cctgctcttg     60
ttcctcgtga tctcccactc ctgccgcgcc gcttacgact acaagcaggt gttgcgggac    120
tcgctactat tctatgaggc ccagagatcc ggccggctcc cagccgacca gaaggtcacg    180
tggaggaagg atagcgcgct gaatgaccag ggtgaccagg gacaagactt gaccggcggc    240
tactttgacg ctggggactt cgtcaagttc gggttcccca tggcttatac cgcaaccgtg    300
ctggcatggg gcctcataga ttttgaggcc ggctacagca gtgccggggc cttggatgat    360
ggacggaagg ctgtcaaatg ggccaccgac tatttcataa aggcccacac aagtcaaaat    420
gagttctatg gtcaggtcgg ccagggtgac gccgatcacg ctttctgggg aagaccagag    480
gatatgacga tggcgcgccc ggcgtacaag atagacacct caaggcctgg ctctgatctg    540
gcaggcgaga cagcggctgc tcttgccgct gcttcaatcg tgttccggaa cgtcgatggc    600
acttactcaa ataacctgtt aacacacgct cgccagctat tcgacttcgc gaacaactac    660
cggggaaagt atagtgactc tattactgac gcaagaaatt tctacgcaag cgcagactac    720
agagacgagt tggtttgggc tgctgcgtgg ttatacagag cgaccaacga caacacctac    780
ctcaacactg ctgagtcact gtacgatgag tttgggctac agaactgggg ggggggcctg    840
aactgggata gcaaggtgtc tggcgtgcag gtgttgttgg ccaagcttac caataagcag    900
gcctacaagg acacggtgca gtcttacgtc aattacctaa ttaataacca gcagaagact    960
cccaagggcc tcctctacat cgacatgtgg ggcacccttc gccacgctgc caacgccgca   1020
ttcatcatgc tcgaagccgc cgagctgggc ttgtccgcct cctcttatag acagttcgcg   1080
```

```
caaacgcaaa tcgactacgc cctgggcgat ggtggccgct cctttgtgtg cgggttcggg   1140

agtaatcctc ctacgagacc gcaccacaga tcctcgtcgt gcccgccagc tcccgctact   1200

tgcgactgga atacattcaa ctcacctgac ccaaactacc acgtcctctc tggggcccta   1260

gtgggcggac ctgatcagaa tgacaactac gtcgatgacc gttcagacta tgttcacaac   1320

gaagtcgcca ctgattacaa cgcgggtttc cagtccgcgt tagctgcttt ggtggccctt   1380

ggttacagcg agaaggacga gctgtga                                       1407


<210> SEQ ID NO 59
<211> LENGTH: 2376
<212> TYPE: DNA
<213> ORGANISM: Artificial Sequence
<220> FEATURE:
<223> OTHER INFORMATION: Synthetic construct, BAASS:P77853:T134-100-101:
      SEKDEL

<400> SEQUENCE: 59

atggcgaaca aacatttgtc cctctccctc ttcctcgtcc tccttggcct gtcggccagc     60

ttggcctccg ggcaacaaac aagcattact ctgacatcca acgcatccgg tacgtttgac    120

ggttactatt acgaactctg gaaggatact ggcaatacaa caatgacggt ctacactcaa    180

ggtcgctttt cctgccagtg gtcgaacatc aataacgcgt tgtttaggac cgggaagaaa    240

tacaaccaga attggcagtc tcttggcaca atccggatca cgtactctgc gacttacaac    300

ccaaacggga actcctactt gtgtatctat ggctggtcta ccaacccatt ggtcgagttc    360

tacatcgttg agtcctgggg gaactggaga ccgcctggtg cctgcctggc cgagggctcg    420

ctcgtcttgg acgcggctac cggcagaggg gtccctatcg aaaaggtgcg tccggggatg    480

gaagttttct ccttgggacc tgattacaga ctgtatcggg tgcccgtttt ggaggtcctt    540

gagagcgggg ttagggaagt tgtgcgcctc agaactcggt cagggagaac gctggtgttg    600

acaccagatc acccgctttt gacccccgaa ggttggaaac ctctttgtga cctcccgctt    660

ggaactccaa ttgcagtccc cgcagaactg cctgtggcgg gccacttggc ccccacctgaa    720

gaacgtgtta cgctcctggc tcttctgttg ggggatggga acacaaagct gtcgggtcgg    780

agaggtacac gtcctaatgc cttcttctac agcaaaaacc ccgaattgct cgcggcttat    840

cgccggtgtg cagaagcctt gggtgcaaag gtgaaagcat acgtccaccc gactacgggg    900

gtggttacac tcgcaaccct cgctccacgt cctggagctc aagatcctgt caaacgcctc    960

gttgtcgagg cgggaatggt tgctaaagcc gaagagaaga gggtcccgga ggaggtgttt   1020

cgttaccggc gtgaggcgtt ggcccttttc ttgggccgtt tgttctcgac agacggctct   1080

gttgaaaaga agaggatctc ttattcaagt gccagtttgg gactggccca ggatgtcgca   1140

catctcttgc tgcgccttgg aattacatct caactccgtt cgagagggcc acgggctcac   1200

gaggttctta tatcgggccg cgaggatatt ttgcggtttg ctgaacttat cggaccctac   1260

ctcttggggg ccaagaggga gagacttgca gcgctggaag ctgaggcccg caggcgtttg   1320

cctggacagg gatggcactt gcggcttgtt cttcctgccg tggcgtacag agtgggcgag   1380

gcggaaaggc gctcgggatt ttcgtggagt gaagccggtc ggcgcgtcgc agttgcggga   1440

tcgtgtttgt catctggact caacctcaaa ttgcccagac gctacctttc tcggcaccgg   1500

ttgtcgctgc tcggtgaggc ttttgccgac cctgggctgg aagcgctcgc ggaaggccaa   1560

gtgctctggg accctattgt tgctgtcgaa ccggccggta aggcgagaac attcgacttg   1620

cgcgttccac cctttgcaaa cttcgtgagc gaggacctgg tggtgcataa caccgtcccc   1680
```

```
ctgggccaag tgacaatcga tggcgggacc tacgacatct ataggacgac acgcgtcaac   1740

cagccttcca ttgtggggac agccacgttc gatcagtact ggagcgtgcg cacctctaag   1800

cggacttcag gaacagtgac cgtgaccgat cacttccgcg cctgggcgaa ccggggcctg   1860

aacctcggca caatagacca aattacattg tgcgtggagg gttaccaaag ctctggatca   1920

gccaacatca cccagaacac cttctctcag ggctcttctt ccggcagttc gggtggctca   1980

tccggctcca caacgactac tcgcatcgag tgtgagaaca tgtccttgtc cggaccctac   2040

gttagcagga tcaccaatcc ctttaatggt attgcgctgt acgccaacgg agacacagcc   2100

cgcgctaccg ttaacttccc cgcaagtcgc aactacaatt tccgcctgcg gggttgcggc   2160

aacaacaata atcttgcccg tgtggacctg aggatcgacg gacggaccgt cgggaccttt   2220

tattaccagg gcacataccc ctgggaggcc ccaattgaca atgtttatgt cagtgcgggg   2280

agtcatacag tcgaaatcac tgttactgcg gataacggca catgggacgt gtatgccgac   2340

tacctggtga tacagagcga gaaggacgag ctgtga                              2376
```

<210> SEQ ID NO 60
<211> LENGTH: 1446
<212> TYPE: DNA
<213> ORGANISM: Artificial Sequence
<220> FEATURE:
<223> OTHER INFORMATION: Synthetic construct, HvAleSP:NtEGM:SEKDEL

<400> SEQUENCE: 60

```
atggcccacg cccgcgtcct cctcctggcg ctcgccgtcc tggccaccgc cgccgtcgcc     60

gtcgcctcct cctcctcctt cgccgactcc aacccgatcc gcccggtgac cgaccgcgcc    120

gcctccaccg cttacgacta caagcaggtg ttgcgggact cgctactatt ctatgaggcc    180

cagagatccg gccggctccc agccgaccag aaggtcacgt ggaggaagga tagcgcgctg    240

aatgaccagg gtgaccaggg acaagacttg accggcggct actttgacgc tggggacttc    300

gtcaagttcg ggttccccat ggcttatacc gcaaccgtgc tggcatgggg cctcatagat    360

tttgaggccg gctacagcag tgccggggcc ttggatgatg gacggaaggc tgtcaaatgg    420

gccaccgact atttcataaa ggcccacaca agtcaaaatg agttctatgg tcaggtcggc    480

cagggtgacg ccgatcacgc tttctgggga agaccagagg atatgacgat ggcgcgcccg    540

gcgtacaaga tagacacctc aaggcctggc tctgatctgg caggcgagac agcggctgct    600

cttgccgctg cttcaatcgt gttccggaac gtcgatggca cttactcaaa taacctgtta    660

acacacgctc gccagctatt cgacttcgcg aacaactacc ggggaaagta tagtgactct    720

attactgacg caagaaattt ctacgcaagc gcagactaca gagacgagtt ggtttgggct    780

gctgcgtggt tatacagagc gaccaacgac aacacctacc tcaacactgc tgagtcactg    840

tacgatgagt ttgggctaca gaactggggg gggggcctga actgggatag caaggtgtct    900

ggcgtgcagg tgttgttggc caagcttacc aataagcagg cctacaagga cacggtgcag    960

tcttacgtca attacctaat taataaccag cagaagactc ccaagggcct cctctacatc   1020

gacatgtggg gcacccttcg ccacgctgcc aacgccgcat tcatcatgct cgaagccgcc   1080

gagctgggct tgtccgcctc ctcttataga cagttcgcgc aaacgcaaat cgactacgcc   1140

ctgggcgatg gtggccgctc ctttgtgtgc gggttcggga gtaatcctcc tacgagaccg   1200

caccacagat cctcgtcgtg cccgccagct cccgctactt gcgactggaa tacattcaac   1260

tcacctgacc caaactacca cgtcctctct ggggccctag tgggcggacc tgatcagaat   1320

gacaactacg tcgatgaccg ttcagactat gttcacaacg aagtcgccac tgattacaac   1380
```

gcgggtttcc agtccgcgtt agctgctttg gtggcccttg gttacagcga gaaggacgag 1440
ctgtga 1446

<210> SEQ ID NO 61
<211> LENGTH: 717
<212> TYPE: DNA
<213> ORGANISM: Artificial Sequence
<220> FEATURE:
<223> OTHER INFORMATION: Synthetic construct, BAASS:O43097:SEKDEL

<400> SEQUENCE: 61
atggcgaaca aacatttgtc cctctccctc ttcctcgtcc tccttggcct gtcggccagc 60
ttggcctccg ggcaagtctt cccagctgga aacgcaacgg aattggagaa aagacaaacc 120
acccctaact ctgagggctg gcatgacgga tactactact cttggtggag cgatggtggt 180
gcacaggcca cctatacaaa cctcgaaggc ggcacttatg agatttcatg ggtgacggt 240 ggcaaccttg tcggcggaaa ggggtggaac cccggactta acgccagggc aatccacttc 300
gaaggggtgt accagcccaa tggcaactca tacctggccg tctacgggtg gacgcgcaat 360
ccgctggttg agtactatat cgtggagaat ttcggaactt atgaccctag ctccggtgcc 420
acggacctcg ggacagtcga gtgtgacgga agcatctaca ggctgggtaa aactacccgc 480
gttaatgctc catcgatcga cggcacgcaa acatttgatc aatactggtc cgtgcggcag 540
gataagagga caagcggcac agttcagacg ggttgccact ttgatgcctg ggcaagagcg 600
gggctcaatg tgaatgggga ccactactat cagattgtgg cgaccgaggg ctatttctcc 660
agtggctatg cgcgtataac cgtcgctgat gttggaagcg agaaggacga gctgtga 717

<210> SEQ ID NO 62
<211> LENGTH: 1596
<212> TYPE: DNA
<213> ORGANISM: Artificial Sequence
<220> FEATURE:
<223> OTHER INFORMATION: Synthetic construct, xGZein27ss-02:BD22308:
HvVSD-01

<400> SEQUENCE: 62
atgcgcgtgc tgctcgtggc cctggccctg ctggctcttg ctgccagcgc cacctctcag 60
cagatcggca cctacaccgc cgagacccac ccaagcctga gctggtccac ctgcaagagc 120
ggcggttcct gcacgaccaa cagcggcgcc atcacccttg atgcgaactg gcgctgggtg 180
cacggcgtga acaccagcac caactgctac acgggtaaca cgtggaacac cgccatctgc 240
gacacggacg cttcctgcgc ccaggactgc gcgcttgatg gcgccgacta ctccggcacc 300
tacggcatca ccacctccgg caacagcctg cgcctgaact tcgtgaccgg cagcaatgtg 360
ggcagccgca cctacctgat ggccgacaac acccactacc agatcttcga cctgctgaac 420
caggagttca ccttcaccgt cgacgtgtcc cacctgccct gcggcctgaa cggcgccctc 480
tacttcgtga cgatggacgc cgacggcggc gtgtccaagt acccgaacaa caaggctggc 540
gcccagtacg gtgtgggcta ctgcgacagc cagtgcccga gggacctgaa gttcatcgcc 600
ggccaggcca acgtggaggg ctggaccccg agcagcaaca acgccaacac cggcctgggc 660
aaccacggcg cctgctgcgc cgagctggac atctgggagg ccaacagcat cagcgaggcc 720
ctgaccccac acccatgcga caccccaggc ctgtctgtgt gcaccaccga cgcctgcggc 780
ggcacctact ccagcgaccg ctacgccggc acctgcgacc cagacggctg cgacttcaac 840
ccgtaccgcc tgggcgtgac cgacttctac ggcagcggca agaccgtgga caccaccaag 900

```
ccgatcaccg tggtgaccca gttcgtgacc gacgacggca ccagcaccgg caccctgagc    960

gagatccgcc gctactacgt ccagaacggc gtggtgatcc cgcagccgag cagcaagatc   1020

agcggcgtgt ccggcaacgt gatcaacagc gacttctgcg acgccgagat cagcaccttc   1080

ggcgagaccg ccagcttcag caagcacggc ggcctggcca agatgggcgc tggcatggaa   1140

gccggcatgg tgctggtgat gagcctgtgg gacgactact ccgtgaacat gctgtggctg   1200

gacagcacct acccgaccaa cgccaccggg acgccaggcg ctgccagggg cagctgccca   1260

accacctcgg gcgaccccaa gaccgtcgag agccagagcg gcagcagcta cgtgaccttc   1320

agcgacatcc gcgtgggccc gttcaactcc acgttcagcg gtggctctag cacgggcggc   1380

tcctccacca ccaccgccag cggcaccacc accaccaagg cctccagcac gtctactagc   1440

tccacctcta ccggcaccgg cgttgctgcc cattggggcc agtgcggtgg ccagggctgg   1500

acgggtccaa cgacttgcgc ctccggcacc acctgcaccg tggtcaatcc gtactactcc   1560

cagtgcctgg acgagctgaa ggccgaggcc aagtga                             1596
```

<210> SEQ ID NO 63
<211> LENGTH: 13321
<212> TYPE: DNA
<213> ORGANISM: Artificial Sequence
<220> FEATURE:
<223> OTHER INFORMATION: Synthetic construct, vector pAG2015

<400> SEQUENCE: 63

```
aattcatact aaagcttgca tgcctgcagg tcgactctag taacggccgc cagtgtgctg     60

gaattaattc ggcttgtcga ccacccaacc ccatatcgac agaggatgtg aagaacaggt    120

aaatcacgca gaagaaccca tctctgatag cagctatcga ttagaacaac gaatccatat    180

tgggtccgtg ggaaatactt actgcacagg aagggggcga tctgacgagg ccccgccacc    240

ggcctcgacc cgaggccgag gccgacgaag cgccggcgag tacggcgccg cggcggcctc    300

tgcccgtgcc ctctgcgcgt gggagggaga ggccgcggtg gtgggggcgc gcgcgcgcgc    360

gcgcgcagct ggtgcggcgg cgcgggggtc agccgccgag ccggcggcga cggaggagca    420

gggcggcgtg gacgcgaact tccgatcggt tggtcagagt gcgcgagttg ggcttagcca    480

attaggtctc aacaatctat tgggccgtaa aattcatggg ccctggtttg tctaggccca    540

atatcccgtt catttcagcc cacaaatatt tccccagagg attattaagg cccacacgca    600

gcttatagca gatcaagtac gatgtttcct gatcgttgga tcggaaacgt acggtcttga    660

tcaggcatgc cgacttcgtc aaagagaggc ggcatgacct gacgcggagt tggttccggg    720

caccgtctgg atggtcgtac cgggaccgga cacgtgtcgc gcctccaact acatggacac    780

gtgtggtgct gccattgggc cgtacgcgtg gcggtgaccg caccggatgc tgcctcgcac    840

cgccttgccc acgctttata tagagaggtt ttctctccat taatcgcata gcgagtcgaa    900

tcgaccgaag ggagggggga gcgaagcttt gcgttctcta atcgcctcgt caaggtaact    960

aatcaatcac ctcgtcctaa tcctcgaatc tctcgtggtg cccgtctaat ctcgcgattt   1020

tgatgctcgt ggtggaaagc gtaggaggat cccgtgcgag ttagtctcaa tctctcaggg   1080

tttcgtgcga ttttagggtg atccacctct taatcgagtt acggtttcgt gcgattttag   1140

ggtaatcctc ttaatctctc attgatttag ggtttcgtga gaatcgaggt agggatctgt   1200

gttatttata tcgatctaat agatggattg gttttgagat tgttctgtca gatggggatt   1260

gtttcgatat attaccctaa tgatgtgtca gatggggatt gtttcgatat attaccctaa   1320
```

```
tgatgtgtca gatggggatt gtttcgatat attaccctaa tgatggataa taagagtagt   1380

tcacagttat gttttgatcc tgccacatag tttgagtttt gtgatcagat ttagttttac   1440

ttatttgtgc ttagttcgga tgggattgtt ctgatattgt tccaatagat gaatagctcg   1500

ttaggttaaa atctttaggt tgagttaggc gacacatagt ttatttcctc tggatttgga   1560

ttggaattgt gttcttagtt tttttcccct ggatttggat tggaattgtg tggagctggg   1620

ttagagaatt acatctgtat cgtgtacacc tacttgaact gtagagcttg ggttctaagg   1680

tcaatttaat ctgtattgta tctggctctt tgcctagttg aactgtagtg ctgatgttgt   1740

actgtgtttt tttacccgtt ttatttgctt tactcgtgca aatcaaatct gtcagatgct   1800

agaactaggt ggctttattc tgtgttctta catagatctg ttgtcctgta gttacttatg   1860

tcagttttgt tattatctga agatattttt ggttgttgct tgttgatgtg gtgtgagctg   1920

tgagcagcgc tcttatgatt aatgatgctg tccaattgta gtgtagtatg atgtgattga   1980

tatgttcatc tattttgagc tgacagtacc gatatcgtag gatctggtgc caacttattc   2040

tccagctgct ttttttacc tatgttaatt ccaatccttt cttgcctctt ccagatccag   2100

ataatgcaga aactcattaa ctcagtgcaa aactatgcct ggggcagcaa aacggcgttg   2160

actgaacttt atggtatgga aaatccgtcc agccagccga tggccgagct gtggatgggc   2220

gcacatccga aaagcagttc acgagtgcag aatgccgccg gagatatcgt ttcactgcgt   2280

gatgtgattg agagtgataa atcgactctg ctcggagagg ccgttgccaa acgctttggc   2340

gaactgcctt tcctgttcaa agtattatgc gcagcacagc cactctccat tcaggttcat   2400

ccaaacaaac acaattctga aatcggtttt gccaaagaaa atgccgcagg tatcccgatg   2460

gatgccgccg agcgtaacta taaagatcct aaccacaagc cggagctggt ttttgcgctg   2520

acgcctttcc ttgcgatgaa cgcgtttcgt gaattttccg agattgtctc cctactccag   2580

ccggtcgcag gtgcacatcc ggcgattgct cactttttac aacagcctga tgccgaacgt   2640

ttaagcgaac tgttcgccag cctgttgaat atgcagggtg aagaaaaatc ccgcgcgctg   2700

gcgattttaa aatcggccct cgatagccag cagggtgaac cgtggcaaac gattcgttta   2760

atttctgaat ttacccgga agacagcggt ctgttctccc cgctattgct gaatgtggtg   2820

aaattgaacc ctggcgaagc gatgttcctg ttcgctgaaa caccgcacgc ttacctgcaa   2880

ggcgtggcgc tggaagtgat ggcaaactcc gataacgtgc tgcgtgcggg tctgacgcct   2940

aaatacattg atattccgga actggttgcc aatgtgaaat tcgaagccaa accggctaac   3000

cagttgttga cccagccggt gaaacaaggt gcagaactgg acttcccgat tccagtggat   3060

gattttgcct tctcgctgca tgaccttagt gataaagaaa ccaccattag ccagcagagt   3120

gccgccattt tgttctgcgt cgaaggcgat gcaacgttgt ggaaaggttc tcagcagtta   3180

cagcttaaac cgggtgaatc agcgtttatt gccgccaacg aatcaccggt gactgtcaaa   3240

ggccacggcc gtttagcgcg tgtttacaac aagctgtaag agcttactga aaaaattaac   3300

atctcttgct aagctgggag ctctagatcc ccgaatttcc ccgatcgttc aaacatttgg   3360

caataaagtt tcttaagatt gaatcctgtt gccggtcttg cgatgattat catataattt   3420

ctgttgaatt acgttaagca tgtaataatt aacatgtaat gcatgacgtt atttatgaga   3480

tgggttttta tgattagagt cccgcaatta tacatttaat acgcgataga aaacaaaata   3540

tagcgcgcaa actaggataa attatcgcgc gcggtgtcat ctatgttact agatcgggaa   3600

ttggcgagct cgaattaatt cagtacatta aaaacgtccg caatgtgtta ttaagttgtc   3660

taagcgtcaa tttgtttaca ccacaatata tcctgccacc agccagccaa cagctccccg   3720
```

```
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc ccccttttggg gtgtagaaca   4440
tccttttgcc agatgtggaa aagaagttcg ttgtcccatt gttggcaatg acgtagtagc   4500
cggcgaaagt gcgagaccca tttgcgctat atataagcct acgatttccg ttgcgactat   4560
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
cgacatcctt cggcgcgatt ttgccggtta ctgcgctgta ccaaatgcgg gacaacgtaa   5100
gcactacatt tcgctcatcg ccagcccagt cgggcggcga gttccatagc gttaaggttt   5160
catttagcgc ctcaaataga tcctgttcag gaaccggatc aaagagttcc tccgccgctg   5220
gacctaccaa ggcaacgcta tgttctcttg cttttgtcag caagatagcc agatcaatgt   5280
cgatcgtggc tggctcgaag atacctgcaa gaatgtcatt gcgctgccat tctccaaatt   5340
gcagttcgcg cttagctgga taacgccacg gaatgatgtc gtcgtgcaca acaatggtga   5400
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
```

```
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aacccttttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
```

```
gtcccccccc cccccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg ccctttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
```

```
ttaatcgcat agcgagtcga atcgaccgaa ggggaggggg agcgaagctt tgcgttctct  10860

aatcgcctcg tcaaggtaac taatcaatca cctcgtccta atcctcgaat ctctcgtggt  10920

gcccgtctaa tctcgcgatt ttgatgctcg tggtggaaag cgtaggagga tcccgtgcga  10980

gttagtctca atctctcagg gtttcgtgcg attttagggt gatccacctc ttaatcgagt  11040

tacggtttcg tgcgatttta gggtaatcct cttaatctct cattgattta gggtttcgtg  11100

agaatcgagg tagggatctg tgttatttat atcgatctaa tagatggatt ggtttttgaga  11160

ttgttctgtc agatggggat tgtttcgata tattacccta atgatgtgtc agatggggat  11220

tgtttcgata tattacccta atgatgtgtc agatggggat tgtttcgata tattacccta  11280

atgatggata ataagagtag ttcacagtta tgttttgatc ctgccacata gtttgagttt  11340

tgtgatcaga tttagtttta cttatttgtg cttagttcgg atgggattgt tctgatattg  11400

ttccaataga tgaatagctc gttaggttaa aatctttagg ttgagttagg cgacacatag  11460

tttatttcct ctggatttgg attggaattg tgttcttagt ttttttcccc tggatttgga  11520

ttggaattgt gtggagctgg gttagagaat tacatctgta tcgtgtacac ctacttgaac  11580

tgtagagctt gggttctaag gtcaatttaa tctgtattgt atctggctct ttgcctagtt  11640

gaactgtagt gctgatgttg tactgtgttt ttttacccgt tttatttgct ttactcgtgc  11700

aaatcaaatc tgtcagatgc tagaactagg tggctttatt ctgtgttctt acatagatct  11760

gttgtcctgt agttacttat gtcagttttg ttattatctg aagatatttt tggttgttgc  11820

ttgttgatgt ggtgtgagct gtgagcagcg ctcttatgat taatgatgct gtccaattgt  11880

agtgtagtat gatgtgattg atatgttcat ctattttgag ctgacagtac cgatatcgta  11940

ggatctggtg ccaacttatt ctccagctgc tttttttttac ctatgttaat tccaatcctt  12000

tcttgcctct tccagatcca gataatgcaa acaagcatta ctctgacatc caacgcatcc  12060

ggtacgtttg acggttacta ttacgaactc tggaaggata ctggcaatac aacaatgacg  12120

gtctacactc aaggtcgctt ttcctgccag tggtcgaaca tcaataacgc gttgtttagg  12180

accgggaaga aatacaacca gaattggcag tctcttggca caatccggat cacgtactct  12240

gcgacttaca acccaaacgg gaactcctac ttgtgtatct atggctggtc taccaaccca  12300

ttggtcgagt tctacatcgt tgagtcctgg gggaactgga gaccgcctgg tgccacgtcc  12360

ctgggccaag tgacaatcga tggcgggacc tacgacatct ataggacgac acgcgtcaac  12420

cagccttcca ttgtggggac agccacgttc gatcagtact ggagcgtgcg cacctctaag  12480

cggacttcag gaacagtgac cgtgaccgat cacttccgcg cctgggcgaa ccggggcctg  12540

aacctcggca caatagacca aattacattg tgcgtggagg gttaccaaag ctctggatca  12600

gccaacatca cccagaacac cttctctcag ggctcttctt ccggcagttc gggtggctca  12660

tccggctcca caacgactac tcgcatcgag tgtgagaaca tgtccttgtc cggaccctac  12720

gttagcagga tcaccaatcc ctttaatggt attgcgctgt acgccaacgg agacacagcc  12780

cgcgctaccg ttaacttccc cgcaagtcgc aactacaatt tccgcctgcg ggttgcggc  12840

aacaacaata atcttgcccg tgtggacctg aggatcgacg gacggaccgt cgggaccttt  12900

tattaccagg gcacataccc ctgggaggcc ccaattgaca atgtttatgt cagtgcgggg  12960

agtcatacag tcgaaatcac tgttactgcg gataacggca catgggacgt gtatgccgac  13020

tacctggtga tacagtgacc taggtccccg aatttccccg atcgttcaaa catttggcaa  13080

taaagtttct taagattgaa tcctgttgcc ggtcttgcga tgattatcat ataatttctg  13140

ttgaattacg ttaagcatgt aataattaac atgtaatgca tgacgttatt tatgagatgg  13200
```

gtttttatga ttagagtccc gcaattatac atttaatacg cgatagaaaa caaaatatag 13260
cgcgcaaact aggataaatt atcgcgcgcg gtgtcatcta tgttactaga tcgggaattg 13320
g 13321

<210> SEQ ID NO 64
<211> LENGTH: 13735
<212> TYPE: DNA
<213> ORGANISM: Artificial Sequence
<220> FEATURE:
<223> OTHER INFORMATION: Synthetic construct, vector pAG2048

<400> SEQUENCE: 64
aattcatact aaagcttgca tgcctgcagg tcgactctag taacggccgc cagtgtgctg 60
gaattaattc ggcttgtcga ccacccaacc ccatatcgac agaggatgtg aagaacaggt 120
aaatcacgca gaagaaccca tctctgatag cagctatcga ttagaacaac gaatccatat 180
tgggtccgtg ggaaatactt actgcacagg aagggggcga tctgacgagg ccccgccacc 240
ggcctcgacc cgaggccgag gccgacgaag cgccggcgag tacggcgccg cggcggcctc 300
tgcccgtgcc ctctgcgcgt gggagggaga ggccgcggtg gtgggggcgc gcgcgcgcgc 360
gcgcgcagct ggtgcggcgg cgcgggggtc agccgccgag ccggcggcga cggaggagca 420
gggcggcgtg gacgcgaact tccgatcggt tggtcagagt gcgcgagttg ggcttagcca 480
attaggtctc aacaatctat tgggccgtaa aattcatggg ccctggtttg tctaggccca 540
atatcccgtt catttcagcc cacaaatatt tccccagagg attattaagg cccacacgca 600
gcttatagca gatcaagtac gatgtttcct gatcgttgga tcggaaacgt acggtcttga 660
tcaggcatgc cgacttcgtc aaagagaggc ggcatgacct gacgcggagt tggttccggg 720
caccgtctgg atggtcgtac cgggaccgga cacgtgtcgc gcctccaact acatggacac 780
gtgtggtgct gccattgggc cgtacgcgtg gcggtgaccg caccggatgc tgcctcgcac 840
cgccttgccc acgctttata tagagaggtt ttctctccat taatcgcata gcgagtcgaa 900
tcgaccgaag ggagggggga gcgaagcttt gcgttctcta atcgcctcgt caaggtaact 960
aatcaatcac ctcgtcctaa tcctcgaatc tctcgtggtg cccgtctaat ctcgcgattt 1020
tgatgctcgt ggtggaaagc gtaggaggat cccgtgcgag ttagtctcaa tctctcaggg 1080
tttcgtgcga ttttagggtg atccacctct taatcgagtt acggtttcgt gcgattttag 1140
ggtaatcctc ttaatctctc attgatttag ggtttcgtga gaatcgaggt agggatctgt 1200
gttatttata tcgatctaat agatggattg gttttgagat tgttctgtca gatggggatt 1260
gtttcgatat attaccctaa tgatgtgtca gatggggatt gtttcgatat attaccctaa 1320
tgatgtgtca gatggggatt gtttcgatat attaccctaa tgatggataa taagagtagt 1380
tcacagttat gttttgatcc tgccacatag tttgagtttt gtgatcagat ttagttttac 1440
ttatttgtgc ttagttcgga tgggattgtt ctgatattgt tccaatagat gaatagctcg 1500
ttaggttaaa atctttaggt tgagttaggc gacacatagt ttatttcctc tggatttgga 1560
ttggaattgt gttcttagtt tttttcccct ggatttggat tggaattgtg tggagctggg 1620
ttagagaatt acatctgtat cgtgtacacc tacttgaact gtagagcttg ggttctaagg 1680
tcaatttaat ctgtattgta tctggctctt tgcctagttg aactgtagtg ctgatgttgt 1740
actgtgtttt tttacccgtt ttatttgctt tactcgtgca aatcaaatct gtcagatgct 1800
agaactaggt ggctttattc tgtgttctta catagatctg ttgtcctgta gttacttatg 1860

```
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct tttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt ttttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
```

```
cgactagatg ttgaggccta acattttatt agagagcagg ctagttgctt agatacatga   4320

tcttcaggcc gttatctgtc agggcaagcg aaaattggcc atttatgacg accaatgccc   4380

cgcagaagct cccatctttg ccgccataga cgccgcgccc ccctttttggg gtgtagaaca   4440

tcctttgcc agatgtggaa aagaagttcg ttgtcccatt gttggcaatg acgtagtagc   4500

cggcgaaagt gcgagaccca tttgcgctat atataagcct acgatttccg ttgcgactat   4560

tgtcgtaatt ggatgaacta ttatcgtagt tgctctcaga gttgtcgtaa tttgatggac   4620

tattgtcgta attgcttatg gagttgtcgt agttgcttgg agaaatgtcg tagttggatg   4680

gggagtagtc atagggaaga cgagcttcat ccactaaaac aattggcagg tcagcaagtg   4740

cctgccccga tgccatcgca agtacgaggc ttagaaccac cttcaacaga tcgcgcatag   4800

tcttccccag ctctctaacg cttgagttaa gccgcgccgc gaagcggcgt cggcttgaac   4860

gaattgttag acattatttg ccgactacct tggtgatctc gcctttcacg tagtgaacaa   4920

attcttccaa ctgatctgcg cgcgaggcca agcgatcttc ttgtccaaga taagcctgcc   4980

tagcttcaag tatgacgggc tgatactggg ccggcaggcg ctccattgcc cagtcggcag   5040

cgacatcctt cggcgcgatt ttgccggtta ctgcgctgta ccaaatgcgg gacaacgtaa   5100

gcactacatt tcgctcatcg ccagcccagt cgggcggcga gttccatagc gttaaggttt   5160

catttagcgc ctcaaataga tcctgttcag gaaccggatc aaagagttcc tccgccgctg   5220

gacctaccaa ggcaacgcta tgttctcttg cttttgtcag caagatagcc agatcaatgt   5280

cgatcgtggc tggctcgaag atacctgcaa gaatgtcatt gcgctgccat tctccaaatt   5340

gcagttcgcg cttagctgga taacgccacg gaatgatgtc gtcgtgcaca acaatggtga   5400

cttctacagc gcggagaatc tcgctctctc caggggaagc cgaagtttcc aaaaggtcgt   5460

tgatcaaagc tcgccgcgtt gtttcatcaa gccttacggt caccgtaacc agcaaatcaa   5520

tatcactgtg tggcttcagg ccgccatcca ctgcggagcc gtacaaatgt acggccagca   5580

acgtcggttc gagatggcgc tcgatgacgc caactacctc tgatagttga gtcgatactt   5640

cggcgatcac cgcttccctc atgatgttta actcctgaat taagccgcgc cgcgaagcgg   5700

tgtcggcttg aatgaattgt taggcgtcat cctgtgctcc cgagaaccag taccagtaca   5760

tcgctgtttc gttcgagact tgaggtctag ttttatacgt gaacaggtca atgccgccga   5820

gagtaaagcc acattttgcg tacaaattgc aggcaggtac attgttcgtt tgtgtctcta   5880

atcgtatgcc aaggagctgt ctgcttagtg cccacttttt cgcaaattcg atgagactgt   5940

gcgcgactcc tttgcctcgg tgcgtgtgcg acacaacaat gtgttcgata gaggctagat   6000

cgttccatgt tgagttgagt tcaatcttcc cgacaagctc ttggtcgatg aatgcgccat   6060

agcaagcaga gtcttcatca gagtcatcat ccgagatgta atccttccgg taggggctca   6120

cacttctggt agatagttca aagccttggt cggataggtg cacatcgaac acttcacgaa   6180

caatgaaatg gttctcagca tccaatgttt ccgccacctg ctcagggatc accgaaatct   6240

tcatatgacg cctaacgcct ggcacagcgg atcgcaaacc tggcgcggct tttggcacaa   6300

aaggcgtgac aggtttgcga atccgttgct gccacttgtt aacccttttg ccagatttgg   6360

taactataat ttatgttaga ggcgaagtct tgggtaaaaa ctggcctaaa attgctgggg   6420

atttcaggaa agtaaacatc accttccggc tcgatgtcta ttgtagatat atgtagtgta   6480

tctacttgat cgggggatct gctgcctcgc gcgtttcggt gatgacggtg aaaacctctg   6540

acacatgcag ctcccggaga cggtcacagc ttgtctgtaa gcggatgccg ggagcagaca   6600
```

```
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
```

```
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atcttttgg aatgctgctc    9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg ccctttaaa tatccgatta ttctaataaa cgctcttttc tcttaggttt    9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
```

```
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
gaactgtagt gctgatgttg tactgtgttt ttttacccgt tttatttgct ttactcgtgc  11700
aaatcaaatc tgtcagatgc tagaactagg tggctttatt ctgtgttctt acatagatct  11760
gttgtcctgt agttacttat gtcagttttg ttattatctg aagatatttt tggttgttgc  11820
ttgttgatgt ggtgtgagct gtgagcagcg ctcttatgat taatgatgct gtccaattgt  11880
agtgtagtat gatgtgattg atatgttcat ctattttgag ctgacagtac cgatatcgta  11940
ggatctggtg ccaacttatt ctccagctgc tttttttttac ctatgttaat tccaatcctt  12000
tcttgcctct tccagatcca gataatggcc cacgcccgcg tcctcctcct ggcgctcgcc  12060
gtcctggcca ccgccgccgt cgccgtcgcc tcctcctcct ccttcgccga ctccaacccg  12120
atccgcccgg tgaccgaccg cgccgcctcc accgcttacg actacaagca ggtgttgcgg  12180
gactcgctac tattctatga ggcccagaga tccggccggc tcccagccga ccagaaggtc  12240
acgtggagga aggatagcgc gctgaatgac cagggtgacc agggacaaga cttgaccggc  12300
ggctactttg acgctgggga cttcgtcaag ttcgggttcc ccatggctta taccgcaacc  12360
gtgctggcat ggggcctcat agattttgag gccggctaca gcagtgccgg ggccttggat  12420
gatggacgga aggctgtcaa atgggccacc gactatttca taaaggccca cacaagtcaa  12480
aatgagttct atggtcaggt cggccagggt gacgccgatc acgctttctg ggaagacca  12540
gaggatatga cgatggcgcg cccggcgtac aagatagaca cctcaaggcc tggctctgat  12600
ctggcaggcg agacagcggc tgctcttgcc gctgcttcaa tcgtgttccg gaacgtcgat  12660
ggcacttact caaataacct gttaacacac gctcgccagc tattcgactt cgcgaacaac  12720
taccggggaa agtatagtga ctctattact gacgcaagaa atttctacgc aagcgcagac  12780
tacagagacg agttggtttg ggctgctgcg tggttataca gagcgaccaa cgacaacacc  12840
tacctcaaca ctgctgagtc actgtacgat gagtttgggc tacagaactg gggggggggc  12900
ctgaactggg atagcaaggt gtctggcgtg caggtgttgt tggccaagct taccaataag  12960
caggcctaca aggacacggt gcagtcttac gtcaattacc taattaataa ccagcagaag  13020
actcccaagg gcctcctcta catcgacatg tggggcaccc ttcgccacgc tgccaacgcc  13080
gcattcatca tgctcgaagc cgccgagctg ggcttgtccg cctcctctta tagacagttc  13140
gcgcaaacgc aaatcgacta cgccctgggc gatggtggcc gctcctttgt gtgcgggttc  13200
gggagtaatc ctcctacgag accgcaccac agatcctcgt cgtgcccgcc agctcccgct  13260
acttgcgact ggaatacatt caactcacct gacccaaact accacgtcct ctctggggcc  13320
ctagtgggcg gacctgatca gaatgacaac tacgtcgatg accgttcaga ctatgttcac  13380
aacgaagtcg ccactgatta caacgcgggt ttccagtccg cgttagctgc tttggtggcc  13440
cttggttact gacctaggtc cccgaatttc cccgatcgtt caaacatttg gcaataaagt  13500
ttcttaagat tgaatcctgt tgccggtctt gcgatgatta tcatataatt tctgttgaat  13560
tacgttaagc atgtaataat taacatgtaa tgcatgacgt tatttatgag atgggttttt  13620
atgattagag tcccgcaatt atacatttaa tacgcgatag aaaacaaaat atagcgcgca  13680
aactaggata aattatcgcg cgcggtgtca tctatgttac tagatcggga attgg       13735
```

<210> SEQ ID NO 65
<211> LENGTH: 13753
<212> TYPE: DNA
<213> ORGANISM: Artificial Sequence
<220> FEATURE:
<223> OTHER INFORMATION: Synthetic construct vector pAG2049

<400> SEQUENCE: 65

```
aattcatact aaagcttgca tgcctgcagg tcgactctag taacggccgc cagtgtgctg      60
gaattaattc ggcttgtcga ccacccaacc ccatatcgac agaggatgtg aagaacaggt     120
aaatcacgca gaagaaccca tctctgatag cagctatcga ttagaacaac gaatccatat     180
tgggtccgtg ggaaatactt actgcacagg aaggggggcga tctgacgagg ccccgccacc     240
ggcctcgacc cgaggccgag gccgacgaag cgccggcgag tacggcgccg cggcggcctc     300
tgcccgtgcc ctctgcgcgt gggagggaga ggccgcggtg gtgggggcgc gcgcgcgcgc     360
gcgcgcagct ggtgcggcgg cgcgggggtc agccgccgag ccggcggcga cggaggagca     420
gggcggcgtg gacgcgaact tccgatcggt tggtcagagt gcgcgagttg ggcttagcca     480
attaggtctc aacaatctat tggccgtaa aattcatggg ccctggtttg tctaggccca     540
atatcccgtt catttcagcc cacaaatatt tccccagagg attattaagg cccacacgca     600
gcttatagca gatcaagtac gatgtttcct gatcgttgga tcggaaacgt acggtcttga     660
tcaggcatgc cgacttcgtc aaagagaggc ggcatgacct gacgcggagt tggttccggg     720
caccgtctgg atggtcgtac cgggaccgga cacgtgtcgc gcctccaact acatggacac     780
gtgtggtgct gccattgggc cgtacgcgtg gcggtgaccg caccggatgc tgcctcgcac     840
cgccttgccc acgctttata tagagaggtt ttctctccat taatcgcata gcgagtcgaa     900
tcgaccgaag gggagggggga gcgaagcttt gcgttctcta atcgcctcgt caaggtaact     960
aatcaatcac ctcgtcctaa tcctcgaatc tctcgtggtg cccgtctaat ctcgcgattt    1020
tgatgctcgt ggtggaaagc gtaggaggat cccgtgcgag ttagtctcaa tctctcaggg    1080
tttcgtgcga ttttagggtg atccacctct taatcgagtt acggtttcgt gcgattttag    1140
ggtaatcctc ttaatctctc attgatttag ggtttcgtga gaatcgaggt agggatctgt    1200
gttatttata tcgatctaat agatggattg gttttgagat tgttctgtca gatggggatt    1260
gtttcgatat attaccctaa tgatgtgtca gatggggatt gtttcgatat attaccctaa    1320
tgatgtgtca gatggggatt gtttcgatat attaccctaa tgatggataa taagagtagt    1380
tcacagttat gttttgatcc tgccacatag tttgagtttt gtgatcagat ttagttttac    1440
ttatttgtgc ttagttcgga tgggattgtt ctgatattgt tccaatagat gaatagctcg    1500
ttaggttaaa atctttaggt tgagttaggc gacacatagt ttatttcctc tggatttgga    1560
ttggaattgt gttcttagtt tttttcccct ggatttggat tggaattgtg tggagctggg    1620
ttagagaatt acatctgtat cgtgtacacc tacttgaact gtagagcttg ggttctaagg    1680
tcaatttaat ctgtattgta tctggctctt tgcctagttg aactgtagtg ctgatgttgt    1740
actgtgtttt tttacccgtt ttatttgctt tactcgtgca aatcaaatct gtcagatgct    1800
agaactaggt ggctttattc tgtgttctta catagatctg ttgtcctgta gttacttatg    1860
tcagttttgt tattatctga agatattttt ggttgttgct tgttgatgtg gtgtgagctg    1920
tgagcagcgc tcttatgatt aatgatgctg tccaattgta gtgtagtatg atgtgattga    1980
tatgttcatc tattttgagc tgacagtacc gatatcgtag gatctggtgc caacttattc    2040
```

```
tccagctgct ttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt tttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc ccttttgggg gtgtagaaca   4440
```

```
tccttttgcc agatgtggaa aagaagttcg ttgtcccatt gttggcaatg acgtagtagc   4500
cggcgaaagt gcgagaccca tttgcgctat atataagcct acgatttccg ttgcgactat   4560
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
cgacatcctt cggcgcgatt ttgccggtta ctgcgctgta ccaaatgcgg gacaacgtaa   5100
gcactacatt tcgctcatcg ccagcccagt cgggcggcga gttccatagc gttaaggttt   5160
catttagcgc ctcaaataga tcctgttcag gaaccggatc aaagagttcc tccgccgctg   5220
gacctaccaa ggcaacgcta tgttctcttg cttttgtcag caagatagcc agatcaatgt   5280
cgatcgtggc tggctcgaag atacctgcaa gaatgtcatt gcgctgccat tctccaaatt   5340
gcagttcgcg cttagctgga taacgccacg gaatgatgtc gtcgtgcaca acaatggtga   5400
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aaccctttttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
```

-continued

```
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
```

```
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg cccttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
```

```
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
gaactgtagt gctgatgttg tactgtgttt ttttacccgt tttatttgct ttactcgtgc  11700
aaatcaaatc tgtcagatgc tagaactagg tggctttatt ctgtgttctt acatagatct  11760
gttgtcctgt agttacttat gtcagttttg ttattatctg aagatatttt tggttgttgc  11820
ttgttgatgt ggtgtgagct gtgagcagcg ctcttatgat taatgatgct gtccaattgt  11880
agtgtagtat gatgtgattg atatgttcat ctattttgag ctgacagtac cgatatcgta  11940
ggatctggtg ccaacttatt ctccagctgc ttttttttac ctatgttaat tccaatcctt  12000
tcttgcctct tccagatcca gataatggcc cacgcccgcg tcctcctcct ggcgctcgcc  12060
gtcctggcca ccgccgccgt cgccgtcgcc tcctcctcct ccttcgccga ctccaacccg  12120
atccgcccgg tgaccgaccg cgccgcctcc accgcttacg actacaagca ggtgttgcgg  12180
gactcgctac tattctatga ggcccagaga tccggccggc tcccagccga ccagaaggtc  12240
acgtggagga aggatagcgc gctgaatgac cagggtgacc agggacaaga cttgaccggc  12300
ggctactttg acgctgggga cttcgtcaag ttcgggttcc ccatggctta taccgcaacc  12360
gtgctggcat ggggcctcat agattttgag gccggctaca gcagtgccgg ggccttggat  12420
gatggacgga aggctgtcaa atgggccacc gactatttca taaaggccca cacaagtcaa  12480
aatgagttct atggtcaggt cggccagggt gacgccgatc acgctttctg ggaagaccca  12540
gaggatatga cgatggcgcg cccggcgtac aagatagaca cctcaaggcc tggctctgat  12600
ctggcaggcg agacagcggc tgctcttgcc gctgcttcaa tcgtgttccg gaacgtcgat  12660
ggcacttact caaataacct gttaacacac gctcgccagc tattcgactt cgcgaacaac  12720
taccggggaa agtatagtga ctctattact gacgcaagaa atttctacgc aagcgcagac  12780
tacagagacg agttggtttg ggctgctgcg tggttataca gagcgaccaa cgacaacacc  12840
tacctcaaca ctgctgagtc actgtacgat gagtttgggc tacagaactg gggggggggc  12900
ctgaactggg atagcaaggt gtctggcgtg caggtgttgt tggccaagct taccaataag  12960
caggcctaca aggacacggt gcagtcttac gtcaattacc taattaataa ccagcagaag  13020
actcccaagg gcctcctcta catcgacatg tggggcaccc ttcgccacgc tgccaacgcc  13080
gcattcatca tgctcgaagc cgccgagctg ggcttgtccg cctcctctta tagacagttc  13140
gcgcaaacgc aaatcgacta cgccctgggc gatggtggcc gctcctttgt gtgcgggttc  13200
gggagtaatc ctcctacgag accgcaccac agatcctcgt cgtgcccgcc agctcccgct  13260
acttgcgact ggaatacatt caactcacct gacccaaact accacgtcct ctctggggcc  13320
ctagtgggcg gacctgatca gaatgacaac tacgtcgatg accgttcaga ctatgttcac  13380
aacgaagtcg ccactgatta caacgcgggt ttccagtccg cgttagctgc tttggtggcc  13440
cttggttaca gcgagaagga cgagctgtga cctaggtccc cgaatttccc cgatcgttca  13500
aacatttggc aataaagttt cttaagattg aatcctgttg ccggtcttgc gatgattatc  13560
atataatttc tgttgaatta cgttaagcat gtaataatta acatgtaatg catgacgtta  13620
tttatgagat gggtttttat gattagagtc ccgcaattat acatttaata cgcgatagaa  13680
aacaaaatat agcgcgcaaa ctaggataaa ttatcgcgcg cggtgtcatc tatgttacta  13740
gatcgggaat tgg                                                     13753
```

<210> SEQ ID NO 66
<211> LENGTH: 13024

<212> TYPE: DNA
<213> ORGANISM: Artificial Sequence
<220> FEATURE:
<223> OTHER INFORMATION: Synthetic construct, vector pAG2063

<400> SEQUENCE: 66

```
aattcatact aaagcttgca tgcctgcagg tcgactctag taacggccgc cagtgtgctg     60
gaattaattc ggcttgtcga ccacccaacc ccatatcgac agaggatgtg aagaacaggt    120
aaatcacgca gaagaaccca tctctgatag cagctatcga ttagaacaac gaatccatat    180
tgggtccgtg ggaaatactt actgcacagg aagggggcga tctgacgagg ccccgccacc    240
ggcctcgacc cgaggccgag gccgacgaag cgccggcgag tacggcgccg cggcggcctc    300
tgcccgtgcc ctctgcgcgt gggagggaga ggccgcggtg gtgggggcgc gcgcgcgcgc    360
gcgcgcagct ggtgcggcgg cgcgggggtc agccgccgag ccggcggcga cggaggagca    420
gggcggcgtg gacgcgaact tccgatcggt tggtcagagt gcgcgagttg ggcttagcca    480
attaggtctc aacaatctat tggccgtaa aattcatggg ccctggtttg tctaggccca    540
atatcccgtt catttcagcc cacaaatatt tccccagagg attattaagg cccacacgca    600
gcttatagca gatcaagtac gatgtttcct gatcgttgga tcggaaacgt acggtcttga    660
tcaggcatgc cgacttcgtc aaagagaggc ggcatgacct gacgcggagt tggttccggg    720
caccgtctgg atggtcgtac cgggaccgga cacgtgtcgc gcctccaact acatggacac    780
gtgtggtgct gccattgggc cgtacgcgtg gcggtgaccg caccggatgc tgcctcgcac    840
cgccttgccc acgctttata tagagaggtt ttctctccat taatcgcata gcgagtcgaa    900
tcgaccgaag gggagggga gcgaagcttt gcgttctcta atcgcctcgt caaggtaact    960
aatcaatcac ctcgtcctaa tcctcgaatc tctcgtggtg cccgtctaat ctcgcgattt   1020
tgatgctcgt ggtggaaagc gtaggaggat cccgtgcgag ttagtctcaa tctctcaggg   1080
tttcgtgcga ttttagggtg atccacctct taatcgagtt acggtttcgt gcgattttag   1140
ggtaatcctc ttaatctctc attgatttag ggtttcgtga gaatcgaggt agggatctgt   1200
gttatttata tcgatctaat agatggattg gttttgagat tgttctgtca gatggggatt   1260
gtttcgatat attaccctaa tgatgtgtca gatggggatt gtttcgatat attaccctaa   1320
tgatgtgtca gatggggatt gtttcgatat attaccctaa tgatggataa taagagtagt   1380
tcacagttat gttttgatcc tgccacatag tttgagtttt gtgatcagat ttagttttac   1440
ttatttgtgc ttagttcgga tgggattgtt ctgatattgt tccaatagat gaatagctcg   1500
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct ttttttacc tatgttaatt ccaatccttt cttgcctctt ccagatccag   2100
ataatgcaga aactcattaa ctcagtgcaa aactatgcct ggggcagcaa aacggcgttg   2160
```

```
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt ttttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc ccccttttggg gtgtagaaca   4440
tccttttgcc agatgtggaa aagaagttcg ttgtcccatt gttggcaatg acgtagtagc   4500
cggcgaaagt gcgagaccca tttgcgctat atataagcct acgatttccg ttgcgactat   4560
```

```
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
cgacatcctt cggcgcgatt ttgccggtta ctgcgctgta ccaaatgcgg gacaacgtaa   5100
gcactacatt tcgctcatcg ccagcccagt cgggcggcga gttccatagc gttaaggttt   5160
catttagcgc ctcaaataga tcctgttcag gaaccggatc aaagagttcc tccgccgctg   5220
gacctaccaa ggcaacgcta tgttctcttg cttttgtcag caagatagcc agatcaatgt   5280
cgatcgtggc tggctcgaag atacctgcaa gaatgtcatt gcgctgccat tctccaaatt   5340
gcagttcgcg cttagctgga taacgccacg gaatgatgtc gtcgtgcaca acaatggtga   5400
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aacccttttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
```

-continued

```
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
```

```
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atcttttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg cccttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
```

gaactgtagt gctgatgttg tactgtgttt ttttacccgt tttatttgct ttactcgtgc 11700
aaatcaaatc tgtcagatgc tagaactagg tggctttatt ctgtgttctt acatagatct 11760
gttgtcctgt agttacttat gtcagttttg ttattatctg aagatatttt tggttgttgc 11820
ttgttgatgt ggtgtgagct gtgagcagcg ctcttatgat taatgatgct gtccaattgt 11880
agtgtagtat gatgtgattg atatgttcat ctattttgag ctgacagtac cgatatcgta 11940
ggatctggtg ccaacttatt ctccagctgc ttttttttac ctatgttaat tccaatcctt 12000
tcttgcctct tccagatcca gataatggcg aacaaacatt tgtccctctc cctcttcctc 12060
gtcctccttg gcctgtcggc cagcttggcc tccgggcaag tcttcccagc tggaaacgca 12120
acggaattgg agaaaagaca aaccacccct aactctgagg gctggcatga cggatactac 12180
tactcttggt ggagcgatgg tggtgcacag gccacctata caaacctcga aggcggcact 12240
tatgagattt catggggtga cggtggcaac cttgtcggcg gaaaggggtg gaaccccgga 12300
cttaacgcca gggcaatcca cttcgaaggg gtgtaccagc ccaatggcaa ctcatacctg 12360
gccgtctacg ggtggacgcg caatccgctg gttgagtact atatcgtgga gaatttcgga 12420
acttatgacc ctagctccgg tgccacggac ctcgggacag tcgagtgtga cggaagcatc 12480
tacaggctgg gtaaaactac ccgcgttaat gctccatcga tcgacggcac gcaaacattt 12540
gatcaatact ggtccgtgcg gcaggataag aggacaagcg gcacagttca gacgggttgc 12600
cactttgatg cctgggcaag agcggggctc aatgtgaatg ggaccacta ctatcagatt 12660 gtggcgaccg agggctattt ctccagtggc tatgcgcgta taaccgtcgc tgatgttgga 12720
agcgagaagg acgagctgtg acctaggtcc ccgaatttcc ccgatcgttc aaacatttgg 12780
caataaagtt tcttaagatt gaatcctgtt gccggtcttg cgatgattat catataattt 12840
ctgttgaatt acgttaagca tgtaataatt aacatgtaat gcatgacgtt atttatgaga 12900
tgggttttta tgattagagt cccgcaatta tacatttaat acgcgataga aaacaaaata 12960
tagcgcgcaa actaggataa attatcgcgc gcggtgtcat ctatgttact agatcgggaa 13020
ttgg 13024

<210> SEQ ID NO 67
<211> LENGTH: 14917
<212> TYPE: DNA
<213> ORGANISM: Artificial Sequence
<220> FEATURE:
<223> OTHER INFORMATION: Synthetic construct, vector pAG2069

<400> SEQUENCE: 67
aattcatact aaagcttgca tgcctgcagg tcgactctag taacggccgc cagtgtgctg 60
gaattaattc ggcttgtcga ccacccaacc ccatatcgac agaggatgtg aagaacaggt 120
aaatcacgca gaagaaccca tctctgatag cagctatcga ttagaacaac gaatccatat 180
tgggtccgtg ggaaatactt actgcacagg aagggggcga tctgacgagg ccccgccacc 240
ggcctcgacc cgaggccgag gccgacgaag cgccggcgag tacggcgccg cggcggcctc 300
tgcccgtgcc ctctgcgcgt gggagggaga ggccgcggtg gtgggggcgc gcgcgcgcgc 360
gcgcgcagct ggtgcggcgg cgcgggggtc agccgccgag ccggcggcga cggaggagca 420
gggcggcgtg gacgcgaact tccgatcggt tggtcagagt gcgcgagttg ggcttagcca 480
attaggtctc aacaatctat tgggccgtaa aattcatggg ccctggtttg tctaggccca 540
atatcccgtt catttcagcc cacaaatatt tccccagagg attattaagg cccacacgca 600
gcttatagca gatcaagtac gatgtttcct gatcgttgga tcggaaacgt acggtcttga 660

```
tcaggcatgc cgacttcgtc aaagagaggc ggcatgacct gacgcggagt tggttccggg    720
caccgtctgg atggtcgtac cgggaccgga cacgtgtcgc gcctccaact acatggacac    780
gtgtggtgct gccattgggc cgtacgcgtg gcggtgaccg caccggatgc tgcctcgcac    840
cgccttgccc acgctttata tagagaggtt ttctctccat taatcgcata gcgagtcgaa    900
tcgaccgaag ggagggggga gcgaagcttt gcgttctcta atcgcctcgt caaggtaact    960
aatcaatcac ctcgtcctaa tcctcgaatc tctcgtggtg cccgtctaat ctcgcgattt   1020
tgatgctcgt ggtggaaagc gtaggaggat cccgtgcgag ttagtctcaa tctctcaggg   1080
tttcgtgcga ttttagggtg atccacctct taatcgagtt acggtttcgt gcgattttag   1140
ggtaatcctc ttaatctctc attgatttag ggtttcgtga gaatcgaggt agggatctgt   1200
gttatttata tcgatctaat agatggattg gttttgagat tgttctgtca gatggggatt   1260
gtttcgatat attaccctaa tgatgtgtca gatggggatt gtttcgatat attaccctaa   1320
tgatgtgtca gatggggatt gtttcgatat attaccctaa tgatggataa taagagtagt   1380
tcacagttat gttttgatcc tgccacatag tttgagtttt gtgatcagat ttagttttac   1440
ttatttgtgc ttagttcgga tgggattgtt ctgatattgt tccaatagat gaatagctcg   1500
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct ttttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt tttgcgctg    2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
```

```
cagttgttga cccagccggt gaaacaaggt gcagaactgg acttcccgat tccagtggat   3060

gattttgcct tctcgctgca tgaccttagt gataaagaaa ccaccattag ccagcagagt   3120

gccgccattt tgttctgcgt cgaaggcgat gcaacgttgt ggaaaggttc tcagcagtta   3180

cagcttaaac cgggtgaatc agcgtttatt gccgccaacg aatcaccggt gactgtcaaa   3240

ggccacggcc gtttagcgcg tgtttacaac aagctgtaag agcttactga aaaaattaac   3300

atctcttgct aagctgggag ctctagatcc ccgaatttcc ccgatcgttc aaacatttgg   3360

caataaagtt tcttaagatt gaatcctgtt gccggtcttg cgatgattat catataattt   3420

ctgttgaatt acgttaagca tgtaataatt aacatgtaat gcatgacgtt atttatgaga   3480

tgggttttta tgattagagt cccgcaatta tacatttaat acgcgataga aaacaaaata   3540

tagcgcgcaa actaggataa attatcgcgc gcggtgtcat ctatgttact agatcgggaa   3600

ttggcgagct cgaattaatt cagtacatta aaaacgtccg caatgtgtta ttaagttgtc   3660

taagcgtcaa tttgtttaca ccacaatata tcctgccacc agccagccaa cagctccccg   3720

accggcagct cggcacaaaa tcaccactcg atacaggcag cccatcagtc cgggacggcg   3780

tcagcgggag agccgttgta aggcggcaga ctttgctcat gttaccgatg ctattcggaa   3840

gaacggcaac taagctgccg ggtttgaaac acggatgatc tcgcggaggg tagcatgttg   3900

attgtaacga tgacagagcg ttgctgcctg tgatcaaata tcatctccct cgcagagatc   3960

cgaattatca gccttcttat tcatttctcg cttaaccgtg acaggctgtc gatcttgaga   4020

actatgccga cataatagga aatcgctgga taaagccgct gaggaagctg agtggcgcta   4080

tttctttaga agtgaacgtt gacgatcgtc gaccgtaccc cgatgaatta attcggacgt   4140

acgttctgaa cacagctgga tacttacttg ggcgattgtc atacatgaca tcaacaatgt   4200

acccgtttgt gtaaccgtct cttggaggtt cgtatgacac tagtggttcc cctcagcttg   4260

cgactagatg ttgaggccta acattttatt agagagcagg ctagttgctt agatacatga   4320

tcttcaggcc gttatctgtc agggcaagcg aaaattggcc atttatgacg accaatgccc   4380

cgcagaagct cccatctttg ccgccataga cgccgcgccc ccttttgggg gtgtagaaca   4440

tccttttgcc agatgtggaa aagaagttcg ttgtcccatt gttggcaatg acgtagtagc   4500

cggcgaaagt gcgagaccca tttgcgctat atataagcct acgatttccg ttgcgactat   4560

tgtcgtaatt ggatgaacta ttatcgtagt tgctctcaga gttgtcgtaa tttgatggac   4620

tattgtcgta attgcttatg gagttgtcgt agttgcttgg agaaatgtcg tagttggatg   4680

gggagtagtc atagggaaga cgagcttcat ccactaaaac aattggcagg tcagcaagtg   4740

cctgccccga tgccatcgca agtacgaggc ttagaaccac cttcaacaga tcgcgcatag   4800

tcttccccag ctctctaacg cttgagttaa gccgcgccgc gaagcggcgt cggcttgaac   4860

gaattgttag acattatttg ccgactacct tggtgatctc gcctttcacg tagtgaacaa   4920

attcttccaa ctgatctgcg cgcgaggcca agcgatcttc ttgtccaaga taagcctgcc   4980

tagcttcaag tatgacgggc tgatactggg ccggcaggcg ctccattgcc cagtcggcag   5040

cgacatcctt cggcgcgatt ttgccggtta ctgcgctgta ccaaatgcgg gacaacgtaa   5100

gcactacatt tcgctcatcg ccagcccagt cgggcggcga gttccatagc gttaaggttt   5160

catttagcgc ctcaaataga tcctgttcag gaaccggatc aaagagttcc tccgccgctg   5220

gacctaccaa ggcaacgcta tgttctcttg cttttgtcag caagatagcc agatcaatgt   5280

cgatcgtggc tggctcgaag atacctgcaa gaatgtcatt gcgctgccat tctccaaatt   5340

gcagttcgcg cttagctgga taacgccacg gaatgatgtc gtcgtgcaca acaatggtga   5400
```

```
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aaccctttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
```

```
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg ccctttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
```

```
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
gaactgtagt gctgatgttg tactgtgttt ttttacccgt tttatttgct ttactcgtgc  11700
aaatcaaatc tgtcagatgc tagaactagg tggctttatt ctgtgttctt acatagatct  11760
gttgtcctgt agttacttat gtcagttttg ttattatctg aagatatttt tggttgttgc  11820
ttgttgatgt ggtgtgagct gtgagcagcg ctcttatgat taatgatgct gtccaattgt  11880
agtgtagtat gatgtgattg atatgttcat ctattttgag ctgacagtac cgatatcgta  11940
ggatctggtg ccaacttatt ctccagctgc ttttttttac ctatgttaat tccaatcctt  12000
tcttgcctct tccagatcca gataatgctg gaggacaagt ctcccaaact gcctgattat  12060
aagaacgacc ttctgtacga acgcacattc gacgaggggc tctgcttccc gtggcacacg  12120
tgcgaagatt caggagggaa atgcgatttt gccgtggtcg acgttccagg cgagcctggg  12180
aacaaggcgt tcaggctcac tgttatcgat aagggtcaga acaagtggtc ggtccaaatg  12240
agacaccggg gtatcacgtt ggagcagggg cacacataca ccgttcggtt tactatctgg  12300
agcgacaaga gctgccgcgt gtatgccaaa atcggccaaa tgggtgaacc ctacacggag  12360
tactggaaca ataactggaa tccgttcaac ctcactccgg ggcagaaatt gacggtggaa  12420
cagaacttta ctatgaatta tcccacggac gacacgtgtg agtttacctt ccacttggga  12480
```

ggggaactgg cagccgggac cccttactac gtgtacctcg acgacgtttc tctttacgat 12540
ccccgctttg tcaagccagt ggaatacgtc ctgcctcaac cggatgtcag ggttaatcaa 12600
gttggatacc tccctttttgc taagaaatat gctactgtcg tgtcatcgag cacgtcccca 12660
ttgaagtggc aacttctgaa tagtgcaaac caagttgtct tggagggcaa tacaatcccc 12720
aagggactgg acaaagattc acaagactac gttcattgga tcgatttctc gaactttaag 12780
accgaaggca aggggtacta tttcaagttg cccactgtga actccgatac taactactcc 12840
cacccgtttg atatttctgc agatatctat tcaaagatga agttcgacgc gctcgctttc 12900
ttttaccata aaaggtcggg aataccaatc gagatgccct acgccggggg agagcagtgg 12960
acaaggcccg cagggcacat tggtgtcgcg ccgaacaagg gcgacacgaa tgtgccaact 13020
tggccccagg atgacgaata tgctggacgc ccccagaaat actatacgaa agacgtgacc 13080
ggcgggtggt acgatgccgg tgaccacggc aagtacgtcg tgaacggggg tatcgcagtt 13140
tggaccctta tgaatatgta cgagagagca aagattagag gaatcgctaa ccagggtgcc 13200
tacaaagatg gaggaatgaa tatcccggaa aggaataacg gctatcctga tattctggac 13260
gaggccagat gggagatcga attttttaag aagatgcaag tcactgagaa agaagatccg 13320
tcgattgcag gtatggtgca ccacaagatc cacgatttca ggtggacggc gctcggaatg 13380
ttgcctcacg aggaccccca gccacgctac cttcggcccg tcagcacagc ggcaaccctg 13440
aatttcgcag cgaccctcgc tcagtctgcc agattgtgga aggattacga cccgactttt 13500
gcagcggact gccttgagaa agctgaaatt gcctggcaag cagcactcaa acacccggac 13560
atctacgctg agtacacgcc aggaagcggt gggccgggtg gaggtcctta taatgacgat 13620
tatgtcgggg acgagttcta ctgggccgct tgtgaactct atgtgacaac cggtaaggat 13680
gagtacaaga attacttgat gaatagtccg cactatctgg aaatgccagc gaagatgggc 13740
gagaacggag gggctaacgg cgaggacaac ggtctctggg gctgctttac ttggggaacg 13800
acacaggggt tgggtacaat taccccttgcc ctcgttgaaa acggcctccc ttcggcggat 13860
attcaaaagg cccgcaacaa tatcgctaaa gccgcagata agtggcttga gaatattgaa 13920
gaacaaggtt accgcctgcc tatcaaacaa gcggaggatg aacggggcgg atacccgtgg 13980
ggtagtaatt ctttcattct caaccagatg atcgtcatgg gctacgctta cgacttcacg 14040
ggaaacagca agtatcttga cgggatgcag gacggcatgt cctacctgct cggtagaaac 14100
ggacttgatc aatcgtacgt tactgggtac ggggagaggc cacttcagaa cccccacgac 14160
cgcttttgga cccctcaaac ttcgaagaaa ttcccggccc cacccccctgg tattatcgca 14220
ggcgggccga atagccggtt tgaagatcca acgatcactg cagcggttaa gaaggataca 14280
cccccgcaga agtgctatat tgaccacacc gattcctggt ctactaacga gatcacgatt 14340
aattggaacg ccccccttcgc gtgggtcaca gcgtatctgg acgaaattga cttgattacc 14400
ccacccggcg gagtggaccc tgaagagccg gaagttatct acggtgattg taacggcgac 14460
ggaaaggtta attcgaccga tgctgtggcc cttaaaaggt atatcctccg cagcggtatc 14520
tcgatcaaca cggacaacgc ggacgttaat gcagatggtc gcgtgaatag cactgacctc 14580
gctattttga agcgctatat tttgaaggag atcgatgttc ttcctcacaa gtgacctagg 14640
tccccgaatt tccccgatcg ttcaaacatt tggcaataaa gtttcttaag attgaatcct 14700
gttgccggtc ttgcgatgat tatcatataa tttctgttga attacgttaa gcatgtaata 14760
attaacatgt aatgcatgac gttatttatg agatgggttt ttatgattag agtcccgcaa 14820
ttatacattt aatacgcgat agaaaacaaa atatagcgcg caaactagga taaattatcg 14880
cgcgcggtgt catctatgtt actagatcgg gaattgg 14917

<210> SEQ ID NO 68
<211> LENGTH: 16551
<212> TYPE: DNA
<213> ORGANISM: Artificial Sequence
<220> FEATURE:
<223> OTHER INFORMATION: Synthetic construct, vector pAG2091

<400> SEQUENCE: 68
catggaatca aggtaccgtc gactctagta acggccgcca gtgtgctgga attaattcgg 60
cttgtcgacc acccaacccc atatcgacag aggatgtgaa gaacaggtaa atcacgcaga 120
agaacccatc tctgatagca gctatcgatt agaacaacga atccatattg ggtccgtggg 180
aaatacttac tgcacaggaa gggggcgatc tgacgaggcc ccgccaccgg cctcgacccg 240
aggccgaggc cgacgaagcg ccggcgagta cggcgccgcg gcggcctctg cccgtgccct 300
ctgcgcgtgg gagggagagg ccgcggtggt gggggcgcgc gcgcgcgcgc gcgcagctgg 360
tgcggcggcg cgggggtcag ccgccgagcc ggcggcgacg gaggagcagg gcggcgtgga 420
cgcgaacttc cgatcggttg gtcagagtgc gcgagttggg cttagccaat taggtctcaa 480
caatctattg ggccgtaaaa ttcatgggcc ctggtttgtc taggcccaat atcccgttca 540
tttcagccca caaatatttc cccagaggat tattaaggcc cacacgcagc ttatagcaga 600
tcaagtacga tgtttcctga tcgttggatc ggaaacgtac ggtcttgatc aggcatgccg 660
acttcgtcaa agagaggcgg catgacctga cgcggagttg gttccgggca ccgtctggat 720
ggtcgtaccg ggaccggaca cgtgtcgcgc ctccaactac atggacacgt gtggtgctgc 780
cattgggccg tacgcgtggc ggtgaccgca ccggatgctg cctcgcaccg ccttgcccac 840
gctttatata gagaggtttt ctctccatta atcgcatagc gagtcgaatc gaccgaaggg 900
gagggggagc gaagctttgc gttctctaat cgcctcgtca aggtaactaa tcaatcacct 960
cgtcctaatc ctcgaatctc tcgtggtgcc cgtctaatct cgcgattttg atgctcgtgg 1020
tggaaagcgt aggaggatcc cgtgcgagtt agtctcaatc tctcagggtt tcgtgcgatt 1080
ttagggtgat ccacctctta atcgagttac ggtttcgtgc gattttaggg taatcctctt 1140
aatctctcat tgatttaggg tttcgtgaga atcgaggtag ggatctgtgt tatttatatc 1200
gatctaatag atggattggt tttgagattg ttctgtcaga tggggattgt ttcgatatat 1260
taccctaatg atgtgtcaga tggggattgt ttcgatatat taccctaatg atgtgtcaga 1320
tggggattgt ttcgatatat taccctaatg atggataata agagtagttc acagttatgt 1380
tttgatcctg ccacatagtt tgagttttgt gatcagattt agttttactt atttgtgctt 1440
agttcggatg ggattgttct gatattgttc caatagatga atagctcgtt aggttaaaat 1500
ctttaggttg agttaggcga cacatagttt atttcctctg gatttggatt ggaattgtgt 1560
tcttagtttt tttcccctgg atttggattg gaattgtgtg gagctgggtt agagaattac 1620
atctgtatcg tgtacaccta cttgaactgt agagcttggg ttctaaggtc aatttaatct 1680
gtattgtatc tggctctttg cctagttgaa ctgtagtgct gatgttgtac tgtgtttttt 1740
tacccgtttt atttgcttta ctcgtgcaaa tcaaatctgt cagatgctag aactaggtgg 1800
ctttattctg tgttcttaca tagatctgtt gtcctgtagt tacttatgtc agttttgtta 1860
ttatctgaag atatttttgg ttgttgcttg ttgatgtggt gtgagctgtg agcagcgctc 1920
ttatgattaa tgatgctgtc caattgtagt gtagtatgat gtgattgata tgttcatcta 1980

-continued

```
ttttgagctg acagtaccga tatcgtagga tctggtgcca acttattctc cagctgcttt   2040
tttttaccta tgttaattcc aatcctttct tgcctcttcc agatccagat aatggcgaac   2100
aaacatttgt ccctctccct cttcctcgtc ctccttggcc tgtcggccag cttggcctcc   2160
gggcaacaaa caagcattac tctgacatcc aacgcatccg gtacgtttga cggttactat   2220
tacgaactct ggaaggatac tggcaataca acaatgacgg tctacactca aggtcgcttt   2280
tcctgccagt ggtcgaacat caataacgcg ttgtttagga ccgggaagaa atacaaccag   2340
aattggcagt ctcttggcac aatccggatc acgtactctg cgacttacaa cccaaacggg   2400
aactcctact tgtgtatcta tggctggtct accaacccat tggtcgagtt ctacatcgtt   2460
gagtcctggg ggaactggag accgcctggt gccacgtccc tgggccaagt gacaatcgat   2520
ggcgggacct acgacatcta taggacgaca cgcgtcaacc agccttccat tgtggggaca   2580
gccacgttcg atcagtactg gagcgtgcgc acctctaagc ggacttcagg aacagtgacc   2640
gtgaccgatc acttccgcgc ctgggcgaac cggggcctga acctcggcac aatagaccaa   2700
attacattgt gcgtggaggg ttaccaaagc tctggatcag ccaacatcac ccagaacacc   2760
ttctctcagg gctcttcttc cggcagttcg ggtggctcat ccggctccac aacgactact   2820
cgcatcgagt gtgagaacat gtccttgtcc ggaccctacg ttagcaggat caccaatccc   2880
tttaatggta ttgcgctgta cgccaacgga gacacagccc gcgctaccgt taacttcccc   2940
gcaagtcgca actacaattt ccgcctgcgg ggttgcggca acaacaataa tcttgcccgt   3000
gtggacctga ggatcgacgg acggaccgtc gggacctttt attaccaggg cacatacccc   3060
tgggaggccc caattgacaa tgtttatgtc agtgcgggga gtcatacagt cgaaatcact   3120
gttactgcgg ataacggcac atgggacgtg tatgccgact acctggtgat acagtgacct   3180
aggtccccga atttccccga tcgttcaaac atttggcaat aaagtttctt aagattgaat   3240
cctgttgccg gtcttgcgat gattatcata taatttctgt tgaattacgt taagcatgta   3300
ataattaaca tgtaatgcat gacgttattt atgagatggg tttttatgat tagagtcccg   3360
caattataca tttaatacgc gatagaaaac aaaatatagc gcgcaaacta ggataaatta   3420
tcgcgcgcgg tgtcatctat gttactagat cgggaattgg aattcatact aaagcttgca   3480
tgcctgcagg tcgactctag taacggccgc cagtgtgctg gaattaattc ggcttgtcga   3540
ccacccaacc ccatatcgac agaggatgtg aagaacaggt aaatcacgca gaagaaccca   3600
tctctgatag cagctatcga ttagaacaac gaatccatat tgggtccgtg ggaaatactt   3660
actgcacagg aagggggcga tctgacgagg ccccgccacc ggcctcgacc cgaggccgag   3720
gccgacgaag cgccggcgag tacggcgccg cggcggcctc tgcccgtgcc ctctgcgcgt   3780
gggagggaga ggccgcggtg gtgggggcgc gcgcgcgcgc gcgcgcagct ggtgcggcgg   3840
cgcgggggtc agccgccgag ccggcggcga cggaggagca gggcggcgtg gacgcgaact   3900
tccgatcggt tggtcagagt gcgcgagttg ggcttagcca attaggtctc aacaatctat   3960
tgggccgtaa aattcatggg ccctggtttg tctaggccca atatcccgtt catttcagcc   4020
cacaaatatt tccccagagg attattaagg cccacacgca gcttatagca gatcaagtac   4080
gatgtttcct gatcgttgga tcggaaacgt acggtcttga tcaggcatgc cgacttcgtc   4140
aaagagaggc ggcatgacct gacgcggagt tggttccggg caccgtctgg atggtcgtac   4200
cgggaccgga cacgtgtcgc gcctccaact acatggacac gtgtggtgct gccattgggc   4260
cgtacgcgtg gcggtgaccg caccggatgc tgcctcgcac cgccttgccc acgctttata   4320
tagagaggtt ttctctccat taatcgcata gcgagtcgaa tcgaccgaag ggagggggga   4380
```

```
gcgaagcttt gcgttctcta atcgcctcgt caaggtaact aatcaatcac ctcgtcctaa   4440
tcctcgaatc tctcgtggtg cccgtctaat ctcgcgattt tgatgctcgt ggtggaaagc   4500
gtaggaggat cccgtgcgag ttagtctcaa tctctcaggg tttcgtgcga ttttagggtg   4560
atccacctct taatcgagtt acggtttcgt gcgattttag ggtaatcctc ttaatctctc   4620
attgatttag ggtttcgtga gaatcgaggt agggatctgt gttatttata tcgatctaat   4680
agatggattg gttttgagat tgttctgtca gatggggatt gtttcgatat attaccctaa   4740
tgatgtgtca gatggggatt gtttcgatat attaccctaa tgatgtgtca gatggggatt   4800
gtttcgatat attaccctaa tgatggataa taagagtagt tcacagttat gttttgatcc   4860
tgccacatag tttgagtttt gtgatcagat ttagttttac ttatttgtgc ttagttcgga   4920
tgggattgtt ctgatattgt tccaatagat gaatagctcg ttaggttaaa atctttaggt   4980
tgagttaggc gacacatagt ttatttcctc tggatttgga ttggaattgt gttcttagtt   5040
tttttcccct ggatttggat tggaattgtg tggagctggg ttagagaatt acatctgtat   5100
cgtgtacacc tacttgaact gtagagcttg ggttctaagg tcaatttaat ctgtattgta   5160
tctggctctt tgcctagttg aactgtagtg ctgatgttgt actgtgtttt tttacccgtt   5220
ttatttgctt tactcgtgca aatcaaatct gtcagatgct agaactaggt ggctttattc   5280
tgtgttctta catagatctg ttgtcctgta gttacttatg tcagttttgt tattatctga   5340
agatattttt ggttgttgct tgttgatgtg gtgtgagctg tgagcagcgc tcttatgatt   5400
aatgatgctg tccaattgta gtgtagtatg atgtgattga tatgttcatc tattttgagc   5460
tgacagtacc gatatcgtag gatctggtgc caacttattc tccagctgct ttttttttacc   5520
tatgttaatt ccaatccttt cttgcctctt ccagatccag ataatgcaga aactcattaa   5580
ctcagtgcaa aactatgcct ggggcagcaa aacggcgttg actgaacttt atggtatgga   5640
aaatccgtcc agccagccga tggccgagct gtggatgggc gcacatccga aaagcagttc   5700
acgagtgcag aatgccgccg gagatatcgt ttcactgcgt gatgtgattg agagtgataa   5760
atcgactctg ctcggagagg ccgttgccaa acgctttggc gaactgcctt tcctgttcaa   5820
agtattatgc gcagcacagc cactctccat tcaggttcat ccaaacaaac acaattctga   5880
aatcggtttt gccaaagaaa atgccgcagg tatcccgatg gatgccgccg agcgtaacta   5940
taaagatcct aaccacaagc cggagctggt ttttgcgctg acgcctttcc ttgcgatgaa   6000
cgcgtttcgt gaattttccg agattgtctc cctactccag ccggtcgcag gtgcacatcc   6060
ggcgattgct cactttttac aacagcctga tgccgaacgt ttaagcgaac tgttcgccag   6120
cctgttgaat atgcagggtg aagaaaaatc ccgcgcgctg gcgattttaa aatcggccct   6180
cgatagccag cagggtgaac cgtggcaaac gattcgttta atttctgaat tttacccgga   6240
agacagcggt ctgttctccc cgctattgct gaatgtggtg aaattgaacc ctggcgaagc   6300
gatgttcctg ttcgctgaaa caccgcacgc ttacctgcaa ggcgtggcgc tggaagtgat   6360
ggcaaactcc gataacgtgc tgcgtgcggg tctgacgcct aaatacattg atattccgga   6420
actggttgcc aatgtgaaat tcgaagccaa accggctaac cagttgttga cccagccggt   6480
gaaacaaggt gcagaactgg acttcccgat tccagtggat gattttgcct tctcgctgca   6540
tgaccttagt gataaagaaa ccaccattag ccagcagagt gccgccattt tgttctgcgt   6600
cgaaggcgat gcaacgttgt ggaaaggttc tcagcagtta cagcttaaac cgggtgaatc   6660
agcgtttatt gccgccaacg aatcaccggt gactgtcaaa ggccacggcc gtttagcgcg   6720
```

-continued

```
tgtttacaac aagctgtaag agcttactga aaaaattaac atctcttgct aagctgggag   6780
ctctagatcc ccgaatttcc ccgatcgttc aaacatttgg caataaagtt tcttaagatt   6840
gaatcctgtt gccggtcttg cgatgattat catataattt ctgttgaatt acgttaagca   6900
tgtaataatt aacatgtaat gcatgacgtt atttatgaga tgggttttta tgattagagt   6960
cccgcaatta tacatttaat acgcgataga aaacaaaata tagcgcgcaa actaggataa   7020
attatcgcgc gcggtgtcat ctatgttact agatcgggaa ttggcgagct cgaattaatt   7080
cagtacatta aaaacgtccg caatgtgtta ttaagttgtc taagcgtcaa tttgtttaca   7140
ccacaatata tcctgccacc agccagccaa cagctccccg accggcagct cggcacaaaa   7200
tcaccactcg atacaggcag cccatcagtc cgggacggcg tcagcgggag agccgttgta   7260
aggcggcaga ctttgctcat gttaccgatg ctattcggaa gaacggcaac taagctgccg   7320
ggtttgaaac acggatgatc tcgcggaggg tagcatgttg attgtaacga tgacagagcg   7380
ttgctgcctg tgatcaaata tcatctccct cgcagagatc cgaattatca gccttcttat   7440
tcatttctcg cttaaccgtg acaggctgtc gatcttgaga actatgccga cataatagga   7500
aatcgctgga taaagccgct gaggaagctg agtggcgcta tttctttaga agtgaacgtt   7560
gacgatcgtc gaccgtaccc cgatgaatta attcggacgt acgttctgaa cacagctgga   7620
tacttacttg ggcgattgtc atacatgaca tcaacaatgt acccgtttgt gtaaccgtct   7680
cttggaggtt cgtatgacac tagtggttcc cctcagcttg cgactagatg ttgaggccta   7740
acattttatt agagagcagg ctagttgctt agatacatga tcttcaggcc gttatctgtc   7800
agggcaagcg aaaattggcc atttatgacg accaatgccc cgcagaagct cccatctttg   7860
ccgccataga cgccgcgccc ccttttggg gtgtagaaca tccttttgcc agatgtggaa   7920
aagaagttcg ttgtcccatt gttggcaatg acgtagtagc cggcgaaagt gcgagaccca   7980
tttgcgctat atataagcct acgatttccg ttgcgactat tgtcgtaatt ggatgaacta   8040
ttatcgtagt tgctctcaga gttgtcgtaa tttgatggac tattgtcgta attgcttatg   8100
gagttgtcgt agttgcttgg agaaatgtcg tagttggatg gggagtagtc atagggaaga   8160
cgagcttcat ccactaaaac aattggcagg tcagcaagtg cctgccccga tgccatcgca   8220
agtacgaggc ttagaaccac cttcaacaga tcgcgcatag tcttccccag ctctctaacg   8280
cttgagttaa gccgcgccgc gaagcggcgt cggcttgaac gaattgttag acattatttg   8340
ccgactacct tggtgatctc gcctttcacg tagtgaacaa attcttccaa ctgatctgcg   8400
cgcgaggcca agcgatcttc ttgtccaaga taagcctgcc tagcttcaag tatgacgggc   8460
tgatactggg ccggcaggcg ctccattgcc cagtcggcag cgacatcctt cggcgcgatt   8520
ttgccggtta ctgcgctgta ccaaatgcgg gacaacgtaa gcactacatt tcgctcatcg   8580
ccagcccagt cgggcggcga gttccatagc gttaaggttt catttagcgc ctcaaataga   8640
tcctgttcag gaaccggatc aaagagttcc tccgccgctg gacctaccaa ggcaacgcta   8700
tgttctcttg cttttgtcag caagatagcc agatcaatgt cgatcgtggc tggctcgaag   8760
atacctgcaa gaatgtcatt gcgctgccat tctccaaatt gcagttcgcg cttagctgga   8820
taacgccacg gaatgatgtc gtcgtgcaca acaatggtga cttctacagc gcggagaatc   8880
tcgctctctc caggggaagc cgaagtttcc aaaaggtcgt tgatcaaagc tcgccgcgtt   8940
gtttcatcaa gccttacggt caccgtaacc agcaaatcaa tatcactgtg tggcttcagg   9000
ccgccatcca ctgcggagcc gtacaaatgt acggccagca acgtcggttc gagatggcgc   9060
tcgatgacgc caactacctc tgatagttga gtcgatactt cggcgatcac cgcttccctc   9120
```

```
atgatgttta actcctgaat taagccgcgc cgcgaagcgg tgtcggcttg aatgaattgt   9180
taggcgtcat cctgtgctcc cgagaaccag taccagtaca tcgctgtttc gttcgagact   9240
tgaggtctag ttttatacgt gaacaggtca atgccgccga gagtaaagcc acattttgcg   9300
tacaaattgc aggcaggtac attgttcgtt tgtgtctcta atcgtatgcc aaggagctgt   9360
ctgcttagtg cccacttttt cgcaaattcg atgagactgt gcgcgactcc tttgcctcgg   9420
tgcgtgtgcg acacaacaat gtgttcgata gaggctagat cgttccatgt tgagttgagt   9480
tcaatcttcc cgacaagctc ttggtcgatg aatgcgccat agcaagcaga gtcttcatca   9540
gagtcatcat ccgagatgta atccttccgg taggggctca cacttctggt agatagttca   9600
aagccttggt cggataggtg cacatcgaac acttcacgaa caatgaaatg gttctcagca   9660
tccaatgttt ccgccacctg ctcagggatc accgaaatct tcatatgacg cctaacgcct   9720
ggcacagcgg atcgcaaacc tggcgcggct tttggcacaa aaggcgtgac aggtttgcga   9780
atccgttgct gccacttgtt aaccctttttg ccagatttgg taactataat ttatgttaga   9840
ggcgaagtct tgggtaaaaa ctggcctaaa attgctgggg atttcaggaa agtaaacatc   9900
accttccggc tcgatgtcta ttgtagatat atgtagtgta tctacttgat cgggggatct   9960
gctgcctcgc gcgtttcggt gatgacggtg aaaacctctg acacatgcag ctcccggaga  10020
cggtcacagc ttgtctgtaa gcggatgccg ggagcagaca agcccgtcag ggcgcgtcag  10080
cgggtgttgg cgggtgtcgg ggcgcagcca tgacccagtc acgtagcgat agcggagtgt  10140
atactggctt aactatgcgg catcagagca gattgtactg agagtgcacc atatgcggtg  10200
tgaaataccg cacagatgcg taaggagaaa ataccgcatc aggcgctctt ccgcttcctc  10260
gctcactgac tcgctgcgct cggtcgttcg gctgcggcga gcggtatcag ctcactcaaa  10320
ggcggtaata cggttatcca cagaatcagg ggataacgca ggaaagaaca tgtgagcaaa  10380
aggccagcaa aaggccagga accgtaaaaa ggccgcgttg ctggcgtttt tccataggct  10440
ccgcccccct gacgagcatc acaaaaatcg acgctcaagt cagaggtggc gaaacccgac  10500
aggactataa agataccagg cgtttccccc tggaagctcc ctcgtgcgct ctcctgttcc  10560
gaccctgccg cttaccggat acctgtccgc ctttctccct tcgggaagcg tggcgctttc  10620
tcatagctca cgctgtaggt atctcagttc ggtgtaggtc gttcgctcca agctgggctg  10680
tgtgcacgaa ccccccgttc agcccgaccg ctgcgcctta tccggtaact atcgtcttga  10740
gtccaacccg gtaagacacg acttatcgcc actggcagca gccactggta acaggattag  10800
cagagcgagg tatgtaggcg gtgctacaga gttcttgaag tggtggccta actacggcta  10860
cactagaagg acagtatttg gtatctgcgc tctgctgaag ccagttacct tcggaaaaag  10920
agttggtagc tcttgatccg gcaaacaaac caccgctggt agcggtggtt tttttgtttg  10980
caagcagcag attacgcgca gaaaaaaagg atctcaagaa gatcctttga tcttttctac  11040
ggggtctgac gctcagtgga acgaaaactc acgttaaggg attttggtca tgagattatc  11100
aaaaaggatc ttcacctaga tccttttaaa ttaaaaatga agttttaaat caatctaaag  11160
tatatatgag taaacttggt ctgacagtta ccaatgctta atcagtgagg cacctatctc  11220
agcgatctgt ctatttcgtt catccatagt tgcctgactc cccgtcgtgt agataactac  11280
gatacgggag ggcttaccat ctggccccag tgctgcaatg ataccgcgag acccacgctc  11340
accggctcca gatttatcag caataaacca gccagccgga agggccgagc gcagaagtgg  11400
tcctgcaact ttatccgcct ccatccagtc tattaattgt tgccgggaag ctagagtaag  11460
```

-continued

```
tagttcgcca gttaatagtt tgcgcaacgt tgttgccatt gctgcagggg gggggggggg  11520
ggggttccat tgttcattcc acggacaaaa acagagaaag gaaacgacag aggccaaaaa  11580
gctcgctttc agcacctgtc gtttcctttc ttttcagagg gtattttaaa taaaaacatt  11640
aagttatgac gaagaagaac ggaaacgcct taaaccggaa aattttcata aatagcgaaa  11700
acccgcgagg tcgccgcccc gtaacctgtc ggatcaccgg aaaggacccg taaagtgata  11760
atgattatca tctacatatc acaacgtgcg tggaggccat caaaccacgt caaataatca  11820
attatgacgc aggtatcgta ttaattgatc tgcatcaact taacgtaaaa acaacttcag  11880
acaatacaaa tcagcgacac tgaatacggg gcaacctcat gtcccccccc cccccccct  11940
gcaggcatcg tggtgtcacg ctcgtcgttt ggtatggctt cattcagctc cggttcccaa  12000
cgatcaaggc gagttacatg atcccccatg ttgtgcaaaa aagcggttag ctccttcggt  12060
cctccgatcg ttgtcagaag taagttggcc gcagtgttat cactcatggt tatggcagca  12120
ctgcataatt ctcttactgt catgccatcc gtaagatgct tttctgtgac tggtgagtac  12180
tcaaccaagt cattctgaga atagtgtatg cggcgaccga gttgctcttg cccggcgtca  12240
acacgggata ataccgcgcc acatagcaga actttaaaag tgctcatcat tggaaaacgt  12300
tcttcggggc gaaaactctc aaggatctta ccgctgttga gatccagttc gatgtaaccc  12360
actcgtgcac ccaactgatc ttcagcatct tttactttca ccagcgtttc tgggtgagca  12420
aaaacaggaa ggcaaaatgc cgcaaaaaag ggaataaggg cgacacggaa atgttgaata  12480
ctcatactct tcctttttca atattattga agcatttatc agggttattg tctcatgagc  12540
ggatacatat ttgaatgtat ttagaaaaat aaacaaatag gggttccgcg cacatttccc  12600
cgaaaagtgc cacctgacgt ctaagaaacc attattatca tgacattaac ctataaaaat  12660
aggcgtatca cgaggccctt tcgtcttcaa gaattggtcg acgatcttgc tgcgttcgga  12720
tattttcgtg gagttcccgc cacagacccg gattgaaggc gagatccagc aactcgcgcc  12780
agatcatcct gtgacggaac tttggcgcgt gatgactggc caggacgtcg gccgaaagag  12840
cgacaagcag atcacgcttt tcgacagcgt cggatttgcg atcgaggatt tttcggcgct  12900
gcgctacgtc cgcgaccgcg ttgagggatc aagccacagc agcccactcg accttctagc  12960
cgacccagac gagccaaggg atcttttttgg aatgctgctc cgtcgtcagg ctttccgacg  13020
tttgggtggt tgaacagaag tcattatcgc acggaatgcc aagcactccc gaggggaacc  13080
ctgtggttgg catgcacata caaatggacg aacggataaa ccttttcacg cccttttaaa  13140
tatccgatta ttctaataaa cgctcttttc tcttaggttt acccgccaat atatcctgtc  13200
aaacactgat agtttaaact gaaggcggga aacgacaacc tgatcatgag cggagaatta  13260
agggagtcac gttatgaccc ccgccgatga cgcgggacaa gccgttttac gtttggaact  13320
gacagaaccg caacgttgaa ggagccactc agcttaatta agtctaactc gagcacccaa  13380
ccccatatcg acagaggatg tgaagaacag gtaaatcacg cagaagaacc catctctgat  13440
agcagctatc gattagaaca acgaatccat attgggtccg tgggaaatac ttactgcaca  13500
ggaagggggc gatctgacga ggccccgcca ccggcctcga cccgaggccg aggccgacga  13560
agcgccggcg agtacggcgc cgcggcggcc tctgcccgtg ccctctgcgc gtgggaggga  13620
gaggccgcgg tggtgggggc gcgcgcgcgc gcgcgcgcag ctggtgcggc ggcgcggggg  13680
tcagccgccg agccggcggc gacggaggag cagggcggcg tggacgcgaa cttccgatcg  13740
gttggtcaga gtgcgcgagt tgggcttagc caattaggtc tcaacaatct attgggccgt  13800
aaaattcatg ggccctggtt tgtctaggcc caatatcccg ttcatttcag cccacaaata  13860
```

```
tttccccaga ggattattaa ggcccacacg cagcttatag cagatcaagt acgatgtttc  13920
ctgatcgttg gatcggaaac gtacggtctt gatcaggcat gccgacttcg tcaaagagag  13980
gcggcatgac ctgacgcgga gttggttccg ggcaccgtct ggatggtcgt accgggaccg  14040
gacacgtgtc gcgcctccaa ctacatggac acgtgtggtg ctgccattgg gccgtacgcg  14100
tggcggtgac cgcaccggat gctgcctcgc accgccttgc ccacgcttta tatagagagg  14160
ttttctctcc attaatcgca tagcgagtcg aatcgaccga aggggagggg gagcgaagct  14220
ttgcgttctc taatcgcctc gtcaaggtaa ctaatcaatc acctcgtcct aatcctcgaa  14280
tctctcgtgg tgcccgtcta atctcgcgat tttgatgctc gtggtggaaa gcgtaggagg  14340
atcccgtgcg agttagtctc aatctctcag ggtttcgtgc gattttaggg tgatccacct  14400
cttaatcgag ttacggtttc gtgcgatttt agggtaatcc tcttaatctc tcattgattt  14460
agggtttcgt gagaatcgag gtagggatct gtgttattta tatcgatcta atagatggat  14520
tggttttgag attgttctgt cagatgggga ttgtttcgat atattaccct aatgatgtgt  14580
cagatgggga ttgtttcgat atattaccct aatgatgtgt cagatgggga ttgtttcgat  14640
atattaccct aatgatggat aataagagta gttcacagtt atgttttgat cctgccacat  14700
agtttgagtt ttgtgatcag atttagtttt acttatttgt gcttagttcg gatgggattg  14760
ttctgatatt gttccaatag atgaatagct cgttaggtta aaatctttag gttgagttag  14820
gcgacacata gtttatttcc tctggatttg gattggaatt gtgttcttag tttttttccc  14880
ctggatttgg attggaattg tgtggagctg ggttagagaa ttacatctgt atcgtgtaca  14940
cctacttgaa ctgtagagct tgggttctaa ggtcaattta atctgtattg tatctggctc  15000
tttgcctagt tgaactgtag tgctgatgtt gtactgtgtt tttttacccg ttttatttgc  15060
tttactcgtg caaatcaaat ctgtcagatg ctagaactag gtggctttat tctgtgttct  15120
tacatagatc tgttgtcctg tagttactta tgtcagtttt gttattatct gaagatattt  15180
ttggttgttg cttgttgatg tggtgtgagc tgtgagcagc gctcttatga ttaatgatgc  15240
tgtccaattg tagtgtagta tgatgtgatt gatatgttca tctattttga gctgacagta  15300
ccgatatcgt aggatctggt gccaacttat tctccagctg cttttttta cctatgttaa  15360
ttccaatcct ttcttgcctc ttccagatcc agataatggc gaacaaacat ttgtccctct  15420
ccctcttcct cgtcctcctt ggcctgtcgg ccagcttggc ctccgggcaa gtcgcatcca  15480
cgcagggtat ctctgaggac ctgtataatc gcctcgtgga aatggccaca atttcacaag  15540
cggcttacgc agatctttgt aatatccctt cgacaattat caagggagag aaaatctata  15600
acgcccagac tgacatcaac ggctggatac tgcgggatga cacgagcaag gaaattatca  15660
cagtctttag agggaccggt tccgatacaa atttgcagtt ggacacgaat tacacactga  15720
ccccccttcga tactctccct caatgcaacg actgtgaggt tcacggtggg tactatattg  15780
gctggatctc tgttcaagac caagtcgagt cacttgttaa gcagcaagcg tcgcagtacc  15840
cggactacgc attgacggtg acagggcaca gcctgggtgc ctcgatggca gcgctcaccg  15900
ctgcccagct ttctgcaacc tacgataatg tcaggctgta cactttcgga gaaccacgct  15960
caggcaacca agcgtttgct tcgtatatga acgacgcttt ccaggttagc tcccccgaga  16020
cgacacaata ctttcgggtg acccattcta acgacgggat tcctaacctc ccgccagccg  16080
acgaaggtta cgcacacggg ggtgtcgagt actggtcagt ggacccctac agcgcgcaga  16140
atactttcgt ttgcacgggc gatgaggtcc agtgctgtga agctcaaggg ggtcagggag  16200
```

```
tgaatgatgc acacacaacc tatttcggaa tgacttccgg ggcttgcacg tggagcgaga  16260

aggacgagct gtgatccccg aatttccccg atcgttcaaa catttggcaa taaagtttct  16320

taagattgaa tcctgttgcc ggtcttgcga tgattatcat ataatttctg ttgaattacg  16380

ttaagcatgt aataattaac atgtaatgca tgacgttatt tatgagatgg gtttttatga  16440

ttagagtccc gcaattatac atttaatacg cgatagaaaa caaaatatag cgcgcaaact  16500

aggataaatt atcgcgcgcg gtgtcatcta tgttactaga tcgggaattg c           16551


<210> SEQ ID NO 69
<211> LENGTH: 17296
<212> TYPE: DNA
<213> ORGANISM: Artificial Sequence
<220> FEATURE:
<223> OTHER INFORMATION: Synthetic construct, vector pAG2092

<400> SEQUENCE: 69

cgtcgactct agtaacggcc gccagtgtgc tggaattaat tcggcttgtc gaccacccaa     60

ccccatatcg acagaggatg tgaagaacag gtaaatcacg cagaagaacc catctctgat    120

agcagctatc gattagaaca acgaatccat attgggtccg tgggaaatac ttactgcaca    180

ggaagggggc gatctgacga ggccccgcca ccggcctcga cccgaggccg aggccgacga    240

agcgccggcg agtacggcgc cgcggcggcc tctgcccgtg ccctctgcgc gtgggaggga    300

gaggccgcgg tggtgggggc gcgcgcgcgc gcgcgcgcag ctggtgcggc ggcgcggggg    360

tcagccgccg agccggcggc gacggaggag cagggcggcg tggacgcgaa cttccgatcg    420

gttggtcaga gtgcgcgagt tgggcttagc caattaggtc tcaacaatct attgggccgt    480

aaaattcatg ggccctggtt tgtctaggcc caatatcccg ttcatttcag cccacaaata    540

tttccccaga ggattattaa ggcccacacg cagcttatag cagatcaagt acgatgtttc    600

ctgatcgttg gatcggaaac gtacggtctt gatcaggcat gccgacttcg tcaaagagag    660

gcggcatgac ctgacgcgga gttggttccg ggcaccgtct ggatggtcgt accgggaccg    720

gacacgtgtc gcgcctccaa ctacatggac acgtgtggtg ctgccattgg gccgtacgcg    780

tggcggtgac cgcaccggat gctgcctcgc accgccttgc ccacgcttta tatagagagg    840

ttttctctcc attaatcgca tagcgagtcg aatcgaccga aggggagggg gagcgaagct    900

ttgcgttctc taatcgcctc gtcaaggtaa ctaatcaatc acctcgtcct aatcctcgaa    960

tctctcgtgg tgcccgtcta atctcgcgat tttgatgctc gtggtggaaa gcgtaggagg   1020

atcccgtgcg agttagtctc aatctctcag ggtttcgtgc gattttaggg tgatccacct   1080

cttaatcgag ttacggtttc gtgcgatttt agggtaatcc tcttaatctc tcattgattt   1140

agggtttcgt gagaatcgag gtagggatct gtgttattta tatcgatcta atagatggat   1200

tggttttgag attgttctgt cagatgggga ttgtttcgat atattaccct aatgatgtgt   1260

cagatgggga ttgtttcgat atattaccct aatgatgtgt cagatgggga ttgtttcgat   1320

atattaccct aatgatggat aataagagta gttcacagtt atgttttgat cctgccacat   1380

agtttgagtt ttgtgatcag atttagtttt acttatttgt gcttagttcg gatgggattg   1440

ttctgatatt gttccaatag atgaatagct cgttaggtta aaatctttag gttgagttag   1500

gcgacacata gtttatttcc tctggatttg gattggaatt gtgttcttag ttttttttccc  1560

ctggatttgg attggaattg tgtggagctg ggttagagaa ttacatctgt atcgtgtaca   1620

cctacttgaa ctgtagagct tgggttctaa ggtcaattta atctgtattg tatctggctc   1680

tttgcctagt tgaactgtag tgctgatgtt gtactgtgtt tttttacccg ttttatttgc   1740
```

```
tttactcgtg caaatcaaat ctgtcagatg ctagaactag gtggctttat tctgtgttct   1800
tacatagatc tgttgtcctg tagttactta tgtcagtttt gttattatct gaagatattt   1860
ttggttgttg cttgttgatg tggtgtgagc tgtgagcagc gctcttatga ttaatgatgc   1920
tgtccaattg tagtgtagta tgatgtgatt gatatgttca tctattttga gctgacagta   1980
ccgatatcgt aggatctggt gccaacttat tctccagctg cttttttta cctatgttaa    2040
ttccaatcct ttcttgcctc ttccagatcc agataatggc gaacaaacat ttgtccctct   2100
ccctcttcct cgtcctcctt ggcctgtcgg ccagcttggc ctccgggcaa caaacaagca   2160
ttactctgac atccaacgca tccggtacgt ttgacggtta ctattacgaa ctctggaagg   2220
atactggcaa tacaacaatg acggtctaca ctcaaggtcg cttttcctgc cagtggtcga   2280
acatcaataa cgcgttgttt aggaccggga agaaatacaa ccagaattgg cagtctcttg   2340
gcacaatccg gatcacgtac tctgcgactt acaacccaaa cgggaactcc tacttgtgta   2400
tctatggctg gtctaccaac ccattggtcg agttctacat cgttgagtcc tgggggaact   2460
ggagaccgcc tggtgccacg tccctgggcc aagtgacaat cgatggcggg acctacgaca   2520
tctataggac gacacgcgtc aaccagcctt ccattgtggg gacagccacg ttcgatcagt   2580
actggagcgt gcgcacctct aagcggactt caggaacagt gaccgtgacc gatcacttcc   2640
gcgcctgggc gaaccggggc ctgaacctcg gcacaataga ccaaattaca ttgtgcgtgg   2700
agggttacca aagctctgga tcagccaaca tcacccagaa caccttctct caggctcttc   2760
cttccggcag ttcgggtggc tcatccggct ccacaacgac tactcgcatc gagtgtgaga   2820
acatgtcctt gtccggaccc tacgttagca ggatcaccaa tccctttaat ggtattgcgc   2880
tgtacgccaa cggagacaca gcccgcgcta ccgttaactt ccccgcaagt cgcaactaca   2940
atttccgcct gcggggttgc ggcaacaaca ataatcttgc ccgtgtggac ctgaggatcg   3000
acggacggac cgtcgggacc ttttattacc agggcacata cccctgggag gccccaattg   3060
acaatgttta tgtcagtgcg gggagtcata cagtcgaaat cactgttact gcggataacg   3120
gcacatggga cgtgtatgcc gactacctgg tgatacagtg acctaggtcc ccgaatttcc   3180
ccgatcgttc aaacatttgg caataaagtt tcttaagatt gaatcctgtt gccggtcttg   3240
cgatgattat catataattt ctgttgaatt acgttaagca tgtaataatt aacatgtaat   3300
gcatgacgtt atttatgaga tgggttttta tgattagagt cccgcaatta tacatttaat   3360
acgcgataga aaacaaaata tagcgcgcaa actaggataa attatcgcgc gcggtgtcat   3420
ctatgttact agatcgggaa ttggaattca tactaaagct tgcatgcctg caggtcgact   3480
ctagtaacgg ccgccagtgt gctggaatta attcggcttg tcgaccaccc aaccccatat   3540
cgacagagga tgtgaagaac aggtaaatca cgcagaagaa cccatctctg atagcagcta   3600
tcgattagaa caacgaatcc atattgggtc cgtgggaaat acttactgca caggaagggg   3660
gcgatctgac gaggccccgc caccggcctc gacccgaggc cgaggccgac gaagcgccgg   3720
cgagtacggc gccgcggcgg cctctgcccg tgccctctgc gcgtgggagg gagaggccgc   3780
ggtggtgggg gcgcgcgcgc gcgcgcgcgc agctggtgcg gcggcgcggg ggtcagccgc   3840
cgagccggcg gcgacggagg agcagggcgg cgtggacgcg aacttccgat cggttggtca   3900
gagtgcgcga gttgggctta gccaattagg tctcaacaat ctattgggcc gtaaaattca   3960
tgggccctgg tttgtctagg cccaatatcc cgttcatttc agcccacaaa tatttcccca   4020
gaggattatt aaggcccaca cgcagcttat agcagatcaa gtacgatgtt tcctgatcgt   4080
```

```
tggatcggaa acgtacggtc ttgatcaggc atgccgactt cgtcaaagag aggcggcatg   4140
acctgacgcg gagttggttc cgggcaccgt ctggatggtc gtaccgggac cggacacgtg   4200
tcgcgcctcc aactacatgg acacgtgtgg tgctgccatt gggccgtacg cgtggcggtg   4260
accgcaccgg atgctgcctc gcaccgcctt gcccacgctt tatatagaga ggttttctct   4320
ccattaatcg catagcgagt cgaatcgacc gaaggggagg gggagcgaag ctttgcgttc   4380
tctaatcgcc tcgtcaaggt aactaatcaa tcacctcgtc ctaatcctcg aatctctcgt   4440
ggtgcccgtc taatctcgcg attttgatgc tcgtggtgga aagcgtagga ggatcccgtg   4500
cgagttagtc tcaatctctc agggtttcgt gcgattttag ggtgatccac ctcttaatcg   4560
agttacggtt tcgtgcgatt ttagggtaat cctcttaatc tctcattgat ttagggtttc   4620
gtgagaatcg aggtagggat ctgtgttatt tatatcgatc taatagatgg attggttttg   4680
agattgttct gtcagatggg gattgtttcg atatattacc ctaatgatgt gtcagatggg   4740
gattgtttcg atatattacc ctaatgatgt gtcagatggg gattgtttcg atatattacc   4800
ctaatgatgg ataataagag tagttcacag ttatgttttg atcctgccac atagtttgag   4860
ttttgtgatc agatttagtt ttacttattt gtgcttagtt cggatgggat tgttctgata   4920
ttgttccaat agatgaatag ctcgttaggt taaaatcttt aggttgagtt aggcgacaca   4980
tagtttattt cctctggatt tggattggaa ttgtgttctt agttttttttc ccctggattt   5040
ggattggaat tgtgtggagc tgggttagag aattacatct gtatcgtgta cacctacttg   5100
aactgtagag cttgggttct aaggtcaatt taatctgtat tgtatctggc tctttgccta   5160
gttgaactgt agtgctgatg ttgtactgtg tttttttacc cgttttattt gctttactcg   5220
tgcaaatcaa atctgtcaga tgctagaact aggtggcttt attctgtgtt cttacataga   5280
tctgttgtcc tgtagttact tatgtcagtt ttgttattat ctgaagatat ttttggttgt   5340
tgcttgttga tgtggtgtga gctgtgagca gcgctcttat gattaatgat gctgtccaat   5400
tgtagtgtag tatgatgtga ttgatatgtt catctatttt gagctgacag taccgatatc   5460
gtaggatctg gtgccaactt attctccagc tgcttttttt tacctatgtt aattccaatc   5520
ctttcttgcc tcttccagat ccagataatg cagaaactca ttaactcagt gcaaaactat   5580
gcctggggca gcaaaacggc gttgactgaa ctttatggta tggaaaatcc gtccagccag   5640
ccgatggccg agctgtggat gggcgcacat ccgaaaagca gttcacgagt gcagaatgcc   5700
gccggagata tcgtttcact gcgtgatgtg attgagagtg ataaatcgac tctgctcgga   5760
gaggccgttg ccaaacgctt tggcgaactg cctttcctgt tcaaagtatt atgcgcagca   5820
cagccactct ccattcaggt tcatccaaac aaacacaatt ctgaaatcgg ttttgccaaa   5880
gaaaatgccg caggtatccc gatggatgcc gccgagcgta actataaaga tcctaaccac   5940
aagccggagc tggtttttgc gctgacgcct ttccttgcga tgaacgcgtt tcgtgaattt   6000
tccgagattg tctccctact ccagccggtc gcaggtgcac atccggcgat tgctcacttt   6060
ttacaacagc ctgatgccga acgtttaagc gaactgttcg ccagcctgtt gaatatgcag   6120
ggtgaagaaa aatcccgcgc gctggcgatt ttaaaatcgg ccctcgatag ccagcagggt   6180
gaaccgtggc aaacgattcg tttaatttct gaattttacc cggaagacag cggtctgttc   6240
tccccgctat tgctgaatgt ggtgaaattg aaccctggcg aagcgatgtt cctgttcgct   6300
gaaacaccgc acgcttacct gcaaggcgtg gcgctggaag tgatggcaaa ctccgataac   6360
gtgctgcgtg cgggtctgac gcctaaatac attgatattc cggaactggt tgccaatgtg   6420
aaattcgaag ccaaaccggc taaccagttg ttgacccagc cggtgaaaca aggtgcagaa   6480
```

```
ctggacttcc cgattccagt ggatgatttt gccttctcgc tgcatgacct tagtgataaa   6540
gaaaccacca ttagccagca gagtgccgcc attttgttct gcgtcgaagg cgatgcaacg   6600
ttgtggaaag gttctcagca gttacagctt aaaccgggtg aatcagcgtt tattgccgcc   6660
aacgaatcac cggtgactgt caaaggccac ggccgtttag cgcgtgttta caacaagctg   6720
taagagctta ctgaaaaaat taacatctct tgctaagctg ggagctctag atccccgaat   6780
ttccccgatc gttcaaacat ttggcaataa agtttcttaa gattgaatcc tgttgccggt   6840
cttgcgatga ttatcatata atttctgttg aattacgtta agcatgtaat aattaacatg   6900
taatgcatga cgttatttat gagatgggtt tttatgatta gagtcccgca attatacatt   6960
taatacgcga tagaaaacaa aatatagcgc gcaaactagg ataaattatc gcgcgcggtg   7020
tcatctatgt tactagatcg ggaattggcg agctcgaatt aattcagtac attaaaaacg   7080
tccgcaatgt gttattaagt tgtctaagcg tcaatttgtt tacaccacaa tatatcctgc   7140
caccagccag ccaacagctc cccgaccggc agctcggcac aaaatcacca ctcgatacag   7200
gcagcccatc agtccgggac ggcgtcagcg ggagagccgt tgtaaggcgg cagactttgc   7260
tcatgttacc gatgctattc ggaagaacgg caactaagct gccgggtttg aaacacggat   7320
gatctcgcgg agggtagcat gttgattgta acgatgacag agcgttgctg cctgtgatca   7380
aatatcatct ccctcgcaga gatccgaatt atcagccttc ttattcattt ctcgcttaac   7440
cgtgacaggc tgtcgatctt gagaactatg ccgacataat aggaaatcgc tggataaagc   7500
cgctgaggaa gctgagtggc gctatttctt tagaagtgaa cgttgacgat cgtcgaccgt   7560
accccgatga attaattcgg acgtacgttc tgaacacagc tggatactta cttgggcgat   7620
tgtcatacat gacatcaaca atgtacccgt ttgtgtaacc gtctcttgga ggttcgtatg   7680
acactagtgg ttcccctcag cttgcgacta gatgttgagg cctaacattt tattagagag   7740
caggctagtt gcttagatac atgatcttca ggccgttatc tgtcagggca agcgaaaatt   7800
ggccatttat gacgaccaat gccccgcaga agctcccatc tttgccgcca tagacgccgc   7860
gcccccccttt tggggtgtag aacatccttt tgccagatgt ggaaaagaag ttcgttgtcc   7920
cattgttggc aatgacgtag tagccggcga aagtgcgaga cccatttgcg ctatatataa   7980
gcctacgatt tccgttgcga ctattgtcgt aattggatga actattatcg tagttgctct   8040
cagagttgtc gtaatttgat ggactattgt cgtaattgct tatggagttg tcgtagttgc   8100
ttggagaaat gtcgtagttg gatggggagt agtcataggg aagacgagct tcatccacta   8160
aaacaattgg caggtcagca agtgcctgcc ccgatgccat cgcaagtacg aggcttagaa   8220
ccaccttcaa cagatcgcgc atagtcttcc ccagctctct aacgcttgag ttaagccgcg   8280
ccgcgaagcg gcgtcggctt gaacgaattg ttagacatta tttgccgact accttggtga   8340
tctcgccttt cacgtagtga acaaattctt ccaactgatc tgcgcgcgag gccaagcgat   8400
cttcttgtcc aagataagcc tgcctagctt caagtatgac gggctgatac tgggccggca   8460
ggcgctccat tgcccagtcg gcagcgacat ccttcggcgc gattttgccg gttactgcgc   8520
tgtaccaaat gcgggacaac gtaagcacta catttcgctc atcgccagcc cagtcgggcg   8580
gcgagttcca tagcgttaag gtttcattta gcgcctcaaa tagatcctgt tcaggaaccg   8640
gatcaaagag ttcctccgcc gctggaccta ccaaggcaac gctatgttct cttgcttttg   8700
tcagcaagat agccagatca atgtcgatcg tggctggctc gaagatacct gcaagaatgt   8760
cattgcgctg ccattctcca aattgcagtt cgcgcttagc tggataacgc cacggaatga   8820
```

```
tgtcgtcgtg cacaacaatg gtgacttcta cagcgcggag aatctcgctc tctccagggg   8880
aagccgaagt ttccaaaagg tcgttgatca aagctcgccg cgttgtttca tcaagcctta   8940
cggtcaccgt aaccagcaaa tcaatatcac tgtgtggctt caggccgcca tccactgcgg   9000
agccgtacaa atgtacggcc agcaacgtcg gttcgagatg gcgctcgatg acgccaacta   9060
cctctgatag ttgagtcgat acttcggcga tcaccgcttc cctcatgatg tttaactcct   9120
gaattaagcc gcgccgcgaa gcggtgtcgg cttgaatgaa ttgttaggcg tcatcctgtg   9180
ctcccgagaa ccagtaccag tacatcgctg tttcgttcga gacttgaggt ctagttttat   9240
acgtgaacag gtcaatgccg ccgagagtaa agccacattt tgcgtacaaa ttgcaggcag   9300
gtacattgtt cgtttgtgtc tctaatcgta tgccaaggag ctgtctgctt agtgcccact   9360
ttttcgcaaa ttcgatgaga ctgtgcgcga ctcctttgcc tcggtgcgtg tgcgacacaa   9420
caatgtgttc gatagaggct agatcgttcc atgttgagtt gagttcaatc ttcccgacaa   9480
gctcttggtc gatgaatgcg ccatagcaag cagagtcttc atcagagtca tcatccgaga   9540
tgtaatcctt ccggtagggg ctcacacttc tggtagatag ttcaaagcct tggtcggata   9600
ggtgcacatc gaacacttca cgaacaatga aatggttctc agcatccaat gtttccgcca   9660
cctgctcagg gatcaccgaa atcttcatat gacgcctaac gcctggcaca gcggatcgca   9720
aacctggcgc ggcttttggc acaaaaggcg tgacaggttt gcgaatccgt tgctgccact   9780
tgttaaccct tttgccagat ttggtaacta taatttatgt tagaggcgaa gtcttgggta   9840
aaaactggcc taaaattgct ggggatttca ggaaagtaaa catcaccttc cggctcgatg   9900
tctattgtag atatatgtag tgtatctact tgatcggggg atctgctgcc tcgcgcgttt   9960
cggtgatgac ggtgaaaacc tctgacacat gcagctcccg gagacggtca cagcttgtct  10020
gtaagcggat gccgggagca gacaagcccg tcagggcgcg tcagcgggtg ttggcgggtg  10080
tcggggcgca gccatgaccc agtcacgtag cgatagcgga gtgtatactg gcttaactat  10140
gcggcatcag agcagattgt actgagagtg caccatatgc ggtgtgaaat accgcacaga  10200
tgcgtaagga gaaaataccg catcaggcgc tcttccgctt cctcgctcac tgactcgctg  10260
cgctcggtcg ttcggctgcg gcgagcggta tcagctcact caaaggcggt aatacggtta  10320
tccacagaat caggggataa cgcaggaaag aacatgtgag caaaaggcca gcaaaaggcc  10380
aggaaccgta aaaaggccgc gttgctggcg tttttccata ggctccgccc ccctgacgag  10440
catcacaaaa atcgacgctc aagtcagagg tggcgaaacc cgacaggact ataaagatac  10500
caggcgtttc cccctggaag ctccctcgtg cgctctcctg ttccgaccct gccgcttacc  10560
ggatacctgt ccgcctttct cccttcggga agcgtggcgc tttctcatag ctcacgctgt  10620
aggtatctca gttcggtgta ggtcgttcgc tccaagctgg gctgtgtgca cgaacccccc  10680
gttcagcccg accgctgcgc cttatccggt aactatcgtc ttgagtccaa cccggtaaga  10740
cacgacttat cgccactggc agcagccact ggtaacagga ttagcagagc gaggtatgta  10800
ggcggtgcta cagagttctt gaagtggtgg cctaactacg gctacactag aaggacagta  10860
tttggtatct gcgctctgct gaagccagtt accttcggaa aaagagttgg tagctcttga  10920
tccggcaaac aaaccaccgc tggtagcggt ggtttttttg tttgcaagca gcagattacg  10980
cgcagaaaaa aaggatctca agaagatcct ttgatctttt ctacggggtc tgacgctcag  11040
tggaacgaaa actcacgtta agggattttg gtcatgagat tatcaaaaag gatcttcacc  11100
tagatccttt taaattaaaa atgaagtttt aaatcaatct aaagtatata tgagtaaact  11160
tggtctgaca gttaccaatg cttaatcagt gaggcaccta tctcagcgat ctgtctattt  11220
```

```
cgttcatcca tagttgcctg actccccgtc gtgtagataa ctacgatacg ggagggctta  11280
ccatctggcc ccagtgctgc aatgataccg cgagacccac gctcaccggc tccagattta  11340
tcagcaataa accagccagc cggaagggcc gagcgcagaa gtggtcctgc aactttatcc  11400
gcctccatcc agtctattaa ttgttgccgg gaagctagag taagtagttc gccagttaat  11460
agtttgcgca acgttgttgc cattgctgca gggggggggg ggggggggtt ccattgttca  11520
ttccacggac aaaaacagag aaaggaaacg acagaggcca aaaagctcgc tttcagcacc  11580
tgtcgtttcc tttcttttca gagggtattt taaataaaaa cattaagtta tgacgaagaa  11640
gaacggaaac gccttaaacc ggaaaatttt cataaatagc gaaaacccgc gaggtcgccg  11700
ccccgtaacc tgtcggatca ccggaaagga cccgtaaagt gataatgatt atcatctaca  11760
tatcacaacg tgcgtggagg ccatcaaacc acgtcaaata atcaattatg acgcaggtat  11820
cgtattaatt gatctgcatc aacttaacgt aaaaacaact tcagacaata caaatcagcg  11880
acactgaata cggggcaacc tcatgtcccc cccccccccc ccctgcaggc atcgtggtgt  11940
cacgctcgtc gtttggtatg gcttcattca gctccggttc ccaacgatca aggcgagtta  12000
catgatcccc catgttgtgc aaaaaagcgg ttagctcctt cggtcctccg atcgttgtca  12060
gaagtaagtt ggccgcagtg ttatcactca tggttatggc agcactgcat aattctctta  12120
ctgtcatgcc atccgtaaga tgcttttctg tgactggtga gtactcaacc aagtcattct  12180
gagaatagtg tatgcggcga ccgagttgct cttgcccggc gtcaacacgg gataataccg  12240
cgccacatag cagaacttta aaagtgctca tcattggaaa acgttcttcg gggcgaaaac  12300
tctcaaggat cttaccgctg ttgagatcca gttcgatgta acccactcgt gcacccaact  12360
gatcttcagc atcttttact ttcaccagcg tttctgggtg agcaaaaaca ggaaggcaaa  12420
atgccgcaaa aaagggaata agggcgacac ggaaatgttg aatactcata ctcttccttt  12480
ttcaatatta ttgaagcatt tatcagggtt attgtctcat gagcggatac atatttgaat  12540
gtatttagaa aaataaacaa ataggggttc cgcgcacatt tccccgaaaa gtgccacctg  12600
acgtctaaga aaccattatt atcatgacat taacctataa aaataggcgt atcacgaggc  12660
cctttcgtct tcaagaattg gtcgacgatc ttgctgcgtt cggatatttt cgtggagttc  12720
ccgccacaga cccggattga aggcgagatc cagcaactcg cgccagatca tcctgtgacg  12780
gaactttggc gcgtgatgac tggccaggac gtcggccgaa agagcgacaa gcagatcacg  12840
cttttcgaca gcgtcggatt tgcgatcgag gatttttcgg cgctgcgcta cgtccgcgac  12900
cgcgttgagg gatcaagcca cagcagccca ctcgaccttc tagccgaccc agacgagcca  12960
agggatcttt ttggaatgct gctccgtcgt caggctttcc gacgtttggg tggttgaaca  13020
gaagtcatta tcgcacggaa tgccaagcac tcccgagggg aaccctgtgg ttggcatgca  13080
catacaaatg gacgaacgga taaacctttt cacgcccttt taaatatccg attattctaa  13140
taaacgctct tttctcttag gtttacccgc caatatatcc tgtcaaacac tgatagttta  13200
aactgaaggc gggaaacgac aacctgatca tgagcggaga attaagggag tcacgttatg  13260
acccccgccg atgacgcggg acaagccgtt ttacgtttgg aactgacaga accgcaacgt  13320
tgaaggagcc actcagctta attaagtcta actcgagtta ctggtacgta ccaaatccat  13380
ggcacccaac cccatatcga cagaggatgt gaagaacagg taaatcacgc agaagaaccc  13440
atctctgata gcagctatcg attagaacaa cgaatccata ttgggtccgt gggaaatact  13500
tactgcacag gaagggggcg atctgacgag gccccgccac cggcctcgac ccgaggccga  13560
```

```
ggccgacgaa gcgccggcga gtacggcgcc gcggcggcct ctgcccgtgc cctctgcgcg  13620

tgggagggag aggccgcggt ggtgggggcg cgcgcgcgcg cgcgcgcagc tggtgcggcg  13680

gcgcgggggt cagccgccga gccggcggcg acggaggagc agggcggcgt ggacgcgaac  13740

ttccgatcgg ttggtcagag tgcgcgagtt gggcttagcc aattaggtct caacaatcta  13800

ttgggccgta aaattcatgg gccctggttt gtctaggccc aatatcccgt tcatttcagc  13860

ccacaaatat ttccccagag gattattaag gcccacacgc agcttatagc agatcaagta  13920

cgatgtttcc tgatcgttgg atcggaaacg tacggtcttg atcaggcatg ccgacttcgt  13980

caaagagagg cggcatgacc tgacgcggag ttggttccgg gcaccgtctg gatggtcgta  14040

ccgggaccgg acacgtgtcg cgcctccaac tacatggaca cgtgtggtgc tgccattggg  14100

ccgtacgcgt ggcggtgacc gcaccggatg ctgcctcgca ccgccttgcc cacgctttat  14160

atagagaggt tttctctcca ttaatcgcat agcgagtcga atcgaccgaa ggggaggggg  14220

agcgaagctt tgcgttctct aatcgcctcg tcaaggtaac taatcaatca cctcgtccta  14280

atcctcgaat ctctcgtggt gcccgtctaa tctcgcgatt ttgatgctcg tggtggaaag  14340

cgtaggagga tcccgtgcga gttagtctca atctctcagg gtttcgtgcg attttagggt  14400

gatccacctc ttaatcgagt tacggtttcg tgcgatttta gggtaatcct cttaatctct  14460

cattgattta gggtttcgtg agaatcgagg tagggatctg tgttatttat atcgatctaa  14520

tagatggatt ggttttgaga ttgttctgtc agatggggat tgtttcgata tattacccta  14580

atgatgtgtc agatggggat tgtttcgata tattacccta atgatgtgtc agatggggat  14640

tgtttcgata tattacccta atgatggata ataagagtag ttcacagtta tgttttgatc  14700

ctgccacata gtttgagttt tgtgatcaga tttagtttta cttatttgtg cttagttcgg  14760

atgggattgt tctgatattg ttccaataga tgaatagctc gttaggttaa aatctttagg  14820

ttgagttagg cgacacatag tttatttcct ctggatttgg attggaattg tgttcttagt  14880

tttttccccc tggatttgga ttggaattgt gtggagctgg gttagagaat tacatctgta  14940

tcgtgtacac ctacttgaac tgtagagctt gggttctaag gtcaatttaa tctgtattgt  15000

atctggctct ttgcctagtt gaactgtagt gctgatgttg tactgtgttt ttttacccgt  15060

tttatttgct ttactcgtgc aaatcaaatc tgtcagatgc tagaactagg tggctttatt  15120

ctgtgttctt acatagatct gttgtcctgt agttacttat gtcagttttg ttattatctg  15180

aagatatttt tggttgttgc ttgttgatgt ggtgtgagct gtgagcagcg ctcttatgat  15240

taatgatgct gtccaattgt agtgtagtat gatgtgattg atatgttcat ctattttgag  15300

ctgacagtac cgatatcgta ggatctggtg ccaacttatt ctccagctgc ttttttttac  15360

ctatgttaat tccaatcctt tcttgcctct tccagatcca gataatggcg aacaaacatt  15420

tgtccctctc cctcttcctc gtcctccttg gcctgtcggc cagcttggcc tccgggcaag  15480

tcgctactga tcccttccag tctcgctgta acgagtttca aaacaaaatt gatatcgcaa  15540

acgtcacggt taggtcggtc gcctacgtcg cggctggtca gaatatctct caagcagaag  15600

tcgcttcggt ttgcaaggca agcgtccagg cctccgtgga cctctgtaga gtgacaatga  15660

atattagcac ctcggatagg agccaccttt gggccgaggc ttggctgcct cgcaattata  15720

ctggacggtt cgtctccact gggaacgggg gcctggctgg atgcgtgcag gaaacagact  15780

tgaatttcgc tgccaacttt ggcttcgcaa ccgttggcac taatggaggg cacgatggag  15840

acacggcgaa atactttctg aataactctg aggtcctcgc tgatttcgcc tatcgcagcg  15900

ttcacgaggg cactgtggtc gggaagcaac ttacccagtt gttctacgac gaaggttaca  15960
```

```
attattcgta ctatctgggc tgcagcaccg gaggcaggca aggctatcag caagtgcagc  16020

gctttccgga tgactacgat ggtgttattg ccggaagtgc agcgatgaac tttatcaatt  16080

tgatttcttg ggcgcttttt ctttggaagg ccacgggact cgcagacgac ccagatttta  16140

tctcagcgaa cctctggagc gttatccacc aggagattgt gcggcagtgt gacttggttg  16200

atggtgctct tgacggaatt attgaagatc ctgacttctg cgcccctgtt atcgagagac  16260

tgatttgtga tgggactacc aacggcacct cctgtatcac tggggcacaa gcggctaaag  16320

tgaatagggc cctctcggac ttttatggtc cggatgggac agtctactat ccacgcttga  16380

actacggagg ggaggcagac tctgcgagcc tgtacttcac aggctccatg tattcacgga  16440

ccgaagagtg gtacaagtac gtcgtgtaca acgatactaa ctggaatagt tctcaatgga  16500

cgctcgaaag cgctaagttg gccttggagc agaacccctt taatattcag gcattcgacc  16560

ctaatatcac agcgttcagg gaccgcggtg gaaaactctt gagctaccac ggcacccaag  16620

atccgattat ttcatcgact gacagcaagt tgtattacag aagagttgct aacgccctta  16680

acgctgcccc atccgaactc gacgagtttt atcgcttctt tcagatctct gggatgggtc  16740

actgcggcga cggaaccggg gcttcataca ttggccaggg atacggcacg tatacctcga  16800

aggccccaca ggtcaacttg cttcggacta tggtggattg ggttgagaat ggaaaagctc  16860

cggaatatat gcctgggaat aagttgaacg ccaacggttc gatcgagtat atgagaaagc  16920

actgtcgtta cccaaaacac aatattcaca cgggcccagg taactacacg gaccctaact  16980

cctggacctg cgtcagcgag aaggacgagc tgtgatcccc gaatttcccc gatcgttcaa  17040

acatttggca ataaagtttc ttaagattga atcctgttgc cggtcttgcg atgattatca  17100

tataatttct gttgaattac gttaagcatg taataattaa catgtaatgc atgacgttat  17160

ttatgagatg ggtttttatg attagagtcc cgcaattata catttaatac gcgatagaaa  17220

acaaaatata gcgcgcaaac taggataaat tatcgcgcgc ggtgtcatct atgttactag  17280

atcgggaatt gggtac                                                  17296
```

<210> SEQ ID NO 70
<211> LENGTH: 20454
<212> TYPE: DNA
<213> ORGANISM: Artificial Sequence
<220> FEATURE:
<223> OTHER INFORMATION: Synthetic construct, vector pAG2096

<400> SEQUENCE: 70

```
cgtcgactct agtaacggcc gccagtgtgc tggaattaat tcggcttgtc gaccacccaa     60

ccccatatcg acagaggatg tgaagaacag gtaaatcacg cagaagaacc catctctgat    120

agcagctatc gattagaaca acgaatccat attgggtccg tgggaaatac ttactgcaca    180

ggaagggggc gatctgacga ggccccgcca ccggcctcga cccgaggccg aggccgacga    240

agcgccggcg agtacggcgc cgcggcggcc tctgcccgtg ccctctgcgc gtgggaggga    300

gaggccgcgg tggtgggggc gcgcgcgcgc gcgcgcgcag ctggtgcggc ggcgcggggg    360

tcagccgccg agccggcggc gacggaggag cagggcggcg tggacgcgaa cttccgatcg    420

gttggtcaga gtgcgcgagt tgggcttagc caattaggtc tcaacaatct attgggccgt    480

aaaattcatg ggccctggtt tgtctaggcc caatatcccg ttcatttcag cccacaaata    540

tttccccaga ggattattaa ggcccacacg cagcttatag cagatcaagt acgatgtttc    600

ctgatcgttg gatcggaaac gtacggtctt gatcaggcat gccgacttcg tcaaagagag    660
```

```
gcggcatgac ctgacgcgga gttggttccg ggcaccgtct ggatggtcgt accgggaccg    720
gacacgtgtc gcgcctccaa ctacatggac acgtgtggtg ctgccattgg gccgtacgcg    780
tggcggtgac cgcaccggat gctgcctcgc accgccttgc ccacgcttta tatagagagg    840
ttttctctcc attaatcgca tagcgagtcg aatcgaccga aggggagggg gagcgaagct    900
ttgcgttctc taatcgcctc gtcaaggtaa ctaatcaatc acctcgtcct aatcctcgaa    960
tctctcgtgg tgcccgtcta atctcgcgat tttgatgctc gtggtggaaa gcgtaggagg   1020
atcccgtgcg agttagtctc aatctctcag ggtttcgtgc gattttaggg tgatccacct   1080
cttaatcgag ttacggtttc gtgcgatttt agggtaatcc tcttaatctc tcattgattt   1140
agggtttcgt gagaatcgag gtagggatct gtgttattta tatcgatcta atagatggat   1200
tggttttgag attgttctgt cagatgggga ttgtttcgat atattaccct aatgatgtgt   1260
cagatgggga ttgtttcgat atattaccct aatgatgtgt cagatgggga ttgtttcgat   1320
atattaccct aatgatggat aataagagta gttcacagtt atgttttgat cctgccacat   1380
agtttgagtt ttgtgatcag atttagtttt acttatttgt gcttagttcg gatgggattg   1440
ttctgatatt gttccaatag atgaatagct cgttaggtta aaatctttag gttgagttag   1500
gcgacacata gtttatttcc tctggatttg gattggaatt gtgttcttag tttttttccc   1560
ctggatttgg attggaattg tgtggagctg ggttagagaa ttacatctgt atcgtgtaca   1620
cctacttgaa ctgtagagct tgggttctaa ggtcaattta atctgtattg tatctggctc   1680
tttgcctagt tgaactgtag tgctgatgtt gtactgtgtt tttttacccg ttttatttgc   1740
tttactcgtg caaatcaaat ctgtcagatg ctagaactag gtggctttat tctgtgttct   1800
tacatagatc tgttgtcctg tagttactta tgtcagtttt gttattatct gaagatattt   1860
ttggttgttg cttgttgatg tggtgtgagc tgtgagcagc gctcttatga ttaatgatgc   1920
tgtccaattg tagtgtagta tgatgtgatt gatatgttca tctattttga gctgacagta   1980
ccgatatcgt aggatctggt gccaacttat tctccagctg ctttttttta cctatgttaa   2040
ttccaatcct ttcttgcctc ttccagatcc agataatggc gaacaaacat ttgtccctct   2100
ccctcttcct cgtcctcctt ggcctgtcgg ccagcttggc ctccgggcaa caaacaagca   2160
ttactctgac atccaacgca tccggtacgt ttgacggtta ctattacgaa ctctggaagg   2220
atactggcaa tacaacaatg acggtctaca ctcaaggtcg cttttcctgc cagtggtcga   2280
acatcaataa cgcgttgttt aggaccggga agaaatacaa ccagaattgg cagtctcttg   2340
gcacaatccg gatcacgtac tctgcgactt acaacccaaa cgggaactcc tacttgtgta   2400
tctatggctg gtctaccaac ccattggtcg agttctacat cgttgagtcc tgggggaact   2460
ggagaccgcc tggtgccacg tccctgggcc aagtgacaat cgatggcggg acctacgaca   2520
tctataggac gacacgcgtc aaccagcctt ccattgtggg gacagccacg ttcgatcagt   2580
actggagcgt gcgcacctct aagcggactt caggaacagt gaccgtgacc gatcacttcc   2640
gcgcctgggc gaaccggggc ctgaacctcg gcacaataga ccaaattaca ttgtgcgtgg   2700
agggttacca aagctctgga tcagccaaca tcacccagaa caccttctct cagggctctt   2760
cttccggcag ttcgggtggc tcatccggct ccacaacgac tactcgcatc gagtgtgaga   2820
acatgtcctt gtccggaccc tacgttagca ggatcaccaa tccctttaat ggtattgcgc   2880
tgtacgccaa cggagacaca gcccgcgcta ccgttaactt ccccgcaagt cgcaactaca   2940
atttccgcct gcggggttgc ggcaacaaca ataatcttgc ccgtgtggac ctgaggatcg   3000
acggacggac cgtcgggacc ttttattacc agggcacata cccctgggag gccccaattg   3060
```

```
acaatgttta tgtcagtgcg gggagtcata cagtcgaaat cactgttact gcggataacg   3120
gcacatggga cgtgtatgcc gactacctgg tgatacagtg acctaggtcc ccgaatttcc   3180
ccgatcgttc aaacatttgg caataaagtt tcttaagatt gaatcctgtt gccggtcttg   3240
cgatgattat catataattt ctgttgaatt acgttaagca tgtaataatt aacatgtaat   3300
gcatgacgtt atttatgaga tgggttttta tgattagagt cccgcaatta tacatttaat   3360
acgcgataga aaacaaaata tagcgcgcaa actaggataa attatcgcgc gcggtgtcat   3420
ctatgttact agatcgggaa ttggaattca tactaaagct tgcatgcctg caggtcgact   3480
ctagtaacgg ccgccagtgt gctggaatta attcggcttg tcgaccaccc aaccccatat   3540
cgacagagga tgtgaagaac aggtaaatca cgcagaagaa cccatctctg atagcagcta   3600
tcgattagaa caacgaatcc atattgggtc cgtgggaaat acttactgca caggaagggg   3660
gcgatctgac gaggccccgc caccggcctc gacccgaggc cgaggccgac gaagcgccgg   3720
cgagtacggc gccgcggcgg cctctgcccg tgccctctgc gcgtgggagg gagaggccgc   3780
ggtggtgggg gcgcgcgcgc gcgcgcgcgc agctggtgcg gcggcgcggg ggtcagccgc   3840
cgagccggcg gcgacggagg agcagggcgg cgtggacgcg aacttccgat cggttggtca   3900
gagtgcgcga gttgggctta gccaattagg tctcaacaat ctattgggcc gtaaaattca   3960
tgggccctgg tttgtctagg cccaatatcc cgttcatttc agcccacaaa tatttcccca   4020
gaggattatt aaggcccaca cgcagcttat agcagatcaa gtacgatgtt tcctgatcgt   4080
tggatcggaa acgtacggtc ttgatcaggc atgccgactt cgtcaaagag aggcggcatg   4140
acctgacgcg gagttggttc cgggcaccgt ctggatggtc gtaccgggac cggacacgtg   4200
tcgcgcctcc aactacatgg acacgtgtgg tgctgccatt gggccgtacg cgtggcggtg   4260
accgcaccgg atgctgcctc gcaccgcctt gcccacgctt tatatagaga ggttttctct   4320
ccattaatcg catagcgagt cgaatcgacc gaaggggagg gggagcgaag ctttgcgttc   4380
tctaatcgcc tcgtcaaggt aactaatcaa tcacctcgtc ctaatcctcg aatctctcgt   4440
ggtgcccgtc taatctcgcg attttgatgc tcgtggtgga aagcgtagga ggatcccgtg   4500
cgagttagtc tcaatctctc agggtttcgt gcgattttag ggtgatccac ctcttaatcg   4560
agttacggtt tcgtgcgatt ttagggtaat cctcttaatc tctcattgat ttagggtttc   4620
gtgagaatcg aggtagggat ctgtgttatt tatatcgatc taatagatgg attggttttg   4680
agattgttct gtcagatggg gattgtttcg atatattacc ctaatgatgt gtcagatggg   4740
gattgtttcg atatattacc ctaatgatgt gtcagatggg gattgtttcg atatattacc   4800
ctaatgatgg ataataagag tagttcacag ttatgttttg atcctgccac atagtttgag   4860
ttttgtgatc agatttagtt ttacttattt gtgcttagtt cggatgggat tgttctgata   4920
ttgttccaat agatgaatag ctcgttaggt taaaatcttt aggttgagtt aggcgacaca   4980
tagtttattt cctctggatt tggattggaa ttgtgttctt agttttttttc ccctggattt   5040
ggattggaat tgtgtggagc tgggttagag aattacatct gtatcgtgta cacctacttg   5100
aactgtagag cttgggttct aaggtcaatt taatctgtat tgtatctggc tctttgccta   5160
gttgaactgt agtgctgatg ttgtactgtg tttttttacc cgttttattt gctttactcg   5220
tgcaaatcaa atctgtcaga tgctagaact aggtggcttt attctgtgtt cttacataga   5280
tctgttgtcc tgtagttact tatgtcagtt ttgttattat ctgaagatat ttttggttgt   5340
tgcttgttga tgtggtgtga gctgtgagca gcgctcttat gattaatgat gctgtccaat   5400
```

```
tgtagtgtag tatgatgtga ttgatatgtt catctatttt gagctgacag taccgatatc   5460
gtaggatctg gtgccaactt attctccagc tgcttttttt tacctatgtt aattccaatc   5520
ctttcttgcc tcttccagat ccagataatg cagaaactca ttaactcagt gcaaaactat   5580
gcctggggca gcaaaacggc gttgactgaa ctttatggta tggaaaatcc gtccagccag   5640
ccgatggccg agctgtggat gggcgcacat ccgaaaagca gttcacgagt gcagaatgcc   5700
gccggagata tcgtttcact gcgtgatgtg attgagagtg ataaatcgac tctgctcgga   5760
gaggccgttg ccaaacgctt tggcgaactg cctttcctgt tcaaagtatt atgcgcagca   5820
cagccactct ccattcaggt tcatccaaac aaacacaatt ctgaaatcgg ttttgccaaa   5880
gaaaatgccg caggtatccc gatggatgcc gccgagcgta actataaaga tcctaaccac   5940
aagccggagc tggtttttgc gctgacgcct ttccttgcga tgaacgcgtt tcgtgaattt   6000
tccgagattg tctccctact ccagccggtc gcaggtgcac atccggcgat tgctcacttt   6060
ttacaacagc ctgatgccga acgtttaagc gaactgttcg ccagcctgtt gaatatgcag   6120
ggtgaagaaa aatcccgcgc gctggcgatt ttaaaatcgg ccctcgatag ccagcagggt   6180
gaaccgtggc aaacgattcg tttaatttct gaattttacc cggaagacag cggtctgttc   6240
tccccgctat tgctgaatgt ggtgaaattg aaccctggcg aagcgatgtt cctgttcgct   6300
gaaacaccgc acgcttacct gcaaggcgtg gcgctggaag tgatggcaaa ctccgataac   6360
gtgctgcgtg cgggtctgac gcctaaatac attgatattc cggaactggt tgccaatgtg   6420
aaattcgaag ccaaaccggc taaccagttg ttgacccagc cggtgaaaca aggtgcagaa   6480
ctggacttcc cgattccagt ggatgatttt gccttctcgc tgcatgacct tagtgataaa   6540
gaaaccacca ttagccagca gagtgccgcc attttgttct gcgtcgaagg cgatgcaacg   6600
ttgtggaaag gttctcagca gttacagctt aaaccgggtg aatcagcgtt tattgccgcc   6660
aacgaatcac cggtgactgt caaaggccac ggccgtttag cgcgtgttta caacaagctg   6720
taagagctta ctgaaaaaat taacatctct tgctaagctg ggagctctag atccccgaat   6780
ttccccgatc gttcaaacat ttggcaataa agtttcttaa gattgaatcc tgttgccggt   6840
cttgcgatga ttatcatata atttctgttg aattacgtta agcatgtaat aattaacatg   6900
taatgcatga cgttatttat gagatgggtt tttatgatta gagtcccgca attatacatt   6960
taatacgcga tagaaaacaa aatatagcgc gcaaactagg ataaattatc gcgcgcggtg   7020
tcatctatgt tactagatcg ggaattggcg agctcgaatt aattcagtac attaaaaacg   7080
tccgcaatgt gttattaagt tgtctaagcg tcaatttgtt tacaccacaa tatatcctgc   7140
caccagccag ccaacagctc cccgaccggc agctcggcac aaaatcacca ctcgatacag   7200
gcagcccatc agtccgggac ggcgtcagcg ggagagccgt tgtaaggcgg cagactttgc   7260
tcatgttacc gatgctattc ggaagaacgg caactaagct gccgggtttg aaacacggat   7320
gatctcgcgg agggtagcat gttgattgta acgatgacag agcgttgctg cctgtgatca   7380
aatatcatct ccctcgcaga gatccgaatt atcagccttc ttattcattt ctcgcttaac   7440
cgtgacaggc tgtcgatctt gagaactatg ccgacataat aggaaatcgc tggataaagc   7500
cgctgaggaa gctgagtggc gctatttctt tagaagtgaa cgttgacgat cgtcgaccgt   7560
accccgatga attaattcgg acgtacgttc tgaacacagc tggatactta cttgggcgat   7620
tgtcatacat gacatcaaca atgtacccgt ttgtgtaacc gtctcttgga ggttcgtatg   7680
acactagtgg ttcccctcag cttgcgacta gatgttgagg cctaacattt tattagagag   7740
caggctagtt gcttagatac atgatcttca ggccgttatc tgtcagggca agcgaaaatt   7800
```

```
ggccatttat gacgaccaat gccccgcaga agctcccatc tttgccgcca tagacgccgc   7860
gcccccccttt tggggtgtag aacatccttt tgccagatgt ggaaaagaag ttcgttgtcc   7920
cattgttggc aatgacgtag tagccggcga aagtgcgaga cccatttgcg ctatatataa   7980
gcctacgatt tccgttgcga ctattgtcgt aattggatga actattatcg tagttgctct   8040
cagagttgtc gtaatttgat ggactattgt cgtaattgct tatggagttg tcgtagttgc   8100
ttggagaaat gtcgtagttg gatggggagt agtcataggg aagacgagct tcatccacta   8160
aaacaattgg caggtcagca agtgcctgcc ccgatgccat cgcaagtacg aggcttagaa   8220
ccaccttcaa cagatcgcgc atagtcttcc ccagctctct aacgcttgag ttaagccgcg   8280
ccgcgaagcg gcgtcggctt gaacgaattg ttagacatta tttgccgact accttggtga   8340
tctcgccttt cacgtagtga acaaattctt ccaactgatc tgcgcgcgag gccaagcgat   8400
cttcttgtcc aagataagcc tgcctagctt caagtatgac gggctgatac tgggccggca   8460
ggcgctccat tgcccagtcg gcagcgacat ccttcggcgc gattttgccg gttactgcgc   8520
tgtaccaaat gcgggacaac gtaagcacta catttcgctc atcgccagcc cagtcgggcg   8580
gcgagttcca tagcgttaag gtttcattta gcgcctcaaa tagatcctgt tcaggaaccg   8640
gatcaaagag ttcctccgcc gctggaccta ccaaggcaac gctatgttct cttgcttttg   8700
tcagcaagat agccagatca atgtcgatcg tggctggctc gaagatacct gcaagaatgt   8760
cattgcgctg ccattctcca aattgcagtt cgcgcttagc tggataacgc cacggaatga   8820
tgtcgtcgtg cacaacaatg gtgacttcta cagcgcggag aatctcgctc tctccagggg   8880
aagccgaagt ttccaaaagg tcgttgatca aagctcgccg cgttgtttca tcaagcctta   8940
cggtcaccgt aaccagcaaa tcaatatcac tgtgtggctt caggccgcca tccactgcgg   9000
agccgtacaa atgtacggcc agcaacgtcg gttcgagatg gcgctcgatg acgccaacta   9060
cctctgatag ttgagtcgat acttcggcga tcaccgcttc cctcatgatg tttaactcct   9120
gaattaagcc gcgccgcgaa gcggtgtcgg cttgaatgaa ttgttaggcg tcatcctgtg   9180
ctcccgagaa ccagtaccag tacatcgctg tttcgttcga gacttgaggt ctagttttat   9240
acgtgaacag gtcaatgccg ccgagagtaa agccacattt tgcgtacaaa ttgcaggcag   9300
gtacattgtt cgtttgtgtc tctaatcgta tgccaaggag ctgtctgctt agtgcccact   9360
ttttcgcaaa ttcgatgaga ctgtgcgcga ctcctttgcc tcggtgcgtg tgcgacacaa   9420
caatgtgttc gatagaggct agatcgttcc atgttgagtt gagttcaatc ttcccgacaa   9480
gctcttggtc gatgaatgcg ccatagcaag cagagtcttc atcagagtca tcatccgaga   9540
tgtaatcctt ccggtagggg ctcacacttc tggtagatag ttcaaagcct tggtcggata   9600
ggtgcacatc gaacacttca cgaacaatga aatggttctc agcatccaat gtttccgcca   9660
cctgctcagg gatcaccgaa atcttcatat gacgcctaac gcctggcaca gcggatcgca   9720
aacctggcgc ggcttttggc acaaaaggcg tgacaggttt gcgaatccgt tgctgccact   9780
tgttaaccct tttgccagat ttggtaacta taatttatgt tagaggcgaa gtcttgggta   9840
aaaactggcc taaaattgct ggggatttca ggaaagtaaa catcaccttc cggctcgatg   9900
tctattgtag atatatgtag tgtatctact tgatcggggg atctgctgcc tcgcgcgttt   9960
cggtgatgac ggtgaaaacc tctgacacat gcagctcccg gagacggtca cagcttgtct  10020
gtaagcggat gccgggagca gacaagcccg tcagggcgcg tcagcgggtg ttggcgggtg  10080
tcggggcgca gccatgaccc agtcacgtag cgatagcgga gtgtatactg gcttaactat  10140
```

```
gcggcatcag agcagattgt actgagagtg caccatatgc ggtgtgaaat accgcacaga  10200
tgcgtaagga gaaaataccg catcaggcgc tcttccgctt cctcgctcac tgactcgctg  10260
cgctcggtcg ttcggctgcg gcgagcggta tcagctcact caaaggcggt aatacggtta  10320
tccacagaat caggggataa cgcaggaaag aacatgtgag caaaaggcca gcaaaaggcc  10380
aggaaccgta aaaaggccgc gttgctggcg tttttccata ggctccgccc ccctgacgag  10440
catcacaaaa atcgacgctc aagtcagagg tggcgaaacc cgacaggact ataaagatac  10500
caggcgtttc cccctggaag ctccctcgtg cgctctcctg ttccgaccct gccgcttacc  10560
ggatacctgt ccgcctttct cccttcggga agcgtggcgc tttctcatag ctcacgctgt  10620
aggtatctca gttcggtgta ggtcgttcgc tccaagctgg gctgtgtgca cgaacccccc  10680
gttcagcccg accgctgcgc cttatccggt aactatcgtc ttgagtccaa cccggtaaga  10740
cacgacttat cgccactggc agcagccact ggtaacagga ttagcagagc gaggtatgta  10800
ggcggtgcta cagagttctt gaagtggtgg cctaactacg gctacactag aaggacagta  10860
tttggtatct gcgctctgct gaagccagtt accttcggaa aaagagttgg tagctcttga  10920
tccggcaaac aaaccaccgc tggtagcggt ggtttttttg tttgcaagca gcagattacg  10980
cgcagaaaaa aaggatctca agaagatcct ttgatctttt ctacggggtc tgacgctcag  11040
tggaacgaaa actcacgtta agggattttg gtcatgagat tatcaaaaag gatcttcacc  11100
tagatccttt taaattaaaa atgaagtttt aaatcaatct aaagtatata tgagtaaact  11160
tggtctgaca gttaccaatg cttaatcagt gaggcaccta tctcagcgat ctgtctattt  11220
cgttcatcca tagttgcctg actccccgtc gtgtagataa ctacgatacg ggagggctta  11280
ccatctggcc ccagtgctgc aatgataccg cgagacccac gctcaccggc tccagattta  11340
tcagcaataa accagccagc cggaagggcc gagcgcagaa gtggtcctgc aactttatcc  11400
gcctccatcc agtctattaa ttgttgccgg gaagctagag taagtagttc gccagttaat  11460
agtttgcgca acgttgttgc cattgctgca gggggggggg ggggggggtt ccattgttca  11520
ttccacggac aaaaacagag aaaggaaacg acagaggcca aaaagctcgc tttcagcacc  11580
tgtcgtttcc tttcttttca gagggtattt taaataaaaa cattaagtta tgacgaagaa  11640
gaacggaaac gccttaaacc ggaaaatttt cataaatagc gaaaacccgc gaggtcgccg  11700
ccccgtaacc tgtcggatca ccggaaagga cccgtaaagt gataatgatt atcatctaca  11760
tatcacaacg tgcgtggagg ccatcaaacc acgtcaaata atcaattatg acgcaggtat  11820
cgtattaatt gatctgcatc aacttaacgt aaaaacaact tcagacaata caaatcagcg  11880
acactgaata cggggcaacc tcatgtcccc cccccccccc ccctgcaggc atcgtggtgt  11940
cacgctcgtc gtttggtatg gcttcattca gctccggttc ccaacgatca aggcgagtta  12000
catgatcccc catgttgtgc aaaaaagcgg ttagctcctt cggtcctccg atcgttgtca  12060
gaagtaagtt ggccgcagtg ttatcactca tggttatggc agcactgcat aattctctta  12120
ctgtcatgcc atccgtaaga tgcttttctg tgactggtga gtactcaacc aagtcattct  12180
gagaatagtg tatgcggcga ccgagttgct cttgcccggc gtcaacacgg gataataccg  12240
cgccacatag cagaacttta aaagtgctca tcattggaaa acgttcttcg gggcgaaaac  12300
tctcaaggat cttaccgctg ttgagatcca gttcgatgta acccactcgt gcacccaact  12360
gatcttcagc atcttttact ttcaccagcg tttctgggtg agcaaaaaca ggaaggcaaa  12420
atgccgcaaa aaagggaata agggcgacac ggaaatgttg aatactcata ctcttccttt  12480
ttcaatatta ttgaagcatt tatcagggtt attgtctcat gagcggatac atatttgaat  12540
```

gtatttagaa aaataaacaa ataggggttc cgcgcacatt tccccgaaaa gtgccacctg 12600
acgtctaaga aaccattatt atcatgacat taacctataa aaataggcgt atcacgaggc 12660
cctttcgtct tcaagaattg gtcgacgatc ttgctgcgtt cggatatttt cgtggagttc 12720
ccgccacaga cccggattga aggcgagatc cagcaactcg cgccagatca tcctgtgacg 12780
gaactttggc gcgtgatgac tggccaggac gtcggccgaa agagcgacaa gcagatcacg 12840
cttttcgaca gcgtcggatt tgcgatcgag gatttttcgg cgctgcgcta cgtccgcgac 12900
cgcgttgagg gatcaagcca cagcagccca ctcgaccttc tagccgaccc agacgagcca 12960
agggatcttt ttggaatgct gctccgtcgt caggctttcc gacgtttggg tggttgaaca 13020
gaagtcatta tcgcacggaa tgccaagcac tcccgagggg aaccctgtgg ttggcatgca 13080
catacaaatg gacgaacgga taaacctttt cacgcccttt taaatatccg attattctaa 13140
taaacgctct tttctcttag gtttacccgc caatatatcc tgtcaaacac tgatagttta 13200
aactgaaggc gggaaacgac aacctgatca tgagcggaga attaagggag tcacgttatg 13260
acccccgccg atgacgcggg acaagccgtt ttacgtttgg aactgacaga accgcaacgt 13320
tgaaggagcc actcagctta attaagtcta actcgagcac ccaaccccat atcgacagag 13380
gatgtgaaga acaggtaaat cacgcagaag aacccatctc tgatagcagc tatcgattag 13440
aacaacgaat ccatattggg tccgtgggaa atacttactg cacaggaagg gggcgatctg 13500
acgaggcccc gccaccggcc tcgacccgag gccgaggccg acgaagcgcc ggcgagtacg 13560
gcgccgcggc ggcctctgcc cgtgccctct gcgcgtggga gggagaggcc gcggtggtgg 13620
gggcgcgcgc gcgcgcgcgc gcagctggtg cggcggcgcg ggggtcagcc gccgagccgg 13680
cggcgacgga ggagcagggc ggcgtggacg cgaacttccg atcggttggt cagagtgcgc 13740
gagttgggct tagccaatta ggtctcaaca atctattggg ccgtaaaatt catgggccct 13800
ggtttgtcta ggcccaatat cccgttcatt tcagcccaca aatatttccc cagaggatta 13860
ttaaggccca cacgcagctt atagcagatc aagtacgatg tttcctgatc gttggatcgg 13920
aaacgtacgg tcttgatcag gcatgccgac ttcgtcaaag agaggcggca tgacctgacg 13980
cggagttggt tccgggcacc gtctggatgg tcgtaccggg accggacacg tgtcgcgcct 14040
ccaactacat ggacacgtgt ggtgctgcca ttgggccgta cgcgtggcgg tgaccgcacc 14100
ggatgctgcc tcgcaccgcc ttgcccacgc tttatataga gaggttttct ctccattaat 14160
cgcatagcga gtcgaatcga ccgaagggga gggggagcga agctttgcgt tctctaatcg 14220
cctcgtcaag gtaactaatc aatcacctcg tcctaatcct cgaatctctc gtggtgcccg 14280
tctaatctcg cgattttgat gctcgtggtg gaaagcgtag gaggatcccg tgcgagttag 14340
tctcaatctc tcagggtttc gtgcgatttt agggtgatcc acctcttaat cgagttacgg 14400
tttcgtgcga ttttagggta atcctcttaa tctctcattg atttagggtt tcgtgagaat 14460
cgaggtaggg atctgtgtta tttatatcga tctaatagat ggattggttt tgagattgtt 14520
ctgtcagatg gggattgttt cgatatatta ccctaatgat gtgtcagatg gggattgttt 14580
cgatatatta ccctaatgat gtgtcagatg gggattgttt cgatatatta ccctaatgat 14640
ggataataag agtagttcac agttatgttt tgatcctgcc acatagtttg agttttgtga 14700
tcagatttag ttttacttat ttgtgcttag ttcggatggg attgttctga tattgttcca 14760
atagatgaat agctcgttag gttaaaatct ttaggttgag ttaggcgaca catagtttat 14820
ttcctctgga tttggattgg aattgtgttc ttagtttttt tcccctggat ttggattgga 14880

```
attgtgtgga gctgggttag agaattacat ctgtatcgtg tacacctact tgaactgtag  14940
agcttgggtt ctaaggtcaa tttaatctgt attgtatctg gctctttgcc tagttgaact  15000
gtagtgctga tgttgtactg tgttttttta cccgttttat ttgctttact cgtgcaaatc  15060
aaatctgtca gatgctagaa ctaggtggct ttattctgtg ttcttacata gatctgttgt  15120
cctgtagtta cttatgtcag ttttgttatt atctgaagat atttttggtt gttgcttgtt  15180
gatgtggtgt gagctgtgag cagcgctctt atgattaatg atgctgtcca attgtagtgt  15240
agtatgatgt gattgatatg ttcatctatt ttgagctgac agtaccgata tcgtaggatc  15300
tggtgccaac ttattctcca gctgcttttt tttacctatg ttaattccaa tcctttcttg  15360
cctcttccag atccagataa tggcgaacaa acatttgtcc ctctccctct tcctcgtcct  15420
ccttggcctg tcggccagct tggcctccgg gcaagtcgca tccacgcagg gtatctctga  15480
ggacctgtat aatcgcctcg tggaaatggc cacaatttca caagcggctt acgcagatct  15540
ttgtaatatc ccttcgacaa ttatcaaggg agagaaaatc tataacgccc agactgacat  15600
caacggctgg atactgcggg atgacacgag caaggaaatt atcacagtct ttagagggac  15660
cggttccgat acaaatttgc agttggacac gaattacaca ctgaccccct tcgatactct  15720
ccctcaatgc aacgactgtg aggttcacgg tgggtactat attggctgga tctctgttca  15780
agaccaagtc gagtcacttg ttaagcagca agcgtcgcag tacccggact acgcattgac  15840
ggtgacaggg cacagcctgg gtgcctcgat ggcagcgctc accgctgccc agctttctgc  15900
aacctacgat aatgtcaggc tgtacacttt cggagaacca cgctcaggca accaagcgtt  15960
tgcttcgtat atgaacgacg ctttccaggt tagctccccc gagacgacac aatactttcg  16020
ggtgacccat tctaacgacg ggattcctaa cctcccgcca gccgacgaag gttacgcaca  16080
cgggggtgtc gagtactggt cagtggaccc ctacagcgcg cagaatactt tcgtttgcac  16140
gggcgatgag gtccagtgct gtgaagctca agggggtcag ggagtgaatg atgcacacac  16200
aacctatttc ggaatgactt ccggggcttg cacgtggagc gagaaggacg agctgtgatc  16260
cccgaatttc cccgatcgtt caaacatttg gcaataaagt ttcttaagat tgaatcctgt  16320
tgccggtctt gcgatgatta tcatataatt tctgttgaat tacgttaagc atgtaataat  16380
taacatgtaa tgcatgacgt tatttatgag atgggttttt atgattagag tcccgcaatt  16440
atacatttaa tacgcgatag aaaacaaaat atagcgcgca aactaggata aattatcgcg  16500
cgcggtgtca tctatgttac tagatcggga attgccatgg cacccaaccc catatcgaca  16560
gaggatgtga agaacaggta aatcacgcag aagaacccat ctctgatagc agctatcgat  16620
tagaacaacg aatccatatt gggtccgtgg gaaatactta ctgcacagga agggggcgat  16680
ctgacgaggc cccgccaccg gcctcgaccc gaggccgagg ccgacgaagc gccggcgagt  16740
acggcgccgc ggcggcctct gcccgtgccc tctgcgcgtg ggagggagag gccgcggtgg  16800
tgggggcgcg cgcgcgcgcg cgcgcagctg gtgcggcggc gcgggggtca gccgccgagc  16860
cggcggcgac ggaggagcag ggcggcgtgg acgcgaactt ccgatcggtt ggtcagagtg  16920
cgcgagttgg gcttagccaa ttaggtctca acaatctatt gggccgtaaa attcatgggc  16980
cctggtttgt ctaggcccaa tatcccgttc atttcagccc acaaatattt ccccagagga  17040
ttattaaggc ccacacgcag cttatagcag atcaagtacg atgtttcctg atcgttggat  17100
cggaaacgta cggtcttgat caggcatgcc gacttcgtca aagagaggcg gcatgacctg  17160
acgcggagtt ggttccgggc accgtctgga tggtcgtacc gggaccggac acgtgtcgcg  17220
cctccaacta catggacacg tgtggtgctg ccattgggcc gtacgcgtgg cggtgaccgc  17280
```

```
accggatgct gcctcgcacc gccttgccca cgctttatat agagaggttt tctctccatt  17340
aatcgcatag cgagtcgaat cgaccgaagg ggaggggggag cgaagctttg cgttctctaa  17400
tcgcctcgtc aaggtaacta atcaatcacc tcgtcctaat cctcgaatct ctcgtggtgc  17460
ccgtctaatc tcgcgatttt gatgctcgtg gtggaaagcg taggaggatc ccgtgcgagt  17520
tagtctcaat ctctcagggt ttcgtgcgat tttagggtga tccacctctt aatcgagtta  17580
cggtttcgtg cgattttagg gtaatcctct taatctctca ttgatttagg gtttcgtgag  17640
aatcgaggta gggatctgtg ttatttatat cgatctaata gatggattgg ttttgagatt  17700
gttctgtcag atggggattg tttcgatata ttaccctaat gatgtgtcag atggggattg  17760
tttcgatata ttaccctaat gatgtgtcag atggggattg tttcgatata ttaccctaat  17820
gatggataat aagagtagtt cacagttatg ttttgatcct gccacatagt ttgagttttg  17880
tgatcagatt tagttttact tatttgtgct tagttcggat gggattgttc tgatattgtt  17940
ccaatagatg aatagctcgt taggttaaaa tctttaggtt gagttaggcg acacatagtt  18000
tatttcctct ggatttggat tggaattgtg ttcttagttt ttttcccctg gatttggatt  18060
ggaattgtgt ggagctgggt tagagaatta catctgtatc gtgtacacct acttgaactg  18120
tagagcttgg gttctaaggt caatttaatc tgtattgtat ctggctcttt gcctagttga  18180
actgtagtgc tgatgttgta ctgtgttttt ttacccgttt tatttgcttt actcgtgcaa  18240
atcaaatctg tcagatgcta gaactaggtg gctttattct gtgttcttac atagatctgt  18300
tgtcctgtag ttacttatgt cagttttgtt attatctgaa gatatttttg gttgttgctt  18360
gttgatgtgg tgtgagctgt gagcagcgct cttatgatta atgatgctgt ccaattgtag  18420
tgtagtatga tgtgattgat atgttcatct attttgagct gacagtaccg atatcgtagg  18480
atctggtgcc aacttattct ccagctgctt ttttttacct atgttaattc caatcctttc  18540
ttgcctcttc cagatccaga taatggcgaa caaacatttg tccctctccc tcttcctcgt  18600
cctccttggc ctgtcggcca gcttggcctc cgggcaagtc gctactgatc ccttccagtc  18660
tcgctgtaac gagtttcaaa acaaaattga tatcgcaaac gtcacggtta ggtcggtcgc  18720
ctacgtcgcg gctggtcaga atatctctca agcagaagtc gcttcggttt gcaaggcaag  18780
cgtccaggcc tccgtggacc tctgtagagt gacaatgaat attagcacct cggataggag  18840
ccacctttgg gccgaggctt ggctgcctcg caattatact ggacggttcg tctccactgg  18900
gaacgggggc ctggctggat gcgtgcagga aacagacttg aatttcgctg ccaactttgg  18960
cttcgcaacc gttggcacta atggagggca cgatggagac acggcgaaat actttctgaa  19020
taactctgag gtcctcgctg atttcgccta tcgcagcgtt cacgagggca ctgtggtcgg  19080
gaagcaactt acccagttgt tctacgacga aggttacaat tattcgtact atctgggctg  19140
cagcaccgga ggcaggcaag gctatcagca agtgcagcgc tttccggatg actacgatgg  19200
tgttattgcc ggaagtgcag cgatgaactt tatcaatttg atttcttggg gcgcttttct  19260
ttggaaggcc acgggactcg cagacgaccc agattttatc tcagcgaacc tctggagcgt  19320
tatccaccag gagattgtgc ggcagtgtga cttggttgat ggtgctcttg acggaattat  19380
tgaagatcct gacttctgcg cccctgttat cgagagactg atttgtgatg ggactaccaa  19440
cggcacctcc tgtatcactg gggcacaagc ggctaaagtg aatagggccc tctcggactt  19500
ttatggtccg gatgggacag tctactatcc acgcttgaac tacggagggg aggcagactc  19560
tgcgagcctg tacttcacag gctccatgta ttcacggacc gaagagtggt acaagtacgt  19620
```

cgtgtacaac gatactaact ggaatagttc tcaatggacg ctcgaaagcg ctaagttggc 19680
cttggagcag aacccctta atattcaggc attcgaccct aatatcacag cgttcaggga 19740
ccgcggtgga aaactcttga gctaccacgg cacccaagat ccgattattt catcgactga 19800
cagcaagttg tattacagaa gagttgctaa cgcccttaac gctgccccat ccgaactcga 19860
cgagttttat cgcttctttc agatctctgg gatgggtcac tgcggcgacg gaaccggggc 19920
ttcatacatt ggccagggat acggcacgta tacctcgaag gccccacagg tcaacttgct 19980
tcggactatg gtggattggg ttgagaatgg aaaagctccg gaatatatgc ctgggaataa 20040
gttgaacgcc aacggttcga tcgagtatat gagaaagcac tgtcgttacc caaaacacaa 20100
tattcacacg ggcccaggta actacacgga ccctaactcc tggacctgcg tcagcgagaa 20160
ggacgagctg tgatccccga atttccccga tcgttcaaac atttggcaat aaagtttctt 20220
aagattgaat cctgttgccg gtcttgcgat gattatcata taatttctgt tgaattacgt 20280
taagcatgta ataattaaca tgtaatgcat gacgttattt atgagatggg tttttatgat 20340
tagagtcccg caattataca tttaatacgc gatagaaaac aaaatatagc gcgcaaacta 20400
ggataaatta tcgcgcgcgg tgtcatctat gttactagat cgggaattgg gtac 20454

<210> SEQ ID NO 71
<211> LENGTH: 13540
<212> TYPE: DNA
<213> ORGANISM: Artificial Sequence
<220> FEATURE:
<223> OTHER INFORMATION: Synthetic construct, vector pAG2201

<400> SEQUENCE: 71
aattcatact aaagcttgca tgcctgcagg tcgactctag taacggccgc cagtgtgctg 60
gaattaattc ggcttgtcga ccacccaacc ccatatcgac agaggatgtg aagaacaggt 120
aaatcacgca gaagaaccca tctctgatag cagctatcga ttagaacaac gaatccatat 180
tgggtccgtg ggaaatactt actgcacagg aagggggcga tctgacgagg ccccgccacc 240
ggcctcgacc cgaggccgag gccgacgaag cgccggcgag tacggcgccg cggcggcctc 300
tgcccgtgcc ctctgcgcgt gggagggaga ggccgcggtg gtgggggcgc gcgcgcgcgc 360
gcgcgcagct ggtgcggcgg cgcgggggtc agccgccgag ccggcggcga cggaggagca 420
gggcggcgtg gacgcgaact tccgatcggt tggtcagagt gcgcgagttg ggcttagcca 480
attaggtctc aacaatctat tgggccgtaa aattcatggg ccctggtttg tctaggccca 540
atatcccgtt catttcagcc cacaaatatt tccccagagg attattaagg cccacacgca 600
gcttatagca gatcaagtac gatgtttcct gatcgttgga tcggaaacgt acggtcttga 660
tcaggcatgc cgacttcgtc aaagagaggc ggcatgacct gacgcggagt tggttccggg 720
caccgtctgg atggtcgtac cgggaccgga cacgtgtcgc gcctccaact acatggacac 780
gtgtggtgct gccattgggc cgtacgcgtg gcggtgaccg caccggatgc tgcctcgcac 840
cgccttgccc acgctttata tagagaggtt ttctctccat taatcgcata gcgagtcgaa 900
tcgaccgaag gggagggga gcgaagcttt gcgttctcta atcgcctcgt caaggtaact 960
aatcaatcac ctcgtcctaa tcctcgaatc tctcgtggtg cccgtctaat ctcgcgattt 1020
tgatgctcgt ggtggaaagc gtaggaggat cccgtgcgag ttagtctcaa tctctcaggg 1080
tttcgtgcga ttttagggtg atccacctct taatcgagtt acggtttcgt gcgattttag 1140
ggtaatcctc ttaatctctc attgatttag ggtttcgtga gaatcgaggt agggatctgt 1200
gttatttata tcgatctaat agatggattg gttttgagat tgttctgtca gatggggatt 1260

-continued

```
gtttcgatat attaccctaa tgatgtgtca gatggggatt gtttcgatat attaccctaa   1320
tgatgtgtca gatggggatt gtttcgatat attaccctaa tgatggataa taagagtagt   1380
tcacagttat gttttgatcc tgccacatag tttgagtttt gtgatcagat ttagttttac   1440
ttatttgtgc ttagttcgga tgggattgtt ctgatattgt tccaatagat gaatagctcg   1500
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct ttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt ttttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
```

```
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc ccttttgggg gtgtagaaca   4440
tccttttgcc agatgtggaa aagaagttcg ttgtcccatt gttggcaatg acgtagtagc   4500
cggcgaaagt gcgagaccca tttgcgctat atataagcct acgatttccg ttgcgactat   4560
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
cgacatcctt cggcgcgatt ttgccggtta ctgcgctgta ccaaatgcgg gacaacgtaa   5100
gcactacatt tcgctcatcg ccagcccagt cgggcggcga gttccatagc gttaaggttt   5160
catttagcgc ctcaaataga tcctgttcag gaaccggatc aaagagttcc tccgccgctg   5220
gacctaccaa ggcaacgcta tgttctcttg cttttgtcag caagatagcc agatcaatgt   5280
cgatcgtggc tggctcgaag atacctgcaa gaatgtcatt gcgctgccat tctccaaatt   5340
gcagttcgcg cttagctgga taacgccacg gaatgatgtc gtcgtgcaca acaatggtga   5400
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
```

```
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aacccttttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
```

```
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg cccttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
```

```
gcaccggatg ctgcctcgca ccgccttgcc cacgctttat atagagaggt tttctctcca  10800

ttaatcgcat agcgagtcga atcgaccgaa ggggaggggg agcgaagctt tgcgttctct  10860

aatcgcctcg tcaaggtaac taatcaatca cctcgtccta atcctcgaat ctctcgtggt  10920

gcccgtctaa tctcgcgatt ttgatgctcg tggtggaaag cgtaggagga tcccgtgcga  10980

gttagtctca atctctcagg gtttcgtgcg attttagggt gatccacctc ttaatcgagt  11040

tacggtttcg tgcgatttta gggtaatcct cttaatctct cattgattta gggtttcgtg  11100

agaatcgagg tagggatctg tgttatttat atcgatctaa tagatggatt ggttttgaga  11160

ttgttctgtc agatggggat tgtttcgata tattacccta atgatgtgtc agatggggat  11220

tgtttcgata tattacccta atgatgtgtc agatggggat tgtttcgata tattacccta  11280

atgatggata ataagagtag ttcacagtta tgttttgatc ctgccacata gtttgagttt  11340

tgtgatcaga tttagtttta cttatttgtg cttagttcgg atgggattgt tctgatattg  11400

ttccaataga tgaatagctc gttaggttaa aatctttagg ttgagttagg cgacacatag  11460

tttatttcct ctggatttgg attggaattg tgttcttagt tttttcccc tggatttgga  11520

ttggaattgt gtggagctgg gttagagaat tacatctgta tcgtgtacac ctacttgaac  11580

tgtagagctt gggttctaag gtcaatttaa tctgtattgt atctggctct ttgcctagtt  11640

gaactgtagt gctgatgttg tactgtgttt ttttacccgt tttatttgct ttactcgtgc  11700

aaatcaaatc tgtcagatgc tagaactagg tggctttatt ctgtgttctt acatagatct  11760

gttgtcctgt agttacttat gtcagttttg ttattatctg aagatatttt tggttgttgc  11820

ttgttgatgt ggtgtgagct gtgagcagcg ctcttatgat taatgatgct gtccaattgt  11880

agtgtagtat gatgtgattg atatgttcat ctattttgag ctgacagtac cgatatcgta  11940

ggatctggtg ccaacttatt ctccagctgc ttttttttac ctatgttaat tccaatcctt  12000

tcttgcctct tccagatgca gatctttgtg aagaccctga ccggcaagac tatcaccctc  12060

gaggtggagt cttctgacac cattgacaat gtcaaggcca agatccagga caaggagggc  12120

atccccccag accagcagcg gctcatcttt gctggcaagc agctggagga cgggcgcacg  12180

cttgcggact acaacatcca gaaggagagc accctccacc tggtgctccg cctcagggga  12240

ggcatgcaaa caagcattac tctgacatcc aacgcatccg gtacgtttga cggttactat  12300

tacgaactct ggaaggatac tggcaataca acaatgacgg tctacactca aggtcgcttt  12360

tcctgccagt ggtcgaacat caataacgcg ttgtttagga ccgggaagaa atacaaccag  12420

aattggcagt ctcttggcac aatccggatc acgtactctg cgacttacaa cccaaacggg  12480

aactcctact tgtgtatcta tggctggtct accaacccat tggtcgagtt ctacatcgtt  12540

gagtcctggg ggaactggag accgcctggt gccacgtccc tgggccaagt gacaatcgat  12600

ggcgggacct acgacatcta taggacgaca cgcgtcaacc agccttccat tgtggggaca  12660

gccacgttcg atcagtactg gagcgtgcgc acctctaagc ggacttcagg aacagtgacc  12720

gtgaccgatc acttccgcgc ctgggcgaac cggggcctga acctcggcac aatagaccaa  12780

attacattgt gcgtggaggg ttaccaaagc tctggatcag ccaacatcac ccagaacacc  12840

ttctctcagg gctcttcttc cggcagttcg ggtggctcat ccggctccac aacgactact  12900

cgcatcgagt gtgagaacat gtccttgtcc ggaccctacg ttagcaggat caccaatccc  12960

tttaatggta ttgcgctgta cgccaacgga gacacagccc gcgctaccgt taacttcccc  13020

gcaagtcgca actacaattt ccgcctgcgg ggttgcggca acaacaataa tcttgcccgt  13080
```

```
gtggacctga ggatcgacgg acggaccgtc gggacctttt attaccaggg cacataccc  13140

tgggaggccc caattgacaa tgtttatgtc agtgcgggga gtcatacagt cgaaatcact  13200

gttactgcgg ataacggcac atgggacgtg tatgccgact acctggtgat acagtgacct  13260

aggtccccga atttccccga tcgttcaaac atttggcaat aaagtttctt aagattgaat  13320

cctgttgccg gtcttgcgat gattatcata taatttctgt tgaattacgt taagcatgta  13380

ataattaaca tgtaatgcat gacgttattt atgagatggg tttttatgat tagagtcccg  13440

caattataca tttaatacgc gatagaaaac aaaatatagc gcgcaaacta ggataaatta  13500

tcgcgcgcgg tgtcatctat gttactagat cgggaattgg                       13540
```

<210> SEQ ID NO 72
<211> LENGTH: 14683
<212> TYPE: DNA
<213> ORGANISM: Artificial Sequence
<220> FEATURE:
<223> OTHER INFORMATION: Synthetic construct, vector pAG2229

<400> SEQUENCE: 72

```
aattcatact aaagcttgca tgcctgcagg tcgactctag taacggccgc cagtgtgctg     60

gaattaattc ggcttgtcga ccacccaacc ccatatcgac agaggatgtg aagaacaggt    120

aaatcacgca gaagaaccca tctctgatag cagctatcga ttagaacaac gaatccatat    180

tgggtccgtg ggaaatactt actgcacagg aagggggcga tctgacgagg ccccgccacc    240

ggcctcgacc cgaggccgag gccgacgaag cgccggcgag tacggcgccg cggcggcctc    300

tgcccgtgcc ctctgcgcgt gggagggaga ggccgcggtg gtgggggcgc gcgcgcgcgc    360

gcgcgcagct ggtgcggcgg cgcgggggtc agccgccgag ccggcggcga cggaggagca    420

gggcggcgtg gacgcgaact tccgatcggt tggtcagagt gcgcgagttg ggcttagcca    480

attaggtctc aacaatctat tgggccgtaa aattcatggg ccctggtttg tctaggccca    540

atatcccgtt catttcagcc cacaaatatt tccccagagg attattaagg cccacacgca    600

gcttatagca gatcaagtac gatgtttcct gatcgttgga tcggaaacgt acggtcttga    660

tcaggcatgc cgacttcgtc aaagagaggc ggcatgacct gacgcggagt tggttccggg    720

caccgtctgg atggtcgtac cgggaccgga cacgtgtcgc gcctccaact acatggacac    780

gtgtggtgct gccattgggc cgtacgcgtg gcggtgaccg caccggatgc tgcctcgcac    840

cgccttgccc acgctttata tagagaggtt ttctctccat taatcgcata gcgagtcgaa    900

tcgaccgaag gggagggga gcgaagcttt gcgttctcta atcgcctcgt caaggtaact    960

aatcaatcac ctcgtcctaa tcctcgaatc tctcgtggtg cccgtctaat ctcgcgattt   1020

tgatgctcgt ggtggaaagc gtaggaggat cccgtgcgag ttagtctcaa tctctcaggg   1080

tttcgtgcga ttttagggtg atccacctct taatcgagtt acggtttcgt gcgattttag   1140

ggtaatcctc ttaatctctc attgatttag ggtttcgtga gaatcgaggt agggatctgt   1200

gttatttata tcgatctaat agatggattg gttttgagat tgttctgtca gatggggatt   1260

gtttcgatat attaccctaa tgatgtgtca gatggggatt gtttcgatat attaccctaa   1320

tgatgtgtca gatggggatt gtttcgatat attaccctaa tgatggataa taagagtagt   1380

tcacagttat gttttgatcc tgccacatag tttgagtttt gtgatcagat ttagttttac   1440

ttatttgtgc ttagttcgga tgggattgtt ctgatattgt tccaatagat gaatagctcg   1500

ttaggttaaa atctttaggt tgagttaggc gacacatagt ttatttcctc tggatttgga   1560

ttggaattgt gttcttagtt tttttcccct ggatttggat tggaattgtg tggagctggg   1620
```

```
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct ttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt tttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
```

```
cgaattatca gccttcttat tcatttctcg cttaaccgtg acaggctgtc gatcttgaga   4020

actatgccga cataatagga aatcgctgga taaagccgct gaggaagctg agtggcgcta   4080

tttctttaga agtgaacgtt gacgatcgtc gaccgtaccc cgatgaatta attcggacgt   4140

acgttctgaa cacagctgga tacttacttg ggcgattgtc atacatgaca tcaacaatgt   4200

acccgtttgt gtaaccgtct cttggaggtt cgtatgacac tagtggttcc cctcagcttg   4260

cgactagatg ttgaggccta acattttatt agagagcagg ctagttgctt agatacatga   4320

tcttcaggcc gttatctgtc agggcaagcg aaaattggcc atttatgacg accaatgccc   4380

cgcagaagct cccatctttg ccgccataga cgccgcgccc cccttttggg gtgtagaaca   4440

tccttttgcc agatgtggaa aagaagttcg ttgtcccatt gttggcaatg acgtagtagc   4500

cggcgaaagt gcgagaccca tttgcgctat atataagcct acgatttccg ttgcgactat   4560

tgtcgtaatt ggatgaacta ttatcgtagt tgctctcaga gttgtcgtaa tttgatggac   4620

tattgtcgta attgcttatg gagttgtcgt agttgcttgg agaaatgtcg tagttggatg   4680

gggagtagtc atagggaaga cgagcttcat ccactaaaac aattggcagg tcagcaagtg   4740

cctgccccga tgccatcgca agtacgaggc ttagaaccac cttcaacaga tcgcgcatag   4800

tcttccccag ctctctaacg cttgagttaa gccgcgccgc gaagcggcgt cggcttgaac   4860

gaattgttag acattatttg ccgactacct tggtgatctc gcctttcacg tagtgaacaa   4920

attcttccaa ctgatctgcg cgcgaggcca agcgatcttc ttgtccaaga taagcctgcc   4980

tagcttcaag tatgacgggc tgatactggg ccggcaggcg ctccattgcc cagtcggcag   5040

cgacatcctt cggcgcgatt ttgccggtta ctgcgctgta ccaaatgcgg gacaacgtaa   5100

gcactacatt tcgctcatcg ccagcccagt cgggcggcga gttccatagc gttaaggttt   5160

catttagcgc ctcaaataga tcctgttcag gaaccggatc aaagagttcc tccgccgctg   5220

gacctaccaa ggcaacgcta tgttctcttg cttttgtcag caagatagcc agatcaatgt   5280

cgatcgtggc tggctcgaag atacctgcaa gaatgtcatt gcgctgccat tctccaaatt   5340

gcagttcgcg cttagctgga taacgccacg gaatgatgtc gtcgtgcaca acaatggtga   5400

cttctacagc gcggagaatc tcgctctctc caggggaagc cgaagtttcc aaaaggtcgt   5460

tgatcaaagc tcgccgcgtt gtttcatcaa gccttacggt caccgtaacc agcaaatcaa   5520

tatcactgtg tggcttcagg ccgccatcca ctgcggagcc gtacaaatgt acggccagca   5580

acgtcggttc gagatggcgc tcgatgacgc caactacctc tgatagttga gtcgatactt   5640

cggcgatcac cgcttccctc atgatgttta actcctgaat taagccgcgc cgcgaagcgg   5700

tgtcggcttg aatgaattgt taggcgtcat cctgtgctcc cgagaaccag taccagtaca   5760

tcgctgtttc gttcgagact tgaggtctag ttttatacgt gaacaggtca atgccgccga   5820

gagtaaagcc acattttgcg tacaaattgc aggcaggtac attgttcgtt tgtgtctcta   5880

atcgtatgcc aaggagctgt ctgcttagtg cccacttttt cgcaaattcg atgagactgt   5940

gcgcgactcc tttgcctcgg tgcgtgtgcg acacaacaat gtgttcgata gaggctagat   6000

cgttccatgt tgagttgagt tcaatcttcc cgacaagctc ttggtcgatg aatgcgccat   6060

agcaagcaga gtcttcatca gagtcatcat ccgagatgta atccttccgg taggggctca   6120

cacttctggt agatagttca aagccttggt cggataggtg cacatcgaac acttcacgaa   6180

caatgaaatg gttctcagca tccaatgttt ccgccacctg ctcagggatc accgaaatct   6240

tcatatgacg cctaacgcct ggcacagcgg atcgcaaacc tggcgcggct tttggcacaa   6300

aaggcgtgac aggtttgcga atccgttgct gccacttgtt aacccttttg ccagatttgg   6360
```

```
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
```

```
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg ccctttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
```

```
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
gaactgtagt gctgatgttg tactgtgttt ttttacccgt tttatttgct ttactcgtgc  11700
aaatcaaatc tgtcagatgc tagaactagg tggctttatt ctgtgttctt acatagatct  11760
gttgtcctgt agttacttat gtcagttttg ttattatctg aagatatttt tggttgttgc  11820
ttgttgatgt ggtgtgagct gtgagcagcg ctcttatgat taatgatgct gtccaattgt  11880
agtgtagtat gatgtgattg atatgttcat ctattttgag ctgacagtac cgatatcgta  11940
ggatctggtg ccaacttatt ctccagctgc ttttttttac ctatgttaat tccaatcctt  12000
tcttgcctct tccagatcca gataatggcg aacaaacatt tgtccctctc cctcttcctc  12060
gtcctccttg gcctgtcggc cagcttggcc tccgggcaac aaacaagcat tactctgaca  12120
tccaacgcat ccggtacgtt tgacggttac tattacgaac tctggaagga tactggcaat  12180
acaacaatga cggtctacac tcaaggtcgc ttttcctgcc agtggtcgaa catcaataac  12240
gcgttgttta ggaccgggaa gaaatacaac cagaattggc agtctcttgg cacaatccgg  12300
atcacgtact ctgcgactta caacccaaac gggaactcct acttgtgtat ctatggctgg  12360
tctaccaacc cattggtcga gttctacatc gttgagtcct gggggaactg gagaccgcct  12420
ggtgcctgcc tggccgaggg ctcgctcgtc ttggacgcgg ctaccgggca gagggtccct  12480
atcgaaaagg tgcgtccggg gatggaagtt ttctccttgg gacctgatta cagactgtat  12540
cgggtgcccg ttttggaggt ccttgagagc ggggttaggg aagttgtgcg cctcagaact  12600
cggtcaggga gaacgctggt gttgacacca gatcacccgc ttttgacccc cgaaggttgg  12660
aaacctcttt gtgacctccc gcttggaact ccaattgcag tccccgcaga actgcctgtg  12720
gcgggccact tggccccacc tgaagaacgt gttacgctcc tggctcttct gttgggggat  12780
gggaacacaa agctgtcggg tcggagaggt acacgtccta atgccttctt ctacagcaaa  12840
aaccccgaat tgctcgcggc ttatcgccgg tgtgcagaag ccttgggtgc aaaggtgaaa  12900
gcatacgtcc acccgactac gggggtggtt acactcgcaa ccctcgctcc acgtcctgga  12960
gctcaagatc ctgtcaaacg cctcgttgtc gaggcgggaa tggttgctaa agccgaagag  13020
aagagggtcc cggaggaggt gtttcgttac cggcgtgagg cgttggccct tttcttgggc  13080
cgtttgttct cgacagacgg ctctgttgaa aagaagagga tctcttattc aagtgccagt  13140
ttgggactgg cccaggatgt cgcacatctc ttgctgcgcc ttggaattac atctcaactc  13200
cgttcgagag ggccacgggc tcacgaggtt cttatatcgg gccgcgagga tattttgcgg  13260
tttgctgaac ttatcggacc ctacctcttg gggggccaaga gggagagact tgcagcgctg  13320
gaagctgagg cccgcaggcg tttgcctgga cagggatggc acttgcggct tgttcttcct  13380
gccgtggcgt acagagtggg cgaggcggaa aggcgctcgg gattttcgtg gagtgaagcc  13440
```

```
ggtcggcgcg tcgcagttgc gggatcgtgt ttgtcatctg gactcaacct caaattgccc  13500
agacgctacc tttctcggca ccggttgtcg ctgctcggtg aggcttttgc cgaccctggg  13560
ctggaagcgc tcgcggaagg ccaagtgctc tgggacccta ttgttgctgt cgaaccggcc  13620
ggtaaggcga gaacattcga cttgcgcgtt ccaccctttg caaacttcgt gagcgaggac  13680
ctggtggtgc ataacaccgt cccccctgggc caagtgacaa tcgatggcgg gacctacgac  13740
atctatagga cgacacgcgt caaccagcct tccattgtgg ggacagccac gttcgatcag  13800
tactggagcg tgcgcacctc taagcggact tcaggaacag tgaccgtgac cgatcacttc  13860
cgcgcctggg cgaaccgggg cctgaacctc ggcacaatag accaaattac attgtgcgtg  13920
gagggttacc aaagctctgg atcagccaac atcacccaga acaccttctc tcagggctct  13980
tcttccggca gttcgggtgg ctcatccggc tccacaacga ctactcgcat cgagtgtgag  14040
aacatgtcct tgtccggacc ctacgttagc aggatcacca atccctttaa tggtattgcg  14100
ctgtacgcca acggagacac agcccgcgct accgttaact tccccgcaag tcgcaactac  14160
aatttccgcc tgcggggttg cggcaacaac aataatcttg cccgtgtgga cctgaggatc  14220
gacggacgga ccgtcgggac cttttattac cagggcacat accccctggga ggccccaatt  14280
gacaatgttt atgtcagtgc ggggagtcat acagtcgaaa tcactgttac tgcggataac  14340
ggcacatggg acgtgtatgc cgactacctg gtgatacaga gcgagaagga cgagctgtga  14400
cctaggtccc cgaatttccc cgatcgttca aacatttggc aataaagttt cttaagattg  14460
aatcctgttg ccggtcttgc gatgattatc atataatttc tgttgaatta cgttaagcat  14520
gtaataatta acatgtaatg catgacgtta tttatgagat gggtttttat gattagagtc  14580
ccgcaattat acatttaata cgcgatagaa aacaaaatat agcgcgcaaa ctaggataaa  14640
ttatcgcgcg cggtgtcatc tatgttacta gatcgggaat tgg                    14683
```

<210> SEQ ID NO 73
<211> LENGTH: 14590
<212> TYPE: DNA
<213> ORGANISM: Artificial Sequence
<220> FEATURE:
<223> OTHER INFORMATION: Synthetic construct, vector pAG2233

<400> SEQUENCE: 73

```
aattcatact aaagcttgca tgcctgcagg tcgactctag taacggccgc cagtgtgctg     60
gaattaattc ggcttgtcga ccacccaacc ccatatcgac agaggatgtg aagaacaggt    120
aaatcacgca gaagaaccca tctctgatag cagctatcga ttagaacaac gaatccatat    180
tgggtccgtg ggaaatactt actgcacagg aaggggcga tctgacgagg ccccgccacc    240
ggcctcgacc cgaggccgag gccgacgaag cgccggcgag tacggcgccg cggcggcctc    300
tgcccgtgcc ctctgcgcgt gggagggaga ggccgcggtg gtgggggcgc gcgcgcgcgc    360
gcgcgcagct ggtgcggcgg cgcgggggtc agccgccgag ccggcggcga cggaggagca    420
gggcggcgtg gacgcgaact tccgatcggt tggtcagagt gcgcgagttg ggcttagcca    480
attaggtctc aacaatctat tgggccgtaa aattcatggg ccctggtttg tctaggccca    540
atatcccgtt catttcagcc cacaaatatt tccccagagg attattaagg cccacacgca    600
gcttatagca gatcaagtac gatgtttcct gatcgttgga tcggaaacgt acggtcttga    660
tcaggcatgc cgacttcgtc aaagagaggc ggcatgacct gacgcggagt tggttccggg    720
caccgtctgg atggtcgtac cgggaccgga cacgtgtcgc gcctccaact acatggacac    780
gtgtggtgct gccattgggc cgtacgcgtg gcggtgaccg caccggatgc tgcctcgcac    840
```

```
cgccttgccc acgctttata tagagaggtt ttctctccat taatcgcata gcgagtcgaa    900
tcgaccgaag gggaggggga gcgaagcttt gcgttctcta atcgcctcgt caaggtaact    960
aatcaatcac ctcgtcctaa tcctcgaatc tctcgtggtg cccgtctaat ctcgcgattt   1020
tgatgctcgt ggtggaaagc gtaggaggat cccgtgcgag ttagtctcaa tctctcaggg   1080
tttcgtgcga ttttagggtg atccacctct taatcgagtt acggtttcgt gcgattttag   1140
ggtaatcctc ttaatctctc attgatttag ggtttcgtga gaatcgaggt agggatctgt   1200
gttatttata tcgatctaat agatggattg gttttgagat tgttctgtca gatggggatt   1260
gtttcgatat attaccctaa tgatgtgtca gatggggatt gtttcgatat attaccctaa   1320
tgatgtgtca gatggggatt gtttcgatat attaccctaa tgatggataa taagagtagt   1380
tcacagttat gttttgatcc tgccacatag tttgagtttt gtgatcagat ttagttttac   1440
ttatttgtgc ttagttcgga tgggattgtt ctgatattgt tccaatagat gaatagctcg   1500
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct ttttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt ttttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
```

```
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc ccttttgggg gtgtagaaca   4440
tccttttgcc agatgtggaa aagaagttcg ttgtcccatt gttggcaatg acgtagtagc   4500
cggcgaaagt gcgagaccca tttgcgctat atataagcct acgatttccg ttgcgactat   4560
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
cgacatcctt cggcgcgatt ttgccggtta ctgcgctgta ccaaatgcgg gacaacgtaa   5100
gcactacatt tcgctcatcg ccagcccagt cgggcggcga gttccatagc gttaaggttt   5160
catttagcgc ctcaaataga tcctgttcag gaaccggatc aaagagttcc tccgccgctg   5220
gacctaccaa ggcaacgcta tgttctcttg cttttgtcag caagatagcc agatcaatgt   5280
cgatcgtggc tggctcgaag atacctgcaa gaatgtcatt gcgctgccat tctccaaatt   5340
gcagttcgcg cttagctgga taacgccacg gaatgatgtc gtcgtgcaca acaatggtga   5400
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
```

```
acgtcggttc gagatggcgc tcgatgacgc caactacctc tgatagttga gtcgatactt   5640

cggcgatcac cgcttccctc atgatgttta actcctgaat taagccgcgc cgcgaagcgg   5700

tgtcggcttg aatgaattgt taggcgtcat cctgtgctcc cgagaaccag taccagtaca   5760

tcgctgtttc gttcgagact tgaggtctag ttttatacgt gaacaggtca atgccgccga   5820

gagtaaagcc acattttgcg tacaaattgc aggcaggtac attgttcgtt tgtgtctcta   5880

atcgtatgcc aaggagctgt ctgcttagtg cccacttttt cgcaaattcg atgagactgt   5940

gcgcgactcc tttgcctcgg tgcgtgtgcg acacaacaat gtgttcgata gaggctagat   6000

cgttccatgt tgagttgagt tcaatcttcc cgacaagctc ttggtcgatg aatgcgccat   6060

agcaagcaga gtcttcatca gagtcatcat ccgagatgta atccttccgg taggggctca   6120

cacttctggt agatagttca aagccttggt cggataggtg cacatcgaac acttcacgaa   6180

caatgaaatg gttctcagca tccaatgttt ccgccacctg ctcagggatc accgaaatct   6240

tcatatgacg cctaacgcct ggcacagcgg atcgcaaacc tggcgcggct tttggcacaa   6300

aaggcgtgac aggtttgcga atccgttgct gccacttgtt aacccttttg ccagatttgg   6360

taactataat ttatgttaga ggcgaagtct tgggtaaaaa ctggcctaaa attgctgggg   6420

atttcaggaa agtaaacatc accttccggc tcgatgtcta ttgtagatat atgtagtgta   6480

tctacttgat cgggggatct gctgcctcgc gcgtttcggt gatgacggtg aaaacctctg   6540

acacatgcag ctcccggaga cggtcacagc ttgtctgtaa gcggatgccg ggagcagaca   6600

agcccgtcag ggcgcgtcag cgggtgttgg cgggtgtcgg ggcgcagcca tgacccagtc   6660

acgtagcgat agcggagtgt atactggctt aactatgcgg catcagagca gattgtactg   6720

agagtgcacc atatgcggtg tgaaataccg cacagatgcg taaggagaaa ataccgcatc   6780

aggcgctctt ccgcttcctc gctcactgac tcgctgcgct cggtcgttcg gctgcggcga   6840

gcggtatcag ctcactcaaa ggcggtaata cggttatcca cagaatcagg ggataacgca   6900

ggaaagaaca tgtgagcaaa aggccagcaa aaggccagga accgtaaaaa ggccgcgttg   6960

ctggcgtttt tccataggct ccgcccccct gacgagcatc acaaaaatcg acgctcaagt   7020

cagaggtggc gaaacccgac aggactataa agataccagg cgtttccccc tggaagctcc   7080

ctcgtgcgct ctcctgttcc gaccctgccg cttaccggat acctgtccgc ctttctccct   7140

tcgggaagcg tggcgctttc tcatagctca cgctgtaggt atctcagttc ggtgtaggtc   7200

gttcgctcca agctgggctg tgtgcacgaa ccccccgttc agcccgaccg ctgcgcctta   7260

tccggtaact atcgtcttga gtccaacccg gtaagacacg acttatcgcc actggcagca   7320

gccactggta acaggattag cagagcgagg tatgtaggcg gtgctacaga gttcttgaag   7380

tggtggccta actacggcta cactagaagg acagtatttg gtatctgcgc tctgctgaag   7440

ccagttacct tcggaaaaag agttggtagc tcttgatccg gcaaacaaac caccgctggt   7500

agcggtggtt tttttgtttg caagcagcag attacgcgca gaaaaaaagg atctcaagaa   7560

gatcctttga tcttttctac ggggtctgac gctcagtgga acgaaaactc acgttaaggg   7620

attttggtca tgagattatc aaaaaggatc ttcacctaga tccttttaaa ttaaaaatga   7680

agttttaaat caatctaaag tatatatgag taaacttggt ctgacagtta ccaatgctta   7740

atcagtgagg cacctatctc agcgatctgt ctatttcgtt catccatagt tgcctgactc   7800

cccgtcgtgt agataactac gatacgggag ggcttaccat ctggccccag tgctgcaatg   7860

ataccgcgag acccacgctc accggctcca gatttatcag caataaacca gccagccgga   7920
```

```
agggccgagc gcagaagtgg tcctgcaact ttatccgcct ccatccagtc tattaattgt   7980

tgccgggaag ctagagtaag tagttcgcca gttaatagtt tgcgcaacgt tgttgccatt   8040

gctgcagggg gggggggggg ggggttccat tgttcattcc acggacaaaa acagagaaag   8100

gaaacgacag aggccaaaaa gctcgctttc agcacctgtc gtttcctttc ttttcagagg   8160

gtattttaaa taaaaacatt aagttatgac gaagaagaac ggaaacgcct taaaccggaa   8220

aattttcata aatagcgaaa acccgcgagg tcgccgcccc gtaacctgtc ggatcaccgg   8280

aaaggacccg taaagtgata atgattatca tctacatatc acaacgtgcg tggaggccat   8340

caaaccacgt caaataatca attatgacgc aggtatcgta ttaattgatc tgcatcaact   8400

taacgtaaaa acaacttcag acaatacaaa tcagcgacac tgaatacggg gcaacctcat   8460

gtcccccccc cccccccccct gcaggcatcg tggtgtcacg ctcgtcgttt ggtatggctt   8520

cattcagctc cggttcccaa cgatcaaggc gagttacatg atcccccatg ttgtgcaaaa   8580

aagcggttag ctccttcggt cctccgatcg ttgtcagaag taagttggcc gcagtgttat   8640

cactcatggt tatggcagca ctgcataatt ctcttactgt catgccatcc gtaagatgct   8700

tttctgtgac tggtgagtac tcaaccaagt cattctgaga atagtgtatg cggcgaccga   8760

gttgctcttg cccggcgtca acacgggata ataccgcgcc acatagcaga actttaaaag   8820

tgctcatcat tggaaaacgt tcttcggggc gaaaactctc aaggatctta ccgctgttga   8880

gatccagttc gatgtaaccc actcgtgcac ccaactgatc ttcagcatct tttactttca   8940

ccagcgtttc tgggtgagca aaaacaggaa ggcaaaatgc cgcaaaaaag ggaataaggg   9000

cgacacggaa atgttgaata ctcatactct tcctttttca atattattga agcatttatc   9060

agggttattg tctcatgagc ggatacatat ttgaatgtat ttagaaaaat aaacaaatag   9120

gggttccgcg cacatttccc cgaaaagtgc cacctgacgt ctaagaaacc attattatca   9180

tgacattaac ctataaaaat aggcgtatca cgaggccctt tcgtcttcaa gaattggtcg   9240

acgatcttgc tgcgttcgga tattttcgtg gagttcccgc cacagacccg gattgaaggc   9300

gagatccagc aactcgcgcc agatcatcct gtgacggaac tttggcgcgt gatgactggc   9360

caggacgtcg gccgaaagag cgacaagcag atcacgcttt tcgacagcgt cggatttgcg   9420

atcgaggatt tttcggcgct gcgctacgtc cgcgaccgcg ttgagggatc aagccacagc   9480

agcccactcg accttctagc cgacccagac gagccaaggg atctttttgg aatgctgctc   9540

cgtcgtcagg ctttccgacg tttgggtggt tgaacagaag tcattatcgc acggaatgcc   9600

aagcactccc gaggggaacc ctgtggttgg catgcacata caaatggacg aacggataaa   9660

ccttttcacg cccttttaaa tatccgatta ttctaataaa cgctcttttc tcttaggttt   9720

acccgccaat atatcctgtc aaacactgat agtttaaact gaaggcggga aacgacaacc   9780

tgatcatgag cggagaatta agggagtcac gttatgaccc ccgccgatga cgcgggacaa   9840

gccgttttac gtttggaact gacagaaccg caacgttgaa ggagccactc agcttaatta   9900

agtctaactc gagttactgg tacgtaccaa atccatggaa tcaaggtacc gtcgactcta   9960

gtaacggccg ccagtgtgct ggaattaatt cggcttgtcg accacccaac cccatatcga  10020

cagaggatgt gaagaacagg taaatcacgc agaagaaccc atctctgata gcagctatcg  10080

attagaacaa cgaatccata ttgggtccgt gggaaatact tactgcacag gaagggggcg  10140

atctgacgag gccccgccac cggcctcgac ccgaggccga ggccgacgaa gcgccggcga  10200

gtacggcgcc gcggcggcct ctgcccgtgc cctctgcgcg tgggagggag aggccgcggt  10260

ggtgggggcg cgcgcgcgcg cgcgcgcagc tggtgcggcg gcgcgggggt cagccgccga  10320
```

```
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
gaactgtagt gctgatgttg tactgtgttt ttttacccgt tttatttgct ttactcgtgc  11700
aaatcaaatc tgtcagatgc tagaactagg tggctttatt ctgtgttctt acatagatct  11760
gttgtcctgt agttacttat gtcagttttg ttattatctg aagatatttt tggttgttgc  11820
ttgttgatgt ggtgtgagct gtgagcagcg ctcttatgat taatgatgct gtccaattgt  11880
agtgtagtat gatgtgattg atatgttcat ctattttgag ctgacagtac cgatatcgta  11940
ggatctggtg ccaacttatt ctccagctgc ttttttttac ctatgttaat tccaatcctt  12000
tcttgcctct tccagatcca gataatgcaa acaagcatta ctctgacatc caacgcatcc  12060
ggtacgtttg acggttacaa ttacgaactc tggaaggata ctggcaatac aacaatgacg  12120
gtctacactc aaggtcgctt ttcctgccag tggtcgaaca tcaataacgc gttgtttagg  12180
accgggaaga aatacaacca gaattggcag tctctcggca caatccggat cacgtactct  12240
gcgacttaca acccaaacgg gaactcctac atgtgtatct atggctggtc taccaaccca  12300
ttggtcgagt tctacatcgt tgagtcctgg gggaactgga gaccgcctgg tgccacgtcc  12360
ctgggccaag tgacaatcga tggcgggacc tacgacatct ataggacgac acgcgtcaac  12420
cagccttgcc tggccgaggg ctcgctcgtc ttggacgcgg ctaccgggca gagggtccct  12480
atcgaaaagg tgcgtccggg gatggaagtt ttctccttgg gacctgatta cagactgtat  12540
cgggtgcccg ttttggaggt ccttgagagc ggggttgggg aagttgtgcg cctccgaact  12600
cggtcaggga gaacgctggt gttgacacca gaacacccgc ttttgacccc cgaaggttgg  12660
```

```
aaacctcttt gtgacctccc gcttggaact ccaattgcag tccccgcaga actgcctgtg  12720

gcgggccact tggccccacc tgaagaacgt gttatgctcc tggctcttct gttgggggat  12780

gggaacacaa agctgtcggg tcggagaggt acacgtccta atgccttctt ctacagcaaa  12840

gactccgaat tgctcgcggc ttatcgccgg tgtgcagaag ccttgggtgc aaaggtgaaa  12900

gcatacgtcc acccgactac gggggtggtt acactcgcaa ccctcgctcc acgtcctgga  12960

gctcaagatc ctgtcaaacg cctcgttgtc gaggcgggaa tggttgctaa agtcgaagag  13020

aagagggtcc cggaggaggt gtttcgttac cggcgtgagg cgttggccct tttcttgggc  13080

cgtttgttct cgacagacgg ctctgttgaa aagaagagga tctcttattc aagtgccagt  13140

ttgggactgg cccaggatgt cgcacatctc ttgctgcgcc ttggaattac atctcaactc  13200

cgttcgagag ggccacgggc tcacaaggtt cttatatcgg gccgcgagga tattttgcgg  13260

tttgctgaac ttatcggacc ctacctcttg gggggccaaga gggagagact tgcagcgctg  13320

gaagctgagg cccgcaggcg tttgcctgga cagggatggc acttgcggcc tgttcttcct  13380

gccgtggcgt acagagtgag cgaggctaaa aggcgctcgg gattttcgtg gagtgaagcc  13440

ggtcggcgcg tcgcagttgc gggatcgtgt ttgtcatctg gactcaacct caaattgccc  13500

agacgctacc tttctcggca ccggttgtcg ctgctcggtg aggcttttgc cgaccctggg  13560

ctggaagcgc tcgcggaagg ccaagtgctc tgggacccta ttgttgctgt cgaaccggcc  13620

ggtaaggcga gaacattcga cttgcgcgtc ccaccctttg caaacttcgt gagcgaggac  13680

ctggtggtgc ataactccat tgtggggaca gccacgttcg atcagtactg gagcgtgcgc  13740

acctctaagc ggacttcagg aacagtgacc gtgaccgatc acttccgcgc ctgggcgaac  13800

cggggcctga acctcggcac aatagaccaa attacattgt gcgtggaggg ttaccaaagc  13860

tctggatcag ccaacatcac ccagaacacc ttctctcagg gctcttcttc cggcagttcg  13920

ggtggctcat ccggctccac aacgactact cgcatcgagt gtgagaacat gtccttgtcc  13980

ggaccctacg ttagcaggat caccaatccc tttaatggta ttgcgctgta cgccaacgga  14040

gacacagccc gcgctaccgt taacttcccc gcaagtcgca actacaattt ccgcctgcgg  14100

ggttgcggca acagcaataa tcttgcccgt gtggacctga ggatcgacgg acggaccgtc  14160

gggacctttt attaccaggg cacatacccc tgggaggccc caattgacaa tgtttatgtc  14220

agtgcgggga gtcatacagt cgaaatcact gttactgcgg ataacggcac acgggacgtg  14280

tatgccgact acctggtgat acagtgacct aggtccccga atttccccga tcgttcaaac  14340

atttggcaat aaagtttctt aagattgaat cctgttgccg gtcttgcgat gattatcata  14400

taatttctgt tgaattacgt taagcatgta ataattaaca tgtaatgcat gacgttattt  14460

atgagatggg tttttatgat tagagtcccg caattataca tttaatacgc gatagaaaac  14520

aaaatatagc gcgcaaacta ggataaatta tcgcgcgcgg tgtcatctat gttactagat  14580

cgggaattgg                                                         14590
```

<210> SEQ ID NO 74
<211> LENGTH: 14662
<212> TYPE: DNA
<213> ORGANISM: Artificial Sequence
<220> FEATURE:
<223> OTHER INFORMATION: Synthetic construct, vector pAG2234

<400> SEQUENCE: 74

```
aattcatact aaagcttgca tgcctgcagg tcgactctag taacggccgc cagtgtgctg     60

gaattaattc ggcttgtcga ccacccaacc ccatatcgac agaggatgtg aagaacaggt    120
```

```
aaatcacgca gaagaaccca tctctgatag cagctatcga ttagaacaac gaatccatat    180
tgggtccgtg ggaaatactt actgcacagg aagggggcga tctgacgagg ccccgccacc    240
ggcctcgacc cgaggccgag gccgacgaag cgccggcgag tacggcgccg cggcggcctc    300
tgcccgtgcc ctctgcgcgt gggagggaga ggccgcggtg gtgggggcgc gcgcgcgcgc    360
gcgcgcagct ggtgcggcgg cgcgggggtc agccgccgag ccggcggcga cggaggagca    420
gggcggcgtg gacgcgaact tccgatcggt tggtcagagt gcgcgagttg ggcttagcca    480
attaggtctc aacaatctat tggccgtaa aattcatggg ccctggtttg tctaggccca    540
atatcccgtt catttcagcc cacaaatatt tccccagagg attattaagg cccacacgca    600
gcttatagca gatcaagtac gatgtttcct gatcgttgga tcggaaacgt acggtcttga    660
tcaggcatgc cgacttcgtc aaagagaggc ggcatgacct gacgcggagt tggttccggg    720
caccgtctgg atggtcgtac cgggaccgga cacgtgtcgc gcctccaact acatggacac    780
gtgtggtgct gccattgggc cgtacgcgtg gcggtgaccg caccggatgc tgcctcgcac    840
cgccttgccc acgctttata tagagaggtt ttctctccat taatcgcata gcgagtcgaa    900
tcgaccgaag gggaggggga gcgaagcttt gcgttctcta atcgcctcgt caaggtaact    960
aatcaatcac ctcgtcctaa tcctcgaatc tctcgtggtg cccgtctaat ctcgcgattt   1020
tgatgctcgt ggtggaaagc gtaggaggat cccgtgcgag ttagtctcaa tctctcaggg   1080
tttcgtgcga ttttagggtg atccacctct taatcgagtt acggtttcgt gcgattttag   1140
ggtaatcctc ttaatctctc attgatttag ggtttcgtga gaatcgaggt agggatctgt   1200
gttatttata tcgatctaat agatggattg gttttgagat tgttctgtca gatggggatt   1260
gtttcgatat attaccctaa tgatgtgtca gatggggatt gtttcgatat attaccctaa   1320
tgatgtgtca gatggggatt gtttcgatat attaccctaa tgatggataa taagagtagt   1380
tcacagttat gttttgatcc tgccacatag tttgagtttt gtgatcagat ttagttttac   1440
ttatttgtgc ttagttcgga tgggattgtt ctgatattgt tccaatagat gaatagctcg   1500
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct ttttttacc tatgttaatt ccaatccttt cttgcctctt ccagatccag    2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
```

```
gatgccgccg agcgtaacta taaagatcct aaccacaagc cggagctggt ttttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc cccttttggg gtgtagaaca   4440
tccttttgcc agatgtggaa aagaagttcg ttgtcccatt gttggcaatg acgtagtagc   4500
cggcgaaagt gcgagaccca tttgcgctat atataagcct acgatttccg ttgcgactat   4560
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
```

```
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
cgacatcctt cggcgcgatt ttgccggtta ctgcgctgta ccaaatgcgg gacaacgtaa   5100
gcactacatt tcgctcatcg ccagcccagt cgggcggcga gttccatagc gttaaggttt   5160
catttagcgc ctcaaataga tcctgttcag gaaccggatc aaagagttcc tccgccgctg   5220
gacctaccaa ggcaacgcta tgttctcttg cttttgtcag caagatagcc agatcaatgt   5280
cgatcgtggc tggctcgaag atacctgcaa gaatgtcatt gcgctgccat tctccaaatt   5340
gcagttcgcg cttagctgga taacgccacg gaatgatgtc gtcgtgcaca acaatggtga   5400
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aaccctttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
```

-continued

```
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atcttttttgg aatgctgctc   9540
cgtcgtcagg ctttccgacg tttgggtggt tgaacagaag tcattatcgc acggaatgcc   9600
```

```
aagcactccc gaggggaacc ctgtggttgg catgcacata caaatggacg aacggataaa   9660
ccttttcacg cccttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
gaactgtagt gctgatgttg tactgtgttt ttttacccgt tttatttgct ttactcgtgc  11700
aaatcaaatc tgtcagatgc tagaactagg tggctttatt ctgtgttctt acatagatct  11760
gttgtcctgt agttacttat gtcagttttg ttattatctg aagatatttt tggttgttgc  11820
ttgttgatgt ggtgtgagct gtgagcagcg ctcttatgat taatgatgct gtccaattgt  11880
agtgtagtat gatgtgattg atatgttcat ctattttgag ctgacagtac cgatatcgta  11940
```

```
ggatctggtg ccaacttatt ctccagctgc ttttttttac ctatgttaat tccaatcctt  12000
tcttgcctct tccagatcca gataatggcg aacaaacatt tgtccctctc cctcttcctc  12060
gtcctccttg gcctgtcggc cagcttggcc tccgggcaac aaacaagcat tactctgaca  12120
tccaacgcat ccggtacgtt tgacggttac aattacgaac tctggaagga tactggcaat  12180
acaacaatga cggtctacac tcaaggtcgc ttttcctgcc agtggtcgaa catcaataac  12240
gcgttgttta ggaccgggaa gaaatacaac cagaattggc agtctctcgg cacaatccgg  12300
atcacgtact ctgcgactta caacccaaac gggaactcct acatgtgtat ctatggctgg  12360
tctaccaacc cattggtcga gttctacatc gttgagtcct gggggaactg gagaccgcct  12420
ggtgccacgt ccctgggcca agtgacaatc gatggcggga cctacgacat ctataggacg  12480
acacgcgtca accagccttg cctggccgag ggctcgctcg tcttggacgc ggctaccggg  12540
cagagggtcc ctatcgaaaa ggtgcgtccg gggatggaag ttttctcctt gggacctgat  12600
tacagactgt atcgggtgcc cgttttggag gtccttgaga gcggggttgg ggaagttgtg  12660
cgcctccgaa ctcggtcagg gagaacgctg gtgttgacac cagaacaccc gcttttgacc  12720
cccgaaggtt ggaaacctct ttgtgacctc ccgcttggaa ctccaattgc agtccccgca  12780
gaactgcctg tggcgggcca cttggcccca cctgaagaac gtgttatgct cctggctctt  12840
ctgttggggg atgggaacac aaagctgtcg ggtcggagag gtacacgtcc taatgccttc  12900
ttctacagca aagactccga attgctcgcg gcttatcgcc ggtgtgcaga agccttgggt  12960
gcaaaggtga aagcatacgt ccacccgact acgggggtgg ttacactcgc aaccctcgct  13020
ccacgtcctg gagctcaaga tcctgtcaaa cgcctcgttg tcgaggcggg aatggttgct  13080
aaagtcgaag agaagagggt cccggaggag gtgtttcgtt accggcgtga ggcgttggcc  13140
cttttcttgg gccgtttgtt ctcgacagac ggctctgttg aaaagaagag gatctcttat  13200
tcaagtgcca gtttgggact ggcccaggat gtcgcacatc tcttgctgcg ccttggaatt  13260
acatctcaac tccgttcgag agggccacgg gctcacaagg ttcttatatc gggccgcgag  13320
gatattttgc ggtttgctga acttatcgga ccctacctct tgggggccaa gagggagaga  13380
cttgcagcgc tggaagctga ggcccgcagg cgtttgcctg gacagggatg gcacttgcgg  13440
cctgttcttc ctgccgtggc gtacagagtg agcgaggcta aaaggcgctc gggattttcg  13500
tggagtgaag ccggtcggcg cgtcgcagtt gcgggatcgt gtttgtcatc tggactcaac  13560
ctcaaattgc ccagacgcta cctttctcgg caccggttgt cgctgctcgg tgaggctttt  13620
gccgaccctg ggctggaagc gctcgcggaa ggccaagtgc tctgggaccc tattgttgct  13680
gtcgaaccgg ccggtaaggc gagaacattc gacttgcgcg tcccaccctt tgcaaacttc  13740
gtgagcgagg acctggtggt gcataactcc attgtgggga cagccacgtt cgatcagtac  13800
tggagcgtgc gcacctctaa gcggacttca ggaacagtga ccgtgaccga tcacttccgc  13860
gcctgggcga accggggcct gaacctcggc acaatagacc aaattacatt gtgcgtggag  13920
ggttaccaaa gctctggatc agccaacatc acccagaaca ccttctctca gggctcttct  13980
tccggcagtt cgggtggctc atccggctcc acaacgacta ctcgcatcga gtgtgagaac  14040
atgtccttgt ccggacccta cgttagcagg atcaccaatc cctttaatgg tattgcgctg  14100
tacgccaacg gagacacagc ccgcgctacc gttaacttcc ccgcaagtcg caactacaat  14160
ttccgcctgc ggggttgcgg caacagcaat aatcttgccc gtgtggacct gaggatcgac  14220
ggacggaccg tcgggacctt ttattaccag ggcacatacc cctgggaggc ccccaattgac  14280
aatgtttatg tcagtgcggg gagtcataca gtcgaaatca ctgttactgc ggataacggc  14340
```

```
acacgggacg tgtatgccga ctacctggtg atacagtgac ctaggtcccc gaatttcccc  14400

gatcgttcaa acatttggca ataaagtttc ttaagattga atcctgttgc cggtcttgcg  14460

atgattatca tataatttct gttgaattac gttaagcatg taataattaa catgtaatgc  14520

atgacgttat ttatgagatg ggtttttatg attagagtcc cgcaattata catttaatac  14580

gcgatagaaa acaaaatata gcgcgcaaac taggataaat tatcgcgcgc ggtgtcatct  14640

atgttactag atcgggaatt gg                                          14662
```

<210> SEQ ID NO 75
<211> LENGTH: 17309
<212> TYPE: DNA
<213> ORGANISM: Artificial Sequence
<220> FEATURE:
<223> OTHER INFORMATION: Synthetic constrcut, vector pAG2242

<400> SEQUENCE: 75

```
cgtcgactct agtaacggcc gccagtgtgc tggaattaat tcggcttgtc gaccacccaa     60

ccccatatcg acagaggatg tgaagaacag gtaaatcacg cagaagaacc catctctgat    120

agcagctatc gattagaaca acgaatccat attgggtccg tgggaaatac ttactgcaca    180

ggaagggggc gatctgacga ggccccgcca ccggcctcga cccgaggccg aggccgacga    240

agcgccggcg agtacggcgc cgcggcggcc tctgcccgtg ccctctgcgc gtgggaggga    300

gaggccgcgg tggtgggggc gcgcgcgcgc gcgcgcgcag ctggtgcggc ggcgcggggg    360

tcagccgccg agccggcggc gacggaggag cagggcggcg tggacgcgaa cttccgatcg    420

gttggtcaga gtgcgcgagt tgggcttagc caattaggtc tcaacaatct attgggccgt    480

aaaattcatg ggccctggtt tgtctaggcc caatatcccg ttcatttcag cccacaaata    540

tttccccaga ggattattaa ggcccacacg cagcttatag cagatcaagt acgatgtttc    600

ctgatcgttg gatcggaaac gtacggtctt gatcaggcat gccgacttcg tcaaagagag    660

gcggcatgac ctgacgcgga gttggttccg ggcaccgtct ggatggtcgt accgggaccg    720

gacacgtgtc gcgcctccaa ctacatggac acgtgtggtg ctgccattgg gccgtacgcg    780

tggcggtgac cgcaccggat gctgcctcgc accgccttgc ccacgcttta tatagagagg    840

ttttctctcc attaatcgca tagcgagtcg aatcgaccga aggggagggg gagcgaagct    900

ttgcgttctc taatcgcctc gtcaaggtaa ctaatcaatc acctcgtcct aatcctcgaa    960

tctctcgtgg tgcccgtcta atctcgcgat tttgatgctc gtggtggaaa gcgtaggagg   1020

atcccgtgcg agttagtctc aatctctcag ggtttcgtgc gattttaggg tgatccacct   1080

cttaatcgag ttacggtttc gtgcgatttt agggtaatcc tcttaatctc tcattgattt   1140

agggtttcgt gagaatcgag gtagggatct gtgttattta tatcgatcta atagatggat   1200

tggttttgag attgttctgt cagatgggga ttgtttcgat atattaccct aatgatgtgt   1260

cagatgggga ttgtttcgat atattaccct aatgatgtgt cagatgggga ttgtttcgat   1320

atattaccct aatgatggat aataagagta gttcacagtt atgttttgat cctgccacat   1380

agtttgagtt ttgtgatcag atttagtttt acttatttgt gcttagttcg gatgggattg   1440

ttctgatatt gttccaatag atgaatagct cgttaggtta aaatctttag gttgagttag   1500

gcgacacata gtttatttcc tctggatttg gattggaatt gtgttcttag tttttttccc   1560

ctggatttgg attggaattg tgtggagctg ggttagagaa ttacatctgt atcgtgtaca   1620

cctacttgaa ctgtagagct tgggttctaa ggtcaattta atctgtattg tatctggctc   1680
```

```
tttgcctagt tgaactgtag tgctgatgtt gtactgtgtt tttttacccg ttttatttgc   1740
tttactcgtg caaatcaaat ctgtcagatg ctagaactag gtggctttat tctgtgttct   1800
tacatagatc tgttgtcctg tagttactta tgtcagtttt gttattatct gaagatattt   1860
ttggttgttg cttgttgatg tggtgtgagc tgtgagcagc gctcttatga ttaatgatgc   1920
tgtccaattg tagtgtagta tgatgtgatt gatatgttca tctattttga gctgacagta   1980
ccgatatcgt aggatctggt gccaacttat tctccagctg ctttttttta cctatgttaa   2040
ttccaatcct ttcttgcctc ttccagatgc agatctttgt gaagaccctg accggcaaga   2100
ctatcaccct cgaggtggag tcttctgaca ccattgacaa tgtcaaggcc aagatccagg   2160
acaaggaggg catcccccca gaccagcagc ggctcatctt tgctggcaag cagctggagg   2220
acgggcgcac gcttgcggac tacaacatcc agaaggagag caccctccac ctggtgctcc   2280
gcctcagggg aggcatgcaa acaagcatta ctctgacatc caacgcatcc ggtacgtttg   2340
acggttacta ttacgaactc tggaaggata ctggcaatac aacaatgacg gtctacactc   2400
aaggtcgctt ttcctgccag tggtcgaaca tcaataacgc gttgtttagg accgggaaga   2460
aatacaacca gaattggcag tctcttggca caatccggat cacgtactct gcgacttaca   2520
acccaaacgg gaactcctac ttgtgtatct atggctggtc taccaaccca ttggtcgagt   2580
tctacatcgt tgagtcctgg gggaactgga gaccgcctgg tgccacgtcc ctgggccaag   2640
tgacaatcga tggcgggacc tacgacatct ataggacgac acgcgtcaac cagccttcca   2700
ttgtggggac agccacgttc gatcagtact ggagcgtgcg cacctctaag cggacttcag   2760
gaacagtgac cgtgaccgat cacttccgcg cctgggcgaa ccggggcctg aacctcggca   2820
caatagacca aattacattg tgcgtggagg gttaccaaag ctctggatca gccaacatca   2880
cccagaacac cttctctcag ggctcttctt ccggcagttc gggtggctca tccggctcca   2940
caacgactac tcgcatcgag tgtgagaaca tgtccttgtc cggaccctac gttagcagga   3000
tcaccaatcc ctttaatggt attgcgctgt acgccaacgg agacacagcc cgcgctaccg   3060
ttaacttccc cgcaagtcgc aactacaatt tccgcctgcg ggttgcggc aacaacaata    3120
atcttgcccg tgtggacctg aggatcgacg gacggaccgt cgggaccttt tattaccagg   3180
gcacataccc ctgggaggcc ccaattgaca atgtttatgt cagtgcgggg agtcatacag   3240
tcgaaatcac tgttactgcg gataacggca catgggacgt gtatgccgac tacctggtga   3300
tacagtgacc taggtccccg aatttccccg atcgttcaaa catttggcaa taaagtttct   3360
taagattgaa tcctgttgcc ggtcttgcga tgattatcat ataatttctg ttgaattacg   3420
ttaagcatgt aataattaac atgtaatgca tgacgttatt tatgagatgg gtttttatga   3480
ttagagtccc gcaattatac atttaatacg cgatagaaaa caaaatatag cgcgcaaact   3540
aggataaatt atcgcgcgcg gtgtcatcta tgttactaga tcgggaattg gaattcatac   3600
taaagcttgc atgcctgcag gtcgactcta gtaacggccg ccagtgtgct ggaattaatt   3660
cggcttgtcg accacccaac cccatatcga cagaggatgt gaagaacagg taaatcacgc   3720
agaagaaccc atctctgata gcagctatcg attagaacaa cgaatccata ttgggtccgt   3780
gggaaatact tactgcacag gaagggggcg atctgacgag gccccgccac cggcctcgac   3840
ccgaggccga ggccgacgaa gcgccggcga gtacggcgcc gcggcggcct ctgcccgtgc   3900
cctctgcgcg tgggagggag aggccgcggt ggtgggggcg cgcgcgcgcg cgcgcgcagc   3960
tggtgcggcg gcgcgggggt cagccgccga gccggcggcg acggaggagc agggcggcgt   4020
ggacgcgaac ttccgatcgg ttggtcagag tgcgcgagtt gggcttagcc aattaggtct   4080
```

```
caacaatcta ttgggccgta aaattcatgg gccctggttt gtctaggccc aatatcccgt   4140
tcatttcagc ccacaaatat ttccccagag gattattaag gcccacacgc agcttatagc   4200
agatcaagta cgatgtttcc tgatcgttgg atcggaaacg tacggtcttg atcaggcatg   4260
ccgacttcgt caaagagagg cggcatgacc tgacgcggag ttggttccgg gcaccgtctg   4320
gatggtcgta ccgggaccgg acacgtgtcg cgcctccaac tacatggaca cgtgtggtgc   4380
tgccattggg ccgtacgcgt ggcggtgacc gcaccggatg ctgcctcgca ccgccttgcc   4440
cacgctttat atagagaggt tttctctcca ttaatcgcat agcgagtcga atcgaccgaa   4500
ggggaggggg agcgaagctt tgcgttctct aatcgcctcg tcaaggtaac taatcaatca   4560
cctcgtccta atcctcgaat ctctcgtggt gcccgtctaa tctcgcgatt ttgatgctcg   4620
tggtggaaag cgtaggagga tcccgtgcga gttagtctca atctctcagg gtttcgtgcg   4680
attttagggt gatccacctc ttaatcgagt tacggtttcg tgcgatttta gggtaatcct   4740
cttaatctct cattgattta gggtttcgtg agaatcgagg tagggatctg tgttatttat   4800
atcgatctaa tagatggatt ggttttgaga ttgttctgtc agatggggat tgtttcgata   4860
tattacccta atgatgtgtc agatggggat tgtttcgata tattacccta atgatgtgtc   4920
agatggggat tgtttcgata tattacccta atgatggata ataagagtag ttcacagtta   4980
tgttttgatc ctgccacata gtttgagttt tgtgatcaga tttagtttta cttatttgtg   5040
cttagttcgg atgggattgt tctgatattg ttccaataga tgaatagctc gttaggttaa   5100
aatctttagg ttgagttagg cgacacatag tttatttcct ctggatttgg attggaattg   5160
tgttcttagt ttttttcccc tggatttgga ttggaattgt gtggagctgg gttagagaat   5220
tacatctgta tcgtgtacac ctacttgaac tgtagagctt gggttctaag gtcaatttaa   5280
tctgtattgt atctggctct ttgcctagtt gaactgtagt gctgatgttg tactgtgttt   5340
ttttacccgt tttatttgct ttactcgtgc aaatcaaatc tgtcagatgc tagaactagg   5400
tggctttatt ctgtgttctt acatagatct gttgtcctgt agttacttat gtcagttttg   5460
ttattatctg aagatatttt tggttgttgc ttgttgatgt ggtgtgagct gtgagcagcg   5520
ctcttatgat taatgatgct gtccaattgt agtgtagtat gatgtgattg atatgttcat   5580
ctattttgag ctgacagtac cgatatcgta ggatctggtg ccaacttatt ctccagctgc   5640
tttttttac ctatgttaat tccaatcctt tcttgcctct tccagatcca gataatgcag   5700
aaactcatta actcagtgca aaactatgcc tggggcagca aaacggcgtt gactgaactt   5760
tatggtatgg aaaatccgtc cagccagccg atggccgagc tgtggatggg cgcacatccg   5820
aaaagcagtt cacgagtgca gaatgccgcc ggagatatcg tttcactgcg tgatgtgatt   5880
gagagtgata aatcgactct gctcggagag gccgttgcca aacgctttgg cgaactgcct   5940
ttcctgttca aagtattatg cgcagcacag ccactctcca ttcaggttca tccaaacaaa   6000
cacaattctg aaatcggttt tgccaaagaa aatgccgcag gtatcccgat ggatgccgcc   6060
gagcgtaact ataaagatcc taaccacaag ccggagctgg tttttgcgct gacgcctttc   6120
cttgcgatga acgcgtttcg tgaattttcc gagattgtct ccctactcca gccggtcgca   6180
ggtgcacatc cggcgattgc tcacttttta caacagcctg atgccgaacg tttaagcgaa   6240
ctgttcgcca gcctgttgaa tatgcagggt gaagaaaaat cccgcgcgct ggcgatttta   6300
aaatcggccc tcgatagcca gcagggtgaa ccgtggcaaa cgattcgttt aatttctgaa   6360
ttttacccgg aagacagcgg tctgttctcc ccgctattgc tgaatgtggt gaaattgaac   6420
```

```
cctggcgaag cgatgttcct gttcgctgaa acaccgcacg cttacctgca aggcgtggcg   6480
ctggaagtga tggcaaactc cgataacgtg ctgcgtgcgg gtctgacgcc taaatacatt   6540
gatattccgg aactggttgc caatgtgaaa ttcgaagcca aaccggctaa ccagttgttg   6600
acccagccgg tgaaacaagg tgcagaactg gacttcccga ttccagtgga tgattttgcc   6660
ttctcgctgc atgaccttag tgataaagaa accaccatta gccagcagag tgccgccatt   6720
ttgttctgcg tcgaaggcga tgcaacgttg tggaaaggtt ctcagcagtt acagcttaaa   6780
ccgggtgaat cagcgtttat tgccgccaac gaatcaccgg tgactgtcaa aggccacggc   6840
cgtttagcgc gtgtttacaa caagctgtaa gagcttactg aaaaaattaa catctcttgc   6900
taagctggga gctctagatc cccgaatttc cccgatcgtt caaacatttg gcaataaagt   6960
ttcttaagat tgaatcctgt tgccggtctt gcgatgatta tcatataatt tctgttgaat   7020
tacgttaagc atgtaataat taacatgtaa tgcatgacgt tatttatgag atgggttttt   7080
atgattagag tcccgcaatt atacatttaa tacgcgatag aaaacaaaat atagcgcgca   7140
aactaggata aattatcgcg cgcggtgtca tctatgttac tagatcggga attggcgagc   7200
tcgaattaat tcagtacatt aaaaacgtcc gcaatgtgtt attaagttgt ctaagcgtca   7260
atttgtttac accacaatat atcctgccac cagccagcca acagctcccc gaccggcagc   7320
tcggcacaaa atcaccactc gatacaggca gcccatcagt ccgggacggc gtcagcggga   7380
gagccgttgt aaggcggcag actttgctca tgttaccgat gctattcgga agaacggcaa   7440
ctaagctgcc gggtttgaaa cacggatgat ctcgcggagg gtagcatgtt gattgtaacg   7500
atgacagagc gttgctgcct gtgatcaaat atcatctccc tcgcagagat ccgaattatc   7560
agccttctta ttcatttctc gcttaaccgt gacaggctgt cgatcttgag aactatgccg   7620
acataatagg aaatcgctgg ataaagccgc tgaggaagct gagtggcgct atttctttag   7680
aagtgaacgt tgacgatcgt cgaccgtacc ccgatgaatt aattcggacg tacgttctga   7740
acacagctgg atacttactt gggcgattgt catacatgac atcaacaatg tacccgtttg   7800
tgtaaccgtc tcttggaggt tcgtatgaca ctagtggttc ccctcagctt gcgactagat   7860
gttgaggcct aacattttat tagagagcag gctagttgct tagatacatg atcttcaggc   7920
cgttatctgt cagggcaagc gaaaattggc catttatgac gaccaatgcc ccgcagaagc   7980
tcccatcttt gccgccatag acgccgcgcc ccccttttgg ggtgtagaac atccttttgc   8040
cagatgtgga aaagaagttc gttgtcccat tgttggcaat gacgtagtag ccggcgaaag   8100
tgcgagaccc atttgcgcta tatataagcc tacgatttcc gttgcgacta ttgtcgtaat   8160
tggatgaact attatcgtag ttgctctcag agttgtcgta atttgatgga ctattgtcgt   8220
aattgcttat ggagttgtcg tagttgcttg gagaaatgtc gtagttggat ggggagtagt   8280
catagggaag acgagcttca tccactaaaa caattggcag gtcagcaagt gcctgccccg   8340
atgccatcgc aagtacgagg cttagaacca ccttcaacag atcgcgcata gtcttcccca   8400
gctctctaac gcttgagtta agccgcgccg cgaagcggcg tcggcttgaa cgaattgtta   8460
gacattattt gccgactacc ttggtgatct cgcctttcac gtagtgaaca aattcttcca   8520
actgatctgc gcgcgaggcc aagcgatctt cttgtccaag ataagcctgc ctagcttcaa   8580
gtatgacggg ctgatactgg gccggcaggc gctccattgc ccagtcggca gcgacatcct   8640
tcggcgcgat tttgccggtt actgcgctgt accaaatgcg ggacaacgta agcactacat   8700
ttcgctcatc gccagcccag tcgggcggcg agttccatag cgttaaggtt tcatttagcg   8760
cctcaaatag atcctgttca ggaaccggat caaagagttc ctccgccgct ggacctacca   8820
```

```
aggcaacgct atgttctctt gcttttgtca gcaagatagc cagatcaatg tcgatcgtgg   8880
ctggctcgaa gatacctgca agaatgtcat tgcgctgcca ttctccaaat tgcagttcgc   8940
gcttagctgg ataacgccac ggaatgatgt cgtcgtgcac aacaatggtg acttctacag   9000
cgcggagaat ctcgctctct ccaggggaag ccgaagtttc caaaaggtcg ttgatcaaag   9060
ctcgccgcgt tgtttcatca agccttacgg tcaccgtaac cagcaaatca atatcactgt   9120
gtggcttcag gccgccatcc actgcggagc cgtacaaatg tacggccagc aacgtcggtt   9180
cgagatggcg ctcgatgacg ccaactacct ctgatagttg agtcgatact tcggcgatca   9240
ccgcttccct catgatgttt aactcctgaa ttaagccgcg ccgcgaagcg gtgtcggctt   9300
gaatgaattg ttaggcgtca tcctgtgctc ccgagaacca gtaccagtac atcgctgttt   9360
cgttcgagac ttgaggtcta gttttatacg tgaacaggtc aatgccgccg agagtaaagc   9420
cacattttgc gtacaaattg caggcaggta cattgttcgt ttgtgtctct aatcgtatgc   9480
caaggagctg tctgcttagt gcccactttt tcgcaaattc gatgagactg tgcgcgactc   9540
ctttgcctcg gtgcgtgtgc gacacaacaa tgtgttcgat agaggctaga tcgttccatg   9600
ttgagttgag ttcaatcttc ccgacaagct cttggtcgat gaatgcgcca tagcaagcag   9660
agtcttcatc agagtcatca tccgagatgt aatccttccg gtaggggctc acacttctgg   9720
tagatagttc aaagccttgg tcggataggt gcacatcgaa cacttcacga acaatgaaat   9780
ggttctcagc atccaatgtt tccgccacct gctcagggat caccgaaatc ttcatatgac   9840
gcctaacgcc tggcacagcg gatcgcaaac ctggcgcggc ttttggcaca aaaggcgtga   9900
caggtttgcg aatccgttgc tgccacttgt taaccctttt gccagatttg gtaactataa   9960
tttatgttag aggcgaagtc ttgggtaaaa actggcctaa aattgctggg gatttcagga  10020
aagtaaacat caccttccgg ctcgatgtct attgtagata tatgtagtgt atctacttga  10080
tcgggggatc tgctgcctcg cgcgtttcgg tgatgacggt gaaaacctct gacacatgca  10140
gctcccggag acggtcacag cttgtctgta agcggatgcc gggagcagac aagcccgtca  10200
gggcgcgtca gcgggtgttg gcgggtgtcg gggcgcagcc atgacccagt cacgtagcga  10260
tagcggagtg tatactggct taactatgcg gcatcagagc agattgtact gagagtgcac  10320
catatgcggt gtgaaatacc gcacagatgc gtaaggagaa aataccgcat caggcgctct  10380
tccgcttcct cgctcactga ctcgctgcgc tcggtcgttc ggctgcggcg agcggtatca  10440
gctcactcaa aggcggtaat acggttatcc acagaatcag gggataacgc aggaaagaac  10500
atgtgagcaa aaggccagca aaaggccagg aaccgtaaaa aggccgcgtt gctggcgttt  10560
ttccataggc tccgcccccc tgacgagcat cacaaaaatc gacgctcaag tcagaggtgg  10620
cgaaacccga caggactata aagataccag gcgtttcccc ctggaagctc cctcgtgcgc  10680
tctcctgttc cgaccctgcc gcttaccgga tacctgtccg cctttctccc ttcgggaagc  10740
gtggcgcttt ctcatagctc acgctgtagg tatctcagtt cggtgtaggt cgttcgctcc  10800
aagctgggct gtgtgcacga accccccgtt cagcccgacc gctgcgcctt atccggtaac  10860
tatcgtcttg agtccaaccc ggtaagacac gacttatcgc cactggcagc agccactggt  10920
aacaggatta gcagagcgag gtatgtaggc ggtgctacag agttcttgaa gtggtggcct  10980
aactacggct acactagaag gacagtattt ggtatctgcg ctctgctgaa gccagttacc  11040
ttcggaaaaa gagttggtag ctcttgatcc ggcaaacaaa ccaccgctgg tagcggtggt  11100
tttttgtttg caagcagcag attacgcgca gaaaaaaagg atctcaagaa gatcctttga  11160
```

```
atcttttcta cggggtctga cgctcagtgg aacgaaaact cacgttaagg gattttggtc  11220
atgagattat caaaaaggat cttcacctag atccttttaa attaaaaatg aagttttaaa  11280
tcaatctaaa gtatatatga gtaaacttgg tctgacagtt accaatgctt aatcagtgag  11340
gcacctatct cagcgatctg tctatttcgt tcatccatag ttgcctgact ccccgtcgtg  11400
tagataacta cgatacggga gggcttacca tctggcccca gtgctgcaat gataccgcga  11460
gacccacgct caccggctcc agatttatca gcaataaacc agccagccgg aagggccgag  11520
cgcagaagtg gtcctgcaac tttatccgcc tccatccagt ctattaattg ttgccgggaa  11580
gctagagtaa gtagttcgcc agttaatagt ttgcgcaacg ttgttgccat tgctgcaggg  11640
gggggggggg gggggttcca ttgttcattc cacggacaaa aacagagaaa ggaaacgaca  11700
gaggccaaaa agctcgcttt cagcacctgt cgtttccttt cttttcagag ggtattttaa  11760
ataaaaacat taagttatga cgaagaagaa cggaaacgcc ttaaaccgga aaattttcat  11820
aaatagcgaa aacccgcgag gtcgccgccc cgtaacctgt cggatcaccg gaaaggaccc  11880
gtaaagtgat aatgattatc atctacatat cacaacgtgc gtggaggcca tcaaaccacg  11940
tcaaataatc aattatgacg caggtatcgt attaattgat ctgcatcaac ttaacgtaaa  12000
aacaacttca gacaatacaa atcagcgaca ctgaatacgg ggcaacctca tgtccccccc  12060
cccccccccc tgcaggcatc gtggtgtcac gctcgtcgtt tggtatggct tcattcagct  12120
ccggttccca acgatcaagg cgagttacat gatcccccat gttgtgcaaa aaagcggtta  12180
gctccttcgg tcctccgatc gttgtcagaa gtaagttggc cgcagtgtta tcactcatgg  12240
ttatggcagc actgcataat tctcttactg tcatgccatc cgtaagatgc ttttctgtga  12300
ctggtgagta ctcaaccaag tcattctgag aatagtgtat gcggcgaccg agttgctctt  12360
gcccggcgtc aacacgggat aataccgcgc cacatagcag aactttaaaa gtgctcatca  12420
ttggaaaacg ttcttcgggg cgaaaactct caaggatctt accgctgttg agatccagtt  12480
cgatgtaacc cactcgtgca cccaactgat cttcagcatc ttttactttc accagcgttt  12540
ctgggtgagc aaaaacagga aggcaaaatg ccgcaaaaaa gggaataagg gcgacacgga  12600
aatgttgaat actcatactc ttcctttttc aatattattg aagcatttat cagggttatt  12660
gtctcatgag cggatacata tttgaatgta tttagaaaaa taaacaaata ggggttccgc  12720
gcacatttcc ccgaaaagtg ccacctgacg tctaagaaac cattattatc atgacattaa  12780
cctataaaaa taggcgtatc acgaggccct ttcgtcttca agaattggtc gacgatcttg  12840
ctgcgttcgg atattttcgt ggagttcccg ccacagaccc ggattgaagg cgagatccag  12900
caactcgcgc cagatcatcc tgtgacggaa ctttggcgcg tgatgactgg ccaggacgtc  12960
ggccgaaaga gcgacaagca gatcacgctt ttcgacagcg tcggatttgc gatcgaggat  13020
ttttcggcgc tgcgctacgt ccgcgaccgc gttgagggat caagccacag cagcccactc  13080
gaccttctag ccgacccaga cgagccaagg gatctttttg gaatgctgct ccgtcgtcag  13140
gctttccgac gtttgggtgg ttgaacagaa gtcattatcg cacggaatgc caagcactcc  13200
cgaggggaac cctgtggttg gcatgcacat acaaatggac gaacggataa accttttcac  13260
gcccttttaa atatccgatt attctaataa acgctctttt ctcttaggtt tacccgccaa  13320
tatatcctgt caaacactga tagtttaaac tgaaggcggg aaacgacaac ctgatcatga  13380
gcggagaatt aagggagtca cgttatgacc cccgccgatg acgcgggaca agccgtttta  13440
cgtttggaac tgacagaacc gcaacgttga aggagccact cagcttaatt aagtctaact  13500
cgagttactg gtacgtacca aatccatgga atcaaggtac cgtcgactct agtaacggcc  13560
```

```
gccagtgtgc tggaattaat tcggcttgtc gaccacccaa ccccatatcg acagaggatg  13620
tgaagaacag gtaaatcacg cagaagaacc catctctgat agcagctatc gattagaaca  13680
acgaatccat attgggtccg tgggaaatac ttactgcaca ggaagggggc gatctgacga  13740
ggccccgcca ccggcctcga cccgaggccg aggccgacga agcgccggcg agtacggcgc  13800
cgcggcggcc tctgcccgtg ccctctgcgc gtgggaggga gaggccgcgg tggtgggggc  13860
gcgcgcgcgc gcgcgcgcag ctggtgcggc ggcgcggggg tcagccgccg agccggcggc  13920
gacggaggag cagggcggcg tggacgcgaa cttccgatcg gttggtcaga gtgcgcgagt  13980
tgggcttagc caattaggtc tcaacaatct attgggccgt aaaattcatg ggccctggtt  14040
tgtctaggcc caatatcccg ttcatttcag cccacaaata tttccccaga ggattattaa  14100
ggcccacacg cagcttatag cagatcaagt acgatgtttc ctgatcgttg gatcggaaac  14160
gtacggtctt gatcaggcat gccgacttcg tcaaagagag gcggcatgac ctgacgcgga  14220
gttggttccg ggcaccgtct ggatggtcgt accgggaccg gacacgtgtc gcgcctccaa  14280
ctacatggac acgtgtggtg ctgccattgg gccgtacgcg tggcggtgac cgcaccggat  14340
gctgcctcgc accgccttgc ccacgcttta tatagagagg ttttctctcc attaatcgca  14400
tagcgagtcg aatcgaccga aggggagggg gagcgaagct ttgcgttctc taatcgcctc  14460
gtcaaggtaa ctaatcaatc acctcgtcct aatcctcgaa tctctcgtgg tgcccgtcta  14520
atctcgcgat tttgatgctc gtggtggaaa gcgtaggagg atcccgtgcg agttagtctc  14580
aatctctcag ggtttcgtgc gattttaggg tgatccacct cttaatcgag ttacggtttc  14640
gtgcgatttt agggtaatcc tcttaatctc tcattgattt agggtttcgt gagaatcgag  14700
gtagggatct gtgttattta tatcgatcta atagatggat tggttttgag attgttctgt  14760
cagatgggga ttgtttcgat atattaccct aatgatgtgt cagatgggga ttgtttcgat  14820
atattaccct aatgatgtgt cagatgggga ttgtttcgat atattaccct aatgatggat  14880
aataagagta gttcacagtt atgttttgat cctgccacat agtttgagtt ttgtgatcag  14940
atttagtttt acttatttgt gcttagttcg gatgggattg ttctgatatt gttccaatag  15000
atgaatagct cgttaggtta aaatctttag gttgagttag gcgacacata gtttatttcc  15060
tctggatttg gattggaatt gtgttcttag tttttttccc ctggatttgg attggaattg  15120
tgtggagctg ggttagagaa ttacatctgt atcgtgtaca cctacttgaa ctgtagagct  15180
tgggttctaa ggtcaattta atctgtattg tatctggctc tttgcctagt tgaactgtag  15240
tgctgatgtt gtactgtgtt tttttacccg ttttatttgc tttactcgtg caaatcaaat  15300
ctgtcagatg ctagaactag gtggctttat tctgtgttct tacatagatc tgttgtcctg  15360
tagttactta tgtcagtttt gttattatct gaagatattt ttggttgttg cttgttgatg  15420
tggtgtgagc tgtgagcagc gctcttatga ttaatgatgc tgtccaattg tagtgtagta  15480
tgatgtgatt gatatgttca tctattttga gctgacagta ccgatatcgt aggatctggt  15540
gccaacttat tctccagctg cttttttttta cctatgttaa ttccaatcct ttcttgcctc  15600
ttccagatcc agataatggg cttcgtgctc ttctcccagc tgccttcctt ccttcttgtc  15660
tccaccctgc tcttgttcct cgtgatctcc cactcctgcc gcgccgctta cgactacaag  15720
caggtgttgc gggactcgct actattctat gaggcccaga gatccggccg gctcccagcc  15780
gaccagaagg tcacgtggag gaaggatagc gcgctgaatg accagggtga ccagggacaa  15840
gacttgaccg gcggctactt tgacgctggg gacttcgtca agttcgggtt ccccatggct  15900
```

tataccgcaa ccgtgctggc atggggcctc atagattttg aggccggcta cagcagtgcc 15960
ggggccttgg atgatggacg gaaggctgtc aaatgggcca ccgactattt cataaaggcc 16020
cacacaagtc aaaatgagtt ctatggtcag gtcggccagg gtgacgccga tcacgctttc 16080
tggggaagac cagaggatat gacgatggcg cgcccggcgt acaagataga cacctcaagg 16140
cctggctctg atctggcagg cgagacagcg gctgctcttg ccgctgcttc aatcgtgttc 16200
cggaacgtcg atggcactta ctcaaataac ctgttaacac acgctcgcca gctattcgac 16260
ttcgcgaaca actaccgggg aaagtatagt gactctatta ctgacgcaag aaatttctac 16320
gcaagcgcag actacagaga cgagttggtt tgggctgctg cgtggttata cagagcgacc 16380
aacgacaaca cctacctcaa cactgctgag tcactgtacg atgagtttgg gctacagaac 16440 tgggggggg gcctgaactg ggatagcaag gtgtctggcg tgcaggtgtt gttggccaag 16500
cttaccaata agcaggccta caaggacacg gtgcagtctt acgtcaatta cctaattaat 16560
aaccagcaga agactcccaa gggcctcctc tacatcgaca tgtggggcac ccttcgccac 16620
gctgccaacg ccgcattcat catgctcgaa gccgccgagc tgggcttgtc cgcctcctct 16680
tatagacagt tcgcgcaaac gcaaatcgac tacgccctgg gcgatggtgg ccgctccttt 16740
gtgtgcgggt tcgggagtaa tcctcctacg agaccgcacc acagatcctc gtcgtgcccg 16800
ccagctcccg ctacttgcga ctggaataca ttcaactcac ctgacccaaa ctaccacgtc 16860
ctctctgggg ccctagtggg cggacctgat cagaatgaca actacgtcga tgaccgttca 16920
gactatgttc acaacgaagt cgccactgat tacaacgcgg gtttccagtc cgcgttagct 16980
gctttggtgg cccttggtta cagcgagaag gacgagctgt gacctaggtc cccgaatttc 17040
cccgatcgtt caaacatttg gcaataaagt ttcttaagat tgaatcctgt tgccggtctt 17100
gcgatgatta tcatataatt tctgttgaat tacgttaagc atgtaataat taacatgtaa 17160
tgcatgacgt tatttatgag atgggttttt atgattagag tcccgcaatt atacatttaa 17220
tacgcgatag aaaacaaaat atagcgcgca aactaggata aattatcgcg cgcggtgtca 17280
tctatgttac tagatcggga attgggtac 17309

<210> SEQ ID NO 76
<211> LENGTH: 13042
<212> TYPE: DNA
<213> ORGANISM: Artificial Sequence
<220> FEATURE:
<223> OTHER INFORMATION: Synthetic construct, vector pAG2252

<400> SEQUENCE: 76
aattcatact aaagcttgca tgcctgcagg tcgactctag taacggccgc cagtgtgctg 60
gaattaattc ggcttgtcga ccacccaacc ccatatcgac agaggatgtg aagaacaggt 120
aaatcacgca gaagaaccca tctctgatag cagctatcga ttagaacaac gaatccatat 180
tgggtccgtg ggaaatactt actgcacagg aagggggcga tctgacgagg ccccgccacc 240
ggcctcgacc cgaggccgag gccgacgaag cgccggcgag tacggcgccg cggcggcctc 300
tgcccgtgcc ctctgcgcgt gggagggaga ggccgcggtg gtgggggcgc gcgcgcgcgc 360
gcgcgcagct ggtgcggcgg cgcgggggtc agccgccgag ccggcggcga cggaggagca 420
gggcggcgtg gacgcgaact tccgatcggt tggtcagagt gcgcgagttg ggcttagcca 480
attaggtctc aacaatctat tgggccgtaa aattcatggg ccctggtttg tctaggccca 540
atatcccgtt catttcagcc cacaaatatt tccccagagg attattaagg cccacacgca 600
gcttatagca gatcaagtac gatgtttcct gatcgttgga tcggaaacgt acggtcttga 660

```
tcaggcatgc cgacttcgtc aaagagaggc ggcatgacct gacgcggagt tggttccggg    720
caccgtctgg atggtcgtac cgggaccgga cacgtgtcgc gcctccaact acatggacac    780
gtgtggtgct gccattgggc cgtacgcgtg gcggtgaccg caccggatgc tgcctcgcac    840
cgccttgccc acgctttata tagagaggtt ttctctccat taatcgcata gcgagtcgaa    900
tcgaccgaag gggaggggga gcgaagcttt gcgttctcta atcgcctcgt caaggtaact    960
aatcaatcac ctcgtcctaa tcctcgaatc tctcgtggtg cccgtctaat ctcgcgattt   1020
tgatgctcgt ggtggaaagc gtaggaggat cccgtgcgag ttagtctcaa tctctcaggg   1080
tttcgtgcga ttttagggtg atccacctct taatcgagtt acggtttcgt gcgattttag   1140
ggtaatcctc ttaatctctc attgatttag ggtttcgtga gaatcgaggt agggatctgt   1200
gttatttata tcgatctaat agatggattg gttttgagat tgttctgtca gatggggatt   1260
gtttcgatat attaccctaa tgatgtgtca gatggggatt gtttcgatat attaccctaa   1320
tgatgtgtca gatggggatt gtttcgatat attaccctaa tgatggataa taagagtagt   1380
tcacagttat gttttgatcc tgccacatag tttgagtttt gtgatcagat ttagttttac   1440
ttatttgtgc ttagttcgga tgggattgtt ctgatattgt tccaatagat gaatagctcg   1500
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct tttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt ttttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
```

cagttgttga cccagccggt gaaacaaggt gcagaactgg acttcccgat tccagtggat 3060
gattttgcct tctcgctgca tgaccttagt gataaagaaa ccaccattag ccagcagagt 3120
gccgccattt tgttctgcgt cgaaggcgat gcaacgttgt ggaaaggttc tcagcagtta 3180
cagcttaaac cgggtgaatc agcgtttatt gccgccaacg aatcaccggt gactgtcaaa 3240
ggccacggcc gtttagcgcg tgtttacaac aagctgtaag agcttactga aaaaattaac 3300
atctcttgct aagctgggag ctctagatcc ccgaatttcc ccgatcgttc aaacatttgg 3360
caataaagtt tcttaagatt gaatcctgtt gccggtcttg cgatgattat catataattt 3420
ctgttgaatt acgttaagca tgtaataatt aacatgtaat gcatgacgtt atttatgaga 3480
tgggttttta tgattagagt cccgcaatta tacatttaat acgcgataga aaacaaaata 3540
tagcgcgcaa actaggataa attatcgcgc gcggtgtcat ctatgttact agatcgggaa 3600
ttggcgagct cgaattaatt cagtacatta aaaacgtccg caatgtgtta ttaagttgtc 3660
taagcgtcaa tttgtttaca ccacaatata tcctgccacc agccagccaa cagctccccg 3720
accggcagct cggcacaaaa tcaccactcg atacaggcag cccatcagtc cgggacggcg 3780
tcagcgggag agccgttgta aggcggcaga ctttgctcat gttaccgatg ctattcggaa 3840
gaacggcaac taagctgccg ggtttgaaac acggatgatc tcgcggaggg tagcatgttg 3900
attgtaacga tgacagagcg ttgctgcctg tgatcaaata tcatctccct cgcagagatc 3960
cgaattatca gccttcttat tcatttctcg cttaaccgtg acaggctgtc gatcttgaga 4020
actatgccga cataatagga aatcgctgga taaagccgct gaggaagctg agtggcgcta 4080
tttctttaga agtgaacgtt gacgatcgtc gaccgtaccc cgatgaatta attcggacgt 4140
acgttctgaa cacagctgga tacttacttg ggcgattgtc atacatgaca tcaacaatgt 4200
acccgtttgt gtaaccgtct cttggaggtt cgtatgacac tagtggttcc cctcagcttg 4260
cgactagatg ttgaggccta acattttatt agagagcagg ctagttgctt agatacatga 4320
tcttcaggcc gttatctgtc agggcaagcg aaaattggcc atttatgacg accaatgccc 4380
cgcagaagct cccatctttg ccgccataga cgccgcgccc cccttttggg gtgtagaaca 4440
tccttttgcc agatgtggaa aagaagttcg ttgtcccatt gttggcaatg acgtagtagc 4500
cggcgaaagt gcgagaccca tttgcgctat atataagcct acgatttccg ttgcgactat 4560
tgtcgtaatt ggatgaacta ttatcgtagt tgctctcaga gttgtcgtaa tttgatggac 4620
tattgtcgta attgcttatg gagttgtcgt agttgcttgg agaaatgtcg tagttggatg 4680
gggagtagtc atagggaaga cgagcttcat ccactaaaac aattggcagg tcagcaagtg 4740
cctgccccga tgccatcgca agtacgaggc ttagaaccac cttcaacaga tcgcgcatag 4800
tcttccccag ctctctaacg cttgagttaa gccgcgccgc gaagcggcgt cggcttgaac 4860
gaattgttag acattatttg ccgactacct tggtgatctc gcctttcacg tagtgaacaa 4920
attcttccaa ctgatctgcg cgcgaggcca agcgatcttc ttgtccaaga taagcctgcc 4980
tagcttcaag tatgacgggc tgatactggg ccggcaggcg ctccattgcc cagtcggcag 5040
cgacatcctt cggcgcgatt ttgccggtta ctgcgctgta ccaaatgcgg gacaacgtaa 5100
gcactacatt tcgctcatcg ccagcccagt cgggcggcga gttccatagc gttaaggttt 5160
catttagcgc ctcaaataga tcctgttcag gaaccggatc aaagagttcc tccgccgctg 5220
gacctaccaa ggcaacgcta tgttctcttg cttttgtcag caagatagcc agatcaatgt 5280
cgatcgtggc tggctcgaag atacctgcaa gaatgtcatt gcgctgccat tctccaaatt 5340
gcagttcgcg cttagctgga taacgccacg gaatgatgtc gtcgtgcaca acaatggtga 5400

```
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aaccctttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
```

```
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg cccttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
```

atctgacgag gccccgccac cggcctcgac ccgaggccga ggccgacgaa gcgccggcga 10200
gtacggcgcc gcggcggcct ctgcccgtgc cctctgcgcg tgggagggag aggccgcggt 10260
ggtgggggcg cgcgcgcgcg cgcgcgcagc tggtgcggcg gcgcgggggt cagccgccga 10320
gccggcggcg acggaggagc agggcggcgt ggacgcgaac ttccgatcgg ttggtcagag 10380
tgcgcgagtt gggcttagcc aattaggtct caacaatcta ttgggccgta aaattcatgg 10440
gccctggttt gtctaggccc aatatcccgt tcatttcagc ccacaaatat ttccccagag 10500
gattattaag gcccacacgc agcttatagc agatcaagta cgatgtttcc tgatcgttgg 10560
atcggaaacg tacggtcttg atcaggcatg ccgacttcgt caaagagagg cggcatgacc 10620
tgacgcggag ttggttccgg gcaccgtctg gatggtcgta ccgggaccgg acacgtgtcg 10680
cgcctccaac tacatggaca cgtgtggtgc tgccattggg ccgtacgcgt ggcggtgacc 10740
gcaccggatg ctgcctcgca ccgccttgcc cacgctttat atagagaggt tttctctcca 10800
ttaatcgcat agcgagtcga atcgaccgaa ggggaggggg agcgaagctt tgcgttctct 10860
aatcgcctcg tcaaggtaac taatcaatca cctcgtccta atcctcgaat ctctcgtggt 10920
gcccgtctaa tctcgcgatt ttgatgctcg tggtggaaag cgtaggagga tcccgtgcga 10980
gttagtctca atctctcagg gtttcgtgcg attttagggt gatccacctc ttaatcgagt 11040
tacggtttcg tgcgatttta gggtaatcct cttaatctct cattgattta gggtttcgtg 11100
agaatcgagg tagggatctg tgttatttat atcgatctaa tagatggatt ggttttgaga 11160
ttgttctgtc agatggggat tgtttcgata tattacccta atgatgtgtc agatggggat 11220
tgtttcgata tattacccta atgatgtgtc agatggggat tgtttcgata tattacccta 11280
atgatggata ataagagtag ttcacagtta tgttttgatc ctgccacata gtttgagttt 11340
tgtgatcaga tttagtttta cttatttgtg cttagttcgg atgggattgt tctgatattg 11400
ttccaataga tgaatagctc gttaggttaa aatctttagg ttgagttagg cgacacatag 11460
tttatttcct ctggatttgg attggaattg tgttcttagt ttttttcccc tggatttgga 11520
ttggaattgt gtggagctgg gttagagaat tacatctgta tcgtgtacac ctacttgaac 11580
tgtagagctt gggttctaag gtcaatttaa tctgtattgt atctggctct ttgcctagtt 11640
gaactgtagt gctgatgttg tactgtgttt ttttacccgt tttatttgct ttactcgtgc 11700
aaatcaaatc tgtcagatgc tagaactagg tggctttatt ctgtgttctt acatagatct 11760
gttgtcctgt agttacttat gtcagttttg ttattatctg aagatatttt tggttgttgc 11820
ttgttgatgt ggtgtgagct gtgagcagcg ctcttatgat taatgatgct gtccaattgt 11880
agtgtagtat gatgtgattg atatgttcat ctattttgag ctgacagtac cgatatcgta 11940
ggatctggtg ccaacttatt ctccagctgc tttttttttac ctatgttaat tccaatcctt 12000
tcttgcctct tccagatcca gataatgtgc gattggctgt tccctgatgg agataatgga 12060
aaggagcccg aaccagaacc agaaccaacg gtagagctct gcggaagatg ggatgcaaga 12120
gacgtagcgg gaggaagata tagagttatt aacaatgtgt ggggggccga aacagcacag 12180
tgtatagaag taggtcttga aacaggtaat tttacgataa caagagccga tcatgacaat 12240
ggtaataatg ttgcagcata tccagcaatt tacttcggat gtcattgggc accagcgaga 12300
gcaataaggg attgtgccgc gcgtgcggga gcggttagga gagcacacga attggatgtt 12360
acaccaatta ccacgggaag atggaacgca gcttacgata tatggtttag tccggtaaca 12420
aactctggta acgggtactc gggaggcgcc gaacttatga tatggctgaa ttggaatggt 12480

```
ggcgtaatgc caggaggatc acgggtagca actgtcgaat tggctggagc gacatgggaa  12540

gtgtggtatg cagattggga ttggaattac atcgcatata gaagaacgac tccgacaacc  12600

tcagtgagtg aacttgactt gaaagccttt attgatgatg cagtagcgag aggatacata  12660

aggccagaat ggtatctgca tgcagtggaa acgggatttg aattgtggga aggggggct  12720

gggttgagga cagcagattt tagcgtaact gtacagtgac ctaggtcccc gaatttcccc  12780

gatcgttcaa acatttggca ataaagtttc ttaagattga atcctgttgc cggtcttgcg  12840

atgattatca tataatttct gttgaattac gttaagcatg taataattaa catgtaatgc  12900

atgacgttat ttatgagatg ggtttttatg attagagtcc cgcaattata catttaatac  12960

gcgatagaaa acaaaatata gcgcgcaaac taggataaat tatcgcgcgc ggtgtcatct  13020

atgttactag atcgggaatt gg                                           13042
```

<210> SEQ ID NO 77
<211> LENGTH: 13120
<212> TYPE: DNA
<213> ORGANISM: Artificial Sequence
<220> FEATURE:
<223> OTHER INFORMATION: Synthetic construct, vector pAG2253

<400> SEQUENCE: 77

```
aattcatact aaagcttgca tgcctgcagg tcgactctag taacggccgc cagtgtgctg     60

gaattaattc ggcttgtcga ccacccaacc ccatatcgac agaggatgtg aagaacaggt    120

aaatcacgca gaagaaccca tctctgatag cagctatcga ttagaacaac gaatccatat    180

tgggtccgtg ggaaatactt actgcacagg aagggggcga tctgacgagg ccccgccacc    240

ggcctcgacc cgaggccgag gccgacgaag cgccggcgag tacggcgccg cggcggcctc    300

tgcccgtgcc ctctgcgcgt gggagggaga ggccgcggtg gtgggggcgc gcgcgcgcgc    360

gcgcgcagct ggtgcggcgg cgcgggggtc agccgccgag ccggcggcga cggaggagca    420

gggcggcgtg gacgcgaact tccgatcggt tggtcagagt gcgcgagttg ggcttagcca    480

attaggtctc aacaatctat tgggccgtaa aattcatggg ccctggtttg tctaggccca    540

atatcccgtt catttcagcc cacaaatatt tccccagagg attattaagg cccacacgca    600

gcttatagca gatcaagtac gatgtttcct gatcgttgga tcggaaacgt acggtcttga    660

tcaggcatgc cgacttcgtc aaagagaggc ggcatgacct gacgcggagt tggttccggg    720

caccgtctgg atggtcgtac cgggaccgga cacgtgtcgc gcctccaact acatggacac    780

gtgtggtgct gccattgggc cgtacgcgtg gcggtgaccg caccggatgc tgcctcgcac    840

cgccttgccc acgctttata tagagaggtt ttctctccat taatcgcata gcgagtcgaa    900

tcgaccgaag ggagggggga gcgaagcttt gcgttctcta atcgcctcgt caaggtaact    960

aatcaatcac ctcgtcctaa tcctcgaatc tctcgtggtg cccgtctaat ctcgcgattt   1020

tgatgctcgt ggtggaaagc gtaggaggat cccgtgcgag ttagtctcaa tctctcaggg   1080

tttcgtgcga ttttagggtg atccacctct taatcgagtt acggtttcgt gcgattttag   1140

ggtaatcctc ttaatctctc attgatttag ggtttcgtga gaatcgaggt agggatctgt   1200

gttatttata tcgatctaat agatggattg gttttgagat tgttctgtca gatggggatt   1260

gtttcgatat attaccctaa tgatgtgtca gatggggatt gtttcgatat attaccctaa   1320

tgatgtgtca gatggggatt gtttcgatat attaccctaa tgatggataa taagagtagt   1380

tcacagttat gttttgatcc tgccacatag tttgagtttt gtgatcagat ttagttttac   1440

ttatttgtgc ttagttcgga tgggattgtt ctgatattgt tccaatagat gaatagctcg   1500
```

```
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct ttttttaccc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt ttttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
```

```
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc ccccttttggg gtgtagaaca   4440
tcctttttgcc agatgtggaa aagaagttcg ttgtcccatt gttggcaatg acgtagtagc   4500
cggcgaaagt gcgagaccca tttgcgctat atataagcct acgatttccg ttgcgactat   4560
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
cgacatcctt cggcgcgatt ttgccggtta ctgcgctgta ccaaatgcgg gacaacgtaa   5100
gcactacatt tcgctcatcg ccagcccagt cgggcggcga gttccatagc gttaaggttt   5160
catttagcgc ctcaaataga tcctgttcag gaaccggatc aaagagttcc tccgccgctg   5220
gacctaccaa ggcaacgcta tgttctcttg cttttgtcag caagatagcc agatcaatgt   5280
cgatcgtggc tggctcgaag atacctgcaa gaatgtcatt gcgctgccat tctccaaatt   5340
gcagttcgcg cttagctgga taacgccacg gaatgatgtc gtcgtgcaca acaatggtga   5400
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
```

```
tcatatgacg cctaacgcct ggcacagcgg atcgcaaacc tggcgcggct tttggcacaa   6300
aaggcgtgac aggtttgcga atccgttgct gccacttgtt aacccttttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
```

```
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg cccttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
```

```
gttagtctca atctctcagg gtttcgtgcg attttagggt gatccacctc ttaatcgagt  11040

tacggtttcg tgcgatttta gggtaatcct cttaatctct cattgattta gggtttcgtg  11100

agaatcgagg tagggatctg tgttatttat atcgatctaa tagatggatt ggttttgaga  11160

ttgttctgtc agatggggat tgtttcgata tattacccta atgatgtgtc agatggggat  11220

tgtttcgata tattacccta atgatgtgtc agatggggat tgtttcgata tattacccta  11280

atgatggata ataagagtag ttcacagtta tgttttgatc ctgccacata gtttgagttt  11340

tgtgatcaga tttagtttta cttatttgtg cttagttcgg atgggattgt tctgatattg  11400

ttccaataga tgaatagctc gttaggttaa aatctttagg ttgagttagg cgacacatag  11460

tttatttcct ctggatttgg attggaattg tgttcttagt ttttttcccc tggatttgga  11520

ttggaattgt gtggagctgg gttagagaat tacatctgta tcgtgtacac ctacttgaac  11580

tgtagagctt gggttctaag gtcaatttaa tctgtattgt atctggctct ttgcctagtt  11640

gaactgtagt gctgatgttg tactgtgttt ttttacccgt tttatttgct ttactcgtgc  11700

aaatcaaatc tgtcagatgc tagaactagg tggctttatt ctgtgttctt acatagatct  11760

gttgtcctgt agttacttat gtcagttttg ttattatctg aagatatttt tggttgttgc  11820

ttgttgatgt ggtgtgagct gtgagcagcg ctcttatgat taatgatgct gtccaattgt  11880

agtgtagtat gatgtgattg atatgttcat ctattttgag ctgacagtac cgatatcgta  11940

ggatctggtg ccaacttatt ctccagctgc tttttttac ctatgttaat tccaatcctt  12000

tcttgcctct tccagatcca gataatggcg aacaaacatt tgtccctctc cctcttcctc  12060

gtcctccttg gcctgtcggc cagcttggcc tccgggcaac aggtgtgcga ttggctgttc  12120

cctgatggag ataatggaaa ggagcccgaa ccagaaccag aaccaacggt agagctctgc  12180

ggaagatggg atgcaagaga cgtagcggga ggaagatata gagttattaa caatgtgtgg  12240

ggggccgaaa cagcacagtg tatagaagta ggtcttgaaa caggtaattt tacgataaca  12300

agagccgatc atgacaatgg taataatgtt gcagcatatc cagcaattta cttcggatgt  12360

cattgggcac cagcgagagc aataagggat tgtgccgcgc gtgcgggagc ggttaggaga  12420

gcacacgaat tggatgttac accaattacc acgggaagat ggaacgcagc ttacgatata  12480

tggtttagtc cggtaacaaa ctctggtaac gggtactcgg gaggcgccga acttatgata  12540

tggctgaatt ggaatggtgg cgtaatgcca ggaggatcac gggtagcaac tgtcgaattg  12600

gctggagcga catgggaagt gtggtatgca gattgggatt ggaattacat cgcatataga  12660

agaacgactc cgacaacctc agtgagtgaa cttgacttga aagcctttat tgatgatgca  12720

gtagcgagag gatacataag gccagaatgg tatctgcatg cagtggaaac gggatttgaa  12780

ttgtgggaag ggggggctgg gttgaggaca gcagatttta gcgtaactgt acagtgacct  12840

aggtccccga atttccccga tcgttcaaac atttggcaat aaagtttctt aagattgaat  12900

cctgttgccg gtcttgcgat gattatcata taatttctgt tgaattacgt taagcatgta  12960

ataattaaca tgtaatgcat gacgttattt atgagatggg tttttatgat tagagtcccg  13020

caattataca tttaatacgc gatagaaaac aaaatatagc gcgcaaacta ggataaatta  13080

tcgcgcgcgg tgtcatctat gttactagat cgggaattgg                       13120
```

<210> SEQ ID NO 78
<211> LENGTH: 17111
<212> TYPE: DNA
<213> ORGANISM: Artificial Sequence
<220> FEATURE:

<223> OTHER INFORMATION: Synthetic construct, vector pAG2309

<400> SEQUENCE: 78

```
cgtcgactct agtaacggcc gccagtgtgc tggaattaat tcggcttgtc gaccacccaa     60
ccccatatcg acagaggatg tgaagaacag gtaaatcacg cagaagaacc catctctgat    120
agcagctatc gattagaaca acgaatccat attgggtccg tgggaaatac ttactgcaca    180
ggaagggggc gatctgacga ggccccgcca ccggcctcga cccgaggccg aggccgacga    240
agcgccggcg agtacggcgc cgcggcggcc tctgcccgtg ccctctgcgc gtgggaggga    300
gaggccgcgg tggtgggggc gcgcgcgcgc gcgcgcgcag ctggtgcggc ggcgcggggg    360
tcagccgccg agccggcggc gacggaggag cagggcggcg tggacgcgaa cttccgatcg    420
gttggtcaga gtgcgcgagt tgggcttagc caattaggtc tcaacaatct attgggccgt    480
aaaattcatg ggccctggtt tgtctaggcc caatatcccg ttcatttcag cccacaaata    540
tttccccaga ggattattaa ggcccacacg cagcttatag cagatcaagt acgatgtttc    600
ctgatcgttg gatcggaaac gtacggtctt gatcaggcat gccgacttcg tcaaagagag    660
gcggcatgac ctgacgcgga gttggttccg ggcaccgtct ggatggtcgt accgggaccg    720
gacacgtgtc gcgcctccaa ctacatggac acgtgtggtg ctgccattgg gccgtacgcg    780
tggcggtgac cgcaccggat gctgcctcgc accgccttgc ccacgcttta tatagagagg    840
ttttctctcc attaatcgca tagcgagtcg aatcgaccga aggggagggg gagcgaagct    900
ttgcgttctc taatcgcctc gtcaaggtaa ctaatcaatc acctcgtcct aatcctcgaa    960
tctctcgtgg tgcccgtcta atctcgcgat tttgatgctc gtggtggaaa gcgtaggagg   1020
atcccgtgcg agttagtctc aatctctcag ggtttcgtgc gattttaggg tgatccacct   1080
cttaatcgag ttacggtttc gtgcgatttt agggtaatcc tcttaatctc tcattgattt   1140
agggtttcgt gagaatcgag gtagggatct gtgttattta tatcgatcta atagatggat   1200
tggttttgag attgttctgt cagatgggga ttgtttcgat atattaccct aatgatgtgt   1260
cagatgggga ttgtttcgat atattaccct aatgatgtgt cagatgggga ttgtttcgat   1320
atattaccct aatgatggat aataagagta gttcacagtt atgttttgat cctgccacat   1380
agtttgagtt ttgtgatcag atttagtttt acttatttgt gcttagttcg gatgggattg   1440
ttctgatatt gttccaatag atgaatagct cgttaggtta aaatctttag gttgagttag   1500
gcgacacata gtttatttcc tctggatttg gattggaatt gtgttcttag ttttttttccc   1560
ctggatttgg attggaattg tgtggagctg ggttagagaa ttacatctgt atcgtgtaca   1620
cctacttgaa ctgtagagct tgggttctaa ggtcaattta atctgtattg tatctggctc   1680
tttgcctagt tgaactgtag tgctgatgtt gtactgtgtt tttttacccg ttttatttgc   1740
tttactcgtg caaatcaaat ctgtcagatg ctagaactag gtggctttat tctgtgttct   1800
tacatagatc tgttgtcctg tagttactta tgtcagtttt gttattatct gaagatattt   1860
ttggttgttg cttgttgatg tggtgtgagc tgtgagcagc gctcttatga ttaatgatgc   1920
tgtccaattg tagtgtagta tgatgtgatt gatatgttca tctattttga gctgacagta   1980
ccgatatcgt aggatctggt gccaacttat tctccagctg cttttttttta cctatgttaa   2040
ttccaatcct ttcttgcctc ttccagatcc agataatgca aacaagcatt actctgacat   2100
ccaacgcatc cggtacgttt gacggttact attacgaact ctggaaggat actggcaata   2160
caacaatgac ggtctacact caaggtcgct tttcctgcca gtggtcgaac atcaataacg   2220
cgttgtttag gaccgggaag aaatacaacc agaattggca gtctcttggc acaatccgga   2280
```

```
tcacgtactc tgcgacttac aacccaaacg ggaactccta cttgtgtatc tatggctggt   2340
ctaccaaccc attggtcgag ttctacatcg ttgagtcctg gggggaactgg agaccgcctg   2400
gtgccacgtc cctgggccaa gtgacaatcg atggcgggac ctacgacatc tataggacga   2460
cacgcgtcaa ccagccttcc attgtgggga cagccacgtt cgatcagtac tggagcgtgc   2520
gcacctctaa gcggacttca ggaacagtga ccgtgaccga tcacttccgc gcctgggcga   2580
accggggcct gaacctcggc acaatagacc aaattacatt gtgcgtggag ggttaccaaa   2640
gctctggatc agccaacatc acccagaaca ccttctctca gggctcttct tccggcagtt   2700
cgggtggctc atccggctcc acaacgacta ctcgcatcga gtgtgagaac atgtccttgt   2760
ccggacccta cgttagcagg atcaccaatc cctttaatgg tattgcgctg tacgccaacg   2820
gagacacagc ccgcgctacc gttaacttcc ccgcaagtcg caactacaat ttccgcctgc   2880
ggggttgcgg caacaacaat aatcttgccc gtgtggacct gaggatcgac ggacggaccg   2940
tcgggacctt ttattaccag ggcacatacc cctgggaggc cccaattgac aatgtttatg   3000
tcagtgcggg gagtcataca gtcgaaatca ctgttactgc ggataacggc acatgggacg   3060
tgtatgccga ctacctggtg atacagtgac ctaggtcccc gaatttcccc gatcgttcaa   3120
acatttggca ataaagtttc ttaagattga atcctgttgc cggtcttgcg atgattatca   3180
tataatttct gttgaattac gttaagcatg taataattaa catgtaatgc atgacgttat   3240
ttatgagatg ggtttttatg attagagtcc cgcaattata catttaatac gcgatagaaa   3300
acaaaatata gcgcgcaaac taggataaat tatcgcgcgc ggtgtcatct atgttactag   3360
atcgggaatt ggaattcata ctaaagcttg catgcctgca ggtcgactct agtaacggcc   3420
gccagtgtgc tggaattaat tcggcttgtc gaccacccaa ccccatatcg acagaggatg   3480
tgaagaacag gtaaatcacg cagaagaacc catctctgat agcagctatc gattagaaca   3540
acgaatccat attgggtccg tgggaaatac ttactgcaca ggaagggggc gatctgacga   3600
ggccccgcca ccggcctcga cccgaggccg aggccgacga agcgccggcg agtacggcgc   3660
cgcggcggcc tctgcccgtg ccctctgcgc gtgggaggga gaggccgcgg tggtgggggc   3720
gcgcgcgcgc gcgcgcgcag ctggtgcggc ggcgcggggg tcagccgccg agccggcggc   3780
gacggaggag cagggcggcg tggacgcgaa cttccgatcg gttggtcaga gtgcgcgagt   3840
tgggcttagc caattaggtc tcaacaatct attgggccgt aaaattcatg ggccctggtt   3900
tgtctaggcc caatatcccg ttcatttcag cccacaaata tttccccaga ggattattaa   3960
ggcccacacg cagcttatag cagatcaagt acgatgtttc ctgatcgttg gatcggaaac   4020
gtacggtctt gatcaggcat gccgacttcg tcaaagagag gcggcatgac ctgacgcgga   4080
gttggttccg ggcaccgtct ggatggtcgt accgggaccg gacacgtgtc gcgcctccaa   4140
ctacatggac acgtgtggtg ctgccattgg gccgtacgcg tggcggtgac cgcaccggat   4200
gctgcctcgc accgccttgc ccacgcttta tatagagagg ttttctctcc attaatcgca   4260
tagcgagtcg aatcgaccga aggggagggg gagcgaagct ttgcgttctc taatcgcctc   4320
gtcaaggtaa ctaatcaatc acctcgtcct aatcctcgaa tctctcgtgg tgcccgtcta   4380
atctcgcgat tttgatgctc gtggtggaaa gcgtaggagg atcccgtgcg agttagtctc   4440
aatctctcag ggtttcgtgc gattttaggg tgatccacct cttaatcgag ttacggtttc   4500
gtgcgatttt agggtaatcc tcttaatctc tcattgattt agggtttcgt gagaatcgag   4560
gtagggatct gtgttattta tatcgatcta atagatggat tggttttgag attgttctgt   4620
```

```
cagatgggga ttgtttcgat atattaccct aatgatgtgt cagatgggga ttgtttcgat   4680
atattaccct aatgatgtgt cagatgggga ttgtttcgat atattaccct aatgatggat   4740
aataagagta gttcacagtt atgttttgat cctgccacat agtttgagtt ttgtgatcag   4800
atttagtttt acttatttgt gcttagttcg gatgggattg ttctgatatt gttccaatag   4860
atgaatagct cgttaggtta aaatctttag gttgagttag gcgacacata gtttatttcc   4920
tctggatttg gattggaatt gtgttcttag tttttttccc ctggatttgg attggaattg   4980
tgtggagctg ggttagagaa ttacatctgt atcgtgtaca cctacttgaa ctgtagagct   5040
tgggttctaa ggtcaattta atctgtattg tatctggctc tttgcctagt tgaactgtag   5100
tgctgatgtt gtactgtgtt tttttacccg ttttatttgc tttactcgtg caaatcaaat   5160
ctgtcagatg ctagaactag gtggctttat tctgtgttct tacatagatc tgttgtcctg   5220
tagttactta tgtcagtttt gttattatct gaagatattt ttggttgttg cttgttgatg   5280
tggtgtgagc tgtgagcagc gctcttatga ttaatgatgc tgtccaattg tagtgtagta   5340
tgatgtgatt gatatgttca tctattttga gctgacagta ccgatatcgt aggatctggt   5400
gccaacttat tctccagctg cttttttta cctatgttaa ttccaatcct ttcttgcctc   5460
ttccagatcc agataatgca gaaactcatt aactcagtgc aaaactatgc ctggggcagc   5520
aaaacggcgt tgactgaact ttatggtatg gaaaatccgt ccagccagcc gatggccgag   5580
ctgtggatgg gcgcacatcc gaaaagcagt tcacgagtgc agaatgccgc cggagatatc   5640
gtttcactgc gtgatgtgat tgagagtgat aaatcgactc tgctcggaga ggccgttgcc   5700
aaacgctttg gcgaactgcc tttcctgttc aaagtattat gcgcagcaca gccactctcc   5760
attcaggttc atccaaacaa acacaattct gaaatcggtt ttgccaaaga aaatgccgca   5820
ggtatcccga tggatgccgc cgagcgtaac tataaagatc ctaaccacaa gccggagctg   5880
gtttttgcgc tgacgccttt ccttgcgatg aacgcgtttc gtgaattttc cgagattgtc   5940
tccctactcc agccggtcgc aggtgcacat ccggcgattg ctcacttttt acaacagcct   6000
gatgccgaac gtttaagcga actgttcgcc agcctgttga atatgcaggg tgaagaaaaa   6060
tcccgcgcgc tggcgatttt aaaatcggcc ctcgatagcc agcagggtga accgtggcaa   6120
acgattcgtt taatttctga attttacccg gaagacagcg gtctgttctc cccgctattg   6180
ctgaatgtgg tgaaattgaa ccctggcgaa gcgatgttcc tgttcgctga aacaccgcac   6240
gcttacctgc aaggcgtggc gctggaagtg atggcaaact ccgataacgt gctgcgtgcg   6300
ggtctgacgc ctaaatacat tgatattccg gaactggttg ccaatgtgaa attcgaagcc   6360
aaaccggcta accagttgtt gacccagccg gtgaaacaag gtgcagaact ggacttcccg   6420
attccagtgg atgattttgc cttctcgctg catgacctta gtgataaaga aaccaccatt   6480
agccagcaga gtgccgccat tttgttctgc gtcgaaggcg atgcaacgtt gtggaaaggt   6540
tctcagcagt tacagcttaa accgggtgaa tcagcgttta ttgccgccaa cgaatcaccg   6600
gtgactgtca aaggccacgg ccgtttagcg cgtgtttaca acaagctgta agagcttact   6660
gaaaaaatta acatctcttg ctaagctggg agctctagat ccccgaattt ccccgatcgt   6720
tcaaacattt ggcaataaag tttcttaaga ttgaatcctg ttgccggtct tgcgatgatt   6780
atcatataat ttctgttgaa ttacgttaag catgtaataa ttaacatgta atgcatgacg   6840
ttatttatga gatgggtttt tatgattaga gtcccgcaat tatacattta atacgcgata   6900
gaaaacaaaa tatagcgcgc aaactaggat aaattatcgc gcgcggtgtc atctatgtta   6960
ctagatcggg aattggcgag ctcgaattaa ttcagtacat taaaaacgtc cgcaatgtgt   7020
```

```
tattaagttg tctaagcgtc aatttgttta caccacaata tatcctgcca ccagccagcc   7080

aacagctccc cgaccggcag ctcggcacaa aatcaccact cgatacaggc agcccatcag   7140

tccgggacgg cgtcagcggg agagccgttg taaggcggca gactttgctc atgttaccga   7200

tgctattcgg aagaacggca actaagctgc cgggtttgaa acacggatga tctcgcggag   7260

ggtagcatgt tgattgtaac gatgacagag cgttgctgcc tgtgatcaaa tatcatctcc   7320

ctcgcagaga tccgaattat cagccttctt attcatttct cgcttaaccg tgacaggctg   7380

tcgatcttga gaactatgcc gacataatag gaaatcgctg gataaagccg ctgaggaagc   7440

tgagtggcgc tatttcttta gaagtgaacg ttgacgatcg tcgaccgtac cccgatgaat   7500

taattcggac gtacgttctg aacacagctg gatacttact tgggcgattg tcatacatga   7560

catcaacaat gtacccgttt gtgtaaccgt ctcttggagg ttcgtatgac actagtggtt   7620

cccctcagct tgcgactaga tgttgaggcc taacatttta ttagagagca ggctagttgc   7680

ttagatacat gatcttcagg ccgttatctg tcagggcaag cgaaaattgg ccatttatga   7740

cgaccaatgc cccgcagaag ctcccatctt tgccgccata gacgccgcgc ccccctttg   7800

gggtgtagaa catccttttg ccagatgtgg aaaagaagtt cgttgtccca ttgttggcaa   7860

tgacgtagta gccggcgaaa gtgcgagacc catttgcgct atatataagc ctacgatttc   7920

cgttgcgact attgtcgtaa ttggatgaac tattatcgta gttgctctca gagttgtcgt   7980

aatttgatgg actattgtcg taattgctta tggagttgtc gtagttgctt ggagaaatgt   8040

cgtagttgga tggggagtag tcatagggaa gacgagcttc atccactaaa acaattggca   8100

ggtcagcaag tgcctgcccc gatgccatcg caagtacgag gcttagaacc accttcaaca   8160

gatcgcgcat agtcttcccc agctctctaa cgcttgagtt aagccgcgcc gcgaagcggc   8220

gtcggcttga acgaattgtt agacattatt tgccgactac cttggtgatc tcgcctttca   8280

cgtagtgaac aaattcttcc aactgatctg cgcgcgaggc caagcgatct tcttgtccaa   8340

gataagcctg cctagcttca agtatgacgg gctgatactg ggccggcagg cgctccattg   8400

cccagtcggc agcgacatcc ttcggcgcga ttttgccggt tactgcgctg taccaaatgc   8460

gggacaacgt aagcactaca tttcgctcat cgccagccca gtcgggcggc gagttccata   8520

gcgttaaggt ttcatttagc gcctcaaata gatcctgttc aggaaccgga tcaaagagtt   8580

cctccgccgc tggacctacc aaggcaacgc tatgttctct tgcttttgtc agcaagatag   8640

ccagatcaat gtcgatcgtg gctggctcga agatacctgc aagaatgtca ttgcgctgcc   8700

attctccaaa ttgcagttcg cgcttagctg gataacgcca cggaatgatg tcgtcgtgca   8760

caacaatggt gacttctaca gcgcggagaa tctcgctctc tccaggggaa gccgaagttt   8820

ccaaaaggtc gttgatcaaa gctcgccgcg ttgtttcatc aagccttacg gtcaccgtaa   8880

ccagcaaatc aatatcactg tgtggcttca ggccgccatc cactgcggag ccgtacaaat   8940

gtacggccag caacgtcggt tcgagatggc gctcgatgac gccaactacc tctgatagtt   9000

gagtcgatac ttcggcgatc accgcttccc tcatgatgtt taactcctga attaagccgc   9060

gccgcgaagc ggtgtcggct tgaatgaatt gttaggcgtc atcctgtgct cccgagaacc   9120

agtaccagta catcgctgtt tcgttcgaga cttgaggtct agttttatac gtgaacaggt   9180

caatgccgcc gagagtaaag ccacattttg cgtacaaatt gcaggcaggt acattgttcg   9240

tttgtgtctc taatcgtatg ccaaggagct gtctgcttag tgcccacttt ttcgcaaatt   9300

cgatgagact gtgcgcgact cctttgcctc ggtgcgtgtg cgacacaaca atgtgttcga   9360
```

```
tagaggctag atcgttccat gttgagttga gttcaatctt cccgacaagc tcttggtcga   9420
tgaatgcgcc atagcaagca gagtcttcat cagagtcatc atccgagatg taatccttcc   9480
ggtaggggct cacacttctg gtagatagtt caaagccttg gtcggatagg tgcacatcga   9540
acacttcacg aacaatgaaa tggttctcag catccaatgt ttccgccacc tgctcaggga   9600
tcaccgaaat cttcatatga cgcctaacgc ctggcacagc ggatcgcaaa cctggcgcgg   9660
cttttggcac aaaaggcgtg acaggtttgc gaatccgttg ctgccacttg ttaacccttt   9720
tgccagattt ggtaactata atttatgtta gaggcgaagt cttgggtaaa aactggccta   9780
aaattgctgg ggatttcagg aaagtaaaca tcaccttccg gctcgatgtc tattgtagat   9840
atatgtagtg tatctacttg atcgggggat ctgctgcctc gcgcgtttcg gtgatgacgg   9900
tgaaaacctc tgacacatgc agctcccgga gacggtcaca gcttgtctgt aagcggatgc   9960
cgggagcaga caagcccgtc agggcgcgtc agcgggtgtt ggcgggtgtc ggggcgcagc  10020
catgacccag tcacgtagcg atagcggagt gtatactggc ttaactatgc ggcatcagag  10080
cagattgtac tgagagtgca ccatatgcgg tgtgaaatac cgcacagatg cgtaaggaga  10140
aaataccgca tcaggcgctc ttccgcttcc tcgctcactg actcgctgcg ctcggtcgtt  10200
cggctgcggc gagcggtatc agctcactca aaggcggtaa tacggttatc cacagaatca  10260
ggggataacg caggaaagaa catgtgagca aaaggccagc aaaaggccag gaaccgtaaa  10320
aaggccgcgt tgctggcgtt tttccatagg ctccgccccc ctgacgagca tcacaaaaat  10380
cgacgctcaa gtcagaggtg gcgaaacccg acaggactat aaagatacca ggcgtttccc  10440
cctggaagct ccctcgtgcg ctctcctgtt ccgaccctgc cgcttaccgg atacctgtcc  10500
gcctttctcc cttcgggaag cgtggcgctt tctcatagct cacgctgtag gtatctcagt  10560
tcggtgtagg tcgttcgctc caagctgggc tgtgtgcacg aaccccccgt tcagcccgac  10620
cgctgcgcct tatccggtaa ctatcgtctt gagtccaacc cggtaagaca cgacttatcg  10680
ccactggcag cagccactgg taacaggatt agcagagcga ggtatgtagg cggtgctaca  10740
gagttcttga agtggtggcc taactacggc tacactagaa ggacagtatt tggtatctgc  10800
gctctgctga agccagttac cttcggaaaa agagttggta gctcttgatc cggcaaacaa  10860
accaccgctg gtagcggtgg tttttttgtt tgcaagcagc agattacgcg cagaaaaaaa  10920
ggatctcaag aagatccttt gatcttttct acggggtctg acgctcagtg gaacgaaaac  10980
tcacgttaag ggattttggt catgagatta tcaaaaagga tcttcaccta gatcctttta  11040
aattaaaaat gaagttttaa atcaatctaa agtatatatg agtaaacttg gtctgacagt  11100
taccaatgct taatcagtga ggcacctatc tcagcgatct gtctatttcg ttcatccata  11160
gttgcctgac tccccgtcgt gtagataact acgatacggg agggcttacc atctggcccc  11220
agtgctgcaa tgataccgcg agacccacgc tcaccggctc cagatttatc agcaataaac  11280
cagccagccg gaagggccga gcgcagaagt ggtcctgcaa ctttatccgc ctccatccag  11340
tctattaatt gttgccggga agctagagta agtagttcgc cagttaatag tttgcgcaac  11400
gttgttgcca ttgctgcagg gggggggggg gggggggttcc attgttcatt ccacggacaa  11460
aaacagagaa aggaaacgac agaggccaaa aagctcgctt tcagcacctg tcgtttcctt  11520
tcttttcaga gggtatttta aataaaaaca ttaagttatg acgaagaaga acggaaacgc  11580
cttaaaccgg aaaattttca taaatagcga aaacccgcga ggtcgccgcc ccgtaacctg  11640
tcggatcacc ggaaaggacc cgtaaagtga taatgattat catctacata tcacaacgtg  11700
cgtggaggcc atcaaaccac gtcaaataat caattatgac gcaggtatcg tattaattga  11760
```

```
tctgcatcaa cttaacgtaa aaacaacttc agacaataca aatcagcgac actgaatacg  11820
gggcaacctc atgtcccccc cccccccccc ctgcaggcat cgtggtgtca cgctcgtcgt  11880
ttggtatggc ttcattcagc tccggttccc aacgatcaag gcgagttaca tgatccccca  11940
tgttgtgcaa aaaagcggtt agctccttcg gtcctccgat cgttgtcaga agtaagttgg  12000
ccgcagtgtt atcactcatg gttatggcag cactgcataa ttctcttact gtcatgccat  12060
ccgtaagatg cttttctgtg actggtgagt actcaaccaa gtcattctga gaatagtgta  12120
tgcggcgacc gagttgctct tgcccggcgt caacacggga taataccgcg ccacatagca  12180
gaactttaaa agtgctcatc attggaaaac gttcttcggg gcgaaaactc tcaaggatct  12240
taccgctgtt gagatccagt tcgatgtaac ccactcgtgc acccaactga tcttcagcat  12300
cttttacttt caccagcgtt tctgggtgag caaaaacagg aaggcaaaat gccgcaaaaa  12360
agggaataag ggcgacacgg aaatgttgaa tactcatact cttccttttt caatattatt  12420
gaagcattta tcagggttat tgtctcatga gcggatacat atttgaatgt atttagaaaa  12480
ataaacaaat aggggttccg cgcacatttc cccgaaaagt gccacctgac gtctaagaaa  12540
ccattattat catgacatta acctataaaa ataggcgtat cacgaggccc tttcgtcttc  12600
aagaattggt cgacgatctt gctgcgttcg gatattttcg tggagttccc gccacagacc  12660
cggattgaag gcgagatcca gcaactcgcg ccagatcatc ctgtgacgga actttggcgc  12720
gtgatgactg gccaggacgt cggccgaaag agcgacaagc agatcacgct tttcgacagc  12780
gtcggatttg cgatcgagga tttttcggcg ctgcgctacg tccgcgaccg cgttgaggga  12840
tcaagccaca gcagcccact cgaccttcta gccgacccag acgagccaag ggatcttttt  12900
ggaatgctgc tccgtcgtca ggctttccga cgtttgggtg gttgaacaga agtcattatc  12960
gcacggaatg ccaagcactc ccgaggggaa ccctgtggtt ggcatgcaca tacaaatgga  13020
cgaacggata aacctttca cgccctttta aatatccgat tattctaata aacgctcttt  13080
tctcttaggt ttacccgcca atatatcctg tcaaacactg atagtttaaa ctgaaggcgg  13140
gaaacgacaa cctgatcatg agcggagaat taagggagtc acgttatgac ccccgccgat  13200
gacgcgggac aagccgtttt acgtttggaa ctgacagaac cgcaacgttg aaggagccac  13260
tcagcttaat taagtctaac tcgagttact ggtacgtacc aaatccatgg aatcaaggta  13320
ccgtcgactc tagtaacggc cgccagtgtg ctggaattaa ttcggcttgt cgaccaccca  13380
accccatatc gacagaggat gtgaagaaca ggtaaatcac gcagaagaac ccatctctga  13440
tagcagctat cgattagaac aacgaatcca tattgggtcc gtgggaaata cttactgcac  13500
aggaaggggg cgatctgacg aggccccgcc accggcctcg acccgaggcc gaggccgacg  13560
aagcgccggc gagtacggcg ccgcggcggc ctctgcccgt gccctctgcg cgtgggaggg  13620
agaggccgcg gtggtggggg cgcgcgcgcg cgcgcgcgca gctggtgcgg cggcgcgggg  13680
gtcagccgcc gagccggcgg cgacggagga gcagggcggc gtggacgcga acttccgatc  13740
ggttggtcag agtgcgcgag ttgggcttag ccaattaggt ctcaacaatc tattgggccg  13800
taaaattcat gggccctggt ttgtctaggc ccaatatccc gttcatttca gcccacaaat  13860
atttccccag aggattatta aggcccacac gcagcttata gcagatcaag tacgatgttt  13920
cctgatcgtt ggatcggaaa cgtacggtct tgatcaggca tgccgacttc gtcaaagaga  13980
ggcggcatga cctgacgcgg agttggttcc gggcaccgtc tggatggtcg taccgggacc  14040
ggacacgtgt cgcgcctcca actacatgga cacgtgtggt gctgccattg ggccgtacgc  14100
```

```
gtggcggtga ccgcaccgga tgctgcctcg caccgccttg cccacgcttt atatagagag  14160
gttttctctc cattaatcgc atagcgagtc gaatcgaccg aaggggaggg ggagcgaagc  14220
tttgcgttct ctaatcgcct cgtcaaggta actaatcaat cacctcgtcc taatcctcga  14280
atctctcgtg gtgcccgtct aatctcgcga ttttgatgct cgtggtggaa agcgtaggag  14340
gatcccgtgc gagttagtct caatctctca gggtttcgtg cgattttagg gtgatccacc  14400
tcttaatcga gttacggttt cgtgcgattt tagggtaatc ctcttaatct ctcattgatt  14460
tagggtttcg tgagaatcga ggtagggatc tgtgttattt atatcgatct aatagatgga  14520
ttggttttga gattgttctg tcagatgggg attgtttcga tatattaccc taatgatgtg  14580
tcagatgggg attgtttcga tatattaccc taatgatgtg tcagatgggg attgtttcga  14640
tatattaccc taatgatgga taataagagt agttcacagt tatgttttga tcctgccaca  14700
tagtttgagt tttgtgatca gatttagttt tacttatttg tgcttagttc ggatgggatt  14760
gttctgatat tgttccaata gatgaatagc tcgttaggtt aaaatcttta ggttgagtta  14820
ggcgacacat agtttatttc ctctggattt ggattggaat tgtgttctta gttttttttcc  14880
cctggatttg gattggaatt gtgtggagct gggttagaga attacatctg tatcgtgtac  14940
acctacttga actgtagagc ttgggttcta aggtcaattt aatctgtatt gtatctggct  15000
ctttgcctag ttgaactgta gtgctgatgt tgtactgtgt ttttttaccc gttttatttg  15060
ctttactcgt gcaaatcaaa tctgtcagat gctagaacta ggtggcttta ttctgtgttc  15120
ttacatagat ctgttgtcct gtagttactt atgtcagttt tgttattatc tgaagatatt  15180
tttggttgtt gcttgttgat gtggtgtgag ctgtgagcag cgctcttatg attaatgatg  15240
ctgtccaatt gtagtgtagt atgatgtgat tgatatgttc atctattttg agctgacagt  15300
accgatatcg taggatctgg tgccaactta ttctccagct gctttttttt acctatgtta  15360
attccaatcc tttcttgcct cttccagatc cagataatgg cccacgcccg cgtcctcctc  15420
ctggcgctcg ccgtcctggc caccgccgcc gtcgccgtcg cctcctcctc ctccttcgcc  15480
gactccaacc cgatccgccc ggtgaccgac cgcgccgcct ccaccgctta cgactacaag  15540
caggtgttgc gggactcgct actattctat gaggcccaga gatccggccg gctcccagcc  15600
gaccagaagg tcacgtggag gaaggatagc gcgctgaatg accagggtga ccagggacaa  15660
gacttgaccg gcggctactt tgacgctggg gacttcgtca agttcgggtt ccccatggct  15720
tataccgcaa ccgtgctggc atggggcctc atagattttg aggccggcta cagcagtgcc  15780
ggggccttgg atgatggacg gaaggctgtc aaatgggcca ccgactattt cataaaggcc  15840
cacacaagtc aaaatgagtt ctatggtcag gtcggccagg gtgacgccga tcacgctttc  15900
tggggaagac cagaggatat gacgatggcg cgcccggcgt acaagataga cacctcaagg  15960
cctggctctg atctggcagg cgagacagcg gctgctcttg ccgctgcttc aatcgtgttc  16020
cggaacgtcg atggcactta ctcaaataac ctgttaacac acgctcgcca gctattcgac  16080
ttcgcgaaca actaccgggg aaagtatagt gactctatta ctgacgcaag aaatttctac  16140
gcaagcgcag actacagaga cgagttggtt tgggctgctg cgtggttata cagagcgacc  16200
aacgacaaca cctacctcaa cactgctgag tcactgtacg atgagtttgg gctacagaac  16260
tgggggggggg gcctgaactg ggatagcaag gtgtctggcg tgcaggtgtt gttggccaag  16320
cttaccaata agcaggccta caaggacacg gtgcagtctt acgtcaatta cctaattaat  16380
aaccagcaga agactcccaa gggcctcctc tacatcgaca tgtggggcac ccttcgccac  16440
gctgccaacg ccgcattcat catgctcgaa gccgccgagc tgggcttgtc cgcctcctct  16500
```

```
tatagacagt tcgcgcaaac gcaaatcgac tacgccctgg gcgatggtgg ccgctccttt  16560
gtgtgcgggt tcgggagtaa tcctcctacg agaccgcacc acagatcctc gtcgtgcccg  16620
ccagctcccg ctacttgcga ctggaataca ttcaactcac ctgacccaaa ctaccacgtc  16680
ctctctgggg ccctagtggg cggacctgat cagaatgaca actacgtcga tgaccgttca  16740
gactatgttc acaacgaagt cgccactgat tacaacgcgg gtttccagtc cgcgttagct  16800
gctttggtgg cccttggtta ctgacctagg tccccgaatt tccccgatcg ttcaaacatt  16860
tggcaataaa gtttcttaag attgaatcct gttgccggtc ttgcgatgat tatcatataa  16920
tttctgttga attacgttaa gcatgtaata attaacatgt aatgcatgac gttatttatg  16980
agatgggttt ttatgattag agtcccgcaa ttatacattt aatacgcgat agaaaacaaa  17040
atatagcgcg caaactagga taaattatcg cgcgcggtgt catctatgtt actagatcgg  17100
gaattgggta c                                                       17111
```

<210> SEQ ID NO 79
<211> LENGTH: 12892
<212> TYPE: DNA
<213> ORGANISM: Artificial Sequence
<220> FEATURE:
<223> OTHER INFORMATION: Synthetic construct, vector pAG2310

<400> SEQUENCE: 79

```
ctaggtcccc gaatttcccc gatcgttcaa acatttggca ataaagtttc ttaagattga     60
atcctgttgc cggtcttgcg atgattatca tataatttct gttgaattac gttaagcatg    120
taataattaa catgtaatgc atgacgttat ttatgagatg ggtttttatg attagagtcc    180
cgcaattata catttaatac gcgatagaaa acaaaatata gcgcgcaaac taggataaat    240
tatcgcgcgc ggtgtcatct atgttactag atcgggaatt ggaattcata ctaaagcttg    300
catgcctgca ggtcgactct agtaacggcc gccagtgtgc tggaattaat tcggcttgtc    360
gaccacccaa ccccatatcg acagaggatg tgaagaacag gtaaatcacg cagaagaacc    420
catctctgat agcagctatc gattagaaca acgaatccat attgggtccg tgggaaatac    480
ttactgcaca ggaagggggc gatctgacga ggccccgcca ccggcctcga cccgaggccg    540
aggccgacga agcgccggcg agtacggcgc cgcggcggcc tctgcccgtg ccctctgcgc    600
gtgggaggga gaggccgcgg tggtgggggc gcgcgcgcgc gcgcgcgcag ctggtgcggc    660
ggcgcggggg tcagccgccg agccggcggc gacggaggag cagggcggcg tggacgcgaa    720
cttccgatcg gttggtcaga gtgcgcgagt tgggcttagc caattaggtc tcaacaatct    780
attgggccgt aaaattcatg ggccctggtt tgtctaggcc caatatcccg ttcatttcag    840
cccacaaata tttccccaga ggattattaa ggcccacacg cagcttatag cagatcaagt    900
acgatgtttc ctgatcgttg gatcggaaac gtacggtctt gatcaggcat gccgacttcg    960
tcaaagagag gcggcatgac ctgacgcgga gttggttccg ggcaccgtct ggatggtcgt   1020
accgggaccg gacacgtgtc gcgcctccaa ctacatggac acgtgtggtg ctgccattgg   1080
gccgtacgcg tggcggtgac cgcaccggat gctgcctcgc accgccttgc ccacgcttta   1140
tatagagagg ttttctctcc attaatcgca tagcgagtcg aatcgaccga aggggagggg   1200
gagcgaagct ttgcgttctc taatcgcctc gtcaaggtaa ctaatcaatc acctcgtcct   1260
aatcctcgaa tctctcgtgg tgcccgtcta atctcgcgat tttgatgctc gtggtggaaa   1320
gcgtaggagg atcccgtgcg agttagtctc aatctctcag ggtttcgtgc gattttaggg   1380
```

```
tgatccacct cttaatcgag ttacggtttc gtgcgatttt agggtaatcc tcttaatctc   1440
tcattgattt agggtttcgt gagaatcgag gtagggatct gtgttattta tatcgatcta   1500
atagatggat tggttttgag attgttctgt cagatgggga ttgtttcgat atattaccct   1560
aatgatgtgt cagatgggga ttgtttcgat atattaccct aatgatgtgt cagatgggga   1620
ttgtttcgat atattaccct aatgatggat aataagagta gttcacagtt atgttttgat   1680
cctgccacat agtttgagtt ttgtgatcag atttagtttt acttatttgt gcttagttcg   1740
gatgggattg ttctgatatt gttccaatag atgaatagct cgttaggtta aaatctttag   1800
gttgagttag gcgacacata gtttatttcc tctggatttg gattggaatt gtgttcttag   1860
ttttttcccc ctggatttgg attggaattg tgtggagctg ggttagagaa ttacatctgt   1920
atcgtgtaca cctacttgaa ctgtagagct tgggttctaa ggtcaattta atctgtattg   1980
tatctggctc tttgcctagt tgaactgtag tgctgatgtt gtactgtgtt tttttacccg   2040
ttttatttgc tttactcgtg caaatcaaat ctgtcagatg ctagaactag gtggctttat   2100
tctgtgttct tacatagatc tgttgtcctg tagttactta tgtcagtttt gttattatct   2160
gaagatattt ttggttgttg cttgttgatg tggtgtgagc tgtgagcagc gctcttatga   2220
ttaatgatgc tgtccaattg tagtgtagta tgatgtgatt gatatgttca tctattttga   2280
gctgacagta ccgatatcgt aggatctggt gccaacttat tctccagctg ctttttttta   2340
cctatgttaa ttccaatcct ttcttgcctc ttccagatcc agataatgca gaaactcatt   2400
aactcagtgc aaaactatgc ctggggcagc aaaacggcgt tgactgaact ttatggtatg   2460
gaaaatccgt ccagccagcc gatggccgag ctgtggatgg gcgcacatcc gaaaagcagt   2520
tcacgagtgc agaatgccgc cggagatatc gtttcactgc gtgatgtgat tgagagtgat   2580
aaatcgactc tgctcggaga ggccgttgcc aaacgctttg gcgaactgcc tttcctgttc   2640
aaagtattat gcgcagcaca gccactctcc attcaggttc atccaaacaa acacaattct   2700
gaaatcggtt ttgccaaaga aaatgccgca ggtatcccga tggatgccgc cgagcgtaac   2760
tataaagatc ctaaccacaa gccggagctg gtttttgcgc tgacgccttt ccttgcgatg   2820
aacgcgtttc gtgaattttc cgagattgtc tccctactcc agccggtcgc aggtgcacat   2880
ccggcgattg ctcacttttt acaacagcct gatgccgaac gtttaagcga actgttcgcc   2940
agcctgttga atatgcaggg tgaagaaaaa tcccgcgcgc tggcgatttt aaaatcggcc   3000
ctcgatagcc agcagggtga accgtggcaa acgattcgtt taatttctga attttacccg   3060
gaagacagcg gtctgttctc cccgctattg ctgaatgtgg tgaaattgaa ccctggcgaa   3120
gcgatgttcc tgttcgctga aacaccgcac gcttacctgc aaggcgtggc gctggaagtg   3180
atggcaaact ccgataacgt gctgcgtgcg ggtctgacgc ctaaatacat tgatattccg   3240
gaactggttg ccaatgtgaa attcgaagcc aaaccggcta accagttgtt gacccagccg   3300
gtgaaacaag gtgcagaact ggacttcccg attccagtgg atgattttgc cttctcgctg   3360
catgacctta gtgataaaga aaccaccatt agccagcaga gtgccgccat tttgttctgc   3420
gtcgaaggcg atgcaacgtt gtggaaaggt tctcagcagt tacagcttaa accgggtgaa   3480
tcagcgttta ttgccgccaa cgaatcaccg gtgactgtca aaggccacgg ccgtttagcg   3540
cgtgtttaca acaagctgta agagcttact gaaaaaatta acatctcttg ctaagctggg   3600
agctctagat ccccgaattt ccccgatcgt tcaaacattt ggcaataaag tttcttaaga   3660
ttgaatcctg ttgccggtct tgcgatgatt atcatataat ttctgttgaa ttacgttaag   3720
catgtaataa ttaacatgta atgcatgacg ttatttatga gatgggtttt tatgattaga   3780
```

-continued

```
gtcccgcaat tatacattta atacgcgata gaaaacaaaa tatagcgcgc aaactaggat   3840
aaattatcgc gcgcggtgtc atctatgtta ctagatcggg aattggcgag ctcgaattaa   3900
ttcagtacat taaaaacgtc cgcaatgtgt tattaagttg tctaagcgtc aatttgttta   3960
caccacaata tatcctgcca ccagccagcc aacagctccc cgaccggcag ctcggcacaa   4020
aatcaccact cgatacaggc agcccatcag tccgggacgg cgtcagcggg agagccgttg   4080
taaggcggca gactttgctc atgttaccga tgctattcgg aagaacggca actaagctgc   4140
cgggtttgaa acacggatga tctcgcggag ggtagcatgt tgattgtaac gatgacagag   4200
cgttgctgcc tgtgatcaaa tatcatctcc ctcgcagaga tccgaattat cagccttctt   4260
attcatttct cgcttaaccg tgacaggctg tcgatcttga gaactatgcc gacataatag   4320
gaaatcgctg gataaagccg ctgaggaagc tgagtggcgc tatttcttta gaagtgaacg   4380
ttgacgatcg tcgaccgtac cccgatgaat taattcggac gtacgttctg aacacagctg   4440
gatacttact tgggcgattg tcatacatga catcaacaat gtacccgttt gtgtaaccgt   4500
ctcttggagg ttcgtatgac actagtggtt cccctcagct tgcgactaga tgttgaggcc   4560
taacatttta ttagagagca ggctagttgc ttagatacat gatcttcagg ccgttatctg   4620
tcagggcaag cgaaaattgg ccatttatga cgaccaatgc cccgcagaag ctcccatctt   4680
tgccgccata gacgccgcgc ccccttttg gggtgtagaa catccttttg ccagatgtgg    4740
aaaagaagtt cgttgtccca ttgttggcaa tgacgtagta gccggcgaaa gtgcgagacc   4800
catttgcgct atatataagc ctacgatttc cgttgcgact attgtcgtaa ttggatgaac   4860
tattatcgta gttgctctca gagttgtcgt aatttgatgg actattgtcg taattgctta   4920
tggagttgtc gtagttgctt ggagaaatgt cgtagttgga tggggagtag tcatagggaa   4980
gacgagcttc atccactaaa acaattggca ggtcagcaag tgcctgcccc gatgccatcg   5040
caagtacgag gcttagaacc accttcaaca gatcgcgcat agtcttcccc agctctctaa   5100
cgcttgagtt aagccgcgcc gcgaagcggc gtcggcttga acgaattgtt agacattatt   5160
tgccgactac cttggtgatc tcgcctttca cgtagtgaac aaattcttcc aactgatctg   5220
cgcgcgaggc caagcgatct tcttgtccaa gataagcctg cctagcttca agtatgacgg   5280
gctgatactg ggccggcagg cgctccattg cccagtcggc agcgacatcc ttcggcgcga   5340
ttttgccggt tactgcgctg taccaaatgc gggacaacgt aagcactaca tttcgctcat   5400
cgccagccca gtcgggcggc gagttccata gcgttaaggt ttcatttagc gcctcaaata   5460
gatcctgttc aggaaccgga tcaaagagtt cctccgccgc tggacctacc aaggcaacgc   5520
tatgttctct tgcttttgtc agcaagatag ccagatcaat gtcgatcgtg gctggctcga   5580
agatacctgc aagaatgtca ttgcgctgcc attctccaaa ttgcagttcg cgcttagctg   5640
gataacgcca cggaatgatg tcgtcgtgca caacaatggt gacttctaca gcgcggagaa   5700
tctcgctctc tccaggggaa gccgaagttt ccaaaaggtc gttgatcaaa gctcgccgcg   5760
ttgtttcatc aagccttacg gtcaccgtaa ccagcaaatc aatatcactg tgtggcttca   5820
ggccgccatc cactgcggag ccgtacaaat gtacggccag caacgtcggt tcgagatggc   5880
gctcgatgac gccaactacc tctgatagtt gagtcgatac ttcggcgatc accgcttccc   5940
tcatgatgtt taactcctga attaagccgc gccgcgaagc ggtgtcggct tgaatgaatt   6000
gttaggcgtc atcctgtgct cccgagaacc agtaccagta catcgctgtt tcgttcgaga   6060
cttgaggtct agttttatac gtgaacaggt caatgccgcc gagagtaaag ccacattttg   6120
```

```
cgtacaaatt gcaggcaggt acattgttcg tttgtgtctc taatcgtatg ccaaggagct   6180
gtctgcttag tgcccacttt ttcgcaaatt cgatgagact gtgcgcgact cctttgcctc   6240
ggtgcgtgtg cgacacaaca atgtgttcga tagaggctag atcgttccat gttgagttga   6300
gttcaatctt cccgacaagc tcttggtcga tgaatgcgcc atagcaagca gagtcttcat   6360
cagagtcatc atccgagatg taatccttcc ggtaggggct cacacttctg gtagatagtt   6420
caaagccttg gtcggatagg tgcacatcga acacttcacg aacaatgaaa tggttctcag   6480
catccaatgt ttccgccacc tgctcaggga tcaccgaaat cttcatatga cgcctaacgc   6540
ctggcacagc ggatcgcaaa cctggcgcgg cttttggcac aaaaggcgtg acaggtttgc   6600
gaatccgttg ctgccacttg ttaacccttt tgccagattt ggtaactata atttatgtta   6660
gaggcgaagt cttgggtaaa aactggccta aaattgctgg ggatttcagg aaagtaaaca   6720
tcaccttccg gctcgatgtc tattgtagat atatgtagtg tatctacttg atcgggggat   6780
ctgctgcctc gcgcgtttcg gtgatgacgg tgaaaacctc tgacacatgc agctcccgga   6840
gacggtcaca gcttgtctgt aagcggatgc cgggagcaga caagcccgtc agggcgcgtc   6900
agcgggtgtt ggcgggtgtc ggggcgcagc catgacccag tcacgtagcg atagcggagt   6960
gtatactggc ttaactatgc ggcatcagag cagattgtac tgagagtgca ccatatgcgg   7020
tgtgaaatac cgcacagatg cgtaaggaga aaataccgca tcaggcgctc ttccgcttcc   7080
tcgctcactg actcgctgcg ctcggtcgtt cggctgcggc gagcggtatc agctcactca   7140
aaggcggtaa tacggttatc cacagaatca ggggataacg caggaaagaa catgtgagca   7200
aaaggccagc aaaaggccag gaaccgtaaa aaggccgcgt tgctggcgtt tttccatagg   7260
ctccgccccc ctgacgagca tcacaaaaat cgacgctcaa gtcagaggtg gcgaaacccg   7320
acaggactat aaagatacca ggcgtttccc cctggaagct ccctcgtgcg ctctcctgtt   7380
ccgaccctgc cgcttaccgg atacctgtcc gcctttctcc cttcgggaag cgtggcgctt   7440
tctcatagct cacgctgtag gtatctcagt tcggtgtagg tcgttcgctc caagctgggc   7500
tgtgtgcacg aaccccccgt tcagcccgac cgctgcgcct tatccggtaa ctatcgtctt   7560
gagtccaacc cggtaagaca cgacttatcg ccactggcag cagccactgg taacaggatt   7620
agcagagcga ggtatgtagg cggtgctaca gagttcttga agtggtggcc taactacggc   7680
tacactagaa ggacagtatt tggtatctgc gctctgctga agccagttac cttcggaaaa   7740
agagttggta gctcttgatc cggcaaacaa accaccgctg gtagcggtgg tttttttgtt   7800
tgcaagcagc agattacgcg cagaaaaaaa ggatctcaag aagatccttt gatcttttct   7860
acggggtctg acgctcagtg gaacgaaaac tcacgttaag ggattttggt catgagatta   7920
tcaaaaagga tcttcaccta gatcctttta aattaaaaat gaagttttaa atcaatctaa   7980
agtatatatg agtaaacttg gtctgacagt taccaatgct taatcagtga ggcacctatc   8040
tcagcgatct gtctatttcg ttcatccata gttgcctgac tccccgtcgt gtagataact   8100
acgatacggg agggcttacc atctggcccc agtgctgcaa tgataccgcg agacccacgc   8160
tcaccggctc cagatttatc agcaataaac cagccagccg gaagggccga gcgcagaagt   8220
ggtcctgcaa ctttatccgc ctccatccag tctattaatt gttgccggga agctagagta   8280
agtagttcgc cagttaatag tttgcgcaac gttgttgcca ttgctgcagg gggggggggg   8340
ggggggttcc attgttcatt ccacggacaa aaacagagaa aggaaacgac agaggccaaa   8400
aagctcgctt tcagcacctg tcgtttcctt tcttttcaga gggtatttta aataaaaaca   8460
ttaagttatg acgaagaaga acggaaacgc cttaaaccgg aaaattttca taaatagcga   8520
```

```
aaacccgcga ggtcgccgcc ccgtaacctg tcggatcacc ggaaaggacc cgtaaagtga   8580
taatgattat catctacata tcacaacgtg cgtggaggcc atcaaaccac gtcaaataat   8640
caattatgac gcaggtatcg tattaattga tctgcatcaa cttaacgtaa aaacaacttc   8700
agacaataca aatcagcgac actgaatacg ggcaacctc atgtcccccc cccccccccc   8760
ctgcaggcat cgtggtgtca cgctcgtcgt ttggtatggc ttcattcagc tccggttccc   8820
aacgatcaag gcgagttaca tgatccccca tgttgtgcaa aaaagcggtt agctccttcg   8880
gtcctccgat cgttgtcaga agtaagttgg ccgcagtgtt atcactcatg gttatggcag   8940
cactgcataa ttctcttact gtcatgccat ccgtaagatg cttttctgtg actggtgagt   9000
actcaaccaa gtcattctga gaatagtgta tgcggcgacc gagttgctct tgcccggcgt   9060
caacacggga taataccgcg ccacatagca gaactttaaa agtgctcatc attggaaaac   9120
gttcttcggg gcgaaaactc tcaaggatct taccgctgtt gagatccagt tcgatgtaac   9180
ccactcgtgc acccaactga tcttcagcat cttttacttt caccagcgtt tctgggtgag   9240
caaaaacagg aaggcaaaat gccgcaaaaa agggaataag ggcgacacgg aaatgttgaa   9300
tactcatact cttccttttt caatattatt gaagcattta tcagggttat tgtctcatga   9360
gcggatacat atttgaatgt atttagaaaa ataaacaaat aggggttccg cgcacatttc   9420
cccgaaaagt gccacctgac gtctaagaaa ccattattat catgacatta acctataaaa   9480
ataggcgtat cacgaggccc tttcgtcttc aagaattggt cgacgatctt gctgcgttcg   9540
gatattttcg tggagttccc gccacagacc cggattgaag gcgagatcca gcaactcgcg   9600
ccagatcatc ctgtgacgga actttggcgc gtgatgactg gccaggacgt cggccgaaag   9660
agcgacaagc agatcacgct tttcgacagc gtcggatttg cgatcgagga tttttcggcg   9720
ctgcgctacg tccgcgaccg cgttgaggga tcaagccaca gcagcccact cgaccttcta   9780
gccgacccag acgagccaag ggatcttttt ggaatgctgc tccgtcgtca ggctttccga   9840
cgtttgggtg gttgaacaga agtcattatc gcacggaatg ccaagcactc ccgaggggaa   9900
ccctgtggtt ggcatgcaca tacaaatgga cgaacggata aaccttttca cgccctttta   9960
aatatccgat tattctaata aacgctcttt tctcttaggt ttacccgcca atatatcctg   10020
tcaaacactg atagtttaaa ctgaaggcgg gaaacgacaa cctgatcatg agcggagaat   10080
taagggagtc acgttatgac ccccgccgat gacgcgggac aagccgtttt acgtttggaa   10140
ctgacagaac cgcaacgttg aaggagccac tcagcttaat taagtctaac tcgagttact   10200
ggtacgtacc aaatccatgg aatcaaggta ccgtcgactc tagtaacggc cgccagtgtg   10260
ctggaattaa ttcggcttgt cgaccaccca accccatatc gacagaggat gtgaagaaca   10320
ggtaaatcac gcagaagaac ccatctctga tagcagctat cgattagaac aacgaatcca   10380
tattgggtcc gtgggaaata cttactgcac aggaaggggg cgatctgacg aggccccgcc   10440
accggcctcg acccgaggcc gaggccgacg aagcgccggc gagtacggcg ccgcggcggc   10500
ctctgcccgt gccctctgcg cgtgggaggg agaggccgcg gtggtggggg cgcgcgcgcg   10560
cgcgcgcgca gctggtgcgg cggcgcgggg gtcagccgcc gagccggcgg cgacggagga   10620
gcagggcggc gtggacgcga acttccgatc ggttggtcag agtgcgcgag ttgggcttag   10680
ccaattaggt ctcaacaatc tattgggccg taaaattcat gggccctggt ttgtctaggc   10740
ccaatatccc gttcatttca gcccacaaat atttccccag aggattatta aggcccacac   10800
gcagcttata gcagatcaag tacgatgttt cctgatcgtt ggatcggaaa cgtacggtct   10860
```

```
tgatcaggca tgccgacttc gtcaaagaga ggcggcatga cctgacgcgg agttggttcc  10920
gggcaccgtc tggatggtcg taccgggacc ggacacgtgt cgcgcctcca actacatgga  10980
cacgtgtggt gctgccattg ggccgtacgc gtggcggtga ccgcaccgga tgctgcctcg  11040
caccgccttg cccacgcttt atatagagag gttttctctc cattaatcgc atagcgagtc  11100
gaatcgaccg aaggggaggg ggagcgaagc tttgcgttct ctaatcgcct cgtcaaggta  11160
actaatcaat cacctcgtcc taatcctcga atctctcgtg gtgcccgtct aatctcgcga  11220
ttttgatgct cgtggtggaa agcgtaggag gatcccgtgc gagttagtct caatctctca  11280
gggtttcgtg cgattttagg gtgatccacc tcttaatcga gttacggttt cgtgcgattt  11340
tagggtaatc ctcttaatct ctcattgatt tagggtttcg tgagaatcga ggtagggatc  11400
tgtgttattt atatcgatct aatagatgga ttggttttga gattgttctg tcagatgggg  11460
attgtttcga tatattaccc taatgatgtg tcagatgggg attgtttcga tatattaccc  11520
taatgatgtg tcagatgggg attgtttcga tatattaccc taatgatgga taataagagt  11580
agttcacagt tatgttttga tcctgccaca tagtttgagt tttgtgatca gatttagttt  11640
tacttatttg tgcttagttc ggatgggatt gttctgatat tgttccaata gatgaatagc  11700
tcgttaggtt aaaatcttta ggttgagtta ggcgacacat agtttatttc ctctggattt  11760
ggattggaat tgtgttctta gttttttttcc cctggatttg gattggaatt gtgtggagct  11820
gggttagaga attacatctg tatcgtgtac acctacttga actgtagagc ttgggttcta  11880
aggtcaattt aatctgtatt gtatctggct ctttgcctag ttgaactgta gtgctgatgt  11940
tgtactgtgt ttttttaccc gttttatttg ctttactcgt gcaaatcaaa tctgtcagat  12000
gctagaacta ggtggcttta ttctgtgttc ttacatagat ctgttgtcct gtagttactt  12060
atgtcagttt tgttattatc tgaagatatt tttggttgtt gcttgttgat gtggtgtgag  12120
ctgtgagcag cgctcttatg attaatgatg ctgtccaatt gtagtgtagt atgatgtgat  12180
tgatatgttc atctattttg agctgacagt accgatatcg taggatctgg tgccaactta  12240
ttctccagct gcttttttttt acctatgtta attccaatcc tttcttgcct cttccagatc  12300
cagataatgg cccaaacatg tctgaccagc ccacaaacag gattccacaa cggcttcttt  12360
tactcgtttt ggaaagattc tcctggtact gttaactttt gccttcttga agggggaaga  12420
tatacctcca attggtctgg gataaacaat tgggtcggtg gcaagggctg gcagaccggt  12480
agtaggcgca acatcacgta ttccgggagc ttcaatacac cagggaatgg atacctggct  12540
ctctacggtt ggaccaccaa cccgttggtt gagtactatg ttgtcgatag ctggggctcc  12600
tggcgccctc ccggaagtga tgggacattt cttggcacag tgaactcaga cggcggcacg  12660
tatgacatct acagggcgca aagagtcaac gcaccgagca tcattggcaa tgccaccttc  12720
taccagtatt ggtccgtgcg gcagtccaag cgtgtcggtg ggacaatcac gactggcaac  12780
cacttcgacg cgtgggccag cgtgggcctc aacctcggga ctcataacta ccagataatg  12840
gctactgagg gttaccagtc gtcaggatct tcagacatta cggtgtcatg ac          12892
```

```
<210> SEQ ID NO 80
<211> LENGTH: 21051
<212> TYPE: DNA
<213> ORGANISM: Artificial Sequence
<220> FEATURE:
<223> OTHER INFORMATION: Synthetic construct, vector pAG2339

<400> SEQUENCE: 80

catggaatca aggtaccgtc gactctagta acggccgcca gtgtgctgga attaattcgg     60
```

```
cttgtcgacc acccaacccc atatcgacag aggatgtgaa gaacaggtaa atcacgcaga    120

agaacccatc tctgatagca gctatcgatt agaacaacga atccatattg ggtccgtggg    180

aaatacttac tgcacaggaa gggggcgatc tgacgaggcc ccgccaccgg cctcgacccg    240

aggccgaggc cgacgaagcg ccggcgagta cggcgccgcg gcggcctctg cccgtgccct    300

ctgcgcgtgg gagggagagg ccgcggtggt gggggcgcgc gcgcgcgcgc gcgcagctgg    360

tgcggcggcg cgggggtcag ccgccgagcc ggcggcgacg gaggagcagg gcggcgtgga    420

cgcgaacttc cgatcggttg gtcagagtgc gcgagttggg cttagccaat taggtctcaa    480

caatctattg ggccgtaaaa ttcatgggcc ctggtttgtc taggcccaat atcccgttca    540

tttcagccca caaatatttc cccagaggat tattaaggcc cacacgcagc ttatagcaga    600

tcaagtacga tgtttcctga tcgttggatc ggaaacgtac ggtcttgatc aggcatgccg    660

acttcgtcaa agagaggcgg catgacctga cgcggagttg gttccgggca ccgtctggat    720

ggtcgtaccg ggaccggaca cgtgtcgcgc ctccaactac atggacacgt gtggtgctgc    780

cattgggccg tacgcgtggc ggtgaccgca ccggatgctg cctcgcaccg ccttgcccac    840

gctttatata gagaggtttt ctctccatta atcgcatagc gagtcgaatc gaccgaaggg    900

gagggggagc gaagctttgc gttctctaat cgcctcgtca aggtaactaa tcaatcacct    960

cgtcctaatc ctcgaatctc tcgtggtgcc cgtctaatct cgcgattttg atgctcgtgg   1020

tggaaagcgt aggaggatcc cgtgcgagtt agtctcaatc tctcagggtt tcgtgcgatt   1080

ttagggtgat ccacctctta atcgagttac ggtttcgtgc gattttaggg taatcctctt   1140

aatctctcat tgatttaggg tttcgtgaga atcgaggtag ggatctgtgt tatttatatc   1200

gatctaatag atggattggt tttgagattg ttctgtcaga tggggattgt ttcgatatat   1260

taccctaatg atgtgtcaga tggggattgt ttcgatatat taccctaatg atgtgtcaga   1320

tggggattgt ttcgatatat taccctaatg atggataata agagtagttc acagttatgt   1380

tttgatcctg ccacatagtt tgagttttgt gatcagattt agttttactt atttgtgctt   1440

agttcggatg ggattgttct gatattgttc caatagatga atagctcgtt aggttaaaat   1500

ctttaggttg agttaggcga cacatagttt atttcctctg gatttggatt ggaattgtgt   1560

tcttagtttt tttcccctgg atttggattg gaattgtgtg gagctgggtt agagaattac   1620

atctgtatcg tgtacaccta cttgaactgt agagcttggg ttctaaggtc aatttaatct   1680

gtattgtatc tggctctttg cctagttgaa ctgtagtgct gatgttgtac tgtgtttttt   1740

tacccgtttt atttgcttta ctcgtgcaaa tcaaatctgt cagatgctag aactaggtgg   1800

ctttattctg tgttcttaca tagatctgtt gtcctgtagt tacttatgtc agttttgtta   1860

ttatctgaag atatttttgg ttgttgcttg ttgatgtggt gtgagctgtg agcagcgctc   1920

ttatgattaa tgatgctgtc caattgtagt gtagtatgat gtgattgata tgttcatcta   1980

ttttgagctg acagtaccga tatcgtagga tctggtgcca acttattctc cagctgcttt   2040

tttttaccta tgttaattcc aatcctttct tgcctcttcc agatccagat aatggcgaac   2100

aaacatttgt ccctctccct cttcctcgtc ctccttggcc tgtcggccag cttggcctcc   2160

gggcaacagg tgtgcgattg gctgttccct gatggagata atggaaagga gcccgaacca   2220

gaaccagaac caacggtaga gctctgcgga agatgggatg caagagacgt agcgggagga   2280

agatatagag ttattaacaa tgtgtggggg gccgaaacag cacagtgtat agaagtaggt   2340

cttgaaacag gtaattttac gataacaaga gccgatcatg acaatggtaa taatgttgca   2400
```

```
gcatatccag caatttactt cggatgtcat tgggcaccag cgagagcaat aagggattgt   2460
gccgcgcgtg cgggagcggt taggagagca cacgaattgg atgttacacc aattaccacg   2520
ggaagatgga acgcagctta cgatatatgg tttagtccgg taacaaactc tggtaacggg   2580
tactcgggag gcgccgaact tatgatatgg ctgaattgga atggtggcgt aatgccagga   2640
ggatcacggg tagcaactgt cgaattggct ggagcgacat gggaagtgtg gtatgcagat   2700
tgggattgga attacatcgc atatagaaga acgactccga caacctcagt gagtgaactt   2760
gacttgaaag cctttattga tgatgcagta gcgagaggat acataaggcc agaatggtat   2820
ctgcatgcag tggaaacggg atttgaattg tgggaagggg gggctgggtt gaggacagca   2880
gattttagcg taactgtaca gtgacctagg tccccgaatt tccccgatcg ttcaaacatt   2940
tggcaataaa gtttcttaag attgaatcct gttgccggtc ttgcgatgat tatcatataa   3000
tttctgttga attacgttaa gcatgtaata attaacatgt aatgcatgac gttatttatg   3060
agatgggttt ttatgattag agtcccgcaa ttatacattt aatacgcgat agaaaacaaa   3120
atatagcgcg caaactagga taaattatcg cgcgcggtgt catctatgtt actagatcgg   3180
gaattgggta ccgtcgactc tagtaacggc cgccagtgtg ctggaattaa ttcggcttgt   3240
cgaccaccca accccatatc gacagaggat gtgaagaaca ggtaaatcac gcagaagaac   3300
ccatctctga tagcagctat cgattagaac aacgaatcca tattgggtcc gtgggaaata   3360
cttactgcac aggaaggggg cgatctgacg aggccccgcc accggcctcg acccgaggcc   3420
gaggccgacg aagcgccggc gagtacggcg ccgcggcggc ctctgcccgt gccctctgcg   3480
cgtgggaggg agaggccgcg gtggtggggg cgcgcgcgcg cgcgcgcgca gctggtgcgg   3540
cggcgcgggg gtcagccgcc gagccggcgg cgacggagga gcagggcggc gtggacgcga   3600
acttccgatc ggttggtcag agtgcgcgag ttgggcttag ccaattaggt ctcaacaatc   3660
tattgggccg taaaattcat gggccctggt ttgtctaggc ccaatatccc gttcatttca   3720
gcccacaaat atttccccag aggattatta aggcccacac gcagcttata gcagatcaag   3780
tacgatgttt cctgatcgtt ggatcggaaa cgtacggtct tgatcaggca tgccgacttc   3840
gtcaaagaga ggcggcatga cctgacgcgg agttggttcc gggcaccgtc tggatggtcg   3900
taccgggacc ggacacgtgt cgcgcctcca actacatgga cacgtgtggt gctgccattg   3960
ggccgtacgc gtggcggtga ccgcaccgga tgctgcctcg caccgccttg cccacgcttt   4020
atatagagag gttttctctc cattaatcgc atagcgagtc gaatcgaccg aaggggaggg   4080
ggagcgaagc tttgcgttct ctaatcgcct cgtcaaggta actaatcaat cacctcgtcc   4140
taatcctcga atctctcgtg gtgcccgtct aatctcgcga ttttgatgct cgtggtggaa   4200
agcgtaggag gatcccgtgc gagttagtct caatctctca gggtttcgtg cgattttagg   4260
gtgatccacc tcttaatcga gttacggttt cgtgcgattt tagggtaatc ctcttaatct   4320
ctcattgatt tagggtttcg tgagaatcga ggtagggatc tgtgttattt atatcgatct   4380
aatagatgga ttggttttga gattgttctg tcagatgggg attgtttcga tatattaccc   4440
taatgatgtg tcagatgggg attgtttcga tatattaccc taatgatgtg tcagatgggg   4500
attgtttcga tatattaccc taatgatgga taataagagt agttcacagt tatgttttga   4560
tcctgccaca tagtttgagt tttgtgatca gatttagttt tacttatttg tgcttagttc   4620
ggatgggatt gttctgatat tgttccaata gatgaatagc tcgttaggtt aaaatcttta   4680
ggttgagtta ggcgacacat agtttatttc ctctggattt ggattggaat tgtgttctta   4740
gttttttcc cctggatttg gattggaatt gtgtggagct gggttagaga attacatctg   4800
```

```
tatcgtgtac acctacttga actgtagagc ttgggttcta aggtcaattt aatctgtatt   4860
gtatctggct ctttgcctag ttgaactgta gtgctgatgt tgtactgtgt tttttaccc   4920
gttttatttg ctttactcgt gcaaatcaaa tctgtcagat gctagaacta ggtggcttta   4980
ttctgtgttc ttacatagat ctgttgtcct gtagttactt atgtcagttt tgttattatc   5040
tgaagatatt tttggttgtt gcttgttgat gtggtgtgag ctgtgagcag cgctcttatg   5100
attaatgatg ctgtccaatt gtagtgtagt atgatgtgat tgatatgttc atctattttg   5160
agctgacagt accgatatcg taggatctgg tgccaactta ttctccagct gctttttttt   5220
acctatgtta attccaatcc tttcttgcct cttccagatc cagataatgg cccaaacatg   5280
tctgaccagc ccacaaacag gattccacaa cggcttcttt tactcgtttt ggaaagattc   5340
tcctggtact gttaactttt gccttcttga agggggaaga tatacctcca attggtctgg   5400
gataaacaat tgggtcggtg gcaagggctg gcagaccggt agtaggcgca acatcacgta   5460
ttccgggagc ttcaatacac cagggaatgg atacctggct ctctacggtt ggaccaccaa   5520
cccgttggtt gagtactatg ttgtcgatag ctggggctcc tggcgccctc ccggaagtga   5580
tgggacattt cttggcacag tgaactcaga cggcggcacg tatgacatct acagggcgca   5640
aagagtcaac gcaccgagca tcattggcaa tgccaccttc taccagtatt ggtccgtgcg   5700
gcagtccaag cgtgtcggtg ggacaatcac gactggcaac cacttcgacg cgtgggccag   5760
cgtgggcctc aacctcggga ctcataacta ccagataatg gctactgagg gttaccagtc   5820
gtcaggatct tcagacatta cggtgtcatg acctaggtcc ccgaatttcc ccgatcgttc   5880
aaacatttgg caataaagtt tcttaagatt gaatcctgtt gccggtcttg cgatgattat   5940
catataattt ctgttgaatt acgttaagca tgtaataatt aacatgtaat gcatgacgtt   6000
atttatgaga tgggttttta tgattagagt cccgcaatta tacatttaat acgcgataga   6060
aaacaaaata tagcgcgcaa actaggataa attatcgcgc gcggtgtcat ctatgttact   6120
agatcgggaa ttggaattca tactaaagct tgcatgcctg caggtcgact ctagtaacgg   6180
ccgccagtgt gctggaatta attcggcttg tcgaccaccc aaccccatat cgacagagga   6240
tgtgaagaac aggtaaatca cgcagaagaa cccatctctg atagcagcta tcgattagaa   6300
caacgaatcc atattgggtc cgtgggaaat acttactgca caggaagggg gcgatctgac   6360
gaggccccgc caccggcctc gacccgaggc cgaggccgac gaagcgccgg cgagtacggc   6420
gccgcggcgg cctctgcccg tgccctctgc gcgtgggagg gagaggccgc ggtggtgggg   6480
gcgcgcgcgc gcgcgcgcgc agctggtgcg gcggcgcggg ggtcagccgc cgagccggcg   6540
gcgacggagg agcagggcgg cgtggacgcg aacttccgat cggttggtca gagtgcgcga   6600
gttgggctta gccaattagg tctcaacaat ctattgggcc gtaaaattca tgggccctgg   6660
tttgtctagg cccaatatcc cgttcatttc agcccacaaa tatttcccca gaggattatt   6720
aaggcccaca cgcagcttat agcagatcaa gtacgatgtt tcctgatcgt tggatcggaa   6780
acgtacggtc ttgatcaggc atgccgactt cgtcaaagag aggcggcatg acctgacgcg   6840
gagttggttc cgggcaccgt ctggatggtc gtaccgggac cggacacgtg tcgcgcctcc   6900
aactacatgg acacgtgtgg tgctgccatt gggccgtacg cgtggcggtg accgcaccgg   6960
atgctgcctc gcaccgcctt gcccacgctt tatatagaga ggttttctct ccattaatcg   7020
catagcgagt cgaatcgacc gaaggggagg gggagcgaag ctttgcgttc tctaatcgcc   7080
tcgtcaaggt aactaatcaa tcacctcgtc ctaatcctcg aatctctcgt ggtgcccgtc   7140
```

```
taatctcgcg attttgatgc tcgtggtgga aagcgtagga ggatcccgtg cgagttagtc   7200
tcaatctctc agggtttcgt gcgattttag ggtgatccac ctcttaatcg agttacggtt   7260
tcgtgcgatt ttagggtaat cctcttaatc tctcattgat ttagggtttc gtgagaatcg   7320
aggtagggat ctgtgttatt tatatcgatc taatagatgg attggttttg agattgttct   7380
gtcagatggg gattgtttcg atatattacc ctaatgatgt gtcagatggg gattgtttcg   7440
atatattacc ctaatgatgt gtcagatggg gattgtttcg atatattacc ctaatgatgg   7500
ataataagag tagttcacag ttatgttttg atcctgccac atagtttgag ttttgtgatc   7560
agatttagtt ttacttattt gtgcttagtt cggatgggat tgttctgata ttgttccaat   7620
agatgaatag ctcgttaggt taaaatcttt aggttgagtt aggcgacaca tagtttattt   7680
cctctggatt tggattggaa ttgtgttctt agttttttttc ccctggattt ggattggaat   7740
tgtgtggagc tgggttagag aattacatct gtatcgtgta cacctacttg aactgtagag   7800
cttgggttct aaggtcaatt taatctgtat tgtatctggc tctttgccta gttgaactgt   7860
agtgctgatg ttgtactgtg tttttttacc cgttttattt gctttactcg tgcaaatcaa   7920
atctgtcaga tgctagaact aggtggcttt attctgtgtt cttacataga tctgttgtcc   7980
tgtagttact tatgtcagtt ttgttattat ctgaagatat ttttggttgt tgcttgttga   8040
tgtggtgtga gctgtgagca gcgctcttat gattaatgat gctgtccaat tgtagtgtag   8100
tatgatgtga ttgatatgtt catctatttt gagctgacag taccgatatc gtaggatctg   8160
gtgccaactt attctccagc tgcttttttt tacctatgtt aattccaatc ctttcttgcc   8220
tcttccagat ccagataatg cagaaactca ttaactcagt gcaaaactat gcctggggca   8280
gcaaaacggc gttgactgaa ctttatggta tggaaaatcc gtccagccag ccgatggccg   8340
agctgtggat gggcgcacat ccgaaaagca gttcacgagt gcagaatgcc gccggagata   8400
tcgtttcact gcgtgatgtg attgagagtg ataaatcgac tctgctcgga gaggccgttg   8460
ccaaacgctt tggcgaactg cctttcctgt tcaaagtatt atgcgcagca cagccactct   8520
ccattcaggt tcatccaaac aaacacaatt ctgaaatcgg ttttgccaaa gaaaatgccg   8580
caggtatccc gatggatgcc gccgagcgta actataaaga tcctaaccac aagccggagc   8640
tggtttttgc gctgacgcct ttccttgcga tgaacgcgtt tcgtgaattt tccgagattg   8700
tctccctact ccagccggtc gcaggtgcac atccggcgat tgctcacttt ttacaacagc   8760
ctgatgccga acgtttaagc gaactgttcg ccagcctgtt gaatatgcag ggtgaagaaa   8820
aatcccgcgc gctggcgatt ttaaaatcgg ccctcgatag ccagcagggt gaaccgtggc   8880
aaacgattcg tttaatttct gaattttacc cggaagacag cggtctgttc tccccgctat   8940
tgctgaatgt ggtgaaattg aaccctggcg aagcgatgtt cctgttcgct gaaacaccgc   9000
acgcttacct gcaaggcgtg gcgctggaag tgatggcaaa ctccgataac gtgctgcgtg   9060
cgggtctgac gcctaaatac attgatattc cggaactggt tgccaatgtg aaattcgaag   9120
ccaaaccggc taaccagttg ttgacccagc cggtgaaaca aggtgcagaa ctggacttcc   9180
cgattccagt ggatgatttt gccttctcgc tgcatgacct tagtgataaa gaaaccacca   9240
ttagccagca gagtgccgcc attttgttct gcgtcgaagg cgatgcaacg ttgtggaaag   9300
gttctcagca gttacagctt aaaccgggtg aatcagcgtt tattgccgcc aacgaatcac   9360
cggtgactgt caaaggccac ggccgtttag cgcgtgttta caacaagctg taagagctta   9420
ctgaaaaaat taacatctct tgctaagctg ggagctctag atccccgaat ttccccgatc   9480
gttcaaacat ttggcaataa agtttcttaa gattgaatcc tgttgccggt cttgcgatga   9540
```

```
ttatcatata atttctgttg aattacgtta agcatgtaat aattaacatg taatgcatga   9600
cgttatttat gagatgggtt tttatgatta gagtcccgca attatacatt taatacgcga   9660
tagaaaacaa aatatagcgc gcaaactagg ataaattatc gcgcgcggtg tcatctatgt   9720
tactagatcg ggaattggcg agctcgaatt aattcagtac attaaaaacg tccgcaatgt   9780
gttattaagt tgtctaagcg tcaatttgtt tacaccacaa tatatcctgc caccagccag   9840
ccaacagctc cccgaccggc agctcggcac aaaatcacca ctcgatacag gcagcccatc   9900
agtccgggac ggcgtcagcg ggagagccgt tgtaaggcgg cagactttgc tcatgttacc   9960
gatgctattc ggaagaacgg caactaagct gccgggtttg aaacacggat gatctcgcgg  10020
agggtagcat gttgattgta acgatgacag agcgttgctg cctgtgatca aatatcatct  10080
ccctcgcaga gatccgaatt atcagccttc ttattcattt ctcgcttaac cgtgacaggc  10140
tgtcgatctt gagaactatg ccgacataat aggaaatcgc tggataaagc cgctgaggaa  10200
gctgagtggc gctatttctt tagaagtgaa cgttgacgat cgtcgaccgt accccgatga  10260
attaattcgg acgtacgttc tgaacacagc tggatactta cttgggcgat tgtcatacat  10320
gacatcaaca atgtacccgt ttgtgtaacc gtctcttgga ggttcgtatg acactagtgg  10380
ttcccctcag cttgcgacta gatgttgagg cctaacattt tattagagag caggctagtt  10440
gcttagatac atgatcttca ggccgttatc tgtcagggca agcgaaaatt ggccatttat  10500
gacgaccaat gccccgcaga agctcccatc tttgccgcca tagacgccgc gcccccttt  10560
tggggtgtag aacatccttt tgccagatgt ggaaaagaag ttcgttgtcc cattgttggc  10620
aatgacgtag tagccggcga aagtgcgaga cccatttgcg ctatatataa gcctacgatt  10680
tccgttgcga ctattgtcgt aattggatga actattatcg tagttgctct cagagttgtc  10740
gtaatttgat ggactattgt cgtaattgct tatggagttg tcgtagttgc ttggagaaat  10800
gtcgtagttg gatggggagt agtcataggg aagacgagct tcatccacta aaacaattgg  10860
caggtcagca agtgcctgcc ccgatgccat cgcaagtacg aggcttagaa ccaccttcaa  10920
cagatcgcgc atagtcttcc ccagctctct aacgcttgag ttaagccgcg ccgcgaagcg  10980
gcgtcggctt gaacgaattg ttagacatta tttgccgact accttggtga tctcgccttt  11040
cacgtagtga acaaattctt ccaactgatc tgcgcgcgag gccaagcgat cttcttgtcc  11100
aagataagcc tgcctagctt caagtatgac gggctgatac tgggccggca ggcgctccat  11160
tgcccagtcg gcagcgacat ccttcggcgc gattttgccg gttactgcgc tgtaccaaat  11220
gcgggacaac gtaagcacta catttcgctc atcgccagcc cagtcgggcg gcgagttcca  11280
tagcgttaag gtttcattta gcgcctcaaa tagatcctgt tcaggaaccg gatcaaagag  11340
ttcctccgcc gctggaccta ccaaggcaac gctatgttct cttgcttttg tcagcaagat  11400
agccagatca atgtcgatcg tggctggctc gaagatacct gcaagaatgt cattgcgctg  11460
ccattctcca aattgcagtt cgcgcttagc tggataacgc cacggaatga tgtcgtcgtg  11520
cacaacaatg gtgacttcta cagcgcggag aatctcgctc tctccagggg aagccgaagt  11580
ttccaaaagg tcgttgatca aagctcgccg cgttgtttca tcaagcctta cggtcaccgt  11640
aaccagcaaa tcaatatcac tgtgtggctt caggccgcca tccactgcgg agccgtacaa  11700
atgtacggcc agcaacgtcg gttcgagatg gcgctcgatg acgccaacta cctctgatag  11760
ttgagtcgat acttcggcga tcaccgcttc cctcatgatg tttaactcct gaattaagcc  11820
gcgccgcgaa gcggtgtcgg cttgaatgaa ttgttaggcg tcatcctgtg ctcccgagaa  11880
```

```
ccagtaccag tacatcgctg tttcgttcga gacttgaggt ctagttttat acgtgaacag  11940
gtcaatgccg ccgagagtaa agccacattt tgcgtacaaa ttgcaggcag gtacattgtt  12000
cgtttgtgtc tctaatcgta tgccaaggag ctgtctgctt agtgcccact tttcgcaaa  12060
ttcgatgaga ctgtgcgcga ctcctttgcc tcggtgcgtg tgcgacacaa caatgtgttc  12120
gatagaggct agatcgttcc atgttgagtt gagttcaatc ttcccgacaa gctcttggtc  12180
gatgaatgcg ccatagcaag cagagtcttc atcagagtca tcatccgaga tgtaatcctt  12240
ccggtagggg ctcacacttc tggtagatag ttcaaagcct tggtcggata ggtgcacatc  12300
gaacacttca cgaacaatga aatggttctc agcatccaat gtttccgcca cctgctcagg  12360
gatcaccgaa atcttcatat gacgcctaac gcctggcaca gcggatcgca aacctggcgc  12420
ggcttttggc acaaaaggcg tgacaggttt gcgaatccgt tgctgccact tgttaaccct  12480
tttgccagat ttggtaacta taatttatgt tagaggcgaa gtcttgggta aaaactggcc  12540
taaaattgct ggggatttca ggaaagtaaa catcaccttc cggctcgatg tctattgtag  12600
atatatgtag tgtatctact tgatcggggg atctgctgcc tcgcgcgttt cggtgatgac  12660
ggtgaaaacc tctgacacat gcagctcccg gagacggtca cagcttgtct gtaagcggat  12720
gccgggagca gacaagcccg tcagggcgcg tcagcgggtg ttggcgggtg tcggggcgca  12780
gccatgaccc agtcacgtag cgatagcgga gtgtatactg gcttaactat gcggcatcag  12840
agcagattgt actgagagtg caccatatgc ggtgtgaaat accgcacaga tgcgtaagga  12900
gaaaataccg catcaggcgc tcttccgctt cctcgctcac tgactcgctg cgctcggtcg  12960
ttcggctgcg gcgagcggta tcagctcact caaaggcggt aatacggtta tccacagaat  13020
caggggataa cgcaggaaag aacatgtgag caaaaggcca gcaaaaggcc aggaaccgta  13080
aaaaggccgc gttgctggcg tttttccata ggctccgccc ccctgacgag catcacaaaa  13140
atcgacgctc aagtcagagg tggcgaaacc cgacaggact ataaagatac caggcgtttc  13200
cccctggaag ctccctcgtg cgctctcctg ttccgaccct gccgcttacc ggatacctgt  13260
ccgcctttct cccttcggga agcgtggcgc tttctcatag ctcacgctgt aggtatctca  13320
gttcggtgta ggtcgttcgc tccaagctgg gctgtgtgca cgaacccccc gttcagcccg  13380
accgctgcgc cttatccggt aactatcgtc ttgagtccaa cccggtaaga cacgacttat  13440
cgccactggc agcagccact ggtaacagga ttagcagagc gaggtatgta ggcggtgcta  13500
cagagttctt gaagtggtgg cctaactacg gctacactag aaggacagta tttggtatct  13560
gcgctctgct gaagccagtt accttcggaa aaagagttgg tagctcttga tccggcaaac  13620
aaaccaccgc tggtagcggt ggtttttttg tttgcaagca gcagattacg cgcagaaaaa  13680
aaggatctca agaagatcct ttgatctttt ctacggggtc tgacgctcag tggaacgaaa  13740
actcacgtta agggattttg gtcatgagat tatcaaaaag gatcttcacc tagatccttt  13800
taaattaaaa atgaagtttt aaatcaatct aaagtatata tgagtaaact tggtctgaca  13860
gttaccaatg cttaatcagt gaggcaccta tctcagcgat ctgtctattt cgttcatcca  13920
tagttgcctg actccccgtc gtgtagataa ctacgatacg ggagggctta ccatctggcc  13980
ccagtgctgc aatgataccg cgagacccac gctcaccggc tccagattta tcagcaataa  14040
accagccagc cggaagggcc gagcgcagaa gtggtcctgc aactttatcc gcctccatcc  14100
agtctattaa ttgttgccgg gaagctagag taagtagttc gccagttaat agtttgcgca  14160
acgttgttgc cattgctgca gggggggggg gggggggggtt ccattgttca ttccacggac  14220
aaaaacagag aaaggaaacg acagaggcca aaaagctcgc tttcagcacc tgtcgtttcc  14280
```

```
tttcttttca gagggtattt taaataaaaa cattaagtta tgacgaagaa gaacggaaac  14340
gccttaaacc ggaaaatttt cataaatagc gaaaacccgc gaggtcgccg ccccgtaacc  14400
tgtcggatca ccggaaagga cccgtaaagt gataatgatt atcatctaca tatcacaacg  14460
tgcgtggagg ccatcaaacc acgtcaaata atcaattatg acgcaggtat cgtattaatt  14520
gatctgcatc aacttaacgt aaaaacaact tcagacaata caaatcagcg acactgaata  14580
cggggcaacc tcatgtcccc cccccccccc ccctgcaggc atcgtggtgt cacgctcgtc  14640
gtttggtatg gcttcattca gctccggttc ccaacgatca aggcgagtta catgatcccc  14700
catgttgtgc aaaaaagcgg ttagctcctt cggtcctccg atcgttgtca gaagtaagtt  14760
ggccgcagtg ttatcactca tggttatggc agcactgcat aattctctta ctgtcatgcc  14820
atccgtaaga tgcttttctg tgactggtga gtactcaacc aagtcattct gagaatagtg  14880
tatgcggcga ccgagttgct cttgcccggc gtcaacacgg gataataccg cgccacatag  14940
cagaacttta aaagtgctca tcattggaaa acgttcttcg gggcgaaaac tctcaaggat  15000
cttaccgctg ttgagatcca gttcgatgta acccactcgt gcacccaact gatcttcagc  15060
atcttttact ttcaccagcg tttctgggtg agcaaaaaca ggaaggcaaa atgccgcaaa  15120
aaagggaata agggcgacac ggaaatgttg aatactcata ctcttccttt ttcaatatta  15180
ttgaagcatt tatcagggtt attgtctcat gagcggatac atatttgaat gtatttagaa  15240
aaataaacaa ataggggttc cgcgcacatt tccccgaaaa gtgccacctg acgtctaaga  15300
aaccattatt atcatgacat taacctataa aaataggcgt atcacgaggc cctttcgtct  15360
tcaagaattg gtcgacgatc ttgctgcgtt cggatatttt cgtggagttc ccgccacaga  15420
cccggattga aggcgagatc cagcaactcg cgccagatca tcctgtgacg gaactttggc  15480
gcgtgatgac tggccaggac gtcggccgaa agagcgacaa gcagatcacg cttttcgaca  15540
gcgtcggatt tgcgatcgag gatttttcgg cgctgcgcta cgtccgcgac cgcgttgagg  15600
gatcaagcca cagcagccca ctcgaccttc tagccgaccc agacgagcca agggatcttt  15660
ttggaatgct gctccgtcgt caggctttcc gacgtttggg tggttgaaca gaagtcatta  15720
tcgcacggaa tgccaagcac tcccgagggg aaccctgtgg ttggcatgca catacaaatg  15780
gacgaacgga taaacctttt cacgcccttt taaatatccg attattctaa taaacgctct  15840
tttctcttag gtttacccgc caatatatcc tgtcaaacac tgatagttta aactgaaggc  15900
gggaaacgac aacctgatca tgagcggaga attaagggag tcacgttatg acccccgccg  15960
atgacgcggg acaagccgtt ttacgtttgg aactgacaga accgcaacgt tgaaggagcc  16020
actcagctta attaagtcta actcgagtta ctggtacgta ccaaatccat ggaatcaagg  16080
taccgtcgac tctagtaacg gccgccagtg tgctggaatt aattcggctt gtcgaccacc  16140
caaccccata tcgacagagg atgtgaagaa caggtaaatc acgcagaaga acccatctct  16200
gatagcagct atcgattaga acaacgaatc catattgggt ccgtgggaaa tacttactgc  16260
acaggaaggg ggcgatctga cgaggccccg ccaccggcct cgacccgagg ccgaggccga  16320
cgaagcgccg gcgagtacgg cgccgcggcg gcctctgccc gtgccctctg cgcgtgggag  16380
ggagaggccg cggtggtggg ggcgcgcgcg cgcgcgcgcg cagctggtgc ggcggcgcgg  16440
gggtcagccg ccgagccggc ggcgacggag gagcagggcg gcgtggacgc gaacttccga  16500
tcggttggtc agagtgcgcg agttgggctt agccaattag gtctcaacaa tctattgggc  16560
cgtaaaattc atgggccctg gtttgtctag gcccaatatc ccgttcattt cagcccacaa  16620
```

atatttcccc agaggattat taaggcccac acgcagctta tagcagatca agtacgatgt 16680
ttcctgatcg ttggatcgga aacgtacggt cttgatcagg catgccgact tcgtcaaaga 16740
gaggcggcat gacctgacgc ggagttggtt ccgggcaccg tctggatggt cgtaccggga 16800
ccggacacgt gtcgcgcctc caactacatg gacacgtgtg gtgctgccat tgggccgtac 16860
gcgtggcggt gaccgcaccg gatgctgcct cgcaccgcct tgcccacgct ttatatagag 16920
aggttttctc tccattaatc gcatagcgag tcgaatcgac cgaaggggag ggggagcgaa 16980
gctttgcgtt ctctaatcgc ctcgtcaagg taactaatca atcacctcgt cctaatcctc 17040
gaatctctcg tggtgcccgt ctaatctcgc gattttgatg ctcgtggtgg aaagcgtagg 17100
aggatcccgt gcgagttagt ctcaatctct cagggtttcg tgcgatttta gggtgatcca 17160
cctcttaatc gagttacggt ttcgtgcgat tttagggtaa tcctcttaat ctctcattga 17220
tttagggttt cgtgagaatc gaggtaggga tctgtgttat ttatatcgat ctaatagatg 17280
gattggtttt gagattgttc tgtcagatgg ggattgtttc gatatattac cctaatgatg 17340
tgtcagatgg ggattgtttc gatatattac cctaatgatg tgtcagatgg ggattgtttc 17400
gatatattac cctaatgatg gataataaga gtagttcaca gttatgtttt gatcctgcca 17460
catagtttga gttttgtgat cagatttagt tttacttatt tgtgcttagt tcggatggga 17520
ttgttctgat attgttccaa tagatgaata gctcgttagg ttaaaatctt taggttgagt 17580
taggcgacac atagtttatt tcctctggat ttggattgga attgtgttct tagttttttt 17640
cccctggatt tggattggaa ttgtgtggag ctgggttaga gaattacatc tgtatcgtgt 17700
acacctactt gaactgtaga gcttgggttc taaggtcaat ttaatctgta ttgtatctgg 17760
ctctttgcct agttgaactg tagtgctgat gttgtactgt gtttttttac ccgttttatt 17820
tgctttactc gtgcaaatca aatctgtcag atgctagaac taggtggctt tattctgtgt 17880
tcttacatag atctgttgtc ctgtagttac ttatgtcagt tttgttatta tctgaagata 17940
tttttggttg ttgcttgttg atgtggtgtg agctgtgagc agcgctctta tgattaatga 18000
tgctgtccaa ttgtagtgta gtatgatgtg attgatatgt tcatctattt tgagctgaca 18060
gtaccgatat cgtaggatct ggtgccaact tattctccag ctgctttttt ttacctatgt 18120
taattccaat cctttcttgc ctcttccaga tccagataat gctggaggac aagtctccca 18180
aactgcctga ttataagaac gaccttctgt acgaacgcac attcgacgag ggctctgct 18240 tcccgtggca cacgtgcgaa gattcaggag ggaaatgcga ttttgccgtg gtcgacgttc 18300
caggcgagcc tgggaacaag gcgttcaggc tcactgttat cgataagggt cagaacaagt 18360
ggtcggtcca aatgagacac cggggtatca cgttggagca ggggcacaca tacaccgttc 18420
ggtttactat ctggagcgac aagagctgcc gcgtgtatgc caaaatcggc caaatgggtg 18480
aaccctacac ggagtactgg aacaataact ggaatccgtt caacctcact ccggggcaga 18540
aattgacggt ggaacagaac tttactatga attatcccac ggacgacacg tgtgagttta 18600
ccttccactt gggaggggaa ctggcagccg ggacccctta ctacgtgtac ctcgacgacg 18660
tttctcttta cgatccccgc tttgtcaagc cagtggaata cgtcctgcct caaccggatg 18720
tcagggttaa tcaagttgga tacctccctt ttgctaagaa atatgctact gtcgtgtcat 18780
cgagcacgtc cccattgaag tggcaacttc tgaatagtgc aaaccaagtt gtcttggagg 18840
gcaatacaat ccccaaggga ctggacaaag attcacaaga ctacgttcat tggatcgatt 18900
tctcgaactt taagaccgaa ggcaaggggt actatttcaa gttgcccact gtgaactccg 18960
atactaacta ctcccacccg tttgatattt ctgcagatat ctattcaaag atgaagttcg 19020

```
acgcgctcgc tttcttttac cataaaaggt cgggaatacc aatcgagatg ccctacgccg  19080

ggggagagca gtggacaagg cccgcagggc acattggtgt cgcgccgaac aagggcgaca  19140

cgaatgtgcc aacttggccc caggatgacg aatatgctgg acgcccccag aaatactata  19200

cgaaagacgt gaccggcggg tggtacgatg ccggtgacca cggcaagtac gtcgtgaacg  19260

ggggtatcgc agtttggacc cttatgaata tgtacgagag agcaaagatt agaggaatcg  19320

ctaaccaggg tgcctacaaa gatggaggaa tgaatatccc ggaaaggaat aacggctatc  19380

ctgatattct ggacgaggcc agatgggaga tcgaattttt taagaagatg caagtcactg  19440

agaaagaaga tccgtcgatt gcaggtatgg tgcaccacaa gatccacgat ttcaggtgga  19500

cggcgctcgg aatgttgcct cacgaggacc cccagccacg ctaccttcgg cccgtcagca  19560

cagcggcaac cctgaatttc gcagcgaccc tcgctcagtc tgccagattg tggaaggatt  19620

acgacccgac ttttgcagcg gactgccttg agaaagctga aattgcctgg caagcagcac  19680

tcaaacaccc ggacatctac gctgagtaca cgccaggaag cggtgggccg ggtggaggtc  19740

cttataatga cgattatgtc ggggacgagt tctactgggc cgcttgtgaa ctctatgtga  19800

caaccggtaa ggatgagtac aagaattact tgatgaatag tccgcactat ctggaaatgc  19860

cagcgaagat gggcgagaac ggaggggcta acggcgagga caacggtctc tggggctgct  19920

ttacttgggg aacgacacag ggtttgggta caattaccct tgccctcgtt gaaaacggcc  19980

tcccttcggc ggatattcaa aaggcccgca acaatatcgc taaagccgca gataagtggc  20040

ttgagaatat tgaagaacaa ggttaccgcc tgcctatcaa acaagcggag gatgaacggg  20100

gcggataccc gtggggtagt aattctttca ttctcaacca gatgatcgtc atgggctacg  20160

cttacgactt cacgggaaac agcaagtatc ttgacgggat gcaggacggc atgtcctacc  20220

tgctcggtag aaacggactt gatcaatcgt acgttactgg gtacggggag aggccacttc  20280

agaaccccca cgaccgcttt tggacccctc aaacttcgaa gaaattcccg gccccacccc  20340

ctggtattat cgcaggcggg ccgaatagcc ggtttgaaga tccaacgatc actgcagcgg  20400

ttaagaagga tacacccccg cagaagtgct atattgacca caccgattcc tggtctacta  20460

acgagatcac gattaattgg aacgcccccct tcgcgtgggt cacagcgtat ctggacgaaa  20520

ttgacttgat taccccaccc ggcggagtgg accctgaaga gccggaagtt atctacggtg  20580

attgtaacgg cgacggaaag gttaattcga ccgatgctgt ggcccttaaa aggtatatcc  20640

tccgcagcgg tatctcgatc aacacggaca acgcggacgt taatgcagat ggtcgcgtga  20700

atagcactga cctcgctatt ttgaagcgct atattttgaa ggagatcgat gttcttcctc  20760

acaagtgacc taggtccccg aatttccccg atcgttcaaa catttggcaa taaagtttct  20820

taagattgaa tcctgttgcc ggtcttgcga tgattatcat ataatttctg ttgaattacg  20880

ttaagcatgt aataattaac atgtaatgca tgacgttatt tatgagatgg gtttttatga  20940

ttagagtccc gcaattatac atttaatacg cgatagaaaa caaaatatag cgcgcaaact  21000

aggataaatt atcgcgcgcg gtgtcatcta tgttactaga tcgggaattg c           21051
```

<210> SEQ ID NO 81
<211> LENGTH: 17129
<212> TYPE: DNA
<213> ORGANISM: Artificial Sequence
<220> FEATURE:
<223> OTHER INFORMATION: Synthetic construct, vector pAG2342

<400> SEQUENCE: 81

```
cgtcgactct agtaacggcc gccagtgtgc tggaattaat tcggcttgtc gaccacccaa     60
ccccatatcg acagaggatg tgaagaacag gtaaatcacg cagaagaacc catctctgat    120
agcagctatc gattagaaca acgaatccat attgggtccg tgggaaatac ttactgcaca    180
ggaagggggc gatctgacga ggccccgcca ccggcctcga cccgaggccg aggccgacga    240
agcgccggcg agtacggcgc cgcggcggcc tctgcccgtg ccctctgcgc gtgggaggga    300
gaggccgcgg tggtgggggc gcgcgcgcgc gcgcgcgcag ctggtgcggc ggcgcggggg    360
tcagccgccg agccggcggc gacggaggag cagggcggcg tggacgcgaa cttccgatcg    420
gttggtcaga gtgcgcgagt tgggcttagc caattaggtc tcaacaatct attgggccgt    480
aaaattcatg ggccctggtt tgtctaggcc caatatcccg ttcatttcag cccacaaata    540
tttccccaga ggattattaa ggcccacacg cagcttatag cagatcaagt acgatgtttc    600
ctgatcgttg gatcggaaac gtacggtctt gatcaggcat gccgacttcg tcaaagagag    660
gcggcatgac ctgacgcgga gttggttccg ggcaccgtct ggatggtcgt accgggaccg    720
gacacgtgtc gcgcctccaa ctacatggac acgtgtggtg ctgccattgg gccgtacgcg    780
tggcggtgac cgcaccggat gctgcctcgc accgccttgc ccacgcttta tatagagagg    840
ttttctctcc attaatcgca tagcgagtcg aatcgaccga aggggagggg gagcgaagct    900
ttgcgttctc taatcgcctc gtcaaggtaa ctaatcaatc acctcgtcct aatcctcgaa    960
tctctcgtgg tgcccgtcta atctcgcgat tttgatgctc gtggtggaaa gcgtaggagg   1020
atcccgtgcg agttagtctc aatctctcag ggtttcgtgc gattttaggg tgatccacct   1080
cttaatcgag ttacggtttc gtgcgatttt agggtaatcc tcttaatctc tcattgattt   1140
agggtttcgt gagaatcgag gtagggatct gtgttattta tatcgatcta atagatggat   1200
tggttttgag attgttctgt cagatgggga ttgtttcgat atattaccct aatgatgtgt   1260
cagatgggga ttgtttcgat atattaccct aatgatgtgt cagatgggga ttgtttcgat   1320
atattaccct aatgatggat aataagagta gttcacagtt atgttttgat cctgccacat   1380
agtttgagtt ttgtgatcag atttagtttt acttatttgt gcttagttcg gatgggattg   1440
ttctgatatt gttccaatag atgaatagct cgttaggtta aaatctttag gttgagttag   1500
gcgacacata gtttatttcc tctggatttg gattggaatt gtgttcttag tttttttccc   1560
ctggatttgg attggaattg tgtggagctg ggttagagaa ttacatctgt atcgtgtaca   1620
cctacttgaa ctgtagagct tgggttctaa ggtcaattta atctgtattg tatctggctc   1680
tttgcctagt tgaactgtag tgctgatgtt gtactgtgtt tttttacccg ttttatttgc   1740
tttactcgtg caaatcaaat ctgtcagatg ctagaactag gtggctttat tctgtgttct   1800
tacatagatc tgttgtcctg tagttactta tgtcagtttt gttattatct gaagatattt   1860
ttggttgttg cttgttgatg tggtgtgagc tgtgagcagc gctcttatga ttaatgatgc   1920
tgtccaattg tagtgtagta tgatgtgatt gatatgttca tctattttga gctgacagta   1980
ccgatatcgt aggatctggt gccaacttat tctccagctg cttttttttta cctatgttaa   2040
ttccaatcct ttcttgcctc ttccagatcc agataatgca aacaagcatt actctgacat   2100
ccaacgcatc cggtacgttt gacggttact attacgaact ctggaaggat actggcaata   2160
caacaatgac ggtctacact caaggtcgct tttcctgcca gtggtcgaac atcaataacg   2220
cgttgtttag gaccgggaag aaatacaacc agaattggca gtctcttggc acaatccgga   2280
tcacgtactc tgcgacttac aacccaaacg ggaactccta cttgtgtatc tatggctggt   2340
ctaccaaccc attggtcgag ttctacatcg ttgagtcctg gggggaactgg agaccgcctg   2400
```

```
gtgccacgtc cctgggccaa gtgacaatcg atggcgggac ctacgacatc tataggacga   2460
cacgcgtcaa ccagccttcc attgtgggga cagccacgtt cgatcagtac tggagcgtgc   2520
gcacctctaa gcggacttca ggaacagtga ccgtgaccga tcacttccgc gcctgggcga   2580
accggggcct gaacctcggc acaatagacc aaattacatt gtgcgtggag ggttaccaaa   2640
gctctggatc agccaacatc acccagaaca ccttctctca gggctcttct tccggcagtt   2700
cgggtggctc atccggctcc acaacgacta ctcgcatcga gtgtgagaac atgtccttgt   2760
ccggacccta cgttagcagg atcaccaatc cctttaatgg tattgcgctg tacgccaacg   2820
gagacacagc ccgcgctacc gttaacttcc ccgcaagtcg caactacaat ttccgcctgc   2880
ggggttgcgg caacaacaat aatcttgccc gtgtggacct gaggatcgac ggacggaccg   2940
tcgggacctt ttattaccag ggcacatacc cctgggaggc ccaattgac aatgtttatg    3000
tcagtgcggg gagtcataca gtcgaaatca ctgttactgc ggataacggc acatgggacg   3060
tgtatgccga ctacctggtg atacagtgac ctaggtcccc gaatttcccc gatcgttcaa   3120
acatttggca ataaagtttc ttaagattga atcctgttgc cggtcttgcg atgattatca   3180
tataatttct gttgaattac gttaagcatg taataattaa catgtaatgc atgacgttat   3240
ttatgagatg ggtttttatg attagagtcc cgcaattata catttaatac gcgatagaaa   3300
acaaaatata gcgcgcaaac taggataaat tatcgcgcgc ggtgtcatct atgttactag   3360
atcgggaatt ggaattcata ctaaagcttg catgcctgca ggtcgactct agtaacggcc   3420
gccagtgtgc tggaattaat tcggcttgtc gaccacccaa ccccatatcg acagaggatg   3480
tgaagaacag gtaaatcacg cagaagaacc catctctgat agcagctatc gattagaaca   3540
acgaatccat attgggtccg tgggaaatac ttactgcaca ggaagggggc gatctgacga   3600
ggccccgcca ccggcctcga cccgaggccg aggccgacga agcgccggcg agtacggcgc   3660
cgcggcggcc tctgcccgtg ccctctgcgc gtgggaggga gaggccgcgg tggtgggggc   3720
gcgcgcgcgc gcgcgcgcag ctggtgcggc ggcgcggggg tcagccgccg agccggcggc   3780
gacggaggag cagggcggcg tggacgcgaa cttccgatcg gttggtcaga gtgcgcgagt   3840
tgggcttagc caattaggtc tcaacaatct attgggccgt aaaattcatg ggccctggtt   3900
tgtctaggcc caatatcccg ttcatttcag cccacaaata tttccccaga ggattattaa   3960
ggcccacacg cagcttatag cagatcaagt acgatgtttc ctgatcgttg gatcggaaac   4020
gtacggtctt gatcaggcat gccgacttcg tcaaagagag gcggcatgac ctgacgcgga   4080
gttggttccg ggcaccgtct ggatggtcgt accgggaccg gacacgtgtc gcgcctccaa   4140
ctacatggac acgtgtggtg ctgccattgg gccgtacgcg tggcggtgac cgcaccggat   4200
gctgcctcgc accgccttgc ccacgcttta tatagagagg ttttctctcc attaatcgca   4260
tagcgagtcg aatcgaccga aggggagggg gagcgaagct ttgcgttctc taatcgcctc   4320
gtcaaggtaa ctaatcaatc acctcgtcct aatcctcgaa tctctcgtgg tgcccgtcta   4380
atctcgcgat tttgatgctc gtggtggaaa gcgtaggagg atcccgtgcg agttagtctc   4440
aatctctcag ggtttcgtgc gattttaggg tgatccacct cttaatcgag ttacggtttc   4500
gtgcgatttt agggtaatcc tcttaatctc tcattgattt agggtttcgt gagaatcgag   4560
gtagggatct gtgttattta tatcgatcta atagatggat tggttttgag attgttctgt   4620
cagatgggga ttgtttcgat atattaccct aatgatgtgt cagatgggga ttgtttcgat   4680
atattaccct aatgatgtgt cagatgggga ttgtttcgat atattaccct aatgatggat   4740
```

```
aataagagta gttcacagtt atgttttgat cctgccacat agtttgagtt ttgtgatcag   4800
atttagtttt acttatttgt gcttagttcg gatgggattg ttctgatatt gttccaatag   4860
atgaatagct cgttaggtta aaatctttag gttgagttag gcgacacata gtttatttcc   4920
tctggatttg gattggaatt gtgttcttag tttttttccc ctggatttgg attggaattg   4980
tgtggagctg ggttagagaa ttacatctgt atcgtgtaca cctacttgaa ctgtagagct   5040
tgggttctaa ggtcaattta atctgtattg tatctggctc tttgcctagt tgaactgtag   5100
tgctgatgtt gtactgtgtt tttttacccg ttttatttgc tttactcgtg caaatcaaat   5160
ctgtcagatg ctagaactag gtggctttat tctgtgttct tacatagatc tgttgtcctg   5220
tagttactta tgtcagtttt gttattatct gaagatattt ttggttgttg cttgttgatg   5280
tggtgtgagc tgtgagcagc gctcttatga ttaatgatgc tgtccaattg tagtgtagta   5340
tgatgtgatt gatatgttca tctattttga gctgacagta ccgatatcgt aggatctggt   5400
gccaacttat tctccagctg cttttttta cctatgttaa ttccaatcct ttcttgcctc   5460
ttccagatcc agataatgca gaaactcatt aactcagtgc aaaactatgc ctggggcagc   5520
aaaacggcgt tgactgaact ttatggtatg gaaaatccgt ccagccagcc gatggccgag   5580
ctgtggatgg gcgcacatcc gaaaagcagt tcacgagtgc agaatgccgc cggagatatc   5640
gtttcactgc gtgatgtgat tgagagtgat aaatcgactc tgctcggaga ggccgttgcc   5700
aaacgctttg gcgaactgcc tttcctgttc aaagtattat gcgcagcaca gccactctcc   5760
attcaggttc atccaaacaa acacaattct gaaatcggtt ttgccaaaga aaatgccgca   5820
ggtatcccga tggatgccgc cgagcgtaac tataaagatc ctaaccacaa gccggagctg   5880
gtttttgcgc tgacgccttt ccttgcgatg aacgcgtttc gtgaattttc cgagattgtc   5940
tccctactcc agccggtcgc aggtgcacat ccggcgattg ctcacttttt acaacagcct   6000
gatgccgaac gtttaagcga actgttcgcc agcctgttga atatgcaggg tgaagaaaaa   6060
tcccgcgcgc tggcgatttt aaaatcggcc ctcgatagcc agcagggtga accgtggcaa   6120
acgattcgtt taatttctga attttacccg gaagacagcg gtctgttctc cccgctattg   6180
ctgaatgtgg tgaaattgaa ccctggcgaa gcgatgttcc tgttcgctga aacaccgcac   6240
gcttacctgc aaggcgtggc gctggaagtg atggcaaact ccgataacgt gctgcgtgcg   6300
ggtctgacgc ctaaatacat tgatattccg gaactggttg ccaatgtgaa attcgaagcc   6360
aaaccggcta accagttgtt gacccagccg gtgaaacaag gtgcagaact ggacttcccg   6420
attccagtgg atgattttgc cttctcgctg catgacctta gtgataaaga aaccaccatt   6480
agccagcaga gtgccgccat tttgttctgc gtcgaaggcg atgcaacgtt gtggaaaggt   6540
tctcagcagt tacagcttaa accgggtgaa tcagcgttta ttgccgccaa cgaatcaccg   6600
gtgactgtca aaggccacgg ccgtttagcg cgtgtttaca acaagctgta agagcttact   6660
gaaaaaatta acatctcttg ctaagctggg agctctagat ccccgaattt ccccgatcgt   6720
tcaaacattt ggcaataaag tttcttaaga ttgaatcctg ttgccggtct tgcgatgatt   6780
atcatataat ttctgttgaa ttacgttaag catgtaataa ttaacatgta atgcatgacg   6840
ttatttatga gatgggtttt tatgattaga gtcccgcaat tatacattta atacgcgata   6900
gaaaacaaaa tatagcgcgc aaactaggat aaattatcgc gcgcggtgtc atctatgtta   6960
ctagatcggg aattggcgag ctcgaattaa ttcagtacat taaaaacgtc cgcaatgtgt   7020
tattaagttg tctaagcgtc aatttgttta caccacaata tatcctgcca ccagccagcc   7080
aacagctccc cgaccggcag ctcggcacaa aatcaccact cgatacaggc agcccatcag   7140
```

```
tccgggacgg cgtcagcggg agagccgttg taaggcggca gactttgctc atgttaccga   7200
tgctattcgg aagaacggca actaagctgc cgggtttgaa acacggatga tctcgcggag   7260
ggtagcatgt tgattgtaac gatgacagag cgttgctgcc tgtgatcaaa tatcatctcc   7320
ctcgcagaga tccgaattat cagccttctt attcatttct cgcttaaccg tgacaggctg   7380
tcgatcttga gaactatgcc gacataatag gaaatcgctg gataaagccg ctgaggaagc   7440
tgagtggcgc tatttcttta gaagtgaacg ttgacgatcg tcgaccgtac cccgatgaat   7500
taattcggac gtacgttctg aacacagctg gatacttact tgggcgattg tcatacatga   7560
catcaacaat gtacccgttt gtgtaaccgt ctcttggagg ttcgtatgac actagtggtt   7620
cccctcagct tgcgactaga tgttgaggcc taacatttta ttagagagca ggctagttgc   7680
ttagatacat gatcttcagg ccgttatctg tcagggcaag cgaaaattgg ccatttatga   7740
cgaccaatgc cccgcagaag ctcccatctt tgccgccata gacgccgcgc ccccctttg   7800
gggtgtagaa catccttttg ccagatgtgg aaaagaagtt cgttgtccca ttgttggcaa   7860
tgacgtagta gccggcgaaa gtgcgagacc catttgcgct atatataagc ctacgatttc   7920
cgttgcgact attgtcgtaa ttggatgaac tattatcgta gttgctctca gagttgtcgt   7980
aatttgatgg actattgtcg taattgctta tggagttgtc gtagttgctt ggagaaatgt   8040
cgtagttgga tggggagtag tcatagggaa gacgagcttc atccactaaa acaattggca   8100
ggtcagcaag tgcctgcccc gatgccatcg caagtacgag gcttagaacc accttcaaca   8160
gatcgcgcat agtcttcccc agctctctaa cgcttgagtt aagccgcgcc gcgaagcggc   8220
gtcggcttga acgaattgtt agacattatt tgccgactac cttggtgatc tcgcctttca   8280
cgtagtgaac aaattcttcc aactgatctg cgcgcgaggc caagcgatct tcttgtccaa   8340
gataagcctg cctagcttca agtatgacgg gctgatactg ggccggcagg cgctccattg   8400
cccagtcggc agcgacatcc ttcggcgcga ttttgccggt tactgcgctg taccaaatgc   8460
gggacaacgt aagcactaca tttcgctcat cgccagccca gtcgggcggc gagttccata   8520
gcgttaaggt ttcatttagc gcctcaaata gatcctgttc aggaaccgga tcaaagagtt   8580
cctccgccgc tggacctacc aaggcaacgc tatgttctct tgcttttgtc agcaagatag   8640
ccagatcaat gtcgatcgtg gctggctcga agatacctgc aagaatgtca ttgcgctgcc   8700
attctccaaa ttgcagttcg cgcttagctg gataacgcca cggaatgatg tcgtcgtgca   8760
caacaatggt gacttctaca gcgcggagaa tctcgctctc tccaggggaa gccgaagttt   8820
ccaaaaggtc gttgatcaaa gctcgccgcg ttgtttcatc aagccttacg gtcaccgtaa   8880
ccagcaaatc aatatcactg tgtggcttca ggccgccatc cactgcggag ccgtacaaat   8940
gtacggccag caacgtcggt tcgagatggc gctcgatgac gccaactacc tctgatagtt   9000
gagtcgatac ttcggcgatc accgcttccc tcatgatgtt taactcctga attaagccgc   9060
gccgcgaagc ggtgtcggct tgaatgaatt gttaggcgtc atcctgtgct cccgagaacc   9120
agtaccagta catcgctgtt tcgttcgaga cttgaggtct agttttatac gtgaacaggt   9180
caatgccgcc gagagtaaag ccacattttg cgtacaaatt gcaggcaggt acattgttcg   9240
tttgtgtctc taatcgtatg ccaaggagct gtctgcttag tgcccacttt ttcgcaaatt   9300
cgatgagact gtgcgcgact cctttgcctc ggtgcgtgtg cgacacaaca atgtgttcga   9360
tagaggctag atcgttccat gttgagttga gttcaatctt cccgacaagc tcttggtcga   9420
tgaatgcgcc atagcaagca gagtcttcat cagagtcatc atccgagatg taatccttcc   9480
```

```
ggtaggggct cacacttctg gtagatagtt caaagccttg gtcggatagg tgcacatcga   9540
acacttcacg aacaatgaaa tggttctcag catccaatgt ttccgccacc tgctcaggga   9600
tcaccgaaat cttcatatga cgcctaacgc ctggcacagc ggatcgcaaa cctggcgcgg   9660
cttttggcac aaaaggcgtg acaggtttgc gaatccgttg ctgccacttg ttaacccttt   9720
tgccagattt ggtaactata atttatgtta gaggcgaagt cttgggtaaa aactggccta   9780
aaattgctgg ggatttcagg aaagtaaaca tcaccttccg gctcgatgtc tattgtagat   9840
atatgtagtg tatctacttg atcgggggat ctgctgcctc gcgcgtttcg gtgatgacgg   9900
tgaaaacctc tgacacatgc agctcccgga gacggtcaca gcttgtctgt aagcggatgc   9960
cgggagcaga caagcccgtc agggcgcgtc agcgggtgtt ggcgggtgtc ggggcgcagc  10020
catgacccag tcacgtagcg atagcggagt gtatactggc ttaactatgc ggcatcagag  10080
cagattgtac tgagagtgca ccatatgcgg tgtgaaatac cgcacagatg cgtaaggaga  10140
aaataccgca tcaggcgctc ttccgcttcc tcgctcactg actcgctgcg ctcggtcgtt  10200
cggctgcggc gagcggtatc agctcactca aaggcggtaa tacggttatc cacagaatca  10260
ggggataacg caggaaagaa catgtgagca aaaggccagc aaaaggccag gaaccgtaaa  10320
aaggccgcgt tgctggcgtt tttccatagg ctccgccccc ctgacgagca tcacaaaaat  10380
cgacgctcaa gtcagaggtg gcgaaacccg acaggactat aaagatacca ggcgtttccc  10440
cctggaagct ccctcgtgcg ctctcctgtt ccgaccctgc cgcttaccgg atacctgtcc  10500
gcctttctcc cttcgggaag cgtggcgctt tctcatagct cacgctgtag gtatctcagt  10560
tcggtgtagg tcgttcgctc caagctgggc tgtgtgcacg aaccccccgt tcagcccgac  10620
cgctgcgcct tatccggtaa ctatcgtctt gagtccaacc cggtaagaca cgacttatcg  10680
ccactggcag cagccactgg taacaggatt agcagagcga ggtatgtagg cggtgctaca  10740
gagttcttga agtggtggcc taactacggc tacactagaa ggacagtatt tggtatctgc  10800
gctctgctga agccagttac cttcggaaaa agagttggta gctcttgatc cggcaaacaa  10860
accaccgctg gtagcggtgg tttttttgtt tgcaagcagc agattacgcg cagaaaaaaa  10920
ggatctcaag aagatccttt gatcttttct acggggtctg acgctcagtg gaacgaaaac  10980
tcacgttaag ggattttggt catgagatta tcaaaaagga tcttcaccta gatcctttta  11040
aattaaaaat gaagttttaa atcaatctaa agtatatatg agtaaacttg gtctgacagt  11100
taccaatgct taatcagtga ggcacctatc tcagcgatct gtctatttcg ttcatccata  11160
gttgcctgac tccccgtcgt gtagataact acgatacggg agggcttacc atctggcccc  11220
agtgctgcaa tgataccgcg agacccacgc tcaccggctc cagatttatc agcaataaac  11280
cagccagccg gaagggccga gcgcagaagt ggtcctgcaa ctttatccgc ctccatccag  11340
tctattaatt gttgccggga agctagagta agtagttcgc cagttaatag tttgcgcaac  11400
gttgttgcca ttgctgcagg gggggggggg ggggggttcc attgttcatt ccacggacaa  11460
aaacagagaa aggaaacgac agaggccaaa aagctcgctt tcagcacctg tcgtttcctt  11520
tcttttcaga gggtatttta aataaaaaca ttaagttatg acgaagaaga acggaaacgc  11580
cttaaaccgg aaaattttca taaatagcga aaacccgcga ggtcgccgcc ccgtaacctg  11640
tcggatcacc ggaaaggacc cgtaaagtga taatgattat catctacata tcacaacgtg  11700
cgtggaggcc atcaaaccac gtcaaataat caattatgac gcaggtatcg tattaattga  11760
tctgcatcaa cttaacgtaa aaacaacttc agacaataca aatcagcgac actgaatacg  11820
gggcaacctc atgtcccccc cccccccccc ctgcaggcat cgtggtgtca cgctcgtcgt  11880
```

```
ttggtatggc ttcattcagc tccggttccc aacgatcaag gcgagttaca tgatccccca  11940
tgttgtgcaa aaaagcggtt agctccttcg gtcctccgat cgttgtcaga agtaagttgg  12000
ccgcagtgtt atcactcatg gttatggcag cactgcataa ttctcttact gtcatgccat  12060
ccgtaagatg cttttctgtg actggtgagt actcaaccaa gtcattctga gaatagtgta  12120
tgcggcgacc gagttgctct tgcccggcgt caacacggga taataccgcg ccacatagca  12180
gaactttaaa agtgctcatc attggaaaac gttcttcggg gcgaaaactc tcaaggatct  12240
taccgctgtt gagatccagt tcgatgtaac ccactcgtgc acccaactga tcttcagcat  12300
cttttacttt caccagcgtt tctgggtgag caaaaacagg aaggcaaaat gccgcaaaaa  12360
agggaataag ggcgacacgg aaatgttgaa tactcatact cttccttttt caatattatt  12420
gaagcattta tcagggttat tgtctcatga gcggatacat atttgaatgt atttagaaaa  12480
ataaacaaat aggggttccg cgcacatttc cccgaaaagt gccacctgac gtctaagaaa  12540
ccattattat catgacatta acctataaaa ataggcgtat cacgaggccc tttcgtcttc  12600
aagaattggt cgacgatctt gctgcgttcg gatattttcg tggagttccc gccacagacc  12660
cggattgaag gcgagatcca gcaactcgcg ccagatcatc ctgtgacgga actttggcgc  12720
gtgatgactg gccaggacgt cggccgaaag agcgacaagc agatcacgct tttcgacagc  12780
gtcggatttg cgatcgagga tttttcggcg ctgcgctacg tccgcgaccg cgttgaggga  12840
tcaagccaca gcagcccact cgaccttcta gccgacccag acgagccaag ggatcttttt  12900
ggaatgctgc tccgtcgtca ggctttccga cgtttgggtg gttgaacaga agtcattatc  12960
gcacggaatg ccaagcactc ccgaggggaa ccctgtggtt ggcatgcaca tacaaatgga  13020
cgaacggata aaccttttca cgccctttta aatatccgat tattctaata aacgctcttt  13080
tctcttaggt ttacccgcca atatatcctg tcaaacactg atagtttaaa ctgaaggcgg  13140
gaaacgacaa cctgatcatg agcggagaat taagggagtc acgttatgac ccccgccgat  13200
gacgcgggac aagccgtttt acgtttggaa ctgacagaac cgcaacgttg aaggagccac  13260
tcagcttaat taagtctaac tcgagttact ggtacgtacc aaatccatgg aatcaaggta  13320
ccgtcgactc tagtaacggc cgccagtgtg ctggaattaa ttcggcttgt cgaccaccca  13380
accccatatc gacagaggat gtgaagaaca ggtaaatcac gcagaagaac ccatctctga  13440
tagcagctat cgattagaac aacgaatcca tattgggtcc gtgggaaata cttactgcac  13500
aggaaggggg cgatctgacg aggccccgcc accggcctcg acccgaggcc gaggccgacg  13560
aagcgccggc gagtacggcg ccgcggcggc ctctgcccgt gccctctgcg cgtgggaggg  13620
agaggccgcg gtggtggggg cgcgcgcgcg cgcgcgcgca gctggtgcgg cggcgcgggg  13680
gtcagccgcc gagccggcgg cgacggagga gcagggcggc gtggacgcga acttccgatc  13740
ggttggtcag agtgcgcgag ttgggcttag ccaattaggt ctcaacaatc tattgggccg  13800
taaaattcat gggccctggt ttgtctaggc ccaatatccc gttcatttca gcccacaaat  13860
atttccccag aggattatta aggcccacac gcagcttata gcagatcaag tacgatgttt  13920
cctgatcgtt ggatcggaaa cgtacggtct tgatcaggca tgccgacttc gtcaaagaga  13980
ggcggcatga cctgacgcgg agttggttcc gggcaccgtc tggatggtcg taccgggacc  14040
ggacacgtgt cgcgcctcca actacatgga cacgtgtggt gctgccattg ggccgtacgc  14100
gtggcggtga ccgcaccgga tgctgcctcg caccgccttg cccacgcttt atatagagag  14160
gttttctctc cattaatcgc atagcgagtc gaatcgaccg aaggggaggg ggagcgaagc  14220
```

```
tttgcgttct ctaatcgcct cgtcaaggta actaatcaat cacctcgtcc taatcctcga  14280
atctctcgtg gtgcccgtct aatctcgcga ttttgatgct cgtggtggaa agcgtaggag  14340
gatcccgtgc gagttagtct caatctctca gggtttcgtg cgattttagg gtgatccacc  14400
tcttaatcga gttacggttt cgtgcgattt tagggtaatc ctcttaatct ctcattgatt  14460
tagggtttcg tgagaatcga ggtagggatc tgtgttattt atatcgatct aatagatgga  14520
ttggttttga gattgttctg tcagatgggg attgtttcga tatattaccc taatgatgtg  14580
tcagatgggg attgtttcga tatattaccc taatgatgtg tcagatgggg attgtttcga  14640
tatattaccc taatgatgga taataagagt agttcacagt tatgttttga tcctgccaca  14700
tagtttgagt tttgtgatca gatttagttt tacttatttg tgcttagttc ggatgggatt  14760
gttctgatat tgttccaata gatgaatagc tcgttaggtt aaaatcttta ggttgagtta  14820
ggcgacacat agtttatttc ctctggattt ggattggaat tgtgttctta gttttttttcc  14880
cctggatttg gattggaatt gtgtggagct gggttagaga attacatctg tatcgtgtac  14940
acctacttga actgtagagc ttgggttcta aggtcaattt aatctgtatt gtatctggct  15000
ctttgcctag ttgaactgta gtgctgatgt tgtactgtgt ttttttaccc gttttatttg  15060
ctttactcgt gcaaatcaaa tctgtcagat gctagaacta ggtggcttta ttctgtgttc  15120
ttacatagat ctgttgtcct gtagttactt atgtcagttt tgttattatc tgaagatatt  15180
tttggttgtt gcttgttgat gtggtgtgag ctgtgagcag cgctcttatg attaatgatg  15240
ctgtccaatt gtagtgtagt atgatgtgat tgatatgttc atctattttg agctgacagt  15300
accgatatcg taggatctgg tgccaactta ttctccagct gctttttttt acctatgtta  15360
attccaatcc tttcttgcct cttccagatc cagataatgg cccacgcccg cgtcctcctc  15420
ctggcgctcg ccgtcctggc caccgccgcc gtcgccgtcg cctcctcctc ctccttcgcc  15480
gactccaacc cgatccgccc ggtgaccgac cgcgccgcct ccaccgctta cgactacaag  15540
caggtgttgc gggactcgct actattctat gaggcccaga gatccggccg gctcccagcc  15600
gaccagaagg tcacgtggag gaaggatagc gcgctgaatg accagggtga ccagggacaa  15660
gacttgaccg gcggctactt tgacgctggg gacttcgtca agttcgggtt ccccatggct  15720
tataccgcaa ccgtgctggc atggggcctc atagattttg aggccggcta cagcagtgcc  15780
ggggccttgg atgatggacg gaaggctgtc aaatgggcca ccgactattt cataaaggcc  15840
cacacaagtc aaaatgagtt ctatggtcag gtcggccagg gtgacgccga tcacgctttc  15900
tggggaagac cagaggatat gacgatggcg cgcccggcgt acaagataga cacctcaagg  15960
cctggctctg atctggcagg cgagacagcg gctgctcttg ccgctgcttc aatcgtgttc  16020
cggaacgtcg atggcactta ctcaaataac ctgttaacac acgctcgcca gctattcgac  16080
ttcgcgaaca actaccgggg aaagtatagt gactctatta ctgacgcaag aaatttctac  16140
gcaagcgcag actacagaga cgagttggtt tgggctgctg cgtggttata cagagcgacc  16200
aacgacaaca cctacctcaa cactgctgag tcactgtacg atgagtttgg gctacagaac  16260
tggggggggg gcctgaactg ggatagcaag gtgtctggcg tgcaggtgtt gttggccaag  16320
cttaccaata agcaggccta caaggacacg gtgcagtctt acgtcaatta cctaattaat  16380
aaccagcaga agactcccaa gggcctcctc tacatcgaca tgtggggcac ccttcgccac  16440
gctgccaacg ccgcattcat catgctcgaa gccgccgagc tgggcttgtc cgcctcctct  16500
tatagacagt tcgcgcaaac gcaaatcgac tacgccctgg gcgatggtgg ccgctccttt  16560
gtgtgcgggt tcgggagtaa tcctcctacg agaccgcacc acagatcctc gtcgtgcccg  16620
```

```
ccagctcccg ctacttgcga ctggaataca ttcaactcac ctgacccaaa ctaccacgtc  16680

ctctctgggg ccctagtggg cggacctgat cagaatgaca actacgtcga tgaccgttca  16740

gactatgttc acaacgaagt cgccactgat tacaacgcgg gtttccagtc cgcgttagct  16800

gctttggtgg cccttggtta cagcgagaag gacgagctgt gacctaggtc cccgaatttc  16860

cccgatcgtt caaacatttg gcaataaagt ttcttaagat tgaatcctgt tgccggtctt  16920

gcgatgatta tcatataatt tctgttgaat tacgttaagc atgtaataat taacatgtaa  16980

tgcatgacgt tatttatgag atgggttttt atgattagag tcccgcaatt atacatttaa  17040

tacgcgatag aaaacaaaat atagcgcgca aactaggata aattatcgcg cgcggtgtca  17100

tctatgttac tagatcggga attgggtac                                    17129
```

<210> SEQ ID NO 82
<211> LENGTH: 21841
<212> TYPE: DNA
<213> ORGANISM: Artificial Sequence
<220> FEATURE:
<223> OTHER INFORMATION: Synthetic construct, vector pAG2345

<400> SEQUENCE: 82

```
tcgagttact ggtacgtacc aaatccatgg aatcaaggta ccgtcgactc tagtaacggc     60

cgccagtgtg ctggaattaa ttcggcttgt cgaccaccca accccatatc gacagaggat    120

gtgaagaaca ggtaaatcac gcagaagaac ccatctctga tagcagctat cgattagaac    180

aacgaatcca tattgggtcc gtgggaaata cttactgcac aggaaggggg cgatctgacg    240

aggccccgcc accggcctcg acccgaggcc gaggccgacg aagcgccggc gagtacggcg    300

ccgcggcggc ctctgcccgt gccctctgcg cgtgggaggg agaggccgcg gtggtggggg    360

cgcgcgcgcg cgcgcgcgca gctggtgcgg cggcgcgggg gtcagccgcc gagccggcgg    420

cgacggagga gcagggcggc gtggacgcga acttccgatc ggttggtcag agtgcgcgag    480

ttgggcttag ccaattaggt ctcaacaatc tattgggccg taaaattcat gggccctggt    540

ttgtctaggc ccaatatccc gttcatttca gcccacaaat atttccccag aggattatta    600

aggcccacac gcagcttata gcagatcaag tacgatgttt cctgatcgtt ggatcggaaa    660

cgtacggtct tgatcaggca tgccgacttc gtcaaagaga ggcggcatga cctgacgcgg    720

agttggttcc gggcaccgtc tggatggtcg taccgggacc ggacacgtgt cgcgcctcca    780

actacatgga cacgtgtggt gctgccattg ggccgtacgc gtggcggtga ccgcaccgga    840

tgctgcctcg caccgccttg cccacgcttt atatagagag gttttctctc cattaatcgc    900

atagcgagtc gaatcgaccg aaggggaggg ggagcgaagc tttgcgttct ctaatcgcct    960

cgtcaaggta actaatcaat cacctcgtcc taatcctcga atctctcgtg gtgcccgtct   1020

aatctcgcga ttttgatgct cgtggtggaa agcgtaggag gatcccgtgc gagttagtct   1080

caatctctca gggtttcgtg cgattttagg gtgatccacc tcttaatcga gttacggttt   1140

cgtgcgattt tagggtaatc ctcttaatct ctcattgatt tagggtttcg tgagaatcga   1200

ggtagggatc tgtgttattt atatcgatct aatagatgga ttggttttga gattgttctg   1260

tcagatgggg attgtttcga tatattaccc taatgatgtg tcagatgggg attgtttcga   1320

tatattaccc taatgatgtg tcagatgggg attgtttcga tatattaccc taatgatgga   1380

taataagagt agttcacagt tatgttttga tcctgccaca tagtttgagt tttgtgatca   1440

gatttagttt tacttatttg tgcttagttc ggatgggatt gttctgatat tgttccaata   1500
```

```
gatgaatagc tcgttaggtt aaaatcttta ggttgagtta ggcgacacat agtttatttc   1560
ctctggattt ggattggaat tgtgttctta gttttttttcc cctggatttg gattggaatt   1620
gtgtggagct gggttagaga attacatctg tatcgtgtac acctacttga actgtagagc   1680
ttgggttcta aggtcaattt aatctgtatt gtatctggct ctttgcctag ttgaactgta   1740
gtgctgatgt tgtactgtgt ttttttaccc gttttatttg ctttactcgt gcaaatcaaa   1800
tctgtcagat gctagaacta ggtggcttta ttctgtgttc ttacatagat ctgttgtcct   1860
gtagttactt atgtcagttt tgttattatc tgaagatatt tttggttgtt gcttgttgat   1920
gtggtgtgag ctgtgagcag cgctcttatg attaatgatg ctgtccaatt gtagtgtagt   1980
atgatgtgat tgatatgttc atctattttg agctgacagt accgatatcg taggatctgg   2040
tgccaactta ttctccagct gctttttttt acctatgtta attccaatcc tttcttgcct   2100
cttccagatc cagataatgg cccacgcccg cgtcctcctc ctggcgctcg ccgtcctggc   2160
caccgccgcc gtcgccgtcg cctcctcctc ctccttcgcc gactccaacc cgatccgccc   2220
ggtgaccgac cgcgccgcct ccaccgctta cgactacaag caggtgttgc gggactcgct   2280
actattctat gaggcccaga gatccggccg gctcccagcc gaccagaagg tcacgtggag   2340
gaaggatagc gcgctgaatg accagggtga ccagggacaa gacttgaccg gcggctactt   2400
tgacgctggg gacttcgtca agttcgggtt ccccatggct tataccgcaa ccgtgctggc   2460
atggggcctc atagattttg aggccggcta cagcagtgcc ggggccttgg atgatggacg   2520
gaaggctgtc aaatgggcca ccgactattt cataaaggcc cacacaagtc aaaatgagtt   2580
ctatggtcag gtcggccagg gtgacgccga tcacgctttc tggggaagac cagaggatat   2640
gacgatggcg cgcccggcgt acaagataga cacctcaagg cctggctctg atctggcagg   2700
cgagacagcg gctgctcttg ccgctgcttc aatcgtgttc cggaacgtcg atggcactta   2760
ctcaaataac ctgttaacac acgctcgcca gctattcgac ttcgcgaaca actaccgggg   2820
aaagtatagt gactctatta ctgacgcaag aaatttctac gcaagcgcag actacagaga   2880
cgagttggtt tgggctgctg cgtggttata cagagcgacc aacgacaaca cctacctcaa   2940
cactgctgag tcactgtacg atgagtttgg gctacagaac tggggggggg gcctgaactg   3000
ggatagcaag gtgtctggcg tgcaggtgtt gttggccaag cttaccaata agcaggccta   3060
caaggacacg gtgcagtctt acgtcaatta cctaattaat aaccagcaga agactcccaa   3120
gggcctcctc tacatcgaca tgtggggcac ccttcgccac gctgccaacg ccgcattcat   3180
catgctcgaa gccgccgagc tgggcttgtc cgcctcctct tatagacagt tcgcgcaaac   3240
gcaaatcgac tacgccctgg gcgatggtgg ccgctccttt gtgtgcgggt tcgggagtaa   3300
tcctcctacg agaccgcacc acagatcctc gtcgtgcccg ccagctcccg ctacttgcga   3360
ctggaataca ttcaactcac ctgacccaaa ctaccacgtc ctctctgggg ccctagtggg   3420
cggacctgat cagaatgaca actacgtcga tgaccgttca gactatgttc acaacgaagt   3480
cgccactgat tacaacgcgg gtttccagtc cgcgttagct gctttggtgg cccttggtta   3540
cagcgagaag gacgagctgt gacctaggtc cccgaatttc cccgatcgtt caaacatttg   3600
gcaataaagt ttcttaagat tgaatcctgt tgccggtctt gcgatgatta tcatataatt   3660
tctgttgaat tacgttaagc atgtaataat taacatgtaa tgcatgacgt tatttatgag   3720
atgggttttt atgattagag tcccgcaatt atacatttaa tacgcgatag aaaacaaaat   3780
atagcgcgca aactaggata aattatcgcg cgcggtgtca tctatgttac tagatcggga   3840
attgggtacc gtcgactcta gtaacggccg ccagtgtgct ggaattaatt cggcttgtcg   3900
```

accacccaac cccatatcga cagaggatgt gaagaacagg taaatcacgc agaagaaccc 3960
atctctgata gcagctatcg attagaacaa cgaatccata ttgggtccgt gggaaatact 4020
tactgcacag gaagggggcg atctgacgag gccccgccac cggcctcgac ccgaggccga 4080
ggccgacgaa gcgccggcga gtacggcgcc gcggcggcct ctgcccgtgc cctctgcgcg 4140
tgggagggag aggccgcggt ggtgggggcg cgcgcgcgcg cgcgcgcagc tggtgcggcg 4200
gcgcgggggt cagccgccga gccggcggcg acggaggagc agggcggcgt ggacgcgaac 4260
ttccgatcgg ttggtcagag tgcgcgagtt gggcttagcc aattaggtct caacaatcta 4320
ttgggccgta aaattcatgg gccctggttt gtctaggccc aatatcccgt tcatttcagc 4380
ccacaaatat ttccccagag gattattaag gcccacacgc agcttatagc agatcaagta 4440
cgatgtttcc tgatcgttgg atcggaaacg tacggtcttg atcaggcatg ccgacttcgt 4500
caaagagagg cggcatgacc tgacgcggag ttggttccgg gcaccgtctg gatggtcgta 4560
ccgggaccgg acacgtgtcg cgcctccaac tacatggaca cgtgtggtgc tgccattggg 4620
ccgtacgcgt ggcggtgacc gcaccggatg ctgcctcgca ccgccttgcc cacgctttat 4680
atagagaggt tttctctcca ttaatcgcat agcgagtcga atcgaccgaa ggggaggggg 4740
agcgaagctt tgcgttctct aatcgcctcg tcaaggtaac taatcaatca cctcgtccta 4800
atcctcgaat ctctcgtggt gcccgtctaa tctcgcgatt ttgatgctcg tggtggaaag 4860
cgtaggagga tcccgtgcga gttagtctca atctctcagg gtttcgtgcg attttagggt 4920
gatccacctc ttaatcgagt tacggtttcg tgcgatttta gggtaatcct cttaatctct 4980
cattgattta gggtttcgtg agaatcgagg tagggatctg tgttatttat atcgatctaa 5040
tagatggatt ggttttgaga ttgttctgtc agatggggat tgtttcgata tattacccta 5100
atgatgtgtc agatggggat tgtttcgata tattacccta atgatgtgtc agatggggat 5160
tgtttcgata tattacccta atgatggata ataagagtag ttcacagtta tgttttgatc 5220
ctgccacata gtttgagttt tgtgatcaga tttagtttta cttatttgtg cttagttcgg 5280
atgggattgt tctgatattg ttccaataga tgaatagctc gttaggttaa aatctttagg 5340
ttgagttagg cgacacatag tttatttcct ctggatttgg attggaattg tgttcttagt 5400
ttttttcccc tggatttgga ttggaattgt gtggagctgg gttagagaat tacatctgta 5460
tcgtgtacac ctacttgaac tgtagagctt gggttctaag gtcaatttaa tctgtattgt 5520
atctggctct ttgcctagtt gaactgtagt gctgatgttg tactgtgttt ttttacccgt 5580
tttatttgct ttactcgtgc aaatcaaatc tgtcagatgc tagaactagg tggctttatt 5640
ctgtgttctt acatagatct gttgtcctgt agttacttat gtcagttttg ttattatctg 5700
aagatatttt tggttgttgc ttgttgatgt ggtgtgagct gtgagcagcg ctcttatgat 5760
taatgatgct gtccaattgt agtgtagtat gatgtgattg atatgttcat ctattttgag 5820
ctgacagtac cgatatcgta ggatctggtg ccaacttatt ctccagctgc ttttttttac 5880
ctatgttaat tccaatcctt tcttgcctct tccagatcca gataatggcg aacaaacatt 5940
tgtccctctc cctcttcctc gtcctccttg gcctgtcggc cagcttggcc tccgggcaag 6000
tcttcccagc tggaaacgca acggaattgg agaaaagaca aaccacccct aactctgagg 6060
gctggcatga cggatactac tactcttggt ggagcgatgg tggtgcacag gccacctata 6120
caaacctcga aggcggcact tatgagattt catggggtga cggtggcaac cttgtcggcg 6180
gaaaggggtg gaaccccgga cttaacgcca gggcaatcca cttcgaaggg gtgtaccagc 6240

```
ccaatggcaa ctcatacctg gccgtctacg ggtggacgcg caatccgctg gttgagtact   6300
atatcgtgga gaatttcgga acttatgacc ctagctccgg tgccacggac ctcgggacag   6360
tcgagtgtga cggaagcatc tacaggctgg gtaaaactac ccgcgttaat gctccatcga   6420
tcgacggcac gcaaacattt gatcaatact ggtccgtgcg gcaggataag aggacaagcg   6480
gcacagttca gacgggttgc cactttgatg cctgggcaag agcggggctc aatgtgaatg   6540
gggaccacta ctatcagatt gtggcgaccg agggctattt ctccagtggc tatgcgcgta   6600
taaccgtcgc tgatgttgga agcgagaagg acgagctgtg acctaggtcc ccgaatttcc   6660
ccgatcgttc aaacatttgg caataaagtt tcttaagatt gaatcctgtt gccggtcttg   6720
cgatgattat catataattt ctgttgaatt acgttaagca tgtaataatt aacatgtaat   6780
gcatgacgtt atttatgaga tgggttttta tgattagagt cccgcaatta tacatttaat   6840
acgcgataga aaacaaaata tagcgcgcaa actaggataa attatcgcgc gcggtgtcat   6900
ctatgttact agatcgggaa ttggaattca tactaaagct tgcatgcctg caggtcgact   6960
ctagtaacgg ccgccagtgt gctggaatta attcggcttg tcgaccaccc aaccccatat   7020
cgacagagga tgtgaagaac aggtaaatca cgcagaagaa cccatctctg atagcagcta   7080
tcgattagaa caacgaatcc atattgggtc cgtgggaaat acttactgca caggaagggg   7140
gcgatctgac gaggccccgc caccggcctc gacccgaggc cgaggccgac gaagcgccgg   7200
cgagtacggc gccgcggcgg cctctgcccg tgccctctgc gcgtgggagg gagaggccgc   7260
ggtggtgggg gcgcgcgcgc gcgcgcgcgc agctggtgcg gcggcgcggg ggtcagccgc   7320
cgagccggcg gcgacggagg agcagggcgg cgtggacgcg aacttccgat cggttggtca   7380
gagtgcgcga gttgggctta gccaattagg tctcaacaat ctattgggcc gtaaaattca   7440
tgggccctgg tttgtctagg cccaatatcc cgttcatttc agcccacaaa tatttcccca   7500
gaggattatt aaggcccaca cgcagcttat agcagatcaa gtacgatgtt tcctgatcgt   7560
tggatcggaa acgtacggtc ttgatcaggc atgccgactt cgtcaaagag aggcggcatg   7620
acctgacgcg gagttggttc cgggcaccgt ctggatggtc gtaccgggac cggacacgtg   7680
tcgcgcctcc aactacatgg acacgtgtgg tgctgccatt gggccgtacg cgtggcggtg   7740
accgcaccgg atgctgcctc gcaccgcctt gcccacgctt tatatagaga ggttttctct   7800
ccattaatcg catagcgagt cgaatcgacc gaaggggagg gggagcgaag ctttgcgttc   7860
tctaatcgcc tcgtcaaggt aactaatcaa tcacctcgtc ctaatcctcg aatctctcgt   7920
ggtgcccgtc taatctcgcg attttgatgc tcgtggtgga aagcgtagga ggatcccgtg   7980
cgagttagtc tcaatctctc agggtttcgt gcgattttag ggtgatccac ctcttaatcg   8040
agttacggtt tcgtgcgatt ttagggtaat cctcttaatc tctcattgat ttagggtttc   8100
gtgagaatcg aggtagggat ctgtgttatt tatatcgatc taatagatgg attggttttg   8160
agattgttct gtcagatggg gattgtttcg atatattacc ctaatgatgt gtcagatggg   8220
gattgtttcg atatattacc ctaatgatgt gtcagatggg gattgtttcg atatattacc   8280
ctaatgatgg ataataagag tagttcacag ttatgttttg atcctgccac atagtttgag   8340
ttttgtgatc agatttagtt ttacttattt gtgcttagtt cggatgggat tgttctgata   8400
ttgttccaat agatgaatag ctcgttaggt taaaatcttt aggttgagtt aggcgacaca   8460
tagtttattt cctctggatt tggattggaa ttgtgttctt agttttttc ccctggattt   8520
ggattggaat tgtgtggagc tgggttagag aattacatct gtatcgtgta cacctacttg   8580
aactgtagag cttgggttct aaggtcaatt taatctgtat tgtatctggc tctttgccta   8640
```

```
gttgaactgt agtgctgatg ttgtactgtg tttttttacc cgttttattt gctttactcg   8700
tgcaaatcaa atctgtcaga tgctagaact aggtggcttt attctgtgtt cttacataga   8760
tctgttgtcc tgtagttact tatgtcagtt ttgttattat ctgaagatat ttttggttgt   8820
tgcttgttga tgtggtgtga gctgtgagca gcgctcttat gattaatgat gctgtccaat   8880
tgtagtgtag tatgatgtga ttgatatgtt catctatttt gagctgacag taccgatatc   8940
gtaggatctg gtgccaactt attctccagc tgcttttttt tacctatgtt aattccaatc   9000
ctttcttgcc tcttccagat ccagataatg cagaaactca ttaactcagt gcaaaactat   9060
gcctggggca gcaaaacggc gttgactgaa ctttatggta tggaaaatcc gtccagccag   9120
ccgatggccg agctgtggat gggcgcacat ccgaaaagca gttcacgagt gcagaatgcc   9180
gccggagata tcgtttcact gcgtgatgtg attgagagtg ataaatcgac tctgctcgga   9240
gaggccgttg ccaaacgctt tggcgaactg cctttcctgt tcaaagtatt atgcgcagca   9300
cagccactct ccattcaggt tcatccaaac aaacacaatt ctgaaatcgg ttttgccaaa   9360
gaaaatgccg caggtatccc gatggatgcc gccgagcgta actataaaga tcctaaccac   9420
aagccggagc tggtttttgc gctgacgcct ttccttgcga tgaacgcgtt tcgtgaattt   9480
tccgagattg tctccctact ccagccggtc gcaggtgcac atccggcgat tgctcacttt   9540
ttacaacagc ctgatgccga acgtttaagc gaactgttcg ccagcctgtt gaatatgcag   9600
ggtgaagaaa aatcccgcgc gctggcgatt ttaaaatcgg ccctcgatag ccagcagggt   9660
gaaccgtggc aaacgattcg tttaatttct gaattttacc cggaagacag cggtctgttc   9720
tccccgctat tgctgaatgt ggtgaaattg aaccctggcg aagcgatgtt cctgttcgct   9780
gaaacaccgc acgcttacct gcaaggcgtg gcgctggaag tgatggcaaa ctccgataac   9840
gtgctgcgtg cgggtctgac gcctaaatac attgatattc cggaactggt tgccaatgtg   9900
aaattcgaag ccaaaccggc taaccagttg ttgacccagc cggtgaaaca aggtgcagaa   9960
ctggacttcc cgattccagt ggatgatttt gccttctcgc tgcatgacct tagtgataaa  10020
gaaaccacca ttagccagca gagtgccgcc attttgttct gcgtcgaagg cgatgcaacg  10080
ttgtggaaag gttctcagca gttacagctt aaaccgggtg aatcagcgtt tattgccgcc  10140
aacgaatcac cggtgactgt caaaggccac ggccgtttag cgcgtgttta caacaagctg  10200
taagagctta ctgaaaaaat taacatctct tgctaagctg ggagctctag atccccgaat  10260
ttccccgatc gttcaaacat ttggcaataa agtttcttaa gattgaatcc tgttgccggt  10320
cttgcgatga ttatcatata atttctgttg aattacgtta agcatgtaat aattaacatg  10380
taatgcatga cgttatttat gagatgggtt tttatgatta gagtcccgca attatacatt  10440
taatacgcga tagaaaacaa aatatagcgc gcaaactagg ataaattatc gcgcgcggtg  10500
tcatctatgt tactagatcg ggaattggcg agctcgaatt aattcagtac attaaaaacg  10560
tccgcaatgt gttattaagt tgtctaagcg tcaatttgtt tacaccacaa tatatcctgc  10620
caccagccag ccaacagctc cccgaccggc agctcggcac aaaatcacca ctcgatacag  10680
gcagcccatc agtccgggac ggcgtcagcg ggagagccgt tgtaaggcgg cagactttgc  10740
tcatgttacc gatgctattc ggaagaacgg caactaagct gccgggtttg aaacacggat  10800
gatctcgcgg agggtagcat gttgattgta acgatgacag agcgttgctg cctgtgatca  10860
aatatcatct ccctcgcaga gatccgaatt atcagccttc ttattcattt ctcgcttaac  10920
cgtgacaggc tgtcgatctt gagaactatg ccgacataat aggaaatcgc tggataaagc  10980
```

```
cgctgaggaa gctgagtggc gctatttctt tagaagtgaa cgttgacgat cgtcgaccgt  11040
accccgatga attaattcgg acgtacgttc tgaacacagc tggatactta cttgggcgat  11100
tgtcatacat gacatcaaca atgtacccgt ttgtgtaacc gtctcttgga ggttcgtatg  11160
acactagtgg ttcccctcag cttgcgacta gatgttgagg cctaacattt tattagagag  11220
caggctagtt gcttagatac atgatcttca ggccgttatc tgtcagggca agcgaaaatt  11280
ggccatttat gacgaccaat gccccgcaga agctcccatc tttgccgcca tagacgccgc  11340
gcccccccttt tggggtgtag aacatccttt tgccagatgt ggaaaagaag ttcgttgtcc  11400
cattgttggc aatgacgtag tagccggcga aagtgcgaga cccatttgcg ctatatataa  11460
gcctacgatt tccgttgcga ctattgtcgt aattggatga actattatcg tagttgctct  11520
cagagttgtc gtaatttgat ggactattgt cgtaattgct tatggagttg tcgtagttgc  11580
ttggagaaat gtcgtagttg gatggggagt agtcataggg aagacgagct tcatccacta  11640
aaacaattgg caggtcagca agtgcctgcc ccgatgccat cgcaagtacg aggcttagaa  11700
ccaccttcaa cagatcgcgc atagtcttcc ccagctctct aacgcttgag ttaagccgcg  11760
ccgcgaagcg gcgtcggctt gaacgaattg ttagacatta tttgccgact accttggtga  11820
tctcgccttt cacgtagtga acaaattctt ccaactgatc tgcgcgcgag gccaagcgat  11880
cttcttgtcc aagataagcc tgcctagctt caagtatgac gggctgatac tgggccggca  11940
ggcgctccat tgcccagtcg gcagcgacat ccttcggcgc gattttgccg gttactgcgc  12000
tgtaccaaat gcgggacaac gtaagcacta catttcgctc atcgccagcc cagtcgggcg  12060
gcgagttcca tagcgttaag gtttcattta gcgcctcaaa tagatcctgt tcaggaaccg  12120
gatcaaagag ttcctccgcc gctggaccta ccaaggcaac gctatgttct cttgcttttg  12180
tcagcaagat agccagatca atgtcgatcg tggctggctc gaagatacct gcaagaatgt  12240
cattgcgctg ccattctcca aattgcagtt cgcgcttagc tggataacgc cacggaatga  12300
tgtcgtcgtg cacaacaatg gtgacttcta cagcgcggag aatctcgctc tctccagggg  12360
aagccgaagt ttccaaaagg tcgttgatca aagctcgccg cgttgtttca tcaagcctta  12420
cggtcaccgt aaccagcaaa tcaatatcac tgtgtggctt caggccgcca tccactgcgg  12480
agccgtacaa atgtacggcc agcaacgtcg gttcgagatg gcgctcgatg acgccaacta  12540
cctctgatag ttgagtcgat acttcggcga tcaccgcttc cctcatgatg tttaactcct  12600
gaattaagcc gcgccgcgaa gcggtgtcgg cttgaatgaa ttgttaggcg tcatcctgtg  12660
ctcccgagaa ccagtaccag tacatcgctg tttcgttcga gacttgaggt ctagttttat  12720
acgtgaacag gtcaatgccg ccgagagtaa agccacattt tgcgtacaaa ttgcaggcag  12780
gtacattgtt cgtttgtgtc tctaatcgta tgccaaggag ctgtctgctt agtgcccact  12840
ttttcgcaaa ttcgatgaga ctgtgcgcga ctcctttgcc tcggtgcgtg tgcgacacaa  12900
caatgtgttc gatagaggct agatcgttcc atgttgagtt gagttcaatc ttcccgacaa  12960
gctcttggtc gatgaatgcg ccatagcaag cagagtcttc atcagagtca tcatccgaga  13020
tgtaatcctt ccggtagggg ctcacacttc tggtagatag ttcaaagcct tggtcggata  13080
ggtgcacatc gaacacttca cgaacaatga aatggttctc agcatccaat gtttccgcca  13140
cctgctcagg gatcaccgaa atcttcatat gacgcctaac gcctggcaca gcggatcgca  13200
aacctggcgc ggcttttggc acaaaaggcg tgacaggttt gcgaatccgt tgctgccact  13260
tgttaaccct tttgccagat ttggtaacta taatttatgt tagaggcgaa gtcttgggta  13320
aaaactggcc taaaattgct ggggatttca ggaaagtaaa catcaccttc cggctcgatg  13380
```

```
tctattgtag atatatgtag tgtatctact tgatcggggg atctgctgcc tcgcgcgttt  13440
cggtgatgac ggtgaaaacc tctgacacat gcagctcccg gagacggtca cagcttgtct  13500
gtaagcggat gccgggagca gacaagcccg tcagggcgcg tcagcgggtg ttggcgggtg  13560
tcggggcgca gccatgaccc agtcacgtag cgatagcgga gtgtatactg gcttaactat  13620
gcggcatcag agcagattgt actgagagtg caccatatgc ggtgtgaaat accgcacaga  13680
tgcgtaagga gaaaataccg catcaggcgc tcttccgctt cctcgctcac tgactcgctg  13740
cgctcggtcg ttcggctgcg gcgagcggta tcagctcact caaaggcggt aatacggtta  13800
tccacagaat caggggataa cgcaggaaag aacatgtgag caaaaggcca gcaaaaggcc  13860
aggaaccgta aaaaggccgc gttgctggcg tttttccata ggctccgccc ccctgacgag  13920
catcacaaaa atcgacgctc aagtcagagg tggcgaaacc cgacaggact ataaagatac  13980
caggcgtttc cccctggaag ctccctcgtg cgctctcctg ttccgaccct gccgcttacc  14040
ggatacctgt ccgcctttct cccttcggga agcgtggcgc tttctcatag ctcacgctgt  14100
aggtatctca gttcggtgta ggtcgttcgc tccaagctgg gctgtgtgca cgaacccccc  14160
gttcagcccg accgctgcgc cttatccggt aactatcgtc ttgagtccaa cccggtaaga  14220
cacgacttat cgccactggc agcagccact ggtaacagga ttagcagagc gaggtatgta  14280
ggcggtgcta cagagttctt gaagtggtgg cctaactacg gctacactag aaggacagta  14340
tttggtatct gcgctctgct gaagccagtt accttcggaa aaagagttgg tagctcttga  14400
tccggcaaac aaaccaccgc tggtagcggt ggtttttttg tttgcaagca gcagattacg  14460
cgcagaaaaa aaggatctca agaagatcct ttgatctttt ctacggggtc tgacgctcag  14520
tggaacgaaa actcacgtta agggattttg gtcatgagat tatcaaaaag gatcttcacc  14580
tagatccttt taaattaaaa atgaagtttt aaatcaatct aaagtatata tgagtaaact  14640
tggtctgaca gttaccaatg cttaatcagt gaggcaccta tctcagcgat ctgtctattt  14700
cgttcatcca tagttgcctg actccccgtc gtgtagataa ctacgatacg ggagggctta  14760
ccatctggcc ccagtgctgc aatgataccg cgagacccac gctcaccggc tccagattta  14820
tcagcaataa accagccagc cggaagggcc gagcgcagaa gtggtcctgc aactttatcc  14880
gcctccatcc agtctattaa ttgttgccgg gaagctagag taagtagttc gccagttaat  14940
agtttgcgca acgttgttgc cattgctgca gggggggggg gggggggggtt ccattgttca  15000
ttccacggac aaaaacagag aaaggaaacg acagaggcca aaaagctcgc tttcagcacc  15060
tgtcgtttcc tttcttttca gagggtattt taaataaaaa cattaagtta tgacgaagaa  15120
gaacggaaac gccttaaacc ggaaaatttt cataaatagc gaaaacccgc gaggtcgccg  15180
ccccgtaacc tgtcggatca ccggaaagga cccgtaaagt gataatgatt atcatctaca  15240
tatcacaacg tgcgtggagg ccatcaaacc acgtcaaata atcaattatg acgcaggtat  15300
cgtattaatt gatctgcatc aacttaacgt aaaaacaact tcagacaata caaatcagcg  15360
acactgaata cggggcaacc tcatgtcccc cccccccccc ccctgcaggc atcgtggtgt  15420
cacgctcgtc gtttggtatg gcttcattca gctccggttc ccaacgatca aggcgagtta  15480
catgatcccc catgttgtgc aaaaaagcgg ttagctcctt cggtcctccg atcgttgtca  15540
gaagtaagtt ggccgcagtg ttatcactca tggttatggc agcactgcat aattctctta  15600
ctgtcatgcc atccgtaaga tgcttttctg tgactggtga gtactcaacc aagtcattct  15660
gagaatagtg tatgcggcga ccgagttgct cttgcccggc gtcaacacgg gataataccg  15720
```

```
cgccacatag cagaacttta aaagtgctca tcattggaaa acgttcttcg gggcgaaaac  15780
tctcaaggat cttaccgctg ttgagatcca gttcgatgta acccactcgt gcacccaact  15840
gatcttcagc atcttttact ttcaccagcg tttctgggtg agcaaaaaca ggaaggcaaa  15900
atgccgcaaa aaagggaata agggcgacac ggaaatgttg aatactcata ctcttccttt  15960
ttcaatatta ttgaagcatt tatcagggtt attgtctcat gagcggatac atatttgaat  16020
gtatttagaa aaataaacaa ataggggttc cgcgcacatt tccccgaaaa gtgccacctg  16080
acgtctaaga aaccattatt atcatgacat taacctataa aaataggcgt atcacgaggc  16140
cctttcgtct tcaagaattg gtcgacgatc ttgctgcgtt cggatatttt cgtggagttc  16200
ccgccacaga cccggattga aggcgagatc cagcaactcg cgccagatca tcctgtgacg  16260
gaactttggc gcgtgatgac tggccaggac gtcggccgaa agagcgacaa gcagatcacg  16320
cttttcgaca gcgtcggatt tgcgatcgag gatttttcgg cgctgcgcta cgtccgcgac  16380
cgcgttgagg gatcaagcca cagcagccca ctcgaccttc tagccgaccc agacgagcca  16440
agggatcttt ttggaatgct gctccgtcgt caggctttcc gacgtttggg tggttgaaca  16500
gaagtcatta tcgcacggaa tgccaagcac tcccgagggg aaccctgtgg ttggcatgca  16560
catacaaatg gacgaacgga taaacctttt cacgcccttt taaatatccg attattctaa  16620
taaacgctct tttctcttag gtttacccgc caatatatcc tgtcaaacac tgatagttta  16680
aactgaaggc gggaaacgac aacctgatca tgagcggaga attaagggag tcacgttatg  16740
acccccgccg atgacgcggg acaagccgtt ttacgtttgg aactgacaga accgcaacgt  16800
tgaaggagcc actcagctta attaagtcta actcgagtta ctggtacgta ccaaatccat  16860
ggaatcaagg taccgtcgac tctagtaacg gccgccagtg tgctggaatt aattcggctt  16920
gtcgaccacc caaccccata tcgacagagg atgtgaagaa caggtaaatc acgcagaaga  16980
acccatctct gatagcagct atcgattaga acaacgaatc catattgggt ccgtgggaaa  17040
tacttactgc acaggaaggg ggcgatctga cgaggccccg ccaccggcct cgacccgagg  17100
ccgaggccga cgaagcgccg gcgagtacgg cgccgcggcg gcctctgccc gtgccctctg  17160
cgcgtgggag ggagaggccg cggtggtggg ggcgcgcgcg cgcgcgcgcg cagctggtgc  17220
ggcggcgcgg gggtcagccg ccgagccggc ggcgacggag gagcagggcg gcgtggacgc  17280
gaacttccga tcggttggtc agagtgcgcg agttgggctt agccaattag gtctcaacaa  17340
tctattgggc cgtaaaattc atgggccctg gtttgtctag gcccaatatc ccgttcattt  17400
cagcccacaa atatttcccc agaggattat taaggcccac acgcagctta tagcagatca  17460
agtacgatgt ttcctgatcg ttggatcgga aacgtacggt cttgatcagg catgccgact  17520
tcgtcaaaga gaggcggcat gacctgacgc ggagttggtt ccgggcaccg tctggatggt  17580
cgtaccggga ccggacacgt gtcgcgcctc caactacatg gacacgtgtg gtgctgccat  17640
tgggccgtac gcgtggcggt gaccgcaccg gatgctgcct cgcaccgcct tgcccacgct  17700
ttatatagag aggttttctc tccattaatc gcatagcgag tcgaatcgac cgaaggggag  17760
ggggagcgaa gctttgcgtt ctctaatcgc ctcgtcaagg taactaatca atcacctcgt  17820
cctaatcctc gaatctctcg tggtgcccgt ctaatctcgc gattttgatg ctcgtggtgg  17880
aaagcgtagg aggatcccgt gcgagttagt ctcaatctct cagggtttcg tgcgatttta  17940
gggtgatcca cctcttaatc gagttacggt ttcgtgcgat tttagggtaa tcctcttaat  18000
ctctcattga tttagggttt cgtgagaatc gaggtaggga tctgtgttat ttatatcgat  18060
ctaatagatg gattggtttt gagattgttc tgtcagatgg ggattgtttc gatatattac  18120
```

```
cctaatgatg tgtcagatgg ggattgtttc gatatattac cctaatgatg tgtcagatgg  18180
ggattgtttc gatatattac cctaatgatg gataataaga gtagttcaca gttatgtttt  18240
gatcctgcca catagtttga gttttgtgat cagatttagt tttacttatt tgtgcttagt  18300
tcggatggga ttgttctgat attgttccaa tagatgaata gctcgttagg ttaaaatctt  18360
taggttgagt taggcgacac atagtttatt tcctctggat ttggattgga attgtgttct  18420
tagttttttt cccctggatt tggattggaa ttgtgtggag ctgggttaga gaattacatc  18480
tgtatcgtgt acacctactt gaactgtaga gcttgggttc taaggtcaat ttaatctgta  18540
ttgtatctgg ctctttgcct agttgaactg tagtgctgat gttgtactgt gtttttttac  18600
ccgttttatt tgctttactc gtgcaaatca aatctgtcag atgctagaac taggtggctt  18660
tattctgtgt tcttacatag atctgttgtc ctgtagttac ttatgtcagt tttgttatta  18720
tctgaagata tttttggttg ttgcttgttg atgtggtgtg agctgtgagc agcgctctta  18780
tgattaatga tgctgtccaa ttgtagtgta gtatgatgtg attgatatgt tcatctattt  18840
tgagctgaca gtaccgatat cgtaggatct ggtgccaact tattctccag ctgctttttt  18900
ttacctatgt taattccaat cctttcttgc ctcttccaga tccagataat gctggaggac  18960
aagtctccca aactgcctga ttataagaac gaccttctgt acgaacgcac attcgacgag  19020
gggctctgct tcccgtggca cacgtgcgaa gattcaggag ggaaatgcga ttttgccgtg  19080
gtcgacgttc caggcgagcc tgggaacaag gcgttcaggc tcactgttat cgataagggt  19140
cagaacaagt ggtcggtcca aatgagacac cggggtatca cgttggagca ggggcacaca  19200
tacaccgttc ggtttactat ctggagcgac aagagctgcc gcgtgtatgc caaaatcggc  19260
caaatgggtg aaccctacac ggagtactgg aacaataact ggaatccgtt caacctcact  19320
ccggggcaga aattgacggt ggaacagaac tttactatga attatcccac ggacgacacg  19380
tgtgagttta ccttccactt gggaggggaa ctggcagccg ggacccctta ctacgtgtac  19440
ctcgacgacg tttctcttta cgatccccgc tttgtcaagc cagtggaata cgtcctgcct  19500
caaccggatg tcagggttaa tcaagttgga tacctccctt ttgctaagaa atatgctact  19560
gtcgtgtcat cgagcacgtc cccattgaag tggcaacttc tgaatagtgc aaaccaagtt  19620
gtcttggagg gcaatacaat ccccaaggga ctggacaaag attcacaaga ctacgttcat  19680
tggatcgatt tctcgaactt taagaccgaa ggcaaggggt actatttcaa gttgcccact  19740
gtgaactccg atactaacta ctcccacccg tttgatattt ctgcagatat ctattcaaag  19800
atgaagttcg acgcgctcgc tttcttttac cataaaaggt cgggaatacc aatcgagatg  19860
ccctacgccg gggagagca gtggacaagg cccgcagggc acattggtgt cgcgccgaac  19920
aagggcgaca cgaatgtgcc aacttggccc caggatgacg aatatgctgg acgcccccag  19980
aaatactata cgaaagacgt gaccggcggg tggtacgatg ccggtgacca cggcaagtac  20040
gtcgtgaacg gggtatcgc agtttggacc cttatgaata tgtacgagag agcaaagatt  20100
agaggaatcg ctaaccaggg tgcctacaaa gatggaggaa tgaatatccc ggaaaggaat  20160
aacggctatc ctgatattct ggacgaggcc agatgggaga tcgaattttt taagaagatg  20220
caagtcactg agaaagaaga tccgtcgatt gcaggtatgg tgcaccacaa gatccacgat  20280
ttcaggtgga cggcgctcgg aatgttgcct cacgaggacc cccagccacg ctaccttcgg  20340
cccgtcagca cagcggcaac cctgaatttc gcagcgaccc tcgctcagtc tgccagattg  20400
tggaaggatt acgacccgac ttttgcagcg gactgccttg agaaagctga aattgcctgg  20460
```

```
caagcagcac tcaaacaccc ggacatctac gctgagtaca cgccaggaag cggtgggccg  20520

ggtggaggtc cttataatga cgattatgtc ggggacgagt tctactgggc cgcttgtgaa  20580

ctctatgtga caaccggtaa ggatgagtac aagaattact tgatgaatag tccgcactat  20640

ctggaaatgc cagcgaagat gggcgagaac ggaggggcta acggcgagga caacggtctc  20700

tggggctgct ttacttgggg aacgacacag ggttgggta caattaccct tgccctcgtt  20760

gaaaacggcc tcccttcggc ggatattcaa aaggcccgca acaatatcgc taaagccgca  20820

gataagtggc ttgagaatat tgaagaacaa ggttaccgcc tgcctatcaa acaagcggag  20880

gatgaacggg gcggataccc gtggggtagt aattctttca ttctcaacca gatgatcgtc  20940

atgggctacg cttacgactt cacgggaaac agcaagtatc ttgacgggat gcaggacggc  21000

atgtcctacc tgctcggtag aaacggactt gatcaatcgt acgttactgg gtacggggag  21060

aggccacttc agaaccccca cgaccgcttt tggacccctc aaacttcgaa gaaattcccg  21120

gccccacccc ctggtattat cgcaggcggg ccgaatagcc ggtttgaaga tccaacgatc  21180

actgcagcgg ttaagaagga tacacccccg cagaagtgct atattgacca caccgattcc  21240

tggtctacta acgagatcac gattaattgg aacgcccccct tcgcgtgggt cacagcgtat  21300

ctggacgaaa ttgacttgat taccccaccc ggcggagtgg accctgaaga gccggaagtt  21360

atctacggtg attgtaacgg cgacggaaag gttaattcga ccgatgctgt ggcccttaaa  21420

aggtatatcc tccgcagcgg tatctcgatc aacacggaca acgcggacgt taatgcagat  21480

ggtcgcgtga atagcactga cctcgctatt ttgaagcgct atattttgaa ggagatcgat  21540

gttcttcctc acaagtgacc taggtccccg aatttccccg atcgttcaaa catttggcaa  21600

taaagtttct taagattgaa tcctgttgcc ggtcttgcga tgattatcat ataatttctg  21660

ttgaattacg ttaagcatgt aataattaac atgtaatgca tgacgttatt tatgagatgg  21720

gtttttatga ttagagtccc gcaattatac atttaatacg cgatagaaaa caaaatatag  21780

cgcgcaaact aggataaatt atcgcgcgcg gtgtcatcta tgttactaga tcgggaattg  21840

c                                                                 21841
```

<210> SEQ ID NO 83
<211> LENGTH: 20699
<212> TYPE: DNA
<213> ORGANISM: Artificial Sequence
<220> FEATURE:
<223> OTHER INFORMATION: Synthetic construct, vector pAG2349

<400> SEQUENCE: 83

```
aattcatact aaagcttgca tgcctgcagg tcgactctag taacggccgc cagtgtgctg     60

gaattaattc ggcttgtcga ccacccaacc ccatatcgac agaggatgtg aagaacaggt    120

aaatcacgca gaagaaccca tctctgatag cagctatcga ttagaacaac gaatccatat    180

tgggtccgtg ggaaatactt actgcacagg aagggggcga tctgacgagg ccccgccacc    240

ggcctcgacc cgaggccgag gccgacgaag cgccggcgag tacggcgccg cggcggcctc    300

tgcccgtgcc ctctgcgcgt gggagggaga ggccgcggtg gtgggggcgc gcgcgcgcgc    360

gcgcgcagct ggtgcggcgg cgcgggggtc agccgccgag ccggcggcga cggaggagca    420

gggcggcgtg gacgcgaact tccgatcggt tggtcagagt gcgcgagttg ggcttagcca    480

attaggtctc aacaatctat tgggccgtaa aattcatggg ccctggtttg tctaggccca    540

atatcccgtt catttcagcc cacaaatatt tccccagagg attattaagg cccacacgca    600

gcttatagca gatcaagtac gatgtttcct gatcgttgga tcggaaacgt acggtcttga    660
```

```
tcaggcatgc cgacttcgtc aaagagaggc ggcatgacct gacgcggagt tggttccggg    720
caccgtctgg atggtcgtac cgggaccgga cacgtgtcgc gcctccaact acatggacac    780
gtgtggtgct gccattgggc cgtacgcgtg gcggtgaccg caccggatgc tgcctcgcac    840
cgccttgccc acgctttata tagagaggtt ttctctccat taatcgcata gcgagtcgaa    900
tcgaccgaag ggagggggga gcgaagcttt gcgttctcta atcgcctcgt caaggtaact    960
aatcaatcac ctcgtcctaa tcctcgaatc tctcgtggtg cccgtctaat ctcgcgattt   1020
tgatgctcgt ggtggaaagc gtaggaggat cccgtgcgag ttagtctcaa tctctcaggg   1080
tttcgtgcga ttttagggtg atccacctct taatcgagtt acggtttcgt gcgattttag   1140
ggtaatcctc ttaatctctc attgatttag ggtttcgtga gaatcgaggt agggatctgt   1200
gttatttata tcgatctaat agatggattg gttttgagat tgttctgtca gatggggatt   1260
gtttcgatat attaccctaa tgatgtgtca gatggggatt gtttcgatat attaccctaa   1320
tgatgtgtca gatggggatt gtttcgatat attaccctaa tgatggataa taagagtagt   1380
tcacagttat gttttgatcc tgccacatag tttgagtttt gtgatcagat ttagttttac   1440
ttatttgtgc ttagttcgga tgggattgtt ctgatattgt tccaatagat gaatagctcg   1500
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct tttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt ttttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
```

```
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc ccttttgggg gtgtagaaca   4440
tccttttgcc agatgtggaa aagaagttcg ttgtcccatt gttggcaatg acgtagtagc   4500
cggcgaaagt gcgagaccca tttgcgctat atataagcct acgatttccg ttgcgactat   4560
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
cgacatcctt cggcgcgatt ttgccggtta ctgcgctgta ccaaatgcgg gacaacgtaa   5100
gcactacatt tcgctcatcg ccagcccagt cgggcggcga gttccatagc gttaaggttt   5160
catttagcgc ctcaaataga tcctgttcag gaaccggatc aaagagttcc tccgccgctg   5220
gacctaccaa ggcaacgcta tgttctcttg cttttgtcag caagatagcc agatcaatgt   5280
cgatcgtggc tggctcgaag atacctgcaa gaatgtcatt gcgctgccat tctccaaatt   5340
gcagttcgcg cttagctgga taacgccacg gaatgatgtc gtcgtgcaca acaatggtga   5400
```

```
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aaccctttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
```

```
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg ccctttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtactgc agtgcagcgt gacccggtcg tgcccctctc   9960
tagagataat gagcattgca tgtctaagtt ataaaaaatt accacatatt ttttttgtca  10020
cacttgtttg aagtgcagtt tatctatctt tatacatata tttaaacttt actctacgaa  10080
taatataatc tatagtacta caataatatc agtgttttag agaatcatat aaatgaacag  10140
```

```
ttagacatgg tctaaaggac aattgagtat tttgacaaca ggactctaca gttttatctt  10200
tttagtgtgc atgtgttctc cttttttttt gcaaatagct tcacctatat aatacttcat  10260
ccattttatt agtacatcca tttagggttt agggttaatg gtttttatag actaattttt  10320
ttagtacatc tattttattc tattttagcc tctaaattaa gaaaactaaa actctatttt  10380
agttttttta tttaataatt tagatataaa atagaataaa ataaagtgac taaaaattaa  10440
acaaataccc tttaagaaat taaaaaaact aaggaaacat ttttcttgtt tcgagtagat  10500
aatgccagcc tgttaaacgc cgtcgacgag tctaacggac accaaccagc gaaccagcag  10560
cgtcgcgtcg ggccaagcga agcagacggc acggcatctc tgtcgctgcc tctggacccc  10620
tctcgagagt tccgctccac cgttggactt gctccgctgt cggcatccag aaattgcgtg  10680
gcggagcggc agacgtgagc cggcacggca ggcggcctcc tcctcctctc acggcacggc  10740
agctacgggg gattcctttc ccaccgctcc ttcgctttcc cttcctcgcc cgccgtaata  10800
aatagacacc ccctccacac cctctttccc caacctcgtg ttgttcggag cgcacacaca  10860
cacaaccaga tctcccccaa atccacccgt cggcacctcc gcttcaaggt acgccgctcg  10920
tcctcccccc ccccccctct ctaccttctc tagatcggcg ttccggtcca tggttagggc  10980
ccggtagttc tacttctgtt catgtttgtg ttagatccgt gtttgtgtta gatccgtgct  11040
gctagcgttc gtacacggat gcgacctgta cgtcagacac gttctgattg ctaacttgcc  11100
agtgtttctc tttggggaat cctgggatgg ctctagccgt tccgcagacg ggatcgattt  11160
catgattttt tttgtttcgt tgcatagggt ttggtttgcc cttttccttt atttcaatat  11220
atgccgtgca cttgtttgtc gggtcatctt ttcatgcttt tttttgtctt ggttgtgatg  11280
atgtggtctg gttgggcggt cgttctagat cggagtagaa ttctgtttca aactacctgg  11340
tggatttatt aattttggat ctgtatgtgt gtgccataca tattcatagt tacgaattga  11400
agatgatgga tggaaatatc gatctaggat aggtatacat gttgatgcgg gttttactga  11460
tgcatataca gagatgcttt ttgttcgctt ggttgtgatg atgtggtgtg gttgggcggt  11520
cgttcattcg ttctagatcg gagtagaata ctgtttcaaa ctacctggtg tatttattaa  11580
ttttggaact gtatgtgtgt gtcatacatc ttcatagtta cgagtttaag atggatggaa  11640
atatcgatct aggataggta tacatgttga tgtgggtttt actgatgcat atacatgatg  11700
gcatatgcag catctattca tatgctctaa ccttgagtac ctatctatta taataaacaa  11760
gtatgtttta taattatttt gatcttgata tacttggatg atggcatatg cagcagctat  11820
atgtggattt ttttagccct gccttcatac gctatttatt tgcttggtac tgtttctttt  11880
gtcgatgctc accctgttgt ttggtgttac ttctgcagat ccagatcgga tcctaaacca  11940
tgcgcgtgct gctcgtggcc ctggccctgc tggctcttgc tgccagcgcc acctctcagc  12000
agatcggcac ctacaccgcc gagacccacc caagcctgag ctggtccacc tgcaagagcg  12060
gcggttcctg cacgaccaac agcggcgcca tcacccttga tgcgaactgg cgctgggtgc  12120
acggcgtgaa caccagcacc aactgctaca cgggtaacac gtggaacacc gccatctgcg  12180
acacggacgc ttcctgcgcc caggactgcg cgcttgatgg cgccgactac tccggcacct  12240
acggcatcac cacctccggc aacagcctgc gcctgaactt cgtgaccggc agcaatgtgg  12300
gcagccgcac ctacctgatg gccgacaaca cccactacca gatcttcgac ctgctgaacc  12360
aggagttcac cttcaccgtc gacgtgtccc acctgccctg cggcctgaac ggcgccctct  12420
acttcgtgac gatggacgcc gacggcggcg tgtccaagta cccgaacaac aaggctggcg  12480
```

```
cccagtacgg tgtgggctac tgcgacagcc agtgcccgag ggacctgaag ttcatcgccg  12540
gccaggccaa cgtggagggc tggaccccga gcagcaacaa cgccaacacc ggcctgggca  12600
accacggcgc ctgctgcgcc gagctggaca tctgggaggc caacagcatc agcgaggccc  12660
tgaccccaca cccatgcgac accccaggcc tgtctgtgtg caccaccgac gcctgcggcg  12720
gcacctactc cagcgaccgc tacgccggca cctgcgaccc agacggctgc gacttcaacc  12780
cgtaccgcct gggcgtgacc gacttctacg gcagcggcaa gaccgtggac accaccaagc  12840
cgatcaccgt ggtgacccag ttcgtgaccg acgacggcac cagcaccggc accctgagcg  12900
agatccgccg ctactacgtc cagaacggcg tggtgatccc gcagccgagc agcaagatca  12960
gcggcgtgtc cggcaacgtg atcaacagcg acttctgcga cgccgagatc agcaccttcg  13020
gcgagaccgc cagcttcagc aagcacggcg gcctggccaa gatgggcgct ggcatggaag  13080
ccggcatggt gctggtgatg agcctgtggg acgactactc cgtgaacatg ctgtggctgg  13140
acagcaccta cccgaccaac gccaccggga cgccaggcgc tgccaggggc agctgcccaa  13200
ccacctcggg cgaccccaag accgtcgaga gccagagcgg cagcagctac gtgaccttca  13260
gcgacatccg cgtgggcccg ttcaactcca cgttcagcgg tggctctagc acgggcggct  13320
cctccaccac caccgccagc ggcaccacca ccaccaaggc ctccagcacg tctactagct  13380
ccacctctac cggcaccggc gttgctgccc attggggcca gtgcggtggc cagggctgga  13440
cgggtccaac gacttgcgcc tccggcacca cctgcaccgt ggtcaatccg tactactccc  13500
agtgcctgga cgagctgaag gccgaggcca agtgatcccc gaatttcccc gatcgttcaa  13560
acatttggca ataaagtttc ttaagattga atcctgttgc cggtcttgcg atgattatca  13620
tataatttct gttgaattac gttaagcatg taataattaa catgtaatgc atgacgttat  13680
ttatgagatg ggtttttatg attagagtcc cgcaattata catttaatac gcgatagaaa  13740
acaaaatata gcgcgcaaac taggataaat tatcgcgcgc ggtgtcatct atgttactag  13800
atcgggaatt gggtaccgtc gactctagta acggccgcca gtgtgctgga attaattcgg  13860
cttgtcgacc acccaacccc atatcgacag aggatgtgaa gaacaggtaa atcacgcaga  13920
agaacccatc tctgatagca gctatcgatt agaacaacga atccatattg ggtccgtggg  13980
aaatacttac tgcacaggaa gggggcgatc tgacgaggcc ccgccaccgg cctcgacccg  14040
aggccgaggc cgacgaagcg ccggcgagta cggcgccgcg gcggcctctg cccgtgccct  14100
ctgcgcgtgg gagggagagg ccgcggtggt gggggcgcgc gcgcgcgcgc gcgcagctgg  14160
tgcggcggcg cgggggtcag ccgccgagcc ggcggcgacg gaggagcagg gcggcgtgga  14220
cgcgaacttc cgatcggttg gtcagagtgc gcgagttggg cttagccaat taggtctcaa  14280
caatctattg ggccgtaaaa ttcatgggcc ctggtttgtc taggcccaat atcccgttca  14340
tttcagccca caaatatttc cccagaggat tattaaggcc cacacgcagc ttatagcaga  14400
tcaagtacga tgtttcctga tcgttggatc ggaaacgtac ggtcttgatc aggcatgccg  14460
acttcgtcaa agagaggcgg catgacctga cgcggagttg gttccgggca ccgtctggat  14520
ggtcgtaccg ggaccggaca cgtgtcgcgc ctccaactac atggacacgt gtggtgctgc  14580
cattgggccg tacgcgtggc ggtgaccgca ccggatgctg cctcgcaccg ccttgcccac  14640
gctttatata gagaggtttt ctctccatta atcgcatagc gagtcgaatc gaccgaaggg  14700
gagggggagc gaagctttgc gttctctaat cgcctcgtca aggtaactaa tcaatcacct  14760
cgtcctaatc ctcgaatctc tcgtggtgcc cgtctaatct cgcgattttg atgctcgtgg  14820
tggaaagcgt aggaggatcc cgtgcgagtt agtctcaatc tctcagggtt tcgtgcgatt  14880
```

```
ttagggtgat ccacctctta atcgagttac ggtttcgtgc gattttaggg taatcctctt  14940
aatctctcat tgatttaggg tttcgtgaga atcgaggtag ggatctgtgt tatttatatc  15000
gatctaatag atggattggt tttgagattg ttctgtcaga tggggattgt ttcgatatat  15060
taccctaatg atgtgtcaga tggggattgt ttcgatatat taccctaatg atgtgtcaga  15120
tggggattgt ttcgatatat taccctaatg atggataata agagtagttc acagttatgt  15180
tttgatcctg ccacatagtt tgagttttgt gatcagattt agttttactt atttgtgctt  15240
agttcggatg ggattgttct gatattgttc caatagatga atagctcgtt aggttaaaat  15300
ctttaggttg agttaggcga cacatagttt atttcctctg gatttggatt ggaattgtgt  15360
tcttagtttt tttcccctgg atttggattg gaattgtgtg gagctgggtt agagaattac  15420
atctgtatcg tgtacaccta cttgaactgt agagcttggg ttctaaggtc aatttaatct  15480
gtattgtatc tggctctttg cctagttgaa ctgtagtgct gatgttgtac tgtgtttttt  15540
tacccgtttt atttgcttta ctcgtgcaaa tcaaatctgt cagatgctag aactaggtgg  15600
ctttattctg tgttcttaca tagatctgtt gtcctgtagt tacttatgtc agttttgtta  15660
ttatctgaag atatttttgg ttgttgcttg ttgatgtggt gtgagctgtg agcagcgctc  15720
ttatgattaa tgatgctgtc caattgtagt gtagtatgat gtgattgata tgttcatcta  15780
ttttgagctg acagtaccga tatcgtagga tctggtgcca acttattctc cagctgcttt  15840
tttttaccta tgttaattcc aatcctttct tgcctcttcc agatccagat aatggcccac  15900
gcccgcgtcc tcctcctggc gctcgccgtc ctggccaccg ccgccgtcgc cgtcgcctcc  15960
tcctcctcct tcgccgactc caacccgatc cgcccggtga ccgaccgcgc cgcctccacc  16020
gcttacgact acaagcaggt gttgcgggac tcgctactat tctatgaggc ccagagatcc  16080
ggccggctcc cagccgacca gaaggtcacg tggaggaagg atagcgcgct gaatgaccag  16140
ggtgaccagg gacaagactt gaccggcggc tactttgacg ctggggactt cgtcaagttc  16200
gggttcccca tggcttatac cgcaaccgtg ctggcatggg gcctcataga ttttgaggcc  16260
ggctacagca gtgccggggc cttggatgat ggacggaagg ctgtcaaatg ggccaccgac  16320
tatttcataa aggcccacac aagtcaaaat gagttctatg gtcaggtcgg ccagggtgac  16380
gccgatcacg ctttctgggg aagaccagag gatatgacga tggcgcgccc ggcgtacaag  16440
atagacacct caaggcctgg ctctgatctg gcaggcgaga cagcggctgc tcttgccgct  16500
gcttcaatcg tgttccggaa cgtcgatggc acttactcaa ataacctgtt aacacacgct  16560
cgccagctat tcgacttcgc gaacaactac cggggaaagt atagtgactc tattactgac  16620
gcaagaaatt tctacgcaag cgcagactac agagacgagt tggtttgggc tgctgcgtgg  16680
ttatacagag cgaccaacga caacacctac ctcaacactg ctgagtcact gtacgatgag  16740
tttgggctac agaactgggg ggggggcctg aactgggata gcaaggtgtc tggcgtgcag  16800
gtgttgttgg ccaagcttac caataagcag gcctacaagg acacggtgca gtcttacgtc  16860
aattacctaa ttaataacca gcagaagact cccaagggcc tcctctacat cgacatgtgg  16920
ggcacccttc gccacgctgc caacgccgca ttcatcatgc tcgaagccgc cgagctgggc  16980
ttgtccgcct cctcttatag acagttcgcg caaacgcaaa tcgactacgc cctgggcgat  17040
ggtggccgct cctttgtgtg cgggttcggg agtaatcctc ctacgagacc gcaccacaga  17100
tcctcgtcgt gcccgccagc tcccgctact tgcgactgga atacattcaa ctcacctgac  17160
ccaaactacc acgtcctctc tggggcccta gtgggcggac ctgatcagaa tgacaactac  17220
```

```
gtcgatgacc gttcagacta tgttcacaac gaagtcgcca ctgattacaa cgcgggtttc  17280
cagtccgcgt tagctgcttt ggtggccctt ggttacagcg agaaggacga gctgtgacct  17340
aggtccccga atttccccga tcgttcaaac atttggcaat aaagtttctt aagattgaat  17400
cctgttgccg gtcttgcgat gattatcata taatttctgt tgaattacgt taagcatgta  17460
ataattaaca tgtaatgcat gacgttattt atgagatggg tttttatgat tagagtcccg  17520
caattataca tttaatacgc gatagaaaac aaaatatagc gcgcaaacta ggataaatta  17580
tcgcgcgcgg tgtcatctat gttactagat cgggaattgg gtaccgtcga ctctagtaac  17640
ggccgccagt gtgctggaat taattcggct tgtcgaccac ccaaccccat atcgacagag  17700
gatgtgaaga acaggtaaat cacgcagaag aacccatctc tgatagcagc tatcgattag  17760
aacaacgaat ccatattggg tccgtgggaa atacttactg cacaggaagg gggcgatctg  17820
acgaggcccc gccaccggcc tcgacccgag gccgaggccg acgaagcgcc ggcgagtacg  17880
gcgccgcggc ggcctctgcc cgtgccctct gcgcgtggga gggagaggcc gcggtggtgg  17940
gggcgcgcgc gcgcgcgcgc gcagctggtg cggcggcgcg ggggtcagcc gccgagccgg  18000
cggcgacgga ggagcagggc ggcgtggacg cgaacttccg atcggttggt cagagtgcgc  18060
gagttgggct tagccaatta ggtctcaaca atctattggg ccgtaaaatt catgggccct  18120
ggtttgtcta ggcccaatat cccgttcatt tcagcccaca aatatttccc cagaggatta  18180
ttaaggccca cacgcagctt atagcagatc aagtacgatg tttcctgatc gttggatcgg  18240
aaacgtacgg tcttgatcag gcatgccgac ttcgtcaaag agaggcggca tgacctgacg  18300
cggagttggt tccgggcacc gtctggatgg tcgtaccggg accggacacg tgtcgcgcct  18360
ccaactacat ggacacgtgt ggtgctgcca ttgggccgta cgcgtggcgg tgaccgcacc  18420
ggatgctgcc tcgcaccgcc ttgcccacgc tttatataga gaggttttct ctccattaat  18480
cgcatagcga gtcgaatcga ccgaagggga gggggagcga agctttgcgt tctctaatcg  18540
cctcgtcaag gtaactaatc aatcacctcg tcctaatcct cgaatctctc gtggtgcccg  18600
tctaatctcg cgattttgat gctcgtggtg gaaagcgtag gaggatcccg tgcgagttag  18660
tctcaatctc tcagggtttc gtgcgatttt agggtgatcc acctcttaat cgagttacgg  18720
tttcgtgcga ttttagggta atcctcttaa tctctcattg atttagggtt tcgtgagaat  18780
cgaggtaggg atctgtgtta tttatatcga tctaatagat ggattggttt tgagattgtt  18840
ctgtcagatg gggattgttt cgatatatta ccctaatgat gtgtcagatg gggattgttt  18900
cgatatatta ccctaatgat gtgtcagatg gggattgttt cgatatatta ccctaatgat  18960
ggataataag agtagttcac agttatgttt tgatcctgcc acatagtttg agttttgtga  19020
tcagatttag ttttacttat ttgtgcttag ttcggatggg attgttctga tattgttcca  19080
atagatgaat agctcgttag gttaaaatct ttaggttgag ttaggcgaca catagtttat  19140
ttcctctgga tttggattgg aattgtgttc ttagtttttt tcccctggat ttggattgga  19200
attgtgtgga gctgggttag agaattacat ctgtatcgtg tacacctact tgaactgtag  19260
agcttgggtt ctaaggtcaa tttaatctgt attgtatctg gctctttgcc tagttgaact  19320
gtagtgctga tgttgtactg tgttttttta cccgttttat ttgctttact cgtgcaaatc  19380
aaatctgtca gatgctagaa ctaggtggct ttattctgtg ttcttacata gatctgttgt  19440
cctgtagtta cttatgtcag ttttgttatt atctgaagat atttttggtt gttgcttgtt  19500
gatgtggtgt gagctgtgag cagcgctctt atgattaatg atgctgtcca attgtagtgt  19560
agtatgatgt gattgatatg ttcatctatt ttgagctgac agtaccgata tcgtaggatc  19620
```

```
tggtgccaac ttattctcca gctgcttttt tttacctatg ttaattccaa tcctttcttg  19680

cctcttccag atccagataa tggcgaacaa acatttgtcc ctctccctct tcctcgtcct  19740

ccttggcctg tcggccagct tggcctccgg gcaagtcttc ccagctggaa acgcaacgga  19800

attggagaaa agacaaacca cccctaactc tgagggctgg catgacggat actactactc  19860

ttggtggagc gatggtggtg cacaggccac ctatacaaac ctcgaaggcg gcacttatga  19920

gatttcatgg ggtgacggtg gcaaccttgt cggcggaaag gggtggaacc ccggacttaa  19980

cgccagggca atccacttcg aaggggtgta ccagcccaat ggcaactcat acctggccgt  20040

ctacgggtgg acgcgcaatc cgctggttga gtactatatc gtggagaatt tcggaactta  20100

tgaccctagc tccggtgcca cggacctcgg gacagtcgag tgtgacggaa gcatctacag  20160

gctgggtaaa actacccgcg ttaatgctcc atcgatcgac ggcacgcaaa catttgatca  20220

atactggtcc gtgcggcagg ataagaggac aagcggcaca gttcagacgg gttgccactt  20280

tgatgcctgg gcaagagcgg ggctcaatgt gaatggggac cactactatc agattgtggc  20340

gaccgagggc tatttctcca gtggctatgc gcgtataacc gtcgctgatg ttggaagcga  20400

gaaggacgag ctgtgaccta ggtccccgaa tttccccgat cgttcaaaca tttggcaata  20460

aagtttctta agattgaatc ctgttgccgg tcttgcgatg attatcatat aatttctgtt  20520

gaattacgtt aagcatgtaa taattaacat gtaatgcatg acgttattta tgagatgggt  20580

ttttatgatt agagtcccgc aattatacat ttaatacgcg atagaaaaca aaatatagcg  20640

cgcaaactag gataaattat cgcgcgcggt gtcatctatg ttactagatc gggaattgg   20699
```

<210> SEQ ID NO 84
<211> LENGTH: 14002
<212> TYPE: DNA
<213> ORGANISM: Artificial Sequence
<220> FEATURE:
<223> OTHER INFORMATION: Synthetic construct, vector pAG2042

<400> SEQUENCE: 84

```
aattcatact aaagcttgca tgcctgcagg tcgactctag taacggccgc cagtgtgctg     60

gaattaattc ggcttgtcga ccacccaacc ccatatcgac agaggatgtg aagaacaggt    120

aaatcacgca gaagaaccca tctctgatag cagctatcga ttagaacaac gaatccatat    180

tgggtccgtg ggaaatactt actgcacagg aagggggcga tctgacgagg ccccgccacc    240

ggcctcgacc cgaggccgag gccgacgaag cgccggcgag tacggcgccg cggcggcctc    300

tgcccgtgcc ctctgcgcgt gggagggaga ggccgcggtg gtgggggcgc gcgcgcgcgc    360

gcgcgcagct ggtgcggcgg cgcgggggtc agccgccgag ccggcggcga cggaggagca    420

gggcggcgtg gacgcgaact tccgatcggt tggtcagagt gcgcgagttg ggcttagcca    480

attaggtctc aacaatctat tgggccgtaa aattcatggg ccctggtttg tctaggccca    540

atatcccgtt catttcagcc cacaaatatt tccccagagg attattaagg cccacacgca    600

gcttatagca gatcaagtac gatgtttcct gatcgttgga tcggaaacgt acggtcttga    660

tcaggcatgc cgacttcgtc aaagagaggc ggcatgacct gacgcggagt tggttccggg    720

caccgtctgg atggtcgtac cgggaccgga cacgtgtcgc gcctccaact acatggacac    780

gtgtggtgct gccattgggc cgtacgcgtg gcggtgaccg caccggatgc tgcctcgcac    840

cgccttgccc acgctttata tagagaggtt ttctctccat taatcgcata gcgagtcgaa    900

tcgaccgaag gggaggggga gcgaagcttt gcgttctcta atcgcctcgt caaggtaact    960
```

-continued

```
aatcaatcac ctcgtcctaa tcctcgaatc tctcgtggtg cccgtctaat ctcgcgattt   1020
tgatgctcgt ggtggaaagc gtaggaggat cccgtgcgag ttagtctcaa tctctcaggg   1080
tttcgtgcga ttttagggtg atccacctct taatcgagtt acggtttcgt gcgattttag   1140
ggtaatcctc ttaatctctc attgatttag ggtttcgtga gaatcgaggt agggatctgt   1200
gttatttata tcgatctaat agatggattg gttttgagat tgttctgtca gatggggatt   1260
gtttcgatat attaccctaa tgatgtgtca gatggggatt gtttcgatat attaccctaa   1320
tgatgtgtca gatggggatt gtttcgatat attaccctaa tgatggataa taagagtagt   1380
tcacagttat gttttgatcc tgccacatag tttgagtttt gtgatcagat ttagttttac   1440
ttatttgtgc ttagttcgga tgggattgtt ctgatattgt tccaatagat gaatagctcg   1500
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct ttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt ttttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
```

```
caataaagtt tcttaagatt gaatcctgtt gccggtcttg cgatgattat catataattt   3420

ctgttgaatt acgttaagca tgtaataatt aacatgtaat gcatgacgtt atttatgaga   3480

tgggttttta tgattagagt cccgcaatta tacatttaat acgcgataga aaacaaaata   3540

tagcgcgcaa actaggataa attatcgcgc gcggtgtcat ctatgttact agatcgggaa   3600

ttggcgagct cgaattaatt cagtacatta aaaacgtccg caatgtgtta ttaagttgtc   3660

taagcgtcaa tttgtttaca ccacaatata tcctgccacc agccagccaa cagctccccg   3720

accggcagct cggcacaaaa tcaccactcg atacaggcag cccatcagtc cgggacggcg   3780

tcagcgggag agccgttgta aggcggcaga ctttgctcat gttaccgatg ctattcggaa   3840

gaacggcaac taagctgccg ggtttgaaac acggatgatc tcgcggaggg tagcatgttg   3900

attgtaacga tgacagagcg ttgctgcctg tgatcaaata tcatctccct cgcagagatc   3960

cgaattatca gccttcttat tcatttctcg cttaaccgtg acaggctgtc gatcttgaga   4020

actatgccga cataatagga aatcgctgga taaagccgct gaggaagctg agtggcgcta   4080

tttctttaga agtgaacgtt gacgatcgtc gaccgtaccc cgatgaatta attcggacgt   4140

acgttctgaa cacagctgga tacttacttg ggcgattgtc atacatgaca tcaacaatgt   4200

acccgtttgt gtaaccgtct cttggaggtt cgtatgacac tagtggttcc cctcagcttg   4260

cgactagatg ttgaggccta acattttatt agagagcagg ctagttgctt agatacatga   4320

tcttcaggcc gttatctgtc agggcaagcg aaaattggcc atttatgacg accaatgccc   4380

cgcagaagct cccatctttg ccgccataga cgccgcgccc ccttttgggg gtgtagaaca   4440

tccttttgcc agatgtggaa aagaagttcg ttgtcccatt gttggcaatg acgtagtagc   4500

cggcgaaagt gcgagaccca tttgcgctat atataagcct acgatttccg ttgcgactat   4560

tgtcgtaatt ggatgaacta ttatcgtagt tgctctcaga gttgtcgtaa tttgatggac   4620

tattgtcgta attgcttatg gagttgtcgt agttgcttgg agaaatgtcg tagttggatg   4680

gggagtagtc atagggaaga cgagcttcat ccactaaaac aattggcagg tcagcaagtg   4740

cctgccccga tgccatcgca agtacgaggc ttagaaccac cttcaacaga tcgcgcatag   4800

tcttccccag ctctctaacg cttgagttaa gccgcgccgc gaagcggcgt cggcttgaac   4860

gaattgttag acattatttg ccgactacct tggtgatctc gcctttcacg tagtgaacaa   4920

attcttccaa ctgatctgcg cgcgaggcca agcgatcttc ttgtccaaga taagcctgcc   4980

tagcttcaag tatgacgggc tgatactggg ccggcaggcg ctccattgcc cagtcggcag   5040

cgacatcctt cggcgcgatt ttgccggtta ctgcgctgta ccaaatgcgg gacaacgtaa   5100

gcactacatt tcgctcatcg ccagcccagt cgggcggcga gttccatagc gttaaggttt   5160

catttagcgc ctcaaataga tcctgttcag gaaccggatc aaagagttcc tccgccgctg   5220

gacctaccaa ggcaacgcta tgttctcttg cttttgtcag caagatagcc agatcaatgt   5280

cgatcgtggc tggctcgaag atacctgcaa gaatgtcatt gcgctgccat tctccaaatt   5340

gcagttcgcg cttagctgga taacgccacg gaatgatgtc gtcgtgcaca acaatggtga   5400

cttctacagc gcggagaatc tcgctctctc caggggaagc cgaagtttcc aaaaggtcgt   5460

tgatcaaagc tcgccgcgtt gtttcatcaa gccttacggt caccgtaacc agcaaatcaa   5520

tatcactgtg tggcttcagg ccgccatcca ctgcggagcc gtacaaatgt acggccagca   5580

acgtcggttc gagatggcgc tcgatgacgc caactacctc tgatagttga gtcgatactt   5640

cggcgatcac cgcttccctc atgatgttta actcctgaat taagccgcgc cgcgaagcgg   5700
```

```
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aaccctttttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
```

```
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg cccttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
```

```
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
gaactgtagt gctgatgttg tactgtgttt ttttacccgt tttatttgct ttactcgtgc  11700
aaatcaaatc tgtcagatgc tagaactagg tggctttatt ctgtgttctt acatagatct  11760
gttgtcctgt agttacttat gtcagttttg ttattatctg aagatatttt tggttgttgc  11820
ttgttgatgt ggtgtgagct gtgagcagcg ctcttatgat taatgatgct gtccaattgt  11880
agtgtagtat gatgtgattg atatgttcat ctattttgag ctgacagtac cgatatcgta  11940
ggatctggtg ccaacttatt ctccagctgc ttttttttac ctatgttaat tccaatcctt  12000
tcttgcctct tccagatcca gataatggcc cacgcccgcg tcctcctcct ggcgctcgcc  12060
gtcctggcca ccgccgccgt cgccgtcgcc tcctcctcct ccttcgccga ctccaacccg  12120
atccgcccgg tgaccgaccg cgccgcctcc accgctggag gaggatactg gcacacttcc  12180
ggcagggaga tcctcgacgc aaataacgtt ccagtcagaa tcgccgggat taattggttt  12240
ggcttcgaaa cgtgtaacta cgtggttcac ggcctgtggt ctcgggatta cagatcaatg  12300
ctcgaccaga tcaaatcctt ggggtataat acaattaggc tgccctacag cgatgacatt  12360
cttaagcctg gaaccatgcc gaactcgatt aatttctacc aaatgaacca ggatctgcag  12420
ggattgactt ctctgcaggt tatggacaag atcgtggcgt acgccggcca aatcgggctc  12480
agaattattt tggatcggca caggccagac tgctcaggtc agtcggccct gtggtacaca  12540
agctccgtgt cagaggcaac atggatttca gatcttcaag ccctcgcaca acgctataaa  12600
ggcaacccca cggttgtggg attcgacctt cacaacgaac ctcacgatcc ggcctgttgg  12660
ggctgcgggg acccttcgat cgactggaga ctggcagcgg agagggctgg taacgccgtt  12720
ctcagcgtca atcccaactt gctgatcttt gtggagggag ttcagtccta caacggcgat  12780
tcttactggt ggggcggaaa tctccaaggc gcagggcagt atcctgtcgt gcttaacgtt  12840
```

```
ccgaatcgcc tggtctactc agcacacgac tacgcgacta gcgtgtaccc acagacgtgg  12900

ttctccgatc ccacatttcc taacaatatg ccgggaatct ggaacaagaa ttggggttac  12960

ttgtttaacc aaaacattgc tccagtttgg ttgggtgaat ttggcaccac tcttcagtcg  13020

acgacagacc aaacctggct gaaaaccctc gtccagtatt tgcggccaac tgctcagtac  13080

ggagcagatt cttttcaatg gacgttctgg tcttggaatc ctgactccgg ggatacaggc  13140

ggtatcctga aagacgattg gcagaccgtg gacactgtta aggacgggta cttggcgccg  13200

attaaaagct cgatctttga cccagtcggc gctagcgctt ccccatcttc acaaccttcg  13260

ccgagcgtca gccccagccc aagcccaagc ccgtctgcca gcagaacccc cactcccaca  13320

cctacccccca cggcctcacc aactccgacg ctcactccta cggcgacgcc aacaccaact  13380

gcttcaccca ctcctagccc caccgcagcg agcggggcta ggtgcaccgc ttcttaccag  13440

gtcaactctg actggggtaa tggcttcacc gtgactgtgg cggtcactaa ctcaggaagc  13500

gtcgcgacga aaacctggac tgtgtcctgg acgttcgggg gcaaccaaac aatcaccaac  13560

agctggaacg ctgcagttac gcagaatggg caaagcgtca cggcgcgcaa tatgagctac  13620

aacaacgtga ttcaaccagg ccagaatacc acattcggtt ttcaagcaag ctataccggg  13680

tcaaacgctg ccccaactgt cgcttgtgct gcctcatgac ctaggtcccc gaatttcccc  13740

gatcgttcaa acatttggca ataaagtttc ttaagattga atcctgttgc cggtcttgcg  13800

atgattatca tataatttct gttgaattac gttaagcatg taataattaa catgtaatgc  13860

atgacgttat ttatgagatg ggtttttatg attagagtcc cgcaattata catttaatac  13920

gcgatagaaa acaaaatata gcgcgcaaac taggataaat tatcgcgcgc ggtgtcatct  13980

atgttactag atcgggaatt gg                                          14002
```

<210> SEQ ID NO 85
<211> LENGTH: 9983
<212> TYPE: DNA
<213> ORGANISM: Artificial Sequence
<220> FEATURE:
<223> OTHER INFORMATION: Synthetic construct, vector pAG2004

<400> SEQUENCE: 85

```
ccgatggccg agctgtggat gggcgcacat ccgaaaagca gttcacgagt gcagaatgcc     60

gccggagata tcgtttcact gcgtgatgtg attgagagtg ataaatcgac tctgctcgga    120

gaggccgttg ccaaacgctt tggcgaactg cctttcctgt tcaaagtatt atgcgcagca    180

cagccactct ccattcaggt tcatccaaac aaacacaatt ctgaaatcgg ttttgccaaa    240

gaaaatgccg caggtatccc gatggatgcc gccgagcgta actataaaga tcctaaccac    300

aagccggagc tggtttttgc gctgacgcct ttccttgcga tgaacgcgtt tcgtgaattt    360

tccgagattg tctccctact ccagccggtc gcaggtgcac atccggcgat tgctcacttt    420

ttacaacagc ctgatgccga acgtttaagc gaactgttcg ccagcctgtt gaatatgcag    480

ggtgaagaaa aatcccgcgc gctggcgatt ttaaaatcgg ccctcgatag ccagcagggt    540

gaaccgtggc aaacgattcg tttaatttct gaattttacc cggaagacag cggtctgttc    600

tccccgctat tgctgaatgt ggtgaaattg aaccctggcg aagcgatgtt cctgttcgct    660

gaaacaccgc acgcttacct gcaaggcgtg gcgctggaag tgatggcaaa ctccgataac    720

gtgctgcgtg cgggtctgac gcctaaatac attgatattc cggaactggt tgccaatgtg    780

aaattcgaag ccaaaccggc taaccagttg ttgacccagc cggtgaaaca aggtgcagaa    840
```

```
ctggacttcc cgattccagt ggatgatttt gccttctcgc tgcatgacct tagtgataaa    900
gaaaccacca ttagccagca gagtgccgcc attttgttct gcgtcgaagg cgatgcaacg    960
ttgtggaaag gttctcagca gttacagctt aaaccgggtg aatcagcgtt tattgccgcc   1020
aacgaatcac cggtgactgt caaaggccac ggccgtttag cgcgtgttta caacaagctg   1080
taagagctta ctgaaaaaat taacatctct tgctaagctg ggagctctag atccccgaat   1140
ttccccgatc gttcaaacat ttggcaataa agtttcttaa gattgaatcc tgttgccggt   1200
cttgcgatga ttatcatata atttctgttg aattacgtta agcatgtaat aattaacatg   1260
taatgcatga cgttatttat gagatgggtt tttatgatta gagtcccgca attatacatt   1320
taatacgcga tagaaaacaa aatatagcgc gcaaactagg ataaattatc gcgcgcggtg   1380
tcatctatgt tactagatcg ggaattggcg agctcgaatt aattcagtac attaaaaacg   1440
tccgcaatgt gttattaagt tgtctaagcg tcaatttgtt tacaccacaa tatatcctgc   1500
caccagccag ccaacagctc cccgaccggc agctcggcac aaaatcacca ctcgatacag   1560
gcagcccatc agtccgggac ggcgtcagcg ggagagccgt tgtaaggcgg cagactttgc   1620
tcatgttacc gatgctattc ggaagaacgg caactaagct gccgggtttg aaacacggat   1680
gatctcgcgg agggtagcat gttgattgta acgatgacag agcgttgctg cctgtgatca   1740
aatatcatct ccctcgcaga gatccgaatt atcagccttc ttattcattt ctcgcttaac   1800
cgtgacaggc tgtcgatctt gagaactatg ccgacataat aggaaatcgc tggataaagc   1860
cgctgaggaa gctgagtggc gctatttctt tagaagtgaa cgttgacgat cgtcgaccgt   1920
accccgatga attaattcgg acgtacgttc tgaacacagc tggatactta cttgggcgat   1980
tgtcatacat gacatcaaca atgtacccgt ttgtgtaacc gtctcttgga ggttcgtatg   2040
acactagtgg ttcccctcag cttgcgacta gatgttgagg cctaacattt tattagagag   2100
caggctagtt gcttagatac atgatcttca ggccgttatc tgtcagggca agcgaaaatt   2160
ggccatttat gacgaccaat gccccgcaga agctcccatc tttgccgcca tagacgccgc   2220
gcccccttt tggggtgtag aacatccttt tgccagatgt ggaaaagaag ttcgttgtcc   2280
cattgttggc aatgacgtag tagccggcga aagtgcgaga cccatttgcg ctatatataa   2340
gcctacgatt tccgttgcga ctattgtcgt aattggatga actattatcg tagttgctct   2400
cagagttgtc gtaatttgat ggactattgt cgtaattgct tatggagttg tcgtagttgc   2460
ttggagaaat gtcgtagttg gatggggagt agtcataggg aagacgagct tcatccacta   2520
aaacaattgg caggtcagca agtgcctgcc ccgatgccat cgcaagtacg aggcttagaa   2580
ccaccttcaa cagatcgcgc atagtcttcc ccagctctct aacgcttgag ttaagccgcg   2640
ccgcgaagcg gcgtcggctt gaacgaattg ttagacatta tttgccgact accttggtga   2700
tctcgccttt cacgtagtga acaaattctt ccaactgatc tgcgcgcgag gccaagcgat   2760
cttcttgtcc aagataagcc tgcctagctt caagtatgac gggctgatac tgggccggca   2820
ggcgctccat tgcccagtcg gcagcgacat ccttcggcgc gattttgccg gttactgcgc   2880
tgtaccaaat gcgggacaac gtaagcacta catttcgctc atcgccagcc cagtcgggcg   2940
gcgagttcca tagcgttaag gtttcattta gcgcctcaaa tagatcctgt tcaggaaccg   3000
gatcaaagag ttcctccgcc gctggaccta ccaaggcaac gctatgttct cttgcttttg   3060
tcagcaagat agccagatca atgtcgatcg tggctggctc gaagatacct gcaagaatgt   3120
cattgcgctg ccattctcca aattgcagtt cgcgcttagc tggataacgc cacggaatga   3180
tgtcgtcgtg cacaacaatg gtgacttcta cagcgcggag aatctcgctc tctccagggg   3240
```

```
aagccgaagt ttccaaaagg tcgttgatca aagctcgccg cgttgtttca tcaagcctta   3300
cggtcaccgt aaccagcaaa tcaatatcac tgtgtggctt caggccgcca tccactgcgg   3360
agccgtacaa atgtacggcc agcaacgtcg gttcgagatg gcgctcgatg acgccaacta   3420
cctctgatag ttgagtcgat acttcggcga tcaccgcttc cctcatgatg tttaactcct   3480
gaattaagcc gcgccgcgaa gcggtgtcgg cttgaatgaa ttgttaggcg tcatcctgtg   3540
ctcccgagaa ccagtaccag tacatcgctg tttcgttcga gacttgaggt ctagttttat   3600
acgtgaacag gtcaatgccg ccgagagtaa agccacattt tgcgtacaaa ttgcaggcag   3660
gtacattgtt cgtttgtgtc tctaatcgta tgccaaggag ctgtctgctt agtgcccact   3720
ttttcgcaaa ttcgatgaga ctgtgcgcga ctcctttgcc tcggtgcgtg tgcgacacaa   3780
caatgtgttc gatagaggct agatcgttcc atgttgagtt gagttcaatc ttcccgacaa   3840
gctcttggtc gatgaatgcg ccatagcaag cagagtcttc atcagagtca tcatccgaga   3900
tgtaatcctt ccggtagggg ctcacacttc tggtagatag ttcaaagcct tggtcggata   3960
ggtgcacatc gaacacttca cgaacaatga aatggttctc agcatccaat gtttccgcca   4020
cctgctcagg gatcaccgaa atcttcatat gacgcctaac gcctggcaca gcggatcgca   4080
aacctggcgc ggcttttggc acaaaaggcg tgacaggttt gcgaatccgt tgctgccact   4140
tgttaaccct tttgccagat ttggtaacta taatttatgt tagaggcgaa gtcttgggta   4200
aaaactggcc taaaattgct ggggatttca ggaaagtaaa catcaccttc cggctcgatg   4260
tctattgtag atatatgtag tgtatctact tgatcggggg atctgctgcc tcgcgcgttt   4320
cggtgatgac ggtgaaaacc tctgacacat gcagctcccg gagacggtca cagcttgtct   4380
gtaagcggat gccgggagca gacaagcccg tcagggcgcg tcagcgggtg ttggcgggtg   4440
tcggggcgca gccatgaccc agtcacgtag cgatagcgga gtgtatactg gcttaactat   4500
gcggcatcag agcagattgt actgagagtg caccatatgc ggtgtgaaat accgcacaga   4560
tgcgtaagga gaaaataccg catcaggcgc tcttccgctt cctcgctcac tgactcgctg   4620
cgctcggtcg ttcggctgcg gcgagcggta tcagctcact caaaggcggt aatacggtta   4680
tccacagaat caggggataa cgcaggaaag aacatgtgag caaaaggcca gcaaaaggcc   4740
aggaaccgta aaaaggccgc gttgctggcg tttttccata ggctccgccc ccctgacgag   4800
catcacaaaa atcgacgctc aagtcagagg tggcgaaacc cgacaggact ataaagatac   4860
caggcgtttc cccctggaag ctccctcgtg cgctctcctg ttccgaccct gccgcttacc   4920
ggatacctgt ccgcctttct cccttcggga agcgtggcgc tttctcatag ctcacgctgt   4980
aggtatctca gttcggtgta ggtcgttcgc tccaagctgg gctgtgtgca cgaacccccc   5040
gttcagcccg accgctgcgc cttatccggt aactatcgtc ttgagtccaa cccggtaaga   5100
cacgacttat cgccactggc agcagccact ggtaacagga ttagcagagc gaggtatgta   5160
ggcggtgcta cagagttctt gaagtggtgg cctaactacg gctacactag aaggacagta   5220
tttggtatct gcgctctgct gaagccagtt accttcggaa aaagagttgg tagctcttga   5280
tccggcaaac aaaccaccgc tggtagcggt ggtttttttg tttgcaagca gcagattacg   5340
cgcagaaaaa aaggatctca agaagatcct ttgatctttt ctacggggtc tgacgctcag   5400
tggaacgaaa actcacgtta agggattttg gtcatgagat tatcaaaaag gatcttcacc   5460
tagatccttt taaattaaaa atgaagtttt aaatcaatct aaagtatata tgagtaaact   5520
tggtctgaca gttaccaatg cttaatcagt gaggcaccta tctcagcgat ctgtctattt   5580
```

```
cgttcatcca tagttgcctg actccccgtc gtgtagataa ctacgatacg ggagggctta   5640
ccatctggcc ccagtgctgc aatgataccg cgagacccac gctcaccggc tccagattta   5700
tcagcaataa accagccagc cggaagggcc gagcgcagaa gtggtcctgc aactttatcc   5760
gcctccatcc agtctattaa ttgttgccgg gaagctagag taagtagttc gccagttaat   5820
agtttgcgca acgttgttgc cattgctgca gggggggggg gggggggggtt ccattgttca   5880
ttccacggac aaaaacagag aaaggaaacg acagaggcca aaaagctcgc tttcagcacc   5940
tgtcgtttcc tttcttttca gagggtattt taaataaaaa cattaagtta tgacgaagaa   6000
gaacggaaac gccttaaacc ggaaaatttt cataaatagc gaaaacccgc gaggtcgccg   6060
ccccgtaacc tgtcggatca ccggaaagga cccgtaaagt gataatgatt atcatctaca   6120
tatcacaacg tgcgtggagg ccatcaaacc acgtcaaata atcaattatg acgcaggtat   6180
cgtattaatt gatctgcatc aacttaacgt aaaaacaact tcagacaata caaatcagcg   6240
acactgaata cggggcaacc tcatgtcccc cccccccccc ccctgcaggc atcgtggtgt   6300
cacgctcgtc gtttggtatg gcttcattca gctccggttc ccaacgatca aggcgagtta   6360
catgatcccc catgttgtgc aaaaaagcgg ttagctcctt cggtcctccg atcgttgtca   6420
gaagtaagtt ggccgcagtg ttatcactca tggttatggc agcactgcat aattctctta   6480
ctgtcatgcc atccgtaaga tgcttttctg tgactggtga gtactcaacc aagtcattct   6540
gagaatagtg tatgcggcga ccgagttgct cttgcccggc gtcaacacgg gataataccg   6600
cgccacatag cagaacttta aaagtgctca tcattggaaa acgttcttcg gggcgaaaac   6660
tctcaaggat cttaccgctg ttgagatcca gttcgatgta acccactcgt gcacccaact   6720
gatcttcagc atcttttact ttcaccagcg tttctgggtg agcaaaaaca ggaaggcaaa   6780
atgccgcaaa aaagggaata agggcgacac ggaaatgttg aatactcata ctcttccttt   6840
ttcaatatta ttgaagcatt tatcagggtt attgtctcat gagcggatac atatttgaat   6900
gtatttagaa aaataaacaa ataggggttc cgcgcacatt tccccgaaaa gtgccacctg   6960
acgtctaaga aaccattatt atcatgacat taacctataa aaataggcgt atcacgaggc   7020
cctttcgtct tcaagaattg gtcgacgatc ttgctgcgtt cggatatttt cgtggagttc   7080
ccgccacaga cccggattga aggcgagatc cagcaactcg cgccagatca tcctgtgacg   7140
gaactttggc gcgtgatgac tggccaggac gtcggccgaa agagcgacaa gcagatcacg   7200
cttttcgaca gcgtcggatt tgcgatcgag gatttttcgg cgctgcgcta cgtccgcgac   7260
cgcgttgagg gatcaagcca cagcagccca ctcgaccttc tagccgaccc agacgagcca   7320
agggatcttt ttggaatgct gctccgtcgt caggctttcc gacgtttggg tggttgaaca   7380
gaagtcatta tcgcacggaa tgccaagcac tcccgagggg aaccctgtgg ttggcatgca   7440
catacaaatg gacgaacgga taaacctttt cacgcccttt taaatatccg attattctaa   7500
taaacgctct tttctcttag gtttacccgc caatatatcc tgtcaaacac tgatagttta   7560
aactgaaggc gggaaacgac aacctgatca tgagcggaga attaagggag tcacgttatg   7620
acccccgccg atgacgcggg acaagccgtt ttacgtttgg aactgacaga accgcaacgt   7680
tgaaggagcc actcagctta attaagtcta actcgagtta ctggtacgta ccaaatccat   7740
ggaatcaagg taccatcaat cccgggtatt catcctaggt atccaagaat tcatactaaa   7800
gcttgcatgc ctgcaggtcg actctagtaa cggccgccag tgtgctggaa ttaattcggc   7860
ttgtcgacca cccaacccca tatcgacaga ggatgtgaag aacaggtaaa tcacgcagaa   7920
gaacccatct ctgatagcag ctatcgatta gaacaacgaa tccatattgg gtccgtggga   7980
```

-continued

```
aatacttact gcacaggaag ggggcgatct gacgaggccc cgccaccggc ctcgacccga   8040
ggccgaggcc gacgaagcgc cggcgagtac ggcgccgcgg cggcctctgc ccgtgccctc   8100
tgcgcgtggg agggagaggc cgcggtggtg ggggcgcgcg cgcgcgcgcg cgcagctggt   8160
gcggcggcgc gggggtcagc cgccgagccg gcggcgacgg aggagcaggg cggcgtggac   8220
gcgaacttcc gatcggttgg tcagagtgcg cgagttgggc ttagccaatt aggtctcaac   8280
aatctattgg gccgtaaaat tcatgggccc tggtttgtct aggcccaata tcccgttcat   8340
ttcagcccac aaatatttcc ccagaggatt attaaggccc acacgcagct tatagcagat   8400
caagtacgat gtttcctgat cgttggatcg gaaacgtacg gtcttgatca ggcatgccga   8460
cttcgtcaaa gagaggcggc atgacctgac gcggagttgg ttccgggcac cgtctggatg   8520
gtcgtaccgg gaccggacac gtgtcgcgcc tccaactaca tggacacgtg tggtgctgcc   8580
attgggccgt acgcgtggcg gtgaccgcac cggatgctgc ctcgcaccgc cttgcccacg   8640
ctttatatag agaggttttc tctccattaa tcgcatagcg agtcgaatcg accgaagggg   8700
agggggagcg aagctttgcg ttctctaatc gcctcgtcaa ggtaactaat caatcacctc   8760
gtcctaatcc tcgaatctct cgtggtgccc gtctaatctc gcgattttga tgctcgtggt   8820
ggaaagcgta ggaggatccc gtgcgagtta gtctcaatct ctcagggttt cgtgcgattt   8880
tagggtgatc cacctcttaa tcgagttacg gtttcgtgcg attttagggt aatcctctta   8940
atctctcatt gatttagggt ttcgtgagaa tcgaggtagg gatctgtgtt atttatatcg   9000
atctaataga tggattggtt ttgagattgt tctgtcagat ggggattgtt tcgatatatt   9060
accctaatga tgtgtcagat ggggattgtt tcgatatatt accctaatga tgtgtcagat   9120
ggggattgtt tcgatatatt accctaatga tggataataa gagtagttca cagttatgtt   9180
ttgatcctgc cacatagttt gagttttgtg atcagattta gttttactta tttgtgctta   9240
gttcggatgg gattgttctg atattgttcc aatagatgaa tagctcgtta ggttaaaatc   9300
tttaggttga gttaggcgac acatagttta tttcctctgg atttggattg gaattgtgtt   9360
cttagttttt ttcccctgga tttggattgg aattgtgtgg agctgggtta gagaattaca   9420
tctgtatcgt gtacacctac ttgaactgta gagcttgggt tctaaggtca atttaatctg   9480
tattgtatct ggctctttgc ctagttgaac tgtagtgctg atgttgtact gtgttttttt   9540
acccgtttta tttgctttac tcgtgcaaat caaatctgtc agatgctaga actaggtggc   9600
tttattctgt gttcttacat agatctgttg tcctgtagtt acttatgtca gttttgttat   9660
tatctgaaga tatttttggt tgttgcttgt tgatgtggtg tgagctgtga gcagcgctct   9720
tatgattaat gatgctgtcc aattgtagtg tagtatgatg tgattgatat gttcatctat   9780
tttgagctga cagtaccgat atcgtaggat ctggtgccaa cttattctcc agctgctttt   9840
ttttacctat gttaattcca atcctttctt gcctcttcca gatccagata atgcagaaac   9900
tcattaactc agtgcaaaac tatgcctggg gcagcaaaac ggcgttgact gaactttatg   9960
gtatggaaaa tccgtccagc cag                                           9983
```

CONSOLIDATED PRETREATMENT AND HYDROLYSIS OF PLANT BIOMASS EXPRESSING CELL WALL DEGRADING ENZYMES

This application is a continuation of U.S. patent application Ser. No. 13/414,627, filed Mar. 7, 2012, which claimed the benefit of U.S. provisional application 61/449,769 filed Mar. 7, 2011. U.S. patent application Ser. No. 13/414,627 was a continuation-in-part of U.S. patent application Ser. No. 12/590,444, which was filed Nov. 6, 2009 and issued on Apr. 16, 2013 as U.S. Pat. No. 8,420,387. U.S. patent application Ser. No. 13/414,627 was also a continuation-in-part of U.S. patent application Ser. No. 13/004,713, which was filed Jan. 11, 2011 and issued on Aug. 21, 2012 as U.S. Pat. No. 8,247,647. U.S. patent application Ser. No. 13/414,627 was also a continuation-in-part of International Patent Application Serial No. PCT/US10/55746, which was filed Nov. 5, 2010 and was a continuation-in-part of U.S. patent application Ser. No. 12/590,444, which was filed Nov. 6, 2009, and claimed the benefit of U.S. Provisional Application Ser. No. 61/280,635, filed Nov. 6, 2009, and U.S. Provisional Application Ser. No. 61/398,589, filed Jun. 28, 2010. U.S. patent application Ser. No. 13/414,627 was also a continuation-in-part of International Patent Application Serial No. PCT/US10/55669, which was filed Nov. 5, 2010, and was a continuation-in-part of U.S. patent application Ser. No. 12/590,444, filed Nov. 6, 2009. U.S. patent application Ser. No. 13/414,627 was also a continuation-in-part of International Patent Application Serial No. PCT/US10/55751, which was filed Nov. 5, 2010, and was a continuation-in-part of U.S. patent application Ser. No. 12/590,444. All of the foregoing are incorporated herein by reference as if fully set forth.

The sequence listing electronically filed with this application titled "Sequence Listing," created on Dec. 7, 2015, and having a file size of 616,407 bytes is incorporated herein by reference as if fully set forth.

GOVERNMENT SUPPORT STATEMENT

This invention was made at least in part with government support under the United States Department of Energy Advanced Research Projects Agency-Energy (ARPA-e) Grant No. DE-AR0000042. The Government has certain rights in this invention.

FIELD OF INVENTION

The disclosure relates to methods for producing soluble sugars from plants expressing cell wall degrading enzymes, transgenic plants, expression vectors, nucleic acids, and cell wall degrading proteins.

BACKGROUND

Lignocelluosic biomass is an attractive feedstock for the production of biofuels, chemicals, and bioproducts. Lignocellulosic biomass provides many benefits, including abundant availability, potential low cost, sustainability, and the fact that it is not ordinarily consumed by humans as a source of food (Langeveld J W A et al. 2010 Crop Sci 50: S131-S151). To convert lignocellulosic biomass into renewable energy and biochemicals, bioprocesses convert a portion of the lignocellulosic biomass into simple sugars, which are converted into biofuels or other bioproducts.

The cost of sugar production through biological conversion is expensive due to the costs of biomass pretreatment and enzymatic hydrolysis (Alvira P et al. 2010 Bioresour Technol 101: 4851; Abramson M et at 2010 Plant Science 178: 61; Daniel Klein-Marcuschamer et al. Biotechnol. Bioeng. 2012; 109:1083). Plant cell walls are recalcitrant to enzymatic hydrolysis because the heterogeneity, chemical composition and structural features of the cell wall polysaccharides make them inaccessible to hydrolytic enzymes (Zhu L et al. 2008 Bioresour Technol 99: 3817). For this reason, enzymatic hydrolysis requires a pretreatment that can make plant cell walls accessible. The pretreatment technologies prevalent in industry typically employ harsh conditions such as high temperatures and extreme pHs (Wyman C E et al. 2005 Bioresour Technol 96:1959; Mosier N et at 2005 Bioresour Technol 96: 673). These conditions cause sugar degradation and result in reduced sugar yields and formation of toxic fermentation compounds, requiring expensive additional steps for detoxification, separation and neutralization as well as expensive up-front capital equipment.

Pretreatment costs, high costs of exogenous enzyme loadings, slow hydrolysis rate, and limited supply of enzymes are also concerns for the commercialization of processes involving lignocellulosic biomass.

SUMMARY

In an aspect, the invention relates to a method for producing soluble sugars from engineered plant material. The method includes pretreating by mixing the engineered plant material with a pulping formulation to form a mixture. The engineered plant material includes a first polynucleotide sequence encoding a first protein selected from the group consisting of: a xylanase, an endoglucanase, an exoglucanase, a feruloyl esterase, an intein-modified xylanase, an intein-modified endoglucanase, an intein-modified exoglucanase, and an intein-modified feruloyl esterase. The method also includes providing hydrolysis conditions.

In an aspect, the invention relates to an engineered plant. The engineered plant includes a first polynucleotide sequence encoding an amino acid sequence with at least 90% identity to a first reference sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11.

In an aspect, the invention relates to an expression cassette. The expression cassette includes a first polynucleotide sequence capable of hybridizing under conditions of moderate stringency to a nucleic acid consisting of a first reference sequence selected from the group consisting of: SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39 [P77853:S158-30-108-35]. The expression cassette also includes a second polynucleotide sequence capable of hybridizing under conditions of moderate stringency to a nucleic acid consisting of a second reference sequence selected from the group consisting of: SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID: 43. The SEQ ID NO selected as the first reference sequence is different than the SEQ ID NO selected as the second reference sequence.

In an aspect, the invention relates to an expression cassette. The expression cassette includes a polynucleotide sequence capable of hybridizing under conditions of moderate stringency to a nucleic acid consisting of a reference sequence selected from the group of sequences consisting of: SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62.

In an aspect, the invention relates to an expression vector. The expression vector includes a polynucleotide sequence capable of hybridizing under conditions of moderate stringency to nucleic acid consisting of a sequence selected from the group consisting of: SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, and SEQ ID NO: 83.

BRIEF DESCRIPTION OF THE DRAWINGS

The following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 4B illustrates glucose yield from a transgenic plant expressing endoglucanase B (EGB2042.03) and a transgenic control plant lacking endoglucanase (TGC.2004.8.02).

FIGS. 5A-5D illustrate hydrolysis results with transgenic plants expressing multiple proteins. FIGS. 5A and 5C illustrate glucose yields, and FIGS. 5B and 5D illustrate xylose yields from test transgenic plants and the transgenic control plants with cocktail #1. FIGS. 5A and 5B illustrate results with 1) double stack transgenic plants XynA/AccA/B.2096.05 and XynA/AccA/B.2096.01, which express xylanase A (XynA) and accessory enzymes (Acc) and 2) a transgenic control plant TGC.2004.8.02 in treatments with a full enzyme cocktail (FCt; dark gray (middle)), a full cocktail lacking xylanase (FCt-Xyn; striped bars (right)) and no enzymes (NCt; white bars (left)). FIGS. 5C and 5D illustrate results with 1) a transgenic plant EGA/XynA.2242.09 expressing XynA and EGA and 2) a transgenic control plant TGC.4000.12 in treatments with a full enzyme cocktail (FCt; dark gray (left bar of the four for each sample)), a full cocktail lacking xylanase (Ct-Xyn; diagonal stripes (second from left)), a full cocktail lacking endoglucanase (Ct-EG; white (third from left)) and a full cocktail lacking xylanase and endoglucanase (Ct-Xyn-EG; checked (fourth from left)).

FIG. 7A shows glucose yields from pretreated transgenic switchgrass plants expressing xylanase A (XynA.pv2015.3c, XynA.pv2015.4c) and a pretreated wild-type switchgrass plant (Alamo) following enzymatic hydrolysis with the enzyme cocktail #1 (FCt; gray (middle)); the cocktail #1 lacking xylanase (Ct-Xyn; diagonal stripes (right)); and a control treatment lacking the enzyme cocktail (NCt; white (left)). FIG. 7B shows the xylose yield results from a pretreated first generation transgenic plant expressing xylanase A (XynA.2015.05.T0), a second generation transgenic plant expressing xylanase A (XynA.2015.05.T1) and a pretreated transgenic plant lacking xylanase (TGC.4000.11) following enzymatic hydrolysis with the enzyme cocktail #1 (FCt; gray (middle)); the cocktail #1 lacking xylanase (Ct-Xyn; diagonal stripes (right)); and a control treatment lacking the enzyme cocktail (NCt; white (left)).

(EGA.2049.10.FCt, closed square; TGC.4000.11.FCt, open diamond) and the enzyme cocktail #1 lacking endoglucanase (EGA.2049.10.Ct-EG, closed triangle; TGC.4000.11.Ct-EG, open circle).

Figure 12B:
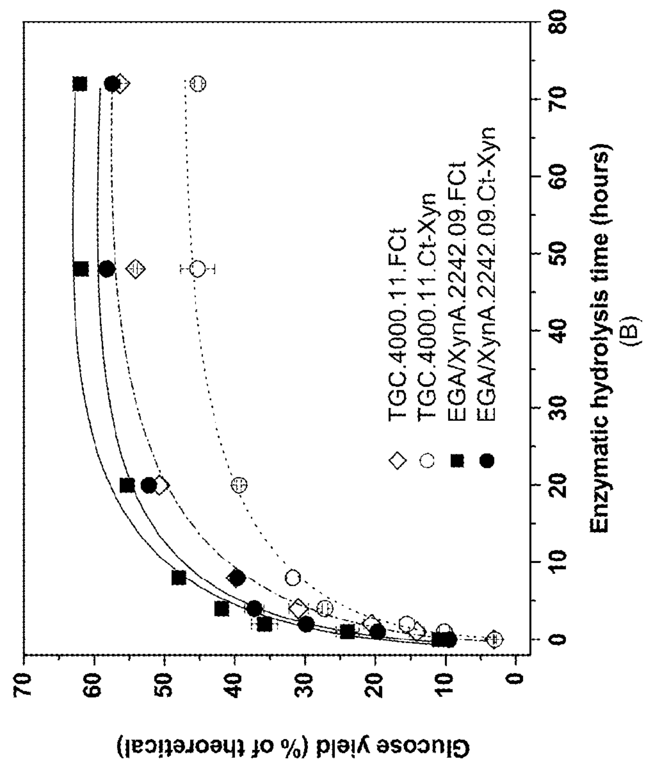
Figure 12A:
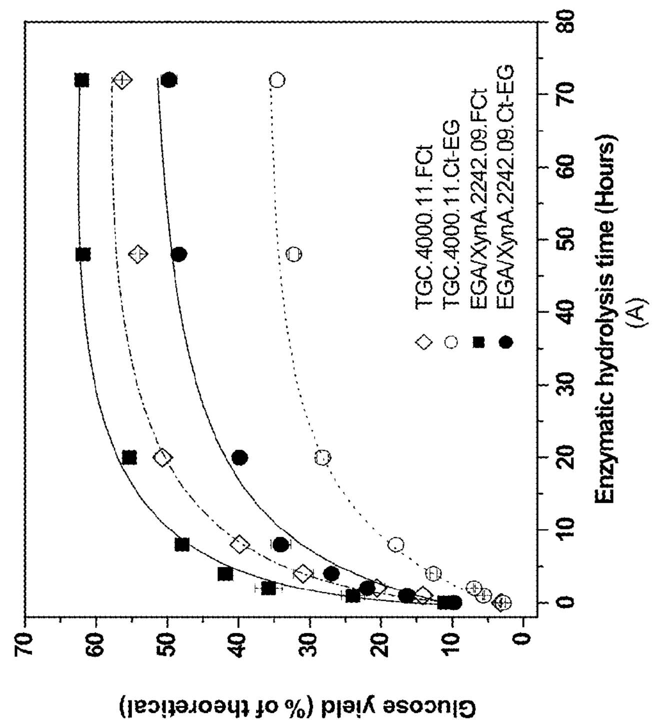

FIGS. 12A-12B illustrate time courses of the glucose yield from enzymatic hydrolysis of a pretreated transgenic plant (EGA/XynA.2242.09) and a pretreated transgenic control plant (TGC.4000.11) using the full enzyme cocktail (EGA/XynA.2242.09.FCt, closed square; TGC.4000.11.FCt, open diamond) compared to treatments using the full enzyme cocktail lacking endoglucanase (EGA/XynA.2242.09.Ct-EG, closed circle; TGC.4000.11.Ct-EG, open circle in FIG. 12A) and the full enzyme cocktail lacking xylanase (EGA/XynA.2242.09.Ct-Xyn, closed circle; TGC.4000.11.Ct-Xyn, open circle).

Figure 13B:
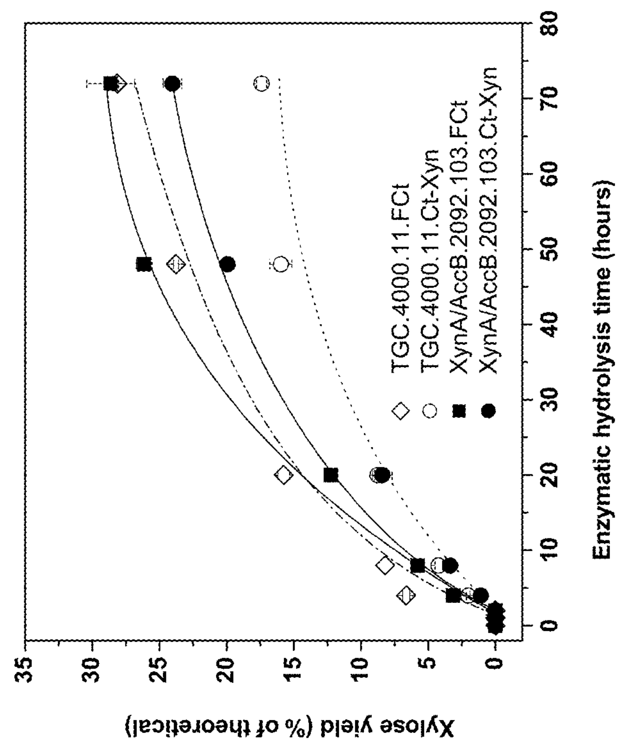
Figure 13A:
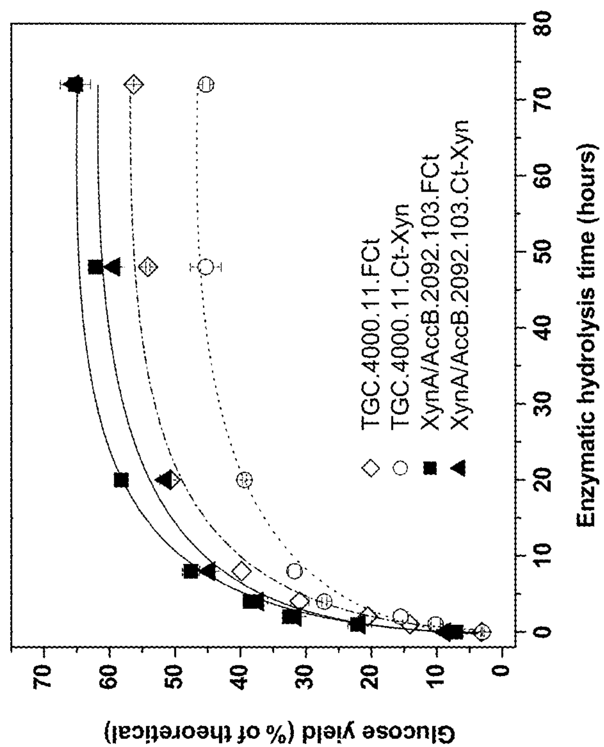

FIGS. 13A-13B illustrate time courses of glucose and xylose yields, respectively, from a pretreated transgenic plant expressing xylanase A and feruloyl esterase B (XynA/AccB.2092.103) and a pretreated transgenic control plant (TGC.4000.11) following enzymatic hydrolysis with the full enzyme cocktail (XynA/AccB.2092.103.FCt, closed square; TGC.4000.11.FCt, open diamond) and the full enzyme cocktail lacking xylanase (XynA/AccB.2092.103.Ct-Xyn, closed triangle; TGC.4000.11.Ct-Xyn, open circle).

Figure 14:
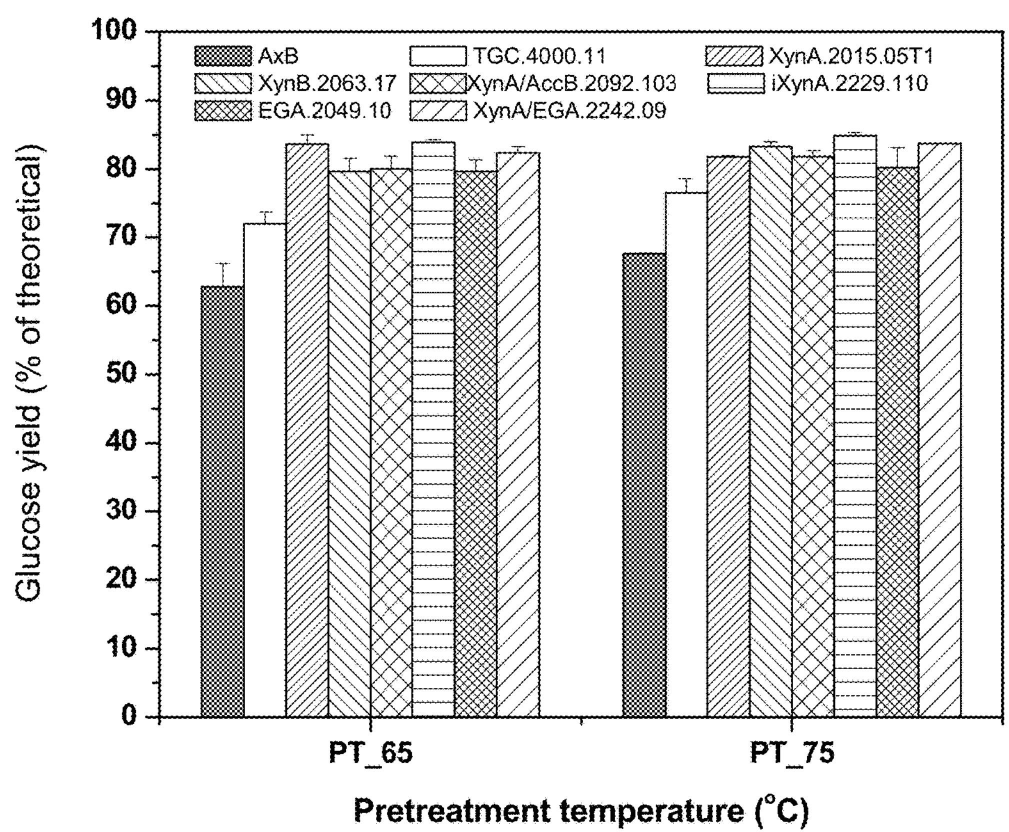

FIG. 14 illustrates glucose yields from enzymatic hydrolysis of pretreated transgenic plant expressing the following proteins: xylanase B (XynB.2063.17), endoglucanase (EGA.2049.10), xylanase A and feruloyl esterase B (XynA/Acc.B.2092.103), xylanase A and endoglucanase (EGA/XynA.2242.09), intein modified xylanase A (iXynA.2229.110) compared to a non-transgenic control plant (AxB) and a transgenic control plant lacking enzymes (TGC.4000.11). Pretreatments were performed at temperatures of 65° C. (PT_65) and 75° C. (PT_75). Enzyme loading includes 0.2 ml Accellerase® 1500 or 0.1 ml Accellerase® XY per gram of biomass and 0.05 μM β-glucosidase (BGL). The bars above each of the PT_65 and PT_75 pretreatment sets present data for the transgenic and control plants from left to right as follows: AxB; TGC.4000.11; XynA.2015.05T1; XynB.2063.17; XynA/AccB.2092.103; iXynA.2229.110; EGA.2049.10; and XynA/EGA.2242.09.

Figure 15:
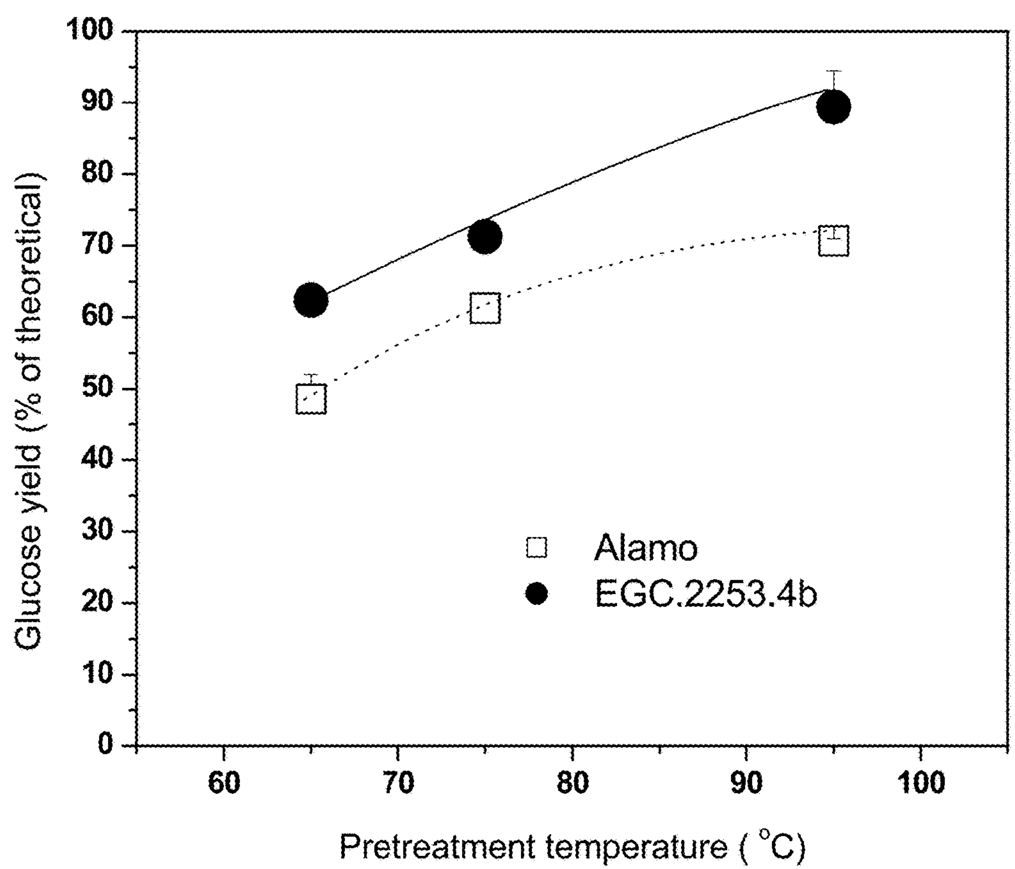

FIG. 15 illustrates glucose yields from enzymatic hydrolysis of pretreated transgenic switchgrass (EGC.2253.4b, closed circle) and a wild type switchgrass (Alamo, open square) with enzyme cocktail #5. Pretreatment temperatures: 65° C., 75° C., and 95° C.

FIGS. 16A-16B illustrate an effect of a pretreatment temperature and time on glucose (FIG. 16A) and xylose (FIG. 16B) yields from enzyme hydrolysis of a pretreated transgenic plant expressing endoglucanase and xylanase A (EGA/XynA.2342.105; black bars (right)) and a pretreated control plant (TGC.2342.01; gray bars (left)).

Figure 17B:
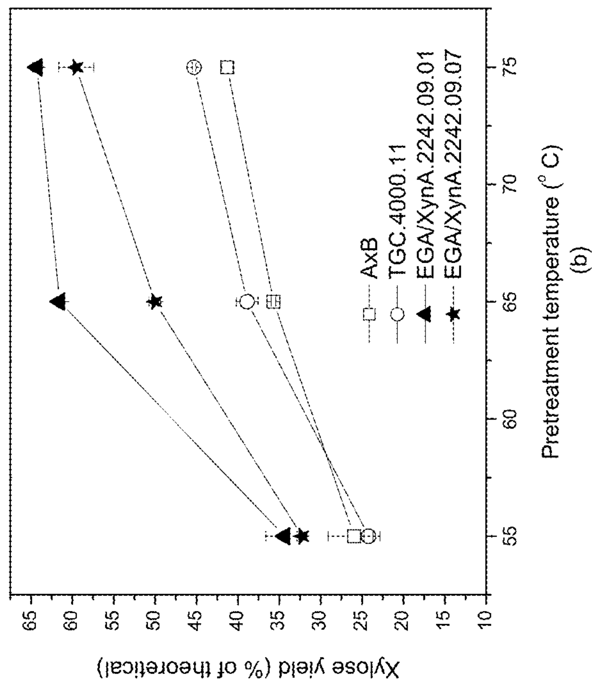
Figure 17A:
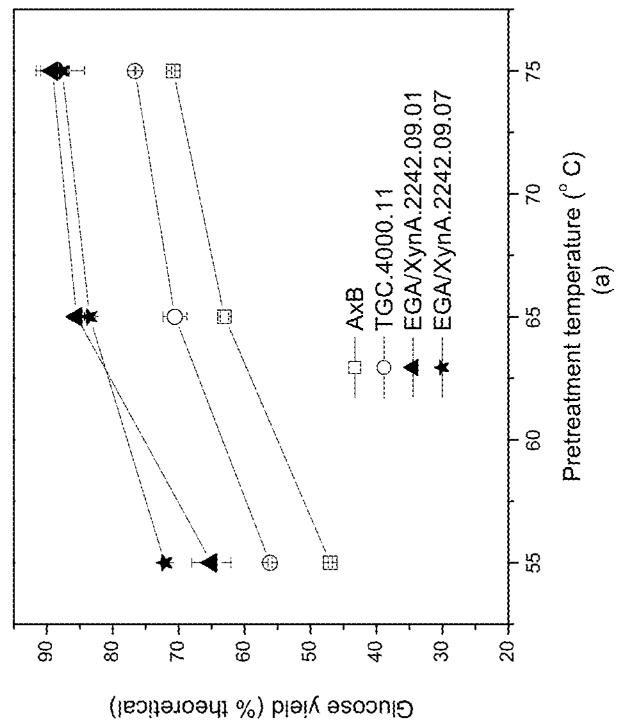

FIGS. 17A-17B illustrate an effect of a pretreatment temperature on glucose (FIG. 17A) and xylose (FIG. 17B) yields from the pretreated transgenic plants EGA/XynA.2242.09.01 and EGA/XynA.2242.09.07 expressing endoglucanase A and xylanase A, and the control plants: wild type AxB and transgenic TGC.4000.11.

Figure 18:
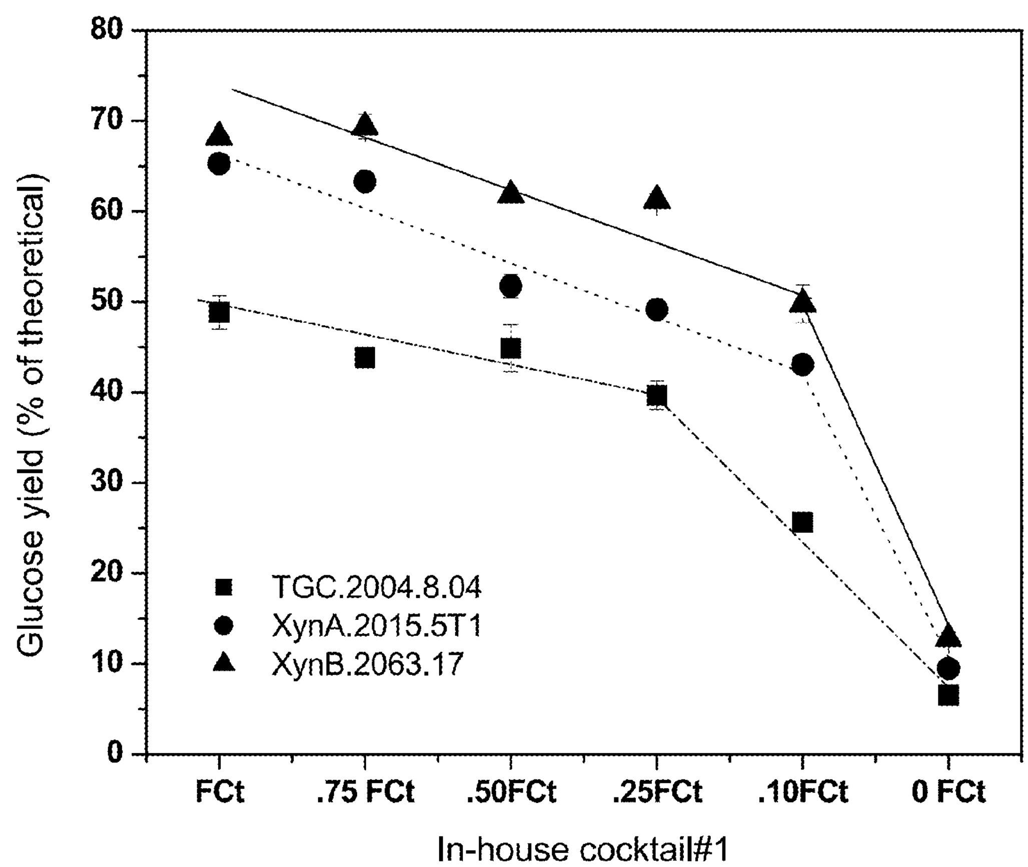

FIG. 18 illustrates an effect of reducing loading of external enzymes on glucose yields from the pretreated transgenic plants XynA.2015.05T1 (closed circle), XynB.2063.17 (closed triangle), and control plant TGC.2004.8.04 (closed square) after hydrolysis with the decreasing enzyme loadings: full cocktail #1 (FCt), 75% full cocktail #1 (0.75 FCt), 50% full cocktail #1 (0.50FCt), 25% full cocktail #1 (0.25FCt), 10% full cocktail #1 (0.10FCt) and no enzymes (OFCt).

Figure 19:
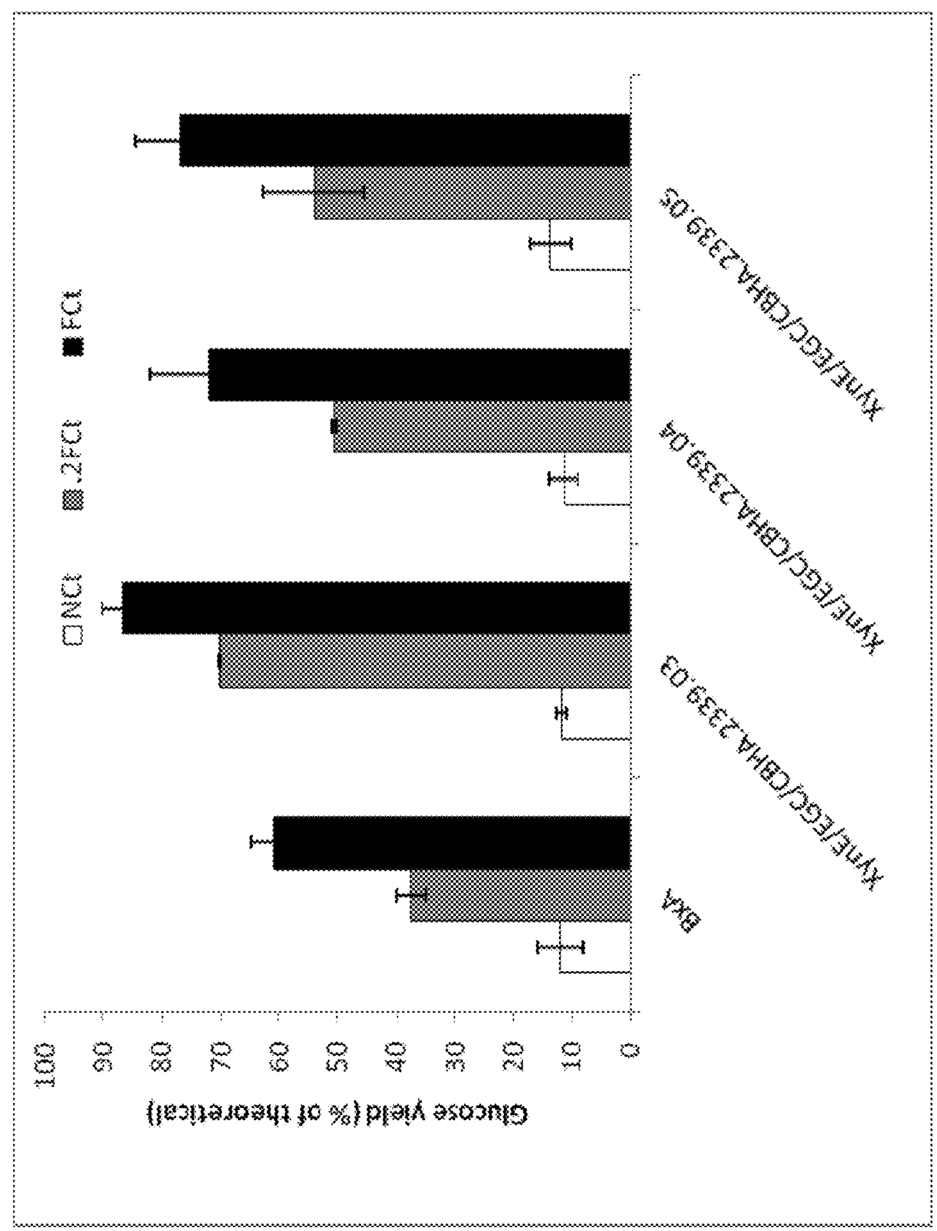

FIG. 19 illustrates an effect of reducing loadings of external enzymes on glucose yields from the transgenic plants XynE/EGC/CBHA.2339.03, XynE/EGC/CBHA.2339.04, and XynE/EGC/CBHA.2339.05, and the control plant BxA. Pretreatment was performed using 0.17 M ammonium bisulfite and ammonium carbonate (pH8.1) at 75° C., at liquid to solid ratio equal to 10 for 16 hours. Enzymatic hydrolysis was conducted at approximately 2% solids content with no enzymes (NCt; white (left)), 20% full cocktail (0.2FCt; gray (middle)) and full cocktail Accellerase® 1500/XY at 0.2 ml/0.1 ml of per gram stover (FCt; black (right)) at 50° C. and pH 5.0 for a period of 3 days.

FIGS. 20A-20B illustrate glucose and xylose yields, respectively, from pretreated plants expressing xylanase A and endoglucanase (Xyn A/EGA.2309.54 and XynA/EGA2309.107) compared to a pretreated non-transgenic control plant (BxA) after enzymatic hydrolysis with a full load of the enzyme cocktail Accelerase® 1500/XY (FCt; black (right)), a 20% load of the cocktail (0.2FCt; gray (middle in FIG. 20A and right in FIG. 20B)) and no enzymes (NCt; white (left in FIG. 20A)).

Figure 21B:
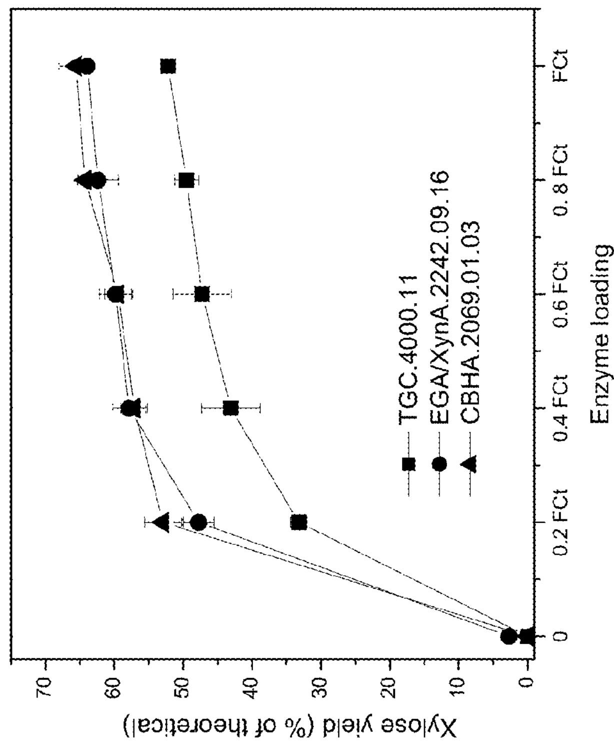
Figure 21A:
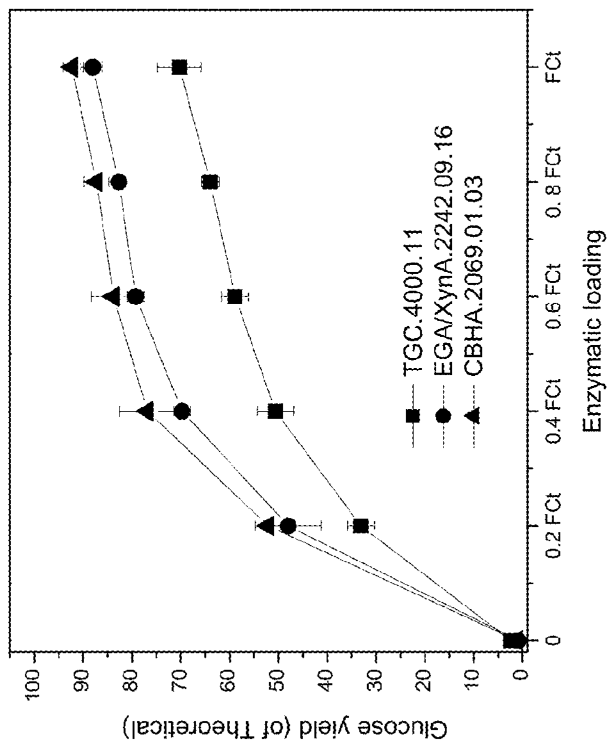

FIGS. 21A-21B illustrate an effect of reducing loadings of external enzymes on glucose (FIG. 21A) and xylose (FIG. 21B) yields from the transgenic plants EGA/XynA.2242.09.16, CBHA.2069.01.03 and the control plant TGC.4000.11 following enzymatic hydrolysis with the full cocktail at 0.2 ml Accellerase® 1500 per gram stover+0.1 ml Accellerase® XY per gram stover (FCt;), 80% full cocktail: 0.16 ml Accellerase® 1500 per gram stover+0.08 ml Accellerase® XY per gram stover (0.8FCt), 60% full cocktail: 0.12 ml Accellerase® 1500 per gram stover+0.06 ml Accellerase® XY per gram stover (0.6FCt), 40% full cocktail: 0.08 mL Accellerase® 1500 per gram stover+0.04 mL Accellerase® XY per gram stover (0.4FCt), 20% full cocktail: 0.04 mL Accellerase® 1500 per gram stover+0.02 mL Accellerase® XY per gram stover (0.2FCt) and no enzymes (OFCt).

Figure 22:
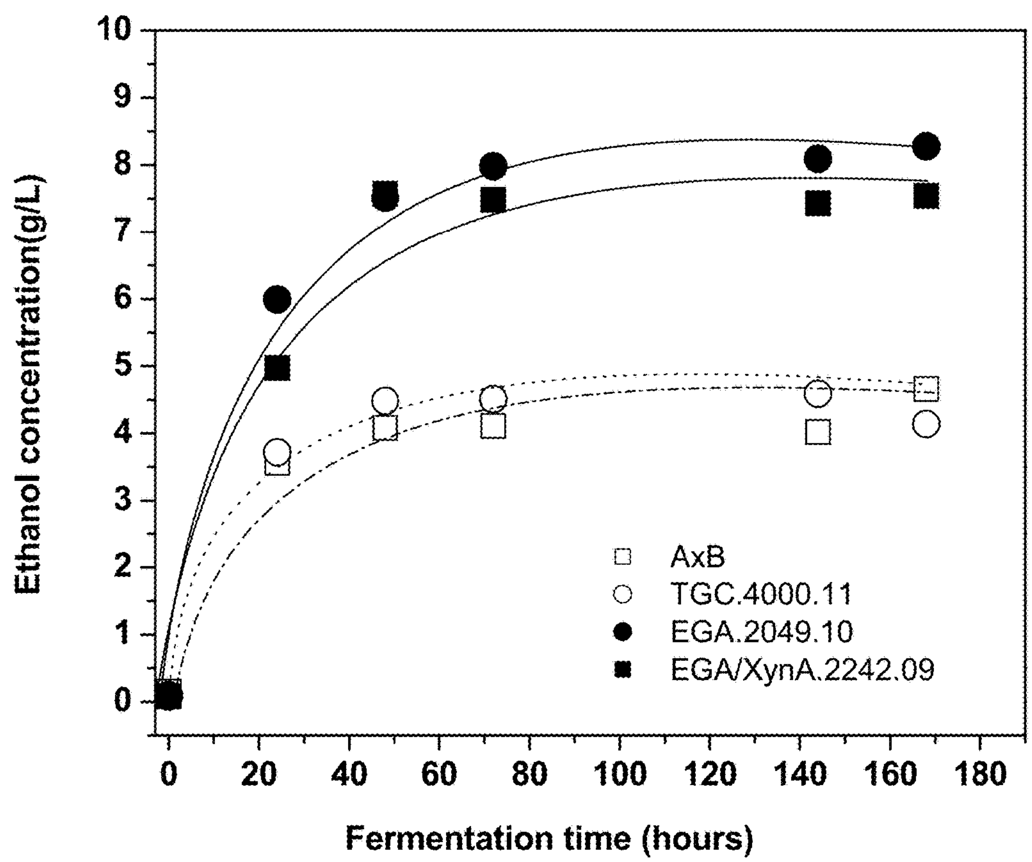

FIG. 22 illustrates ethanol production from simultaneous saccharification and fermentation (SSF) of pretreated transgenic plants EGA.2049.10 and EGA/XynA.2242.09 against control plants using 1) the enzyme cocktails Accellerase® 1500 and Accellerase® XY; and 2) yeast strain *Saccharomyces cerevisiae* D5A.

Figure 23:
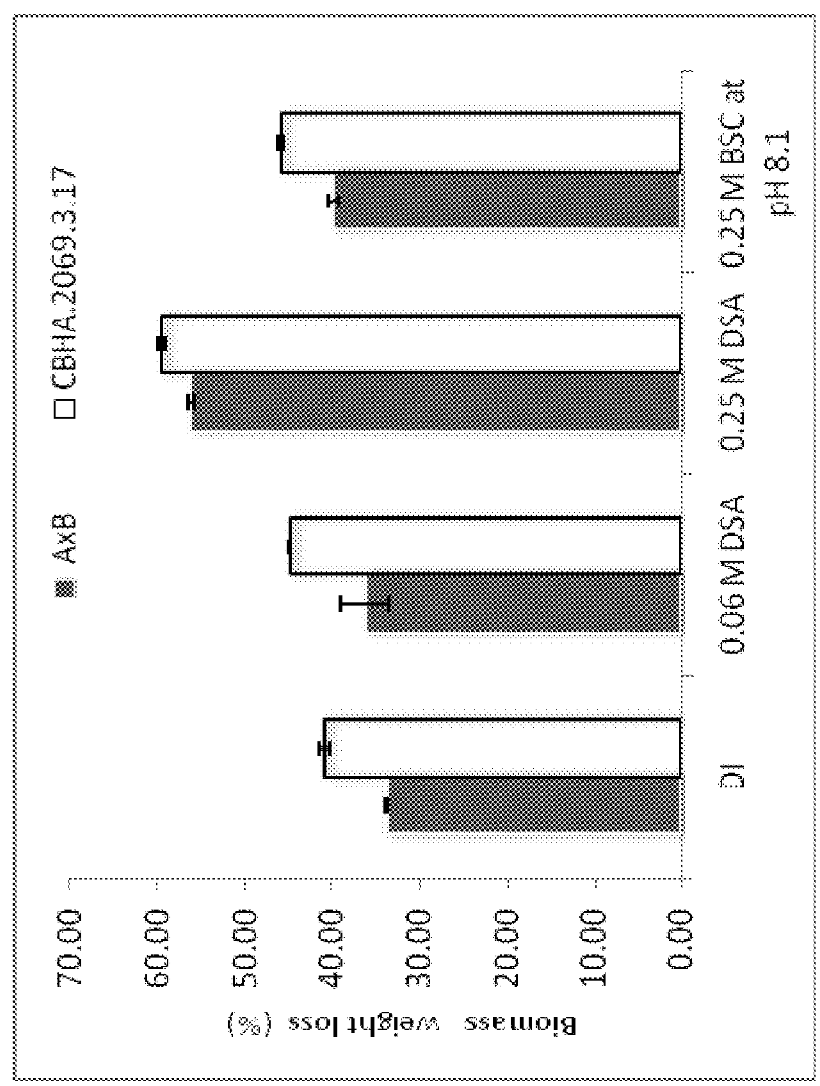

FIG. 23 illustrates biomass solubilization based on weight loss in a transgenic plant expressing exoglucanase CBHA (CBHA.2069.3.17; white) and a wild-type control plant (AxB; gray).

FIGS. 24A-24B illustrate yield of acetic acid (HAc) from a non-transgenic control plant (AxB; FIG. 24A) and a transgenic plant expressing exoglucanase CBHA (CBHA.2063.3.17; FIG. 24B). The treatments were performed at 75° C. for 16 hours (white (left)); 85° C. for 7 hours (striped bars (middle)) and 95° C. (checked (right)).

FIGS. 25A-25B illustrate yield of sugar degradation products hydroxymethylfurfural (HMF) and furfural from a non-transgenic control plant (AxB; FIG. 25A) and a transgenic plant expressing exoglucanase CBHA (CBHA.2063.3.17). The treatments as indicated by white, striped or checked bars were as follows from left to right: white, HMF_75° C. for 16 hours; striped, HMF_85° C. for 7 hours; checked, HMF_95° C. for 16 hours; striped, Furfural_95° C. for 16 hours).

Figure 26:
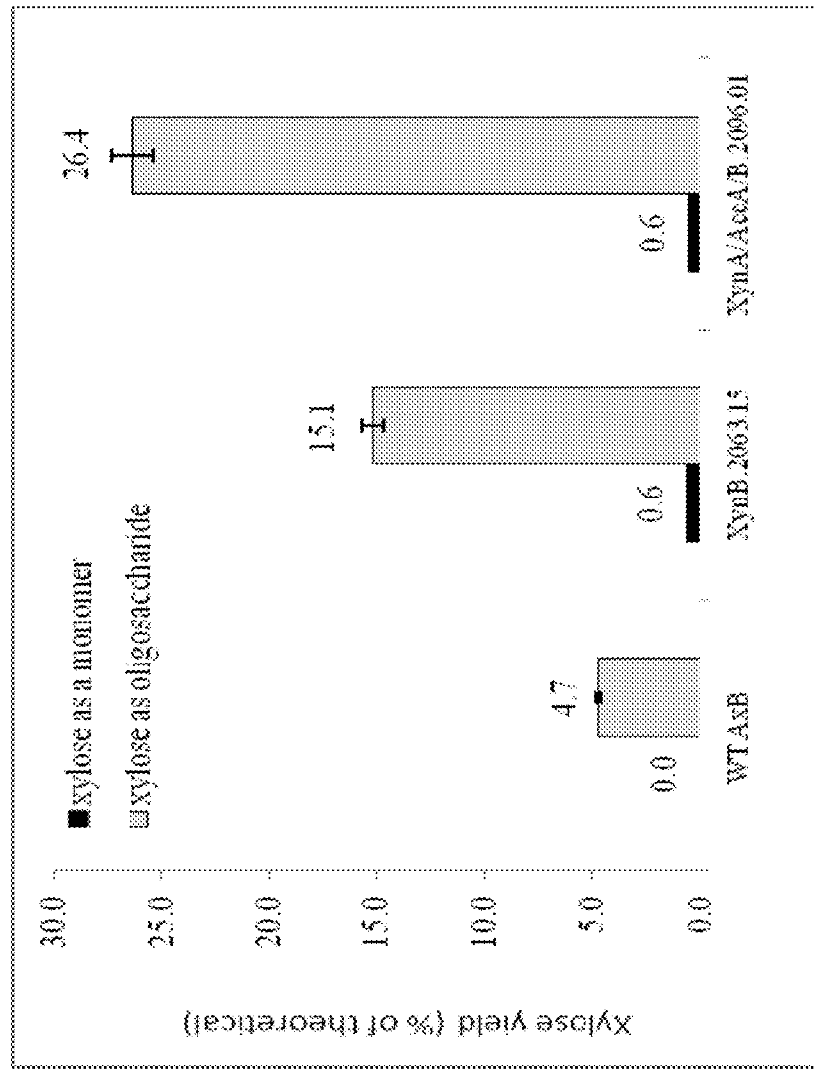

FIG. 26 illustrates xylose yield from a transgenic plant expressing xylanase B alone (XynB.2063.15), a transgenic plant expressing xylanase A and two accessory enzymes A and B (XynA/AccA/B.2096.1) and a non-transgenic control plant (WT AxB) following pretreatment with 0.17M ammonium bisulfite and ammonium carbonate (BSC; pH 8.1) and autohydrolysis. Xylose yield was assessed for xylose as a monomer (black (right)) and xylose as oligosaccharide (gray (left)).

Figure 27:
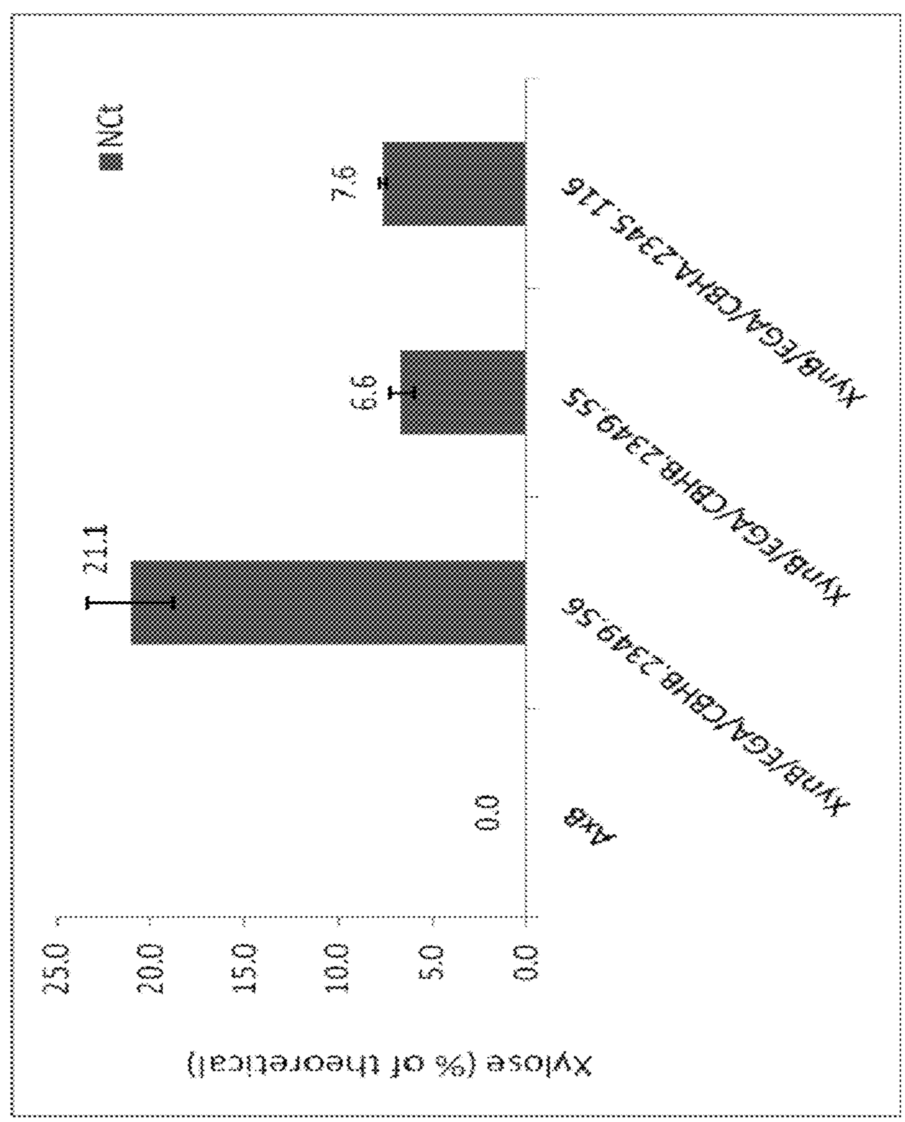
Figure 28B:
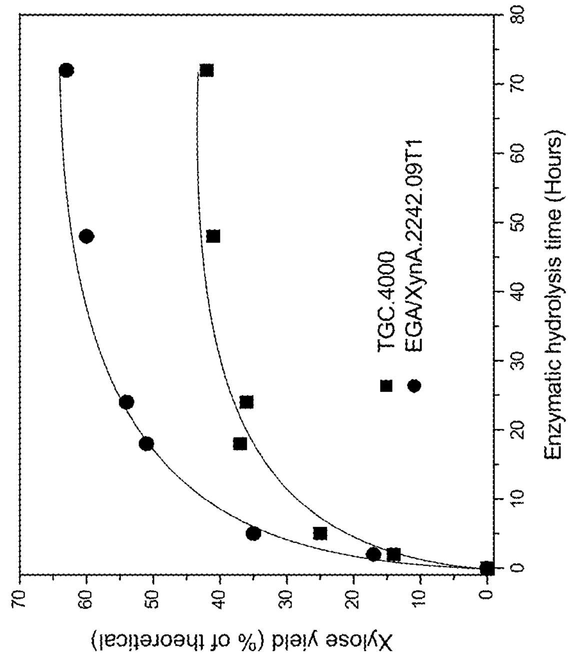
Figure 28A:
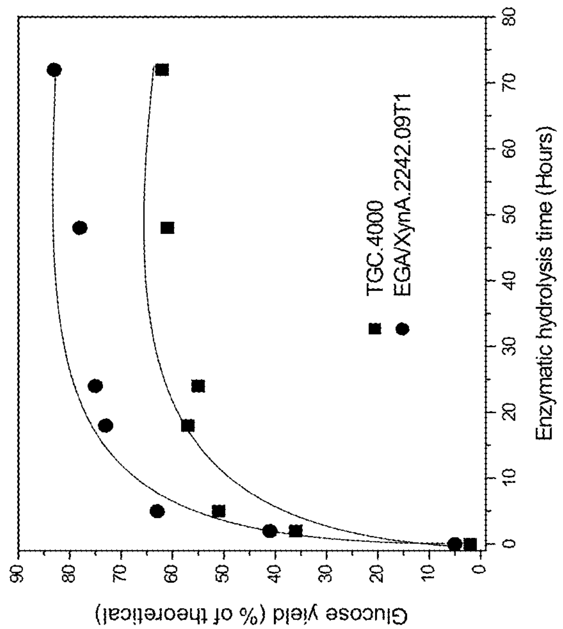

FIG. 27 illustrates xylose yields from two transgenic plant expressing xylanase B, endoglucanase, and CBHB (XynB/EGA/CBHB.2349.56 and XynB/EGA/CBHB.2349.55), a transgenic plant expressing xylanase B, endoglucanase and CBHA (XynB/EGA/CBHA.2345.116) and a non-transgenic control plant (AxB) following pretreatment with 0.17M ammonium bisulfite and 0.165M ammonium carbonate (BSC; pH 8.1) and autohydrolysis FIGS. 28A-28B illustrate glucose and xylose yields, respectively, from pretreated transgenic plants using Accellerase® XY. EGA/XynA.2242.09T1 (closed circle) simultaneously expressed endoglucanase and xylanase A, and the transgenic control plant was TGC.4000 (closed square).

Figure 28D:
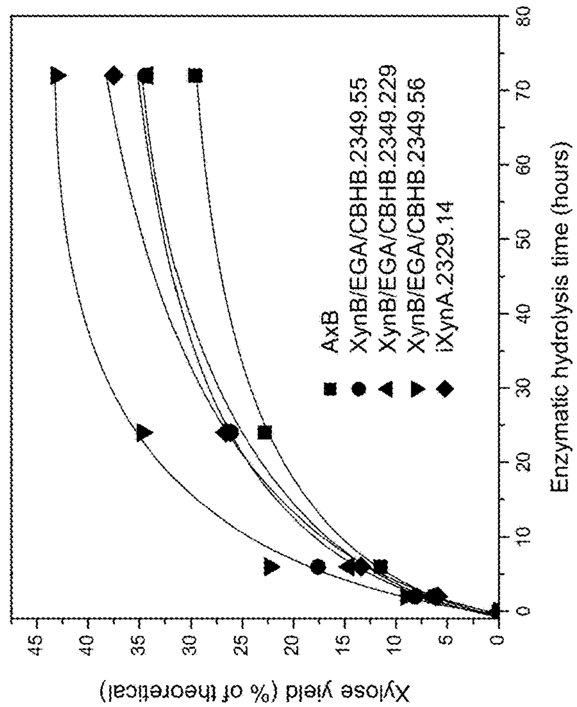
Figure 28C:
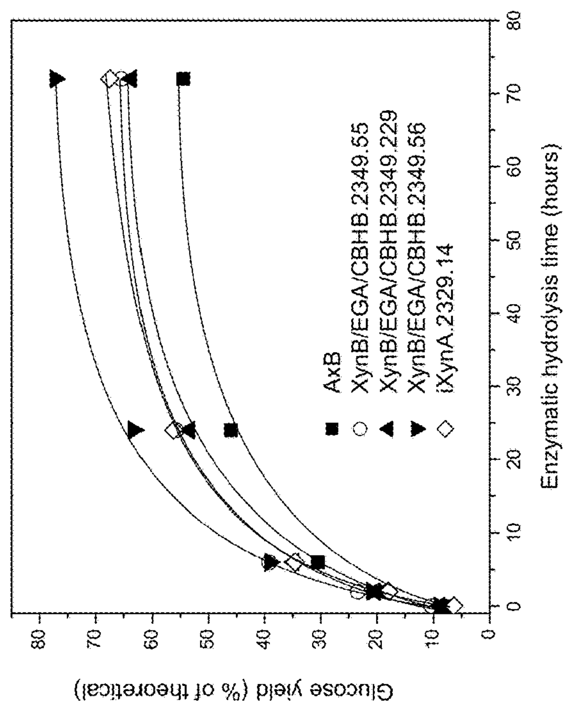

FIGS. 28C-28D show, respectively, glucose and xylose yields from XynB/EGA/CBHB.2349.55 (open circle), XynB/EGA/CBHB.2349.229 (closed triangle, point up), and XynB/EGA/CBHB.2349.56 (closed triangle, point down), each of which simultaneously expressed endoglucanase A, xylanase B, and cellobihydrolase B, and iXynA.2329.14, which expressed intein-modified xylanase A and a wild type control plant AxB.

DETAILED DESCRIPTION OF THE PREFERRED EMBODIMENTS

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

Embodiments herein provide technologies to express a portfolio of cell wall degrading (CWD) proteins in a plant. The CWD proteins may be CWD enzymes or modified forms of the CWD enzymes. The modified forms may be intein modified CWD proteins. The plant may be maize, sorghum, switchgrass, or another plant. Embodiments herein provide for harvesting plant biomass with in planta CWD proteins for use as a feedstock in sugar production. In planta enzyme expression uses the plant as a "factory" rather than microbial fermentation to produce industrial CWD enzymes. This strategy has an advantage of delivering the proteins directly in the biomass feedstocks for fermentable sugar production. Transgenic plant biomass with hydrolytic traits may not require harsh pretreatments to improve cellulose cell wall accessibility to exogenous enzymes. The expression of different classes of CWD proteins in a single plant may create a low cost sugar platform for biofuel and biochemical production. Embodiments herein provide methods for producing soluble sugars using a mild chemical pretreatment of lignocellulosic biomass derived from plants genetically engineered to include one or more types of a CWD protein.

An embodiment provides a method for producing soluble sugars from engineered plant material. The method may include pretreating the engineered plant material through mixing with a pulping formulation to form a mixture. The engineered plant material may include a first polynucleotide sequence encoding a first protein. The first protein may be a CWD enzyme. The first protein may be an intein-modified CWD enzyme. The first protein may be a xylanase, an endoglucanase, an exoglucanase, a feruloyl esterase, an intein-modified xylanase, an intein-modified endoglucanase, an intein-modified exoglucanase, or an intein-modified feruloyl esterase. The first protein may be capable of hydrolyzing a component of the engineered plant material. Being capable of hydrolyzing a component means that the first protein catalyzes hydrolysis of the component under hydrolysis conditions. In the case of an intein modified first protein, being capable of hydrolyzing a component means that after the intein has spliced from the peptide, the protein may hydrolyze the component under hydrolysis conditions. The method may further include providing hydrolysis conditions. The hydrolysis conditions may be suitable for hydrolyzing the component.

The engineered plant material may further include a second polynucleotide sequence encoding a second protein. The second protein may be a CWD protein. The second protein maybe an intein-modified CWD protein. The second protein may be a xylanase, an endoglucanase, an exoglucanase, a feruloyl esterase, an intein-modified xylanase, an intein-modified endoglucanase, an intein-modified exoglucanase, or an intein-modified feruloyl esterase. The protein selected as the second protein may be different than the protein selected as the first protein. The second protein may be capable of hydrolyzing a component of the engineered plant material. Being capable of hydrolyzing a component means that the second protein catalyzes hydrolysis of the component under hydrolysis conditions. In the case of an intein modified second protein, being capable of hydrolyzing a component means that after the intein has spliced from the peptide, the protein may hydrolyze the component under hydrolysis conditions.

The engineered plant material may further include a third polynucleotide sequence encoding a third protein. The third protein may be a CWD protein. The third protein maybe an intein-modified CWD protein. The third protein may be a xylanase, an endoglucanase, an exoglucanase, a feruloyl esterase, an intein-modified xylanase, an intein-modified endoglucanase, an intein-modified exoglucanase, or an intein-modified feruloyl esterase. The protein selected as the third protein may be different than the protein selected as the first protein. The protein selected as the third protein may be different than the protein selected as the second protein. The third protein may be capable of hydrolyzing a component of the engineered plant material. Being capable of hydrolyzing a component means that the third protein catalyzes hydrolysis of the component under hydrolysis conditions. In the case of an intein modified third protein, being capable of hydrolyzing a component means that after the intein has spliced from the peptide, the protein may hydrolyze the component under hydrolysis conditions.

Engineered plant material refers to a transgenic plant, progeny of a transgenic plant, a descendant of a transgenic plant, or a part of any of the foregoing. Engineered plant material may include a cell wall degrading enzyme, which does not occur naturally in the plant, or a gene encoding the same. Engineered plant material may be a transgenic plant expressing a CWD protein, or any part of the transgenic plant. Engineered plant material may be any transgenic plant expressing a modified form of a CWD protein, or any part of the transgenic plant. The transgenic plant may be of any type of plant. The transgenic plant type of plant may be but is not limited to maize, sugar beet, sugar cane, sorghum, switchgrass, *miscanthus, eucalyptus*, willow, or poplar. Engineered plant material may be a whole transgenic plant or parts of the plant. The parts may be but are not limited to leaves, stems, flowers, buds, petals, ovaries, fruits, or seeds. Engineered plant material may be callus from a transgenic plant. Engineered plant material may be regenerated from parts of a transgenic plant or plants. Engineered plant material may be a product of sexual crossing of a first transgenic plant and a second transgenic plant or a non-transgenic plant where the product plant retains a polynucleotide sequence introduced to the first transgenic plant. The transgenic plant may be any one of the transgenic plants provided herein. The transgenic plant may include any vector, expression cassette, or isolated nucleic acid or fragment thereof herein.

Mixing of engineered plant material with a pulping formulation may be done by any combination of the engineered plant mater with the pulping formulation. Mixing may be done by agitation.

The pulping formulation may be a substance that breaks down lignin, which binds the lignocellulose fibers within lignocellulosic plant material together. The substance may break down ligin without seriously degrading the lignocellulose fibers. Pretreating may lead to a partial release of enzymes expressed in the genetically engineered plants and partial degradation of lignin within lignocellulosic plant material.

The method may include activation of a CWD protein before, during or after pretreating. The method may include activation of a CWD protein before, during or after providing hydrolysis conditions. The CWD protein being activated may be a first protein, second protein, or third protein, or any additional lignocellulose processing enzyme. A CWD protein may be modified to include an intein. The intein may be fused to the CWD enzyme on an end of the enzyme or within the enzyme. The intein may be inducible to splice by providing induction conditions. The induction conditions may be a particular temperature of the mixture. The induction conditions may be a temperature provided before, during, or after one of the pretreating or providing hydrolysis steps. Intein modified enzymes and conditions for inducing splicing of the inteins, which could be used as activation conditions, were described in U.S. application Ser. No. 10/886,393 filed Jul. 7, 2004 and PCT/US10/55746 filed Nov. 5, 2010, and PCT/US10/55669 filed Nov. 5, 2010 and PCT/US10/55751 filed Nov. 5, 2010, which are incorporated herein by reference as if fully set forth.

The component may be any moiety desired for processing. The component may be lignocellulosic material. The component may be the substrate for any CWD protein listed herein. The component may be the substrate for a xylanase, an endoglucanase, an exoglucanase, a feruloyl esterase. The component may be a moiety including a substrate for any CWD protein listed herein. The component may be a moiety including a substrate for a xylanase, an endoglucanase, an exoglucanase, a feruloyl esterase.

The method may also include adding other plant material before, during, or after mixing, pretreating, or providing hydrolysis conditions. Other plant material may be any plant biomass, cellulosic or lignocellulosic material other than the engineered plant material. The other plant material may be from biorefineries. Other plant material may include forestry and agricultural residues. The forestry and agricultural residues may be, but are not limited to, corn stover, baggasses, wheat straw, waste wood, forest trimmings, waste paper, and municipal solid wastes (MSW). Other plant material may be any energy crop. The energy crop may be, but is not limited to, switchgrass, sorghum, sugar beet, sugar cane, *miscanthus* and poplar.

A polynucleotide sequence encoding a first protein, a second protein, a third protein, or any additional enzyme may be operably connected to a regulatory sequence. In this context, operably connected means that the regulatory element imparts it function to the polynucleotide sequence. In the case of a regulatory element that is a promoter, the promoter is capable of controlling expression from the polynucleotide sequence when they are operably connected. In the case of a regulatory element that is a terminator, the terminator is capable of terminating transcription from the polynucleotide sequence. Non-limiting examples of regulatory elements are provided below.

At least one of the first protein, the second protein, or the third protein may be but is not limited to an enzyme selected from XynA: Beta-1,4-xylanase 229B from Dictyoglomus *thermophilum* (Uniprot accession P77853); XynB: Endo-1, 4-beta-xylanase from *Thermomyces lanuginosus* (Uniprot accession O43097); EGA: Endo-beta 1,4-endoglucanase from *Nasutitermes takasagoensis* (Uniprot accession O77044); EGB: Endo-beta 1,4-endoglucanase from *Acidothermus cellulolyticus* (Uniprot accession P54583); AccA: Feruloyl esterase A from *Apergillus niger* (Uniprot accession O42807); AccB: Feruloyl esterase B from *Aspergillus niger* (Uniprot accession number Q8WZI8); AccA/B: Feruloyl esterase A and Feruloyl esterase B from *Aspergillus niger*; EGC: Endo-beta 1,4-endoglucanase from *Rhodothermus marinus* (Uniprot accession O33897); P40942: Beta-1, 4-xylanase from *Clostridium stercorarium* F9 (Uniprot accession number P40942); P40943: Beta-1,4-xylanase from *Geobacillus stearothermophilus* T-6 (*Bacillus stearothermophilus*;Uniprot accession number P40943); O30700: Beta-1,4-xylanase from *Bacillus* sp. NG-27(Uniprot accession number O30700); CBHA: cellobiohydrolase A from *Clostridium thermocellum* (Uniprot accession number O68438); CBHB: cellobiohydrolase B (SYT BD22308); or XynE: xylanase (EU591743).

The first protein may include, consist essentially of, or consist of an amino acid sequence with at least 70, 72, 75, 80, 85, 90, 91, 92, 93, 94, 95, 96, 97, 98, 99, or 100% identity to a reference sequence selected from the group consisting of: SEQ ID NO: 1[WT P77853], SEQ ID NO: 2 [AnfaeA], SEQ ID NO: 3 [AnfaeB], SEQ ID NO: 4 [NtEGm], SEQ ID NO: 5 [EU591743], SEQ ID NO: 6 [O43097], SEQ ID NO: 7 [P77853:T134-100-101], SEQ ID NO: 8 [P77853:5158-30-108-35], SEQ ID NO: 9 [O33897], SEQ ID NO: 10 [O68438], and SEQ ID NO: 11 [P54583]. The first protein may include, consist essentially of, or consist of an amino acid sequence with at least 70, 72, 75, 80, 85, 90, 91, 92, 93, 94, 95, 96, 97, 98, 99, or 100% identity to the reference sequence of SEQ ID: 12 [BD22308].

The second protein may include, or consist essentially of, or consist of an amino acid sequence with at least 70, 72, 75, 80, 85, 90, 91, 92, 93, 94, 95, 96, 97, 98, 99, or 100% identity to a second reference sequence selected from the group consisting of: SEQ ID NO: 1[WT P77853], SEQ ID NO: 2 [AnfaeA], SEQ ID NO: 3 [AnfaeB], SEQ ID NO: 4 [NtEGm], SEQ ID NO: 5 [EU591743], SEQ ID NO: 6 [O43097], SEQ ID NO: 7 [P77853:T134-100-101], SEQ ID NO: 8 [P77853:5158-30-108-35], SEQ ID NO: 9 [O33897], SEQ ID NO: 10 [O68438], and SEQ ID NO: 11 [P54583].

The second protein may include, consist essentially of, or consist of an amino acid sequence with at least 70, 72, 75, 80, 85, 90, 91, 92, 93, 94, 95, 96, 97, 98, 99, or 100% identity to the reference sequence of SEQ ID: 12 [BD22308].

The third protein may include, consist essentially of, or consist of an amino acid sequence with at least 70, 72, 75, 80, 85, 90, 91, 92, 93, 94, 95, 96, 97, 98, 99, or 100% identity to a third reference sequence selected from the group consisting of SEQ ID NO: 1[WT P77853], SEQ ID NO: 2 [AnfaeA], SEQ ID NO: 3 [AnfaeB], SEQ ID NO: 4 [NtEGm], SEQ ID NO: 5 [EU591743], SEQ ID NO: 6 [O43097], SEQ ID NO: 7 [P77853:T134-100-101], SEQ ID NO: 8[P77853:5158-30-108-35], SEQ ID NO: 9 [O33897], SEQ ID NO: 10 [O68438], and SEQ ID NO: 11 [P54583]. The third protein may include, consist essentially of, or consist of an amino acid sequence with at least 70, 72, 75, 80, 85, 90, 91, 92, 93, 94, 95, 96, 97, 98, 99, or 100% identity to the reference sequence of SEQ ID: 12 [BD22308].

At least one of the first polynucleotide sequence, the second polynucleotide sequence, or the third polynucleotide sequence may further include a first targeting polynucleotide sequence encoding a respective targeting peptide. For engineered plant material lacking the third polynucleotide sequence, a first targeting polynucleotide sequence may be included on at least one of the first polynucleotides sequence or the second polynucleotide sequence. For engineered plant material lacking the second polynucleotide sequence and the third polynucleotide sequence, a first targeting polynucleotide sequence may be included on the first polynucleotide sequence. Each respective targeting peptide may be independently selected for each of the first, the second, or the third polynucleotide sequence. A targeting peptide may be fused to the first protein, the second protein, or the third protein. Each respective targeting peptide may be independently selected from but is not limited to an amyloplast targeting signal, a cell wall targeting peptide, a mitochondrial targeting peptide, a cytosol localization signal, a chloroplast targeting signal, a nuclear targeting peptide, and a vacuole targeting peptide.

A first targeting polynucleotide may be upstream of the first polynucleotide sequence, the second polynucleotide sequence or the third polynucleotide sequence. A targeting peptide may have at least 70, 72, 75, 80, 85, 90, 91, 92, 93, 94, 95, 96, 97, 98, 99, or 100% identity to one of SEQ ID NO: 13 [BAASS], the barley aleurone sequence SEQ ID NO: 14 [HVAlePS], SEQ ID NO: 15 [PR1a], SEQ ID NO: 16 [the gamma-zein sequence xGZein27ss-02], or SEQ ID NO: 17 [Glu B4SP].

A first targeting polynucleotide sequence in combination with one of the first polynucleotide sequence, the second polynucleotide sequence, or the third polynucleotide sequence together may encode an amino acid sequence with at least 70, 72, 75, 80, 85, 90, 91, 92, 93, 94, 95, 96, 97, 98, 99, or 100% identity to a reference sequence selected from the group consisting of: SEQ ID NO: 18 [BAASS:P77853], SEQ ID NO: 19 [BAASS:O33897], SEQ ID NO: 20 [HVAlePS:NtEGm], and SEQ ID NO: 21 [BAAS:P77853:5158-30-108-35].

At least one of the first polynucleotide sequence, the second polynucleotide sequence, or the third polynucleotide sequence may further include a second targeting polynucleotide sequence encoding a carboxy targeting peptide. For engineered plant material lacking the third polynucleotide sequence, a second targeting polynucleotide sequence may be included on at least one of the first polynucleotide sequence or the second polynucleotide sequence. For engineered plant material lacking the second polynucleotide sequence and the third polynucleotide sequence, a second targeting polynucleotide sequence may be included on the first polynucleotide sequence. A carboxy targeting peptide may be selected from but is not limited to sequence having at least 70, 72, 75, 80, 85, 90, 91, 92, 93, 94, 95, 96, 97, 98, 99, or 100 identity to one of SEQ ID NO: 22 [SEKDEL], the abridged SEQ ID NO: 23 [KDEL], or the barley vacuolar sorting determinant sequence SEQ ID NO: 24 [HvVSD-01]. A carboxy targeting peptide may be fused to at least one of the first protein, the second protein, or the third protein.

At least one of the first protein, the second protein, or the third protein may be provided without the targeting peptide for accumulation in cytoplasm.

The first targeting polynucleotide sequence and the second targeting polynucleotide sequence in combination with one of the first polynucleotide sequence, the second polynucleotide sequence, or the third polynucleotide sequence together may encode an amino acid sequence with at least 70, 72, 75, 80, 85, 90, 91, 92, 93, 94, 95, 96, 97, 98, 99, or 100% identity to a reference sequence selected from the group consisting of: SEQ ID NO: 25 [BAASS: AnfaeB: SEKDEL], SEQ ID NO: 26 [BAASS:AnfaeA:SEKDEL], SEQ ID NO: 27 [PR1a:NtEGm:SEKDEL], SEQ ID NO: 28 [BAASS: P77853:T134-100-101:SEKDEL], SEQ ID NO: 29 [HvAleSP:NtEGm:SEKDEL], SEQ ID NO: 30 [BAASS: O43097:SEKDEL] and SEQ ID NO: 31[xGZein27ss-02: BD22308:HVVSD-01].

At least one of the first, the second or the third polynucleotide sequence may encode a "variant" of a CWD protein. The amino acid sequence of a variant of a CWD protein may differ by deletions, additions, substitutions of amino acid sequences, or other modifications of the CWD protein. A variant of a CWD protein may maintain the biological activity of the CWD protein. To maintain biological activity as used herein means that the variant has at least 60% of the activity of the CWD protein from which it is derived Activity of a xylanase may be assessed in an assay using Xylazyme AX substrate as described herein in the sub-section of Example 1 herein entitled "Stover Enzyme Assay. " Activity of a endoglucanase may be assessed by using Cellazyme substrate as described herein in the sub-section of Example 1 herein entitled "Stover Enzyme Assay." Activity of a exoglucanase may be assessed by using fluorescent 4-methylumbelliferyl-b-D-lactopyranoside (4-MU) as described in Harrison M D et al. 2011 "Accumulation of recombinant cellobiohydrolase and endoglucanase in the leaves of mature transgenic sugar cane," Plant Biotechnology Journal 9: 884-896 and incorporated here by reference as if fully set forth. Activity of a feruloyl esterase may be assessed using an assay using pNP labeled ferulate as a substrate (as described in Hegde S. et al. 2009 "Single-step synthesis of 4-nitrophenyl ferulate for spectrophotometric assay of feruloyl esterases," Analytical Biochemistry 387 (1): 128-129). The foregoing tests for activity of a xylanase, endoglucanase, exoglucanase, or feruloyl esterase may be utilized to determine whether a sequence with less than 100% identity to a CWD degrading protein sequence herein is a variant of the CWD degrading protein. Variants of a CWD protein herein may be modified in amino acid sequence versus the CWD protein based on similarity in hydrophobicity, hydrophilicity, solubility, polarity of amino acid residues. Variants of a CWD protein herein may differ following post-translational modifications. The differing post-translational modification may be but are not limited to glycosylations, acetylations, or phosphorylations. A variant may be developed by any means. A variant may be developed through site-directed mutagenesis or non-targeted mutagenesis. Error-prone PCR may be used to create mutants of a CWD protein herein, and any of the assays above may be used to assess whether the mutant is a variant.

Embodiments include at least one of the first protein, the second protein, or the third protein, or variants thereof, fused to variants of at least one of a targeting peptide, or a carboxy targeting peptide. Variants of a targeting peptide or a carboxy targeting peptide will target the protein it is fused with to the same location as the reference sequence for the targeting peptide or carboxy targeting peptide.

Variants of intein may be provided in a first protein, a second protein, or a third protein. An intein variant may splice from the protein in which it is fused.

For determining percent identity of two amino acid sequences or two nucleic acid sequence may include aligning and comparing the amino acid residues or nucleotides at corresponding positions in the two sequences. If all positions in two sequences are occupied by identical amino acid residues or nucleotides then the sequences are said to be 100% identical. Percent identity may be measured by the Smith Waterman algorithm (Smith T F, Waterman M S 1981 "Identification of Common Molecular Subsequences," J Mol Biol 147: 195-197, which is incorporated herein by reference as if fully set forth).

In an embodiment, a polynucleotide sequence that encodes a protein having less than 100% identity to the cited amino acid reference sequence may encode a variant of the protein having the amino acid reference sequence. In an embodiment, a protein having less than 100% identity to the cited amino acid reference sequence may be a variant of the protein having the amino acid reference sequence. In an embodiment, a polynucleotide sequence that encodes a protein having less than 100% identity to the protein encoded by the cited nucleic acid reference sequence may encode a variant of the protein encoded by the reference sequence.

Figure 1:
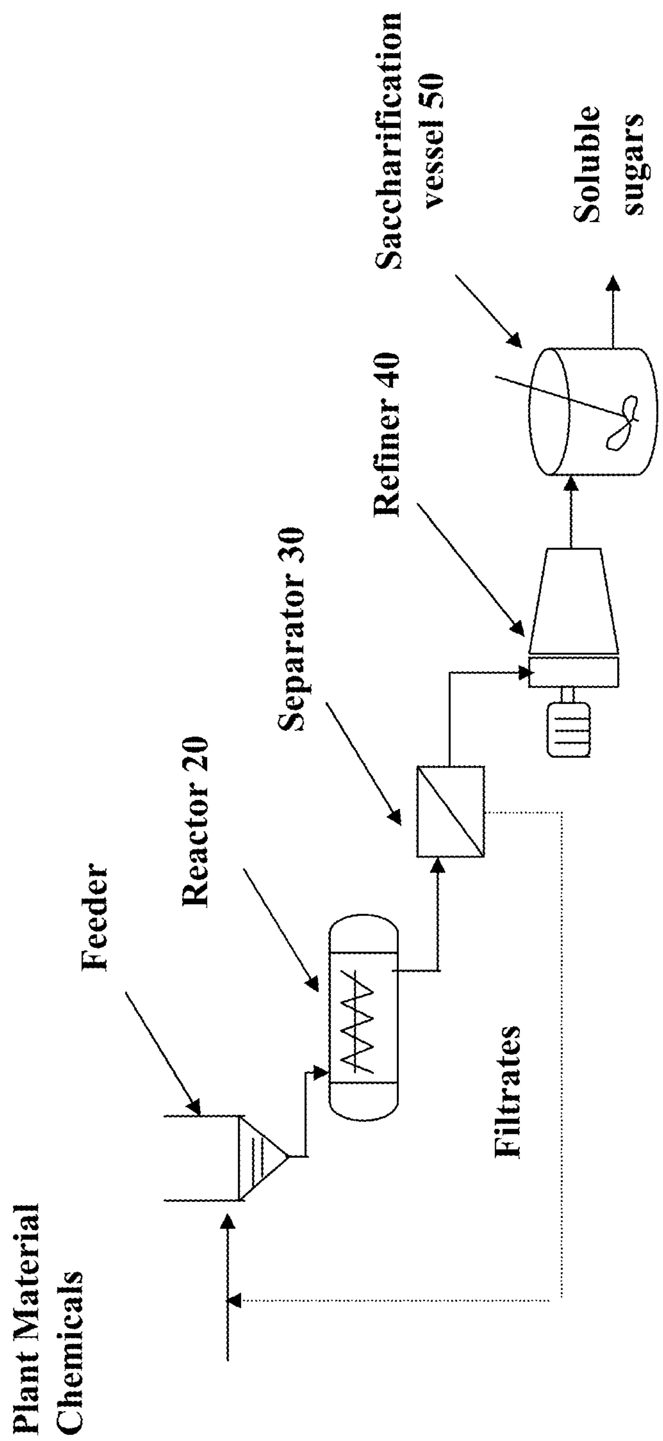
FIG. 1 is a process flow diagram illustrating steps of consolidated pretreatment and hydrolysis of plant biomass expressing cell wall degrading enzymes.

Referring to FIG. 1, a method for producing soluble sugars from engineered plant material is illustrated. FIG. 1 depicts a process flow for consolidated pretreatment and hydrolysis of engineered plant material. Engineered plant material or engineered plant material admixed with other plant material may be added through Feeder 10 to Reactor 20 for chemical pretreatment and enzymatic liquefaction; i.e., the process of conversion of solid lignocellulosic biomass into a liquefied state suitable for further processing and hydrolysis. In Reactor 20, engineered plant material or engineered plant material admixed with other plant material may be mixed with the pulping formulation. The pulping formulation may include at least one moiety having an ion selected from the group consisting of: sulfite, bisulfite, sulfate, carbonate, hydroxide, and oxide. The at least one moiety further may include but is not limited to a counter ion selected from the group consisting of: ammonium, sodium, magnesium, and calcium. The at least one moiety may be a salt. A salt may be but is not limited to a sulfite ($SO_3^{2-}$), a bisulfite ($HSO_3^-$), an oxide ($O^{2-}$) and a hydroxide ($OH^-$). The salt may include a counter ion. A counter ion may be but is not limited to sodium (Nat), calcium ($Ca^{2+}$), hydrogen, potassium ($K^+$), magnesium ($Mg^{2+}$), and ammonium ($NH_4^+$). A pulping formulation may include at least one of calcium oxide (CaO), lime, or calcium hydroxide ($Ca(OH)_2$), shaked lime.

In an embodiment, a pulping formulation may include at least one of ammonium bisulfite and ammonium carbonate. The ammonium bisulfite may be at a concentration of 0.02 M to 0.35 M and the ammonium carbonate may be at a concentration of 0.025 M to 0.25 M. The pulping formulation may be mixed with the engineered plant material or engineered plant material admixed with other plant material at an optimal liquid-to-solid ratio in a mixture. The mixture may have a liquid to solid ratio selected from the value of less than or equal to one of 10, 9, 8, 7, 6, 5, 4, 3, 2, or 1, or any value in a range between any two of the foregoing (endpoints inclusive). For example, the liquid to solid ratio may be a value less than any integer or non-integer number selected from 3 to 7. The liquid-to-solid ratio may be equal to 10, 9, 8, 7, 6, 5, 4, 3, 2, or 1, or any value in a range between any to of the foregoing (endpoints inclusive). For example, the liquid to solid ratio may be a value equal to any integer or non-integer number in the range from 3 to 7.

Pretreating may include incubating the mixture for any period of time. Pretreating may include incubating the mixture for up to 16 hours. Incubating may occur for longer or shorter periods may be performed. Pretreating may include incubating the mixture for a period of less or equal to one of 16, 15, 14, 13, 12, 11, 10, 9, 8, 7, 6, 5, 4, 3, 2, or 1 hour(s).

Pretreating may include providing a mixture temperature of 40° C. to 95° C. A mixture temperature of 40° C. to 95° C. may allow breakage or removal of portions of lignin within the lignocellulosic material in the mixture without deactivating hydrolytic enzymes. Pretreating may include providing a mixture temperature of 55° C., 65° C., 75° C., 95° C., less than 55° C., less than 65° C., less than 75° C., less than 95° C., less than 100° C., 40° C. to 55° C., 40° C. to 65° C., 40° C. to 75° C., 40° C. to 95° C., 40° C. to less than 100° C., 55° C. to 65° C., 55° C. to 75° C., 55° C. to 95° C., 55° C. to less than 100° C., 65° C. to 75° C., 65° C. to 95° C., 65° C. to less than 100° C., 75° C. to 95° C., 75° C. to less than 100° C., or 95° C. to less than 100° C.

Pretreating may include providing a mixture pH ranging from 5.0 to 10. Pretreating may include providing a mixture pH within a range of 6.5 to 8.5. The mixture pH provided may be 5.0, 5.5, 6.0, 7.0, 7.5, 8.0, 9.0, 9.5, or 10, or a pH within a range between any two of the foregoing pH values (endpoints inclusive). The pH of the mixture during pretreating may depend on the type of chemical used and/or type of plant material used. Providing a mixture pH may include adding a pH modifying chemical. A pH modifying chemical may be an acid or an alkali.

At the end of the pretreating step, the mixture may include partially degraded plant material and a liquid phase called a partial filtrate that may include chemicals from the pulping formulation and a low concentration of CWD enzyme or enzymes released from engineered plant material. The method may include separating the partial filtrate from solids of partially degraded plant material in Separator 30. Separation may be achieved through various processes. Separation may be achieved through sedimenting, filtering, or centrifuging the partial filtrate. The method may include at least one of collecting or recycling at least a portion of the partial filtrate in multiple rounds of pretreating. After removal of the partial filtrate, the concentration of solids within the mixture may be increased and may be any integer or non-integer value within a range of 2% to 15% (w/v), or any range within two integer values within the range of 2% to 15% (w/v).

The method may include washing the pretreated engineered plant material with any suitable liquid. The liquid may be deionized water. The liquid may be removed by centrifugation.

The method may further include refining by mechanical grinding, which is performed in Refiner 40 by any known method, such as, but is not limited to, defibrillation, milling, or crashing.

The method may include transferring refined pretreated biomass to Saccharification vessel 50. Hydrolysis by a CWD enzyme released from engineered plant material may occur in Saccharification vessel 5.

Providing hydrolysis conditions may include adjusting the mixture to 2% to 25% solids, to any integer or non-integer value within 2% to 25% solids (endpoints inclusive), or to any integer or non-integer value within a range between any two integers within 2% to 25% solids. Providing hydrolysis conditions may include incubating the mixture for a period of time up to 144 hours, a period of time selected from any one integer or non-integer value up to 144 hours, or a period of time within a range between any two integer values greater than zero and up to 144 hours. Providing hydrolysis conditions may include providing a mixture temperature of 100° C. or less, 65° C. or less, 50° C. or less, 48° C. to 50° C., 48° C. to 65° C., 48° C. to less that 100° C., or 48° C. to 100° C. Providing hydrolysis conditions may include providing a pH ranging from 4.8 to 5.0, a pH of 4.8, a pH of 4.9, or a pH of 5.0. At least one of the temperature, pH, or time of treatment, may be selected based on the specific activity of a CWD enzyme in the engineered plant material.

If the engineered plant material includes multiple CWD enzymes, conditions optimal for at least one of expression, pretreating, or hydrolysis by each of the multiple CWD enzymes may be provided sequentially. Hydrolysis conditions may include providing a pH optimal for activity of one enzyme, followed by a different pH optimal for activity of another enzyme. Hydrolysis conditions may include adjusting temperatures at different periods of time for optimal activity of each enzyme. For example, a xylanase may require a different temperature or pH than an endoglucanase.

The method may include adding one or more exogenous enzymes to at least one of the engineered plant material, other plant material, or the mixture. The exogenous enzymes may be added before, during, or after pretreating. The exogenous enzymes may be added before, during, or after providing hydrolysis conditions. Exogenous enzymes may be added to Saccharification vessel 50. One or more exogenous enzymes may be provided in an enzyme cocktail. An enzyme cocktail may include one or more CWD enzymes. A CWD enzyme provided in an embodiment herein may be but is not limited to a lignin degrading enzyme, a cellulose degrading enzyme, or a hemicellulose degrading enzyme. A CWD enzyme provided in an embodiment herein may be but is not limited to one selected from glycosidases, xylanases, cellulases, endoglucanases, exoglucanases, cellobiohydrolases, β-xylosidases, feruloyl esterases, and amylases. An enzyme cocktail may include a cellulase isolated from *Trichoderma reesii*. An enzyme cocktail may be purchased from a vendor. An enzyme cocktail may be, but is not limited to, Accellerase™ 1000, Accellerase® 1500, and Accellerase® XY available from Genencor International (Rochester, N.Y.). An enzyme cocktail may be Cellic. An enzyme cocktail may include different classes of CWD enzymes. Optimal conditions for different classes of CWD enzymes in a cocktail may be provided. For example, the temperature, pH and time of treatment for hydrolysis may be adjusted during the method to provide optimal conditions for different enzymes in the cocktail. Hydrolysis conditions may include reduced loadings of external enzymes included in an enzyme cocktail. Reduced loadings may include formulations having less of or lacking a CWD protein or proteins expressed in engineered plant material. For example, if a transgenic plant expresses xylanase and endoglucanase, these enzymes may be removed from an enzyme cocktail formulated for hydrolysis of engineered plant material having the transgenic plant.

Efficiency of hydrolysis may be assessed by measuring solubilization of plant material. Methods to measure solubilization of plant material are known in the art and may include determining monosaccharide and disaccharide concentrations, for example by high performance liquid chromatography (HPLC). As described in Examples herein, HPLC may be performed using Shimadzu LC-20 AD binary pump with LC solutions software (Shimadzu, Kyoto, Japan) and sugar concentration may be determined using an Aminex HPX-87P sugar column (Bio-Rad Laboratories). Other methods to measure solubilization of plant material, for example, by determining weight loss, lignin removal, or deacetylation in the pretreated plant material, are available.

The method may further include contacting the mixture and/or products of hydrolysis with a fermenting organism to produce a biochemical product. After enzymatic hydrolysis, soluble sugars may be recovered and used for production of a biochemical product. Alternatively, simultaneous saccharification and fermentation of soluble sugars into a biochemical product may be performed in the method. A biochemical product may be but is not limited to butane, butanediol, butadiene, butanol, isobutanol, propane, propanediol, propylene, propanol, isopropanol, methane, methanol, ethanol, phenol, glycerol, ethylene, toluene, ethyl, benzene, styrene, xylene, ethylene glycol, ethylene oxide, formic acid, carbone dioxide, formaldehyde, acetaldehyde, acetone, a vitamin, ethane, pentane, hexane, heptane, octane, benzene, acetic acid, sorbitol, arabinitol, succinic acid, fumaric acid, malic acid, furan dicarboxylic acid, aspartic acid, glucaric acid, glutamic acid, itaconic acid, levulinic acid, hydroxybutyrolactone, glycerol, sorbitol, xylitol, arabinitol, gluconic acid, lactic acid, malonic acid, propionic acid, citric acid, aconitic acid, xylonic acid, furfural, levoglucosan, alanine, proline, lysine, serine, or threonine (See T. Werpy and G. Petersen, *Top Value Added Chemicals From Biomass*, Volume 1, Results of Screening for Potential Candidates from Sugars and Synthesis Gas, August 2004, Report, PNNL & NREL, which is incorporated herein by reference as if fully set forth). The method may include simultaneous saccharification and fermentation of soluble sugars to produce ethanol. Simultaneous saccharification and fermentation to produce ethanol may include providing *Saccharomyces cerevisiae* D5A before, during or after pretreating or providing hydrolysis conditions.

The conversion of sugars into desired biochemical products may be performed by any suitable fermenting organism. The fermenting organism may be selected based on the desired biochemical product. The fermenting organism may be yeast. The yeast may be but is not limited to one of *Saccharomyces, Kluyveromyces, Pichia, Yarrowia, Spathaspora* or *Scheffersomyces* ssp. The fermenting organism may be a bacterium. A bacterium may be but is not limited to a *Zymomonas, Escherichia, Bacillus, Lactobacillus*, or *Clostridium* ssp. The fermenting organism may be a wild type organism or a genetically engineered recombinant organism.

An embodiment includes an engineered plant including a first polynucleotide sequence encoding a first protein. The first protein may be a CWD protein. The first protein may be an intein-modified CWD protein. The first protein may by any one described with respect to the method for producing soluble sugars from engineered plant material. The first protein may include, consist essentially of, or consist of an amino acid sequence with at least 70, 72, 75, 80, 85, 90, 91, 92, 93, 94, 95, 96, 97, 98, 99, or 100% identity to a first reference sequence selected from the group consisting of: SEQ ID NO: 1[WT P77853], SEQ ID NO: 2 [AnfaeA], SEQ ID NO: 3 [AnfaeB], SEQ ID NO: 4 [NtEGm], SEQ ID NO: 5 [EU591743], SEQ ID NO: 6 [O43097], SEQ ID NO: 7 [P77853:T134-100-101], SEQ ID NO: 8[P77853:5158-30-108-35], SEQ ID NO: 9 [O33897], SEQ ID NO: 10 [O68438], and SEQ ID NO: 11 [P54583]. The first protein may include, consist essentially of, or consist of an amino acid sequence with at least 70, 72, 75, 80, 85, 90, 91, 92, 93, 94, 95, 96, 97, 98, 99, or 100% identity to the reference sequence of SEQ ID: 12 [BD22308].

The engineered plant may further include a second polynucleotide sequence encoding a second protein. The second protein may be a CWD enzyme. The second protein may be an intein-mothfied CWD protein. The second protein may by any one described with respect to the method for producing soluble sugars from engineered plant material. The second protein may include, consist essentially of, or consist of an amino acid sequence with at least 70, 72, 75, 80, 85, 90, 91, 92, 93, 94, 95, 96, 97, 98, 99, or 100% identity to a second reference sequence selected from the group consisting of: SEQ ID NO: 1[WT P77853], SEQ ID NO: 2 [AnfaeA], SEQ ID NO: 3 [AnfaeB], SEQ ID NO: 4 [NtEGm], SEQ ID NO: 5 [EU 591743], SEQ ID NO: 6 [O43097], SEQ ID NO: 7 [P77853:T134-100-101], SEQ ID NO: 8 [P77853:S158-30-108-35], SEQ ID NO: 9 [O33897], SEQ ID NO: 10 [O68438], SEQ ID NO: 11 [P54583], and SEQ ID: 12 [BD22308]. The SEQ ID NO selected as the second reference sequence may be different than the SEQ ID NO selected as the first reference sequence.

The engineered plant may further include a third polynucleotide sequence encoding a third protein. The third protein may be a CWD enzyme. The third protein may be an intein-modified CWD protein. The third protein may by any one described with respect to the method for producing soluble sugars from engineered plant material. The third protein may include, consist essentially of, or consist of an amino acid sequence with at least 70, 72, 75, 80, 85, 90, 91, 92, 93, 94, 95, 96, 97, 98, 99, or 100% identity to a third reference sequence selected from the group consisting of: SEQ ID NO: 1[WT P77853], SEQ ID NO: 2 [AnfaeA], SEQ ID NO: 3 [AnfaeB], SEQ ID NO: 4 [NtEGm], SEQ ID NO: 5 [EU591743], SEQ ID NO: 6 [O43097], SEQ ID NO: 7 [P77853:T134-100-101], SEQ ID NO: 8 [P77853:S158-30-108-35], SEQ ID NO: 9 [O33897], SEQ ID NO: 10 [O68438], SEQ ID NO: 11 [P54583], and SEQ ID: 12 [BD22308]. The SEQ ID NO selected as the third reference sequence may be different than the SEQ ID NO selected as the first reference sequence. The SEQ ID NO selected as the third reference sequence may be different than the SEQ ID NO selected as the second reference sequence.

At least one of the first polynucleotide sequence, the second polynucleotide sequence, or the third polynucleotide sequence in an engineered plant may further include a first targeting polynucleotide sequence encoding a respective targeting peptide. For an engineered plant lacking the third polynucleotide sequence, a first targeting polynucleotide sequence may be included on at least one of the first polynucleotide sequence or the second polynucleotide sequence. For an engineered plant lacking the second polynucleotide sequence and the third polynucleotide sequence, a first targeting polynucleotide sequence may be included on the first polynucleotide sequence. A respective targeting peptide may be independently selected from but is not limited to an amyloplast targeting signal, a cell wall targeting peptide, a mitochondrial targeting peptide, a cytosol localization signal, a chloroplast targeting signal, a nuclear targeting peptide, or a vacuole targeting peptide.

Each respective targeting peptide may be fused to the corresponding first protein, second protein, or third protein. A targeting peptide may have at least 70, 72, 75, 80, 85, 90, 91, 92, 93, 94, 95, 96, 97, 98, 99, or 100% identity to one of SEQ ID NO: 13 [BAASS], SEQ ID NO: 14 [HvAleSP], SEQ ID NO: 1 [PR1a] 5, SEQ ID NO: 16 [xGZein27ss-02], or SEQ ID NO: 17 [GluB4SP].

At least one of the first polynucleotide sequence, the second polynucleotide sequence, or the third polynucleotide sequence in an engineered plant may further include a second targeting polynucleotide sequence encoding a carboxy targeting peptide. For an engineered plant lacking the third polynucleotide sequence, a second targeting polynucleotide sequence may be included on at least one of the first polynucleotide sequence or the second polynucleotide sequence. For an engineered plant lacking the second polynucleotide sequence and the third polynucleotide sequence, a second targeting polynucleotide sequence may be included on the first polynucleotide sequence. A carboxy targeting peptide may be selected from but is not limited to sequence having at least 70, 72, 75, 80, 85, 90, 91, 92, 93, 94, 95, 96, 97, 98, 99, or 100 identity to one of SEQ ID NO: 22 [SEKDEL], the abridged SEQ ID NO: 23 [KDEL], or SEQ ID NO: 24 [the barley vacuolar sorting determinant sequence HvVSD-01]. A carboxy targeting peptide may be fused to at least one of the first protein, the second protein, or the third protein.

An engineered plant may include at least one polynucleotide sequence encoding an amino acid sequence including, consisting essentially of, or consisting of a sequence with at least 70, 72, 75, 80, 85, 90, 91, 92, 93, 94, 95, 96, 97, 98, 99, or 100% identity to a sequence selected from the group consisting of: SEQ ID NO: 18 [BAASS:P77853], SEQ ID NO: 19 [BAASS:O33897], SEQ ID NO: 20 [HVAlePS:NtEGm], SEQ ID NO: 21 [BAASS:P77853:5158-30-108-35], SEQ ID NO: 25 [BAASS: AnfaeB: SEKDEL], SEQ ID NO: 26 [BAASS:AnfaeA:SEKDEL], SEQ ID NO: 27 [PR1a:NtEGm:SEKDEL], SEQ ID NO: 28 [BAASS: P77853:T134-100-101:SEKDEL], SEQ ID NO: 29 [HvAleSP:NtEGm:SEKDEL], SEQ ID NO: 30 [BAASS: O43097:SEKDEL], and SEQ ID NO: 31 [xGZein27ss-02: BD22308:HvVSD-01].

An engineered plant may include at least one amino acid sequence including, consisting essentially of, or consisting of a sequence with at least 70, 72, 75, 80, 85, 90, 91, 92, 93, 94, 95, 96, 97, 98, 99, or 100% identity to a sequence selected from the group consisting of: SEQ ID NO: 18 [BAASS:P77853], SEQ ID NO: 19 [BAASS:O33897], SEQ ID NO: 20 [HVAlePS:NtEGm], SEQ ID NO: 21 [BAASS: P77853:5158-30-108-35], SEQ ID NO: 25 [BAASS: AnfaeB: SEKDEL], SEQ ID NO: 26 [BAASS:AnfaeA: SEKDEL], SEQ ID NO: 27 [PR1a:NtEGm:SEKDEL], SEQ ID NO: 28 [BAASS: P77853:T134-100-101:SEKDEL], SEQ ID NO: 29 [HvAleSP:NtEGm:SEKDEL], SEQ ID NO: 30 [BAASS:O43097:SEKDEL], and SEQ ID NO: 31 [xGZein27ss-02:BD22308:HvVSD-01].

The engineered plant may be a transgenic plant, progeny of a transgenic plant, a descendant of a transgenic plant, or any part of the foregoing. The engineered plant may include a CWD protein, which does not occur naturally in the plant, or a gene encoding the same. The CWD protein may be an intein-modified CWD protein. The transgenic plant may be any type of plant. The transgenic plant type may be maize, sugar cane, sugar beet, sorghum, switchgrass, *miscanthus, eucalyptus*, willow or poplar. The transgenic plant may be created by known methods to express a CWD enzyme or CWD protein in any form. The plant may be created by *Agrobacterium*-mediated transformation using a vector that includes a polynucleotide sequences encoding an enzyme. The transgenic plant may be created by other methods for transforming plants, for example, particle bombardment or direct DNA uptake. The transgenic plant may include any isolated nucleic acid, amino acid sequence, expression cassette, or vector herein.

In an embodiment, an expression cassette is provided that includes at least one of a first polynucleotide sequence, a second polynucleotide sequence, or a third polynucleotide sequence, which encode, respectively, a first protein, a second protein, and a third protein. Any one or more of the first protein, the second protein, or the third protein may be a CWD protein. Any one or more of the first protein, the second protein, or the third protein may be an intein-modified CWD protein. Any one or more of the first protein, the second protein, or the third protein may be one of the proteins described with respect to the method for producing soluble sugars from engineered plant material or the engineered plants. Any one or more of the first protein, the second protein, or the third protein may be a xylanase, an endoglucanase, an exoglucanase, a feruloyl esterase, an intein-modified xylanase, an intein-modified endoglucanase, an intein-modified exoglucanase, or an intein-modified feruloyl esterase. The protein selected as the second protein may be different than the protein selected as the first protein. The protein selected as the third protein may be different than the protein selected as the first protein. The protein selected as the third protein may be different than the protein selected as the second protein.

At least one of the first polynucleotide sequence, the second polynucleotide sequence, or the third polynucleotide sequence encoding a CWD protein in an expression cassette may be modified by insertion of the nucleic acid sequence encoding an intein. An intein-modified polynucleotide may encode an intein-modified protein with a modified function. A modified function may be inactivation of a CWD protein while the intein remains fused to or within the CWD protein. An intein in an intein-modified protein may be inducible to splice form the non-intein-modified protein. The induction condition for splicing may be but is not limited to providing a certain temperature. The temperature provided may be that provided during at least one of pretreating or hydrolysis conditions described with respect to the method for producing soluble sugars from engineered plant material. The induction condition may be any other induction condition that matches the intein selected. The intein-modified protein may be iXynA: i.e., intein-modified XynA. The intein-modified protein may be intein-modified P77853). The intein-modified protein may be P77853:T134-100-101 or P77853:S158-30-108-35.

One or more of the first protein, the second protein, or the third protein in an expression cassette may include, consist essentially of, or consist of an amino acid sequence with at least 70, 72, 75, 80, 85, 90, 91, 92, 93, 94, 95, 96, 97, 98, 99, or 100% identity to a reference sequence selected from the group consisting of: SEQ ID NO: 1[WT P77853], SEQ ID NO: 2 [AnfaeA], SEQ ID NO: 3 [AnfaeB], SEQ ID NO: 4 [NtEGm], SEQ ID NO: 5 [EU 591743], SEQ ID NO: 6 [O43097], SEQ ID NO: 7 [P77853:T134-100-101], SEQ ID NO: 8 [P77853:S158-30-108-35], SEQ ID NO: 9 [O33897], SEQ ID NO: 10 [O68438], and SEQ ID NO: 11 [P54583].

One or more of the first protein, the second protein, or the third protein may include, consist essentially of, or consist of an amino acid sequence with at least 70, 72, 75, 80, 85, 90, 91, 92, 93, 94, 95, 96, 97, 98, 99, or 100% identity to the reference sequence of SEQ ID: 12 [BD22308].

At least one of the first polynucleotide sequence, the second polynucleotide sequence, or the third polynucleotide sequence in an expression cassette may further include a first targeting polynucleotide sequence encoding a respective targeting peptide. For an expression construct lacking the third polynucleotide sequence, a first targeting polynucleotide sequence may be included on at least one of the first polynucleotide sequence or the second polynucleotide sequence. For an expression construct lacking the second polynucleotide sequence and the third polynucleotide sequence, a first targeting polynucleotide sequence may be included on the first polynucleotide sequence. Each respective targeting peptide may be independently selected for each of the first polynucleotide sequence, the second polynucleotide sequence, or the third polynucleotide sequence. A targeting peptide may be fused to the first protein, the second protein, or the third protein. Each respective targeting peptide may be independently selected from but is not limited to an amyloplast targeting signal, a cell wall targeting peptide, a mitochondrial targeting peptide, a cytosol localization signal, a chloroplast targeting signal, a nuclear targeting peptide, and a vacuole targeting peptide. A first targeting polynucleotide may be upstream of the first polynucleotide sequence, the second polynucleotide sequence or the third polynucleotide sequence. A targeting peptide may have at least 70, 72, 75, 80, 85, 90, 91, 92, 93, 94, 95, 96, 97, 98, 99, or 100% identity to one of BAASS (SEQ ID NO: 13), the barley aleurone sequence HVAlePS (SEQ ID NO: 14), PR1a (SEQ ID NO: 15), the gamma-zein sequence xGZein27ss-02 (SEQ ID NO: 16), or GluB4SP (SEQ ID NO: 17). A first targeting polynucleotide sequence in combination with one of the first polynucleotide sequence, the second polynucleotide sequence, or the third polynucleotide sequence together may encode an amino acid sequence with at least 70, 72, 75, 80, 85, 90, 91, 92, 93, 94, 95, 96, 97, 98, 99, or 100% identity to a reference sequence selected from the group consisting of: SEQ ID NO: 18 [BAASS:P77853], SEQ ID NO: 19 [BAASS:O33897], SEQ ID NO: 20 [HVAlePS:NtEGm] and SEQ ID NO: 21 [BAAS:P 77853:5158-30-108-35].

At least one of the first polynucleotide sequence, the second polynucleotide sequence, or the third polynucleotide sequence in an expression cassette may further include a second targeting polynucleotide sequence encoding a carboxy targeting peptide. For an expression construct lacking the third polynucleotide sequence, a second targeting polynucleotide sequence may be included on at least one of the first polynucleotide sequence or the second polynucleotide sequence. For an expression construct lacking the second polynucleotide sequence and the third polynucleotide sequence, a second targeting polynucleotide sequence may be included on the first polynucleotide sequence. A carboxy targeting peptide may be selected from but is not limited to sequence having at least 70, 72, 75, 80, 85, 90, 91, 92, 93, 94, 95, 96, 97, 98, 99, or 100 identity to one of SEKDEL (SEQ ID NO: 22), the abridged KDEL (SEQ ID NO: 23), or the barley vacuolar sorting determinant sequence HvVSD-01 (SEQ ID NO: 24). A carboxy targeting peptide may be fused to at least one of the first protein, the second protein, or the third protein.

An expression cassette may be configured such that at least one of the first protein, the second protein, or the third protein is be provided without the targeting peptide for accumulation in cytoplasm.

In an expression cassette, the first targeting polynucleotide sequence and the second targeting polynucleotide sequence in combination with one of the first polynucleotide sequence, the second polynucleotide sequence, or the third polynucleotide sequence together may encode an amino acid sequence with at least 70, 72, 75, 80, 85, 90, 91, 92, 93, 94, 95, 96, 97, 98, 99, or 100% identity to a reference sequence selected from the group consisting of: SEQ ID NO: 25 [BAASS: AnfaeB: SEKDEL], SEQ ID NO: 26 [BAASS: AnfaeA:SEKDEL], SEQ ID NO: 27 [PR1a:NtEGm: SEKDEL], SEQ ID NO: 28 [BAASS: P77853:T134-100-101:SEKDEL], SEQ ID NO: 29 [HvAleSP:NtEGm: SEKDEL], SEQ ID NO: 30 [BAASS:O43097:SEKDEL] and SEQ ID NO: 31[xGZein27ss-02:BD22308:HvVSD-01].

Embodiments include an expression cassette encoding at least one of the first protein, the second protein, or the third protein, or variants thereof, fused to variants of at least one of a targeting peptide or a carboxy targeting peptide.

In an embodiment, a polynucleotide sequence that encodes a protein in an expression cassette and having less than 100% identity to the cited amino acid reference sequence may encode a variant of the protein having the amino acid reference sequence. In an embodiment, a protein having less than 100% identity to the cited amino acid reference sequence may be a variant of the protein having the amino acid reference sequence. In an embodiment, a polynucleotide sequence that encodes a protein having less than 100% identity to the protein encoded by the cited nucleic acid reference sequence may encode a variant of the protein encoded by the reference sequence.

In an expression cassette, at least one of the first polynucleotide sequence, the second polynucleotide sequence, or the third polynucleotide sequence may be capable of hybridizing to a reference sequence encoding a CWD protein or an intein-modified CWD protein under one of low, moderate, or high stringency conditions. At least one of the first, the second, or the third polynucleotide may be capable of hybridizing under conditions of one of low, moderate or high stringency conditions to a nucleic acid consisting of a reference sequence selected from the group consisting of: SEQ ID NO: 32[WT P77853], SEQ ID NO: 33 [AnfaeA], SEQ ID NO: 34 [AnfaeB], SEQ ID NO: 35 [NtEGm], SEQ ID NO: 36 [EU591743], SEQ ID NO: 37 [O43097], SEQ ID NO: 38 [P77853:T134-100-101], SEQ ID NO: 39 [P77853: S158-30-108-35], SEQ ID NO: 40 [O33897], SEQ ID NO: 41 [O68438], SEQ ID NO: 42 [P54583], and SEQ ID NO: 43 [BD22308]. An expression cassette may include a polynucleotide sequence capable of hybridizing under conditions of one of low, moderate, or high stringency conditions to a nucleic acid consisting of a reference sequence selected from the group of sequences consisting of: SEQ ID NO: [BAASS:P77853], SEQ ID NO: 53 [BAASS:O33897], SEQ ID NO: 54 [HVAlePS:NtEGm], SEQ ID NO: 55 [BAASS: P77853:S158-30-108-35], SEQ ID NO: 56 [BAASS: AnfaeB: SEKDEL], SEQ ID NO: 57 [BAASS:AnfaeA: SEKDEL], SEQ ID NO: 58 [PR1a:NtEGm:SEKDEL], SEQ ID NO: 59 [BAASS: P77853:T134-100-101:SEKDEL], SEQ ID NO: 60 [HvAleSP:NtEGm:SEKDEL], SEQ ID NO: 61 [BAASS:O43097:SEKDEL], and SEQ ID NO: 62 [xGZein27ss-02:BD22308:HvVSD-01].

An expression cassette herein may include a regulatory element.

In an embodiment, a vector including any isolated nucleic acid, polynucleotide sequence, or expression cassette herein is provided. Embodiments herein include a plasmid, chromosome, mitochondrial DNA, plastid DNA, virus or nucleic acid fragment having at least one expression cassette herein incorporated therein. An embodiment provides a vector for expressing CWD proteins in a plant. An embodiment provides a plant transformation vector. The plant transformation vector may be but is not limited to a T-DNA vector, a binary vector or a cointegrate vector. The transformation vector may include any isolated nucleic acid, polynucleotide sequence, or expression cassette herein.

An embodiment includes an expression vector including a polynucleotide sequence capable of hybridizing under conditions of one of low, moderate or high stringency conditions to nucleic acid consisting of a sequence including, consisting essentially of, or consisting of a sequence selected from the group consisting of: SEQ ID NO: 63 [pAG 2015], SEQ ID NO: 64 [pAG2048], SEQ ID NO: 65 [pAG2049], SEQ ID NO: 66 [pAG2063], SEQ ID NO: 67 [pAG2069], SEQ ID NO: 68 [pAG2091], SEQ ID NO: 69 [pAG2092], SEQ ID NO: 70 [pAG2096], SEQ ID NO: 71 [pAG2201], SEQ ID NO: 72 [pAG2229], SEQ ID NO: 73 [pAG2233], SEQ ID NO: 74 [pAG2234], SEQ ID NO: 75 [pAG2242], SEQ ID NO: 76 [pAG2252], SEQ ID NO: 77 [pAG2253], SEQ ID NO: 78 [pAG2309], SEQ ID NO: 79 [pAG2310], SEQ ID NO: 80 [pAG2339], SEQ ID NO: 81 [pAG2342], SEQ ID NO: 82 [pAG2345], and SEQ ID NO: 83 [pAG2349].

An embodiment includes an expression vector including a polynucleotide sequence having at least 70, 72, 75, 80, 85, 90, 91, 92, 93, 94, 95, 96, 97, 98, 99, or 100% identity to a sequence selected from the group consisting of: SEQ ID NO: 63 [pAG 2015], SEQ ID NO: 64 [pAG2048], SEQ ID NO: 65 [pAG2049], SEQ ID NO: 66 [pAG2063], SEQ ID NO: 67 [pAG2069], SEQ ID NO: 68 [pAG2091], SEQ ID NO: 69 [pAG2092], SEQ ID NO: 70 [pAG2096], SEQ ID NO: 71 [pAG2201], SEQ ID NO: 72 [pAG2229], SEQ ID NO: 73 [pAG2233], SEQ ID NO: 74 [pAG2234], SEQ ID NO: 75 [pAG 2242], SEQ ID NO: 76 [pAG2252], SEQ ID NO: 77 [pAG2253], SEQ ID NO: 78 [pAG2309], SEQ ID NO: 79 [pAG2310], SEQ ID NO: 80 [pAG2339], SEQ ID NO: 81 [pAG2342], SEQ ID NO: 82 [pAG2345], and SEQ ID NO: 83 [pAG2349].

Methods of hybridization and stringency conditions are known in the art and are described the following books: Molecular Cloning, T. Maniatis, E. F. Fritsch and J. Sambrook, Cold Spring Harbor Laboratory, 1982, and Current Protocols in Molecular Biology, F. M. Ausubel, R. Brent, R. E. Kingston, D. D. Moore, J. G. Siedman, J. A. Smith, K. Struhl, Volume 1, John Wiley & Sons, 2000, which are incorporated hereby by reference as if fully set forth.

Moderate conditions may be as follows: filters loaded with DNA samples are pretreated for 2-4 hours at 68° C. in a solution containing 6× citrate buffered saline (SSC; Amresco, Inc., Solon, Ohio), 0.5% sodium dodecyl sulfate (SDS; Amresco, Inc., Solon, Ohio), SxDenhardt's solution (Amresco, Inc., Solon, Ohio), and denatured salmon sperm (Invitrogen Life Technologies, Inc. Carlsbad, Calif.). Hybridization is carried in the same solution with the following modifications: 0.01 M EDTA (Amresco, Inc., Solon, Ohio), 100 μg/ml salmon sperm DNA, and 5-20×$10^6$ cpm $^{32}$P-labeled or fluorescently labeled probes. Filters are incubated in hybridization mixture for 16-20 hours and then washed for 15 minutes in a solution containing 2×SSC and 0.1% SDS. The wash solution is replaced for a second wash with a solution containing 0.1×SSC and 0.5% SDS and incubated an additional 2 hours at 20° C. to 29° C. below Tm (melting temperature in ° C.). Tm=81.5+16.61 $Log_{10}([Na^+]/(1.0+0.7[Na^+]))$+0.41(%[G+C])−(500/n)−P−F. [Na+]=Molar concentration of sodium ions. %[G+C]=percent of G+C bases in DNA sequence. N=length of DNA sequence in bases. P=a temperature correction for % mismatched base pairs (~1° C. per 1% mismatch). F=correction for formamide concentration (=0.63° C. per 1% formamide). Filters are exposed for development in an imager or by autoradiography. Low stringency conditions refers to hybridization conditions at low temperatures, for example, between 37° C. and 60° C., and the second wash with higher $[Na^+]$ (up to 0.825M) and at a temperature 40° C. to 48° C. below Tm. High stringency refers to hybridization conditions at high temperatures, for example, over 68° C., and the second wash with [Na+]=0.0165 to 0.0330M at a temperature 5° C. to 10° C. below Tm.

An embodiment provides an isolated nucleic acid sequence having a sequence that hybridizes under one of low, moderate, or high stringency conditions to a nucleic acid consisting of a sequence selected from SEQ ID NO: 32[WT P77853], SEQ ID NO: 33 [AnfaeA], SEQ ID NO: 34 [AnfaeB], SEQ ID NO: 35 [NtEGm], SEQ ID NO: 36 [EU591743], SEQ ID NO: 37 [O43097], SEQ ID NO: 38 [P77853:T134-100-101], and SEQ ID NO: 39 [P77853: S158-30-108-35], of SEQ ID NO: 40 [O33897], SEQ ID NO: 41 [O68438], SEQ ID NO: 42 [P54583], and SEQ ID: 43 [BD22308], SEQ ID NO: 52 [BAASS:P77853], SEQ ID NO: 53 [BAASS:O33897], SEQ ID NO: 54 [HVAlePS: NtEGm], SEQ ID NO: 55 [BAASS: P77853:S158-30-108-35], SEQ ID NO: 56 [BAASS: AnfaeB: SEKDEL], SEQ ID NO: 57 [BAASS:AnfaeA:SEKDEL], SEQ ID NO: 58 [PR1a:NtEGm:SEKDEL], SEQ ID NO: [BAASS: P77853: T134-100-101:SEKDEL], SEQ ID NO: 60 [HvAleSP:NtEGm:SEKDEL], SEQ ID NO: 61 [BAASS:O43097: SEKDEL] and SEQ ID NO: 62 [xGZein27ss-02:BD22308: HvVSD-01], SEQ ID NO: 63 [pAG 2015], SEQ ID NO: 64 [pAG2048], SEQ ID NO: 65 [pAG2049], SEQ ID NO: 66 [pAG2063], SEQ ID NO: 67 [pAG2069], SEQ ID NO: 68 [pAG2091], SEQ ID NO: 69 [pAG2092], SEQ ID NO: 70 [pAG2096], SEQ ID NO: 71 [pAG2201], SEQ ID NO: 72 [pAG2229], SEQ ID NO: 73 [pAG2233], SEQ ID NO: 74 [pAG2234], SEQ ID NO: 75 [pAG 2242], SEQ ID NO: 76 [pAG2252], SEQ ID NO: 77 [pAG2253], SEQ ID NO: 78 [pAG2309], SEQ ID NO: 79 [pAG2310], SEQ ID NO: 80 [pAG2339], SEQ ID NO: 81 [pAG2342], SEQ ID NO: 82 [pAG2345], and SEQ ID NO: 83 [pAG2349], or the complement thereof.

An embodiment provides a fragment of any of the above isolated nucleic acids. The fragment may be a hybridization probe or primer. The probe or primer may have any length. The probe or primer may be 6, 10, 15, 20, 25, 30, 35, 40, 45, or 50 nucleotides in length, or have a length in a range between any two of the foregoing lengths (endpoints inclusive). A fragment may have a length less than the full length and/or include substitutions or deletions in comparison to cited reference sequence. The fragment may be a variant of the cited reference sequence. A peptide encoded by a fragment may have a length less than the full length and/or include substitutions or deletions in comparison to the amino acid sequence encoded by the cited reference sequence. The peptide with a length less than full length may be a variant of the amino acid sequence encoded by the cited reference sequence.

An expression cassette may be generated recombinantly by known methods. An expression cassette may include a series of specified nucleic acid elements, which permit transcription of a particular nucleic acid in a plant cell or plant tissue. The expression cassette may include a polynucleotide sequence encoding a protein. The protein may be a CWD enzyme or an intein-modified CWD enzyme. The CWD enzyme may be selected from the list of CWD enzymes consisting of: xylanases, endoglucanases, exoglucanases, xylosidases, glucosidases and feruloyl esterases.

A polynucleotide sequence in an expression cassette, isolated nucleic acid, vector, or any other DNA construct herein, or utilized in a method herein may be operably connected to one or more regulatory element. A regulatory element included may be a promoter. The promoter may be a constitutive promoter which provides transcription of the polynucleotide sequences throughout the plant in most cells, tissues and organs and during many but not necessarily all stages of development. The promoter may be an inducible promoter, which initiates transcription of the polynucleotide sequences only when exposed to a particular chemical or environmental stimulus. The promoter may be specific to a particular developmental stage, organ or tissue. A tissue specific promoter may be capable of initiating transcription in a particular plant tissue. Plant tissue that may be targeted by a tissue specific promoter may be but is not limited to a stem, leaves, trichomes, anthers, or seed. A constitutive promoter herein may be the rice Ubiquitin 3 promoter (OsUbi3P) or rice Actin 1 promoter. Other known constitutive promoters may be used, and include but are not limited to Cauliflower Mosaic Virus (CAMV) 35S promoter, the Cestrum Yellow Leaf Curling Virus promoter (CMP) or the CMP short version (CMPS), the Rubisco small subunit promoter, and the maize ubiquitin promoter. The tissue specific promoter may include the seed-specific promoter. The seed specific promoter may be but is not limited to the rice GluB4 promoter or the maize zein promoter. Another regulatory element that may be provided is a terminator sequence, which terminates transcription. A terminator sequence may be included at the 3' end of a transcriptional unit of the expression cassette. The terminator may be derived from a variety of plant genes. The terminator may be a terminator sequence from the nopaline synthase or octopine synthase genes of *Agrobacterium tumefaciens*.

Vectors incorporating an expression cassette herein may also include additional genetic elements such as multiple cloning sites to facilitate molecular cloning and selection markers to facilitate selection. A selectable marker that may be included in a vector may be a phosphomannose isomerase (PMI) gene from *Escherichia coli* which confers to the transformed cell the ability to utilize mannose for growth. A Selectable markers that may be included in a vector include but are not limited to a neomycin phosphotransferase (npt) gene conferring resistance to kanamycin, a hygromycin phosphotransferase (hpt) gene conferring resistance to hygromycin, and an enolpyruvylshikimate-3-phosphate synthase gene conferring resistance to glyphosate.

In an embodiment, the vector may be constructed to include polynucleotide sequences encoding multiple CWD enzymes. A vector herein may further include a polynucleotide sequence designed to silence a gene or genes in a plant.

An expression vector may be introduced into suitable host cells, tissues, organs and/or organisms. Suitable hosts may be dicotyledonous (dicots) or monocotyledonous (monocots) plants.

Further embodiments herein may be formed by supplementing an embodiment with one or more element from any one or more other embodiment herein, and/or substituting one or more element from one embodiment with one or more element from one or more other embodiment herein. Further embodiments herein may be described by reference to any one of the appended claims following claim 1 and reading the chosen claim to depend from any one or more preceding claim.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1

Materials and Methods

Vectors

A vector design herein is based on the pSB11 intermediate plasmid available from Japan Tobacco and described in the International application Nos. PCT/US10/55746 filed Nov. 5, 2010, PCT/US10/55669 filed Nov. 5, 2010 and PCT/US10/55751 filed Nov. 5, 2010, which are incorporated herein by reference as if fully set forth. Briefly, the pSB11 plasmid used for cloning is conjugated with the pSB1 acceptor vector, a disarmed Ti plasmid, through homologous recombination using cos and ori sites present in both pSB11 and pSB1. The integrated vector contains virulence genes such as virB, virC and vir G required for T-DNA transfer and may be used for plant transformation. The base transformation vector includes an expression cassette containing a man A gene encoding PMI under the control of the CMPS promoter later replaced by the OsUbi3P promoter. This base vector was used to obtain the vectors listed below, which were used for plant transformation and expression of cell wall degrading enzymes in planta:

1. pAG2015(SEQ ID NO: 63): OsUbi3P:P77853;
2. pAG2048 (SEQ ID NO: 64): OsUbi3P:HvAleSP:NtEGm between rice Ubi3 promoter fused to vacuole;
3. pAG2049 (SEQ ID NO: 65): OsUbi3P:HvAleSP:NtEGm: SEKDEL;
4. pAG2063 (SEQ ID NO: 66): OsUbi3P:BAASS:O43097:SEKDEL;
5. pAG2069 (SEQ ID NO: 67): OsUbi3P:O68438;
6. pAG2091 (SEQ ID NO: 68): OsUbi3P:BAASS:AnfaeA:SEKDEL+OsUbi3P:BAASS:P77853;
7. pAG2092 (SEQ ID NO: 69): OsUbi3P:BAASS:AnfaeB:SEKDEL+OsUbi3P:BAASS:P77853;
8. pAG2096 (SEQ ID NO: 70): OsUbi3P:BAASS:AnfaeA:SEKDEL+OsUbi3P:BAASS:AnfaeB:SEKDEL+OsUbi3P:BAASS:P77853;
9. pAG2201 (SEQ ID NO: 71): OsUbi3P:ZmUBQm:P77853;
10. pAG2229 (SEQ ID NO: 72): OsUbi3P:BAASS:P77853:T134-100-101:SEKDEL (intein modified xylanase);
11. pAG2233 (SEQ ID NO: 73) OsUbi3P:P77853:5158-30-108-35;
12. pAG2234(SEQ ID NO: 74) OsUbi3P:BAASS:P77853:5158-30-108-35;
13. pAG2242 (SEQ ID NO: 75): OsUbi3P:PR1aSP:NtEGm:SEKDEL+OsUbi3P:ZmUBQm:P77853;
14. pAG2252 (SEQ ID NO: 76): OsUbi3P:O33897 (endoglucanase);
15. pAG2253 (SEQ ID NO: 77): OsUbi3P:BAASS:O33897;
16. pAG2309 (SEQ ID NO: 78): OsUbi3P:HvAleSP:NtEGm+OsUbi3P:P77853;
17. pAG2310 (SEQ ID NO: 79): OsUbi3P:EU591743 (xylanase);
18. pAG2339 (SEQ ID NO: 80): OsUbi3P:O68438+OsUbi3P:BAASS:O33897+OsUbi3P:EU591743;
19. pAG2342 (SEQ ID NO: 81): OsUbi3P:HvAleSP:NtEGm: SEKDEL+OsUbi3P:P77853;
20. pAG2345 (SEQ ID NO: 82): OsUbi3P:O68438+OsUbi3P:HvAleSP:NtEGm:SEKDEL+OsUbi3P:BAASS:O43097:SEKDEL;
21. pAG2349 (SEQ ID NO: 83): ZmUbilP:ZmKozak:xGZein27ss-O2:BD22308:HvVSD-01+OsUbi3P:HvAleSP:NtEGm:SEKDEL+OsUbi3P:BAASS: O43097:SEKDEL;
22. pAG2042 (SEQ ID NO: 84): P54583 (endoglucanase EGB)

Production of Transgenic Maize Plants

The methods for maize and switchgrass transformation were described in the International application Nos. PCT/US10/55746 filed Nov. 5, 2010, PCT/US10/55669 filed Nov. 5, 2010, PCT/US10/55751 filed Nov. 5, 2010 and Gray et al. 2011 Plant Biotech J 9:1100, which are all incorporated herein by reference as if fully set forth. Briefly, embryogenic callus from wild-type AxB maize was inoculated with LBA4404 *Agrobacterium* cells harboring the appropriate transformation plasmid. *Agrobacterium*-mediated transformation of immature maize embryos was performed as described previously (Negrotto D et al. 2000 Plant Cell Rep 19: 798; Ishida Y et al. 1996 Nat Biotech 14: 745). The expression cassettes for enzyme genes were cloned into the KpnI-EcoRI sites of the pAG2004 (SEQ ID NO: 85) vector to generate an intermediate vector capable of recombining with the pSB1 vector in triparental mating in *Agrobacterium tumefaciens* strain LBA4404 using procedures reported previously (Ishida Y et al. 1996 Nat Biotech 14: 745; Hiei Y et al. 1994 Plant J 6: 271; Hiei Y and Komari T 2006 Plant Cell Tissue Organ Cult. 85: 27; Komari T et al. 1996 Plant J 10: 165). Maize (*Zea mays* cultivars HiII, A188 or B73) stock plants were grown in a greenhouse under 16 hours of daylight at 28° C. Immature zygotic embryos were isolated from the kernels and inoculated with the *Agrobacterium* solution containing the genes of interest. After inoculation immature embryos were grown in a tissue culture process for 10-12 weeks. Well-developed seedlings with leaves and roots were sampled for PCR analysis to identify transgenic plants containing the genes of interest. PCR positive and rooted plants were rinsed with water to wash off the agar medium, and transplanted to soil and grown in the greenhouse to generate seeds and stover.

Particular transgenic plants are referred to herein by an enzyme designation (e.g.; “P77853,” “P40942,” “O30700,” “NtEGm,” etc.) or transgenic control (e.g.; “TGC,” etc.) followed by a number in the thousands that designates the plasmid used to create the transgenic plant (e.g.; “2014,” “2015,” “2229,” “2092,” etc.). Additional characters are inserted occasionally, but the i) enzyme or control and ii) plasmid designation are clear in context. The plasmids referred to are named pAGXXXX. For example, the designations “2229,” “2252,” “2253,” “2092,” “2096,” or “2042” in a transgenic plant name means that the transgenic plant was made by transformation with “pAG2229,” “pAG2252,” “pAG2253,” “pAG2092,” “pAG2096,” or “pAG2042,” respectively. Reference can be made to the incorporated sequences labeled with the plasmid names to determine sequences used to make a particular transgenic plant.

For generating transgenic switchgrass plants, seeds from *Panicum virgatum*, cv. Alamo were used for initiating embryogenic callus lines subsequently used for transformation using *Agrobacterium* LBA4404 harboring pSB1 plasmid. The presence of the gene of interest was confirmed by PCR using gene specific primers.

The following transgenic plants expressing a CWD enzyme or CWD enzymes and control plants were used for consolidated pretreatment and hydrolysis:

1. Wild type maize plant used as negative controls (AxB; BxA);

2. Maize plants transformed with an empty vector used as negative controls (TGC.4000.12; TGC.4000.11; TGC.2004.8.02; TGC.2004.8.04; TGC.2243.01);

3. A transgenic maize plant XynA.2015.05 made by transformation with pAG2015 and expressing xylanase XynA (P77853);

4. A second generation transgenic maize plant XynA.2015.5T1 made by transformation with pAG2015 and expressing xylanase XynA (P77853);

5. A transgenic maize plant XynB.2063.17 made by transformation with pAG2063 and expressing xylanase XynB (O43097);

6. Transgenic maize plants EGA.2049.02 and EGA.2049.10 made by transformation with pAG2049 and expressing endoglucanase EGA (NtEG);

7. A transgenic maize plant EGB.2042.03 made by transformation with pAG2042 and expressing endoglucanase EGB (P54583);

8. A transgenic maize plant EGC.2253.4b made by transformation with pAG2253 and expressing endoglucanase EGC (O33897);

9. A transgenic maize plant EGA/XynA.2242.09 made by transformation with pAG2242 and expressing endoglucanase EGA (NtEG) and xylanase XynA (P77853);

10. A second generation transgenic maize plant of plant 9, above, called EGA/XynA.2242.09.16T1 and expressing endoglucanase EGA (NtEG) and xylanase XynA (P77853);

11. A transgenic maize plant XynA/AccB.2092.103 made by transformation with pAG2092 and expressing xylanase XynA (P77853) and feruloyl esterase B from *Aspergillus niger;*

12. Transgenic maize plants XynA/AccA/B.2096.01 and XynA/AccA/B.2096.05 made by transformation with pAG2096 and expressing xylanase XynA (P77853), Feruloyl esterase A from *Aspergillus niger*, and feruloyl esterase B from *Aspergillus niger;*

13. A transgenic maize plant CBHA.2069.3.17 made by transformation with pAG2069 and expressing exoglucanase CBH (O68438);

14. Transgenic switchgrass plants XynA.pv2015.3c and XynA.pv2015.4c made by transformation with pAG2015 and expressing xylanase XynA (P77853);

15. A transgenic maize plant iXynA.2229.110 made by transformation with pAG2229 and expressing intein modified xylanase XynA (P77853);

16. Transgenic maize plants XynA/EGA.2309.54 and XynA/EGA.2309.107 made by transformation with pAG2309 and expressing XynA (P77853), endoglucanase EGA(NtEGm);

17. A transgenic maize plant XynA/EGA.2342.105 made by transformation with pAG2342 and expressing XynA (P77853) and EGA(NtEGm);

18. Transgenic maize plants XynE/EGC/CBHA.2339.03, XynE/EGC/CBHA.2339.04, and XynE/EGC/CBHA.2339.05 made by transformation with pAG2339 and expressing XynE (EU591743), endoglucanase EGC (O33897), and CBHA (O68438);

19. A transgenic maize plant XynB/EGA/CBHA.2345.116 made by transformation with pAG2345 and expressing XynB (O43097), endoglucanase EGA(NtEGm), and CBHA (O68438);

20. Transgenic maize plants XynB/EGA/CBHB.2349.55 and XynB/EGA/CBHB.2349.56 made by transformation with pAG2349 and expressing XyanB (O43097), endoglucanase EGA(NtEG), CBHB (BD22308), and ZmUbilP:ZmKozak:xGZein27ss-02:BD22308:HvVSD-01:NosT.

Plant Stover

Harvested greenhouse maize stover was dried in an air circulator at 37° C. for 1-2 weeks. After drying, the stover was cut manually to 1.0-1.5 inch pieces and then milled using an UDY mill (Model 014, UDY Corporation, Fort Collins, Colo.) with a 0.5 mm screen.

Preparation of Plant Protein Extracts

Individual crushed grains or 20 mg milled stover were resuspended in protein extraction buffer that include 100 mM sodium phosphate (pH 6.5), ethylenediaminetetraacetic acid (EDTA;1 mM), Triton X-100 (0.1%, v/v) and phenylmethanesulfonylfluoride(PMSF; 0.1 mM). Resuspended tissue samples were mixed thoroughly, and insoluble material was then sedimented by centrifugation. The supernatant liquid-containing soluble protein was transferred to a new tube.

Chemicals and Enzymes

Sugar standards (glucose, xylose, arabinose, galactose, mannose and cellobiose) were purchased from Acros Organics (Morris Plains, N.J.). All other chemicals used in this study were purchased from Sigma-Aldrich (St. Louis, Mo.). Endoglucanase (C8546), β-glycosidase (49291), and endoxylanase (X2753) for making in house cocktail were all purchased from Sigma (St. Louis, Mo.). The cellobiohydrolase (CBHI) (EC 3.2.1.91) and β-xylosidase (EC 3.2.1.37) were purchased from Megazyme (Wicklow, Ireland). Accellerase® 1500 and Accellerase® XY were generous gifts from Genencor International (Rochester, N.Y.). The yeast *Saccharomyces cerevisiae*, strain D5A was obtained from the American Type Culture Collection (ATCC) (Manassas, Va.).

Stover Enzyme Assays

Protein was extracted from 15 mg stover in 500 μl extraction buffer (100 mM sodium phosphate buffer, pH 6.5; NaOAc, pH 4.5; or Tris, pH 8.0, EDTA (10 mM), and Triton X-100 (0.1%) after incubation for 30 minutes at room temperature. The stover was spun down by centrifugation. The supernatant was collected and transferred to a new Eppendorf tube. For enzyme assays, 50 μl protein extract was resuspended in a buffer. Typically, the buffer included Xylazyme in 100 mM Na phosphate, pH 6.5 or Cellazyme in 100 mM NaOAc, pH 4.5. Xylazyme AX or cellazyme tablets were used as was appropriate for each tube of enzyme assay. The reactions were incubated at the assay temperature (usually approximately 50-60° C., depending on the enzyme being tested) until a blue color was visible in the supernatant liquid. The amount of blue dye was quantified by measuring absorbance of the reaction at 590 nm. Controls for these reaction included microbially raised enzymes and extracts from wild type plants. Hydrolysis substrates may be also determined by using AZCL-conjugated substrate (Megazyme) instead of the xylazyme AX and cellazyme tablets. Using the AZCL-conjugated substrate allows for optimization of both the volume of stover being tested and the concentration of substrate.

Detection of Xylanase Activity

Soluble proteins were assayed using Xylazyme AX (Megazyme, Bray, Co. Wicklow, Ireland) as a substrate in 0.5-ml reactions at 50° C. in HEPES buffer (100 mM, pH 8.0) for BSX or in sodium phosphate (100 mM, pH 6.5) for XynB. To stop the Xylazyme AX reactions, 1 ml 2% (w/v) Tris base was added to the reactions. The insoluble material from the Xylazyme AX reaction was sedimented by centrifugation, and the absorbance of the reaction 100 μL of the supernatant was measured in triplicate spectrophotometrically at 590 nm. For quantification of BSX or XynB accumulation levels, calibration curves were constructed by incubating known amounts of purified, microbially raised BSX or XynB diluted in assay buffer with Xylazyme AX tablets concurrent with the Xylazyme AX assays using transgenic plant material.

Table 1 below demonstrates the enzyme activities detected in transgenic plants. As indicated, the enzyme activities were detected for several xylanases, endoglucanases, cellobiohydrolases and feruloyl esterases. For each transgenic event, the detected enzyme activity was also confirmed by Western blot analysis. "N/A" refers to analysis not yet performed.

TABLE 1

| Transgenic plant | Xylanase | Endoglucanase | CBH | AccA or B |
|---|---|---|---|---|
| A × B | − | − | − | − |
| B × A | − | − | − | − |
| TGC.2243.01 | − | − | − | − |
| TGC.4000.12 | − | − | − | − |
| TGC.4000.11 | − | − | − | − |
| TGC.2004.8.02 | − | − | − | − |
| TGC.2004.8.04 | − | − | − | − |
| TGC.2243.01 | − | − | − | − |
| XynA.2015.05 | + | − | − | − |
| XynA.2015.5T1 | + | − | − | − |
| XynB.2063.17 | + | − | − | − |
| EGA.2049.02 | − | + | − | − |
| EGA.2049.10 | − | + | − | − |
| EGB.2042.03 | − | + | − | − |
| EGC.2253.4b | − | + | − | − |
| EGA/XynA.2242.09 | + | + | − | − |
| EGA/XynA.2242.09.16T1 | + | + | − | − |
| XynA/AccB.2092.103 | + | − | − | + |
| XynA/AccA/B.2096.01 | + | − | − | + |
| XynA/AccA/B.2096.05 | + | − | − | + |
| XynA.pv2015.3c | + | − | − | − |
| XynA.pv2015.4c | + | − | − | − |
| iXynA.2229.110 | + | − | − | − |
| XynA/EGA.2309.54 | + | + | − | − |
| XynA/EGA.2309.107 | + | + | − | − |
| XynA/EGA.2342.105 | + | + | − | − |
| XynE/EGC/CBHA.2339.03 | + | + | N/A | − |
| XynE/EGC/CBHA.2339.04 | + | + | N/A | − |
| XynE/EGC/CBHA.2339.05 | + | + | N/A | − |
| XynB/EGA/CBHA.2345.116 | + | + | N/A | − |
| XynB/EGA/CBHB.2349.55 | + | + | + | − |
| XynB/EGA/CBHB.2349.56 | + | + | + | − |

Biomass Carbohydrate Compositional Analysis

Prior to carbohydrate compositional analysis, duplicates of 3.0 g of air-dried milled stover were refluxed with 90% (v/v) ethanol using a glass Soxhlet extraction system (Fisher Scientific, Pittsburgh, Pa.) to remove the ethanol-extractable materials by following NREL standards (NREL/TP-510-42619). The ethanol containing extracts were vacuum evaporated using a rotary evaporator equipped with a water bath set to 40° C. (Heidolph LR4000 G5B, IL USA). Extract content was determined by the weight of the solids in the flask after oven drying at 50° C. for 48 hours.

The extract-free stover was subject to a two-step acid hydrolysis (NREL/TP-510-42618), which was the first hydrolyzed at 30° C. with 1.5 ml of 72% (w/w) $H_2SO_4$ per 0.16-0.18 g (air dry weight) for 60 min, followed by 121° C. for 1 hour with supplementation of 42.0 ml of water. After acid hydrolysis, sodium hydroxide and calcium hydroxide were added to adjust the pH to between 4.0 and 9.0 and all samples were filtered through a 0.2 μm PVDF filters (Fisher Scientific, Pittsburgh, Pa.) for high performance liquid chromatography (HPLC) analysis.

Consolidated Process with Moderate Pretreatment and Saccharification

To evaluate the effect of plant expressed CWD enzymes on stover hydrolysis, a consolidated process was developed includes a mild pretreatment followed by enzymatic hydrolysis without inter-stage washing of the biomass/detoxification. The consolidated process removes any washing/separation/detoxification steps and allows an integrated pretreatment and simultaneous saccharification and fermentation (SSF) process.

Moderate pretreatment An efficient mild pretreatment was developed that can achieve some pretreatment effects on biomass but not deactivate the hydrolytic enzymes within the plant. The pretreatment chemical was a mixture of 0.02M-0.18 M ammonium bisulfite and 0.025M-0.20 M ammonium carbonate with pH between 5.0 and 9.0, preferably around 8.10. For evaluating plant stover hydrolysis, 20.0 mg milled corn stover was added to 2-ml microcentrifuge tubes with pretreatment chemical solution at a liquor-to-solid (L/S) ratio of 10 or less (preferably 3-6). The pretreatment was incubated in a shaker at 350 rpm and a temperature of 40° C.-95 DC for 0-16 hours. For milled and unmilled stover, a mechanical refining or defibrillation followed the pretreatment with chemicals. Further, the pretreated material was subject to enzymatic hydrolysis without inter-stage washing.

Enzymatic hydrolysis The pretreated stover was subject to enzymatic hydrolysis in Britton-Robinson polybuffer (40 mM phosphate, 40 mM acetate, 40 mM borate) with sodium azide. The enzymatic hydrolysis was conducted at 2% (w/v) solids content, pH 4.9, 50° C. in a New Brunswick shaker (New Brunswick Scientific, New Jersey USA) at 250 rpm for varying time (0-144 hours). Cocktail #1 was loaded as 0.5 μM endoglucanase, 0.1 μM cellobiohydrolase (CBHI), 0.05 μM β-glycosidase, and 0.5 μM endoxylanase based on 10.0 mg stover with 1 ml reaction volume. Cocktail 5# was the cocktail #1 with 0.1 μM β-xylosidase added. In conjunction, three types of enzymatic hydrolysis were run in parallel: No enzyme cocktail (NCt), a full enzyme cocktail (FCt), and an enzyme cocktail lacking the in-planta expressed enzyme (Ct-PE), e.g., an enzyme cocktail lacking endoxylanase (Ct-Xyn) or endoglucanase (Ct-EG) or both (Ct-EG-Xyn) depending on the enzyme expressed in plants. Accellerase® 1500 was loaded at 0.2 ml/g dry mass and Accellerase® XY was loaded at 0.1 ml/g dry mass. Glucose and xylose yields (% of theoretical) were expressed as a percentage of total Glucose and xylose in each substrate. Error bars in the accompanying FIGS. are the standard deviation of the mean from replicate assays.

Simultaneous Saccharification and Fermentation (SSF)

The inoculum was prepared by growing the yeast strain *Saccharomyces cerevisiae* D5A to an $OD_{600}$ of 0.5 in YPD (10 g/l yeast extract, 20 g/l peptone and 20 g/l dextrose) at 30° C. and 250 rpm. The cells were harvested by centrifugation (3000 g for 5 min) and re-suspended in a 1× YP (10 g/l yeast extract and 20 g/l peptone).

SSF experiments were performed in duplicate in 250 ml Erlenmeyer glass flasks with a working volume of 50 ml, consisting of 3.0-4.0 g (dry weight) pretreated biomass, Britton-Robinson buffer, 10× YP (100 g/l yeast extract and 200 g/l peptone), inocula, and hydrolytic enzymes. The flasks were sealed by a rubber stopper with an airlock. The experiments were started by adding yeast inocula and enzymes (Accellerase® 1500 at 10 FPU/g dry mass and Accellerase® XY at 0.1 ml/g dry mass), and were incubated at 35° C. and 120 rpm for 7 days. Samples were withdrawn after 0, 24, 48, 72, 144 and 168 hours and analyzed for ethanol and sugars.

Analysis of Fermentable Sugars and Ethanol

The hydrolysate samples were heated at 90° C. for 20 min and then centrifuged at 10,000 g, following which the supernatants were clarified by passing through 0.20 μm PVDF filters (Cat. #: 09-910-13, Fisher Scientific, Pittsburgh, Pa.). Monosaccharide and disaccharide concentrations were determined by high performance liquid chromatography (HPLC), using a Shimadzu LC-20 AD binary pump with LC solutions software (Shimadzu, Kyoto, Japan). Sugar concentrations were determined using an Aminex HPX-87P sugar column (Bio-Rad Laboratories, Hercules, Calif.) operating at 0.6 ml/min and 80° C. with degassed water as the mobile phase. Ethanol concentration in fermentation broth was analyzed using an Aminex HPX-87H Column (Bio-Rad Laboratories, Hercules, Calif.) acid column operating at 0.6 ml/min, 60° C. with 0.004 M sulfuric acid as the mobile phase. Peak areas for all samples, analyzed with an RI detector (RID 10AD), were integrated and the values were compared to standard curves for quantification.

Example 2

Plant Stover Carbohydrate Compositional Analysis

The stover from transgenic plants was characterized in terms of their structural carbohydrate composition and the sugar content to examine any significant changes caused by genetic modification. Table 2 shows results of the structural carbohydrate analysis of random sampled transgenic and non-transgenic maize and switchgrass events. The glucan and xylan content from a set of transgenic plants, whether expressing a single or multiple CWD enzymes or lacking a transgene encoding a CWD enzyme (transgenic control TGC), are similar to wild-type control plants (AxB).

TABLE 2

Glucan and xylan content of transgenic plants (CWD expressing or TGC) versus non-transgenic wild-type (A × B) plants.

| Plant Stover | # events (n) | Glucan (g/100 g stover) | Xylan (g/100 g stover) |
|---|---|---|---|
| Wild type maize controls | 4 | 31.51 ± 0.33 | 17.12 ± 0.66 |
| Transgenic maize controls | 8 | 30.16 ± 1.02 | 15.99 ± 1.14 |
| Transgenic maize with enzymes | 18 | 31.40 ± 1.52 | 16.59 ± 1.34 |

A Student t-test of the data presented in Table 2 shows no significant difference in the amount of glucan between transgenic maize events expressing CWD enzymes and wild-type maize AxB, or between transgenic maize events expressing CWD enzymes and transgenic control events that do not express a CWD enzyme with a P-value of 0.90 and 0.14, respectively. The corresponding P-values from a t-test on xylan content are 0.57 and 0.36, respectively.

Therefore, in planta expression of enzymes provides an opportunity for producing not only low cost enzymes but also biomass feedstocks with hydrolytic traits for cheap fermentable sugar production.

Example 3

Effect of Plant Expressed CWD Enzymes on Biomass Hydrolysis

Methodology for Plant Biomass Hydrolysis Evaluation

One of the goals of expressing CDW enzymes in planta is to eliminate or reduce the severity of chemical pretreatment conditions for processing lignocellulosic biomass.

To evaluate the effects of plant expressed CWD enzymes on biomass hydrolysis, a consolidated process with moderate chemical pretreatment (pH 5.0-9.0, 55° C. for 16 hours) followed by an enzymatic hydrolysis (pH 4.9, 50° C. for 72 hours) without inter-stage washing was developed and chosen as a standard procedure for the initial plant stover screening. In this process, in-house enzyme cocktails (cocktail#1 and cocktail #5) were used for the evaluation. The in-house cocktail is a combination of individual enzyme components, which enables the omission of any component depending on the identity of the enzyme(s) expressed in planta. For each transgenic plant stover and wild type or transgenic control plant stover, the following treatments for enzymatic hydrolysis were run in parallel: no enzyme cocktail (NCt), full cocktail (FCt), and cocktail lacking the in planta expressed enzyme (Ct-PE; e.g., cocktail lacking xylanase (Ct-Xyn), cocktail lacking endoglucanase (Ct-EG), or cocktail lacking both xylanase and endoglucanase (Ct-Xyn-EG)).

To determine which enzyme or enzymes support good hydrolysis performance, two criteria were used to evaluate the processing characteristics of transgenic events expressing CWD enzymes in the initial screening:

1. Total sugar yield from the full cocktail (FCt) hydrolysis (height (1) in FIGS. 2A-2B).

2. Sugar yield difference between hydrolyses involving the full cocktail (FCt) and the enzyme cocktail without the enzyme that is expressed in planta (Ct-PE) (height (2) in FIGS. 2A-2B).

The total sugar produced (height (1)) from processing is a criterion to be considered because it directly affects the yield of final products, the productivity, and operational cost. With the in planta expression of CWD enzymes, it was demonstrated that enzyme-expressing transgenic plants achieved better overall hydrolysis than a control plant under same processing conditions, which was demonstrated from the total glucose and xylose yields in FIG. 2. The second criterion, the sugar yield difference between FCt and Ct-PE (height (2)) represents an effect of plant expressed enzymes on hydrolysis. When using these transgenic plants as biomass feedstocks, it was observed that external enzymes in the enzyme cocktail can be partially or completely replaced by a CWD enzyme or CWD enzymes expressed in transgenic plants, while achieving similar or equal hydrolysis, which is indicated by a smaller change or no difference in sugar yield between FCt and Ct-PE hydrolysis (FIG. 2B).

Plant Stover Hydrolysis Evaluation

Using the two selection criteria identified above, enzymatic hydrolysis of stover samples with the in-house cocktail was done to screen the performance of different transgenic maize plants expressing CWD enzymes. Based on the results of this screening, the best performing transgenic plant events were identified and included xylanase-expressing transgenic plants XynA.2015.05 and XynB.2063.17; endoglucanase-expressing transgenic plants EGA.2049.10 and EGB.2042.03; and transgenic plants expressing multiple enzymes-XynA/AccA/B.2096.01, XynA/AccB.2092.103, EGA/XynA.2242.09, XynB/EGA/CBHA.2345.116, XynB/EGA/CBHB.2349.55 XynB/EGA/CBHB.2349.56, and XynB/EGA/CBHB.2349.229.

Figure 2B:
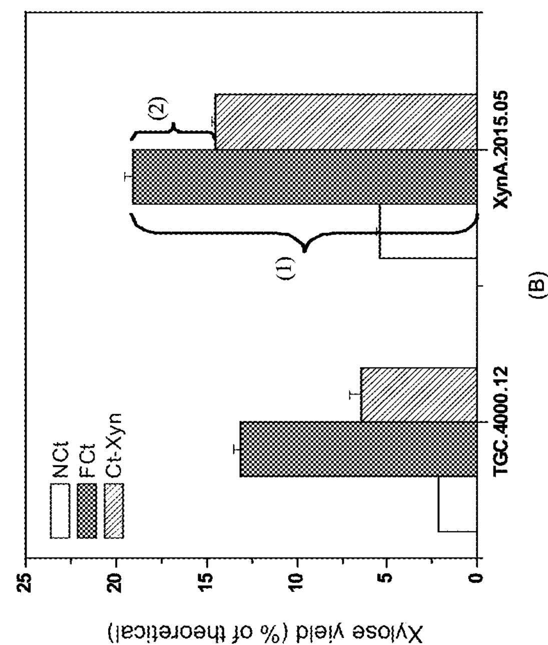
FIGS. 2A-2B illustrate glucose (FIG. 2A) and xylose (FIG. 2B) yields from a pretreated transgenic plant expressing xylanase A (XynA.2015.05) and a transgenic control plant lacking xylanase A (TGC.4000.12) after enzymatic hydrolysis with enzyme cocktail #5 (FCt; gray (middle bar of each set of three)); or the enzyme cocktail #5 lacking xylanase A (Ct-Xyn; diagonal stripes (right)); or no enzymes (NCt; white (left)).
Figure 2A:
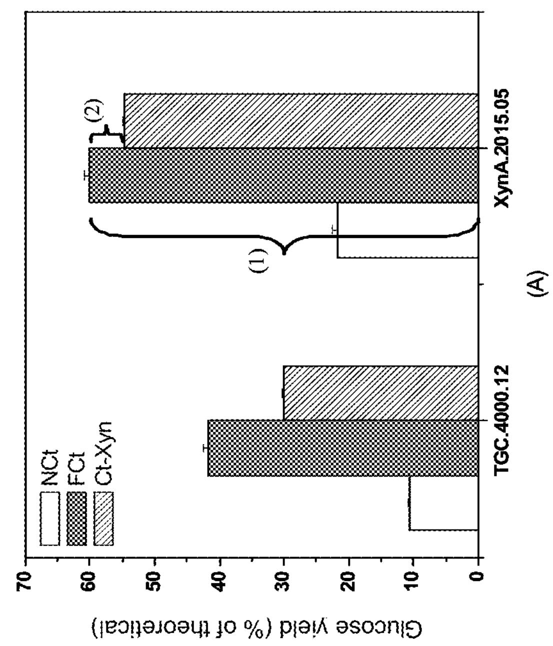

FIG. 2 illustrates glucose (FIG. 2A) and xylose (FIG. 2B) yields after hydrolysis of material from a transgenic plant expressing xylanase A (XynA; XynA.2015.05) and a transgenic control plant TGC.4000.12 that does not express a CWD enzyme (TGC.4000.12). The data on sugar yields from the transgenic event XynA.2015.05 and the transgenic control after enzymatic hydrolysis by FCt (in house cocktail #5), NCt and Ct-Xyn (in house cocktail #5 lacking xylanase A) was evaluated using the above-listed selection criteria. The value of a total glucose yield after FCt treatment (criterion 1) was shown to be higher than the difference in values of glucose yield between FCt and Ct-Xyn treatments (criterion 2) for both XynA.2015.05 and TGC.4000.12. The value of total glucose and xylose yields for all treatments was higher for the transgenic event XynA.2015.05 than for the control plant TGC.4000.12. Interestingly, the difference in glucose and xylose yields after treatments with a full enzyme cocktail and an enzyme cocktail without the plant-expressed xylanase A was very small. Based on these results, xylanase A expressed in a plant was almost as efficient in hydrolyzing the plant stover as xylanase A provided in a full cocktail. Based on the selection criteria 1 and 2, the transgenic event XynA.2015.05 shown in FIG. 2 was identified as a good performer for hydrolysis.

Plants Expressing Xylanase

Xylan is known to be the dominant hemicellulose in hardwood, agricultural residue, biomass, and perennial grasses. Xylan is a heteropolymeric biopolymer that consists of a repeating β-1,4-linked xylose backbone decorated with branch groups and may be cross-linked to lignin by aromatic esters (Dodd D and Cann IO 2009 Glob Change Biol Bioenergy 1: 2). Xylan destruction and removal benefits the hydrolysis of cellulose into fermentable sugars. In a typical hydrolytic enzyme cocktail, xylanases are a major class of CWD enzymes required to hydrolyze hemicellulose polymers since they play key role in making cellulose more accessible to enzymatic hydrolysis. Referring to FIG. 3B, FIGS. 5B-5D, and FIG. 7B, the transgenic plant events expressing XynA or XynB (XynB.2063.17, XynA/Acc/A/B.2096.01, and XynA.2015.05T1) demonstrated 29.80-172.1% higher xylan conversion from Ct-Xyn hydrolysis than the control plants, indicating the enhanced effect of in planta expressed xylanase on biomass xylan hydrolysis. Likewise, these transgenic plants also show 50.1-93.5% higher glucan conversion from Ct-Xyn hydrolysis than did the control plants.

Figure 3B:
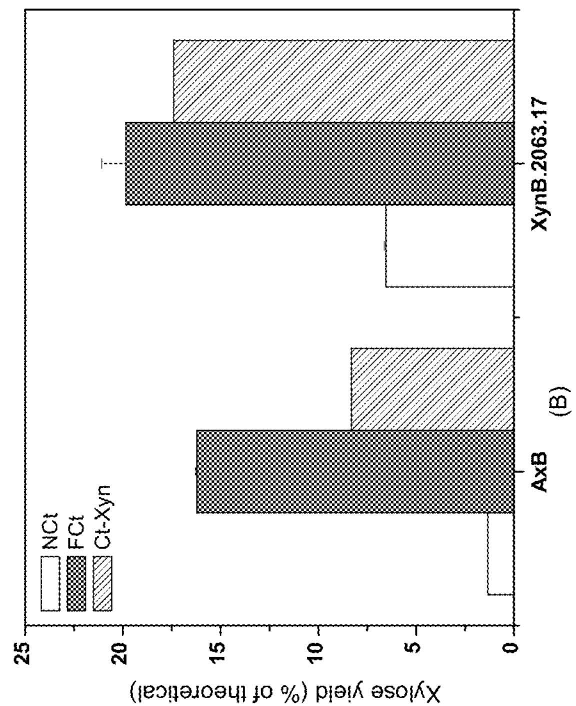
FIGS. 3A-3B illustrate glucose (FIG. 3A) and xylose (FIG. 3B) yields from a pretreated transgenic plant expressing xylanase B (XynB. 2063.17) and a pretreated wild-type control plant (AxB) after enzymatic hydrolysis with enzyme cocktail #1 (FCt; gray (middle)); or the enzymatic cocktail #1 lacking xylanase (Ct-Xyn; diagonal stripes (right)), or no enzymes (NCt; white (left)).
Figure 3A:
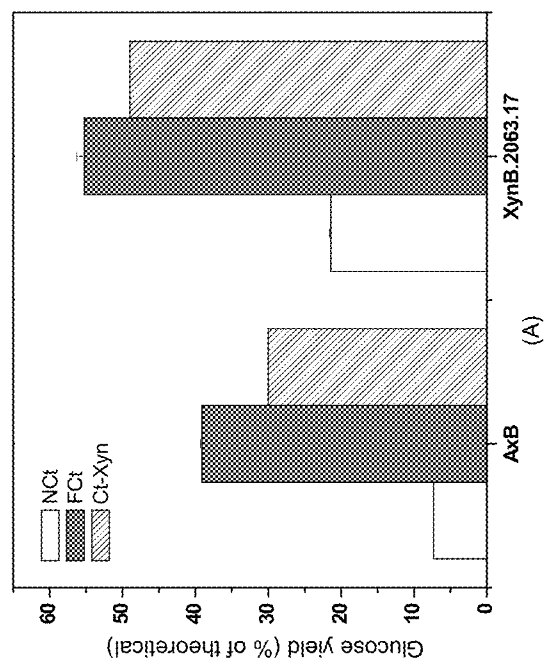

FIGS. 3A-3B illustrate glucose (FIG. 3A) and xylose (FIG. 3B) yields from a pretreated transgenic plant tissue expressing xylanase B (XynB.2063.17) and a wild-type control (AxB) after hydrolysis by the in-house cocktail #1 (FCt), cocktail #1 lacking xylanase B (Ct-Xyn) and no cocktail (NCt). Results for Ct-Xyn treatment demonstrated 63.2% higher glucose yield and 109.4% higher xylose yield from the transgenic event XynB.2063.17 than from the AxB control plant. Improved xylan hydrolysis of the event XynB.2063.17 was also evident from the small difference in values of xylose yield between the FCt and the Ct-Xyn treatments (criterion 2).

These results show surprisingly good performance of xylanase B expressed in planta in hydrolyzing stover in comparison to the enzyme provided in the full cocktail.

Plants Expressing Cellulose

Lignocellulosic biomass is known to be composed of a matrix with multiple intertwined biopolymers (cellulose, hemicelluloses, lignin and extractives), which requires several different classes of enzymes in large quantities to efficiently release fermentable sugars. Among them, cellulase is a key enzyme. Three types of cellulases; endoglucanase, exoglucanase and β-glucosidase, work together to hydrolyze cellulose into glucose. In the hydrolysis process, endoglucanase breaks cross-linkages between cellulose chains while exoglucanase hydrolyzes the individual glucan chains and β-glucosidase breaks down the exoglucanase products to monomers of glucose (Sticklen M B 2008 Nature Reviews Genetics 9:433).

Figure 4B:
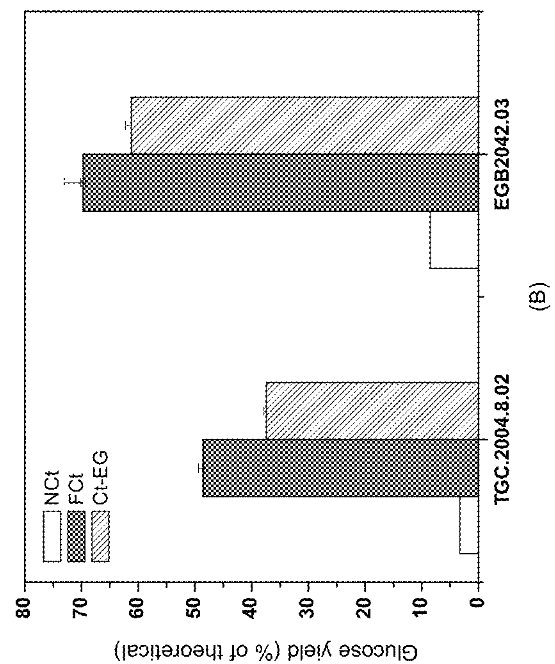
FIGS. 4A-4B illustrate glucose yields from pretreated transgenic plants expressing endoglucanase (EG) following enzymatic hydrolysis with enzyme cocktail #1 (FCt; gray (middle)), or the enzymatic cocktail #1 lacking endoglucanase (Ct-EG(right)), or no enzymes (NCt; white (left)). A illustrates glucose yield from transgenic plants expressing endoglucanase A (EGA.2049.02 and EGA.2049.10) and a transgenic control plant lacking endoglucanase (TGC.4000.12).
Figure 4A:
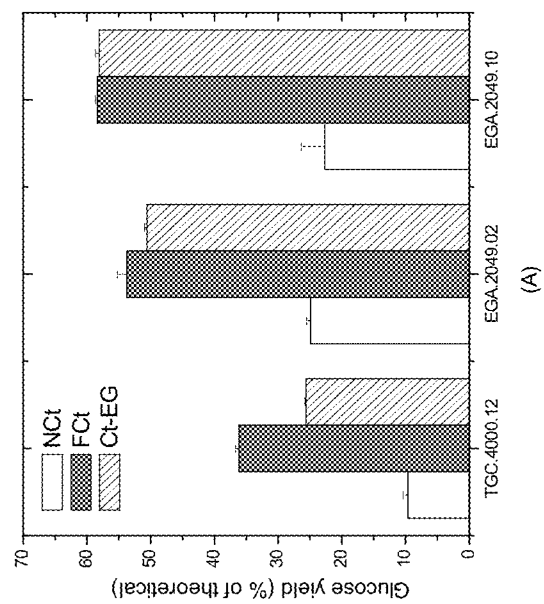

FIGS. 4A-4B show the hydrolysis results for the transgenic plants expressing endoglucanases. These figures illustrate glucose yield from the transgenic events EGA.2049.02 and EGA.2049.10, which express endoglucanase A (EGA), and the transgenic control plant TGC.4000.12, which lacks the enzyme (FIG. 4A). These figures also illustrate glucose yield from the transgenic event EGB.2042.03, which expresses endoglucanase B (EGB), and the transgenic control plant TGC.2004.8.02 (FIG. 4B). Hydrolysis treatments were with the full enzyme cocktail #1 (FCt), enzyme cocktail lacking endoglucanase (Ct-EG) and no enzymes (NCt). For EGA-expressing maize events, both EGA.2049.02 and EGA.2049.10 achieved 48.9-126.9% higher glucan conversion compared to the transgenic control plant (TGC.4000.12) (FIG. 4A). The difference in glucose yields between Ct-EG and FCt hydrolysis is negligible for EGA.2049.10, and about 29.1% lower for TGC.4000.12. Similar observations based on criterion 2 were made for the transgenic event EGA.2049.02. Referring to FIG. 4B, the EGB expressing transgenic plant EGB.2042.0) shows 63.6% higher glucan conversion from Ct-EG hydrolysis than the transgenic control TGC.2004.8.02. Surprising, the glucose yield from Ct-EG hydrolysis of EGB.2042.03 is only 12.2% lower than from FCt hydrolysis compared to 23.0% lower value from the corresponding treatments for TGC.2004.8.02. These data show about 50.0% better hydrolysis from the EGB expressing plant than from the control plant.

Plants Expressing Multiple Enzymes

To develop an efficient and inexpensive enzyme production system for rapid and less expensive biomass depolymerization, several enzymes used in the hydrolytic enzyme cocktail were expressed in maize.

FIGS. 5A-5D and FIGS. 6A-6B show the results from the hydrolysis of the transgenic plants XynA/AccA/B.2096.05, XynA/AccA/B.2096.01, EGA/XynA.2242.09, XynB/EGA/CBHB.2349.56, XynB/EGA/CBHB.2349.55, and XynB/EGA/CBHA.2345.116, which express multiple enzymes.

FIGS. 5A-5B illustrate data from enzymatic hydrolysis of the pretreated transgenic maize plants XynA/AccA/B.2096.01, XynA/AccA/B.2096.05 expressing xylanase A (XynA) and accessory enzymes (Acc) and the transgenic control plant TGC.2004.8.02 following the full cocktail #1 (FCt), cocktail #1 without xylanase (Ct-Xyn) and no-cocktail (NCt) treatments. The glucose yield (FIG. 5A) from the Ct-Xyn hydrolysis of the transgenic events XynA/AccA/B.2096.01, XynA/AccA/B.2096.05 is, respectively, 80.4% and 93.5% higher than from the control plant TGC.2004.8.02.

Referring to FIG. 5C, the surprisingly higher glucose yield from Ct-Xyn-EG hydrolysis of EGA/XynA.2242.09 may be explained by a synergistic hydrolytic effect. Likewise, efficiency of xylan conversion based on xylose yield (FIG. 5B) from CT-Xyn hydrolysis of the transgenic tissues from XynA/AccA/B.2096.01, XynA/AccA/B.2096.05 is, respectively, 143.4% and 172.1% higher than that from the control plant TGC.2004.8.02. The observed high efficiency of xylan conversion for these transgenic events may also be attributed to a synergistic effect of multiple enzymes.

FIG. 5 illustrates glucose (FIG. 5C) and xylose (FIG. 5D) yields from the transgenic maize event EGA/XynA.2242.09 simultaneously expressing endoglucanase A (EGA) and xylanase A (XynA) following enzymatic treatments with the full cocktail #1 (FCt), cocktail #1 lacking xylanase (Ct-Xyn), cocktail #1 lacking endoglucanase (Ct-EG] and cocktail #1 lacking xylanase and endoglucanase (Ct-Xyn-EG). The in planta expression of XynA results in the improved glucose and xylose yields for EGA/XynA.2242.09 after hydrolysis. For example, for the Ct-Xyn treatment transgenic events demonstrated 50.1% higher efficiency of glucan conversion (FIG. 5C) and 29.8% higher efficiency of xylan conversion (FIG. 5D) relative to that of the control plant. The in planta expression of EGA results in an improved efficiency of glucan hydrolysis evident from the difference in glucose yields between FCt, Ct-EG, and Ct-Xyn-EG treatments.

Figures 6A, 6B:
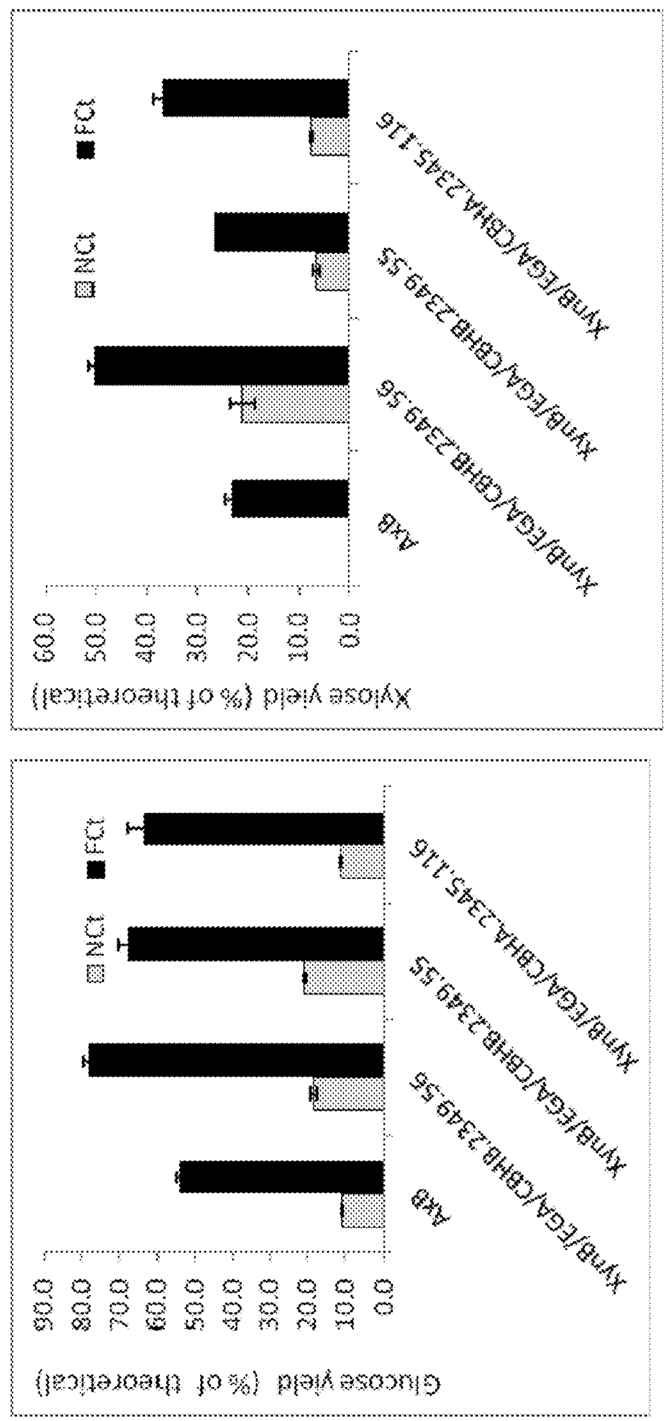
FIGS. 6A-6B illustrate glucose and xylose yields, respectively, from the stover of the pretreated wild type control plant AxB and the transgenic maize plants XynB/EGA/CBHB.2349.56, XynB/EGA/CBHB.2349.55, and XynB/EGA/CBHA.2345.116, which express triple stacked proteins. The yields were measured following enzymatic hydrolysis with the enzyme cocktail Accelerase® 1500/XY (FCt; black bars (right)) compared to a control treatment lacking the enzyme cocktail (NCt; gray bars (left)).

FIGS. 6A-6B illustrate glucose (FIG. 6A) and xylose (FIG. 6B) yields from 1) transgenic events simultaneously expressing three CWD enzymes (XynB/EGA/CBHB.2349.56 and XynB/EGA/CBHB.2349.55, which simultaneously express xylanase B, endoglucanase A (EGA), cellobiohydrolase B, and XynB/EGA/CBHA.2345.116, which simultaneously expresses xylanase B, endoglucanase A (EGA), and cellobiohydrolase A) and 2) wild type control plant AxB. full cocktail (FCt) and no enzyme cocktail (NCt) treatments results are shown. The pretreatment included 0.17 M of ammonium bisulfite and ammonium carbonate (BSC), a liquid to solid ratio equal to 10, at 55° C. for 17 hours. Enzymatic hydrolysis of the stover was performed at 50° C., pH 5.0 for three days using 0. 2/0.1 ml of Accellerase® 1500/XY per gram of stover. Referring to FIG. 6, the results show that glucose and xylose yields from the transgenic plants expressing three CWD enzymes were much higher than that from the wild type control plant. Surprisingly, the best performing event XynB/EGA/CBHB.2345.56 showed 43.6% higher in glucose yield and 117.6% higher in xylose yield than that of the negative control (AxB) after a very moderate chemical pretreatment.

Second Generation Plants Expressing CWD Enzymes

Figure 7B:
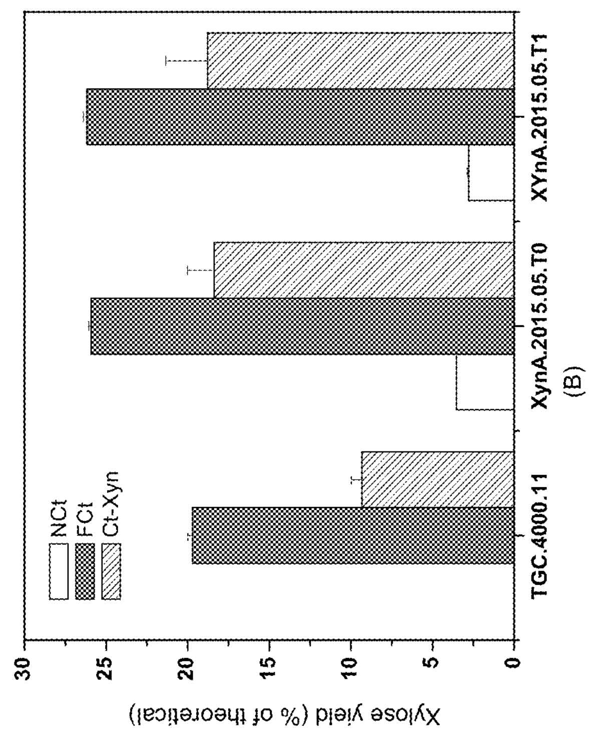
FIGS. 7A-7B illustrate glucose and xylose yields, respectively, from transgenic plants.

The first generation (T0) XynA.2015.05 plant was identified as a good hydrolysis candidate. To further evaluate this event and the corresponding enzyme (XynA) construct, seeds from this event were planted to generate second generation T1 progeny. The hydrolysis evaluation results for T0 and T1 of XynA.2015.05 plants are shown in FIG. 7B.

Figure 7A:
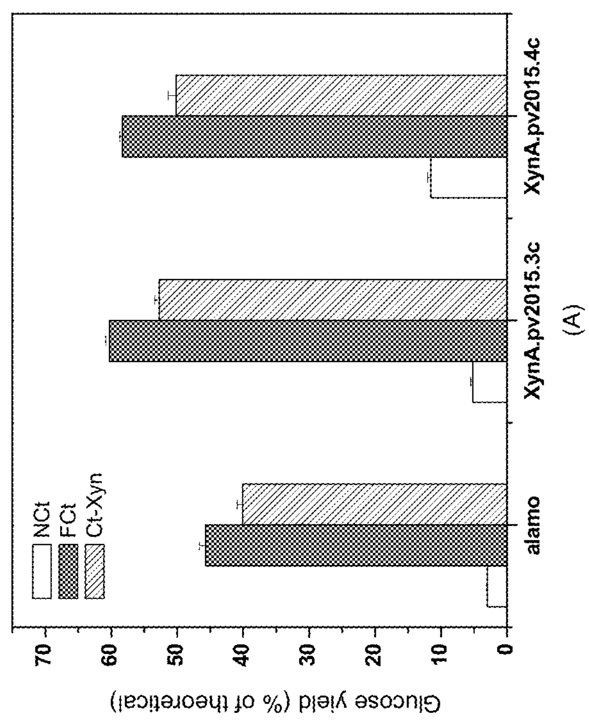

The two criteria used for assessment of the T0 plants were also applied to evaluate efficiency of hydrolysis for the plants produced in T1 and to demonstrate the enzymes can be effective across species. FIG. 7B shows glucose (FIG. 7A) yields from switchgrass plants made using pAG2015 and xylose (FIG. 7B) yields from the T0 transgenic event XynA.2015.05T0 expressing xylanase A, the T1 transgenic event XynA.2015.05T1 expressing xylanase A and the transgenic control plant lacking the enzyme TGC.4000.11. Hydrolysis was done along with the full cocktail (FCt), cocktail lacking xylanase (Ct-Xyn) and no enzyme cocktail (NCt) treatments. For the Ct-Xyn treatment, the first generation transgenic event XynA.2015.05T1 demonstrated 55.3% higher glucan and 101.6% xylan hydrolysis as judged by glucose and xylose yields similar to that of the first generation event XynA.2015.05T0 and higher than sugar yields for the control plant TGC.4000.12.

These data show that enzymes expressed in planta are heritable and preserve activity in subsequent generations of transgenic plants.

Diverse Plant Species

Figure 8B:
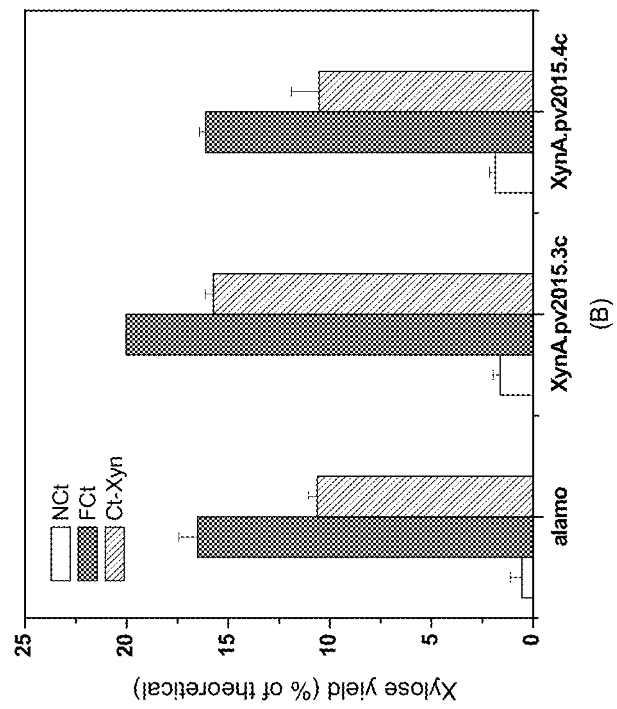
FIGS. 8A-8B illustrate glucose and xylose yields, respectively, from two pretreated transgenic switchgrass plants expressing xylanase A (XynA.pv2015.3c and XynA.pv2015.4c) compared to a control non-transgenic switchgrass plant (Alamo) following enzymatic hydrolysis with enzyme cocktail #1 (FCt; gray (middle)); enzyme cocktail #1 lacking xylanase (Ct-Xyn; diagonal stripes (right)) and a control treatment lacking the enzyme cocktail (NCt; white (left)).
Figure 8A:
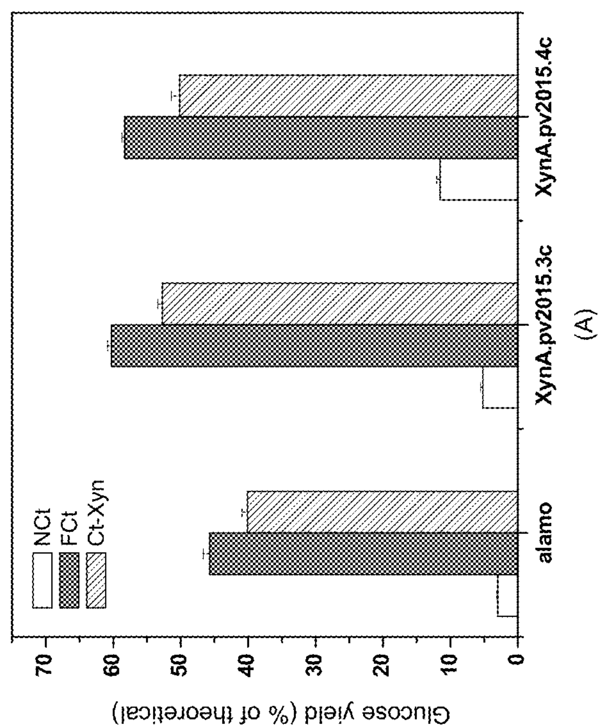

In addition to the transgenic maize events, switchgrass plants expressing xylanase A were obtained through transformation with the vector pAG2015. When xylanase A from a good maize hydrolysis performer XynA.2015.05 was expressed in switchgrass by transformation with the same construct (pAG2015) the resulting transgenic switchgrass XynA.pv2015.3c also demonstrates better glucan and xylan conversion over the control switchgrass Alamo. FIG. 8 illustrates glucose (FIG. 8A) and xylose (FIG. 8B) yields following hydrolysis of the pretreated transgenic switchgrass events XynA.pv2015.3c, XynA.pv2015.4c and the wild type control switchgrass plant (Alamo) in treatments with the full cocktail (FCt), the enzyme cocktail lacking xylanase (Ct-Xyn) and no enzymes (NCT). Both transgenic events XynA.pv2015.3c and XynA.pv2015.4c show better hydrolysis than the control switchgrass (Alamo). The best performing event XynA.pv2015.3c demonstrated about 30.0% higher efficiency in glucan conversion and 50.0% higher efficiency in xylan conversion compared to that of the control plant. These data show that the same hydrolytic trait may be conserved across species expressing enzymes in planta.

Plants Expressing Intein-modified Enzymes

Figure 9B:
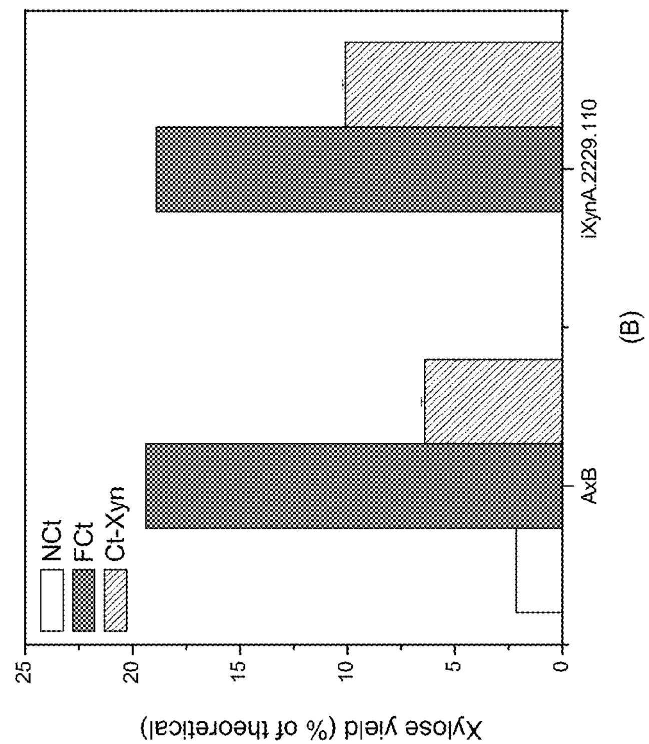
FIGS. 9A-9B illustrate glucose and xylose yields, respectively, from a pretreated transgenic plant (iXynA.2229.110) expressing intein-modified XynA (iXynA) and a pretreated wild-type control plant (AxB) following enzymatic hydrolysis with enzyme cocktail #1(FCt; gray (middle)); enzyme cocktail #1 lacking xylanase (Ct-Xyn; diagonal stripes (right)) and a control treatment lacking the enzyme cocktail (NCt; white (right)).
Figure 9A:
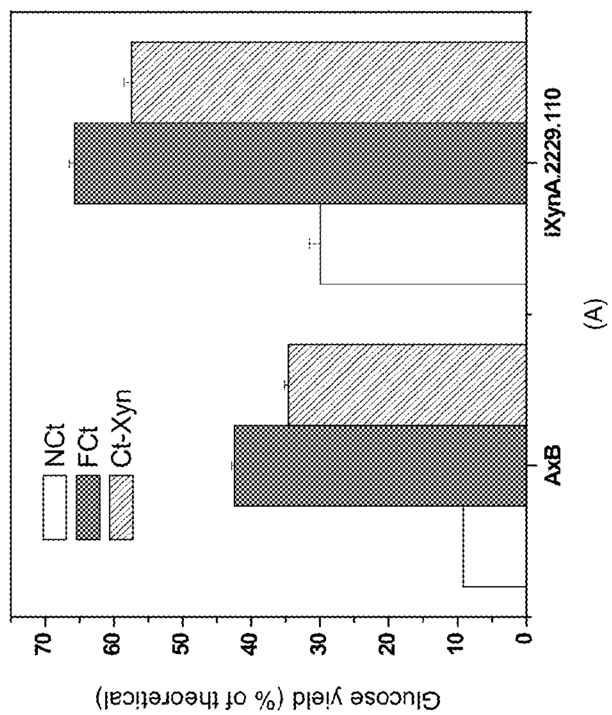

To avoid detrimental effects of in planta accumulation of CWD enzymes on plant growth, intein-modified enzymes were developed and expressed in plants to achieve desirable performance in hydrolysis without causing phenotypical abnormalities in plants. FIG. 9 illustrates glucose (FIG. 9A) and xylose (FIG. 9B) yields following the hydrolysis of a pretreated transgenic plant iXynA.2229.110 expressing intein-modified XynA and a wild type control plant AxB in FCt, Ct-Xyn and NCt treatments. The pretreatment temperature of higher than 500° C. induced intein splicing in iXynA.2229.110. The hydrolysis by Ct-Xyn demonstrates 66.0% higher efficiency of glucan conversion and 57.3% higher efficiency of xylan conversion for iXynA.2229.110 than for the control plant AxB. The transgenic plants iXynA.2229.110 were all normal Data from the carbohydrate compositional analysis showed no significant difference in the amounts of glucan and xylan between the transgenic plants expressing hydrolytic enzyme or enzymes and control plants. Hydrolysis results demonstrated that transgenic plants that express CWD enzymes achieved up to 141% higher glucose yield and 172% higher xylose yield compared the control plants from enzymatic hydrolysis under the experimental conditions.

Example 4

Time Course of Hydrolysis

Figure 10:
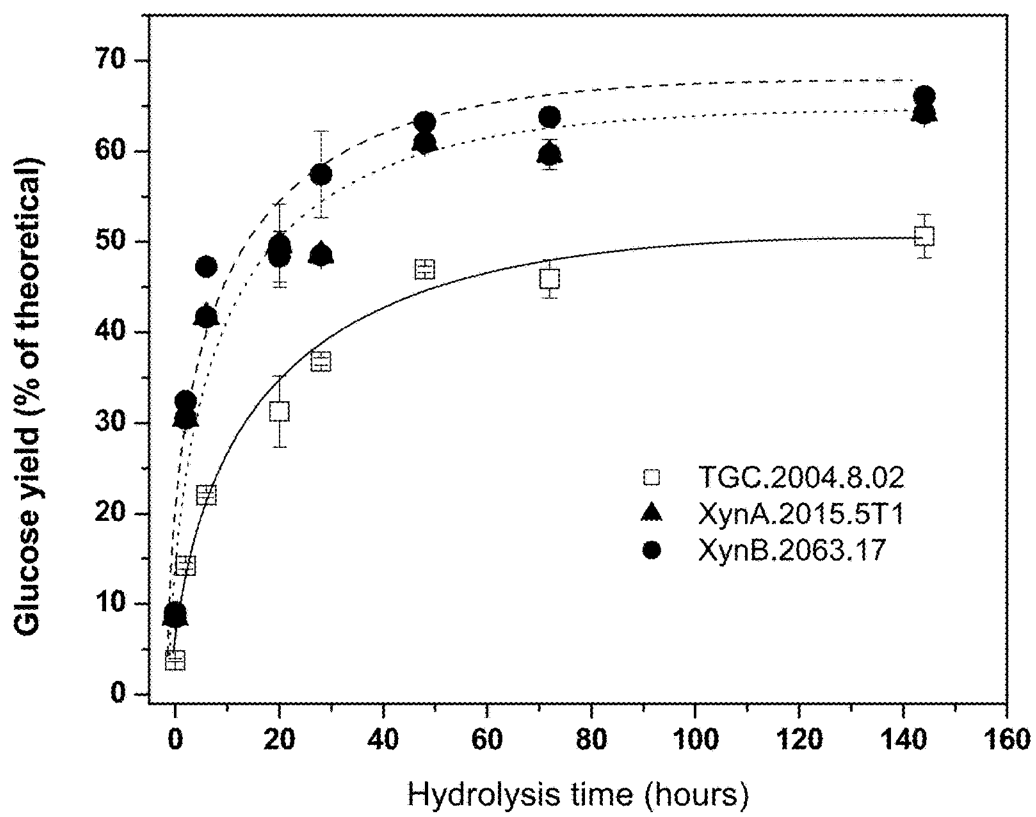
FIG. 10 illustrates the time course of the glucose yield from enzymatic hydrolysis of a pretreated transgenic plant expressing xylanase A (XynA.2015.5T1; closed triangle), and a pretreated transgenic plant expressing xylanase B (Xyn B.2063.17; closed circle) versus a transgenic control plant (TGC.2004.8.02; open square) using enzyme cocktail #1.

To better evaluate the effect of in planta expressed enzymes on hydrolysis, a time course assessment of hydrolysis for candidate transgenic plants was conducted. FIG. 10 compares the time courses for full cocktail (FCt) hydrolysis of a transgenic plant XynB, 2063.17, XynA.2015.05T1 and the control plant TGC.2004.8.02. The kinetics of hydrolysis follows a typical profile: a rapid initial hydrolysis is followed by a slow rising phase and a final plateau. The hydrolysis slows down at 24 hours and levels out after 48 hours. The transgenic plants expressing xylanases in planta demonstrate consistently better hydrolysis than the control plant through the time course, as evident from 30.0-40.0% higher glucose yields for a 3-day hydrolysis. Xylanase expression in planta can be considered as an enzyme pretreatment to improve both biomass hemicellulose and cellulose hydrolysis.

Figure 11:
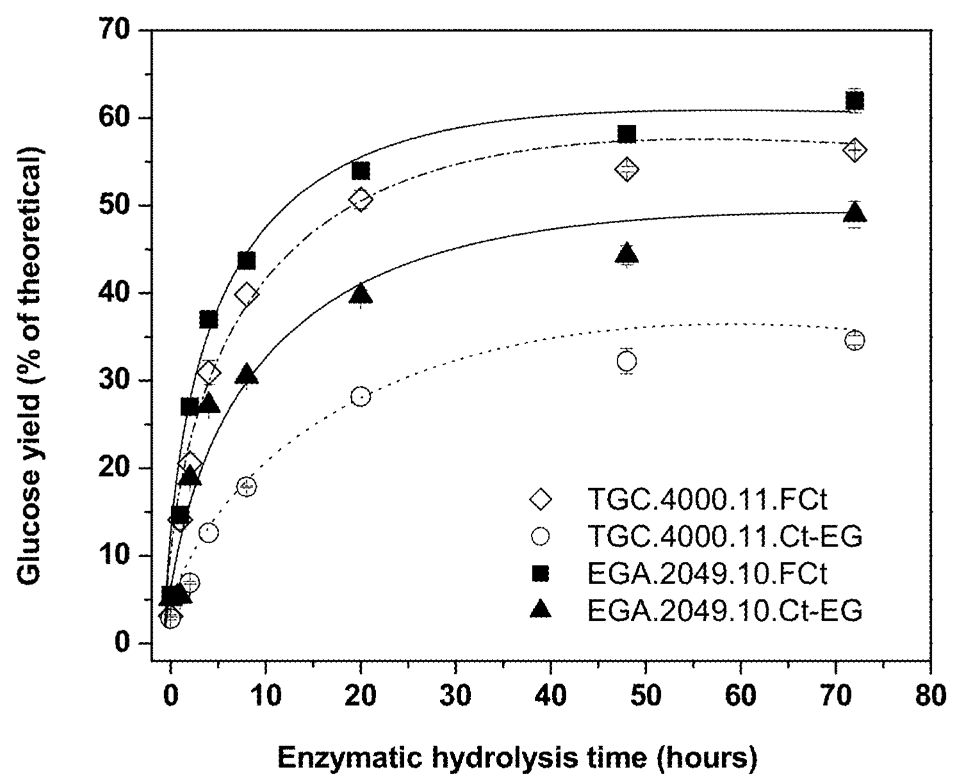
FIG. 11 illustrates the time course of glucose yield from enzymatic hydrolysis of a pretreated transgenic plant (EGA.2049.10) and a pretreated transgenic control (TGC.4000.11) using enzyme cocktail #1

FIG. 11 illustrates the time course of enzymatic hydrolysis of the transgenic plant EGA.2049.10 expressing endoglucanase A (EGA) compared to a transgenic control plant TGC.4000.11 using FCt and Ct-EG. The effect of in planta expressed endoglucanase A on hydrolysis was demonstrated by the difference in glucose yields from these plants throughout the time course of Ct-EG hydrolysis. Throughout the time course, the endoglucanase-expressing plants EGA.2049.10 demonstrated 48.9% and 63.6% consistently higher glucan conversion from Ct-EG hydrolysis than did the control plants TGC.4000.11. Surprisingly, a more efficient and faster hydrolysis has been achieved from the transgenic plants with endoglucanase expression.

FIG. 12 illustrates the time course of enzymatic hydrolysis of the transgenic event EGA/XynA.2242.09 expressing EGA and XynA and the transgenic control plant TGC.4000.11. The transgenic event EGA/XynA.2242.09 demonstrates consistently higher glucose yields (FIG. 12A) and xylose yields (FIG. 12B) using FCt, Ct-EG and Ct-Xyn compared to that of the control plant TGC.4000.11. The data demonstrate that these high sugar yields result from the simultaneous expression of endoglucanase and xylanase in plants.

FIG. 13 illustrates the time course of the enzymatic hydrolysis of the transgenic plant XynA/AccB.2092.103 expressing XynA and an accessory enzyme (*Aspergillus niger* FAE B) and the transgenic control plant TGC.4000.11 using FCt and Ct-Xyn treatments. The Ct-Xyn hydrolysis of the pretreated stover from the transgenic plant XynA/AccB.2092.103 achieved more than 30% higher efficiency in glucan conversion (FIG. 13A) and more than 24% higher efficiency in xylan conversion (FIG. 13B) than a transgenic control plant throughout the time course.

Referring to FIG. 12 and FIG. 13, the better hydrolysis of transgenic plants that express multiple enzymes was also observed in terms of glucose and xylose yields throughout the time course of hydrolysis of XynA/AccB.2092.103 and EGA/XynA.2242.09. The better hydrolysis may be explained by a synergistic effect of the action of multiple enzymes.

Referring to FIGS. 10, 11, 12A and 13A, the results show that in addition to the higher hydrolysis yields achieved through expression of CWD enzymes in plants, the kinetics profiles of the transgenic events expressing CWD enzymes during the time course of hydrolysis show a higher initial slope in the change of glucose yields compared to that of control plants indicating a faster initial hydrolysis.

Referring to FIG. 10, in addition to the better hydrolysis, the transgenic plants expressing hydrolytic enzymes also show faster initial hydrolysis than do the control plant (FIG. 10). After in planta expression, the hydrolytic enzymes have been accumulated within plant cells. During processing, they can start to function immediately in situ without the need for long distance transport and diffusion. The efficiency of these enzymes is therefore expected to be high because of low resistance from mass transfer and an expected decrease in non-selective binding of the in planta enzymes to lignin or other non-target molecules. The over expression of plant biomass degrading enzymes in plants does not appear to result in a decrease in cellulose, but rather loosened xyloglucan intercalation, followed by an irreversible wall modification. All these factors may contribute to the faster hydrolysis for enzyme expressed plants.

Example 5

Hydrolysis Improvements by Increasing Pretreatment Temperature

With the pretreatment chemicals, a relative high temperature for pretreatment typically delivers more pretreatment effects on hydrolysis. To examine the effect of pretreatment temperature, the top hydrolysis performers identified were subject to pretreatments at 65° C. and 75° C. The glucose hydrolysis yields of these plants are shown in FIG. 14.

It has been found that the thermal stability of some CWD enzymes including endoglucanase A (O77044) may improve when expressed in plants. Thermal stability of highly thermostable enzymes such as a family 12 endoglucanase C (O33897) can be further improved after expressing in plants, providing opportunities to apply elevated pretreatment temperatures during processing to achieve improved hydrolysis. FIG. 14 illustrates the effect of a pretreatment temperatures on glucose yield from the top performing transgenic events XynB.2063 (expressing xylanase B), XynA.2015.05T1 (expressing xylanase A), EGA.2049.10 (expressing endoglucanase A), XynA/AccB.2092.103 (expressing xylanase A and accessory enzyme B), XynA/EGA.2242.09 (expressing xylanase A and endoglucanae A), and iXynA.2229.110 (expressing an intein-modified xylanase A) versus the wild type control plant AxB and the transgenic control plant lacking enzyme TGC.4000.11. Hydrolysis of the plants was performed using FCt at a temperature of 65° C. or 75° C. It was demonstrated that increasing a pretreatment temperature from 65° C. to 75° C. improved glucose hydrolysis yields for the control plants AxB and TGC.4000.11 but not for transgenic plants expressing enzymes. This fact may be explained by saturation of the in planta expressed enzymes on available biomass substrate. With a pretreatment temperature of 65° C., all the transgenic plants expressing enzymes showed 11.0-33.4% higher hydrolysis compared to the wild type control plant AxB and the transgenic control TGC.4000.11, reaching 80-84% of theoretical glucose yield.

FIG. 15 illustrates the glucose yield from the transgenic switchgrass plant EGC.2253.4b expressing a highly thermostable endoglucanase A (EGC) following pretreatment with temperatures of 65° C., 75° C., and 95° C. and enzymatic hydrolysis. As shown, the glucose yield from the transgenic event EGC.2253.4b was consistently higher than that from the control plant Alamo, reaching 89.4% and 71.4% respective conversion rates of a pretreatment at 95° C.

FIGS. 16A-16B illustrate an effect of the pretreatment temperature and time on glucose (FIG. 16A) and xylose (FIG. 16B) yields from the transgenic event XynA/EGA.2342.05 and the transgenic control plant lacking enzymes TGC.2243.01 following enzymatic hydrolysis. Pretreatments were performed using 0.175M ammonium bisulfite and ammonium carbonate at a pH 8.1 and temperatures of 55° C., 60° C. and 75° C. for 2, 4, 6 and 16 hours at each temperature and 3000 rpm. Enzymatic hydrolysis was performed using 0.2 ml Accellerase® 1500/g pretreated stover and 0.1 ml Accellerase® XY/g stover, at 2% solids, pH ~5.0, 1× Britton-Robinson Polybuffer (BR; final pH 4.9), 0.02% sodium azide at 50° C. for 72 hours, at 250 rpm. As shown, for all pretreatment temperatures and periods of time, the transgenic event XynA/EGA.2342.105 expressing xylanase A and endoglucanase A performed consistently better than the control plant TGC.2243.01. These data also show that extending the pretreatment time increases both glucose and xylose yield from plants almost linearly and that pretreatment for 16 hours significantly improves hydrolysis from the transgenic and control plants.

FIGS. 17A-17B illustrate an effect of pretreatment temperature on glucose (FIG. 17A) and xylose (FIG. 17B) yields from the transgenic events XynA/EGA.2242.09.01 and XynA/EGA.2242.09.07 (expressing xylanase A and endoglucanase A) and control plants wild type AxB and transgenic TGC.4000.11. The plants were subjected to enzymatic hydrolysis using full Accellerase enzyme cocktail at temperatures 55° C. to 65° C. and 75° C. Enzyme loadings included 0.2 ml of Accellerase® 1500 per gram of pretreated stover and 0.1 ml Accellerase®XY per gram of pretreated stover. Transgenic plants expressing CWD enzymes achieved up to 83.5-89.1% glucose yield and 50.0-64.3% xylose yield compared to control plants achieved only 63.0-76.6% glucose yield and 35.7-45.3% xylose yield.

Significant hydrolysis can be achieved when increasing pretreatment temperature to 65° C. For some maize stover, increasing temperature to 75° C. improved hydrolysis for the control plants but not for the transgenic plants expressing enzymes. Referring to FIG. 15, for the transgenic switchgrass EGC.2253.4b expressing a highly thermostable endoglucanase C (EGC), the improved hydrolysis was found surprisingly to be significantly higher with increased pretreatment temperature, especially at 95° C. than the for the control plant Alamo.

Overall, pretreating stover from the top performing transgenic plants at elevated temperatures (65° C. and 75° C.) achieved over 80% glucose hydrolysis yields, which is 25% higher hydrolysis compared to control plants that do not express heterologous hydrolytic enzymes. Therefore, in planta expression of highly thermostable hydrolytic enzymes will provide more opportunities to achieve target component hydrolysis.

Example 6

Enzyme Loading Reduction and Fermentability

Since the transgenic plants expressing CWD enzymes demonstrated higher hydrolysis yields and more rapid kinetics during the hydrolysis compared to the control plants under similar processing conditions, reduction in exogenous enzyme loadings was tested. FIG. 18 illustrates glucose yields from the transgenic plants XynB.2063.17 expressing xylanase B, XynA.2015.5T1 expressing xylanase A and the control plant TGC.2004.8.4 following hydrolysis treatments using the in-house cocktail #1 with varying loadings such as full cocktail (FCt), 75% cocktail (0.75 FCt), 50% cocktail (0.50 FCt). 25% cocktail (0.25 FCt), 10% cocktail (0.10 FCt), and no enzymes (0 FCt). The data demonstrate feasibility in reducing loadings of exogenous enzymes by application of the transgenic material expressing CWD enzymes without reducing sugar yields. For example, the transgenic event XynA.2015.15T1 achieved more than 60% glucan conversion using 0.75 FCt loading which is similar to approximately 65% glucan conversion achieved using FCt loading. In contrast, the transgenic control TGC.2004.8.4 achieved approximately 50.0% glucan conversion using FCt loading and approximately 40% of glucan conversion using 0.75 FCt loading. These data show that hydrolysis of plants expressing CWD enzymes was more efficient than that from control plants and with lower loadings of external enzymes.

FIG. 19 illustrates glucose yields from the transgenic plants XynE/EGC/CBHA.2339.03, XynE/EGC/CBHA.2339.04, and XynE/EGC/CBHA.2339.05 (expressing xylanase E, endoglucanase C and cellobiohydrolase A) and the wild type control plant BxA following enzymatic hydrolysis with the full cocktail (FCt), 20% full cocktail (0.2 FCt), and no enzymes (NCt) treatments. The data show that 50-70% glucose yield can be achieved from the transgenic plants XynE/EGC/CBHA.2339.03, XynE/EGC/CBHA.2339.04, and XynE/EGC/CBHA.2339.05 using only 20% loadings of the full cocktail which is 35-77% higher than that of the control plants.

Surprisingly, the glucose yield from the transgenic event XynE/EGC/CBHA.2339.03 following hydrolysis with only 20% loading of the full cocktail was still 15% higher than the glucose yield from the control plant BxA after the hydrolysis treatment using the full cocktail.

FIGS. 20A-20B illustrate the effect of reduction in loadings of external enzymes on glucose yield from the transgenic events XynA/EGA.2309.54 and XynA/EGA.2309.107 (expressing xylanase A and endoglucanase A) and the control plants BxA after hydrolysis with full cocktail (FCt), 20% full cocktail (0.2FCt) and no enzymes (NCt). 60-70% glucose yields from the transgenic plants expressing enzymes were achieved by using 20% loadings of full cocktails compared to about 80% glucose yields achieved with the full cocktail. In contrast, the negative control plants yielded only 53% glucose in the 0.2 FCt treatment and 70% glucose in the FCt treatment. Referring to FIG. 20B, approximately 38% xylose yields were achieved from the transgenic plants expressing CWD enzymes in 0.2FCt treatment compared to approximately 47% xylose yields in FCt treatment and much lower xylose yields for the negative control plants in both FCt and 0.2FCt treatments. 20% FCt glucose yield of XynA/EGA.2309.54 and XynA/EGA.2309.107 can achieve 16-29.3% higher glucose yield as well as 27.6-31% higher xylose yield than the negative control.

FIGS. 21A-21B illustrate the effect of reduction in external enzyme loadings on glucose (FIG. 21A) and xylose (FIG. 21B) from the transgenic plants EGA/XynA.2242.09.16 (expressing endoglucanase CBHA.2069.1.3) and the transgenic control TGC.4000.11 after hydrolysis using no enzymes (0), 20% full cocktail (0.2FCt), 40% full cocktail (0.4FCt), 60% full cocktail (0.6FCt), 80% full cocktail (0.8FCt), and Full cocktail (Accellerase® 1500/XY). Pretreatment was performed using 0.25 M ammonium bisulfite and ammonium carbonate (pH 8.56) at a liquid to solid ratio equal to 7, at 75° C. for 20 hours. Enzymatic hydrolysis was performed using approximately 2% solids content, pH 5.0, at 50° C. for three days. Surprisingly, the data shows that 60% FCt hydrolysis can achieve 80% of glucose and approximately 60% xylose theoretical yields for both transgenic plants expressing enzymes while only 60% and 49%, respectively, for the negative control TGC.4000.11.

These results demonstrate the potential for reduction in loadings of external enzymes and simultaneously achieving efficient hydrolysis of plant stover by utilizing the transgenic plants expressing CWD enzymes.

To evaluate the fermentability of the hydrolysates that are produced from transgenic plants expressing CWD enzymes, a simultaneous saccharification and fermentation (SSF) experiment was performed using *Saccharomyces cerevisiae*

D5A. FIG. 22 illustrates the production of ethanol during SSF from the transgenic plants EGA.2049.10 (expressing endoglucanase A) and EGA/XynA.2242.09 (expressing endoglucanase A and xylanase A) and control plants AxB and TGC.4000.11 at a biomass solids content of 6%. These data show about 77.8% higher cellulose conversion was achieved by using the transgenic plants expressing CWD enzymes compared to the control plants. Further, with the moderately pretreated biomass, SSF of the enzyme-expressing plants EGA.2049.10 and EGA/XynA.2242.09 produced ethanol at a concentration of 8.0 g/1, or at 65% ethanol yield, compared to 4.5 g/1, or 42% ethanol yield for the control plants, which corresponds to a 55% improvement in production of ethanol.

The improved hydrolysis has the potential to be translated into the exogenous enzyme loading reduction while still maintaining similar hydrolysis as shown in FIGS. 18-21. Expression of in planta CWD enzymes demonstrated the opportunity to produce low-cost sugar from CWD enzyme-expressing crops or biomass for the production of biofuels, biochemicals, and biomaterials. The benefit of fast initial hydrolysis also provide a potential to achieve similar or better hydrolysis in less operation time, an advantage for a simultaneous saccharification and fermentation process (FIG. 22), and an opportunity to decrease the requirement for equipment capacity and operation cost.

In planta production of cell wall degrading enzymes is a means to lower the costs associated with fermentable sugar production from biomass through the direct hydrolysis of transgenic plants.

Example 7

Thermo-chemical Effect: Biomass Solubilization from Moderate Pretreatment

FIG. 23 illustrates biomass solubilization from moderate pretreatment based on weight loss in a transgenic plant expressing exoglucanase CBHA (CBHA.2069.3.17) and wild type control plant (AxB) after pretreatment with deionized water (DI); 0.06M or 0.25M dilute sulfuric acid (DSA); or 0.25 M ammonium bisulfite and 0.23M ammonium carbonate (BSC; pH 8.1Pretreatment was performed at a temperature of 75° C., a liquid to solids ratio equal to 8, for 16 hours. This figure highlights weight loss data for samples of oven-dried corn stover derived from the transgenic plant and the wild type control plant. Measurements were conducted following wash and centrifugation procedures of the pretreated biomass. Compared to pretreatment with DI, pretreatment with 0.25 M BSC (pH 8.1) results in 17.5% more biomass weight loss for the transgenic plant (CBHA.2069.3.17) and 12.2% more weight loss for the non-transgenic control plant (AxB). The transgenic plant expressing exoglucanase (CBHA.2069.3.17) shows more biomass weight loss from all pretreatments compared to the non-transgenic control plant.

Example 8

Thermo-chemical Effect: Biomass Weight Loss and Lignin Removal from Moderate Pretreatment Biomass weight loss and lignin removal was determined for samples of oven dried stover derived from a transgenic control plant TGC.2209 after pretreatment with deionized water (DI) and 0.17 M ammonium bisulfite with 0.165M ammonium carbonate (BSC) at pH 8.1, a liquid to solid ratio equal to 8, at a temperature of 75° C., for 16 hours. Measurements were conducted following wash and centrifugation procedures of the pretreated biomass. Table 3 shows that pretreatment with 0.17 M BSC (pH 8.1) results in more biomass weight loss and more lignin removal compared to pretreatment with DI water.

TABLE 3

Biomass weight loss after pretreatment and acid insoluble lignin in pretreated biomass

| Pretreatment chemicals | Biomass weight loss (% of stover) | Acid insoluble lignin (% on pretreated biomass) |
|---|---|---|
| DI water | 34.6 | 10.0 |
| 0.17M BSC | 39.9 | 14.6 |

Example 9

Thermo-chemical Effect: Deacetylation from Moderate Pretreatment

FIGS. 24A-24B illustrate the effect of the temperature and time on deacetylation of plant biomass assessed for the oven-dried corn stover derived from a transgenic plant expressing cellobiohydrolase A (CBHA.2063.3.17) and a non-transgenic control plant (AxB). The pretreatments included deionized water (DI), 0.06M dilute sulfuric acid (DSA), 0.25 M DSA, or 0.25 M ammonium bisulfite with 0.23M ammonium carbonate (BSC) and were performed at pH 8.1, a liquid-to solid ratio equal to 8, at temperatures 75° C. or 95° C. for 16 hours, or 85° C. for 7 hours. Acetic acid (HAc) concentration was determined by HPLC analysis of the filtrate samples obtained from the pretreated biomass using HPX-87H Column (Bio-Rad Laboratories, Hercules, Calif.) acid column operating at 0.6 ml/min, 60° C. with 0.004 M sulfuric acid as the mobile phase. Pretreatment with 0.25 M BSC (pH 8.1) resulted in significant deacetylation compared to pretreatment with DI water and 0.06 M DSA.

Example 10

Thermo-chemical Effect: Little/No Sugar Degradation (Furfural and HMF) from Moderate Pretreatment FIGS. 25A-25B illustrate yields of sugar degradation products hydroxymethylfurfural (HMF) and furfural in samples of oven-dried corn stover from a transgenic plant expressing exoglucanase CBHA (CBHA.2069.3.17) and a non-transgenic control plant (AxB) after pretreatment with deionized water (DI), 0.06M dilute sulfuric acid (DSA), 0.25 DSA, or 0.25 M ammonium bisulfite and 0.23M ammonium carbonate (BSC; pH 8.1). Pretreatment was performed at temperatures 75° C. and 95° C. for 16 hours and 85° C. for 7 hours. Concentrations of HMF and furfural in the filtrate of the pretreated biomass were measured by HPLC analysis using HPX-87H Column (Bio-Rad Laboratories, Hercules, Calif.) acid column operating at 0.6 ml/min, 60° C. with 0.004 M sulfuric acid as the mobile phase.

The data show that little to no HMF or furfural were found in samples from a transgenic plant expressing exoglucanase CBHA (CBHA.2069.3.17), or the non-transgenic control plant (AxB) after pretreatment with 0.25 M BSC (pH 8.1) in comparison to pretreatment with deionized water (DI), 0.06

M dilute sulfuric acid (DSA), or 0.25 M DSA, which led to sugar degradation and detection of HMF and furfural in samples.

Example 11

Autohydrolysis from in Planta Enzymes

Examples of autohydrolysis of plants expressing cell wall degrading enzymes are shown in FIG. 26. This figure illustrates results on a pretreated maize plant that expresses XynB (XynB.2063.15) alone and a plant that simultaneously express three enzymes; XynA and accessory enzymes A and B (XynA/AccA/B.2096.01). The results are compared to a pretreated non-transgenic control plant (AxB). Pretreatment was performed using 0.17 M ammonium bisulfite and 0.165 M ammonium carbonate (pH 8.1), liquid to solid ration (L/S) equal to 10, and at 55° C. for 16 hours. Enzymatic hydrolysis was achieved by enzymes produced in planta at 2% solids content with no external enzyme cocktail (NCt) and at a temperature of 50° C., pH 5.0 for 3 days. Post-acid hydrolysis was performed at pH less than 1.0 and a temperature of 121° C. for 60 minutes. Both transgenic plants expressing xylanase show 3-5 fold more xylose yield from autohydrolysis compared to the control AxB plant.

FIG. 27 illustrates results of autohydrolysis for a corn plant simultaneously expressing xylanase B, endoglucanase and CHBA (XynB/EGA/CBHA.2345.116) and a plant expressing xylanase B, endoglucanase and CBHB (XynB/EGA/CBHB.2349.55) compared to a non-transgenic control plant (AxB). The plants were pretreated with 0.17 M ammonium bisulfite and 0.165M ammonium carbonate BSC (pH 8.1) with L/S equal to 10 at 55° C. for 16 hours. No intermediate washing procedures were applied between pretreatment and hydrolysis with enzymes expressed in planta. Hydrolysis was achieved under the following conditions: 2% solids content, no cocktail (NCt), 50° C. and pH 5.0 for 3 days. The transgenic plants expressing xylanase and other cellulases show significantly higher xylose yield from autohydrolysis compared to the control AxB plant.

Example 12

Effect of Mechanical Defibrillation on Processing of Unmilled Stover

Data on the effect of mechanical defibrillation on glucose and xylose yields from processing of un-milled stover are shown in FIGS. 28A-28B. The data were derived from experiments with a pretreated transgenic plant expressing endoglucanase and xylanase A (EGA/XynA.2242.09T1) versus a transgenic control plant TGC.4000. Pretreatment was performed using 0.25M ammonium bisulfite with 0.23 M ammonium carbonate (pH 8.56, L/S equal to 8, 75° C., for 16 hours followed by mechanical defibrillation (6% solid content). Enzymatic hydrolysis was achieved by enzymes produced in planta at 4% solids content using Accelerase® 1500/XY (0.2/0.1 ml per g of stover) at a temperature of 50° C. for up to 3 days and at pH 5.0. The transgenic maize plant simultaneously expressing endoglucanase and xylanase shows consistently higher glucose and xylose yields compared the control TGC.4000 plant through the time-course, reaching 83% and 63% glucose and xylose yields, respectively, for 3-day hydrolysis.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. An engineered plant comprising a first polynucleotide sequence, a second polynucleotide sequence, and a third polynucleotide sequence, wherein the first polynucleotide sequence encodes a xylanase comprising an amino acid sequence of SEQ ID NO: 6, the second polynucleotide sequence encodes an endoglucanase comprising an amino acid sequence of SEQ ID NO: 4, and the third polynucleotide sequence encodes a cellobiohydrolase comprising an amino acid sequence of SEQ ID NO: 10 or 12.

2. The engineered plant of claim 1, wherein at least one of the first polynucleotide sequence, the second polynucleotide sequence, or the third polynucleotide sequence further comprises a targeting polynucleotide sequence encoding a targeting peptide selected from the group consisting of: an amyloplast targeting signal, a cell wall targeting peptide, a vacuole targeting peptide, a mitochondrial targeting peptide, a cytosol localization signal, a chloroplast targeting signal, and a nuclear targeting peptide.

3. The engineered plant of claim 2, wherein the targeting polynucleotide sequence encodes a targeting sequence selected from the group consisting of: SEQ ID NO: 13, SEQ ID NO: 14, SEQ ID NO: 15, SEQ ID NO: 16, SEQ ID NO: 17, SEQ ID NO: 22, SEQ ID NO: 23, and SEQ ID NO: 24.

4. The engineered plant of claim 1, wherein the engineered plant is selected from the group consisting of: corn, sugar cane, sugar beet, sorghum, switchgrass, miscanthus, eucalyptus, willow and poplar.

5. The engineered plant of claim 1, wherein the engineered plant produces more xylose under hydrolysis condition in the absence of exogenous enzymes compared to a non-engineered plant of the same genetic background lacking a xylanase, an endoglucanase and a cellobiohydrolase.

6. The engineered plant of claim 1, wherein the engineered plant produces more glucose under hydrolysis condition in the absence of exogenous enzymes compared to a non-engineered plant of the same genetic background lacking a xylanase, an endoglucanase and a cellobiohydrolase.

7. The engineered plant of claim 1, wherein the engineered plant produces at least 10% more xylose under hydrolysis condition in the absence of exogenous enzymes compared to a non-engineered plant of the same genetic background lacking a xylanase, an endoglucanase and a cellobiohydrolase.

8. The engineered plant of claim 1, wherein the engineered plant produces at least 10% more glucose under hydrolysis condition in the absence of exogenous enzymes compared to a non-engineered plant of the same genetic background lacking a xylanase, an endoglucanase and a cellobiohydrolase.

* * * * *